US009932571B2

(12) United States Patent
Hallen-Adams et al.

(10) Patent No.: US 9,932,571 B2
(45) **Date of Patent: *Apr. 3, 2018**

(54) USE OF GALERINA MARGINATA GENES AND PROTEINS FOR PEPTIDE PRODUCTION

(71) Applicant: Board of Trustees of Michigan State University, East Lansing, MI (US)

(72) Inventors: Heather E. Hallen-Adams, Lincoln, NE (US); John S. Scott-Craig, East Lansing, MI (US); Jonathan D. Walton, East Lansing, MI (US); Hong Luo, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/437,359

(22) Filed: Feb. 20, 2017

(65) Prior Publication Data

US 2017/0275608 A1 Sep. 28, 2017

Related U.S. Application Data

(63) Continuation of application No. 14/933,239, filed on Nov. 5, 2015, now Pat. No. 9,598,686, which is a continuation of application No. 13/362,561, filed on Jan. 31, 2012, now Pat. No. 9,273,100, which is a continuation-in-part of application No. 12/268,229, filed on Nov. 10, 2008, now Pat. No. 9,518,097.

(60) Provisional application No. 61/002,650, filed on Nov. 9, 2007.

(51) Int. Cl.

| | |
|---|---|
| ***C12N 9/58*** | (2006.01) |
| ***C07K 7/64*** | (2006.01) |
| ***C07K 14/375*** | (2006.01) |
| ***C12P 21/06*** | (2006.01) |

(52) U.S. Cl.

CPC .................. *C12N 9/58* (2013.01); *C07K 7/64* (2013.01); *C07K 14/375* (2013.01); *C12P 21/06* (2013.01); *C12Y 304/21026* (2013.01)

(58) Field of Classification Search

CPC ...... C07K 14/375; C07K 7/64; C12Q 1/6895; C12Y 304/21026; C12N 9/58

See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 4,965,188 | A | 10/1990 | Mullis et al. |
| 5,928,906 | A | 7/1999 | Koster et al. |
| 9,273,100 | B2 | 3/2016 | Hallen-Adams et al. |
| 9,598,686 | B2 | 3/2017 | Hallen-Adams et al. |
| 2001/0014445 | A1 | 8/2001 | Urnovitz |
| 2004/0081978 | A1 | 4/2004 | Ziman et al. |
| 2005/0255486 | A1 | 11/2005 | Behlke et al. |
| 2006/0141495 | A1 | 6/2006 | Wu |
| 2008/0076677 | A1 | 3/2008 | Yershov et al. |
| 2009/0093620 | A1 | 4/2009 | Kovalic et al. |
| 2010/0267019 | A1 | 10/2010 | Hallen et al. |
| 2012/0276588 | A1 | 11/2012 | Hallen-Adams et al. |
| 2016/0281075 | A1 | 9/2016 | Hallen-Adams et al. |

FOREIGN PATENT DOCUMENTS

| | | |
|---|---|---|
| CN | 1341362 A | 3/2002 |

OTHER PUBLICATIONS

US 9,067,975, 06/2015, Hallen-Adams et al. (withdrawn)
"U.S. Appl. No. 12/268,229, Advisory Action dated Jun. 13, 2012", 3 pgs.
"U.S. Appl. No. 12/268,229, Advisory Action dated Sep. 18, 2014", 3 pgs.
"U.S. Appl. No. 12/268,229, Advisory Action dated Dec. 15, 2015", 3 pgs.
"U.S. Appl. No. 12/268,229, Examiner Interview Summary dated Jan. 12, 2016", 3 pgs.
"U.S. Appl. No. 12/268,229, Examiner Interview Summary dated Aug. 26, 2014", 4 pgs.
"U.S. Appl. No. 12/268,229, Final Office Action dated Feb. 28, 2013", 7 pgs.
"U.S. Appl. No. 12/268,229, Final Office Action dated Apr. 4, 2012", 8 pgs.
"U.S. Appl. No. 12/268,229, Final Office Action dated Jul. 9, 2014", 9 pgs.
"U.S. Appl. No. 12/268,229, Final Office Action dated Oct. 8, 2015", 16 pgs.
"U.S. Appl. No. 12/268,229, Non Final Office Action dated Mar. 4, 2014", 7 pgs.
"U.S. Appl. No. 12/268,229, Non Final Office Action dated Apr. 6, 2015", 19 pgs.
"U.S. Appl. No. 12/268,229, Non Final Office Action dated Jul. 16, 2012", 9 pgs.
"U.S. Appl. No. 12/268,229, Non Final Office Action dated Jul. 22, 2011", 13 pgs.
"U.S. Appl. No. 12/268,229, Non Final Office Action dated Dec. 21, 2010", 13 pgs.
"U.S. Appl. No. 12/268,229, Notice of Allowance dated Feb. 1, 2016", 10 pgs.
"U.S. Appl. No. 12/268,229, Notice of Allowance dated May 25, 2016", 7 pgs.
"U.S. Appl. No. 12/268,229, Preliminary Amendment dated Jun. 10, 2009", 16 pgs.

(Continued)

*Primary Examiner* — Maryam Monshipouri
(74) *Attorney, Agent, or Firm* — Schwegman Lundberg & Woessner, P.A.

(57) ABSTRACT

The present invention relates to compositions and methods comprising genes and peptides associated with cyclic peptides and cyclic peptide production in mushrooms. In particular, the present invention relates to using genes and proteins from *Galerina* species encoding peptides specifically relating to amatoxins in addition to proteins involved with processing cyclic peptide toxins. In a preferred embodiment, the present invention also relates to methods for making small peptides and small cyclic peptides including peptides similar to amanitin. Further, the present inventions relate to providing kits for making small peptides.

18 Claims, 85 Drawing Sheets

(56) References Cited

OTHER PUBLICATIONS

"U.S. Appl. No. 12/268,229, Response dated Jan. 8, 2016 to Advisory Action dated Dec. 15, 2015 and Final Office Action dated Oct. 8, 2015", 8 pgs.
"U.S. Appl. No. 12/268,229, Response dated May 24, 2013 to Final Office Action dated Feb. 28, 2013", 6 pgs.
"U.S. Appl. No. 12/268,229, Response dated May 27, 2011 to Supplemental Non-Final Office Action dated Dec. 27, 2010", 31 pgs.
"U.S. Appl. No. 12/268,229, Response dated Jun. 4, 2012 to Final Office Action dated Apr. 4, 2012", 13 pgs.
"U.S. Appl. No. 12/268,229, Response dated Jun. 4, 2014 to Non Final Office Action dated Mar. 4, 2014", 11 pgs.
"U.S. Appl. No. 12/268,229, Response dated Jun. 25, 2012 to Advisory Action dated Jun. 13, 2012 and to Final Office Action dated Apr. 4, 2012", 15 pgs.
"U.S. Appl. No. 12/268,229, Response dated Sep. 9, 2014 to Final Office Action dated Jul. 9, 2014", 9 pgs.
"U.S. Appl. No. 12/268,229, Response dated Oct. 18, 2010 to Restriction Requirement dated Sep. 16, 2010", 1 pg.
"U.S. Appl. No. 12/268,229, Response dated Nov. 16, 2012 to Non Final Office Action dated Jul. 16, 2012", 12 pgs.
"U.S. Appl. No. 12/268,229, Response dated Dec. 8, 2015 to Final Office Action dated Oct. 8, 2015", 7 pgs.
"U.S. Appl. No. 12/268,229, Response dated Dec. 22, 2011 to Non Final Office Action dated Jul. 22, 2011", 13 pgs.
"U.S. Appl. No. 12/268,229, Response dated Jul. 6, 2015 to Non Final Office Action dated Apr. 6, 2015", 16 pgs.
"U.S. Appl. No. 12/268,229, Restriction Requirement dated Sep. 16, 2010", 7 pgs.
"U.S. Appl. No. 12/268,229, Supplemental Non Final Office Action dated Dec. 27, 2010", 14 pgs.
"U.S. Appl. No. 13/362,561, Amendment Under 37 CFR dated Oct. 28, 2014", 12 pgs.
"U.S. Appl. No. 13/362,561, Non Final Office Action dated Jan. 28, 2014", 8 pgs.
"U.S. Appl. No. 13/362,561, Notice of Allowability dated Sep. 1, 2015", 6 pgs.
"U.S. Appl. No. 13/362,561, Notice of Allowance dated Aug. 5, 2015", 7 pgs.
"U.S. Appl. No. 13/362,561, Notice of Allowance dated Oct. 8, 2014", 11 pgs.
"U.S. Appl. No. 13/362,561, PTO Response to 312 Communication dated Feb. 5, 2015", 2 pgs.
"U.S. Appl. No. 13/362,561, PTO Response to Rule 312 Communication dated Jan. 28, 2016", 2 pgs.
"U.S. Appl. No. 13/362,561, PTO Response to Rule 312 Communication dated Jun. 5, 2015", 2 pgs.
"U.S. Appl. No. 13/362,561, PTO Response to Rule 312 Communication dated Nov. 7, 2014", 2 pgs.
"U.S. Appl. No. 13/362,561, Response dated Apr. 8, 2014 to Non Final Office Action dated Jan. 28, 2014", 8 pgs.
"U.S. Appl. No. 13/362,561, Response dated Aug. 4, 2014 to Restriction Requirement dated Jun. 3, 2014", 14 pgs.
"U.S. Appl. No. 13/362,561, Response dated Oct. 16, 2013 to Restriction Requirement dated Sep. 17, 2013", 7 pgs.
"U.S. Appl. No. 13/362,561, Restriction Requirement dated Jun. 3, 2014", 6 pgs.
"U.S. Appl. No. 13/362,561, Restriction Requirement dated Sep. 17, 2013", 7 pgs.
"U.S. Appl. No. 13/362,561, Supplemental Amendment Under 37 CFR dated Nov. 7, 2014", 13 pgs.
"U.S. Appl. No. 14/933,239, Non Final Office Action dated Jul. 6, 2016", 8 pgs.
"U.S. Appl. No. 14/933,239, Notice of Allowance dated Nov. 8, 2016", 8 pgs.
"U.S. Appl. No. 14/933,239, Preliminary Amendment dated Nov. 6, 2015", 14 pgs.
"U.S. Appl. No. 14/933,239, Preliminary Amendment dated Apr. 11, 2016", 9 pgs.
"U.S. Appl. No. 14/933,239, Response dated Oct. 6, 2016 to Non Final Office Action dated Jul. 6, 2016", 6 pgs.
"Machine Translation of CN1341362, obtained on Dec. 21, 2010", 7 pgs.
Ahn, J. H., et al., "An Extended Physical Map of the TOX2 Locus of Cochliobolus carbonum Required for Biosynthesis of HC-Toxin", Fungal Genet, Biol., 35(1), (2002), 31-38.
Alves, A. M. C. R., et al., "Highly Efficient Production of Laccase by the Basidiomycete Pycnoporus cinnabarinus.", Appl. Environ. Microbiol., 70(11), (2004), 6379-6384.
Bamburg, J. R., "Proteins of the ADF/cofilin family: essential regulators of actin dynamics.", Annu. Rev. Cell. Dev. Biol., 15, (1999), 185-230.
Benedict, R. G., et al., "Fermentative Production of Amanita Toxins by a Strain of Galerina marginata", J. Bacteriol., 91(3), (1966), 1380-1381.
Beutler, J. A., et al., "Chemical Variation in Amanita", J. Nat. Prod., 44(4), (1981), 422-431.
Brandt, I., et al., "Suggested functions for prolyl oligopeptidase: A puzzling paradox", Clin Chirp Acta, 377(1-2), (2007), 50-61.
Bulaj, G., et al., "Efficient oxidative folding of conotoxins and the radiation of venomous cone snails", Proc Natl. Acad. Sci. USA, 100(2), (2003), 14562-14568.
Bushnell, D. A., et al., "Structural basis of transcription: alpha-amanitin-RNA polymerase II cocrystal at 2.8 A resolution.", Proc. Natl. Acad. Sci. USA, 99(3), (2002), 1218-1222.
Butera, R., et al., "Diagnostic accuracy of urinary amanitin in suspected mushroom poisoning: a pilot study", Clinical Toxicology, 42(6), (2004), 901-912.
Craik, D. J., "Chemistry. Seamless Proteins Tie Up Their Loose Ends", Science, 311(5767), (2006), 1563-1564.
Craik, D. J., et al., "The chemistry and biology of cyclotides", Curr. Opin. Drug Discov. Devel., 10(2), (2007), 176-184.
Crooks, G. E., et al., "WebLogo: A Sequence Logo Generator.", Genome Res, 4(6):, (2004), 1188-1190.
Cunningham, D. F., et al., "Proline specific peptidases", Biochim Biophys Acta, 1343(2), (1997), 160-186.
Duquesne, S., et al., "Two enzymes catalyze the maturation of a lasso peptide in *Escherichia coli*.", Chem Biol., 14(7), (2007), 793-803.
Enjalbert, F., et al., "Treatment of Amatoxin Poisoning: 20-Year Retrospective Analysis, review of poisonings.", J Toxicol. Clin. Toxicok. 40(6), (2002), 715-757.
Escoubas, P., "Molecular diversification in spider venoms: a web of combinatorial peptide libraries.", Mol. Divers., 10(4), (2006), 545-554.
Finking, R., et al., "Biosynthesis of Nonribosomal Peptides", Annu. Rev. Microbiol., 58, (2004), 453-488.
Frohman, M. A., et al., "Rapid Production of Full-Length cDNAs from Rare Transcripts: Amplification Using a Single Gene-Specific Oligonucleotide Primer", Proc. Nat'l. Acad. Sci. USA; 85(23), (1988), 8998-9002.
Garcia-Horsman, J. A., et al., "Deficient activity of mammalian prolyl oligopeptidase on the immunoactive peptide digestion in coeliac disease.", Scand. J. Gastroenterol., 42(5), (2007), 562-571.
Gardiner, D. M., et al., "The sirodesmin biosynthetic gene cluster ofthe plant pathogenic fungus Leptosphaeria maculans.", Mol. Microbiol. 53(5):, (2004), 1307-1318.
Gass, J., et al., "Prolyl endopeptidases", Cell. Mol. Life Sci., 64(3), (2007), 345-355.
Hallen, H. E., et al., "159. The utility of the incomplete genome: the Amanita bisporigera genome project", (Abstract Only), XXIII Fungal Genetics Conference, Fungal Genetics Newsletter, vol. 52—Supplement, (2005), 2 pgs.
Hallen, H. E., et al., "Gene expression shifts during perithecium development in Gibberella zeae (anamorph Fusarium grarninearum), with particular emphasis on ion transport proteins", Fung. Genet. Biol., 44, (2007), 1146-1156.
Hallen, H. E., et al., "Gene family encoding the major toxins ofiethal Amanita mushrooms", Proc. Natl. Acad. Sci. USA, 104(48), (2007), 19097-19101.

(56) References Cited

OTHER PUBLICATIONS

Hallen, H. E., et al., "Taxonomy and toxicity of Conocybe lactea and related species.", Mycol. Res., 107(8), (2003), 969-979.
Keller, N. P., et al., "Fungal secondary metabolism—from biochemistry to genomics.", Nat. Rev. Microbiol., 3(12), (2005), 937-947.
Kroncke, K. D., et al., "alpha-Amanitin Uptake into Hepatocytes—Identification of hepatic membrane transport systems used by amatoxins.", J. Biol. Chem., 261(27), (1986), 12562-12567.
Kuo, M., "Galerina marginata. Retrieved from the MushroomExpert.Com Web site", [online]. [retrieved Sep. 21, 2011]. Retrived from the Internet : <URL: http://www. mushroomexpert.com/galerina marginata.html>, (Aug. 2004), 2 pgs.
Le Quere, A., et al., "Size and complexity of the nuclear genome of the ectomycorrhizal fungus *Paxillus involutus*", Fung. Genet. Biol., 36(3), (2002), 34-241.
Lengsfeld, A. M., et al., "Interaction of Phalloidin with Actin", Proc. Natl. Acad. Sci. USA, 71(7), (1974), 2803-2807.
Letschert, K., et al., "Molecular characterization and inhibition of amanitin uptake into human hepatocytes.", Toxicol Sci., 91(1), (2006), 140-149.
Lindell, T. J., et al., "Specific inhibition of Nuclear RNA Polymerase II by alpha-Arnanitin.", Science, 170(3959), (1970), 447-449.
Lugones, L. G., et al., "Introns are necessary for mRNA accumulation in Schizophyllum commune.", Mol. Microbiol., 32(4), (1999), 681-700.
Malonek, S., et al., "Functional characterization of two cytochrome P450 monooxygenase genes, P450-1 and P450-4, of the gibberellic acid gene cluster in Fusarium proliferatum (Gibberella fujikuroi MP-D).", Appl. Environ. Microbial., 71(3), (2005), 1462-1472.
Maniatis, T., et al., "Regulation of Inducible and Tissue-Specific Gene Expression.", Science, 236(4806), (1987), 1237-1245.
Marqulies, M., et al., "Genome Sequencing in microfabricated high-density picolitre reactors", Nature, 437(7057), (2005), 376-380 May, J. P., et al., "Tryptathionine Bridges in Peptide Synthesis", Biopolymers, 88(5), (2007), 714-724.
May J. P., et al., "Tryptathionine Bridges in Peptide Synthesis", Biopolymers, 88(5), (2007), 714-724.
Muraoka, S., et al., "Detection and Identification of Amanitins in the Wood-Rotting Fungi *Galerina fasciculata* and *Galerina helvoliceps*.", Appl. Environ. Microbiol., 65(9), (1999), 4207-4210.
Muraoka, S., et al., "Effective Production of Amanitins by Two-Step Cultivation of the Basidiomycete, Galerina fasciculata OF-060", J. Biosci. Bioeng., 89(1), (2000), 73-76
Nikolskaya, A. N., et al., "Identification of peptide synthetase-encoding genes from filamentous fungi producing host-selective phytotoxins or analogs.", Gene, 165(2), (1995), 207-211.
Novick, R. P., et al., "Quorum Sensing in Staphylococci", Annu. Rev. Genet., 42, (2008), 541-564.
Olivera, B. M., "Conus Peptides: Biodiversity-based Discovery and Exogenornics", J. Biol. Chem., 281, (2006), 31173-31177.
Panaccione, D. G., "Multiple families of peptide synthetase genes from ergopeptine-producing fungi", Mycological Research, 100(4), (1996), 429-436.
Panaro, F., et al, "Liver transplantation represents the optimal treatment for fulminant hepatic failure from amanita phalloides poisoning.", Transplant International,19(4), (2006), 344-345.
Polgar, L., "The prolyl oligopeptidase family"", Cell. Mol. Life Sci., 59(2), (2002), 349-362.
Richter, K., et al., "cDNAs encoding [D-Ala2]deltorphin precursors from skin of Phyllomedusa bicolor also contain genetic information for three derrnorphin-related opioid peptides.", Proc. Nat. Acad, Sci. USA, 87(10), (1990), 4836-4839.
Rosengren, K. J., et al., "Microcin J25 has a threaded sidechain-to-backbone ring structure and not a head-to-tail cyclized backbone.", J. Am. Chem. Soc., 125(41), (2003), 12464-12474.
Rozen, et al., "Methods in Molecular Biology", (2000), 365-386.
Salamov, A. A., et al., "Ab initio Gene Finding in Drosophila Genomic DNA", Genome Res., 10, (2000), 516-522.
Saska, I., et al., "An Asparaginyl Endopeptidase Mediates in Vivo Protein Backbone Cyclization", J. Biol. Chem., 282(40), (2007), 29721-29728.
Schneider, J., "Mushroom in backyard kills curious puppy.", Lansing State Journal, (Sep. 30, 2008), 4 pgs.
Schuren, F, H., et al., "Highly-efficient transformation of the hornobasidiomycete Schizophyllum commune to phleomycin resistance.", Curr. Genet., 26(2), (1994), 179-183.
Shan, L., et ed., "Identification and analysis of multivalent proteolytically resistant peptides from gluten: implications for celiac sprue.", Proteome Res., 4(5), (2005), 1732-1741.
Shan, L., et al., "Structural Basis for Gluten Intolerence in Celiac Sprue", Science, 297(5590), (2002), 2275-2279.
Singh, L., et al., "The use of heparin as a simple cost-effective means of controlling background in nucleic acid hybridization procedures.", Nucl. Acids Res., 12(14), (1984), 5627-5638.
Szeltner, Z., et al., "Substrate- and pH-dependent contribution of oxyanion binding site to the catalysis of prolyl oligopeptidase, a paradigm of the serine oligopeptidase family.", Protein Sci., 9(2), (2000), 353-360.
Szeltner, Z., et al., "The Noncatalytic beta-Propeller Domain of Prolyl Oligopeptidase Enhances the Catalytic Capability of the Peptidase Domain", J. Biol. Chern., 275(20), (2000), 15000-15005.
Trabi, M., et al., "Circular proteins—no end in sight", Trends Biochem. Sci., 27(3), (2002), 132-138.
Trigueros, V., et al., "Xerocomus chrysenteron lectin: identification of a new pesticidal protein", Biochimica et Biophysica Acta (BBA), 1621(3), (2003), 292-298.
Tudzynski, B., "Characterization of the Final Two Genes of the Gibberellin Biosynthesis Gene Cluster of Gibberella fujikuroi: des and P450-3 encode GA4 desaturase and the 13-hydroxylase, respectively", J. Biol. Chern., 278(31), (2003), 28635-28643.
Tudzynski, B., et al., "Gibberellin Biosynthetic Pathway in Gibberella fujikuroi: Evidence for a Gene Cluster", Fungal Genet. Biol., 25(3), (1998), 157-170.
Tulloss, R. F., et al., "Amanita: Beauty, Danger, and Diversity—Almost Everywhere", Boll. Gr. micol. G. Bres. (n.s.) 43(2), (2000), 13-21.
Tyler, Jr., V. E., et al., "Occurrence of Amanita toxins in American collections of deadly amanitas.", J..Pharm. Sci.., 55(6), (1966), 590-593.
Voss, S. D., et al., "The Role of Enhancers in the Regulation of Cell-Type-Specific Transcriptional Control", Trends Biochem. Sci, 11, (1986), 287-289.
Walton, J. D., "Horizontal Gene Transfer and the Evolution of Secondary Metabolite Gene Clusters in fFngi: An Hypothesis.", Fungal Genet. Biol., 30(3), (2000), 167-171.
Walton, J. D., et al., "Ribosomal Biosynthesis of the Cyclic Peptide Toxins of Amanita Mushrooms.", Peptide Science, 94(5)., (2010), 659-664.
Weiss, M., et al., "Molecular phylogenetic studies in the genus Amanita.", Can. J. Bot., 76(7), (1998), 1170-1180.
Welzel, K., et al., "Characterization of the ferrichrome a biosynthetic gene cluster in the homobasidiomycete Omphalotus olearius.", FEMS Microbiol. Lett., 249(1), (2005), 157-163.
Williams, R. S. B., et al., "Loss of a prolyl oligopeptidase confers resistance to lithium by elevation of inositol (1 ,4,5) trisphosphate.", The EMBO Journal, 18(10), (1999), 2734-2745.
Williams, R. S. B., et al., "Pharmacogenetics in model systems: defining a common mechanism of action for mood stabilisers.", Prog. Neuropsychopharmacol. Biol. Psychiatry, 29(6), (2005), 1029-1037.
Woodward, S. R., et al., "Constant and hypervariable regions in conotoxin propeptides.", The EMBO Journal, 9(4), (1990), 1015-1020.
Yu, Jun, et al., "A Draft Sequence of the Rice Genome (*Oryza sativa* L. ssp. indica).", Science, 296(5565), (2002), 79-92.
Zhang, P., et al., "Production arid characterization of Amanitin toxins from a pure cultureof Amanita exitialis", FEMS Microbiology Letters 252., (2005), 223-228.
"U.S. Appl. No. 62/491,632, Preliminary Amendment dated May 24, 2017", 3 pgs.

AMATOXINS $\alpha$-AMANITIN $R=CH_2C(=O)NH_2$ $\beta$-AMANITIN $R=CH_2C(=O)OH$

PHALLOTOXINS

PHALLOIDIN $R^1=CH_3$, $R^2=CH_3$, $R^3=OH$

PHALLACIDIN $R^1=CH(CH_3)_2$, $R^2=OH$, $R^3=CO_2H$

Amanitin

SEQ ID NO:55    a ccc aac tcc cat tcg aac cta act cca aga cct cta aac ctc aca atc cca M   S   D   I   N   A   T R L P <u>I W G I G C N P</u>
atg tct gac atc aat gct acc cgt ctt ccc <u>atc tgg ggt atc ggt tgc aac ccg</u>

C I G D D V T T L L T R G E A L C *
tgc atc ggt gac gac gtc act aca ctc ctc act cgt ggc gag gc^c ctt tgt
taa
attccccatccatttgtccgctgctatgacacgaag^tagtgggcgatacaagttgtggacgttatcaggc
ttgggccgttgagcctgcatcggaa^acaacttatgttccttcttttttctgttttcatttgttaaaatac
agaacccatgtcgatgatctgtgtttgtagtcaatataaagttgtactgtgtttcttgtcaaaaaaaaaaaa
aaaaaaaaaa Carats indicate the positions of three introns.

SEQ ID NO:55
a ccc aac tcc cat tcg aac cta act cca aga cct cta aac ctc aca atc cca
atg tct gac atc aat gct acc cgt ctt ccc atc tgg ggt atc ggt tgc aac ccg
tgc atc ggt gac gac gtc act aca ctc ctc act cgt ggc gag gcc ctt tgt
taaattccccatccatttgtccgctgctatgacacgaagtagtgggcgatacaagttgtggacgttatcag
gcttgggccgttgagcctgcatcggaaacaacttatgttccttcttttttctgttttcatttgttaaaata
cagaacccatgtcgatgatctgtgtttgtagtcaatataaagttgtactgtgtttcttgtcaaaaaaaaaa
aaaaaaaaaaa SEQ ID NO:56 (coencoding region of the propeptide)
atg tct gac atc aat gct acc cgt ctt ccc atc tgg ggt atc ggt tgc aac ccg
tgc atc ggt gac gac gtc act aca ctc ctc act cgt ggc gag gcc ctt tgt

FIG. 4A

SEQ ID NO:57

Exemplary sequence of genomic DNA covering the amanitin gene. The nucleotides encoding the amanitin peptide are underlined.

CGATCGAAAACAGAAATCACACACTCGGCTAGATGTCCATTAAGTATGGGAGCGGAAGTCTGTTGCCAAAT
ATGGACGACCAGACGTTTTTTAAAATTATGAGTCGCGTGACTCGACCATTAAAGTACGAATACTCAGCATT
GTATAGGTCCCGAATATCATCCGCAGTAGCCGCCATTGTTGGCGGCCACGAGAAGTTGGTAATCGCCGCTC
AAACTATCAAACGTCGTGCACGTCGCACTATTGGCTGTGCTATGTATATACAGTTCATACTGACATCACTG
TGACCTCGTCACTTTCCACCTGTCGAACAAGCCAAGGAAGCTTAAGACGGCCGACGATAGCCGAAAGTACA
ACCTAGAGGTATGGCAGTAGATAAGTCGGACGAACCAAAGTCAAACTACTGACAGGAACTTCACCCTGAAC
TGTTGCCGCGCGATGGTTCAACAGGGGTTGTCATAAGTTTAGCCTGACACGTAATGGTCGCCCAACCGGGC
ATGGATATATGGAGAGCGAGAGGTGTGTGAATGGACAACTACCGCCGAAAAAGGATAACCAGGCTCCCTTG
ACCGAACAGCGGCGGGATCGCAGTTCGTATCACCGCACCATCTTGTCGCGTTTCACTCTGTCAGAACATTC
ATGTAATGAGCTAGTGTGAATGGAAATATTTTCGCTATGTCGAAAAAGGATGAACTTCGGATAGAGAAAGC
CAACGAATGCTTGACCGAACAACGGTAGTACCGCAGTACCACCGCACCAACTTGGTGCAATTCGCTCTGTC
AGAAGATTCATATCAACTCCGCCGAGGAAATGAGTTGGCAAGATGAAAAATTCGCAGATCCCATATGAGAG
CGTGAGGAGACGCTCAGAAACTTCCAGCTTGAAGCGCTTAGCCCAGCAGGCGGACAAGACGTGGTGGTCCT
TAAGATTCCGAGGGAGAATGAAATGAGCCTCGGTCTTATCTTCGTCGAGCCGTGTGGGGAATTTAAGAGTA
CGGAAATATTCTTATAGCCTCAAAACACTCATCTCCGGCAAAAAGTGACCACCTACCCAGGGCACGTAACG
ATGTCCTTGTTCACAGGCCTCTGATCGTGCCGTGCGCAGCAGCGGTCCATACCATAGAAGTCATGCTGCGA
GCCTTTGGATTGGCATGGTTGTCGTCGCCGATGGGGCATAGGTAAACGTGACCAATTTTAATCGATAATCA
TCGGATCAAAGTCGTTGAAACTTGAAGAGGATGAGCCGTTTTAACTGTGACGTCAGTTTAGGAAAATAAGG
AACTAGCCAACACGATGGTCGAGTAAATCATGAATGGAGAAAATATTTCACTATCACCAAGAAAGAATGAC
TAGGCGTGCATGGGAAGGGCTGGCTGATGGTTTGACGAATGGGGGGTCAACCACCGTAACGAAGTGGTCCC
AGTCCCCGTTTCTCAAGGTGACTATAGCAAAACCCTACGGATTTTGCAGGTAGTCCAACAAGATAAGGGTG
AGATGTGTCTGTTGCCGAAAAAAGGAATCCGCTCAAATGCTCACAAAATGTGTTGGACTCCTATCAAGATA
ACATACTTGATGTCAAGTTACTCCGAGAATGGGGTCTTCTATTAGTTCCTTTTGATTCTCTCATTTCGATT
GGGCGAACTGGTGCGAATGGCGACAAGTACTTCGTTACTACCCCCATGGAATAACCAAATTTCTGTGGAAA
AAGAAGCATCTGCCCGCACCTTACGGTATACTACTTTTGTTCCGCATTCGCGCACTGATTCTTCTATCTAT
TRTGTTTCTCAGGCTATTATACCAATTTCTGCGACTCATAGGATTGATTTTACCTCCAACCAACTAGGCAA
TGAYGTATAAAAGGGAYTGTGAATCTCAGCGTTCAGTACCCAACTaaatcCCATTCGAACCTAACTCCAAG
ACCTCTAAACCTCACAATCCCAATGTCTGACATCAATGCTACCCGTCTCCCCATCTGGGGTATCGGTTGCA
ACCCGTGCGTCGGTGACGACGTCACTACRCTYCTCACTCGTGGCGAGGCGTAAGCACGATTTCTCTCCACT
AATGTACTAGTGCACTTATGTGTGTATCAGCCTTTGTTAAATTCCCCWTCCATTTGTCCGCTGCTATGACA
CGAAGGTATCACCATCTCACTTCATAACGGTGATACAAGGCAGTTGTCCTGACTCAAGACGTAGTAGTGGG
CGATACAAGTTGTGGACGTTATCAGGCTTGGACCGTTGAGCCTGCATCGGAAGTAAGGCCTTCAAGTTATT
ATTTGTGGCAAACCACGAGGCTAAATTGTCTTTTGCCAGACAACTTACGTTCTTTCATTTTTTCTGTTCTC
ATTTGTAAAAATACAAAACCCATGTCGATGATCTGTGTTGTAGTCAATATAAAGTTGTACTGTGTTTCTTG
TCAGCAGGAGTGCATTAACTTGTTCAGGAAACGTCACCCTCCGAGTCTGCTCACGATTCATAGCAATACAA
ACTGTTTTTTTTAAGCAGATGCGTCACTCTGAGAACAACTCCGATCG

FIG. 4B

Phallacidin

SEQ ID NO: 619

```
                            M   S   D   I   N   A   T   R   L   P   A
ga cct ctg ctc taa atc aca atg tct gac atc aat gcc acc cgt ctt ccc gct

 W   L   V   D   C   P   C   V   G   D   D   V   N   R   L   L   T   R
tgg ctt gta gat tgc cca tgc gtc ggt gac gat gtc aac cgt ctc ctc act cgt

 G   E   S   L   C   *
ggc gag ag^c ctt tgg taa
atgtctcatccactagtcaag^gcaagttgttgacaatgtcaggcttgcggaccgttgagcctgcatcggaa
^acgactcacgttctttctcattctttctgattctcatttgtaaacatataaacccacgtaaatgatccgt
tgtgctatggaatgcaatatacttgtgaaaaaaaaaaaaaaaaaaaaaaaaa
```

Carats indicate the positions of three introns.

```
SEQ ID NO:79
ga cct ctg ctc taa atc aca atg tct gac atc aat gcc acc cgt ctt ccc gct
tgg ctt gta gat tgc cca tgc gtc ggt gac gat gtc aac cgt ctc ctc act cgt
ggc gag agc ctt tgg taa
atgtctcatccactagtcaaggcaagttgttgacaatgtcaggcttgcggaccgttgagcctgcatcggaa
acgactcacgttctttctcattctttctgattctcatttgtaaacatataaacccacgtaaatgatccgt
tgtgctatggaatgcaatatacttgtgaaaaaaaaaaaaaaaaaaaaaaaaa

SEQ ID NO:81 (coding sequence of proprotein)
atg tct gac atc aat gcc acc cgt ctt ccc gct tgg ctt gta gat tgc cca tgc
gtc ggt gac gat gtc aac cgt ctc ctc act cgt ggc gag agc ctt tgg
```

*FIG. 5A*

SEQ ID NO: 78
Sac<u>I and</u> PvuI
GCTTGGCTTGTAGACTGCCCA

SEQ ID NO:76
>phallacidin sequence #1, 1893 bp, SacI
GAGCTCAGCACGGAGGGTCTCTTGGATTTCTGGCCGGCGTGCAAGTTCAATGAGAGACCACTGAGTGAAGGCTCAGTGA
TAGAACAGCTTGAACACTCGTAGGCGAAGATTACCGTTAGGGTGACTATGAGCAGCACCATTTCACTACATCGGTTATGACGGGGTTGT
TTGATCGCTCTGATGACGGAGAACATGAATCCCATGCTGGCCGATTGTTTTGAGACTGAAACCGTTCTAACCTGATGGGCAGAATTCAA
GCACACGGAGTGAGATTGCGAATTGCTGAAACCGACAGTGGAGAAGACAGTCTCCGTAGTGTGCGATCATGTTAAGTTTATGCCCTAA
TCGTTGAGCGATAAAGAGCCGACCAACCGCTTGTGAGTCTCGCCTCAGAAATAGATATAACATCACCATACTGGAACGACAATGAGGCT
GGCAGCTGAAAAATGGTGCAAAACAAAGACTCGCCAACCTGGCTCAAAGCGGTTGTCCCTGCGAGCCGAGGATATGTGGTGGTATCCTC
GGAATATATGTGTGTGAGCCTTGGGATGGCTCAATACAACATGGCTGTAGCCGATGCCAGTGGGTATCTCGTAAGGCCCATACATTCGT
TCCCAATCCCGATATACCACCGTACTGAGGTTCGCGGAAGGGAAGATCTTGGTGTTACTGAATCTGAAGCTCTCGCTGCGTGGTCCTTG
TAGTCTGGCGTTCTGATACCCTCGGCATCTCCAATAGATAGAAATGACGACGAGCAATGTCAGAGGTCACAATCCTTATCGAATTACCT
TTGAGGTACTCTGCCACATCAGGCCAGAGGCCGTTGGAGTTGAGGTTCAACATCACGGGTGACGGAGTGGACGAGCCGTTATGCAAGGA
AGGAAGGCCATCGGCGATAAGTACTAGTATAGCGACCAACCCAACCAGACGTGGAAATGCCATTGAAGGGTGGGAGTTGCCCGAATACG
AGGAAAACGTTTCTGAGGAGCCGAAACCGTAACCAGGCGCGAGAACTTGACCTATCTATCTCCGGGAACGGTGTTGGGGGTCCATGTTA
CCGTGAAGGTGGATAGGGGCGGATTCGATTCCAGGAAAGTTAGAGCCACATAGTCATAAGTGATGCAACACGCCTGTGCGCGATGGAGA
TAATGCGTCTTTGTTGCATCGGCAAACCGGGTCACACGGACGAAAATCATTACTACATGGTCCATTTCAGGACAAAACCCCTATCTATT
GATCCTACAAACTGCTTGACTGTTCAATCTGTGACCACCGGGACAGAGAAAGGCTGTGCTCAGTGGGTGTTTAATCCAGCGAGAAACG
CGTTAGGCCCAGTCGCCGATCAGGATACGACGAAAAAGTGTAAGGTCAAGACTCCCTTGATGCGATTCAACTATTCTTGACGGGGGGTT
GCCATTGTATTGCACCGTCTTGCCCGACTGGCTGTGCCCGCAAAGACAGAACGTCCCAAAAACAGGAAAGAACAAAGAAGTTTTGTGGA
GCCTGCCAAGAATGTGTGATGAACAGTGACTGACAGCATGAATGGGGATGAATATTGAATACCGAAAAAGGATGATCAGACAACTGTT
TATGGAGATTTTGCGCCAACTCGTCTTCATCTCCGTGTCAGGACAAGATTCTCTTATCTATCGTCCTTTCCGCGGTTTTTGCAACCATG
CGAATTCGTGACTGAGACAGATAAAAGGCGTTGGATTCAGCTTAGCATTCAATATTCAATACTTACCTCCCATTCGAACTCGAGCCCAA
GACCTCTGCTCTAAATCACAATGTCTGACATCAATGCCACCCGTCTTCCT<u>GCTTGGCTTGTAGACTGCCCA</u>TGCGTCGGTGACGATGTC
AACCGTCTCCTCACTCGTGGCGAGAGGTGAGCTC SEQ ID NO:77
>phallacidin sequence #2, 1613 nt, PvuI
CGATCGGGTGGTATGAGCGACGTTGATGCATGGATTAGATAAAAAACTCATTTTTGCCTTGACATTGTAACATGCGAATAAGAGAGCAA
GGACCCCATCAGAGCAAAAAAGGAATCACGGATTTGATATCGACCTGACCCAAGTCGGCAACGGTAATAGGGGCTAGAGCCACATATGA
GTGATGAGCGATGGAGATAATGTTGCATCGGGAAACCGGGTCACACGGCCGATAATCATTCTCATACATGTCCATTTCTATCTATTGGT
CTGTAGGACTGCTTAACGGTTTAAATCTGTGACCACCAGGACAGACAAAGAAAGGCTGTGCTGTTCGAAACGCGTTACTAATTAGGCCC
AGTTCGGCATAAATCGCCGACACGCAGGATACGACGAAAAGTGTAAGCTTAAGGTCAAGACTCCCTCTGATGTGATTCAACAACTTTTGA
CGGGGGGTTGCCATTGTATGCACCGTCTTGCCCGGCTGGCCATGTCCGCAGAACCGAACGCCCCTAACGACAGGAAAGAAGAAAGAAGT
TCACGGATTCCATATAGTAAGCGTGGAGCCTGTGTGATAAACAGTCATGAATGATTCATGGGAATGAAGACCGATCAGACAAACGCTTA
TGGAGATTTTGTGCCAATTTGTCTTTCCATCTACGATTCTCTTATCTATCGTCCTTTCTGCGGTTTTTGCAACCATGCGAAGTCGTGAC
TGAAACAGATAAAAGGCGTTGGATGTGGCTCAGTAGTCAATATTCAATACTTACCTCCCATTCGAACTCGAACCCAAGACCTCTGCTCT
AAATCACAATGTCTGACATCAATGCCACCCGTCTTCCT<u>GCTTGGCTTGTAGACTGCCCA</u>TGCGTCGGTGACGACGTCAACCGTCTCCTC
ACTCGTGGTGAGAGGTGAGCTCAAAATTCCATTTAATAATGTAGCAATGTACTCATGTGTCGTGTATCAGCCTTTGTTAAATGTCTCAT
CCACTAGTCAAGGTATCCGCCTCTGATTTCTTGATGACAATGCATGGTCATGGTACTTACTTTGATGTAGTAGTGGACGACGCAAGTTG
TTGACAATGTTAGGCTTGGACCGTTGAGCCTGCATCGGAAGTAAGGCCTTCAAATTTTTCTGTGATAAGCAGCGAGCTAACTTGGGTTA
GACGACTCACATTCTTTCTCATTCTTTCTCATTCTCATATAAAACCCACGTAAATGATCCGAGCTGTACTATGGAATGCAATGTACGGG
TGTATATGTGTGTGTTGTCAGTAGGAGAGCATTTAGCAATCCGAGCTTGCATGCCGCTGTCGCCAGAGCTGTCTACTTGTCAGCAACAT
ATCGCATATCACATAGGCAGCTGTTGTACCATTGAAAAGCCGTGGGGCGTATAACCTGGAGGAGTTCAAAGAAGGGTCTTTTATGATG
AGTTTGATAGCTCGCATAGTTGTGAAAGTCGGCAAGTTCACAAAAAAGAGTGATTTTATGTTACATGTGACGAGGAGCATGAGACACAA
CTTTGAACTGCACCCGGGAGAAAGCAGGCTTAGCAACACCGATGACGAGGGGGAGGAGAAATACGGGGAGAATGCCGATGATGTAGGCA
TAATGCGATCG

*FIG. 5B*

*FIG. 6A*

| | A | | B | Conserved Regions |
|---|---|---|---|---|
| SEQ ID NO: 626 | MSDINATRLP | IWGIGCNP | CIGDDVTTLLTRALC | (amanitin) |
| SEQ ID NO: 627 | MSDINATRLP | W G P | C GDDV LLTR LC | (consensus) |
| SEQ ID NO: 628 | MSDINATRLP | AWLVDC-P | CVGDDVNRLLTRSLC | (phallacidin) |

*FIG. 6B*

| SEQ ID NO. | Comparisons of sequences BLAST. | Identical amino acids | Percent identity |
|---|---|---|---|
| SEQ ID NO: 180 | Alpha-Amanitin<br>ATGTCTGACATCAATGCTACCCGTCTCCCCATCTGGGGTATCGGTTGCAACCCGT<br>GCATCGGTGACGACGTCACTACTCTCCTCACTCGTGCCCTTTGTTAA | 102/102 | 100% |
| SEQ ID NO: 81 | Phallacidin<br>ATGTCTGACATCAATGCCACCCGTCTTCCCGCTTGGCTTGTAGACTGCCCA<br>TGCGTCGGTGACGATGTCAACCGTCTCCTCACTCGTAGCCTTTGGTAA | 99/99 | 100% |
| | Alpha-Amanitin vs.Phallacidin | 78/102 | 76% |

*FIG. 6C*

SEQ ID NO:183 ECIMO1V01AIXAG S length=115
TTGGGGTTTGGCAGTCGGTTAGTACCCAGTCCTCTTCGAACTCGGAAAACCTTTACTCT
CAATAAACCATGTCTGACATCAATGCCACCCGTCTTCCTATCTGGTGGTACATATA

SEQ ID NO: 184
GVWQSVSTQSSSNSENLYSQ-TMSDINATRLPIWWYI

SEQ ID NO: 185 ECGK9L002IH938 R length=98
GTGGGTACGCGCCGGGGAGACGGGTGGCATTGATGTCCGACATTGCGATTGAGAGTAGA
GGATGCTGTAGGTTTCTGAGGGGTCTTGTGAGTATTGAA

SEQ ID NO: 186
SILTRPLRNLQHPLLSIAMSDINATRLPGAYP

SEQ ID NO: 187 ECGK9L001DOKJN R length=106
CTCACAAGACCCTCACGAAACCTACAGCATCCTCTACTTCTCAATCGCAATGTCGGACA
TCAATGCCACCCGTCTCCCCGGCGCGTACCCACCTGTTCCTTGGCCG

SEQ ID NO: 188
SQDPHETYSILYFSIAMSDINATRLPGAYPPVPWP

SEQ ID NO: 189 cn1104 1266 nt
TGAGGCACGGGAAGTATATGAACCAGAAGATAGGAAGACTGGTGACATTGATGTCAGAC
ATGGTTATCAGTAAAGAGTTTGACGAGGACTGGGTACTAATTGCCAAACCCCAGAACCT
TTATGTGATTCGACAAGAGCAAATATAATTGCAGAACTTGACCCAATGTTTCAGGTGTT
GGCGCTGTCTCAGGCAATGGTAGCGCCGCCTTGTGGGTGGCTCTAGGGTGTAACGTGTA
ACAGTTAGCAATTAGGCTATATGCTGCTCTGCGAAACAGGCTTGCGACGCCTGTCACCT
TGCCGACCGTACTATCTAGCACCATTCAACGCCATGTGATTATGATAGCGTCGGCATTC
CGTGCCAGTTGCATGTGCTTTGAGTTTTCCATGTTTAGTAACCGCGAGCCGCGAGCGTT
CAGAATCATAGTGGTGGCGGTGCTAGAGTTACAACATGTATGTAACATACGAGTCAGGA
ATAAATTACCATAGGAATCTAGTTCTGATGTCCATTGGTCAACTCGACCCAGTACCTTT
CCTCCCTCTCCTTCCACCGCCTTCGTCTCCTTCATTGTCCCCACCACTGGTATACAACG
CCGACGTCGACCGCTGCGCCGTCCTCTCAACAATAGACGTCCCGTCTCTAAATCTTGCC
CTAAACAGCACATTTGCGTTCGTAAACAGCCCTTCCTTCAGTGACACCACTATAAATTG
CGACCCCTTGAACCGCGTCCGGAACAGCTGTCCAATATGCTGCGTGTGCGATAGATCCA
GGGCAGCGTCGATCTCGTCGAGGATGTACATTGGCGCTGGTTTGAATTGGAGGAGCGCC
ATGATGAGCGAGAGCGCGATGAGAGATCTGCAGCATACCGTCAGACGAAGCAACTTGGG
TGTTCAAACGACATACCTCTGGCCCCCACTTAACTCAGTCAAGCTCTCCTTCCAAACGG
TGCCGAGTTGAACTTTGACTTCTAGACCGTCCATAAGATCTTGGCCTTCGGGCGGTACC
AGTTTGGCAAAATTGCCAGGCAAGAGTTCTGCAAAGATCCCGCCAAAGTCGCTTTACCA
CATGCCTTCAATCCCCTTGTCATACAAATGGTGACAAAGTGACTCACCCGTCAACCTTT
TCCCAAGTTTTTTGAAGCGCATCCCTCTTGTACCGGTCTAGTTCTTCGATAGTCTCTTC
AATCTTTTCTTTATCTTTCAGCACCTGACTAAGCATCTTTTTAAGATGTGCCTCTCTGC
TCACGACGCTAGACACGTGGCAGGAAA

FIG. 7A

SEQ ID NO:190
SCHVSSVVSREAHLKKMLSQVLKDKEKIEETIEELDRYKRDALQKYWEKVDG-
VTLSPFV-QGD-
RHVVKRLWRDLCRTLAWQFCQTGTARRPRSYGRSRSQSSTRHRLEGELD-
VKWGPEVCRLNTQVASSDGMLQISHRALAHHGAPPIQTSANVHPRRDRRCPGSIAHAAY
WTAVPDAVQGVAIYSGVTEGRAVYERKCAV-GKI-ERDVYC-
EDGAAVDVGVVYQWWGQ-RRRRRWKERREERYWVELTNGHQN-IPMVIYS-
LVCYIHVVTLAPPPL-F-TLAARGY-TWKTQSTCNWHGMPTLS-SHGVEWC-IVRSAR-
QASQACFAEQHIA-LLTVTRYTLEPPTRRRYHCLRQRQHLKHWVKFCNYICSCRIT-
RFWGLAISTQSSSNSLLITMSDINVTSLPIFWFIYFPCL

SEQ ID NO: 191 W7_54_B09 Length = 554
TATGCTTTTAGTCCAAGCTTTTACTTCACCTGGACGTTGGGATACGTCAGGAATATGTA
CTGACAATAAATATCACCGCAGCGGCGCCGAAACTCACCAATCTTTACTTCACCTGGAC
GTTGGGATAGATGACGTATTCACTGGAAAAGGGTTAGCGGATAACATGGGTCGCATGTC
ATCATGAATATAGTTAGTGCGTCTCCACTCACAATTGTCCAAGTTATTTCGCTTCCGTC
ATTCGCGGACAGTTGAGGTTTGCCCCTGCCCAACTCGGCAATGGGTCATGACTGAGACA
GATAAAAGATGCTGGGGGCGCAAGCATTCAATACTCAGTTCCCCTCCAAATTTGAATCG
TTCAGAAACCTACTACTTCATTTACTCTCTCACAATGTCTGACATCAATACTGCTCGTC
TTCCTTTCTACCAGTTTCCCGATTTTAAGTATCCCTGCGTTGGTGACGACATCGAGATG
GTCCTCGCGCGTGGCGAGAGGTGAATACAACATCCGGCCAAGGCTGTATCAAACGACTT
ACGTGCTACGTATCAGCCTTTGC SEQ ID NO:192
MLLVQAFTSPGRWDTSGICTDNKYHRSGAETHQSLLHLDVGIDDVFTGKGLADNMGRMS
S-I-
LVRLHSQLSKLFRFRHSRTVEVCPCPTRQWVMTETDKRCWGRKHSILSSPPNLNRSETY
YFIYSLTMSDINTARLPFYQFPDFKYPCVGDDIEMVLARGER-
IQHPAKAVSNDLRATYQPL SEQ ID NO: 193 w92k_04_H04_F 684 nt
AATTTGAATCTCTCAGAAACCTACTTACTCTCTCACAATGTCTGACATCAATACTGCTC
GTCTTCCTTTCTTCCAGCCTCCCGAATTTAGGCCTCCCTGCGTCGGTGACGACATCGAG
ATGGTCCTCACGCGTGGTGAGAGGTGAGTACACATCCGGCCAAGGATGTATCAAACCAC
TCACGTGCTACGTATCAGCCTTTGCTAAATGCACGGCCTATCGGTCCACTCCTATGGCA
TGAAGGTGTCGCCGTCGCATTTCAACTACAACGTAAGGCAATTGTACTGACTTGAATGT
AGTAGTGGTCATTATGTTGTTGACGATATCAGGCTTGGACCGTTGAGCCTGCATCAGAA
GTATGACTTTGCTTGTGGTGAAGAAGCACTGGATTTAACCCATCTTTTTTCCTAGATAA
CTCGCTTTCTTTTTCAAGTTTATGTCGAATCCGTTTTGTAGTAAACATATAAAACCCAC
GTCAACGATCCCGTGTTACTTGTTACTTGTTCTTTGTTCTTGAAACCCTCGTCAATGAT
CCGCGTTATAGTCAATAAACTTGTTCTTTGTTCTTGTCAGTGTGAGGGCATTTTGTACG
CGAGTGGTTTCAAGAAATCAGTCAAAAGGTGTCTTTCCAACATATCTGTTGAGCCTGTC
CGGTCCTGAAGCCTGATTGGAGAATCAATCAGTAT

*FIG. 7B*

SEQ ID NO: 194
I~ISQKPTYSLTMSDINTARLPFFQPPEFRPPCVGDDIEMVLTRGER~
VHIRPRMYQTTHVLRISLC~MHGLSVHSYGMKVSPSHFNYNVRQLY~
LECSSGHYVVDDIRLGPLSLHQKYDFACGKEALDLTHLFS~ITRFLFQVYVESVL~
TYKTHVNDPVLLVTCSLFLKPSSMIRVIVNKLVLCSCQCEGILYASGFKKSVKRCLSNI
SVEPVRS~SLIGESIS

SEQ ID NO: 195
ECGK9LO01EMOC5 S length=96
CACAATGTCTGATATCAATACCGCTCGTCTTCCTTGCATCGGGTTCCTTGGCATTCCCT
CCGTCGGTGACGACATCGAGATGGTCCTCAGGCATGG

SEQ ID NO: 196
TMSDINTARLPCIGFLGIPSVGDDIEMVLRH

SEQ ID NO: 629 ECIM01V01BBKCW R length=110
ACCCTTCCGCAATGTCTGACGTCAATGACACCCGTCTTCCCTTCAACTTCTTCCGCTTT
CCCTACCCCTGCATCGGTGACGACAGCGGAAGTGTCCTCAGGCTCGGCGAG

SEQ ID NO: 197
PSAMSDVNDTRLPFNFFRFPYPCIGDDSGSVLRLGE

SEQ ID NO: 198 contig26848 length=93
CCTTCCGAaCCAAGAACCTACAGATACCTTTGCACTCTCACAATGTCTGACATCAATGC
CATCCGTGCTCCCATCCTGATGCTCGCAATTTTG

SEQ ID NO:199
PSEPRTYRYLCTLTMSDINAIRAPILMLAIL

SEQ ID NO:200 W7_17_xp_D11
TTCAATTTAATGCCCCCCTGCGTCGGTGACGACATCAACATGGTCCTCACGCGTGGCGA
GAGGTGAGTACAAATTCCGGCCAACAATGTATCAAACCACTTACGTGCTACGTATTAGC
CTTTGCTAGATGCATTCTATCGGTCCACTCCTGTGGCATGAAGGTGTCGCCGTCTCACT
TAAATTACAACGTAAAGCAATTGTACTGACTTGGATGTAGTAGTGGACACTGTTGTTGA
CGATATCAGGCTCGGACCATTGAGCCTGCATCAGAAGTATGACTTTGGTTGTGGTAAAG
TACTGGGTTAACTCGTCTTTTCTTCCTAGATAACTCACGTTCGTTTTCATTTGAATCTG
CTTTGTAAACATATAAAACCCACGTCTACGATCCGTGCCATACTTGTTCTTTGTTCTTG
TCAGATTTCGAAATTGCCAACGATATGCCAGTTTTCCTGTGTCTGCAAGCTTGGAACTG
TGTGCGTCGGATACTGGATACTGGCGTTTCCTCGTCCTAAAGGTAGCAAAGTGCGCATG
CGGGTGCTAACGGTTGCATGATAAATCATCGCAAGCATCAATGGGTTTCGTTGGCAACG
ATCCAAATGAACGACTGAGGGCTTCGAAATGTGTAGATGGTTGCAAAAACAAAACAAAA
AAACCATTAGACCGTGAATATCGAATCTCTTAGTTACTATTGATTTCGACTTGGAGTAT
CAGCCGCGATCATTTCGTCCTCGGCCCTAGTATCACAACATATGTAATATCATCCTCAG
GATTACATGTATTCTTCAGGTAGCGTGACTGTGATACCTACCTCCCTTC

*FIG. 7C*

SEQ ID NO:201
FNLMPPCVGDDINMVLTRGER~VQIPANNVSNHLRATY~FLLDAFYRSTPVA~
RCRRLT~ITT~SNCTDLDVVVDTVVDDIRLGPLSLHQKYDFGCGKVLG~LVFSS~
ITHVRFHLNLLCKHIKPTSTIRAILVLCSCQISKLPTICQFSCVCKLGTVCVGYWILAF
PRPKGSKVRMRVLTVA~~IIASINGFRWQRSK~TTEGFEMCRWLQKQNKKTIRP~
ISNLLVTIDFDLEYQPRSFRPRP~YHNICNIILRITCILQVA~L~YLPPF

SEQ ID NO:202 cn1466
TCTGGTAAAGGATGAGTTAACCCAATGCTTCACCACAAGGAAACTCATACTTCTGATGC
AGGCTCAACGGTCCAAGCCTGATATCGTCAACAACAGTGTCCACTACTACGTCCAAGTC
AGTACAATTGCCTTCAATGCGTTGAAGTTGAAAAGAGACGGCGACACCTTCATGCCATA
GGAGTGGATCGATATACTGTGCATTTAGGAAAGGCTAATAATACGTAGCACGTAAGTCA
TTTGATACATCGTTGGCCAGATGTTGTACTCACCTCTCGCCACGCGTGAGGACCATCTC
GATGTCGTCACCGACGCAGGGGGCATCCGAACGGGAGGGAGGAAGAGAGGAAGACGAG
CAGTATTGATGTCAGACATCGTAAAAGGAAGCTGTAGGTTTCTGAAAGATTGAAGTTTG
GAGGGGAACTGAGTTTTGAACGCTCCGCCCCCAGCATCTTTTATCTGTCCCAGTCATGG
CCTATTGCTGATTTGGGCAGAGGCAAACCTCAATCCGCCGACGACGGAAGCGAATAACT
TGGATAAGCGACGGTGATTCTTTTTTTATTTATTTAGAGGAACTTCGGCATCAATCATG
TTGATATCTTGCAGAAGTCGTATATCATTGTGATATCATTGTGACAAATGTCACCCACT
ATCTCTTTCCTTGTGAATGTGCCATGTATCCAACGTCCAGGTGAAGTAAACCTTGGTGA
TTCTCGCCGCCGCTGCGGTGATATTGACAGCATAATGATCTGAAAACGTACTGATGGAA
GCGTACTTGACGGCCCGTCCAAACTGACATGGGAGTAATCGCACAGTATTACTATGCTA
TTTGTATTCAGATTCCACAATTCCATTACAGTCACCCGTGAGTTTTCCATATCTGC

SEQ ID NO:203
RYGKLTGDCNGIVESEYK~
HSNTVRLLPCQFGRAVKYASISTFSDHYAVNITAAAARITKVYFTWTLDTWHIHRERDS
G~HLSQ~YHNDIRLLQDINMIDAEVPLNK~
KKNHRRLSKLFASVVGGLRFASAQISNRP~
LGQIKDAGGGAFKTQFPSKLQSFRNLQLPFTMSDINTARLPLFLPPVRMPPCVGDDIEM
VLTRGER~VQHLANDVSNDLRATYY~
PFLNAQYIDPLLWHEGVAVSFQLQRIEGNCTDLDVVVDTVVDDIRLGPLSLHQKYEFPC
GEALG~LILYQ

*FIG. 7D*

SEQ ID NO:204 cn1150 881 nt
CCTCTGAAACTTGCTGCGACGGCACGATCTGACTGGGAGATCTTCGTTGCATCTCTAGG
TTGAGTGAATTCACAATTCCAGTATTCAGTTCGGAGGAGCATGTTGGATCGATTACCGT
ACGTTCTGGCTCTTCATCGACTGGCTTTAGGAACGAACCTTACCAAACTTGTATATCGT
ATTGCAGGTGAATCGAGAAAACACCTTTTACGTCGAGTGTTGTAACCTGGCTCAAAGAT
TCAAAAACTCTCAACGACAAGCAGTTTATTGACTATAACACCGATCGTCGACGTGGGAT
TTGTGTTTACAGAACAAATTCGACAGAGAACGAGAAAGAATGTAAGTTATCTGGGAGAC
AAATTAGACCAGTGCTTCGTGACGAACAAAGTCATACTTCTGATGCAGGCTCAGCGGTC
CAAGCCTGGTATCGTCAACAGCAGAGTCCACTACTACATGCATTTAGCAAAGGCTATAC
GTAGCATGTAAGTGATTTGATACATCATTGGTCAGTTGTTGTACTCACTCCTCGCCACG
CGTGAGGACCACCTGGATGTCGTCATTGACACATGGGGGATGAAGCTCATGAAGACGA
CGTAAGGAAGACGAGCGGTATTGATGTCAGACATTGTGAGAGTTGGAGGGGAACTGAGT
ATTGAATATTGGATATTGAACGCTGCGTCCCAAGCACCTTTTATCTGTCCCAGCCATGG
CCCAGGCCCATTCCTAGTTGAGGCTCGATCTATTGCAAAATTTGACAGCCTGCGTGGTA
TGGAAGACGAAGGACTGACGATGATGCTTAGTTGACATGTGTCAAGCCCACGTACGATA
TCGAAGCCAGAGATAGATCGCGTATTCGTATATCGTACGAGGGATGCTTACTTGG

SEQ ID NO: 205
K-
ASLVRYTNTRSISGFDIVRGLDTCQLSIIVSPSSSIPRRLSNFAIDRASTRNGPGPWLG
QIKGAWDAAFNIQYSILSSPPTLTMSDINTARLPYVVFMSFIPPCVNDDIQVVLTRGEE
-VQQLTNDVSNHLHATYSLC-MHVVVDSAVDDTRLGPLSLHQKYDFVRHEALV-
FVSQITYILSRSLSNLFCKHKSHVDDRCYSQ-TACR-EFLNL-ARLQHST-
KVFSRFTCNTIYKFGKVRS-SQSMKSQNVR-SIQHAPPN-ILEL-IHST-
RCNEDLPVRSCRRSKPQR

SEQ ID NO: 206 contig70115 length=172
GGACCATCAGGATGTCGTCACCGACGCAAGGGAGGAGCATTGGCGAGGAGAGGGGAAGA
CGAGCGGTATTGATGTCAGACATTGTGAGAGAGTAAAGGAAGTTGTAGGTTTCTGAAAG
ATTCAAGTTTGGAGGGGAGGTGAGTATTGAACGCTGCGCCCCCAGCACCTCCAG

SEQ ID NO: 207
LEVLGAQRSILTSPPNLNLSETYNFLYSLTMSDINTARLPLSSPMLLPCVGDDILMV

SEQ ID NO: 208 contig38711 length=234
CCTTCCGAACCAAGAACCTACAGATACCTTTGCACTCTCACAATGTCTGACATCAATGC
CATCCGTGCTCCCATCCTGATGCTCGCAATTTTGCCCTGCGTCGGCGACGACATCGAGG
TCCTCAGGCGTGGCGAGGGGTGAGCCTAACATCCGTCAACGGCGTACAAATGTACTTAT
GCGCTGCGTATCAGCCTTTCCTAAATACCCGGTTCATCAGCTCGCTCCTATGGCATG SEQ ID NO: 209
PSEPRTYRYLCTLIMSDINAIRAPILMLAILPCVGDDIEVLRRGEG-A-
HPSTAYKCTYALRISLS-IPGSSARSYGM

*FIG. 7E*

SEQ ID NO: 210 cn1006
CTTCTAACGTGGGCTTTACGTGTTTATAAATGTGAAAAACCTTAAAAGAAAAAAATCAG
AGTTGTCCCCCACAGACAAAATAAGGACTTACTCCGATGTAGGCTCAACGGTCCAAGCC
TCATATCGTGAACAACTTTGAAAATTTATCACTACATAATACATACGAGTCAGAACGGT
TGCCTTGTATTATACGAGGATGGCGACACCTTTAATGGCACCGAGTTCTCAGCAGAGAC
TAACGCACGCGACATAAGTGTACATCATTGGGTAGATGATATTGCTCACCTCTCGCCAC
GAGTGAGGGTAGGGTTGACGTCGTCACTGACGCACGGAATTCCGAGGGGTATCAAACCA
GGGATGGGAAGACGAGTGCCATTGATATCAGACATTGCGAATGAGAGTAAAGGAGGCTC
TGAGAGGTCTTGGATTCAAGTTGGGAGAGGAACTGGGTATTGTACGCCCTGCCCGATGC
CTTTTTATCTGTCTCAGCCAAGGCCAATTGCCTAGTTGGGCATAGGGAAACCCAAGAGG
CGCTTCGAGTTCGTCCGTGGTCATTCAAGCTCTTTTAGGAGAGCTGGAACCATGATGGG
CCTAATGTAGCTCAACCAGGTATGGAATGGCGCAAGAATTCCGGCCAGAACGGATGATA
TGAGTGGTTCTCATCACGCTGTTCGCTGACTTCCAACGTCCAACGTCTTTGGGTACATG
AAGTACGGCATGTCCTCTTAGAAAAAAAGGCCGGTGGACGATGGACAGTAGCGAACATC
GTGGTGCCTATAGGCTATGGCGTAGCCGGATGTGGGTAGAACAAAGGAGCGGTGCATGT
TGGACAGTAGTGAACAGCGTGGCGTCCTCGTTTCGCACGAGGTACCGCCGCACTGACTC
GTTGTGCGCTGATAAAGGATATCGGCCCTCGATCGCGCACCGCCCCATCATGCGCTCCA
TTGCCACCACGAGGATGTGCATACAGTGCAACCCCCCGAGGACTGCACGACCCAGTTGA
TCCGCGACAAGTACTCCGCGCAGAACGTGGTCGGGAGGTACTGGCGCATACATCACCCG
GCCCAAGCGCAAGCATCCGCGGCTGATCCGAGCTTGCACAAGCTGGTCGAAGACGTAGC
TCTCCCAAACATGTCTGTCCGCCCTTTCGCAAACTGGTCGCTCGACAGCCCTAAAATCT
GCTCCGCCTTCGAGTGCAGATCCGTCCCAGCAGCCTTAGTCCAAGTGTCATCCACCCCA
GTGTCGTCGCGTGATGCATCCCAAATTGCGCATCCCCATACAGCTTGAAATCTACACTT
CCTCAGGGTCCATGTCCGCATCGACTATCGCGTGCCCAGGCGGCACGCACCATCACGGT
TCTGCTTCACATTCAACCACGTCTTTTCGATCGCGCGCCGCATGATGGCGCCTATCGTG
ATCGATGATCACCTGGGGAAGCCTGAAGATCATCCCCCACGTAGAGAAGCAAGAATCCA
CTTCATCGTGACATCGCACCACCAACCGCAAGCGGAAGAAGCTTCCTCCACCAGTCCCA
ACCAATGCCAAACATTCTCTTGTCTCTATTCCGCTTGTTGTCGTCGTCACCCTCGTCGT
CGCAGAGAGCAGGACTATTTGACTCGGGCGACCCGCCCAATCCTTCGATGCTGACGATC
TTATGACATTGCCCGCTTGCCTTCTCACATTAATTTGAGGACGAACTGGATTCG

SEQ ID NO: 211
RIQFVLKLM~EGKRAMS~DRQHRRIGRVARVK~SCSLRRRG~RRQQAE~
RQENVWHWLGLVEEASSACGWWCDVTMKWILASLRGG~SSGFPR~
SSITIGAIMRRAIEKTWLNVKQNRDGACRLGTR~
SMRTWTLRKCRFQAVWGCAIWDASRDDTGVDDTWIKAAGTDLHSKAEQILGLSSDQFAK
GRTDMFGRATSSTSLCKLGSAADACAWAG~
CMRQYLPTTFCAEYLSRINWVVQSSGGCTVCTSSWWQWSA~
WGGARSRADILYQRTTSQCGGTSCETRTPRCSLLSNMHRSFVLPTSGYAIAYRHHDVRY
CPSSTGLFF~EDMPYFMYPKTLDVGSQRTA~~~
EPLISSVLAGILAPFHTWLSYIRPIMVPALLKELE~PRTNSKRLLGFPMPN~AIGLG~
DR~KGIGQGVQYPVPLPT~
IQDLSEPPLLSFAMSDIMGTRLPIPGLIPLGIPCVSDDVNPTLTRGER~AISSTQ~
CTLMSRALVSAENSVPLKVSPSSYNTRQPF~LVCIM~~~~
IFKVVHDMRLGPLSLHRSKSLFCLWGTTLIFFF~GFSHL~TRKAHVR

*FIG. 7F*

SEQ ID NO: 212 contig49252 length=146
AATCTCAGCGTTCAGTACCCAACTCCCATTCGAACCTAACTCCAAGACCTCTAAACCTC
ACAATCCCAATGTCTGACATCAATGCTACCCGTCTCCCCATCTGGGGTATCGGTTGCAA
CCCGTGCGTCGGTGACGACGTCACTACG

SEQ ID NO: 213
SQRSVPNSHSNLTPRPLNLTIPMSDINATRLPIWGIGCNPCVGDDVTT

SEQ ID NO: 214 EEISCGG02IQ8KO R length=103
GTCCGACATCAACGCCACTCGTCTTCCCATGATCCAACGCCCCTTCTACCCGTGCGCCA
GTGACGACGTCACCTCCACCCTCACTCGTGGCGAGAGGTGAGCG

SEQ ID NO: 215
SDINATRLPMIQRPFYPCASDDVTSTLTRGER~A

SEQ ID NO: 216 EEISCGG02HZJKJ R length=103
CCGAACTTAAATCCCAGACCTCACAAAGCCTCTTTATTCTTGAATCGCAATGTCTGATA
TCAATGCCGCTCGTCTTCCCATCATTTTTGAACCAATCATCCCG

SEQ ID NO: 217
RT~IPDLTKPLYS~IAMSDINAARLPIIFEPIIP

SEQ ID NO: 218 contig72700 length=168
TGCTGGCTCACTTCTCGCCCCTAGTGAGGGTGAAATTGTCCGCGTCACCGACGCACGG
CATAGGAACAGGTGGGTACGCGCCGGGGAGACGGGTGGCATTGATGTCCGACATTGCGA
TTGAGAGTAGAGGATGCTGTAGGTTTCTGAGGGGTCTTGTGAGTATTGAA

SEQ ID NO: 219
SILTRPLRNLQHPLLSIAMSDINATRLPGAYPPVPMPCVGDADNFTLTRGEK~AQ

SEQ ID NO: 220
ATGTCTGACATCAATGCCACCCGTCTCCCCCATCCGTTTCCATTAGGATTGCAACCGTG
TGCCGGTGACGTGGACAATTTGACCCTCACTAAAGGCGAAGGGTGA

SEQ ID NO: 221
MSDINATRLPHPFPLGLQPCAGDVDNLTLTKGEG

SEQ ID NO: 222
ATGTCTGACATCAATGCCACCCGTCTCCCCCATCCGTTTCCATTAGGATTGCAACCGTG
TGCCGGTGACGTGGACAATTTGACCCTCACTAAAGGCGAAGGGTGA

SEQ ID NO: 223
MSDINATRLPHPFPLGLQPCAGDVDNLTLTKGEG.

*FIG. 7G*

SEQ ID NO: 224 Beta-amanitin_from_Amanita_phalloides [this sequence was found by PCR with degnerate primers]
ATGTCAGATATCAATGCGACGCGTCTTCCCATATGGGGAATAGGTTGCGACCCGTGCAT
CGGTGACGACGTCACCATACTCCTCACTCGTGGCGAG

SEQ ID NO: 225
MSDINATRLPIWGIGCDPCIGDDVTILLTRGE

SEQ ID NO: 226 Phalloidin_from_Amanita_ocreata [this sequence was also found by PCR with degenerate primers]

ATGTCAGACATTAACGCGACCCGTCTTCCGCCTGGCTCGCCACCTGCCCGTGCGCCGG
TGACGACGTCAACCCTCTCCTCACTCGTGGCGAG

SEQ ID NO: 227
MSDINATRLPAWLATCPCAGDDVNPLLTRGE

FIG. 7H

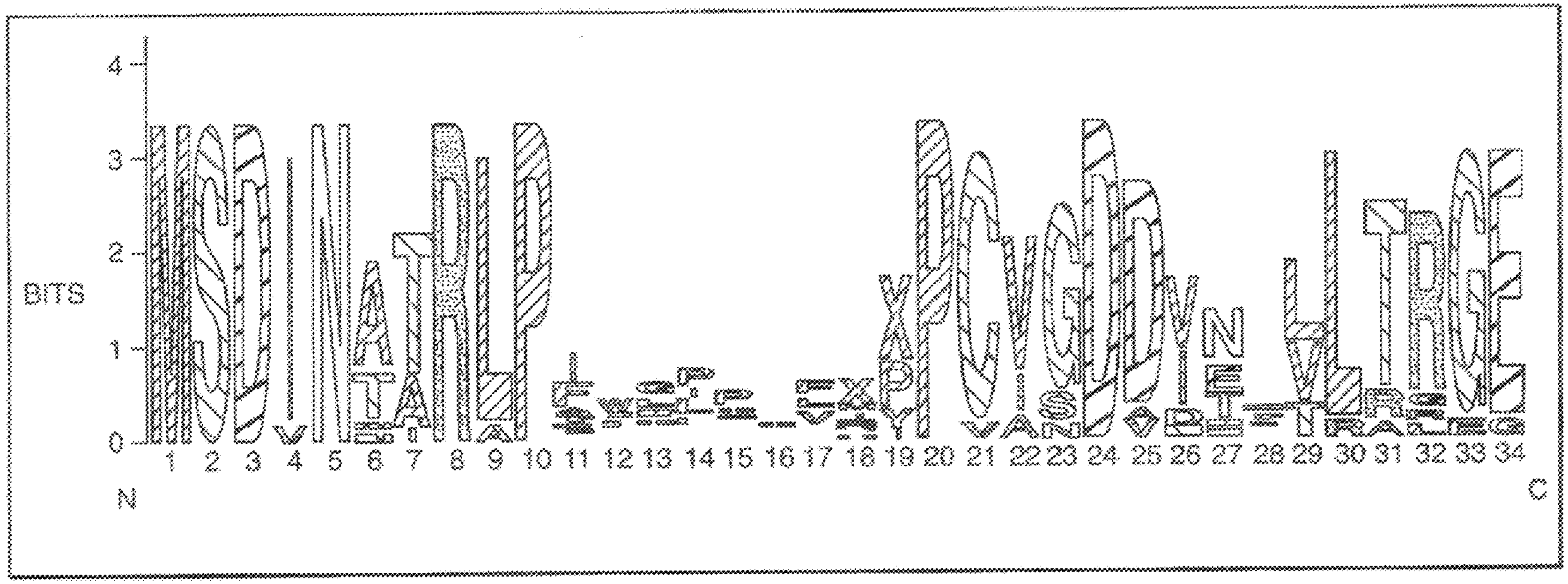

Fifteen new sequences were used for providing a WebLogo (Crooks et al., 2004) showing the relative conservation by Letter size representing amino acids, such that highly conserved amino acids are represented by Large Letters (for example, MSDIN; positions 1-5, and P; positions 10 and 20) while less conserved amino acids have smaller letters (for example A/T, G/S; positions 6 and 23, respectively) and low areas of conserved amin acids have small letters (for example, in regions 11-18). These results showed upstream MSDINATRLP (MSD, N, R, and P are invariant) and downstream conserved consensus CVGDDXXXXLTRGE (D is invariant) SEQ ID NO: 239.

SEQ ID NO:88

*FIG. 9*

A) GmAMA1 Nucleic Acid Sequences.

SEQ ID NO:240
>gi|3087452|lcl|E0UVDMS01BP3R9 length=248
Acacattcaacaaatactaacgcacaacgcatgagtacgtcgaacaagtcaacaacagaaattgagctcactcgttgccactaacgagagtttgatcgacgtgttcagcagtccatgg
Gttgcagccaatacccagattggaagacgagtggagttggtgtcgaacatggtagatattaaggcaagggcgaagatctttggctgattgagttgacggtcggaagattggagactc
ggttttcactgg DNA sequence encoding amanitin propeptide SEQ ID NO:241:
atgttcgacaccaactccactcgtcttccaatctggggtattggctgcaacccatggactgctgaacacgtcgatcaaactctcgttagtggcaacgag DNA sequence encoding alpha-amanitin/gamma-amanitin propeptide SEQ ID NO:242:
atctggggtattggctgcaaccca B) GmAMA1 Amino acid sequences deduced from sequences in A.

SEQ ID NO:243: Translation of frame 3'5' Frame 2:
Q.KPSLQSSDRQLNQPKIFALALISTMFDTNSTRLPIWGIGCNPWTAEHVDQTLVSGNEAQFLLLTCSTYSCVVR.YLLNV
(where . = nonsense codon)

SEQ ID NO: 658

The putative proprotein is underlined; predicted sequence of alpha-amanitin is in bold

SEQ ID NO:244 :
MFDTNSTRLPIWGIGCNPWTAEHVDQTLVSGNE

SEQ ID NO:50 : The bold, larger letters show a sequence of alpha-amanitin/gamma-amanitin:
IWGIGCNP

*FIG. 11*

SEQ ID NO:111
alpha-amanitin/gamma-amanitin from Amanita

```
MSDINATRLPIWGIGCNPCIGDDVTILLTRG-E
|  |  |  | | | | | | | | | | |        |     |   |  |
MFDTNSTRLPIWGIGCNPWTAEHVDQTLVSGNE
```

SEQ ID NO:244 alpha-amanitin/gamma-amanitin from Galerina

GaAMA1

NonToxin producer (nonproducer):

Lane 1: *G. hybrida*, high carbon. Lane 2: *G. hybrida*, low carbon.

Amanitin-producing species of *Galerina* (*G. marginata* and *G. badipes*):

Lane 3: *G. marginata*, high carbon. Lane 4: *G. marginata*, low carbon.

Lane 5: *G. badipes*, high carbon. Lane 6: *G. badipes*, low carbon.

A) GmAMA1/(Ga1MFD2; MFD2) Nucleic Acid Sequences.

SEQ ID NO:246

>GalerinaMFD2(615_bp) GmAMA2 agcttacgtctggcgacatttgacccatgatagactaactttggtagtcgaatcggtacaatcacgactccacggcttttgccactgttcggtgaatcaggttatctctttataggagcct
cttttctgttatctgaaaactccaagccatgtgaggatcgccgcgaccaccttaggtactccttcgtgccgtctgtcaaagtggacaaagatacacctcggcgcgagtttacttgacttac
caccgatctggaacttccccatgggctggtcagatgccctcagatcacagaactccaccaatgaagacagctcctcgtaatggcgtcgaaaatgtcttggacctttattctagaa
gttcacagtcctgcggagtcgttgctatttcctaactcatcagctctattcggtcctcgaaagagataaaggcggtcgtcagtgcaggctgatctccaatcccccaacgcaaac
tcacttaaccaaagattctttttgctctaacatctacaatgttcgacaccaacgccactcgyctcccaatctggggtattggctgcaacccatggactgctgagcacgtcgacca
gactctcgctagtgcaacgagtaa B) GmAMA2/(Ga1MFD2; MFD2) Amino acid sequences deduced from sequences in A.

SEQ ID NO:247, 659, 660, 661, 662, 663, 664, 665

>Ga1MFD2 [predicted amanitin region is underlined and bold]

SLRLATFDP..TNFGSRIGTITTPRLFATVR.IRLSLYRSLFSVLKLQAM.GSPRPP.VLLRAVCQSGQRYTSARVLLD
LPPIWNFPMGWSDALRSQNSTNEDSSS.WRRKCLGPLF.KFTVLRSRCYFLTHQLYSVLERDKRRSSVQADLQSPNA
NSLNQRFFFALTSTMFDTNATRLPIWGIGCNPWTAEHVDQTLASGNE

SEQ ID NO:248 the putative preproprotein is underlined, the toxin sequence is in BOLD.

F.KFTVLRSRCYFLTHQLYSVLERDKRRSSVQADLQSPNANSLNQRFFFALTST
MFDTNATRLPIWGIGCNPWTAEHVDQTLASGNE

C) Amino acid alignment of two Galerina amanitins (GaAMA1 above SEQ ID NO:244, GmAMA2 below, SEQ ID NO:248)

(>gi|3087452|lcl|E0UVDMS01BP3R9 length=248) the putative proprotein is in BOLD

```
GmAMA1                                      KPSLQSSDRQLNQPRIFALALISTMFDTNSTRLPIWGIGCNPWTAEHVDQTLVSGNE
                                                                   |  || ||||||| |||||||||||||||||||||| ||||
MFD2   KFTVLRSRCYFLTHQLYSVLERDKRRSSVQADLQSPNANSLNQRFFFALTSIMFDTNATRLPIWGIGCNPWTAEHVDQTLASGNE.
```

FIG. 14

Prolyloligopeptidase (POP)-like genes in fungi identified using a human POP (GenBank accession no. NP002717) sequence for a BLAST search.

| | | score | e value |
|---|---|---|---|
| gi\|116497644\|gb\|EAU80539.1\| | Coprinus [Coprinopsis] cinereus | 526 | 1e-148 |
| gi\|71022411\|ref\|XP_761435.1\| | Ustilago maydis | 506 | 1e-142 |
| gi\|58259797\|ref\|XP_567311.1\| | Cryptococcus neoformans 1 | 299 | 2e-80 |
| gi\|58259759\|ref\|XP_567292.1\| | Cryptococcus neoformans 2 | 286 | 3e-76 |
| gi\|111059876\|gb\|EAT80996.1\| | Setosphaeria nodorum | 166 | 3e-40 |
| gi\|23476937\|emb\|CAC87723.1\| | Aspergillus niger | 53.1 | 4e-06 |
| gi\|83773722\|dbj\|BAE63849.1\| | Aspergillus niger | 50.4 | 3e-05 |

*FIG. 15*

SEQ ID NO: 666 (Q)
SEQ ID NO: 160 (S)

SEQ ID NO: 228: ECGK9LO02JKSHR R Length = 112; Score = 47.8 bits (112), Expect = 4e-06
Identities = 20/33 (60%), Positives = 26/33 (78%) Frame = +3

```
Query: 436 QTVQIFYFSKDGTKIPMFIVRKKSIKLDGSHPA 468
            ++ Q++Y SKDGTK+PMFIV  KS K DG +PA
Sbjct: 3   ESTQVWYESKDGTKVPMFIVRHKSTKFDGTAPA 101
```

SEQ ID NO: 667
SEQ ID NO: 162

SEQ ID NO: 229: contig26093 length = 206 num Reads = 6; Score = 41.2 bits (95), Expect = 3e-04
Identities = 18/32 (56%), Positives = 23/32 (71%) Frame = +1

```
Query: 440 IFYFSKDGTKIPMFIVRKKSIKLDGSHPAFLY 471
            ++Y S DGTKIPMFIV  K +K +G+ FA  Y
Sbjct: 109 VWYDSYDGTKIPMFIVRHENTKFNGTAPAIQY 204
```

SEQ ID NO: 668
SEQ ID NO: 164

SEQ ID NO: 230: ECIMO1V02ICIO5 S Length = 107; Score = 35.8 bits (81), Expect = 0.014
Identities = 18/27 (66%), Positives = 21/27 (77%), Gaps = 1/27 (3%) Frame = +2

```
Query: 546 KRLTINGGSNGGLLVAAC-ARQRPDLF 571
            ++L I+GGSNGGLLV A     QRPDLF
Sbjct: 26  EKLAISGGSNGGLLVGASRLTQRPDLF 104
```

SEQ ID NO: 669
SEQ ID NO: 166

SEQ ID NO: 231: ECIMO1V01CKHE5 R Length = 94; Score = 35.4 bits (80), Expect = 0.019
Identities = 16/27 (59%), Positives = 19/27 (70%) Frame = +2

```
Query: 120 SDDGTVADKGYAFSEDGEYFAYGLSAS 146
            S DGT +L  Y FS  G+YFAYG+S S
Sbjct: 2   SSDGTASLSMYDFSHCGKYFAYGISLS 82
```

SEQ ID NO: 670
SEQ ID NO: 168

SEQ ID NO: 232: EEISCGG02IHTSV R Length = 106; Score = 33.1 bits (74), Expect = 0.093
Identities = 14/20 (70%), Positives = 15/20 (75%) Frame = -2

```
Query: 669 FLLIRVDTKAGHGAGKPTAK 588
            PLL+ VD KAGHG GK T K
Sbjct: 105 FLLLRVDKKAGHGGGKSTEK 46
```

SEQ ID NO: 671
SEQ ID NO: 169

SEQ ID NO: 233: ECIMO1V02H2WNR S Length = 78; Score = 28.9 bits (63), Expect = 1.7
Identities = 12/16 (75%), Positives = 13/16 (81%) Frame = +2

```
Query: 446 DGTKIPMFIVRKKSIK 46
            DGTK+PMFIV  KS K
Sbjct: 2   DGTKVPMFIVRHKSTK 49
```

*FIG. 16*

SEQ ID NO: 170
POPA: genomic sequence ggacaccccaaccatgtacccttctgctcgccgttcagaccatatagacacatacaggagcgaaacgagaggcgaagtcaaggtgccggacccataccactggctagaggaat
attcagaagagacggacaagtggacgtccgaccaggaggagttcacgaggacatattggacagcaaccctgatcgaaagaagctagaagacgcattcagaaagagtatggat
tatcccaaggtttcttcggcattctattcattctgatggaatggaatcgttgatggctgccaatcttcttccttttatatagttctccgctcctttttgaatgatgacaagcgatggtattggtttac
aataccggccttcaagcacaaacaggtaaacacatcaagctctgtcgtgcgaaatatttacaactttggtagtcatctgcagatcaaaggatgagactcttcccgacttctcagagag
tgactacgtcggggaaacatttttgatgtaagtgtagtttgtcgctggcggtgttcgatatcaatgatagcgttttcgcagccgaacctattatcctcggatggcacagcctcgctctccatg
tatgatttctcacactgtggcaaatacttcgcatatggtatttctcttccgtatgtaatttcaacgagcaaccatcccttccgatgagatgaacttctttttcgtcacaggggagcgatttttca
actatatacgttcggtcaacttcctctccactggcccctggcaacgacagcattagaaatgacgacggtagacttccagacgagcttagatatgtcaaatttcctccatcagctggaca
aaggactcccaaggatttttctatcaggtactacactatggaaagatctgcggacttgactaaattacttgcagcgctatcccggtacaggcactgtgaatggacagaatggcatccaa
actcaaggcgatcgtgatgctatgatttactatcaccggatagggacatcacaatgtatacccccgctcttttgtccaatcctctcatttcaattcgctcttctagccgatgatattctgtgcatg
aagaccaggaacatcctgattgggtatttggcgcagaagtcacggaagatggtaaatatgtggccctgtacacaatgaaggacacatcaagggtatgctttaagtggtcccacctgc
gttgctaaccggttcttgtagaaaaatctattgtggatgctgatcttggacaaaacgaagttggacgaaacatgaaatggaacaagatttgcaacgtttttgactcagaatacgacctgt
aagtccctgaacggtaatacggttgtttttttgcttatttgcgacagaattggcaacgacggttcattactatacatcagaactaataaagctgcacctcaatacaagatttgtcaccttagat
atagagaaaccagaattagggtttaaggaattcataccggaagatcccaaagcatatctctctcaagtcaaaattttaataaggatagactagcactagtatacaagcgtaacgtga
gtccagaacacggcaatatatcgcaggagagcaaattgatggaaaaaataggttataggcgaactctacgtctacaataacactgggtcacgactaatgcgcctagcccgggact
ttgttggctccatgacggtgaccgctcgagaaacggagccatggtttttttgccactctcacgggcttcaatacccctggaatcgtatgcaggtacaatatccagcgacccggaagaaca
gcgttggagcgtatatcgaactgccaaggtcaagggttaaatccgaacgatttcgaggctcgacaggtgactagttggtttatattgcatgaaaagtgcgtctcatgcggtctaggtgt
ggtatgacagctacgatggaacaaagattccaatgttcatcgtccgtcacaagaataccaaatttaatgggacggcgccagctatacaatatggtaggctaaagacagtgaatttatt
accggatgacatgtctaattcactctggcaaggttacggtggctttaatatatctataaatcccttctttagtccaacgattttgacgttcttgcaaaagtatggagcaattctagctgtaccta
atatccgaggaggcggcgagttcggcgagacatggcatgatgctggtatacgagagaaacgagtataacgcacgcctctcccacggtgatagctctgacattatttccaggctaatg
tttacgatgatttcattgcggcaacgtacgtgtcagttgtccttgaattctacattgccatttacttggtaccagtcagttcttggtaaaaaacaagtatgccgcgggcggcaaagtggccat
caacggggggtccaatggaggtctgttggcatgtctttatccaccctcagtctcttatattagccttaggactttttggtcgcggcctgtgtcaatcgtgcacctgaaggaacctttggagctg
ccattgctgaagttggggtcctagacttgctcaaggtttgtccgatcgtgtcttacagagatatatgctccaactcataacctttgatttagttctccaaatttaccataggtatatgatcaaca
ctgctcatgactttgttcttaagtcgatatcaggcaaagcttggactagcgactacggcgatccagaagatccgcgcgatttgatttcatttacacacattcaccacttcataaatatacca
aagaacatggtcttacctccgacgatgcttctgacagctgatcgtgagttggctcccatggtataattgctaggttcctgacgcgacctagatgatgaccgtgtcgtcccaatgcattcatt
taagtatgctgcaatgctacaatacacccctgccgcataatcgtcatccacttctgctacgtgtagacaagaaaggcggggcatggcggaggaaaatctactgagaagaggtgggttt
ttccgttgtcataactcgctgcaattaattatccc

FIG. 17A-1

SEQ ID NO: 171
POPB : genomic sequence accaatggctggaggagaattcaaatgaagtagacgaatggacgacggcgcagacagctttcacgcaagtctatcttgataagaatgcggatagacagaagctcgaggagaaatt
tcgtgcaagcaaggactacgtcaaggtaatcgatgatcgatatagcgttgtgtctgtgctgaagaccttgcccatagtttctgcgccaactctgcttgatagtggacactggtattggttcta
caatagcggcgtacaatcgcaagcaggtatgtacccatctgtctctggcgatgccgaattcagacagtgttcagtcctctaccgctccaagaaacccgttcttcctgatttctcaaagagg
gacgaggaagtcggcgaagtatacttcgatgtagggatctccacgacgttgaatacttcttgacttcactcttgaaagccaaacgtactctctgctgatggcaccgcaattatgggcac
gtgccgattctccctagtggcgagtatttcgcatatgcagtgtcccacttggtgagtaacccacgttcctacatgggccaactcctggtcttatttttgcacagggagttgattatttactatct
atgttcgccctacgagttcatcattgtctcaagctccggaagctgaaggtggggatggtcgattgtcggatgaagtgaaatggtgcaagtttacgactataacgtggacaaaggactcca
aaggatttctttaccaggtatgatacatccagccacccaaccatccgttcgttaacctgtgtcatacagcggtaccctgctcgggaatctcttgtggcgaaagatcgtgataaagatgctat
ggtatgctatcatagggttggaacgactcaatgtagggattacttggcgtcttgacttccccaaactgatccagtagtacagtggaagatatcattgtccaacaagacaaggagaaccc
agactggacatatggaacagatgcgtcagaggacggcaaatatatctacttagtggtatacaaggatgcctcgaaggcaagagtttaagttctatcgcccgacatcaataaccttcata
ctaccagcaaaatcttctgtggggttgcagaattcgacaaggacggggtcaagccggaaattccctggcgaaaagtcatcaatgagtttggggcggattaccatgtgtgagtcctccct
ccttcacgtccccttcacgtcccctttttaactcggcatggtatagtatcacgaaccacggatcttgatctatgtcaagactaacgtgaatgcgccccaatataaagttgtcactatcgacct
ttcgacaggagaacccgaaattcgtgatttcatcccggaacagaaagatgcgaagctcactcaagtcaaatgcgtcaacaaggaatatttcgtcgcgatctacaagcgcaatgtatttt
cattgacaatttgatttcgaatttccctaacgtcgatttgcatcccacaggtcaaagatgaaatatatctttactccaaagcaggcgatcaactcagtcgtctggcgtcggacttcattggcgtt
gcatctataactaacagagagaaacaacctcatttcttcctcactttctctggatttaacacgccgggcaccatttctcgctacgatttacagctccagagacacaacgtctcagcatcctt
agaacgacgaagctaaatggtctgaatgcagatgactttgagagcacacaagtctggtatgagagcaaagacggaacgaaagttccaatgttcatcgttcgtcacaaatcaacgaa
atttgacggaacggcgccggcgattcaaaacggtaatcctttctcatccatcacaaccagtaggaatctctgacaacctgtcttgcttcgcacaggttatggtggtttcgcgattacagccg
atccattctttagtcccatcatgctcacctttatgcagacatatggcgcaatcctggctgtcccgaacatcagaggtggaggtgaattcggcggagaatggcacaaggcagggagacg
agaaaccaaggtttgtgcccattgccttatatttctgttgcatgcagcctggacctccgtaatagggaaatactttgatgatttcatcgctgccgcgtatgtccgccgctattcgaattttcgtg
atttcacaggctcacggaggtctttgttgctacagtcaatttcttgtcaaaaacaagtacgcggctccaggcaaaggtggccatcactggtgcatccaatggcggtaaagtgaccctcgt
tcttgtttcatcccggtactcacctcgcgatggtggaataggttttcttgtctgtggttccgtagttcgggcaccagaggggacattcggcgctgctgtttccgaaggtggtgtcgcggacctc
ctaaaggtatttggttgtccacgatatccgtgctcgttctctaatttctgtatttgagttaataaatttaccggggtgagttgacattggtcttgtgtccaccgctgatttgattaattacatcgtca
gggatggcgtggacgagtgaatatggaaacccttttattaaggaggacttcgactttgtccaagcattgtctcctgtgcataacgtacccaaggatagggttcttcctgccacattacttatg
accaatgcgggtggggtgactctctggagcccagatttaccagtacctgacgctcgactctcatcaggtgacgatcgtgtagttccaatgcattcgcttaagttcgtcgcaaaccttcagtac
aatgtgcctcaaaatcctcatccattgctcatccgtgtggataaatcttggcttggtcattggttttggcaagacaacagacaagcagtaaattgcccctcctttctacgttccattgcttatattt
tacagtactaaagatgctgcggacaagtggagtttcgtagcgcaatcgttagggctagaatggaaaacggttgactaggctgtcaaattaacagatgcggggctcaaaataccgtccac
gttagatgtattcaatgtactctgtttcctgtaaccctgcgtacggcccaatacagccatg

*FIG. 17A-2* cDNA sequences of POPA and POPB.

SEQ ID NO: 234

>PopA_cDNA_full-length

ACACCGTCTCAAATTCAAGCCATGCACCGTTTTTTGCAGCCCGTAAGAGAACGCCTTCGCTCTGCTCTCGCCCGCTACTTTGGTTCGCGGA
TCATGTCTTCTACACAGTGGACACCCAACATGTACCCTTCTGCTCGCCGTTCAGACCATATAGACACATACAGGAGCGAAACGAGAGGCGA
AGTCAAGGTGCCGGACCCGTACCACTGGCTAGAGGAATATTCAGAAGAGACGGACAAGTGGACGTCCGACCAGGAGGAGTTCACGAGGACA
TATTTGGACAGCAACCCTGATCGAAAGAAGCTAGAAGACGCATTCAGAAAGAGTATGGATTATCCCAAGTTCTCCGCTCCTTTTTTGAATG
ATGACAAGCGATGGTATTGGTTTTACAATACCGGCCTTCAAGCACAAACAGTCATCTGCAGATCAAAGGATGAGACTCTTCCCGACTTCTC
AGAGAGTGACTACGTCGGGGAAACATTTTTTGATCCGAACCTATTATCCTCGGATGGCACAGCCTCGCTCTCCATGTATGATTTCTCACAC
TGTGGCAAATACTTCGCATATGGTATTTCTCTTTCCGGGAGCGATTTTTCAACTATATACGTACGGTCAACTTCCTCTCCACTGGCCCCTG
GCAACAACAGCATTAGAAATGACGACGGTAGACTTCCAGACGAGCTTAGATATGTCAAATTTTCCTCCATCAGCTGGACAAAGGACTCCAA
AGGATTTTTCTATCAGCGCTATCCCGGTACAGGCACTGTGAATGGACAGAATGGCATCCAAACTCAAGGCGATCGTGATGCTATGATTTAC
TATCACCGGATAGGGACATCACAATCCGATGATATTCTTGTGCATGAAGACCAGGAACATCCTGATTGGGTATTTGGCGCAGAAGTCACGG
AAGATGGTAAATATGTGGCCCTGTACACAATGAAGGACACATCAAGGAAAAATCTATTGTGGATTGCTGATCTTGGACAAAACGAAGTTGG
ACGAAACATGAAATGGAACAAGATTTGCAACGTTTTTGACTCAGAATACGACCTAATTGGCAACGACGGTTCATTACTATACATCAGAACT
AATAAAGCTGCACCTCAATACAAGATTGTCACCTTAGATATAGAGAAACCAGAATTAGGGTTTAAGGAATTCATACCGGAAGATCCCAAAG
CATATCTCTCTCAAGTCAAAATTTTTAATAAGGATAGACTAGCACTAGTATACAAGCGTAACGTTATAGGCGAACTCTACGTCTACAATAA
CACTGGGTCACGACTAATGCGCCTAGCCCGGGACTTTGTTGGCTCCATGACGGTGACCGCTCGAGAAACGGAGCCATGGTTTTTTGCCACT
CTCACGGGCTTCAATACCCCTGGAATCGTATGCAGGTACAATATCCAGCGACCGGAAGAACAGCGTTGGAGCGTATATCGAACTGCCAAGG
TCAACGGTTTAAATCCGAACGATTTCGAGGCTCGACAGGTGTGGTATGACAGCTACGATGGAACAAAGATTCCAATGTTCATCGTCCGTCA
CAAGAATACCCAATTTAATGGGACGGCGCCAGCTATACAATATGGTTACGGTGGCTTTAATATATCTATAAATCCCTTCTTTAGTCCAACG
ATTTTGACGTTCTTGCAAAAGTATGGAGCAATTCTAGCTGTACCTAATATCCGAGGAGGCGGCGAGTTCGGCGAGACATGGCATGATGCTG
GTATACGAGAGAAACGAGCTAATGTTTACGATGATTTCATTGCGGCAACTCAGTTCTTGGTAAAAAACAAGTATGCCGCGGGCGGCAAAGT
GGCCATCAACGGGGGGTCCAATGGAGGACTTTTGGTCGCGGCCTGTGTCAATCGTGCACGTGAAGGAACCTTTGGAGCTGCCATTGCTGAA
GTTGGGGTCCTAGACTTGCTCAAGTTCCCCAAATTTACCATAGGCAAAGCTTGGATTAGCGACTACGGCGATCCAGAAGATCCGCGTGATT
TTGATTACATTTACACACATTCACCACTTCATAATATACCAAAGAACATGGTCTTACCTCCGACGATGCTTCTGACAGCTGATCATGATGA
CCGTGTCGTCCCAATGCATTCATTTAAGTATGCTGCAATGCTACAATACACCCTGCCGCATAATCGTCATCCACTTCTGCTACGTGTAGAC
AAGAAAGCGGGGCATGGCGGAGGAAAATCTACTGAGAAGAGGTTACAGGAGGCTGCCGACAAATGGGGTTTTGCCGCGCAGTCCATGGGTC
TTGCGTGGAAGGATAGACAAGCTAATCTGTGATGAGTTTCGGCATGCATTCAGCATTTAGACATCTGTTTTACTGTTTGGGCTACATTTTA
CGACACTCACGATTCCAGGTATATTATTTAACGCATTGCACTTGTGCAGGCTAAAAAAAAAAAAAAAAAAAAAAAAA

*FIG. 17B-1*

SEQ ID NO: 235
>PopB_cDNA

ATGCCCCCTACACCATGGGCTCCTCACAGTTATCCTCCTACCCGTCGTTCTGACCACGTTGATGTATATCAGAGCGCAT
CCAGAGGCGAAGTACCAGTACCGGACCCGTACCAATGGCTGGAGGAGAATTCAAATGAAGTCGACGAATGGACGACGGC
GCAGACAGCTTTCACGCAAGGCTATCTTGATAAGAATGCGGATAGACAGAAGCTCGAGGAGAAATTTCGTGCAAGCAAG
GACTACGTCAAGTTTTCTGCGCCAACTCTGCTTGATAGTGGACACTGGTATTGGTTCTACAATAGCGGCGTACAATCGC
AAGCAGTCCTCTACCGCTCCAAGAAACCCGTTCTTCCTGATTTCTCAAAGAGGGACGAGGAAATCGGCGAAGTATACTT
CGATCCAAACGTACTCTCTGCTGATGGCACCGCAATTATGGGCACGTGCCGATTCTCCCCTAGTGGCGAGTATTTCGCA
TATGCAGTGTCCCACTTGGGAGTTGATTATTTTACTATCTATGTTCGCCCTACGAGTTCATCATTGTCTCAAGCTCCGG
AAGCTGAAGGTGGGGATGGTCGATTGTCGGATGAAGTGAAATGGTGCAAGTTTACGACTATAACGTGGACAAAGGACTC
CAAAGGATTTCTTTACCAGCGGTACCCTGCTCGGGAATCTCTTGTGGCGAAAGATCGTGATAAAGATGCTATGGTATGC
TATCATAGGGTTGGAACGACTCAATTGGAAGATATCATTGTCCAACAAGACAAGGAGAACCCAGACTGGACATATGGGA
CAGATGCGTCAGAGGACGGCAAATATATCTACTTAGTGGTATACAAGGATGCCTCGAAGCAAAATCTTCTGTGGGTTGC
AGAATTCGACAAGGACGGGGTCAAGCCGGAAATTCCCTGGCGAAAAGTCATCAATGAGTTTGGGGCGGATTACCATGTT
ATCACGAACCACGGATCTTTGATCTATGTCAAGACTAACGTGAATGCGCCCCAATATAAAGTTGTCACTATCGACCTTT
CGACAGGAGAACCCGAAATTCGTGATTTCATCCCGGAACAGAAAGATGCGAAGCTCACTCAAGTCAAATGCGTCAACAA
GGAATATTTCGTCGCGATCTACAAGCGCAATGTCAAAGATGAAATATATCTTTACTCCAAAGCAGGCGATCAACTCAGT
CGTCTGGCGTCGGACTTCATTGGCGTTGCATCTATAACTAACAGAGAGAAACAACCTCATTTCTTCCTCACTTTCTCTG
GATTTAACACGCCGGGCACCATTTCTCGCTACGATTTTACAGCTCCAGACACACAACGTCTCAGCATCCTTAGGACTAC
GAAGCTAAATGGTCTGAATGCAGATGACTTTGAGAGCACACAAGTCTGGTATAAGAGCAAAGACGGAACGAAAGTTCCA
ATGTTCATCGTTCGTCACAAATCAACAAAATTTGACGGAACGGCGCCGGCGATTCAAAACGGTTATGGTGGTTTCGCTA
TTACAGCCGATCCATTCTTTAGTCCCATCATGCTCACCTTTATGCAGACATATGGCGCAATCCTGGCTGTCCCGAACAT
CAGAGGTGGAGGTGAATTCGGCGGAGAATGGCACAAGGCAGGGAGACGAGAAACCAAGGGAAATACTTTTGATGATTTC
ATCGCTGCCGCTCAATTTCTTGTCAAAAACAAGTACGCGGCTCCAGGCAAGGTGGCCATCACTGGTGCATCCAATGGCG
GTTTTCTTGTCTGTGGTTCCGTAGTTCGGACACCAGAGGGAACATTCGGCGCTGCTGTTTCCGAAGGTGGTGTCGCGGA
CCTCCTAAAGTTTAATAAATTCACCGGGGGGATGGCGTGGACGAGTGAATATGGAAACCCTTTTATTAAGGAGGACTTC
GACTTTGTCCAAGCATTGTCTCCTGTGCATAACGTACCCAAGGATAGGGTTCTTCCTGCCACATTACTTATGACCAATG
CGGGTGACGATCGTGTAGTTCCAATGCATTCGCTCAAGTTCGTCGCAAACCTTCAGTACAATGTGCCTCAAAATCCTCA
TCCATTGCTCATCCGTGTGGATAAATCTTGGCTTGGTCATGGTTTTGGCAAGACAACAGACAAGCATACTAAAGATGCT
GCGGACAAGTGGAGTTTCGTAGCGCAATCGTTAGGGCTAGAATGGAAAACGGTTGA

*FIG. 17B-2*

Amino acid sequences of POPA and POPB

SEQ ID NO: 236
>PopA_amino_acid sequence

MHRFLQPVRERLRSALARYFGSRIMSSTQWTPNMYPSARRSDHIDTYRSETRGEVKVPDPYHWLEEYSEETDKWTSDQEEF
TRTYLDSNPDRKKLEDAFRKSMDYPKFSAPFLNDDKRWYWFYNTGLQAQTVICRSKDETLPDFSESDYVGETFFDPNLLSSD
GTASLSMYDFSHCGKYFAYGISLSGSDFSTIYVRSTSSPLAPGNNSIRNDDGRLPDELRYVKFSSISWTKDSKGFFYQRYPGTG
TVNGQNGIQTQGDRDAMIYYHRIGTSQSDDILVHEDQEHPDWVFGAEVTEDGKYVALYTMKDTSRKNLLWIADLGQNEVG
RNMKWNKICNVFDSEYDLIGNDGSLLYIRTNKAAPQYKIVTLDIEKPELGFKEFIPEDPKAYLSQVKIFNKDRLALVYKRNVI
GELYVYNNTGSRLMRLARDFVGSMTVTARETEPWFFATLTGFNTPGIVCRYNIQRPEEQRWSVYRTAKVKGLNPNDFEARQ
VWYDSYDGTKIPMFIVRHKNTQFNGTAPAIQYGYGGFNISINPFFSPTILTFLQKYGAILAVPNIRGGGEFGETWHDAGIREKR
ANVYDDFIAATQFLVKNKYAAGGKVAINGGSNGGLLVAACVNRAREGTFGAAIAEVGVLDLLKFPKFTIGKAWISDYGDPE
DPRDFDYIYTHSPLHNIPKNMVLPPTMLLTADHDDRVVPMHSFKYAAMLQYTLPHNRHPLLLRVDKKAGHGGGKSTEKRL
QEAADKWGFAAQSMGLAWKDRQANL*

SEQ ID NO: 237
>PopB_amino_acid sequence

MPPTPWAPHSYPPTRRSDHVDVYQSASRGEVPVPDPYQWLEENSNEVDEWTTAQTAFTQGYLDKNADRQKLEEKFRASKD
YVKFSAPTLLDSGHWYWFYNSGVQSQAVLYRSKKPVLPDFQRGTRKVGEVYFDPNVLSADGTAIMGTCRFSPSGEYFAYA
VSHLGVDYFTIYVRPTSSSLSQAPEAEGGDGRLSDGVKWCKFTTITWTKDSKGFLYQRYPARESLVAKDRDKDAMVCYHR
VGTTQLEDIIVQQDKENPDWTYGTDASEDGKYIYLVVYKDASKQNLLWVAEFDKDGVKPEIPWRKVINEFGADYHVITNHG
SLIYVKTNVNAPQYKVVTIDLSTGEPEIRDFIPEQKDAKLTQVKCVNKGYFVAIYKRNVKDEIYLYSKAGDQLSRLASDFIGV
ASITNREKQPHSFLTFSGFNTPGTISRYDFTAPDTQRLSILRTTKLNGLNADDFESTQVWYKSKDGTKVPMFIVRHKSTKFDGT
APAIQNGYGGFAITADPFFSPIMLTFMQTYGAILAVPNIRGGGEFGGEWHKAGRRETKGNTFDDFIAAAQFLVKNKYAAPGK
VAITGASNGGFLVCGSVVRAPEGTFGAAVSEGGVADLLKFNKFTGGMAWTSEYGNPFIKEDFDFVQALSPVHNVPKDRVLP
ATLLMTNAGDDRVVPMHSLKFVANLQYNVPQNPHPLLIRVDKSWLGHGFGKTTDKHTKDAADKWSFVAQSLGLEWKTVD

*FIG. 17C*

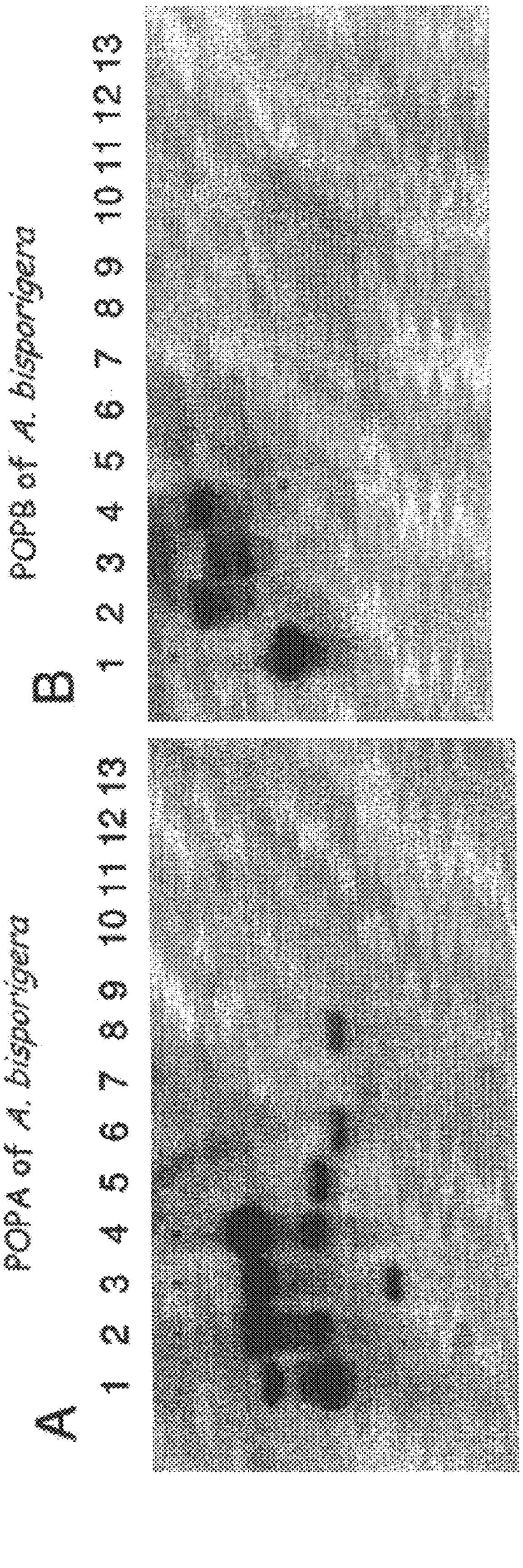

Mushroom Lanes
* Lanes 1 – 4: Amatoxin and phallotoxin producing *Amanita* species in sect. *Phalloideae*
Lanes 5 - 8: Non producers of amatoxin and phallotoxin toxin in *Amanita in* sect. *Validae*
Lanes 9-10: Non producers of amatoxin and phallotoxin toxin in *Amanita* in sect. *Amanita*
Lane 11: Non producers of amatoxin and phallotoxin toxin in *Amanita* in sect. *Caesorea*
Lane 12-13: Non producers of amatoxin and phallotoxin toxin in *Amanita* in sect. *Vaginatae*

*FIG. 18*

- Lane 1: MW standards
- Lane2: Purified single band correlated with peptide cleavage activity shown Figure 20B.

Lane 1: Markers.
Lane 2: POPB purified from inclusion bodies.
Lane 3: Soluble extract of *Amanita bisporigera*.
Lane 4: Immunoblot of POPB inclusion body.
Lane 5: Immunoblot of *Amanita* extract.

| GALERINA POPA SEQUENCES | LENGTH IN NUCLEIC ACIDS | NUMBER OF READS | RELATEDNESS RATING | SEQ ID NO:XX |
|---|---|---|---|---|
| E0UVDMS01DRXPP | LENGTH=241 | NA | 102 7e-23 | SEQ ID NO:250 |
| E0UVDMS01AG5VR | LENGTH=221 | NA | 94 2e-20 | SEQ ID NO:251 |
| E0UVDMS01CLJX8 | LENGTH=243 | NA | 84 2e-19 | SEQ ID NO:252 |
| CONTIG01013 | LENGTH=310 | NUMREADS=5 | 87 1e-18 | SEQ ID NO:253 |
| E0UVDMS02HHTQY | LENGTH=224 | NA | 80 4e-16 | SEQ ID NO:254 |
| E0UVDMS02F8ASH | LENGTH=239 | NA | 57 6e-16 | SEQ ID NO:255 |
| E0UVDMS01ANFQ8 | LENGTH=264 | NA | 64 3e-14 | SEQ ID NO:256 |
| CONTIG18675 | LENGTH=241 | NUMREADS=1 | 64 3e-14 | SEQ ID NO: 256 |
| E0UVDMS01ELV4E | LENGTH=254 | NA | 72 1e-13 | SEQ ID NO:258 |
| E0UVDMS01C7LJ6 | LENGTH=267 | NA | 58 2e-13 | SEQ ID NO:259 |
| E0UVDMS01EUNXT | LENGTH=249 | NA | 65 1e-12 | SEQ ID NO:260 |
| E0UVDMS02GNCLJ | LENGTH=254 | NA | 68 2e-12 | SEQ ID NO:261 |
| E0UVDMS01ASNO8 | LENGTH=254 | NA | 67 3e-12 | SEQ ID NO:262 |
| CONTIG11529 | LENGTH=243 | NUMREADS=2 | 67 4e-12 | SEQ ID NO:263 |
| E0UVDMS01D8GCX | LENGTH=230 | NA | 61 2e-10 | SEQ ID NO:264 |
| CONTIG48857 | LENGTH=169 | NUMREADS=3 | 57 3e-09 | SEQ ID NO:265 |
| E0UVDMS01BH7S5 | LENGTH=262 | NA | 57 5e-09 | SEQ ID NO:266 |
| CONTIG60897 | LENGTH=242 | NUMREADS=4 | 57 5e-09 | SEQ ID NO:267 |
| E0UVDMS02FGJBD | LENGTH=253 | NA | 52 9e-08 | SEQ ID NO:268 |
| E0UVDMS02GQMEJ | LENGTH=280 | NA | 51 3e-07 | SEQ ID NO:269 |
| CONTIG43041 | LENGTH=170 | NUMREADS=2 | 47 1e-06 | SEQ ID NO:270 |
| E0UVDMS02JYI2X | LENGTH=130 | NA | 46 6e-06 | SEQ ID NO:271 |
| CONTIG08963 | LENGTH=360 | NUMREADS=6 | 46 6e-06 | SEQ ID NO:272 |
| CONTIG23635 | LENGTH=193 | NUMREADS=3 | 45 1e-05 | SEQ ID NO:273 |
| CONTIG34645 | LENGTH=176 | NUMREADS=2 | 43 2e-05 | SEQ ID NO:274 |
| CONTIG02145 | LENGTH=325 | NUMREADS=4 | 37 0.003 | SEQ ID NO:275 |
| E0UVDMS02I6F0Q | LENGTH=220 | NA | 36 0.006 | SEQ ID NO:276 |
| E0UVDMS01BQJH3 | LENGTH=263 | NA | 33 0.042 | SEQ ID NO: 69 |

FIG. 22A-1

```
                   >E0UVDMS01DRXPF; LENGTH=241; SCORE =  102 BITS (256), EXPECT = 7e-23; IDENTITIES = 44/77 (57%),
                   POSITIVES = 55/77 (71%); FRAME = -1
SEQ ID NO: 354     QUERY: 26  SSTQWTPNMYPSARRSDHIDTYRSETRGEVKVPDPYHWLEEYSEETDKWTSDQEEFTRTY 85
                              SS  W P  YPS RRSDH+D+Y+S ++GEV VPDPY WLEE ++E DKWT+ Q +  + Y
SEQ ID NO: 356     SBJCT: 238 SSIAWAPGNYPSTRRSDHVDSYQSASKGEVPVPDPYQWLEESTDEVDKWTTAQADLAQAY 59

SEQ ID NO: 355     QUERY: 86  LDSNPDRKKLEDAFRKS 102
                              LD N D +KL D FR S
SEQ ID NO: 357     SBJCT: 58  LDQNADIQKLADKFRAS 8

                   >E0UVDMS01AG5VR; LENGTH=221; SCORE = 94.4 BITS (233), EXPECT = 2e-20; IDENTITIES = 41/64 (64%),
                   POSITIVES = 49/64 (76%); FRAME = +3
SEQ ID NO: 359     QUERY: 44  IDTYRSETRGEVKVPDPYHWLEEYSEETDKWTSDQEEFTRTYLDSNPDRKKLEDAFRKSM 103
                              +D Y+S  RG+V V DPY WLEEY++EIDKWT+ QE FTRTYLD NPD  +LE AF+
SEQ ID NO: 360     SBJCT: 3   VDIYKSALRGDVHVQDPYQWLEEYTDEIDKWTTAQEVFTRTYLDKNPDLPRLEKAFQACN 182

SEQ ID NO: 358     QUERY: 104 DYPK 107
                              DYPK
                   SBJCT: 183 DYPK 194

                   >E0UVDMS01CLJX8; LENGTH=243; SCORE=84.0 BITS(206), EXPECT(2)=2e-19; IDENTITIES=36/70 (51%),
                   POSITIVES=50/70(71%); FRAME=-1
SEQ ID NO: 361     QUERY: 432 GSMTVTARETEPWFFATLIGFNTPGIVCRYNIQRPEEQRWSVYTRAKVKGLNPNDFEARQ 491
                              G+ ++  R+ +  FF TL+GFNTPG = RY+   PE QR+S+ RT KV  L+P+DFE+ Q
SEQ ID NO: 364     SBJCT: 243 GAASOAMRQLQTJFFLTLSGFNTPGTIARYDFTAPETQRFSILRTTKVNELDPDDFESTQ 64

SEQ ID NO: 362     QUERY: 492 VWYDSYDGTK 501
                              VWY+S DG K
SEQ ID NO: 366     SBJCT: 63  VWYESKDGNK 34

                   SCORE = 27.3 BITS(59); EXPECT(2)=2e-19; IDENTITIES=11/12(91%); POSITIVES=12/12(100%); FRAME = -2
SEQ ID NO: 363     QUERY: 500 TKIPMFIVRHKN 511
                              TKIPMFIVRHK+
SEQ ID NO: 365     SBJCT: 38  TKIPMFIVRHKS 3
```

FIG. 22A-2

```
                   >CONTIG01013; LENGTH=310; NUMREADS=5; SCORE = 87.4 BITS(215), EXPECT(2)=1e-18; IDENTITES = 39/50(78%),
                   POSITIVES=44/50 (88%); FRAME=+2
SEQ ID NO: 367     QUERY: 526 GGFNISINPFFSPTILTFLQKYGAILAVPNIRGGGEFGETWHDAGIREKR 575
                              GGF+ISI+PFFS TILTFLQKYG + A+PNIRGGGEFGE WH AG REK+
SEQ ID NO: 368     SBJCT: 2   GGFSISIDPFFSATILTFLQKYGVVFALPNIRGGGEFGEDWHLAGCREKK 151

                   SCORE = 21.2 BITS (43), EXPECT(2) = 1e-18; IDENTITIES = 8/10 (80%), POSITIVES = 9/10 (90%); FRAME = +3
SEQ ID NO: 369     QUERY: 577 NVYDDFIAAT 586
                              N +DDFIAAT
SEQ ID NO: 370     SBJCT: 210 NCFDDFIAAT 239

                   >EOUVDMS02HHTQY; LENGTH=224; SCORE = 80.1 BITS (196), EXPECT = 4e-16; IDENTITIES = 35/46 (76%),
                   POSITIVES = 42/46 (91%); FRAME = -2
SEQ ID NO: 371     QUERY: 690 DDRVVPMHSFKYAAMLQYTLPHNRHPLLLRVDKKAGHGGGKSTEKR 735
                              DDRVVPMHSFK AA LQY+LPHN +PLL+R+DKKAGHG GKST+++
SEQ ID NO: 372     SBJCT: 202 DDRVVPMHSFKLAAELQYSLPHNPNPLLIRIDKKAGHGAGKSTQQK 65

                   >EOUVDMS02F2ASH; LENGTH=239; SCORE = 57.0 BITS(136), EXPECT(2)=6e-16; IDENTITIES=24/34(70%),
                   POSITIVES=30/34(88%); FRAME=-1
SEQ ID NO: 373     QUERY: 702 AAMLQYTLPHNRHPLLLRVDKKAGHGGGKSTEKR 735
                              AA LQY+LPHN +PLL+R+DKK GHG GKST++R
SEQ ID NO: 374     SBJCT: 236 AAELQYSLPHNPNPLLIRIDKKTGHGAGKSTQQR 135

                   SCORE = 42.7 BITS (99), EXPECT(2) = 6e-16; IDENTITIES = 16/22 (72%), POSITIVES = 20/22 (90%); FRAME = -3
SEQ ID NO: 375     QUERY: 735 RLQEAADKWGFAAQSMGLAWKD 756
                              R++E+ADKWGF AQS+GL WKD
SEQ ID NO: 376     SBJCT: 78  RIKESADKWGFVAQSLGLVWKD 13
```

FIG. 22A-3

```
                   >E0UVDMS01ANFQ8; LENGTH=264; SCORE = 63.9 BITS (154), EXPECT(2) = 3e-14; IDENTITIES = 27/34 (79%),
                   POSITIVES = 31/34 (91%); FRAME = +3
SEQ ID NO: 377     QUERY: 491 QVWYDSYDGTKIPMFIVRHKNTQFNGTAPAIQYG 524
                              QVWY+S DGT IPMFIVRHK+T+F+GTAP IQYG
SEQ ID NO: 378     SBJCT: 108 QVWYESKDGTSIPMFIVRHKSTKFDGTAPVIQYG 209

                   SCORE=30.0 BITS(66), EXPECT(2)=3e-14; IDENTITIES=12/20(60%), POSITIVES=15/20(75%); FRAME=+2
SEQ ID NO: 379     QUERY: 473 VYRTAKVKGLNPNDFEARQV 492
                                 +YRT K+ GLN  DF+A QV
SEQ ID NO: 380     SBJCT: 2   IYRTTKLNGLNTEDFKASQV 61

                   >CONTIG10675; LENGTH=241; NUMREADS=1; SCORE=63.9 BITS(154), EXPECT(2)=3e-14; IDENTITIES =27/34(79%),
                   POSITIVES=31/34(91%); FRAME = +3
SEQ ID NO: 256     QUERY; 491 QVWYDSYDGTKIPMFIVRHKNTQFNGTAPAIQYG 524
                              QVWY+S DGT IPMFIVRHK+T+F+GTAP IQYG
SEQ ID NO: 382     SBJCT: 108 QVWYESKDGTSIPMFIVRHKSTKFDGTAPVIQYG 209

                   SCORE=30.0 BITS(66), EXPECT(2)=3e-14; IDENTITIES=12/20(60%), POSITIVES=15/20(75%);FRAME=+2
SEQ ID NO: 379     QUERY: 473 VYRTAKVKGLNPNDFEARQV 492
                              +YRT K+ GLN  DF+A QV
SEQ ID NO: 380     SBJCT: 2   IYRTIKLNGLNTEDFKASQV 61

                   >E0UVDMS01ELV4E; LENGTH=254; SCORE = 72.0 BITS (175), EXPECT = 1e-13; IDENTITIES = 36/60 (60%),
                   POSITIVES = 44/60 (73%); FRAME = -2
SEQ ID NO: 385     QUERY: 189 SDFSTIYVRSTSSPLAPGNNSIRNDDGRLPDELRYVKFSSISWTKDSKGFFYQRYPGTGT 248
                              SDF TIYV ST SPL    +S +ND GRLP+E+++VKFSSI WT DSKGFF +  P T +
SEQ ID NO: 386     SBJCT: 253 SDFVTIYVWSTDSPLTNDVDS-KNDKGRLPEEIKFVKFSSIGWTPDSKGFFIRSIPWTAS 77
```

*FIG. 22A-4*

```
                    >E0UVDMS01C7LJ6; LENGTH=267; SCORE = 58.2 BITS (139), EXPECT(2) = 2e-13; IDENTITIES = 23/35 (65%),
                    POSITIVES = 30/35 (85%); FRAME = -2

SEQ ID NO: 387      QUERY: 211 RNDDGRLPDELRYVKFSSISWTKDSKGFFYQRYPG 245
                               +ND GRLP+E+++VKFSSI WT DSKGFF + +PG
SEQ ID NO: 388      SBJCT: 218 KNDKGRLPEEIKFVKFSSIGWTPDSKGFFIRSFPG 114

                    SCORE = 32.7 BITS (73), EXPECT(2) = 2e-13; IDENTITIES = 15/26 (57%), POSITIVES = 18/26 (69%),
                    GAPS = 1/26 (3%); FRAME = -3

SEQ ID NO: 389      QUERY: 242 RYPGTGTVNGQNG-IQTQGDRDAMIY 266
                               RYP T T   +NG I T+GD DAM+Y
SEQ ID NO: 390      SBJCT: 79  RYPDTSTATQENGPIATEGDLDAMVY 2

                    >E0UVDMS01EUNXT; LENGTH=249; SCORE = 65.1 BITS (157), EXPECT(2) = 1e-12; IDENTITIES = 29/47 (61%),
                    POSITIVES = 37/47 (78%), GAPS = 1/47 (2%); FRAME = -2
SEQ ID NO: 371      QUERY: 690 DDRVVPMHSFKYAAMLQYTLPHNRHPLLLRVDKK-AGHGGGKSTEKR 735
                               DDRVVPMHSFK+ A LQ+ +P N HPLL+++DK   GHG GK T+K+
SEQ ID NO: 394      SBJCT: 230 DDRVVPMHSFKFIATLQHNVPQNPHPLLIKIDKSWLGHGMGKPTDKK 90

                    SCORE = 23.5 BITS (49), EXPECT(2) = 1e-12; IDENTITIES = 8/12 (66%),
                    POSITIVES = 11/12 (91%); FRAME = -1
SEQ ID NO: 396      QUERY: 736 LQEAADKWGFAA 747
                               +++AADKWGF A
SEQ ID NO: 335      SBJCT: 36  VKDAADKWGFIA 1
```

FIG. 22A-5

```
                   >E0UVDMS02GNCLJ; LENGTH=254; SCORE = 67.8 BITS (164), EXPECT = 2e-12; IDENTITIES = 33/54 (61%),
                   POSITIVES = 42/54 (77%); FRAME - -2
SEQ ID NO: 397     QUERY: 188 GSDFSTIYVRSTSSPLAPGNNSIRNDDGRLPDELRYVKFSSISWTKDSKGFFYQ 241
                              G D+STIYVRSTSSPL+  + + +  DGRL DE+++ KFS+I WTKD KGF YQ
SEQ ID NO: 398     SBJCT: 226 GGDYSTIYVRSTSSPLSQSSVA-QGVDGRLSDEVKWFKFSTIIWTKDFKGFLYQ 68

                   >E0UVDMS01ASNO8; LENGTH=254; SCORE = 67.0 BITS (162), EXPECT = 3e-12; IDENTITIES = 39/74 (52%),
                   POSITIVES = 48/74 (64%), GAPS = 2/74 (2%); FRAME = -3
SEQ ID NO: 399     QUERY: 338 VFD--SEYDLIGNDGSLLYIRTNKAAPQYKIVTLDIEKPELGFKEFIPEDPKAYLSQVKI 395
                              VFD    +  I N GSL Y+RTN++APQY+++T+DI K     KE IPE   AYLS +
SEQ ID NO: 400     SBJCT: 234 VFD*SMTFTSITNKGSLFYVRTNESAPQYRVITVDIAKRN-EIKELIPE-TDAYLSSITS 61
SEQ ID NO: 401
                   QUERY: 396 FNKDRLALVYKRNV 409
                               NK   ALVYKRNV
SEQ ID NO: 402     SBJCT: 60  VNKGYFALVYKRNV 19

                   >CONTIG11529; LENGTH=243; NUMREADS=2; SCORE = 66.6 BITS (161), EXPECT = 4e-12; IDENTITIES = 36/64 (56%),
                   POSITIVES = 44/64 (68%); FRAME = -1
SEQ ID NO: 403     QUERY: 346 IGNDGSLLYIRTNKAAPQYKIVTLDIEKPELGFKEFIPEDPKAYLSQVKIFNKDRLALVY 405
                              I N GSL Y+RTN++APQY+++T+DI K     KE IPE   AYLS +   NK   ALVY
SEQ ID NO: 404     SBJCT: 284 ITNKGSLFYVRTNESAPQYRVITVDIAKRN-EIKELIPE-TDAYLSSITSVNKGYFALVY 31

SEQ ID NO: 405     QUERY: 406 KRNV 409
                              KRNV
SEQ ID NO: 406     SBJCT: 30  KRNV 19
```

*FIG. 22A-6*

```
                  >E0UVDMS01D8GCX; LENGTH=230; SCORE = 60.8 BITS (146), EXPECT = 2e-10; IDENTITIES = 31/74 (41%),
                  POSITIVES = 43/74 58%), GAPS = 19/74 (25%); FRAME = +2
SEQ ID NO: 407    QUERY: 643 TIGKAWISDYGPDEDPRDFDYIYTHSPLHNIPKNMVLPPTMLLTAD-------------- 688
                             ++G+AWIS+YG+P  P +FDYIY  SP+HN+  + V+ P ML+T +
SEQ ID NO: 408    SBJCT: 11  SLGQAWISEYGNPSIPEEFDYIYPLSPVHNVQTKDVM-PAMLITVNIGEQLTSSNLIMPH 187

SEQ ID NO: 409    QUERY: 689 -----HDDRVVPMH 697
                                   DDRVVPMH
SEQ ID NO: 410    SBJCT: 188 TRPSPGDDRVVPMH 229

                  >CONTIG48857; LENGTH=169; NUMREADS=3; SCORE = 57.4 BITS (137), EXPECT = 3e-09; IDENTITIES = 24/34 (70%),
                  POSITIVES = 31/34 (91%); FRAME = -1
SEQ ID NO: 373    QUERY: 702 AAMLQYTLPHNRHPLLLRVDKKAGHGGGKSTEKR 735
                             AA LQY+LPHN +PLL+R+DKKAGHG GKST+++
SEQ ID NO: 412    SBJCT: 166 AAELQYSLPHNPNPLLIRIDKKAGHGAGKSTQQK 65

                  >E0UVDMS01BH755; LENGTH=262; SCORE = 56.6 BITS (135), EXPECT = 5e-09; IDENTITIES = 31/86 (36%),
                  POSITIVES = 45/86 (53%); FRAME = -2
SEQ ID NO: 413    QUERY: 552 AVPNIRGGGEFGEIWHDAGIREKRANVYDDFIAATQFLVKNKYAAGGKVAINGGSNGGLL 611
                             AV +IRGG E G  W   G ++K+ N + DFIA  + L+   Y   G++   G S GG+L
SEQ ID NO: 414    SBJCT: 261 AVTHIRGGSEXGWGWFLDGRKDKKPNSFTDFIACAEALIAEGYGTAGRIVAEGRSAGGML 82

SEQ ID NO: 415    QUERY: 612 VAACVNRAREGTFGAAIAEVGVLDLL 637
                             + A  N  R   +   I  V  +D+L
SEQ ID NO: 416    SBJCT: 81  MGAVAN-LRPDLWAGVIGGVPFVDVL 7
```

*FIG. 22A-7*

```
                   >CONTIG60897; LENGTH=242; NUMREALS=4; SCORE = 56/6 BITS (135), EXPECT = 5e=09; IDENTITIES = 30/77 (38%),
                   POSITIVES = 42/77 (54%), GAPS = 20/77 (25%); FRAME = +3
SEQ ID NO: 417     QUERY: 107 KFSAPFLNDDKRWYWFYNTGLQAQT--------------------VICRSKDETLPDFSES 147
                              ++ AP+L+DD RWYW+YN+GL+ QT                    + RSKD  LPD S +
SEQ ID NO: 418     SBJCT: 12  QYYAPYLHDDNRWYWYYNSGLEPQTGERFKQPFRPRWLTSVPAKALYRSKDSNLPOLSTA 191

SEQ ID NO: 419     QUERY: 148 D-YVGETFFDPNLLSSD 163
                              D   G+ FFD   LS++
SEQ ID NO: 420     SBJCT: 192 DGSGGDLFFDVGPLSAN 242

                   >E0UVDMS02FGJBD LENGTH-253; SCORE = 52.4 BITS (124)M EXPECT = 9e-08; IDENTITIES = 19/38 (50%),
                   POSITIVES = 31/38 (81%); FRAME = +2
SEQ ID NO: 421     QUERY: 275 SDDILVHEDQEHPDWVFGAEVTEDGKYVALYTMKDTSR 312
                              ++D L+++D+EH DW+F  +VT+DG Y+ LY +KD+SR
SEQ ID NO: 422     SBJCT: 77  AEDSLIYQDREHRDWMFSIDVTDDGNYLLLYILKDSSR 190

                   >E0UVDMS02GQMEJ LENGTH=280; SCORE = 50.8 BITS (120), EXPECY = 3e-07; IDENTITIES = 24/30 (80%),
                   POSITIVES = 27/30 (90%); FRAME = -3
SEQ ID NO: 423     QUERY: 609 GLLVAACVNRAREGTFGAAIAEVGVLDLLK 638
                              GLLV+ACVNRA EGTFG A+A+VGV DLLK
SEQ ID NO: 424     SBJCT: 269 GLLVSACVNRAPEGTFGCAVADVGVHDLLK 180

                   >CONTIG43041; LENGTH=170; NUMREADS=2; SCORE = 47.0 BITS (110), EXPECT(2) = 1e-06;IDENTITIES = 15/27 (55%),
SEQ ID NO: 425     POSITIVES = 25/27 (92%); FRAME = -1
SEQ ID NO: 427     QUERY: 276 DDILVHEDQEHPDWVFGAEVTEDGKYV 302
                              +DI+V++D EHP+W++GA+ +EDGKY+
SEQ ID NO: 428     SBJCT: 83  EDIIVYQDNEHPEWIYGADTSEDGKYL 3

SEQ ID NO: 429     SCORE = 21.2 BITS (43), EXPECT(2) = 1e-06; IDENTITIES = 6/13 (46%), POSITIVES = 11/13 (84%); FRAME = -2
                   QUERY: 264 NIYYHRIGTSQSD 276
                              M+ YH++GT+Q +
SEQ ID NO: 430     SBJCT: 169 MMCYHKVGTTQGE 131

                   >E0UVDMS02JYIZX; LENGTH=130; SCORE = 46.2 BITS (108), EXPECT = 6e06; IDENTITIES = 18/30 (60%),
SEQ ID NO: 431     POSITIVES = 23/30 (76%); FRAME = +2
                   QUERY: 25 MSSTQWIPNMYPSARRSDHIDTYRSETRGE 54
                             MSS  W P  YPS RRSDH+D+Y+S ++GE
SEQ ID NO: 432     SBJCT: 41 MSSIAWAPGNYPSTRRSDHVDSYQSASKGE 130
```

*FIG. 22A-8*

```
                     >contig08963; length=360; numreads=6; Score = 46.2 bits (108), Expect = 6e-06; Identities = 31/97(31%),
                     Positives = 51/97(52%), Gaps = 11/97(11%); Frame = -3
SEQ ID NO: 433       Query: 452 FNTPGIVCRYN-IQRPEEQR---------WSVYRTAKVKGL-NPNDFEARQVWYDSYDGTK 501
                                F++  I  RY  + RP + R           V +   V G+ N +D+ ++++W  S DGT+
SEQ ID NO: 434       Sbjct: 295 FSSDHIRLRYEALNRPAQIRRLALADGAQQVLKETPVLGVFNADDYVSQRLKATSVDGTQ 116

SEQ ID NO: 435       Query: 502 IPM-FIVAHKNTQFNGTAPAIQYGYGGFNISINPFFS 537
                                -P+  +VRH   Q      P   YGYG +  S++P+FS
SEQ ID NO: 436       Sbjct: 115 VPISLVVRH--DQLGQPTPLYLYGYGAYGHSLDPWFS 11

                     >contig23635; length=193; numreads=3; Score = 45.1 bits (105), Expect = 1e-05; Identities = 21/23 (91%),
                     Positives = 21/23 (91%); Frame = -1
SEQ ID NO: 437       Query: 587 QFLVKNKYAAGGKVAINGGSNGG 609
                                QFLVKNKYAA GKVAING SNGG
SEQ ID NO: 438       Sbjct: 145 QFLVKNKYAAPGKVAINGASNGG 77

                     >contig34645; length=176; numreads=2;  Score = 43.2 bits (100), Expect(2) = 2e-05;  Identities = 20/38 (52%),
                     Positives = 25/38 (65%), Gaps = 5/38 (13%); Frame = -3
SEQ ID NO: 439       Query: 108 FSAPFLNDDKRWYWFYNTGLQAQT-----VICRSKDET 140
                                FSAP L DD  WYWFYN GLQ+Q+      ++ R K +T
SEQ ID NO: 440       Sbjct: 162 FSAPILLDDGHWYWFYNRGLQSQSGRYLFILRRCKTQT 49

                     Score = 20.8 bits (42), Expect(2) = 2e-05; Identities = 8/13 (61%), Positives = 10/13 (76%); Frame = -2
SEQ ID NO: 441       Query: 132 VICRSKDETLPDF 144
                                V+ RSK+  LPDF
SEQ ID NO: 442       Sbjct: 40  VLYRSKEPALPDF 2

                     >contig02145; length=325; numreads=4; Score = 37.4 bits (85), Expect = 0.003; Identities = 22/63 (34%),
                     Positives = 34/63 (53%); Frame = -2
SEQ ID NO: 443       Query: 689 HDDRVVPMHSFKYAAMLQYTLPHNRHPLLLRVDKKAGHGGGKSTEKRLQEAADKWGFAAQ 748
                                +D RV    + K+ A L+ T   + HPLLL+ +  AGHGG      + L++ A ++ F  Q
SEQ ID NO: 444       Sbjct: 321 NDSRVQYWEAAKWVAKLRDTKTDD-HPLLLKTELGAGHGGMSGRYQGLRDVALEYAFCFQ 145

SEQ ID NO: 445       Query: 749 SMG 751
                                  G
SEQ ID NO: 446       Sbjct: 144 GTG 136

                     >E0UVDMSQ2I6FQQ; length=220; Score = 36.2 bits (82), Expect = 0.006; Identities = 12/34 (35%),
                     Positives = 25/34 (73%); Frame = -3
SEQ ID NO: 447       Query: 312 RKNLLWIADLGQNEVGRNMKNNKICNVFDSEYDL 345
                                +KNLLW+A+L ++ V   ++W K+ N + ++Y++
SEQ ID NO: 448       Sbjct: 161 QKNLLWVAELNEDGVKSGIQWRKVVNEYVADYNV 60
```

FIG. 22A-9

| GALERINA POPA SEQUENCES | LENGTH IN NUCLEIC ACIDS | NUMBER OF READS | RELATEDNESS RATING | SEQ ID NO:XX |
|---|---|---|---|---|
| E0UVDMS01CLJX8 | LENGTH=243 | NA | 118 5e-30 | SEQ ID NO:338 |
| E0UVDMS01DRXPF | LENGTH=241 | NA | 123 3e-29 | SEQ ID NO:280 |
| E0UVDMS01EUNXT | LENGTH=249 | NA | 92 3e-21 | SEQ ID NO:339 |
| E0UVDMS01AG5VR | LENGTH=221 | NA | 88 1e-18 | SEQ ID NO:282 |
| E0UVDMS01ANFQ8 | LENGTH=264 | NA | 67 3e-16 | SEQ ID NO:332 |
| CONTIG10675 | LENGTH=241 | NUMREADS=1 | 67 3e-16 | SEQ ID NO:332 |
| E0UVDMS02GNCLJ | LENGTH=254 | NA | 80 5e-16 | SEQ ID NO: 253 |
| CONTIG01013 | LENGTH=310 | NUMREADS=5 | 77 3e-15 | SEQ ID NO: 343 |
| E0UVDMS01ASN08 | LENGTH=254 | NA | 74 3e-14 | SEQ ID NO:286 |
| CONTIG11529 | LENGTH=243 | NUMREADS=2 | 74 3e-14 | SEQ ID NO: 286 |
| E0UVDMS01D8GCX | LENGTH=230 | NA | 70 4e-13 | SEQ ID NO:288 |
| E0UVDMS02HHTQY | LENGTH=224 | NA | 67 3e-12 | SEQ ID NO:289 |
| E0UVDMS02FZASH | LENGTH=239 | NA | 45 9e-11 | SEQ ID NO: 337 |
| CONTIG34645 | LENGTH=176 | NUMREADS=2 | 53 3e-10 | SEQ ID NO: 345 |
| E0UVDMS01BQJH3 | LENGTH=263 | NA | 45 4e-09 | SEQ ID NO: 346 |
| E0UVDMS01BH7S5 | LENGTH=262 | NA | 57 4e-09 | SEQ ID NO:293 |
| CONTIG43041 | LENGTH=170 | NUMREADS=2 | 48 1e-08 | SEQ ID NO: 336 |
| E0UVDMS02I6F0Q | LENGTH=220 | NA | 52 8e-08 | SEQ ID NO: 276 |
| E0UVDMS01ELV4E | LENGTH=254 | NA | 50 3e-07 | SEQ ID NO:296 |
| CONTIG08963 | LENGTH=360 | NUMREADS=6 | 50 3e-07 | SEQ ID NO:297 |
| E0UVDMS02JYIZX | LENGTH=130 | NA | 48 2e-06 | SEQ ID NO: 271 |
| CONTIG60897 | LENGTH=242 | NUMREADS=4 | 48 2e-06 | SEQ ID NO: 267 |
| CONTIG23635 | LENGTH=193 | NUMREADS=3 | 48 2e-06 | SEQ ID NO: 273 |
| CONTIG48857 | LENGTH=169 | NUMREADS=3 | 45 2e-05 | SEQ ID NO: 290 |
| E0UVDMS02FGJBD | LENGTH=253 | NA | 43 5e-05 | SEQ ID NO:302 |

FIG. 22B-1

```
                    >EOUVDMS01CLJX8; LENGTH=243; SCORE=118 BITS (295), EXPECT(2)=5e-30; IDENTITIES = 55/70 (78%),
                    POSITIVES = 61/70 (87%) ; FRAME = -1
SEQ ID NO: 588      QUERY: 403 GVASITNREKQPHSFLTFSGFNTPGTISRYDFTAPDTQRLSILRTTKLNGLNADDFESTQ 462
                               G ASI NR+KQ H FLT SGFNTPGTI+RYDFTAP+TQR SILRTTK+N L+ DDFESTQ
SEQ ID NO: 364      SBJCT: 243 GAASIANRQKQTHFFLTLSGFNTPGTIARYDFTAPETQRFSILRTTKVNELDPDDFESTQ 64

SEQ ID NO: 589      QUERY: 463 VWYKSKDGTK 472
                               VWY+SKDG K
SEQ ID NO: 366      SBJCT: 63      VWYESKDGNK 34

                    SCORE=28.9 BITS 63), EXPECT(2)=5e-30; IDENTITIES=12/15(80%); POSITIVES=13/15(86%); FRAME=-2

SEQ ID NO: 590      QUERY: 468 KDGTKVPMFIVRHKS 482
                               K  TK+PMFIVRHKS
SEQ ID NO: 338      SBJCT: 47  KMATKIPMFIVRHKS 3

                    >EOUVDMS01DRXPF; LENGTH=241; SCORE = 123 BITS (309), EXPECT = 3e-29; IDENTITIES = 55/75 (73%),
                    POSITIVES = 65/75 (86%); FRAME = -1
SEQ ID NO: 352      QUERY: 6   WAPHSYPPTRRSDHVDVYQSASRGEVPVPDPYQWLEENSNEVDEWTTAQTAFTQGYLDKN 65
                               WAP +YP TRRSDHVD YQSAS+GEVPVPDPYQWLEE+++EVD+WTTAQ    Q YLD+N
SEQ ID NO: 353      SBJCT: 226 WAPGNYPSTRRSDHVDSYQSASKGEVPVPDPYQWLEESTDEVDKWITAQADLAQAYLDQN 47

SEQ ID NO: 591      QUERY: 66  ADRQKLEEKFRASKD 80
                               AD QKL +KFRAS++
SEQ ID NO: 592      SBJCT: 46  ADIQKLADKFRASRN 2

                    >EOUVDMS01EUNXT; LENGTH=249; SCORE = 92.0 BITS (227), EXPECT(2) = 3e-21; identities = 39/47 (82%),
                    POSITIVES = 43/47 (91%); FRAME = -2
SEQ ID NO: 449      QUERY: 660 GDDRVVPMHSLKFVANLQYNVPQNPHPLLIRVDKSWLGHGFGKTTDK 706
                               GDDRVVPMHS KF+A LQ+NVPQNPHPLLI++DKSWLGHG GK TDK
SEQ ID NO: 450      SBJCT: 233 GDDRVVPMHSFKFIATLQHNVPQNPHPLLIKIDKSWLGHGMGKPTDK 93

                    SCORE=25.4 BITS(54), EXPECT(2)=3e-21; IDENTITIES=9/11(81%), POSITIVES=10/11(90%); FRAME = -1
SEQ ID NO: 451      QUERY: 709 KDAADKWSFVA 719
                               KDAADKW F+A
SEQ ID NO: 452      SBJCT: 33  KDAADKWGPIA 1
```

*FIG. 22B-2*

```
                 >EOUVDMS01AG5VR; LENGTH=221; SCORE = 88.2 BITS (217), EXPECT = 1e-18; IDENTITIES = 40/70 (57%),
                 POSITIVES = 52/70 (74%); FRAME = +3
SEQ ID NO: 593   QUERY: 20 VDVYQSASRGEVPVPDPYQWLEENSNEVDEWTTAQTAFTQGYLDKNADRQKLEEKFRASK 79
                           VD+Y+SA RG+V V DPYQWLEE ++E D+WTTAQ  FT+ YLDKN D  +LE+ F+A
SEQ ID NO: 360   SBJCT: 3  VDIYKSALRGDVHVQDPYQWLEEYTDETDKWTTAQEVFTRTYLDKNPDLPRLEKAFQACN 182

SEQ ID NO: 594   QUERY; 80 DYVKFSAPTL 89
                           DY K  + T+
SEQ ID NO: 595   SBJCT: 183DYPKVLSATI 212

                 >EOUVDMSOIANFQ8; LENGTH=264; SCORE = 67.0 BITS (162), EXPECT(2)=3e-16; IDENTITIES = 29/34 (85%),
                 POSITIVES = 31/34 (91%); FRAME=+3
SEQ ID NO: 453   QUERY: 462 QVWYKSKDGTKVPMFIVRHKSTKFDGTAPAIQNG 495
                            QVWY+SKDGT +PMFIVRHKSTKFDGTAP IQ G
SEQ ID NO: 378   SBJCT: 108 QVWYESKDGTSIPMFIVRHKSTKFDGTAPVIQYG 209

                 SCORE=33.5 BITS(75), EXPECT(2)=3e-16; IDENTITIES=14/20(70%), POSITIVES=18/20(90%); FRAME=+2
SEQ ID NO: 455   QUERY: 444 ILRTTKLNGLNADDFESTQV 463
                            I RTTKLNGLN +DF+++QV
SEQ ID NO: 380   SBJCT: 2   IYRTTKLNGLNTEDFKASQV 61

                 >CONTIG10675; LENGTH=241; NUMREADS=1; SCORE = 67.0 BITS (162), EXPECT(2) = 3e-16; IDENTITIES 29/34 (85%),
                 POSITIVES = 31/34 (91%); FRAME = +3
SEQ ID NO: 453   QUERY: 462 QVWYKSKDGTKVPMFIVRHKSTKFDGTAPAIQNG 495
                            QVWY+SKDGT +PMFIVRHKSTKFDGTAP IQ G
SEQ ID NO: 378   SBJCT: 108 QVWYESKDGTSIPMFIVRHKSTKFDGTAPVIQYG 209

                 SCORE=33.5 BITS(75), EXPECT(2)=3e-16;IDENTITIES=14/20(70%), POSITIVES=18/20(90%); FRAME=+2
SEQ ID NO: 455   QUERY: 444 ILRTTKLNGLNADDFESTQV 463
                            I RTTKLNGLN +DF+++QV
SEQ ID NO: 380   SBJCT: 2   IYRTTKLNGLNTEDFKASQV 61

                 >EOUVDMS02GNCLG; LENGTH=254; SCORE=79.7 BITS(195), EXPECT=5e-16; IDENTITIES=39/53(73%),
                 POSITIVES = 42/53 (79%); FRAME = -2
SEQ ID NO: 461   QUERY: 165 GVDYPTIYVRPTSSSLSQAPEAEGGDGRLSDGVKWCKFTTITWTKDSKGFLYQ 217
                            G DY TIYVR TSS LSQ+ A+G DGRLSD VKW KF+TI WTKD KGFLYQ
SEQ ID NO: 398   SBJCT: 226 GGDYSTIYVRSTSSPLSQSSVAQGVDGRLSDEVKWPKFSTIIWTKDPKGFLYQ 68
```

FIG. 22B-3

```
                    >CONTIG01013; LENGTH=310; NUMREADS=5; SCORE = 77.0 BITS (188), EXPECT(2) = 3e-15; IDENTITIES 33/50 (66%),
                    POSITIVES = 40/50 (80%); FRAME = +2
SEQ ID NO: 462      QUERY: 497 GGFAITADPFFSPIMLTFMQTYGAILAVPNIRGGGEFGGEWHKAGRRETK 546
SEQ ID NO: 368                 GGF+I+ DPFFS +LTF+Q YG + A+PNIRGGGEFG +WH AG RE K
                    SBJCT: 2   GGFSISIDPFFSATILTFLQKYGVVFALPNIRGGGEFGEDWHLAGCREKK 151
                    SCORE=20.4 BITS(41), EXPECT(2)=3e-15; IDENTITIES=8/9(88%), POSITIVES=8/9(88%); FRAME=+3
SEQ ID NO: 465      QUERY: 548 NTFDDFIAA 556
                               N FDDFIAA
SEQ ID NO: 466      SBJCT: 210 NCFDDFIAA 236

                    >E0UVDMS01ANFQ8; LENGTH=254; SOCRE = 73.9 BITS (180), EXPECT = 3e-14; IDENTITITES= 36/65 (55%),
                    POSITIVES = 49/65 (75%); FRAME = -3
SEQ ID NO: 467      QUERY: 317 ITNHGSLIYVKINVNADPQKVVTIDLSTGEPEIRDSIPEQKDAKLTQVKCVNKGYFVAIY 376
                               ITN GSL YV+TN +APQY+V+T+D++    EI++ IPE  DA L+ +  VNKGYF  +Y
SEQ ID NO: 404      SBJCT: 204 ITNKGSLFYVRTNESAPQYRVITVDIAK-RNEIKELIPE-TDAYLSSITSVNKGYFALVY 31

SEQ ID NO: 469      QUERY: 377 KRNVR 381
                               KRNV+
SEQ ID NO: 470      SBJCT: 30  KRNVR 16

                    >CONTIG11529; LENGTH=243; NUMREADS=2; SCORE = 73.9 BITS (180), EXPECT = 3e-14; IDENTITIES = 36/65 (55%),
                    POSITIVES = 49/65 (75%); FRAME = -1
SEQ ID NO: 467      QUERY: 317 ITNHGSLIYVKTNVNAPQYKVVTIDLSTGEPEIRDFIPEQKDAKLTQVKCVNKGYFVAIY 376
                               ITN GSL YV+TN +APQY+V+T+D++    EI++ IPE  DA L+ +  VNKGYF  +Y
SEQ ID NO: 404      SBJCT: 204 ITNKGSLFYVRTNESAPQYRVITVDIAK-RNEIKELIPE-TDAYLSSITSVNKGYFALVY 31

SEQ ID NO: 469      QUERY: 377 KRNVK 381
                               KRNV+
SEQ ID NO: 470      SBJCT: 30  KRNVR 16

                    >E0UVDMS01D8GCX; LENGTH=230; SOCRE = 70.1 BITS (170), EXPECT = 4e-13; IDENTITIES = 35/71 (49%0,
                    POSITIVES = 41/71 (57%), GAPS = 18/71 (25%);
                     FRAME = +2
SEQ ID NO: 475      QUERY: 616 GMAWTSEYGNPFIKEDFDFVQALSPVHNVPKDRVLPATLLMTN------------------ 658
                               G AW SEYGNP I E+FD++  LSPVRNV  D+V+PA L+  N
SEQ ID NO: 476      SBJCT: 17  GQAWISEYGNPSIPEEFDYIYPLSPVHNVQTDKVMPAMLITVNIGEQLTSSNLIMPHTRP 196
```

FIG. 22B-4

```
SEQ ID NO: 477  QUERY: 659 -AGDDRVVPMH 668
                           GDDRVVPMH
SEQ ID NO: 478  SBJCT: 197 SPGDDRVVPMH 229

                >E0UVDMS02HBTQY; LENGTH=224; SCORE = 67.0 BITS (162), EXPECT = 3e-12; IDENTITIES = 31/49 (63%),
                POSITIVES = 37/49 (75%); FRAME = -2
SEQ ID NO: 479  QUERY: 658 NAGDDRVVPMHSLKFVANLQYNVPQNPHPLLIRVDKSWLGHGFGKTTDK 706
                           N  DDRVVPMHS K  A LQY++P NP+PLLIR+DK   GHG GK+T +
SEQ ID NO: 480  SBJCT: 211 NLDDDRVVPMHSFKLAAELQYSLPHNPNPLLIRIDKK-AGHGAGKSTQQ 68

                >E0UVDMS02F2ASH; LENGTH=239; SCORE = 44.7 BITS(104), EXPECT(2) = 9e-11; IDENTITIES = 20/33(60%),
                POSITIVES = 26/33(78%); FRAME = -1
SEQ ID NO: 481  QUERY: 674 ANLQYNVPQNPHPLLIRVDKSWLGHGFGKTIDK 706
                           A LQY++P NP+PLLIR+DK   GHG GK+T +
SEQ ID NO: 482  SBJCT: 233 AELQYSLPHNPNPLLIRIDKK-TGHGAGKSIQQ 138

                SCORE=37.4 BITS(85) ; EXPECT(2)=9e-11; IDENTITIES=15/19(78%); POSITIVES=17/19(89%); FRAME=-3
SEQ ID NO: 483  QUERY: 709 KDAADKWSFVAQSLGLEWK 727
                           K++ADKW FVAQSLGL WK
SEQ ID NO: 484  SBJCT: 72  KESADKWGFVAQSLGLVWK 16

                >CONTIG34645; LENGTH=176; NUMREADS=2; SCORE = 52.8 BITS (125), EXPECT(2) = 3e-10; IDENTITIES = 21/27 (77%),
                POSITIVES = 23/72 (85%); FRAME = -3
SEQ ID NO: 485  QUERY: 84  FSAPTLLDSGHWYWFYNSGVQSQAVLY 110
                           FSAPTLLD GHWYWFYN G+QSQ+  Y
SEQ ID NO: 486  SBJCT: 162 FSAPTLLDDGHWYWFYNRGLQSQSGRY 82

                SCORE=27.7 BITS(60), EXPECT(2)=3e-10; IDENTITIES=11/13(84%), POSITIVES=12/13(92%); FRAME=-2
SEQ ID NO: 487  QUERY: 108 VLYRSKKPVLPDF 120
                           VLYRSK+P LPDF
SEQ ID NO: 442  SBJCT: 40  VLYRSKEPALPDF 2

                >E0UVDMS01BQJH3; LENGTH=263; SCORE = 45.1 BITS (105), EXPECT(2) = 4e-09; IDENTITIES = 26/46 (56%),
                POSITIVES = 27/46 (58%), GAPS = 18/46 (39%); FRAME = +3
SEQ ID NO: 489  QUERY: 589 RAPEGTFGAAVSEGGVADLLK------------------FNKFIGG 616
                           RAPEGTFGAAV EGGVADLLK                  F+KFTGG
SEQ ID NO: 490  SBJCT: 3   RAPEGTFGAAVFEGGVADLLKVVFVFQLCNSQSLILTLQFHKFTGG 140
```

FIG. 22B-5

```
SCORE=31.6 BITS(70), EXPECT(2)=4e-091; IDENTITIES=12/19(63%), POSITIVES=14/19(73%); FRAME=+2
SEQ ID NO: 491   QUERY: 614 TGGMAWTSEYGNPFIKEDF 632
                            + G AW SEYGNP I E+F
SEQ ID NO: 492   SBJCT: 185 SSGQAWISEYGNPSIPEEF 241

>EOUVDMS01BH755; LENGTH=262; SCORE = 56.6 BITS (135), EXPECT = 4e-09; IDENTITIES = 27/61 (44%),
POSITIVES = 36/61 (59%); FRAME = -2
SEQ ID NO: 493   QUERY: 523 AVPNIRGGGEFGGEWHKAGRRETKGNTFDDFIAAAQFLVKNKYAAPGKVAITGASNGGFL 582
                            AV +IRGG E G  W   GR++ K N+F DFIA A+ L+   Y    G++    G S GG L
SEQ ID NO: 414   SBJCT: 261 AVTHIRGGSEKGWGWFLDGRKDKKPNSFTDFIACAEALIAEGYGTAGRIVAEGRSAGGML 82

SEQ ID NO: 495   QUERY: 583 V 583
                            +
SEQ ID NO: 496   SBJCT: 81  M 79

>CONTIG43041; LENGTH=170; NUMREADS=2; SCORE=47.8 BITS(112), EXPECT(2)=1e-08; IDENTITIES=19/27(70%),
POSITIVES=22/27(81%); FRAME=-1
SEQ ID NO: 497   QUERY: 247 EDIIVQQDKENPDWTYGTDASEDGKYI 273
                            EDIIV QD E+P+W YG D SEDGKY+
SEQ ID NO: 428   SBJCT: 83  EDIIVYQDNEHPEWIYGADTSEDGKYL 3

SCORE=26.9 BITS(58), EXPECT(2)=1e-08; IDENTITIES=10/13(76%), POSITIVES=12/13(92%); FRAME=-2
SEQ ID NO: 499   QUERY: 235 MVCYHRVGTTQLE 247
                            M+CYH+VGTTQ E
SEQ ID NO: 430   SBJCT: 169 MMCYHKVGTTQGE 131

>EOUVDMS02I6F0Q; LENGTH=220; SCORE=52.4 BITS(124),  EXPECT=8e-08; IDENTITIES=22/34(64%),
POSITIVES=29/34(85%); FRAME=-3
SEQ ID NO: 501   QUERY: 283 KQNLLWVAEFDKDGVKPEIPWRKVINEFGADYHV 316
                            ++NLLWVAE ++DGVK  I WRKV+NE+ ADY+V
SEQ ID NO: 448   SBJCT: 161 QKNLLWVAELNEDGVKSGIQWRKVVNEYVADYNV 60

>EOUVDMS01ELV4E; LENGTH=254;  SCORE = 50.4 BITS (119), EXPECT = 3e-07;  IDENTITIES = 23/54 (42%),
POSITIVES = 34/54 (62%); FRAME = -2
SEQ ID NO: 503   QUERY: 167 DYFTIYVRPTSSSLSQAPEAEGGDGRLSDGVKWCKFTTITWTKDSKGFLYQRYP 220
                            D+ TIYV  T S L+    +++     GRL + +K+ KF++I WT DSKGF  +  P
SEQ ID NO: 504   SBJCT: 250 DFVTIYVWSTDSPLTNDVDSKNDKGRLPEEIKFVKFSSIGWTPDSKGFFIRSIP 89
```

FIG. 22B-6

```
                  >CONTIG08963; LENGTH=360; NUMREADS=6; SCORE = 50.4 BITS (119), EXPECT = 3e-07; IDENTITIES = 32/95 (33%),
                  POSITIVES = 45/95 (47%), GAPS = 1/95 (1%); FRAME = -3
SEQ ID NO: 505    QUERY: 415 HSFLTFSGFNTPGTISRYDFTAPDTQRLSILRTTKLNGLNADDFESTQVWYKSKDGTKVP 474
SEQ ID NO: 506               H  L +   N P  I R      D  +  +  T  L    NADD+ S ++W  S DGT+VP
                  SBJCT: 283 HIRLRYEALNRPAQIRR--LALADGAQQVLKETPVLGVFNADDYVSQRLWATSVDGTQVP 110

SEQ ID NO: 508    QUERY: 475 M-FIVRHKSTKFDGTAPAIQNGYGGFAITADPFFS 508
                             +  +VRH    +      P     GYG +  + DP+FS
SEQ ID NO: 507    SBJCT: 109 ISLVVRH--DQLGQPTPLYLYGYGAYGHSLDPWFS 11

                  >EOUVDMS01JYIZX; LENGTH=130; SCORE = 48.1 BITS (113), EXPCET = 2e-06; IDENTITIES = 21/30 (70%),
                  POSITIVES = 23/30 (76%); FRAME = +2
SEQ ID NO: 509    QUERY: 1  MPPTPWAPHSYPPTRRSDHVDVYQSASRGE 30
                            M    WAP +YP TRRSDHVD YQSAS+GE
SEQ ID NO: 432    SBJCT: 41 MSSIAWAPGNYPSTRRSDHVDSYQSASKGE 130

                  >CONTIG60897; LENGTH=242; NUMREADS=4; SCORE = 48.1 BITS (113), EXPECT = 2e-06; IDENTITIES = 25/77 (33%),
                  POSITIVES = 35/77 (45%), GAPS = 19/77 (24%); FRAME = +3
SEQ ID NO: 511    QUERY: 83  KFSAPTLLDSGHWYWFYNSGVQSQA-------------------VLYRSKKPVLPDPQRG 123
                             ++ AP L D   WYW+YNSG++ Q                      LYRSK    LPD
SEQ ID NO: 418    SBJCT: 12  QYYAPYLHDDNRWYWYYNSGLEPQTGERFKQPFRPRWLTSVPAKALYRSKDSNLPDLSTA 191

SEQ ID NO: 513    QUERY: 124 TRKVGEVYFDPNVLSAD 140
                                  G+++FD   LSA+
SEQ ID NO: 420    SBJCT: 192 DGSGGDLFFDVGPLSAN 242

                  >CONTIG23635; LENGTH=193; NUMREADS=3; SCORE = 47.8 BITS (112), EXPECT = 2e-06; IDENTITIES = 22/23 (95%),
                  POSITIVES = 22/23 (95%); FRAME = -1
SEQ ID NO: 515    QUERY: 558 QFLVKNKYAAPGKVAITGASNGG 580
                             QFLVKNKYAAPGKVAI GASNGG
SEQ ID NO: 438    SBJCT: 145 QFLVKNKYAAPKGVAINGASNGG 77
```

FIG. 22B-7

```
                    >CONTIG23635; LENGTH=193; NUMREADS=3; SCORE = 47.8 BITS (112), EXPECT = 2e-06; IDENTITIES = 22/23 (95%),
                    POSITIVES = 22/23 (95%); FRAME = -1
SEQ ID NO: 515      QUERY: 558 QFLVKNKYAAPGKVAITGASNGG 580
                               QFLVKNKYAAPGKVAI GASNGG
SEQ ID NO: 438      SBJCT: 145 QFLVKNKYAAPKGVAINGASNGG 77

                    >CONTIG48857; LENGTH=169  NUMREADS=3; SCORE = 44.7 BITS (104), EXPECT = 2e-05; IDENTITIES = 20/33
                    (60%),
                    POSITIVES = 26/33 (78%); FRAME = -1
SEQ ID NO: 481      QUERY: 674 ANLQYNVPQNPHPLLIRVDKSWLGHGFGKTTDK 706
                               A LQY++P NP+PLLIR+DK   GHG GK+T +
SEQ ID NO: 482      SBJCT: 163 AELQYSLPHNPNPLLIRIDKK-AGHGAGKSTQQ 68

                    >E0UVDMS02FGJBD; LENGTH=253; SCORE = 43.1 BITS (100, EXPECT = 5e-05; IDENTITIES = 15/37 (40%),
                    POSITIVES = 26/37 (70%); FRAME = +2
SEQ ID NO: 519      QUERY: 247 EDIIVQQDKENPDWTYGTDASEDGKYIYLVVYKDASK 283
                               ED ++ QD+E+ DW +  D ++DG Y+ L + KD+S+
SEQ ID NO: 520      SBJCT: 80  EDSLIYQDREHRDWMFSIDVTDDGNYLLLYILKDSSR 190

                    >E0UVDMS01C7LJ6; LENGTH=267; SCORE = 42.4 BITS (98), EXPECT =9e-05; IDENTITIES = 18/43 (41%),
                    POSITIVES = 29/43 (67%); FRAME = -2
SEQ ID NO: 391      QUERY: 178 SSLSQAPEAEGGDGRLSDGVKWCKFTTITWTKDSKGFLYQRYP 220
                               S L++  +A+   GRL + +K+ KF++I WT DSKGF  + +P
SEQ ID NO: 392      SBJCT: 245 SPLTKDVDAKNDKGRLPEEIKFVKFSSIGWTPDSKGFFIRSFP 117

                    >E0UVDMS02GQMEJ; LENGTH=280; SCORE = 40.0 BITS (92), EXPECT = 4e-04; IDENTITIES = 20/30 (66%),
                    POSITIVES = 22/30 (73%); FRAME = -3
SEQ ID NO: 425      QUERY: 580 GFLVCGSVVRAPEGTFGAAVSEGGVADLLK 609
                               G LV   V RAPEGTFG AV++ GV DLLK
SEQ ID NO: 424      SBJCT: 269 GLLVSACVNRAPEGTFGCAVADVGVHDLLK 180
```

FIG. 22B-8

A 13,254 bp lambda clone [red/underlined sequences (portions) are two copies of PHA1 encoding phallacidin] 5' - 3' orientation

SEQ ID NO: 327

GATCCGAGAGAAGTCAGACAAGTTTCACTATTTTCAGCACATCGCAGCCGAAGGCCGGCCGATGTCCATGATGGCAGGGTAGCATAACCAGAAATGGA
TAGAATCGATAATCGATGATGGAAAGTGGAGACGGTGACAGGGGGGACCTAGTAAATCCAAAAGATACAGTAATGGAGATAATGTGTCTCTCACCGA
AAAAAAGGGACGAATCGGAACCATCAGTGCAACCTACGAAACTCAGCATCATCTTCAATCGGAGATTTAACCGATCCACCTACAAGTTTGAAACCTT
TGCCCGTTACCAAGTTAATAACAATGGTCGACTTGCACACCATCTCGTATTCAGCTCTCGTCACTTTCAGGCTTATATTCCAATTCCTCAAGCTATC
TGCAGCTGCATTGACTATCTATGGACTTTACAGAGTCACTCGTGTAATTTATGTTGAGCTGACTTCTCCAATACCCCATCTCCCGGTCCAGCAAAC
GCCAATATATTTCTTGGTAATCTCAAACAGCTCTGGACAGATGTAAGTACAAAATCACCCACCTACCCACCCATTGTTAACCACTATTACCACAGAC
ATATCATTGGCATTCACAATATGGGCCGATGATAAGACTAAATGGATTTCTGGGTGTAACAACCAATCCATTTATTCTGATATAGATAACAATCAAC
TTTAGCTTTCGCATTTATATGTGACGGATCCGCAGGGCTTGAACCACATTTTCAGCAATGGTTACGTTTACAGCAAACCATCGTTTACTCGGCCGCA
GATCGGCAAGTTGTGGGTCCAGGTGCTTTTTCACCTACCATACTTAAGAGGCGATGATCCAACCATACGTCAGGTCTCCCTTTTGTCGAAGGGGAT
CAACATAAAAAGCAGGTGCGTACTTCCGTTGCCTCAACCTAGTTCGTATTATGATATATTACGTTTAACAGCGGAAGATTTTGCTGACTATCTATCC
ATTCCAAATCCTGGTCCATCAGTGTCTCAATCACAACCAGAATCCTGCCTTTGGTCGGGTCCGCATTCGGGAATTCACAGATTGCTTCGTAAAAAA
TCAAAACGGGTCGGTTTTTACTACTCATCCATGCTACCAGTGATGAACTTCGCCTAGCTCCAAGACTCTTGGCCTACTCAATGCTCGAAACAAGTG
GTACTTCCCGCTTAGACATTATGGTAGGCCTTGGTAAGGTGGTGATGGACATCATCAGCTCAACAGGTATGTCTGATGTTCCCAGCATACTTATTAG
TGTTTACCGATGCCATTCGATGGAAAGGCTTCCGTTACGAGCTTGATTCCCTGGATCGTGAAAGTGACTTTAGCCGTGTGGCTACAATTTATCTCA
ATTGAACCTGATTCGTTGCCAACTCCGAAGATTCATCCCACTTCTATGGTTCATAGTATGGAAATTCCAAATCACTGTAACGGAGTTCTCATCGCCT
TGTCTAGCCTGATCCTGTAGAGACACAACTAGACGATATCAAGCAGACCCTTTCTCGGATTACGAGTCGGCTTCTGAACGAGAGCAAGGGATCCGTA
CGTACGAATAATGACAATTCCGGCAGTCGAGATCTCCTATCGCTTTTGGTTCGCACCAATATGTCCCCCGATGTGCCAGAGCACCGTCGTCTATCCG
ATGACGAAGTCAAAGCGGGTGAGGCTGATGTATTTGTCACTGCGAGTATACCTGATCTTTTTTATTTAGAGCTTATCTCATTTCTAATTGCTGGACGT
GAAAGTCCGATGTAAGTCTGAGTCTGTTTATCTGTTTAAGGACTATTCTCGAATATTTGATTGCTAGTAACCTAATGGCGTGGGCTTTTATTTTCTCT
GGCAAAAAACCGTGAAATCCAGGCTAAGCTGCGTAGACAGCTCGTCACCGTCGATACCTGTCAGCCAACGACCGACCAGCTCAATGCACTTTCATAT
TTGGATATGGTAATTAGCGAGACGCTACGTCTGTATCCTTCATCTAGCCCACTCGAGGTGTGTGCCAAGGACGACATTTTACCTTTGGCTAAGCCG
ATCACCGACCGGAGAGGAAACCTATTCTCCAGTATTAGGTGAGGATTCGGTCGTTCCCATATTTCTTTTTAGCGTTCACCGGTCTTATAGTATCAAA
AGAGGGCAAGTAGTCATAATTCCCATTTCTGCCATCCACAAGGACAAGTCGATATGGGTGAAGATGCTTTAGACTTCAGGTAAACATTGCACGTCG
CTGTTGGCTCGTGAGTCATTCAGTTTTGATAGACCAGAACGATGGGAATGTCTACCTGAAGGCGTCAATACCATCCCAGGCGTCTGGAGCCATTTGC
TCAGTTTTTGGCCTGGTCCACGTTCGTGTATCGGATTCAGATTTGCTATCGCCGAGTGAGCAAGTTTTCTCTAGCATTTCGAAGATATAGTGCTGAC
ACTGGTAACGACAAGAATCAAAGCTCTACTCTTCACACTAGTCCGTGCCCTCGAATTTGACTTGGCTGTGCCAGCGGAGCAAATTTCTGTGGAAAGT
GGACTAAGTAACCGACCGATTTTGACCAGGACCCGGCCCGTTATCAGCTCCCGCTCCTCATCAAGCCATATAAAGCTCGAAGTTAAGCCGCCTCGT
GGTTCATTATACCTAGAGGTCTAGGGATCACTGTGTGGAGTTTGTACTGGCATCTATGATATTACATACCAGTCAATTACGAACTGAGTTCGGGGCT
GAGAAATGATGAGAGTAAAATGTGGAGGATGGAAAAGAGCTTGAGCATGCGAGCTGCCGCCGAAGTTTAGTTCATAACCAGGGTTCTAGCCCGTCAA
AGAACCGGTTAGCGATTGAATTTGACAGAAGCTTCTTGCCACTACTAAATGCGTTCTCACCGTGCAGGCACTGCGGATGACGCACCATTGGAACCCG
GCGTTAATGGCCGGAGACTTTAGCGCAAGCCTCGAGATGTCGGTTGGTTGAATCACATCAGTGGGCCCAACTGTTGCCACATGCCATGACTTCCCAA
GCAAAAATTTACAATACGACTCGTATGAGTGACCACCGACTTCATGGCCCCAATGTCGTCGTCTCTTATGGCCGTCATCGATTGACATGGTGTTCG
CACGAGTCTGCTTATCAAGTAGGCGAGCACCAGCACCATGTTTTCTACCCTAGTACAAAAACAGTGGTACGGGGAACGCCTATGTTAACTTTCGCAC
AAGAAGAGGAACTTTTGTACCATCCTCGCCAGCTACCTTGGGGCGCGTAAAATGCCAACTCAGTTCCGTCGATGGCCCATTGGGGAGCTCAAAGGCA
AAATATCTGACCAGAACGGACAGCACAGCCTAGAGATTGTGCAGTCAAACAACCAAACCGCTGACATGGGGTTCAATCGTACCTTCACCTCCAGTAC
GGCGAGGTCTCTGCCTGGACACATCCTGGGACCAGCACCGAAAGTTAAGAGACCCCGGTAGCCAGCTAGTTCTCCCTTGTTTCCTTTCTTATGACCC
TCAGCGTCCAGCCATCTGCTTGGATCGAACATGCCCGCGTCTGGCCCCCACAAGCTTCCGACATATTCACTCCCCCCAAGGGTATACGGACGACCA
TACCTTTCTTCAAAAACAAGCTATCGATCGTCGCTCCAGATGCAATACGTATGGGATTTGTCAACGGTATCACATCGTCTTCGGCTGCCTGCCAAGA
TAATAGGGGGATGCGGGAAGGAATTAAACAATGAAGACGAACCACACGGATTGATTGCATTTCGGGGCATGGAGTCTCAGTATCTCGGCTATAAAA
GCATCGAGGTATTTCAGATCCTTTGTTAGCTGGTCGTATGTAGGACGTTCTCCCTTTGCCAAACATTCTGAGAGCTCAGCACGGAGGCTCTCTTGGA
TTTCTGGCCGGCCGTCCAAGTTCAATGAGAGACCACTGAGTGAAGGCTCAGTAATAGAACAGCTTGAACACTCGTAGGCGAAGATTACCGTTAAGGTG
ACTATGAGCAGCACGGGTCATAGTTATGAGATCTTTGATAAACAAGGACAACCGTTCGCAGAACTTACTTGCTGTTGTTTCATATGCAGCCATGAA
AAGGAAACTCTTCGGTTATATTAACTTACAGAGAATATCAGAGGAGTGGCAAAGGTACCGTACGGCCTACAAAGTATGTTGATTAGGCATCAAGCGA
TGTGCACTTGGCCTACATACCTGGGCCGTGATCTCGGAGAGTGACAAACGGCTGTTGGCATTTGCCGTTTTCTGACTTGACTATACAGGGAAGCGTAG
GCACGAAGAAACATCACCTCATATATTGGTGACATACCCAGAATCCCAAGGACTGATTCGTTGACAGTATCTTCCGGTTCCTTACATGCCTTGCTCA
GGCTGTTAGTTGTAAGCCTATTCAAGTGTGCTACTGATTGTCCGAGCTTCTCTTCTCTGACGCTCATGAGGCTAACTTTAAACAGGCCATAGAGTAT
CGGTGACAGAAAGTGAATAAGCCTTATAAAGGGGGAAGGCTTGACTGTGTGGATAGAGTCAAAGGCGGCCATCATCAAGGACGTGCGGCCCCTGAGA
GTTCCAAAGTCATGGGACAATATAGCTTTCCCTATAGTGTCCAATCTAGGAACATTTCAGGGCAAGGGCGGAATGAAGGCTGGCAACGTACGTGAC
AGAATTCATCCTTGGCGCACAGAGAACAAGGTTAACTAACAATGGGGAGATAGATACAGCAACTTGCCATTTCAGGACATCAATTATGACGGGGTTG
TTTGAGTGCTCTGATGACGGAGAACATGAATCCCATGCTGCTTTGAGCTGTCATTTATGTTGCTCAATCGGCCGATTGTTTTAAGAATGGAACCATT
CTAACCTGATAGGCAGAATCCAAGCACACGGGAGTGAGATTGCCAATTGCTCAGACCGACAGTGGAGAAGACAGGCCTCTCCGTAGTCTGCGATCAT
GTTAAGTTTATGCCCTGATCGTTGACCGATAAAGAGTGACCGACCGCTTGTGAGTCTCGCCCTCAGAAATAGATACAACATCACCATACTGGAACGT
AAATAAGCCTGGCAGCTAAGAAAAATGGTGCAAAACAGATACTCGCCAACTTCCGGCTCAAAGCGGTTGTCCCTGCCGAGCCGACAATATGTGGTGGT
ATCCTTGGAATATATGTGTGTGAGAGCCTTGGGATCGCTTAATACAACATGGCTGGAGCCGATGCCAGTGGGTATCTCGTAAACGGGCCCATACATT
CGTTCCCAATCCCGATATACCACACTGAGGTTGGCCCAAGGGAAGATCTTCTTGGTGTTACCGAAGATGAAGCTCTGGCTGCGTGGTCCTTGCAGTC
TGGCGTTCTGATACCTCGGGTCTTGGATAGATAGAAATGACGACGAGCAAGGTAAAGCCAGAGGTCACAATCCTCATCGAATCGGCTTTGAAATA
CTCTGCTACATCAGGCCAGAGGCCGTTGAAGTTGAGGTTCAACATCACGAAGTGGACGAGCCGTGGAAGGCGATCAAGTTGGCGAATGCGAGGAAA
ATGTTTCTGAGGACCCGAAACCGTAACCAGGCGCGATAAATGCTTGACCTATCTATCTCCGGGGACGGTGTTGGGGTCCATCTTACCGTGAAGGTG
GATAGGGACAGATCCGATTCCGGGAAAGAACAGACGAAACGTTCGTATGATGCAACACAACTGTGAGCGCAAGATGGAGCCGAATGATCGGGACTC

CGTATCCTGATCGGCGACTGGGCCTAACGCGTTTCTCGCTGGATTAAACACCCCACTGAGCACAGCCTTTCTCTGTCCCGGTGGTCACAGATTGAAC
AGTCAAGCAGTTTGTAGGATCAATAGATAGGGGTTTTGTCCTGAAATGGACCATGTAGTAATGATTTTCGTCCGTGTGACCCGGTTTGCCGATGCAA
CAAAGACGCATTATCTCCATCGCGCACAGGCCTGTTGCATCACTTATGACTATGTGGCTCTAACTTTCCTGGAATCGAATCCGGCCCTATCCACCTT
CACCGTAACATGGACCCCCAACACCGTTCCCGGAGATAGATAGGTCAAGTTCTCGGCCCTGGTTACGGTTTCGGCTCCTCAGAAACGTTTTCCTGGT
ATTCGGCGCAACTCCCACCCTTCAATGGCATTTCCACGTCTCGTTGGGTTGGTTGCTATACTAGTACTTATCCGCGATGGCCTTCCTTCCTTGCATAA
CGGCTCGTCCACTCCGTCACCCGTGATGTTGAACCTCAACTCCAACGGCCTCTGGCCTGATGTGGCAGACTATCTCAAAGGTAATTCGATAAGGATT
GTGACCTCTGACATTGCTCGTCGTCATTTCTATCTATGGAGATGCCGACGTATCAGAACGCCCAGACTACAAGGACCACGCAGCCAGAGCTTCAGA
TTCAGTAACACCAAGATCTTCCCTTCCGCGAACCTCAGTACGGTGGTATATCGGGATTGGGAACGAATGTATGGGCCTTACGAGATACCCACTGGCA
TCGGCTACAGCCATGTTGTATTGAGCGATCCCAAGGCTCACACACATATATTCCGAGGATACCACCACATATCCTCGGCTCGCAGGGACAACCGCTT
TGAGCCAGGTTGGCGAGTGTTTGTTTTGCACCATTTTTCAGCTGCCAGCCTCATTGTCGTTCCAGTATGGTGATGTTATATCTATTTCTGAGCGCCA
GACTCACAAGGGGTTGGTCGCTCTTTATCGGTCAACGATTAGGGCATAAACTTAACATGATC

*FIG. 23C*

FGENESH 2.5 Prediction of potential genes in Coprinus genomic DNA

Time : Wed Oct 3 12:42:52 2007
Seq name: test sequence
Length of sequence: 13254
Number of predicted genes 6 in +chain 2 in -chain 4
Number of predicted exons 45 in +chain 26 in -chain 19
Positions of predicted genes and exons: Variant 1 from 1,
Score: 219.729370

| G | Str | Feature | Start | End | Score | ORF | Len |
|---|---|---|---|---|---|---|---|
| 1 | + | 1 CDSf | 315 - | 527 | 13.80 | 315 - 527 | 213 |
| 1 | + | 2 CDSi | 685 - | 799 | 2.33 | 685 - 798 | 114 |
| 1 | + | 3 CDSi | 851 - | 888 | 3.39 | 853 - 888 | 36 |
| 1 | + | 4 CDSi | 945 - | 1028 | 5.81 | 945 - 1028 | 84 |
| 1 | + | 5 CDSi | 1125 - | 1230 | 9.26 | 1125 - 1229 | 105 |
| 1 | + | 6 CDSi | 1262 - | 1413 | -4.15 | 1264 - 1413 | 150 |
| 1 | + | 7 CDSi | 1463 - | 1667 | 3.33 | 1463 - 1666 | 204 |
| 1 | + | 8 CDSi | 1718 - | 1757 | 12.55 | 1720 - 1755 | 36 |
| 1 | + | 9 CDSi | 1814 - | 1968 | 3.64 | 1815 - 1967 | 153 |
| 1 | + | 10 CDSi | 1988 - | 2075 | 6.28 | 1990 - 2073 | 84 |
| 1 | + | 11 CDSi | 2128 - | 2214 | -0.10 | 2129 - 2212 | 84 |
| 1 | + | 12 CDSi | 2264 - | 2383 | 2.36 | 2265 - 2381 | 117 |
| 1 | + | 13 CDSl | 2441 - | 2609 | -0.46 | 2442 - 2609 | 168 |
| 1 | + | PolA | 2730 | | -4.02 | | |
| 2 | - | PolA | 2782 | | -5.12 | | |
| 2 | - | 1 CDSl | 2802 - | 3153 | 11.90 | 2802 - 3152 | 351 |
| 2 | - | 2 CDSi | 3194 - | 3327 | -1.50 | 3196 - 3327 | 132 |
| 2 | - | 3 CDSi | 3381 - | 3677 | 13.49 | 3381 - 3677 | 297 |
| 2 | - | 4 CDSi | 3729 - | 3914 | 7.51 | 3729 - 3914 | 186 |
| 2 | - | 5 CDSi | 4047 - | 4049 | 2.72 | 4047 - 4049 | 3 |
| 2 | - | 6 CDSi | 4104 - | 4139 | 8.59 | 4104 - 4139 | 36 |
| 2 | - | 7 CDSi | 4192 - | 4250 | 6.14 | 4192 - 4248 | 57 |
| 2 | - | 8 CDSi | 4306 - | 4590 | 11.14 | 4307 - 4588 | 282 |
| 2 | - | 9 CDSi | 4856 - | 4937 | 7.69 | 4857 - 4937 | 81 |
| 2 | - | 10 CDSf | 5037 - | 5477 | 24.96 | 5037 - 5477 | 441 |
| 2 | - | TSS | 5711 | | -2.93 | | |
| 3 | - | PolA | 5928 | | -0.32 | | |
| 3 | - | 1 CDSl | 5972 - | 6046 | 9.41 | 5972 - 6046 | 75 |
| 3 | - | 2 CDSi | 6223 - | 6255 | -0.04 | 6223 - 6255 | 33 |
| 3 | - | 3 CDSi | 6307 - | 6339 | 6.29 | 6307 - 6339 | 33 |
| 3 | - | 4 CDSi | 6359 - | 6522 | 3.06 | 6359 - 6520 | 162 |
| 3 | - | 5 CDSi | 6580 - | 6667 | 10.19 | 6581 - 6667 | 87 |
| 3 | - | 6 CDSf | 6708 - | 6719 | -1.18 | 6708 - 6719 | 12 |
| 3 | - | TSS | 6959 | | -1.73 | | |
| 4 | + | TSS | 7029 | | -7.71 | | |
| 4 | + | 1 CDSf | 7173 - | 7184 | -3.79 | 7173 - 7184 | 12 |
| 4 | + | 2 CDSi | 7247 - | 7446 | 10.90 | 7247 - 7444 | 198 |
| 4 | + | 3 CDSi | 7510 - | 7644 | 7.81 | 7511 - 7642 | 132 |
| 4 | + | 4 CDSi | 7755 - | 7832 | 1.96 | 7756 - 7830 | 75 |

FIG. 24A

| | | | | | | | | | | | |
|---|---|---|---|---|---|---|---|---|---|---|---|
| 4 | + | 5 | CDSi | 8245 | - | 8608 | 25.32 | 8246 | - | 8608 | 363 |
| 4 | + | 6 | CDSi | 8764 | - | 8869 | 15.02 | 8764 | - | 8868 | 105 |
| 4 | + | 7 | CDSi | 8906 | - | 8975 | 2.99 | 8908 | - | 8973 | 66 |
| 4 | + | 8 | CDSi | 9099 | - | 9403 | 8.93 | 9100 | - | 9402 | 303 |
| 4 | + | 9 | CDSi | 9460 | - | 9518 | 11.93 | 9462 | - | 9518 | 57 |
| 4 | + | 10 | CDSi | 9569 | - | 9571 | 3.53 | 9569 | - | 9571 | 3 |
| 4 | + | 11 | CDSi | 9625 | - | 9661 | 10.61 | 9625 | - | 9660 | 36 |
| 4 | + | 12 | CDSi | 9753 | - | 9964 | 11.55 | 9755 | - | 9964 | 210 |
| 4 | + | 13 | CDSl | 10019 | - | 10126 | 2.83 | 10019 | - | 10126 | 108 |
| 4 | + | | PolA | 10135 | | | -4.02 | | | | |
| | | | | | | | | | | | |
| 5 | - | | PolA | 10338 | | | 1.88 | | | | |
| 5 | - | 1 | CDSl | 11626 | - | 11635 | 1.39 | 11626 | - | 11634 | 9 |
| 5 | - | 2 | CDSf | 11692 | - | 11786 | 18.50 | 11694 | - | 11786 | 93 |
| 5 | - | | TSS | 11838 | | | -1.30 | | | | |
| | | | | | | | | | | | |
| 6 | - | | PolA | 12087 | | | -5.12 | | | | |
| 6 | - | 1 | CDSo | 12872 | - | 13129 | 13.78 | 12872 | - | 13129 | 258 |
| 6 | - | | TSS | 13184 | | | -1.30 | | | | |

*FIG. 24B*

Predicted cDNA: P450-1 (OP451)

SEQ ID NO:596

```
>FGENESH:[mRNA]   1  13 exon (s)    315  -   2609  1572 bp, chain +
ATGGTCGACTTGCACACCATCTCGTATTCAGCTCTCGTCACTTTCAGGCTTATATTCCAA
TTCCTCAAGCTATCTGCAGCTGCATTGACTATCTATGGACTTTACAGAGTCACTCGTGTA
ATTTATGTTGAGCTGACTTCTCCAATACGCCATCTCCCCGGTCCAGCAAACGCCAATATA
TTTCTTGGTAATCTCAAACAGCTCTGGACAGATCTTTCGCATTTATATGTGACGGATCCG
CAGGCCTTGAACCACATTTTGACGAATGGTTACGTTTACACCAAACCATCGTTTACTCGC
CGCCAGATCGGCAAGTTGTGGGGTCCAGGTCTCCCTTTTGTCGAAGGGGATCAACATAAA
AAGCAGCGGAAGATTTTGGTGACTATCTATCCATTCCAAATCGTGGTCCATCAGTGTCTC
AATCACAACCAGAATCCTGCCTTTGGTCCGCTCCAAGACTCTTGGGCTACTGAATGCTCG
AAACAAGGTGGTACTTGCCGCTTAGACATTATGGTAGGCCTTGGTAAGGTGGTGATGGAC
ATCATCAGCTCAACAGTGTTTACCGATGCCATTCGATGGAAAGGCTTCCGTTACGAGCTT
GATTCCCTGGATCGTGAAAGTGACTTTAGCCGTGTGGCTACAATTTTATCTCAATTGAAC
CTGATTCGTTGGCAACTCCGAAGATTCATCCCACTTCTATGGTTCATACCTGATCCTGTA
GAGACACAACTAGACGATATCAAGCAGACCCTTTCTCGGATTACGAGTCGGCTTCTGAAC
GAGAGCAAGGGATCCGTACGTACGAATAATGACAATTCCGGCAGTCGAGATCTCCTATCG
CTTTTGGTTCGCACCAATATGTCCCCCGATGTGCCAGAGCACCGTCGTCTATCCGATGAC
GAAGTCAAAGCCCAGGTTATCTCATTTGTAATTGCTGGACGTGAAAGTCCGATTAACGTA
ATGGCGTGGGCTTTATTTTCTCTGGCAAAAAACCGTGAAATCCAGGCTAAGCTGCGTAGA
GAGCTGCTCACGGTCGATACCTGTCAGCCAACGACGGACCAGCTCAATGCACTTTCATAT
TTGGATATGGTAATTAGGGAGACGCTACGCCACTCGAGGGTGTGTGCCAAGGACGACATT
TTACCTTTGGCTAAGCCGATCACCGACCGGAGAGGAAACCTATTCTCCAGTATTAGTATC
AAAAGAGGGCAAGTAGTCATAATTCCCATTTCTGCCATCCACAAGGACAAGTCGATATGG
GGTGAAGATGCTTTAGACTTCAGACCAGAACGATGGGAATGTCTACCTGAAGGCGTCAAT
ACCATCCCAGGCGTCTGGAGCCATTTGCTCAGTTTTTGGGGTGGTCCACGTTCGTGTATC
GGATTCAGATTTGCTATCGCCGAAATGAAAGCTCTACTCTTCACACTAGTCCGTGCCCTC
GAATTTGACTTGGCTGTGCCAGCGGAGCAAATTTCTGTGGAAAGTGGACTAAGTAACCGA
CCGATTTTGACCACGGACCCGGGCCGTTATCAGCTCCCGCTGCTCATCAAGCCATATAAA
GCTCGAAGTTAA
```

Predicted protein(s): P450-1 (OP451)

SEQ ID NO: 597

```
>FGENESH:   1  13 exon (s)    315  -   2609   523 aa, chain +
MVDLHTISYSALVTFRLIFQFLKLSAAALTIYGLYRVTRVIYVELTSFIRHLPGPANANI
FLGNLKQLWTDLSHLYVTDPQALNHILTNGYVYTKPSFTRRQIGKLWGPGLPFVEGDQHK
KQRKILVTIYPFQIVVHQCLNHNQNPAFGPLQDSWATECSKQGGTCRLDIMVGLGKVVMD
IISSTVFTDAIRWKGFRYELDSLDRESDFSRVATILSQLNLIRWQLRRFIPLLWFIPDPV
ETQLDDIKQTLSRITSRLLNESKGSVRTNNDNSGSRDLLSLLVRTNMSPDVPEHRRLSDD
EVKAQVISFVIAGRESPINVMAWALFSLAKNREIQAKLRRELLTVDTCQPTTDQLNALSY
LDMVIRETLRHSRVCAKDDILPLAKPITDRRGNLFSSISIKRGQVVIIPISAIHKDKSIW
GEDALDFRPERWECLPEGVNTIPGVWSHLLSFWGGPRSCIGFRFAIAEMKALLFTLVRAL
EFDLAVPAEQISVESGLSNRPILTTDPGRYQLPLLIKPYKARS
```

*FIG. 25A* blastp results of Predicted protein(s): P450-1 (OP451) SEQ ID NO: 597

| | | | |
|---|---|---|---|
| gb\|AAW43869.1\| | Cytochrome P450, putative [Cryptococcus neof... | 232 | 2e-59 |
| gb\|EAL20613.1\| | hypothetical protein CNBF3400 [Cryptococcus ... | 229 | 2e-58 |
| ref\|XP_760336.1\| | hypothetical protein UM04189.1 [Ustilago m... | 179 | 3e-43 |
| ref\|XP_756349.1\| | hypothetical protein UM00202.1 [Ustilago m... | 162 | 3e-38 |
| ref\|XP_758127.1\| | hypothetical protein UM01980.1 [Ustilago m... | 154 | 1e-35 |
| ref\|NP_918020.1\| | putative cytochrome P450 [Oryza sativa (ja... | 149 | 3e-34 |
| gb\|AAR11387.1\| | cytochrome P450 [Triticum aestivum] | 138 | 3e-32 |
| * gb\|AAT68297.1\| | cytochrome P450 CYP709C1 [Triticum aestivum] | 141 | 4e-33 |
| ref\|NP_918024.1\| | putative cytochrome P450 [Oryza sativa (ja... | 144 | 8e-33 |
| ref\|XP_477684.1\| | putative cytochrome P450 [Oryza sativa (ja... | 143 | 2e-32 |
| gb\|EAA52219.1\| | hypothetical protein MG04911.4 [Magnaporthe ... | 142 | 2e-32 |
| gb\|EAA78616.1\| | hypothetical protein FG11303.1 [Gibberella z... | 135 | 3e-30 |
| ref\|NP_918022.1\| | putative cytochrome P450 [Oryza sativa (ja... | 132 | 3e-29 |

* putative homolog shown to have Hydroxylase activity: SEQ ID NO: 599

LOCUS AAT68297 514 aa linear PLN 24-OCT-2005
DEFINITION cytochrome P450 CYP709C1 [Triticum aestivum].
ACCESSION AAT68297
VERSION AAT68297.1 GI:49660016
DBSOURCE accession AY641449.1
ORGANISM Triticum aestivum
AUTHORS Kandel,S., Morant,M., Benveniste,I., Blee,E., Werck-Reichhart,D. and Pinot,F.
TITLE Cloning, Functional Expression, and Characterization of CYP709C1, the First Sub-terminal Hydroxylase of Long Chain Fatty Acid in Plants: INDUCTION BY CHEMICALS AND METHYL JASMONATE
JOURNAL J. Biol. Chem. 280 (43), 35881-35889 (2005)
PUBMED 16120613
REFERENCE 2 (residues 1 to 514)
AUTHORS Morant,M., Werck-Reichhart,D. and Pallett,K.
TITLE Direct Submission
FEATURES Location/Qualifiers
source 1..514
/organism="Triticum aestivum"
/cultivar="Darius"
/note="Cytochrome P450. Cytochrome P450s are haem-thiolate proteins involved in the oxidative degradation of various compounds. They are particularly well known for their role in the degradation of environmental toxins and mutagens; pfam00067"

```
  1 mglwmvaaa vacvlaswaf dalvylvwrp raltrqlraq gvggpgyrff sgnlaslkql
 61 radasgaald lgdhdfvprv gphfrkwipl hgrtflywfg sxpulcisdv nvkqvlsdr
121 gglypksign pblarllgkg lvludgddwk rhrkvvhpaf nmdklkmmtv tmdecgamm
181 sewkakmdkg gsvsidlssq feeltadvis htafgssyeq gkkvflaqre lqflafstvf
241 nvqipsfryl ptkrnlkiwk ldkevrtmlm nlikgrlatk dtmgygndll glmlsacnpe
301 dggnpllsmd eiidecktff faghdtsshl ltwtmrllst hpewqeklre evlrecgngl
361 ptgdnlnklq lvnmfllstl rlypvsalq rkagsdlevg gikvtegtfl tipiatihrd
421 kevwgedank fkpmrfengv tnagkhpnal lafssgprsc lgqnfamiea kavlavilqr
481 fsfslspkyv hapmdvitlr pkfglpmilk slem
```

1: J Biol Chem. 2005 Oct 28;280(43):35881-9. Epub 2005 Aug 23.

Cloning, functional expression, and characterization of CYP709C1, the first sub-terminal hydroxylase of long chain fatty acid in plants. Induction by chemicals and methyl jasmonate.

Kandel S, Morant M, Benveniste I, Blée E, Werck-Reichhart D, Pinot F.
Département Réponse Métabolique à l'Environnement Biotique, IBMP-CNRS, UPR 2357, 28 Rue Goethe, F-67083 Strasbourg Cedex, France.

FIG. 25B-1

We cloned and characterized CYP709C1, a new plant cytochrome P450 belonging to the P450 family, that so far has no identified function except for clustering with a fatty acid metabolizing clade of P450 enzymes. We showed here that CYP709C1 is capable of hydroxylating fatty acids at the omega-1 and omega-2 positions. This work was performed after recoding and heterologous expression of a full-length cDNA isolated from a wheat cDNA library in an engineered yeaststrain. Investigation on substrate specificity indicates that CYP709C1 metabolizes different fatty acids varying in their chain length (C12 to C18)and unsaturation. CYP709C1 is the first identified plant cytochrome P450 that can catalyze sub-terminal hydroxylation of C18 fatty acids. cis-9,10-Epoxystearic acid is metabolized with the highest efficiency, i.e. K(m)(app)) of 8 microM and V(max(app)) of 328 nmol/min/nmol P450. This, together with the fact that wheat possesses a microsomal peroxygenase able to synthesize this compound from oleic acid, strongly suggests that it is a physiological substrate. Hydroxylated fatty acids are implicated in plant defense events. We postulated that CYP709C1 could be involved in plant defense by producing such compounds. This receives support from the observation that (i) sub-terminal hydroxylation of 9,10-epoxystearic acid is induced (15-fold after 3 h) in microsomes of wheat seedlings treated with the stress hormone methyl jasmonate and (ii) CYP709C1 is enhanced at the transcriptional level by this treatment. CYP709C1 transcript also accumulated after treatment with a combination of the safener naphthalic acid anhydride and phenobarbital. This indicates a possible detoxifying function for CYP709C1 that we discussed.

*FIG. 25B-2*

BLASTP of OP45-1 against Coprinus at Broad: the top ID is contemplated to be significant.

| | | |
|---|---|---|
| CC1G_09160: hypothetical protein | 365 | e-101 |
| CC1G_03738: hypothetical protein | 191 | 4e-49 |
| CC1G_06332: hypothetical protein | 183 | 1e-46 |
| CC1G_06814: hypothetical protein | 178 | 4e-45 |
| CC1G_02050: hypothetical protein | 176 | 2e-44 |
| CC1G_00121: hypothetical protein | 160 | 1e-39 |
| CC1G_05308: hypothetical protein | 157 | 8e-39 |
| CC1G_12478: hypothetical protein | 157 | 8e-39 |
| CC1G_04749: hypothetical protein | 156 | 1e-38 |
| CC1G_00122: hypothetical protein | 154 | 5e-38 |
| CC1G_06334: predicted protein | 140 | 7e-34 |
| CC1G_05316: hypothetical protein | 136 | 2e-32 |
| CC1G_12971: predicted protein | 99 | 2e-21 |
| CC1G_02813: predicted protein | 99 | 2e-21 |

*FIG. 25C*

BLASTP of OP45-1 against Coprinus at Broad: the top ID is contemplated to be significant.

| | | |
|---|---|---|
| CC1G_09160: hypothetical protein | 369 | e-101 |
| CC1G_05738: hypothetical protein | 191 | 4e-49 |
| CC1G_06332: hypothetical protein | 183 | 1e-46 |
| CC1G_06814: hypothetical protein | 178 | 6e-45 |
| CC1G_02050: hypothetical protein | 176 | 2e-44 |
| CC1G_00123: hypothetical protein | 160 | 1e-39 |
| CC1G_05306: hypothetical protein | 157 | 8e-39 |
| CC1G_12478: hypothetical protein | 157 | 8e-39 |
| CC1G_04749: hypothetical protein | 156 | 1e-38 |
| CC1G_00122: hypothetical protein | 154 | 5e-38 |
| CC1G_05334: predicted protein | 140 | 7e-34 |
| CC1G_05310: hypothetical protein | 136 | 2e-32 |
| CC1G_12871: predicted protein | 99 | 2e-21 |
| CC1G_02813: predicted protein | 99 | 2e-21 |

* Best Laccaria protein hit:

*FIG. 25D*

SEQ ID NO: 598

>jgi|Lacbi1|315739|eu2.Lbscf0006g04830

MGRTQLLVVSATATLGVYGLYKIAGIVYREWLSPLRVLPGTKSPSFLYGDLKELWEEDTGTSQILVEKY
GTTFRYESLLGISRLYTADTRALSHILMNSYDYEKLPESRAALTNILGAGLLVVEGDKHKQQRKIMNPAF
GPAQIRELTDIFVRKSIQLRDLWAEECTKQGGQGRIEILSWLTWTTLDVIGLAGFNYKFNALMRDSKANE
LSEAFNTIFQAGTSVNVMLILRAFIPALSWILPEAGDVEAKRASSTMSRIGKELLSNSKAAVSQQESLEK
DIWKTRDLLSLLVRANVATDLTESQRMLDEDVLAQIPTFIVAGHETTSNATTWALFALNSQNPDAQIKLR
NELLTVSTDNPIMDELNALPYLDAVVRETLRLHAPVSMTSRVAMKDDVLPLAIPFIDSKGVIHHEIRIRK
GEPLLIPILALNRDKSIWGEDAHEFKPERWESIPDAASSIPGVWGHMLTFLGGPHSCIGYRFALVEMKAL
LFTLIRSFEFELAVPASDIGKKAGIVHRPILLSNPEGGSQMPLFVKAYQPPLEEA*

OP451 as a query sequence for a BLASTP against nr, showing an excellent hit against a Coprinus protein:

gb|EAU81974.1| hypothetical protein CC1G_09160 [Coprinopsis c... 607 6e-172

*FIG. 25E*

Predicted cDNA: P450-2 (OP452)
SEQ ID NO: 600

>FGENESH:[mRNA] 2 10 exon (s) 2802 - 5477 1875 bp, chain -
ATGTTGAACCTCAACTTCAACGGCCTCTGGCCTGATGTAGCACAGTATTTCAAAGGCGAT
TCGATGAGGATTGTGACCTCTGCCTTTACGTTGCTCGTCGTCATTTCTATCTATCGAAGA
CGCCGAGGTATCAGAACGCCCAGACTGCAAGGACCACGCAGCGAGAGCTTCATCTTCGGT
AACACCAAGAAGATCTTCCCTTCGGCGAACCTGAGTGTGGTATATCGGGATTGGGAACGA
ATGTATGGGCCCGTTTACGAGATACCCACTGGCATCGGCTCCAGCCATGTTGTATTAAGC
GATCCCAAGGCTCTCACACACATATATTCCAAGGATACCACCACATATTGTCGGCTCGCA
GGGACAACCGCTTTGAGCCGGAAGTTGGCGAGTATCTGTTTTGCACCATTTTTCTTAGCT
GCCAGCCTTATTTACGTTCCAACTACGGAGAGGCCTGTCTTCTCCACTGTCGGTCTCAGC
AATTCGCAATCTCACTCCCGTGTGCTTGGATTCTGCCTATCAGGGAAAGCTATATTGTCG
CATGACTTTGGAACTCTAAGGGGCCGCACGTCCTTGATGATGGCCGCCTTTGACTCTATC
CACACAGTCAAGCCTTCCCCCTTTATAAGGCTTATTCACTTTCTGTCACCGATACTCTAT
GCCCTGTTTAAAGTTACCCTCATGAGCGTCAGAGAAGAGAAGCTCGCACAATCAGTAGCA
CACTTGAATAGGCTTACAACTAACAGCCTGAACAAGGCATGTAAGGAACCGGAAGATACT
GTCAACGAATCAGTCCTTGGGATTCTGGTCAAGTCAGAAAACGCAAATCCCAACAGCCGT
TTGTCACTCTCCGAGATCACGGCCCAGGCCGTACGTACCTTTGCCACTCCTCTGATATTC
TCTCAATGGTCTCTCATTGAACTTGCACGCCGGCCAGAAATCCAAGAGAGCCTCCGTGCT
GAGCTCTCAGAATGTTTGGCAAAGGGAGAACGTCCTACATACGACCAGCTAACAAAGGAT
CTGAAATACCTCGATGCTTTTATAGCCGAGATACTGAGACTCCATGCCCCCGAAATGCAA
TCAATCCGTGTGGCAGCCGAAGACGATGTGATACCGTTGACAAATCCCATACGTATTGCA
TCTGGAGCGACGATCGATAGCTTGTTTTTGAAGAAAGGTATGGTCGTCCGTATACCCTTG
GGGGGAGTGAATATGTCGGAAGCGTTGTGGGGGCCAGACGCGGGCATGTTCGATCCAAGC
AGATGGCTGGACGCTGAGGGTCATAAGAAAGGAAACAAGGGAGAACTAGCTGGCTACCGG
GGTCTCTTAACTTTCGGTGCTGGTCCCAGGATGTGTCCAGGCAGAGACCTCGCCGTACTG
GAGGTGAAGGCTGTGCTGTCGGTTCTGGTCAGATATTTTGCCTTTGAGCTCCCCAATGGG
CCATCGACGGAACTGAGTTGGCATTTTACGCGCCCCAAGGTAGCTGGCGAGGATGGTACA
AAAGTTCCTCTTCTTGTGCGAAAGGTAGAAAACATGGTGGTGGTGCTCGCCTACTTGATA
AGCAGACTCGTGCGAAACACCATGTCAATCGATGACGGGCATAAGAGACCACGACATTGG
GGCGATGAAGTCGGTGGTGACTCATACGAGTCGTATTGTAAATTTTTGCTTGGGAAGTCA
TGGCATGTCGCAACAGTTGGCCCCACTGATGTCATTCAACCAACCGACATCTCGAGGCTT
GCGCTAAAGTCTCCCGCCATTAACGCCGCGTTCCAATGCTGCGTCATCCGCAGTGCCTGC
ACCGTCAGAACGCATTTAGTAGTGGCAAGAAGCTTCTGTCAAATTCAATCGCTAACCGGT
TCTTTGACGGGCTAG Predicted protein(s): P450-2 (OP452)
SEQ ID NO: 601

>FGENESH: 2 10 exon (s) 2802 - 5477 624 aa, chain -
MLNLNFNGLWPDVAEYFKGDSMRIVTSAFTLLVVISIYRRRRGIRTPRLQGPRSESFIFG
NTKKIFPSANLSVVYRDWERMYGPVYEIPTGIGSSHVVLSDPKALTHIYSKDTTTYCRLA
GTTALSRKLASICFAPFFLAASLIYVPTTERPVFSTVGLSNSQSHSRVLGFCLSGKAILS
HDFGTLRGRTSLMMAAFDSIHTVKPSPFIRLIHFLSPILYALFKVTLMSVREEKLAQSVA
HLNRLTTNSLNKACKEPEDTVNESVLGILVKSENANPNSRLSLSEITAQAVRTFATPLIF
SQWSLIELARRPEIQESLRAELSECLAKGERPTYDQLTKDLKYLDAFIAEILRLHAPEMQ
SIRVAAEDDVIPLTNPIRIASGATIDSLFLKKGMVVRIPLGGVNMSEALWGPDAGMFDPS
RWLDAEGHKKGNKGELAGYRGLLTFGAGPRMCPGRDLAVLEVKAVLSVLVRYFAFELPNG
PSTELSWHFTRPKVAGEDGTKVPLLVRKVENMVVVLAYLISRLVRNTMSIDDGHKRPRHW
GDEVGGDSYESYCKFLLGKSWHVATVGPTDVIQPTDISRLALKSPAINAAFQCCVIRSAC
TVRTHLVVARSFCQIQSLTGSLTG

FIG. 26A

P450-2 (OP452), see 26A.

| | | | |
|---|---|---|---|
| gb\|AAW42869.1\| | Cytochrome P450, putative [Cryptococcus neof... | 128 | 5e-31 |
| gb\|EAL20013.1\| | hypothetical protein CNBF3400 [Cryptococcus ... | 127 | 9e-31 |
| ref\|XP_758127.1\| | hypothetical protein UM01980.1 [Ustilago m... | 118 | 6e-25 |
| ref\|XP_760336.1\| | hypothetical protein UM04189.1 [Ustilago m... | 108 | 2e-21 |
| gb\|EAA77720.1\| | hypothetical protein FG09671.1 [Gibberella z... | 98 | 8e-19 |
| gb\|EAL92111.1\| | cytochrome P450 monooxygenase, putative [Asp... | 95 | 1e-18 |
| gb\|EAA69194.1\| | hypothetical protein FG01048.1 [Gibberella z... | 94 | 2e-17 |
| gb\|EAL91101.1\| | cytochrome P450, putative [Aspergillus fumig... | 93 | 3e-17 |
| ref\|XP_317263.1\| | ENSANGP00000021820 [Anopheles gambiae str.... | 93 | 3e-17 |
| gb\|AAK92957.1\| | cytochrome P450 [Anopheles gambiae] | 92 | 4e-17 |
| ref\|NP_918024.1\| | putative cytochrome P450 [Oryza sativa (ja... | 92 | 6e-17 |
| dbj\|BAB09357.1\| | cytochrome P450-like protein [Arabidopsis t... | 92 | 6e-17 |
| gb\|EAA52219.1\| | hypothetical protein MG04911.4 [Magnaporthe ... | 92 | 6e-17 |
| gb\|EAA72429.1\| | hypothetical protein FG05981.1 [Gibberella z... | 91 | 1e-16 |

*FIG. 26B*

BlastP against Coprinus

| | | |
|---|---|---|
| CC1G_09160: hypothetical protein | 144 | 1e-34 |
| CC1G_07850: hypothetical protein | 143 | 1e-34 |
| CC1G_03738: hypothetical protein | 124 | 1e-28 |
| CC1G_04749: hypothetical protein | 115 | 3e-26 |
| CC1G_06332: hypothetical protein | 113 | 2e-25 |
| CC1G_12478: hypothetical protein | 108 | 7e-24 |
| CC1G_05306: hypothetical protein | 107 | 1e-23 |
| CC1G_06814: hypothetical protein | 107 | 1e-23 |
| CC1G_00121: hypothetical protein | 102 | 3e-22 |
| CC1G_00122: hypothetical protein | 97 | 2e-20 |

*FIG. 26C*

Blast against Laccaria. Again, hits are relatively weak compared to P450-1

| Sequences producing significant alignments: | (bits) Score | E Value | N |
|---|---|---|---|
| jgi\|Lacbi1\|315756\|eu2.Lbscf0006g04400 | 91 | 6e-28 | 3 |
| jgi\|Lacbi1\|324807\|fgenesh3_pg.C_scaffold_6000301 | 91 | 1e-27 | 3 |
| jgi\|Lacbi1\|339066\|estExt_fgenesh3_pg.C_60288 | 91 | 1e-27 | 3 |
| jgi\|Lacbi1\|314449\|eu2.Lbscf0001g00300 | 97 | 1e-27 | 3 |
| jgi\|Lacbi1\|315758\|eu2.Lbscf0006g04420 | 91 | 2e-25 | 2 |
| jgi\|Lacbi1\|334243\|fgenesh3_pg.C_scaffold_61000021 | 94 | 4e-24 | 2 |
| jgi\|Lacbi1\|300937\|eu2.Lbscf0001g03860 | 51 | 4e-24 | 5 |
| jgi\|Lacbi1\|320702\|fgenesh3_pg.C_scaffold_1000272 | 51 | 4e-24 | 5 |

*FIG. 26D*

SEQ ID NO: 602

>FGENESH:[mRNA] 3 6 exon (s) 5972 - 6719 405 bp, chain -
ATGAGAAATAACAAAAACTTGAAGGCCTTACTTCCGATGCAGGCTCAACGCTCCAAGCCT
AACATTGTCAACAACTTGCGTCGTCCACTACTACATCGAATGGATGAGACATTTAGCAAA
GGCTGGTACACGACACATAAGTACATTGCTACATTATTAAATGGAATTTTGAGCTCACCT
CTCACCACGAGTGAGGAGACGGTTGACGTCGTCACCGACGCATGGGCAGTCTACAAGCCA
AGCAGGAAGACGGGTGGCATTGATAGTAGAGGTCTTGGGTTCGAGTTCGAATGGGAGTCA
CGAATTCGCAAGATTGGAAAACCGCAGAAAGGGCGTTCGGTTTCTGCGGACATTCAGCCG
GGCAAGACGGTGCAATACAATGGCAACCCCGTCAAAAGTTGTTGA

SEQ ID NO: 603

>FGENESH: 3 6 exon (s) 5972 - 6719 134 aa, chain -
MRNNKNLKALLPMQAQRSKPNIVNNLRRPLLHRMDETFSKGWYTTHKYIATLLNGILSSP
LTTSEETVDVVTDAWAVYKPSRKTGGIDSRGLGFEFEWESRIRKIGKPQKGRSVSADIQP
GKTVQYNGNPVKSC protein 3: No hits at all. This region overlaps with PHA1-1, which is on + strand (gene 3 is on - strand).

*FIG. 27*

P450-3 (OP453) SEQ ID NO: 604

>FGENESH:[mRNA] 4 13 exon (s) 7173 - 10126 1689 bp, chain +
ATGCGATCGCATTCTCTCAAGGGCCGTTCATTAAAGTTGGCTAAAGTCGCGGGGGAAGGG
CTGGTGATGAGGTATCTTGTGTCGACGCGGGCACAATGGACCATGGGAGGCAGTCGCCGC
ATATCTGAAAAGCTGGGCTCCCGACGTGAAGTGAGGAATCACGAAAATCATATTTGCTTG
GAAGGAAAGCCCATGCAGCTCAGCAAACTCTACCTGAAACCTGCCCTGTCAAGGACATGC
GGCCGCAACCGCGACTGGTTGATGGTAAATCCAAATGCGACGCCCAGTTCGAAAGATGAG
ACATACCTGCGCCAAACAGTGATTACCACAGCCACCTACGAGGCCTCCGTGGCCAGTCGC
GCCTCGGGATTTACCGGCGCGATACAAACGGAAAGTTCTTTCGCAGCGTTCCCACCGCG
CGGCCCCTTTGGCCTTATGTCGCGGAGTACCTCAAAGTCAATTCGATGAGGATAATAGCC
TCTGGCATATCCTTGCTCGTCGTTGTTTCCATTTACCGAAGCCGTCGAGGTCCTAGAACG
CCGAGACTGCAAGGACCACACATGGAGAGCTTCATCCTCGGCAATGCTAGGAAGATCTTC
CCTTCAGCCAACCTCAGTTTGGTGTATCAAGGTTTGGAGCAGACTTACGGGCCCGTCTAT
GAAATAGCCTCTGGCTTTGGCTCCAACCACGTCGTATTGAACGATCCCAAGGCTCTCACA
CACTTATTTTCCAAGGACACTGTCACATATTCTCAGCCTGCTAGGCAGAAAGACATGGGG
CGGAAGTTGAATACGGAGGGTCTTGTCTTCTCCCCTGTCGGTCTCGGCAATCCGCAATTT
CACTCCTATGTGTTTGGATTCCGCCTATCAGGTCAGGACGGTTCCAGCTTTGAGACATCA
TGGGATTCATGTTTCCAGTTGTCAAACAATTCGAACCGTGCTATCGTGCTTGATGCAGAG
AAATGCATGGATAATATTGGAAAAGCTGTATTGTCGTATGACTTCGGCAACATGAGGGGC
CATACGTGTTCGATCTTAGCTGACTTGGATGCTTTCCACGCAGTCAGCCCTTCAGGCCTT
TACATAAGGTTTATTGTGTTTACCCGCGAGATACTTTATAACCTCTTCAAGATTACCTTA
CCGAATGCCAAAGAAAAGCAGTTTGAGGAACTGGCAGCGCACTTTAAAGTACTCGCGACT
GGCTTTCTGCGGGAAGCACGTGAGGCGCCTGAAGATAGCGCCGTTCACCAATCAATCCTT
GGGGTTATGCTCAAGTCCAAAAATGAAAATGCTAACGTCCGTTTATCACTTCCCGAGATC
ACGGCCCAGGCTGGTGGTCTTGTCTTGGCCGGGTATGAAACTACGGCAAAGATCCATCGC
CGAGCTTTCCCTCAGTGGTCCCTCATTGAGCTTGCTCGCCGGGCAGAAATTCAAGAGACT
CTCCGTGCCGAACTCAAGGAGTGCTTGGCAGACGGAGAACGCCCTACATACGACCAGCTG
ACAAAGGATCTGAAATACCTCGATGCTTTTATATCCGAGATACTGAGGTTACATCCCTCA
GAAATGGTACTAACCCGGCTGGCAGCCGAAGACGATGTGATACCGCTGACGGATCCCATA
CGAACTGCATCTGGAGCCGATGATCGACAGCTTGTTCGTGAGGAAAGGCACCGTCTCCGCA
TCCCTTTAG

*FIG. 28A-1*

P450-3 (OP453) SEQ ID NO: 605

>FGENESH: 4 13 exon (s) 7173 - 10126 562 aa, chain +
MRSHSLKGRSLKLAKVAGEGLVMRYLVSTRAQWTMGGSRRISEKLGSRREVRNHENHICL
EGKPMQLSKLYLKPALSRTCGRNRDWLMVNPNATPSSKDETYLRQTVITTATYEASVASR
ASGFTGAIQTESSFAAFPPARPLNPYVAEYLKVNSMRIIASGISLLVVVSIYRSRRGPRT
PRLQGPHMESFILGNARKIFPSANLSLVYQGLEQTYGPVYEIASGFGSNHVVLNDPKALT
HLFSKDTVTYSQPARQKDMGRKLNTEGLVFSPVGLGNPQFHSYVFGPRLSGQDGSSFETS
WDSCFQLSNNSNRAIVLDAEKCMDNIGKAVLSYDFGNMRGHTCSILADLDAFHAVSPSGL
YIRFIVFTREILYNLFKITLPNAKEKQFEELAARFKVLATGFLREAREAPEDSAVHQSIL
GVMLKSENENANVKLSLPEITAQAQGLVLAGYETTAKIHRRAFPQWSLIELAKRAEIQET
LRAELKECLADGERPTYDQLTKDLKYLDAFISEILRLHPSEMVLTRVAAEDDVIPLTDPI
RTASGAMIDSLFVRKGIVSASL

*FIG. 28A-2*

| | | | |
|---|---|---|---|
| gb\|AAW41984.1\| | conserved hypothetical protein [Cryptococcus... | 86 | 3e-15 |
| gb\|EAL22841.1\| | hypothetical protein CNBE0820 [Cryptococcus ... | 78 | 8e-13 |
| gb\|AAW43969.1\| | Cytochrome P450, putative [Cryptococcus neof... | 72 | 5e-11 |
| gb\|EAL20013.1\| | hypothetical protein CNBF3400 [Cryptococcus ... | 72 | 5e-11 |
| gb\|AAT78222.1\| | putative 9782-like cytochrome P450 [Ginkgo b... | 70 | 2e-10 |
| ref\|NP_959532.1\| | hypothetical protein MAP0598c [Mycobacteri... | 69 | 4e-10 |
| ref\|YP_118800.1\| | cytochrome P450 monooxygenase [Nocardia fa... | 69 | 6e-10 |
| ref\|XP_758127.1\| | hypothetical protein UM01980_1 [Ustilago m... | 68 | 1e-09 |
| gb\|AAF40578.1\| | putative cytochrome p450 [Mycobacterium vank... | 65 | 6e-09 |
| ref\|NP_031848.1\| | cytochrome P450, family 3, subfamily a, po... | 65 | 8e-09 |
| gb\|EAL26025.1\| | GA10190-PA [Drosophila pseudoobscura] | 65 | 8e-09 |
| dbj\|BAB63954.1\| | cytochrome P450 [Musca domestica] | 65 | 8e-09 |
| ref\|XP_312050.1\| | ENSANGP00000016967 [Anopheles gambiae str.... | 64 | 1e-08 |

*FIG. 28B*

BLASTP against Coprinus

| Sequences producing significant alignments: | Score (bits) | E Value |
|---|---|---|
| CC1G_02050: hypothetical protein | 127 | 7e-30 |
| CC1G_06332: hypothetical protein | 100 | 2e-21 |
| CC1G_09160: hypothetical protein | 95 | 5e-20 |
| CC1G_12478: hypothetical protein | 79 | 5e-15 |
| CC1G_04749: hypothetical protein | 73 | 2e-13 |
| CC1G_05306: hypothetical protein | 62 | 5e-10 |
| CC1G_06334: predicted protein | 62 | 6e-10 |
| CC1G_00122: hypothetical protein | 61 | 8e-10 |
| CC1G_00121: hypothetical protein | 60 | 2e-09 |
| CC1G_02813: predicted protein | 58 | 7e-09 |

*FIG. 28C*

BLASTP aginast Laccaria:

| Sequences producing significant aligments: | Score (bits) | E Value | N |
|---|---|---|---|
| jgi\|Lacbi1\|314449\|eu2.Lbscf0061g00300 | 73 | 2e-17 | 2 |
| jgi\|Lacbi1\|265411\|e_gww1.61.27.1 | 73 | 4e-12 | 1 |
| jgi\|Lacbi1\|240704\|e_gwh1.61.30.1 | 73 | 4e-12 | 1 |
| jgi\|Lacbi1\|148184\|gww1.61.27.1 | 73 | 4e-12 | 1 |
| jgi\|Lacbi1\|163014\|gwh1.61.30.1 | 73 | 4e-12 | 1 |
| jgi\|Lacbi1\|334243\|fgenesh3_pg.C_scaffold_61000021 | 71 | 2e-11 | 1 |
| jgi\|Lacbi1\|334242\|fgenesh3_pg.C_scaffold_61000020 | 48 | 2e-11 | 3 |
| jgi\|Lacbi1\|341522\|estExt_fgenesh3_pg.C_610019 | 48 | 2e-11 | 3 |
| jgi\|Lacbi1\|309740\|eu2.Lbscf0041g01500 | 42 | 7e-10 | 3 |
| jgi\|Lacbi1\|318101\|eu2.Lbscf0008g02830 | 47 | 1e-09 | 2 |

*FIG. 28D*

SEQ ID NO: 606
>FGENESH:[mRNA] 5 2 exon (s) 11626 - 11786 105 bp, chain -
ATGTCTGACATCAATGCCACCCGTCTTCCCGCTTGGCTTGTAGATTGCCCATGCGTCGGT
GACGATGTCAACCGTCTCCTCACTCGTGGCGAGAGCCTTTGCTAA SEQ ID NO: 607
>FGENESH: 5 2 exon (s) 11626 - 11786 (160 nt) 34 aa, chain -
MSDINATRLPAWLVDCPCVGDDVNRLLTRGESLC No identity hits in any of the genomes of the nontoxic mushrooms. This is a sequence encoding PHA1-2.

SEQ ID NO: 608 Gene 5 rc:
TTAGCAAAGGCTCTCGCCACGAGTGAGGAGACGGTTGACATCGTCACCGACGCATGGGCAATCTACAAGCCAAGCGG
GAAGACGGGTGGCATTGATGTCAGACAT

FIG. 29A

SEQ ID NO: 609
>FGENESH:[mRNA] 6 1 exon (s) 12872 - 13129 258 bp, chain -
ATGGTGCAAAACAAAGACTCGCCAACCTGGCTCAAAGCGGTTGTCCCTGCGAGCCGAGGA
TATGTGGTGGTATCCTCGGAATATATGTGTGTGAGCCTTGGGATCGCTCAATACAACATG
GCTGTAGCCGATGCCAGTGGGTATCTCGTAAGGCCCATACATTCGTTCCCAATCCCGATA
TACCACCGTACTGAGGTTCGCGGAAGGGAAGATCTTGGTGTTACTGAATCTGAAGCTCTC
GCTGCGTGGTCCTTGTAG SEQ ID NO: 610
>FGENESH: 6 1 exon (s) 12872 - 13129 85 aa, chain -
MVQNKDSPTWLKAVVPASRGYVVVSSEYMCVSLGIAQYNMAVADASGYLVRPIHSFPIPI
YHRTEVRGREDLGVTESEALAAWSL No identity hits in any of the mushroom genomes.

FIG. 29B

The alignments of P450 genes 1,2,4 are:

| | | | |
|---|---|---|---|
| gb\|AAW43983.1\| | Cytochrome P450, putative [Cryptococcus neof... | 232 | 3e-59 |
| gb\|EAL20013.1\| | hypothetical protein CNBF3400 [Cryptococcus ... | 229 | 3e-58 |
| ref\|XP_760336.1\| | hypothetical protein UM04189.1 [Ustilago m... | 173 | 3e-43 |
| ref\|XP_756369.1\| | hypothetical protein UM00202.1 [Ustilago m... | 162 | 3e-38 |
| ref\|XP_758127.1\| | hypothetical protein UM01980.1 [Ustilago m... | 154 | 1e-35 |
| ref\|NP_918026.1\| | putative cytochrome P450 [Oryza sativa (ja... | 149 | 3e-34 |
| gb\|AAR11387.1\| | cytochrome P450 [Triticum aestivum] | 145 | 3e-33 |
| gb\|AAT68297.1\| | cytochrome P450 CYP709C1 [Triticum aestivum] | 145 | 4e-33 |
| ref\|NP_918024.1\| | putative cytochrome P450 [Oryza sativa (ja... | 144 | 8e-33 |
| ref\|XP_477684.1\| | putative cytochrome P450 [Oryza sativa (ja... | 143 | 2e-32 |
| gb\|EAA52219.1\| | hypothetical protein MG04911.4 [Magnaporthe ... | 142 | 2e-32 |
| gb\|EAA78616.1\| | hypothetical protein FG11303.1 [Gibberella z... | 135 | 3e-30 |
| ref\|NP_918029.1\| | putative cytochrome P450 [Oryza sativa (ja... | 132 | 3e-29 |

| | | | |
|---|---|---|---|
| gb\|AAW43983.1\| | Cytochrome P450, putative [Cryptococcus neof... | 138 | 5e-31 |
| gb\|EAL20013.1\| | hypothetical protein CNBF3400 [Cryptococcus ... | 137 | 9e-31 |
| ref\|XP_758127.1\| | hypothetical protein UM01980.1 [Ustilago m... | 118 | 6e-25 |
| ref\|XP_760326.1\| | hypothetical protein UM04189.1 [Ustilago m... | 106 | 2e-21 |

FIG. 30A-1

| | | | |
|---|---|---|---|
| gb\|EAA77720.1\| | hypothetical protein FG05971.1 [Gibberella z... | 98 | 8e-19 |
| gb\|EAL92111.1\| | cytochrome P450 monooxygenase, putative [Asp... | 98 | 1e-18 |
| gb\|EAA69194.1\| | hypothetical protein FG01048.1 [Gibberella z... | 94 | 2e-17 |
| gb\|EAL91101.1\| | cytochrome P450, putative [Aspergillus fumig... | 93 | 3e-17 |
| ref\|XP_317263.1\| | ENSANGP00000021820 [Anopheles gambiae str.... | 93 | 3e-17 |
| gb\|AAK32957.1\| | cytochrome P450 [Anopheles gambiae] | 92 | 4e-17 |
| ref\|NP_918024.1\| | putative cytochrome P450 [Oryza sativa (ja... | 92 | 6e-17 |
| dbj\|BAB02357.1\| | cytochrome P450-like protein [Arabidopsis t... | 92 | 6e-17 |
| gb\|EAA52219.1\| | hypothetical protein MG04911.4 [Magnaporthe ... | 92 | 6e-17 |
| gb\|EAA73429.1\| | hypothetical protein FG03561.1 [Gibberella z... | 91 | 1e-16 |

| | | | |
|---|---|---|---|
| gb\|AAW41954.1\| | conserved hypothetical protein [Cryptococcus... | 86 | 3e-15 |
| gb\|EAL22841.1\| | hypothetical protein CNBB0620 [Cryptococcus ... | 78 | 6e-13 |
| * gb\|AAW43969.1\| | Cytochrome P450, putative [Cryptococcus neof... | 72 | 3e-11 |
| gb\|EAL20011.1\| | hypothetical protein CNBF3400 [Cryptococcus ... | 72 | 3e-11 |
| gb\|AAT28722.1\| | putative 9792-like cytochrome P450 [Ginkgo b... | 70 | 2e-10 |
| ref\|NP_959532.1\| | hypothetical protein MAP0998c [Mycobacteri... | 69 | 5e-10 |
| ref\|YP_118806.1\| | cytochrome P450 monooxygenase [Nocardia fa... | 69 | 6e-10 |
| ref\|XP_758127.1\| | hypothetical protein UM01980.1 [Ustilago m... | 68 | 1e-09 |
| gb\|AAT40578.1\| | putative cytochrome p450 [Mycobacterium vanb... | 65 | 6e-09 |
| ref\|NP_031846.1\| | cytochrome P450, family 3, subfamily a, po... | 65 | 8e-09 |
| gb\|EAL26035.1\| | GA10180-PA [Drosophila pseudoobscura] | 65 | 8e-09 |
| dbj\|BAA43954.1\| | cytochrome P450 [Musca domestica] | 65 | 8e-09 |
| ref\|XP_312050.1\| | ENSANGP00000018967 [Anopheles gambiae str.... | 64 | 1e-08 |

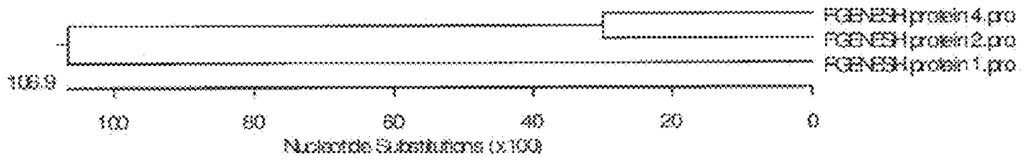

Two and four are closer than either is to one.
Showing approximately 38% identical, however may not be precise due to unmatched N and C termini. There are no identity hits to known Coprinus P450 genes.
* identity to cytochrome P450, putative [Cryptococcus SEQ ID NO: 611
>Crypto AAW43969

MTMELLKVLHHEASQLFPNCIRSSPVACIVLYSFGGIAILLFSVYLWLNPFQYAKLYFRNLFGPPSDSWFWGVVPIL
IKSPPSVPHSMWTDEYGPTVRYRVALGAQRFLTIDPTALNYILSHADLFPKPSRVRKALSDLLGNGLLTAEGHTHKR
QRKALNPSFSPAAVRGMIPVFYDKAYELKAKLLGIIEGDETEQASPIPCKEEDEVEGGKKIDVMKYLGKITLDVIGI
VGFSYDFKALSEPRNELSEAYSKMFQAGMDANFWDFLRGAIPLVNKLPNKRATRIAARKAVILRISKKIVEDKKREV
MSARSEGLEKREDIGDDLLSILIKANMASDVKPEQKLSDEEVLDQITTFMLAGNETSSTALTWILYSLIQHPECQTR
LREEVLAVPDDRPSLETLNNLPYMDAVIREALKLHAPAPGTMREAKEDIVIPLSMPVIGRDGKQIDSVKINKGTMVF
IPILITVNTSPAIWGPDARVFNPDRHLKTSSDSPGGANMHVPGVWGNMLSFLGGARSCIGYKLALAEISTILFVLIRS
FEFQELKSRPEVEKKASVVMRPRIKGEESAGLQMPLMVKPLLM

*FIG. 30A-2*

Whole lambda clone, reverse complement:

SEQ ID NO: 612

GATCATGTTAAGTTTATGCCCTAATCGTTGAGCGATAAAGAGCGACCAACCCCTTGTGAGTCTCGGCTCAGAAATAGAT
ATAACATCACCATACTGGAACGACAATGAGGCTGGCAGCTGAAAAATGGTGCAAAACAAAGACTCGCCAACCTGGCTCAA
AGCGGTTGTCCCTGCGAGCCGAGGATATGTGGTGGTATCCTCGGAATATATGTGTGTGAGCCTTGGGATCGCTCAATACA
ACATGGCTGTAGCCGATGCCAGTGGGTATCTCGTAAGGCCCATACATTCGTTCCCAATCCCGATATACCACCGTACTGAG
GTTCGCGGAAGGGAAGATCTTGGTGTTACTGAATCTGAAGCTCTCGCTGCGTGGTCCTTGTAGTCTGGGCGTTCTGATAC
CTCGGCATCTCCGATAGATAGAAATGACGACGAGCAATGTCAGAGGTCACAATCCTTATCGAATTACCTTTGAGATACTC
TGCCACATCAGCCCAGAGGCCGTTGGAGTTGAGGTTCAACATCACGGGTGACGGAGTGGACGAGCCGTTATGCAAGGAAG
GAAGGCCATCGCGGATAAGTACTAGTATAGCAACCAACCCAACCAGACGTGGAAATGCCATTGAAGGGTGGGAGTTGCGC
GAATACGAGGAAAACGTTTCTGAGGAGCCGAAACCGTAACCAGGCGCGAGAACTTGACCTATCTATCTCCGGGAACGGTG
TTGGGGGTCCATGTTACCGTGAAGGTGGATAGGGGCGGATTCGATTCCAGGAAAGTTAGAGCCACATAGTCATAAGTGAT
GCAACACGCCTGTGCGCGATGGAGATAATGCGTCTTTGTTGCATCGGCAAACCGGGTCACACGGACGAAAATCATTACTA
CATGGTCCATTTCAGGACAAAACCCCTATCTATTGATCCTACAAACTGCTTGACTGTTCAATCTGTGACCACCGGGACAG
ACAAAGCTGTGCTCAGTGGGGTGTTTAATCCAGCGAGAAACGCGTTAGGCCCAGTCGCCGATCAGGATACGACGAAAAA
GTGTAGGGTCAAGACTCCCTTGATGCGATTCAACTATTCTTGACGGGGGGTTGCCATTGTATTGCACCGTCTTGCCCGAC
TGCCTGTGCCCCGCAAAGACAGAACGTCCCAAAAACAGGAAAGAACAAAGAAGTTTTGTGGAGCCTGCCAAGAATGTGTGA
TGAACAGTGACTGACAGCATGAATGGGGATGAATATTGAATACCGAAAAAGGATGATCAGACAACTGTTTATGGAGATT
TTGCGCCAACTCGTCTTCATCTCCGTGTCAGGACAAGATTCTCTTATCTATCGTCCTTTCCGCGGTTTTTGCAACCATGC
GAATTCGTGACTGAGACAGATAAAAGGCGTTGGATTCAGCTTAGCATTCAATATTCAATACTTACCTCCCATTCGAACTC
GAGCCCAAGACCTCTGCTCTAAATCACAATGTCTGACATCAATGCCACCCGTCTTCCCGCTTGGCTTGTAGATTGCCCAT
GCGTCGGTGACGATGTCAACCGTCTCCTCACTCGTGGCGAGAGGTGAGCTCAAAATTCCATTTAATAATGTAGCAATGGA
CTCATGTGTCGTGTATCAGCCTTTGCTAAATGTCTCATCCACTAGTCAAGGTACCCGCCTCGGATTTCATGATAACGAAG
GGTGATTGTGCTGACTATGACGAAGGCAAATTGTAGAACACCTCTTGCTTGCAAAGCGATGATCGTGCCGCTGAACCAGC
GTCTTAAAGATTGTCGTGATAATCATCGGGACACTTGGCTAACACGACTGAAGTACATTACCCTTCTTACTGATTCTCC
TTTGTCAATCTCTAATACCCCCCTCAATGATGCTCTGAGCTGTGCAATGCAATGCACTAGAGAAGGGGGGGGAGGTGTGA
GAGATAGCATCTCAACATTTATCAATGCCAGCTTGTATGCCGCGATCCACAGCAGACCGACCTGACCGACCGTGTCATTG
CTACTTGCGTACTTGAACATATCACATACAACATTGGCAGCTTTTGTACCGTTTAAGAGTCCTGCGGCGTGTAGCCTGGA
AGAATTTCCAGCAGGGGTCCTTCCTGATGAGTTTGACAGCTCGCATAGTTGTAAAAGCGGCAAGTCCACAAAAACAGCGA
TTTTATGTTACATTGCGTGACGAGGAGGTAATGAGAGCATGAGACCGAGCATTTTGCAACCTTGAACTGGCCGAGCACCT
GAGAGAAAGATGCAACGCCGATGAGGAAGAATCATGGTGATGATGTATGTATAGGCATGCGATGGCATGTCCTGGCGACG
ATTGGCAAGAGGCGGAAGGCTCGCTTGGGGCGGAAAACACTGCAGGCTGCAGGCGTGCTCGAGGAGAGATAGACACGCT
ACGTGATTACTACGCCAGCCCTCTCAGGCTGTAATGATCGTTCATCAAAGTTGGTTAGAGTGGGCTGGTGATGATGCATC
TTGTGTCGGTGCGTGGCACGATGGACTATGGGAGGCAAGTTTGGCGTACTAGTAGGTCTATAAGGATGATGTGAAATATG
TGGGTATGCCAGTCATCCAACCTACCATTTACGTCACGATGCTAAGCCTCATCGCCACACATCTGAAAAGCTGGTCCTCC
ACGTGAAGTGAGGAATCATGAAAGTCATTTTTGCTTGGAAGGAAAGCCCATGCGACTCAGTAAACTCTACTAAGACACGA
AACGAACGATGTTGCACATGAGATCCTATGTCAGTCTCGCACAGCATAGGCACTTTCGGACCATCCTCGCCGGCTACCTT
GGGCCGCCCGAACTGCCAACTCAGTTCCGTCGATGGTCCATTGGCGAACTCAAAACTGAAATGGAGGACCAGAATCACAA
GCGCAGCCTGGCAATTGTCAAGTCAAAAATGAATAAAAACCGGCAGGAGTTTCGCCATACCTTCATCTCCAGCAAGGCGA
GGTCTCTTCCCGGACACAGCCTTTGGCCAGCACCGAAAGTCAATAGATTTCGGTAGCCGGGTACTTTCTCCCTTCTTCCT
TTCTTATGACCATCAACTTCCAGCCACCTGCTTGGATCGAATGTCGCCGCATCCGGTCCCCACAACGTCTCTGATATATT
CATTCCTCCTAAAGGGATGCGGAGACGGTGCCTTTCCTCACGAACAAGCTGTCGATCATCGCTCCAGATGCAGTTCGTAT
GGGATCCGTCAGCGGTATCACATCGTCTTCGGCTGCCTAGTCGAAAAGATCGTCATCATAAAAAGATAGGGATGAAAGGA
AGGGACGAACCACGCGGGTTAGTACCATTTCTGAGGGATGTAACCTCAGTATCTCGGATATAAAAGCATCGAGGTATTTC
AGATCCTTTGTCAGCTGGTCGTATGTAGGGCGTTCTCCGTCTGCCAAGCACTCCTTGAGTTCGGCACGGAGAGTCTCTTG
AATTTCTGCCCGGCGAGCAAGCTCAATGAGGGACCACTGAGGGAAAGCTCGGCGATGGATCTCTTGTAGATAAATAACAT
TACCGTCATGGCAACTGTGAACAGCATAGTTAGTGGATTATGAGATCATCGGACTGCTAGTCATAGAACTTACTTGCCGT
AGTTTCATACCCGGCCAAGACAAGACCACCCTTCGGTTATATCAGGTCAGAGTGGATACAAAAGAGATTGCATAGGGACA
TACAGCCTACAAAGGATGTTGATCGAGCACCGACGCCGATGTGTGAAGCAACTTACCTGGCCGTGATCTCGGGAAGTGA
TAAACGGACGTTAGCATTTTCATTTTTGGACTTGACTATATATAGGAAACCTGAAATCTCCTTACACGTGGTCAGGATAG
AGGTAACATACGCATAACCCCAAGGATTGATTGGTGAACGGCGCTATCTTCAGGCGCCTCACGTGCTTCCCGCAGAAAGC
CAGTCGCGAGTACTTTAAAGTGCGCTGCCAGTTCCTCAAACTGCTTTTCTTTGGCATTCGGTAAGGTAATCTTGAAGAGC
TTATAAAGTATCTCGCGGGTAAACACAATAAACCTTATGTAAAGGCCTGAAGGGCTGACTGCGTGGAAAGCATCCAAGTC
AGCTAAGATCGAACACGTATGGCCCCTCATGTTGCCGAAGTCATACGACAATACAGCTTTTCCAATATTATCCATGCTAG
GAATATATTGCAGGTGAGAAGAATGGGGCAGAGTAAAGGTTGCGAGTCATACGTGTAACAGTTCATCCTTGGGCACATAA
TGAACCAATTAAATGAAGGCTAGAAGGAAAGCAACTCACCATTTCTCTGCATCAAGCACGATAGCACGGTTCGAATTGTT
TGACAACTGGAAACATGAATCCCATGATGCTTTGAGCTATCATTTGTGCTGTTCAATCGACTGACTCTCAAAGCTGGAAC
CGTCCTGACCTGATAGGCGGAATCCAAACACATAGGAGTGAAATTGCGGATTGCCGAGACCGACAGGGGAGAAGACAAGA
CCCTCCGTATTCTATAATCCGTTCAATATTAAATTTATGCCATGTTTTCAAGCAGTCAAGAGCGACCAACCTCTTGTGGG

FIG. 30B-1

TCTCCCCTTCCGTGAGCACCAAAATATCACCAAACTGGAACAAGTTAAGTCTGACAGCTCGGGAAAACGCTGGAACAAAC
GCTCACCAACTTCCGCCCCATGTCTTTCTGCCTAGCAGGCTGAGAATATGTGACAGTGTCCTTGGAAAATAAGTGTGTGA
GAGCCTTGGGATCGTTCAATACGACGTGGTTGGAGCCAAAGCCAGAGGCTATTTCATAGACGGCCCGTAAGTCTGCTCC
AAACCTTGATACACCAAACTGAGGTTGGCTGAAGGGAAGATCTTCCTAGCATTGCCGAGGATGAAGCTCTCCATGTGTGG
TCCTTGCAGTCTCGGCGTTCTAGGACCTCGACGGCTTGGGTAAATGGAAACAACGACGAGCAAGGATATGCCAGAGGCTA
TTATCCTCATCGAATTGACTTTGAGGTACTCCGCGACATAAGGCCAAAGGCTGCTGAAATTGAGGTTCAACATCGCGAAG
AGAGCGATCGCGGGCCGTTACAGAGGTGAGACCACCAGTAGGCCATCCAGATATGGATACGACTCAAGATAGAAAATGGG
GTCCTCACCAAAAAAGGATGCCAAACTGGCGAGTCTCCAAGTCATTTCCATCAAGGGCGGACAGCCTCAGCGGGATTTAC
TATTGGCCCAACTGGATATGGATAGTGTGGGGTGAATAGTATAATATTGTGAAGAAGAAGATGATGAGTGGGGGACAGCA
TGAATGCAAGATCTGTCGCTGAAAAAGGATGAAAGGTCACTGATGATCTATGATCAGATTGCTTTCGACGATTCGGCCGA
AGGGATCACATTCTATTCTTGCCGACGGTTTATTTCCTATGGGTGACGGTTTGCACGCTTACGGCCGCGCGGGTGGGAAC
GCTGCGAAAGAACTTTCCGTTTGTATCGGGCCGGTAAATCCCGAGGCGCGACTGGCCACGCTGAGCCAAACAAATGAGCG
TCACTGCGGATTCAGGCACCCTAACTACACGCAGAAGCCCTACTTGGGTGCTCATCTACTGATAGCTAATGAATATTGAG
GCCAACTCACGAGGCCTCGTAGGTGGCTGTGGTAATCACTGTTTGGCGCAGGTATGTCTCATCTTTCGAACTGGGCGTCG
CATTTGGATTTACCATCAACCAGTCGCGGTTGCGGCCGCATGTCCTTGACAGGGCAGGTTTCAGGCTGACTTCATACCAG
AGATCTGATGTCGCAAACATCGCCAGTGATTTCGTTCCGTTGTCTTACTAGAGTTTGCTGAGCTGCATGGGCTTTCCTTC
CAAGCAAATATGATTTCGTGATTCCTCACTTCACGTCGGGAGCCCAGCTTTTCAGATATGCGGCGACTGCCTCCCATGG
TCCATTGTGCCCGGCGTCGACACAACATACCTCATCACCAGCCTTCCCCCGCGACTTTAGCCAACTTTAATGAACGGCCC
TTGAGAGACTGGCGTAGTAATCGCGTAGCGTGTCTATCTCTCCAATCGTCGCCCGTGTTCGCCTACACACATGCGATCGC
ATTATGCCTACATCATCGCCATTCTCTCCTCCCCCTCGTCATCGGGGTTGCTGAGCCTGCTTTTTCCCGGGTGTAGTTCA
AAGTTGCAAATTGCTCGTCTCATGCTCCTCGTCACGCAATGTAACATAAATTCACTGTTTTTGTGAACTTGCCGACTTCC
ACAACTATGCGAGCTATCAAACTCATCATAAAAGACCCTTCTTTGAAATTCCTCCAGGTTATACGCCCCACGGCTTTTCA
ATGGTACAACAGCTGCCTATGTGATATGTGATATGTTGCTGACAAGTAGCAATGATAAGGACAGTCAGGACGGTCAAGCT
CTGGCGACAGCAGCATGCGCTCGGATTGCTAAACGCTCTCTTACTGACAACACACACACATACACACACAAGTATATTGC
ATTCCATAGTACAGCTCGGATCATTTACGTGGGTTTTATATGAGAATGAGAAAGAATGAGAAATAACGTGAGTCGTCTAA
TCCAAGTTGGCTCGCTGCTTATCACAGAAAAACTTGAAGGCCTTACTTCCGATGCAGGCTCAACGCTCCAAGCCTAACAT
TGTCAACAACTTGCGTCGTCCACTACTACATCGAAGTAAGTACCATGACCATGCATTGTCATCAAGAAATCAGAGGCGGA
TACCTTGACTAGTGGATGAGACATTTAGCAAAGGCTGGTACACGACACATAAGTACATTGCTACATTATTAAATGGAATT
TTGAGCTCACCTCTCACCACGACTGAGGAGACGGTTGACGTCGTCACCGACGCATGGGCAGTCTACAACCCAAGCAGGAA
GACGGGTGGCATTGATGTCAGACATTGTGATTTAGAGTAGAGGTCTTGGCTTCGAGTTCGAATGGGAGGTAAGTAATATT
GACAGCTGAGCCGCATCCAACGCCTTTTATCTGTTTCAGTCACGAATTCGCAAGATTGGAAAACCGCAGAAAGTACGATA
GATAAGAGAATCTTGTCCTGACACGGAGATGAGAAGACAAATTGGCGCAAAATCTCCATAAGCGTTTGTCTGATCGGTCT
TCCCATGAATCATTCATGCTGTCCCCCACTCTTTATCACACAGGCTCCACGCTTACTATATGGAATCCGTGAACTTCTTT
GTTTTTAGGGGCGTTCGGTTTCTGCGGACATTCAGCCGGGCAAGACGGTGCAATACAATGGCAACCCCGTCAAAAGTTGT
TGAATCACATCAAGGGAGTCTTGACCTTAAGCTTACACTTTTCATCGTATCCTGCGTGTTGGCGATTTATGCCGAACTGG
GCATAACGCGTTTCGAACACCACTTAGCACAGCCTCTCTTTGTCTGTCCTGGTGGTCACAGATTAAACAGTTAAGTGGCA
GTCCTACAGACCGATAGATAGGTGTTTTGTCCCAAAATGGACATGTATGAGAATGATTATCGGGCGTGTGTATTTAAGAA
TCCCTTCGGCCGAGTTCCCGATCATTCGGCTCCATCTTGCGCTCACACTTGTGTTGCATCATACGAACGTTTCGTCTGTT
CTTTCCCGGAATCGGATCTGTCCCTATCCACCTTCACGGTAAGATGGACCCCCAACACCGTCCCCGGAGATAGATAGGTC
AAGCATTTATCGCGCCTGGTTACGGTTTCGGGTCCTCAGAAACATTTTCCTCGCATTCGGCAACTTGATCGCCTTCCAC
GGCTCGTCCACTTCGTGATGTTGAACCTCAACTTCAACGGCCTCTGGCCTGATGTAGCAGAGTATTTCAAAGGCGATTCG
ATGAGGATTGTGACCTCTGCCTTTACGTTGCTCGTCGTCATTTCTATCTATCGAAGACGCCCGAGGTATCAGAACGCCCAG
ACTGCAAGGACCACGCAGCGAGAGCTTCATCTTCGGTAACACCAAGAAGATCTTCCCTTCGGCGAACCTCAGTGTGGTAT
ATCGGGATTGGGAACGAATGTATGGCCCCGTTTACGAGATACCCACTGGCATCGGCTCCAGCCATGTTGTATTAAGCGAT
CCCAAGGCTCTCACACACATATATTCCAAGGATACCACCACATATTGTCGGCTCGCAGGGACAACGGCTTTGAGCCGGAA
GTTGGCGAGTATCTGTTTTGCACCATTTTTCTTAGCTGCCAGCCTTATTTACGTTCCAGTATGGTGATGTTGTATCTATT
TCTGAGGGCGAGACTCACAAGCGGTCGGTCACTCTTTATCGCTCAACGATCAGGGCATAAACTTAACATGATCGCAGACT
ACGGAGAGGCCTGTCTTCTCCACTGTCGGTCTCAGCAATTCGCAATCTCACTCCCGTGTGCTTGGATTCTGCCTATCAGG
TTAGAATGGTTCCATTCTTAAAACAATCGGCCGATTGACCAACATAAATGACAGCTCAAAGCAGCATGGGATTCATGTTC
TCCGTCATCAGAGCACTCAAACAACCCCGTCATAATTGATGTCGTGAAATGGCAAGTTGCTGTATCTATCTCCCCCATTG
TTAGTTAACCTTGTTCTCTGTGCCCAAGGATGAATTCTGTCACGTACGTTGCGCAGCCTTCATTCCGCCCTTGCCCTGAA
ATGTTCCTAGATTGGACACTATAGGGAAAGCTATATTGTCGCATGACTTTGGAACTCTAAGGGGCCGCACGTCCTTGATG
ATGGCCGCCTTTGACTCTATCCACACAGTCAAGCCTTCCCCCTTTATAAGGCTTATTCACTTTCTGTCACCGATACTCTA
TGCCCTGTTTAAAGTTACCCTCATGAGCGTCAGAGAAGAGAAGCTCGCACAATCAGTAGCACACTTGAATAGGCTTACAA
CTAACAGCCTGAACAAGGCATGTAAGGAACCGGAAGATACTGTCAACGAATCAGTCCTTGGGATTCTGGGTATGTCACCA
ATATATGAGGTGATGTTTCTTCGTGGCTACGCTTGCCTGTATAGTCAAGTCAGAAAACGCAAATCCCAACAGCCGTTTGT
CACTCTCCGAGATCACGGCCCAGGTATGTAGCCCAAGTGCACATCGGCTTGATGCCTAATCAACATACTTTGTAGGCCGT
ACGTACCTTTGCCACTCCTCTGATATTCTCTGTAAGTTAATATAACCGAAGAGTTTCCTTTTCATGGCTGCATATGAAAC
AACAGCAAGTAAGTTCTGCGAACGGTTGTCCTTGTTTATCAAAGATCTCATAAACTATGACCCGTGCTGCTCATAGTCAC
CTTAACGGTAATCTTCGCCTACGAGTGTTCAAGCTGTTCTATTACTGAGCCTTCACTCAGTGGTCTCTCATTGAACTTGC
ACGCCGGCCAGAAATCCAAGAGAGCCTCCGTGCTGAGCTCTCAGAATGTTTGGCAAAGGGAGAACGTCCTACATACGACC
AGCTAACAAAGGATCTGAAATACCTCGATGCTTTATAGCCGAGATACTGAGACTCCATGCCCCCGAAATGCAATCAATC

FIG. 30B-2

CGTGTGGTTCGTCTTCATTGTTTAATTCCTTCCCGGCATCCCCCTATTATCTTGGCAGGCAGCCGAAGACGATGTGATACC
GTTGACAAATCCCATACGTATTGCATCTGGAGCGACGATCGATAGCTTGTTTTTGAAGAAAGGTATGGTCGTCCGTATAC
CCTTGGGGGAGTGAATATGTCGGAAGCGTTGTGGGGGCGAGACGCGGGCATGTTCGATCCAAGCAGATGGCTGGACGCT
GAGGGTCATAAGAAAGGAAACAAGGGAGAACTAGCTGGCTACCGGGGTCTCTTAACTTTCGGTGCTGGTCCCAGGATGTG
TCCAGGCAGAGACCTCGCCGTACTGGAGGTGAAGGTACGATTGAACCCCATGTCAGCGGTTTGGTTGTTTGACTGCACAA
TCTCTAGGCTGTGCTGTGGGTTCTGGTCAGATATTTTGCCTTTGAGCTCCCCAATGGGCCATCGACGGAACTGAGTTGGC
ATTTTACGCGCCCCAAGGTAGCTGGCGAGGATGGTACAAAAGTTCCTCTTCTTGTGGGAAAGTTAACATAGGCGTTCCCC
GTACCACTGTTTTTGTACTAGGGTAGAAAACATGGTGCTGGTGCTCGCCTACTTGATAAGCAGACTCCTGCGAAACACCA
TGTCAATCGATGACGGGCATAACAGACCACGACATTGGGGCGATGAAGTCGGTGGTGACTCATACGAGTCGTATTGTAAA
TTTTTGCTTGGGAAGTCATGGCATGTGGCAACAGTTGGCCCCCACTGATGTCATTCAACCAACCGACATCTCGAGGCTTGC
GCTAAAGTGTCCCGCCATTAACCCCGCGTTCCAATGCTGCGTCATCCGCAGTGCCTGCACCGTCAGAACGCATTTAGTAG
TGGCAAGAAGCTTCTGTCAAATTCAATCGCTAACCGGTTCTTTGACGGGCTAGAACCCTGGTTATGAACTAAACTTCGGC
GGCAGCTCGCATGCTCAAGCTCTTTTCCATCCTCGACATTTTACTCTCATCATTCTCAGCCCGAACTCAGTTGGTAAT
TGACTGCTATGTAATATCATAGATGCCAGTACAAACTCCACACAGTGGTCCCTAGACCTCTAGGTATAATGAACCACGAG
GCGCGTTAACTTCGAGCTTTATATGGCTTGATGAGCAGCGGGACCTGATAACGGCCCGGGTCCGTGGTCAAAATCGGTCG
GTTACTTAGTCCACTTTCCACAGAAATTTGCTCCGCTGGCACAGCCAAGTCAAATTCGAGGGCACGGACTAGTGTGAAGA
GTAGAGCTTTCATTCTTGTCGTTACCAGTGTCAGCACTATATCTTCGAAATGCTAGAGAAAACTTGCTCACTCGGCGATA
GCAAATCTGAATCCGATACACGAACGTGGACCACCCCAAAAACTGAGCAAATGGCTCCAGACGCCTGGGATGGTATTGAC
GCCTTCAGGTAGACATTCCCATCGTTCTGGTCTATCAAAACTGAATGACTCAGCAGCCAACAGCGACGTGCAATATTTAG
CTGAAGTCTAAAGCATCTTCACCCCATATCGACTTGTCCTTGTGGATGGCAGAAATGGGAATTATGACTACTTGCCCTCT
TTTGATACTATAAGACCGGTGAACGCTAAAAAGAAATATGGGAACGACCGAATCCTCACCTAATACTGGAGAATAGGTTT
CCTCTCCGGTCGGTGATCGGCTTAGCCAAAGGTAAAATGTCGTCCTTGGCACACACCCTCGAGTGGCCTAGATGAAGGAT
ACAGACGTAGCGTCTCCCTAATTACCATATCCAAATATGAAAGTGCATTGAGCTGGTCCGTCGTTGGCTGACAGGTATCG
ACCGTGAGCAGCTCTCTACGCAGCTTAGCCTGGATTTCACGGTTTTTTGCCCAGAGAAAATAAAGCCCACGCCATTACGTT
ACTACCAATCAAATATTCGAGAATAGTCCTTAAACAGATAAACAGACTCAGACTTACATCGGACTTTCACGTCCAGCAAT
TACAAATGAGATAACCTCTAAATAAAAAGATCAGGTATACTCGCAGTGACAAATACATCAGCCTCACGCGCTTTGACTTC
GTCATCGGATAGACGACGGTGCTCTGGCACATCGGGGGACATATTGGTGCGAACCAAAAGCGATAGGAGATCTCGACTGC
CGGAATTGTCATTATTCGTACGTACCGATCCCTTGCTCTCGTTCAGAAGCCGACTCGTAATCCGAGAAAGGGTCTGCCTG
ATATCGTCTAGTTGTGTCTCTACAGGATCAGGCTAGACAACGCGATGAGAACTCCGTTACAGTGATTTGGAATTTCCATA
CTATGAACCATAGAAGTGGGATCAATCTTGGAGTTGCCAACGAATCAGGTCAATTGAGATAAAATTGTAGCCACAGG
CTAAAGTCACTTTCACGATCCAGGGAATCAAGCTCGTAACGGAAGCCTTTCCATCGAATGGCATCGGTAAACACTAATAA
GTATGCTGGCAACATCAGACATACCTGTTGAGCTGATGATGTCCATCACCACCTTACCAAGGCCTACCATAATGTCTAAG
CGGCAAGTACCACCTTGTTTCGAGCATTCAGTAGCCCAAGAGTCTTGGAGCTAGGCGAAGTTCATCACTGGTAGCATGGA
TGAGTAGTAAAAACCGACCCGTTTTGATTTTTTACGAAGCAATCTGTGAATTCGCGAATGCGGACCGGACCAAAGGCAG
GATTCTGGTTGTGATTGAGACACTGATGGACCACGATTTGGAATGGATAGATAGTCACCAAAATCTTCCGCTGTTAAACG
TAATATATCATAATACGAACTAGGTTGAGGCAACGGAAGTACGCACCGGCTTTTATGTTGATCCCCTTCGACAAAAGGG
AGACCTGACGTATGGTTGGATCATCGGCTCTTAAGTATGGTAGGTGAAAAAGCACCTGGACCCCAGAACTTGCCGATCTG
GCGGCGAGTAAACGATGGTTGGTGTAAACGTAACCATTCGTCAAAATGTGGTTCAAGGCCTGCGGATCCGTCAGATATA
AATGCGAAAGCTAAACTTGATTGTTATCTATATCAGAATAAATGGATTGGTTCTTACACCGAGAAATCCATTTAGTCTTA
TCATCGGCCCATATTGTGAATGCCAATGATATGTCTGTGGTAATAGTGGTTAACAATGGGTGGGTAGGTGGGTGATTTTG
TACTTACATCTGTCCAGAGCTGTTTGAGATTACCAAGAAATATATTGGCGTTTGCTGGACCGGGGAGATGGCGTATTGGA
GAAGTCAGCTCAACATAAATTACACGAGTGACTCTGTAAAGTCCATAGATAGTCAATGCAGCTGCAGATAGCTTGAGGAA
TTGGAATATAAGCCTGAAAGTGACGAGAGCTGAATACGAGATGGTGTCCAAGTCGACCATTGTTATTAACTTGGTAACGG
GCAAACGTTTCAAACTTGTAGGTGGATCGGTTAAATCTCCGATTGAAGATGATGCTGAGTTTCGTAGGTTGCACTGATGG
TTCCGATTCGTCCCTTTTTTTCGGTGAGAGACACATTATCTTCATTACTGTATCTTTTGGATTTACTAGCTCCCCCCTGT
CACCGTCTCCACTTTCCATCATCGATTATCGATTCTATCCATTTCTTGGTTATGCTACGCTCCCATCATGGACATCGCGGC
CCTTCGGCTGCGATGTGCTGAAAATAGTGAAACTTCTCTGACTTCTCTCCGATC

SEQ ID NO: 613 sequence at ~11,000 (in original orientation):
APTRLHLRVRIRFSYLSSFPRFLQPCEFVTETDERRWIQLSIQYSILTSHSNSSPRPLL-
ITMSDINATRLPAWLVDCPCVGDDVNRLLTRGER-AQNSI---CSNGLMCRVSAFAKCLIR
-SRYPPRIS---RRVIVLTMIRANCRTRLACKAMIVPLNQRLKDCRDNHRGHLANTIEVHY
PSY-FSFVNL-YPPQ-CSELCNAMH-RRGGRCER-RLNIYQCQLVCRDPQQTDLTDRV SEQ ID NO: 614 sequence at ~6400 in original sequence:
LCDKEWGIA-MIHGRTDQINAYGDFAPICLLISVSGQDSLIYRIFCGFPILRIRD-NR-K
ALDAAQLSILLTSHSNSNPRPLL-ITMSDINATRLPAWLVDCPCVGDDVNRLLTRGER-A
QNSI--CSNVLMCRVPAFAKCLIR-SRYPPLIS--QCMVMVLISM-WTTQVVDNVRLGA
LSLHRK-GLQVFL--AASQLGLDDSRYFSFFLILI-NFRK-SELYYGMQYTCVCMCVCCQ
-ESV-QSERMLLSPELDRPDCPYHCYLSATYHISHRQLL

*FIG. 30B-3*

FGENESH of reverse complement: Compared to normal (5'- 3') complement,
genes 1,2,3,5,6 are the same, but gene 4 (gene 3 in RC) is different:

SEQ ID NO: 615 >FGENESH:[mRNA]311 exon(s)3129-5780 1512 bp, chain-

ATGTTTGCGACATCAGATCTCTGGTATGAAGTCAGCCTGAAACCTGCCCTGTCAAGGACA
TGCGGCCGCAACCGCGACTGGTTGATGGTAAATCCAAATGCGACGCCCAGTTCGAAAGAT
GAGACATACCTGCGCCAAACAGTGATTACCACAGCCACCTACGAGGCCTCCGTGGCCAGT
CGCGCCTCGGGATTTACCGGCGCGATACAAACGGAAAGTTCTTTCGCAGCGTTCCCACCC
GCGCGGCCCCTTTGGCCTTATGTCGCGGAGTACCTCAAAGTCAATTCGATGAGGATAATA
GCCTCTGGCATATCCTTGCTCGTCGTTGTTTCCATTTACCGAAGCCGTCGAGGTCCTAGA
ACGCCGAGACTGCAAGGACCACACATGGAGAGCTTCATCCTCGGCAATGCTAGGAAGATC
TTCCCTTCAGCCAACCTCAGTTTGGTGTATCAAGGTTTGGAGCAGACTTACGGGCCCGTC
TATGAAATAGCCTCTGGCTTTGGCTCCAACCACGTCGTATTGAACGATCCCAAGGCTCTC
ACACACTTATTTTCCAAGGACACTGTCACATATTCTCAGCCTGCTAGGCAGAAAGACATG
GGGCGGAAGTTGAATACGGAGGGTCTTGTCTTCTCCCCTGTCGGTCTCGGCAATCCGCAA
TTTCACTCCTATGTGTTTGGATTCCGCCTATCAGGTCAGGACGGTTCCAGCTTTGAGACA
TCATGGGATTCATGTTTCCAGTTGTCAAACAATTCGAACCGTGCTATCGTGCTTGATGCA
GAGAAATGCATGGATAATATTGGAAAAGCTGTATTGTCGTATGACTTCGGCAACATGAGG
GGCCATACGTGTTCGATCTTAGCTGACTTGGATGCTTTCCACGCAGTCAGCCCTTCAGGC
CTTTACATAAGGTTTATTGTGTTTACCCGCGAGATACTTTATAACCTCTTCAAGATTACC
TTACCGAATGCCAAAGAAAAGCAGTTTGAGGAACTGGCAGCGCACTTTAAAGTACTCGCG
ACTGGCTTTCTGCGGGAAGCACGTGAGGCGCCTGAAGATAGCGCCGTTCACCAATCAATC
CTTGGGGTTATGCTCAAGTCCAAAAATGAAAATGCTAACGTCCGTTTATCACTTCCCGAG
ATCACGGCCCAGGCTGGTGGTCTTGTCTTGGCCGGGTATGAAACTACGGCAAAGATCCAT
CGCCGAGCTTTCCCTCAGTGGTCCCTCATTGAGCTTGCTCGCCGGGCAGAAATTCAAGAG
ACTCTCCGTGCCGAACTCAAGGAGTGCTTGGCAGACGGAGAACGCCCTACATACGACCAG
CTGACAAAGGATCTGAAATACCTCGATGCTTTTATATCCGAGATACTGAGGTTACATCCC
TCAGAAATGGTACTAACCCGCGTGGCAGCCGAAGACGATGTGATACCGCTGACCGATCCC
ATACGAACTGCATCTGGAGCCATGATCGACAGCTTGTTCGTGAGGAAAGGCACCGTCTCC
GCATCCCTTTAG

SEQ ID NO: 616 >FGENESH: 311 exon(s)3129 - 5780 503 aa, chain-

MFATSDLWYEVSLKPALSRTCGRNRDWLMVNPNATPSSKDETYLRQTVITTATYEASVAS
RASGFTGAIQTESSFAAFPPARPLWPYVAEYLKVNSMRIIASGISLLVVVSIYRSRRGPR
TPRLQGPHMESFILGNARKIFPSANLSLVYQGLEQTYGPVYEIASGFGSNHVVLNDPKAL
THLFSKDTVTYSQPARQKDMGRKLNTEGLVFSPVGLGNPQFHSYVFGFRLSGQDGSSFET
SWDSCFQLSNNSNRAIVLDAEKCMDNIGKAVLSYDFGNMRGHTCSILADLDAFHAVSPSG
LYIRFIVFTREILYNLFKITLPNAKEKQFEELAAHFKVLATGFLREAREAPEDSAVHQSI
LGVMLKSKNENANVRLSLPEITAQAGGLVLAGYETTAKIHRRAFPQWSLIELARRAEIQE
TLRAELKECLADGERPTYDQLTKDLKYLDAFISEILRLHPSEMVLTRVAAEDDVIPLTDP
IRTASGAMIDSLFVRKGTVSASL

FIG. 30C

New blastp result: (quite different)

| | | | |
|---|---|---|---|
| gb\|EAU91561.1\| | hypothetical protein CC1G_02050 [Coprinopsis c... | 127 | 2e-27 |
| gb\|EAU83619.1\| | hypothetical protein CC1G_06332 [Coprinopsis c... | 97.8 | 1e-18 |
| gb\|EAU81974.1\| | hypothetical protein CC1G_09160 [Coprinopsis c... | 92.8 | 6e-17 |
| ref\|XP_569261.1\| | hypothetical protein [Cryptococcus neoforman... | 84.0 | 2e-14 |
| ref\|XP_777488.1\| | hypothetical protein CNBB0620 [Cryptococcus ... | 80.9 | 2e-13 |
| gb\|EAU84038.1\| | hypothetical protein CC1G_12478 [Coprinopsis c... | 76.6 | 4e-12 |
| ref\|XP_001622363.1\| | hypothetical protein NEMVEDRAFT_v1g176175... | 74.7 | 2e-11 |
| ref\|XP_001602787.1\| | PREDICTED: similar to cytochrome P450 [Nason | 73.6 | 3e-11 |
| gb\|AAY20974.1\| | astaxanthin synthetase [Xanthophyllomyces dend... | 72.8 | 6e-11 |
| ref\|XP_571276.1\| | Cytochrome P450 [Cryptococcus neoformans var... | 72.4 | 6e-11 |
| gb\|EAU83493.1\| | hypothetical protein CC1G_04749 [Coprinopsis c... | 72.4 | 8e-11 |
| ref\|XP_774660.1\| | hypothetical protein CNBF3400 [Cryptococcus ... | 72.0 | 8e-11 |
| ref\|XP_001603146.1\| | PREDICTED: similar to cytochrome P450 [Nason | 71.6 | 1e-10 |
| ref\|XP_970215.1\| | PREDICTED: similar to Probable cytochrome P4... | 71.6 | 1e-10 |

FIG. 30D

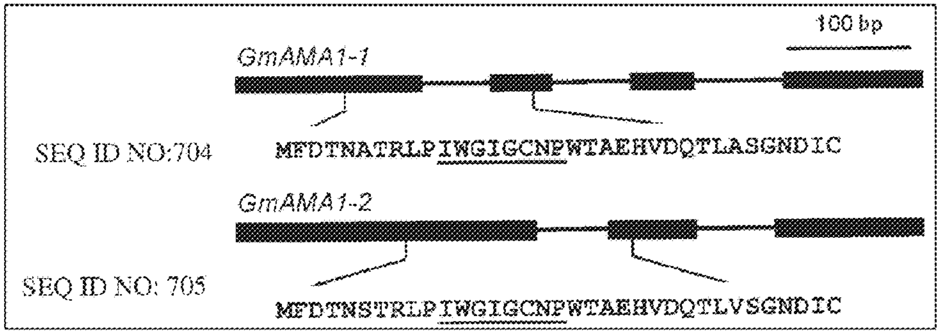

FIG. 32

| | | |
|---|---|---|
| GmAMA1-1 | MFDTNATRLPIWGIGCNPWTAEHVDQTLASGNDIC | SEQ ID NO: 704 |
| GmAMA1-2 | MFDTNSTRLPIWGIGCNPWTAEHVDQTLVSGNDIC | SEQ ID NO: 705 |
| Gm consensus | MFDTN[A/S]TRLPIWGIGCNPWTAEHVDQTL[A/V]SGNDIC | SEQ ID NO: 706 |

FIG. 33A

| | | |
|---|---|---|
| AMA1 | MSDINATRLPIWGIGCNPCIGDDVTTLLTRGEALC | SEQ ID NO: 617 |
| PHA1 | MSDINATRLPAWLVDC-PCVGDDVNRLLTRGESLC | SEQ ID NO: 619 |
| Ab consensus | MSDINATRLP[I/A]W[G/L][I/V][G/D]C[N/-]PC[I/V]GDDV[T/N][T/R]LLTRGE[A/S]LC | SEQ ID NO: 753 |

FIG. 33B

Consensus
(AMA1, GmAMA1-1)
M[F/S]D[T/I]N[A/S]TRLPIWGIGCNP[W/C][T/I][A/G][E/D][H/D]V[Q/T/-][T/L]L[A/V/T][R/S]G[N/E][D/A/S]][I/L]C
SEQ ID NO:707

FIG. 33C

Overall consensus
M[F/S]D[T/I]N[A/S]TRLP[I/A]W[G/L][I/V][G/D]C[N/-]P[W/C][T/I/V][A/G][E/D][H/D]V[Q/T/R][T/L]L[A/V/T][R/S]G[N/E][D/A/S][I/L]C
(AMA1, PHA1, GmAMA1-1, GmAMA1-2)
SEQ ID NO:708

FIG. 33D

E. GmAMA1-1 nucleic acid SEQ ID NO: 709

SEQ ID NO:711
SEQ ID NO:704

```
gatgctctaagatcacagaactccaccaatgaagacaggtcctcgtaatggcgtcgaaa
atgttcttggatctttattctagaagttcacagcttgcggagtcgctgctatttcctaa
ctcatcagctctattcggtcctcgagagagataaaggcgttcgtcagtgagagctgat
    *  SEQ ID NO:710
ctccaatcccccaaccacaaactcacttaaccaaagacctttttgctttaacatctaca

atg ttc gac acc aac gct act cgt ctc cca atc tgg ggt att ggc
 M   F   D   T   N   A   T   R   L  [P]  I   W   G   I   G

tgc aac cca tgg act gct gag cac gtc gac cag act ctc gct agt
 C   N  [P]  W   T   A   E   H   V   D   Q   T   L   A   S

ggc aac ga gtaagcttggtttctgttgttgccgtgttcgacgtactcatgttgtgcgttag
 G   N   D                    Intron 1

c att tgc tga acgtgtcccgcctgtcgttggcccgccgctttaacacgaag
   I   C   ^

gtgtggctatcttactactctcaaagcattgcattcaacaggcctgatatttccgagcag
                          Intron 2

tgggcaacgatacttatcgacgatgttaggcttggaacattgagcctttcgtag
gtcagaccttgtgctttattacgtggtattaaggagtactgacccatctactgtttttccttcatctag
                        Intron 3
ccattctttctcttttgtaaatcgataaaaccatacaccaactcgcatttgtaaattgataaaccctac
Gttgatgatcctcaccgttgaaataaatgtaaattttgagcca
```

* Asterisk indicates the transcriptional start site.

*FIG. 33E*

F. GmAMA1-2 nucleic acid SEQ ID NO:712

* SEQ ID NO:713 cgtcgaaaatgttcgagccatctggaagtttacaactttccgaaagtaatgcgaagcgg
gtgcttcctttcctatctcgtcggctctgtttcgtccttgggagagataaaagcagccc
atgcaagtgaaaaccgaatctccaatcctccaaccatcaactcaaccaaagatcttcgcccttgccttaatatctgcc SEQ ID NO:714 atg ttc gac acc aac tcc act cgt ctt cca atc tgg ggt att ggc tgc aac cca tgg
SEQ ID NO:705 M F D T N S T R L P I W G I G C N P W act gct gaa cac gtc gat caa act ctc gtt agt ggc aac ga
T A E H V D Q T L V S G N D gtgagctcaatttccgttgttgacatgttcgacgtactcatgcgttgtacgttag c
Intron 1 att tgt tga atgtctcctggacttgttgacaatattaggcttggcccgttgagcctttaccgcag
I C ^ gtcagaccatgcatctcatcagtggttttgagaaatgctgacttgcccgttatttctctttgtctag
Intron 2

Gacacgttctgtaacatttctgacccgtgatatgtaaattgtaaaccctacgtcgacgatcgttactgtttgaatgaa
Tgtaacgtttgattcattgcat

* Asterisk indicates the transcriptional start site.

*FIG. 33F*

>GmPOPA cDNA sequence SEQ ID NO:715

GGCTGTCCCTCCGTTCCCTCCCCTTTCCTAGGTCTCTAAGACGCGTTTTCACACTGTATAGGCGCTCCTCGTCGTCTCCT
GCGAACATGGCCCGAACACCGTGGCTTCCCAACGCATATCCACCAGCTCGTCGTTCCGATCACGTTGACATCTATAAGAG
CGCCCTTCGTGGCGACGTACGCGTTCAGGACCCGTACCAGTGGCTAGAGGAATACACCGATGAGACAGACAAATGGACGA
CTGCTCAAGAGGTTTTCACAAGGACTTACCTAGACAAAAACCCTGACCTCCCTCGGCTTGAAAAAGCGTTTCAGGCTTGC
AATGATTATCCCAAGTCCTATGCCCCTTACTTACATGATGACAACCGATGGTACTGGTACTACAATTCTGGCCTGGAGCC
GCAGACGGCCTTGTACCGGTCCAAAGACAGCAGTTTACCGGATCTCTCTACAGCCGATGGCAGTGGTGGCGATTTATTCT
TTGATCCCAATGCCCTTTCCAACGACGGAACTGCCGCTCTTTCAACCTATGCCTTCTCGGATTGTGGCAAATATTTTGCG
TATGGGATCTCTTTCTCTGGCAGTGATTTCGTGACAATCTACGTGCGGTTGACGGATTCCCCTCTCACTAAAGATGTGGA
CGCGAAGAACGACAAAGGTCGCCTTCCAGAGGAAATCAAATTTGTCAAATTTTCATCCATAGGATGGACACCTGATTCCA
AGGGCTTTTTTTATCAGCGTTACCCAGATACCTCCACCGTCACCCAAGAGAACGGGCCTATCGCGACAGAAGGTGACCTG
GATGCCATGGTATATTATCATCGCCTTGGAACACCGCGGTCGGAAGATACTCTGATCTACCAAGACAAAGAACATAGGGA
CTGGATGTTCAGCATTGATGTCACGGACGACGGCAATTACCTCCTCCTTTACATTCTCAAGGACAGCTCAAGGCAAAACT
TACTTTGGATTCCTGCATTTGATCCTGCAAATCTTGGTCCCAATATCAAGTGGCAGAGGGTCTTCGATGAATATCACTCA
GAATACGAGATTATCACAAACAAGGGCTCATTGTTCTATGTTAGAACTAACGAATCCGCTCCCCAGTACAGAGTCATAAC
GGTTGACATTGCCAAAGGGAATGAAATCAATGAACTCATCCCTGAAACCGATGCATACTTGTCCAGCATTACCAGCGTAA
ATAAGGGCTACTTTGCCCTCGTTTACAAGCGCAATGTAAAAGATGAGGTATATGTGTATTCGCATGCTGGAAACCAGCTC
GCTCGCCTGGCTGAGGACTTTGTGGGCGCTGCTCATGTGTCTGGGCGTGAAAAGCATTCCTCCTTCTTTGTCGAACTGAA
TGGCTTTACCTCACCTGGCACAACTGGTAGATACAAGTTTACCGATCCTGAGGAGCAGCGGTGGAGCATTTACCGAACAA
CCAAACTCAACGGCCTAAATACAGAGGATTTCGAAGCTAGCCAAGTATGGTATGAGAGCAAGGACGGCACAGGCATCCCA
ACGTTTATCGTTCGTCACAAATCAACGAAATTTGATGGCACTGCCCCAGTCATACAATACGGTTATGGTGGATTCAGCAT
CTCCATCGACCCCTTTTTCAGCGCGACAATTCTTACATTCCTCCAAAAATACGGCGTCGTGTTTGCGCTTCCAAATATCA
GGGGTGGCGGAGAATTCGGCGAGGACTGGCACTTGGCTGGATGTAGAGAAAAGAAGGGAAATTGCTTCGACGATTTTATC
GCCGCAACCCAATACCTTGTGAAGAATAAGTACGCAGCTCCTGACAAGGTAACAATCAATGGGGGGTCGAATGGCGGTTT
GTTGGTTTCTGCTTGCGTGAACCGCGCCCCGGAGGGTACGTTTGGCTGCGCTGTAGCCGACGTCGGAGTACACGATCTTC
TCAAGTTCCACAAGTTTACTATTGGTAAAGCCTGGACCAGTGATTACGGTAACCCTGACGATCCAAACGACTTTGATTTC
ATTTTCCCCATATCCCCGCTGCAAAACATACCGAAAGACAAGGTGTTCCCTCCAATGTTACTTCTAACTGCTGACCATGA
TGATCGCGTCGTGCCCATGCATTCCTTCAAGCTAGCTGCTGAGCTCCAATACTCGCTCCCACACAACCCGAACCCGTTGC
TCATCCGAATAGACAAGAAAGCCGGTCATGGAGCTGGCAAATCAACTCAACAAAAGATCAAAGAGAGCGCGGACAAGTGG
GGATTTGTCGCGCAATCGCTCGGACTTGTTTGGAAAGACTCCACTGAGCAACCCAATCTCTGATCCATTATTGAAAGTTG
CTAATCGTAGAATCCAGCTCATGAGTATGTTACTCTCTCGTCTGGGCATGTTGTAATTCGGCCTCGCCTCATGACTTTTC
TATGATATAATGGTATATACTTGGGTC

Underlined ATGs are contemplated translational start sites

Exemplary Sequences of prolyl oligopeptidases Isolated from Galerina marginata.

>protein sequence of GmPOPA SEQ ID NO: 716

MARTPWLPNAYPPARRSDHVDIYKSALAGDVRVQDPYQWLEEYTDETDKWTTAQEVFTRTYLDNNPDLPRLEKAFQACND
YPRSYAPYLRDDNRWYWYYNSGLEPQTALYRSEDSSLPDLSTADGSGGDLFFDPNALSNDGTAALSTYAFSDCGKYFAYG
ISFSGSDFVTIYVRLTDSPLTKDVDAKNDRGRLPEEIKFVKFSSIGWTPDSKGFFYQRYPDTSTVTQENGPIATEGDLDA
MVYYHRLGTPRSEDTLLYQDKEHRDWMFSIDVTDDGRYLLLYILKDSSRQNLLWIAAFDPANLGPNIKWQRVFDEYHSEY
EIITNKGSLFYVRTNESAPQYRVITVDIARGNEINELIPETDAYLSSITSVNKGYFALVYKRNVKDKVYVYSHAGNQLAR
LAEDFVGAAHVSGREKHSSFFVELNGFTSPGTTGRYKFTDPEEQRWSIYRTTKLNGLNTEDFEASQVWYESKDGTGIPTF
IVRHKSTKFDGTAPVIQYGYGGFSISIDPFFSATILTFLQKYGVVFALPNIRGGGEFGEDWHLAGCREKKGNCFDDFIAA
TQYLVKNKYAAPDKVTINGGSNGGLLVSACVNRAPEGTFGCAVADVGVHDLLKFHKFTIGKAWTSDYGNPDDPNDFDFIF
PISPLQNIPKDKVFPPMLLLTADHDDRVVPMHSFKLAAELQYSLPHNPNPLLIRIDKKAGHGAGKSTQQKIKESADKWGF
VAQSLGLVWKDSTEQPNL

*FIG. 38A*

>GmPOPB cDNA SEQ ID NO: 717

CTACTTCTCCCTTTTGTCCAGAAGCCCTTTATCATATCTAAAATCGTGACAGTGGCACGGACCGTGGACGTTATCCCAAA
CCAACCCTATTGGTACCCTTAAAAAACAGGGTTTTTCGATGTCCGTCTTCCAGCCGTATCGCTGACCCCACAATTGCGGA
AAACTATGTCGTCTGTAACCTGGGCTCCTGGAAATTATCCCTCTACCCGTCGTTCTGACCATGTCGATACCTATCAGAGC
GCGTCCAAGGGCGAAGTACCTGTGCCGGACCCCTACCAATGGCTGGAAGAGAGCACCGATGAAGTAGACAAATGGACGAC
TGCTCAGGCCGATCTTGCCCAATCATATCTTGATCAGAACGCGGATATTCAGAAACTTGCGGAGAAATTTCGTGCGAGTA
GAAACTACGCAAAGTTTTCCGCACCGACTCTGCTCGATGACGGACATTGGTATTGGTTCTACAACCGAGGCCTGCAATCG
CAGTCAGTTCTTTACCGCTCCAACGAACCGGCGCTTCCTGATTTCTCCAATGGCGACGATAATGTTGGCGACGTATTCTT
CGACCCGAATGTACTCGCTACTGATGGCAGCGCCGGTATGGTCCTCTGTAAATTCTCCCCCGATGGCAAATTTTTCGCCT
ATGCAGTGTCCCATTTGGGAGGCGATTATTCAACTATCTATATTCGTTCAACGAGCTCGCCATTGTCTCAGGCGTCGGCA
GTCCAAGGCACGGACGGCAGACTGTCGGATGAAGTAAAGTGGTTCAAGTTTTCAACGATAATCTGGACGAAGGACTCCAA
AGGTTTTCTTTACCAGCGATATCCTGCTCGTGAACGTCATGAAGGGACACGGCAGCGACAGAAATGCTATGATGTGCTACC
ACAAAGTTGGAACGACTCAAGAGGAGGATATTATCGTGTATCAAGACAATGAACACCCAGAGTGGATATATGGAGCAGAT
ACGTCAGAAGATGGGAAATATCTCTACTTGTATCAGTTCAAGGATACCTCGAAGAAAAACCTTCTGTGGGTTGCAGAACT
CAACGAGGATGGCGTCAAGTCGGGGATTCAGTGGCGAAAAGTCGTTAATGAGTATGTGGCCGACTACAACGTTATAACGA
ACCACGGATCATTGGTGTACATCAAGACCAATCTCAATGCACCCCAGTATAAGGTCATCACCATCGACCTATCGAAAGAC
GAACCTGAAATTCGTGATTTTATCCCGGAAGAGAAAGATGCAAAGCTCGCTCAAGTTAATTGCGCCAACGAAGAATACTT
TGTGGCAATCTACAAGCGCAATGTCAAGGATGAAATATATCTCTACTCGAAGGCTGGCGTACAACTCACCCGTCTTGCGC
CGGACTTTGTTGGCGCTGCGTCTATAGCGAACAGACAGAAACAAACTCATTTCTTCCTCACGCTGTCTGGATTCAATACA
CCTGGCACCATTGCTCGGTACGACTTCACGGCTCCAGAAACGCAACGCTTCAGCATCCTTCGGACGACRAAGGTCAATGA
ACTGGATCCAGATGACTTTGAGTCCACGCAAGTCTGGTATGAGAGTAAAGATGGCACRAAAATTCCCATGTTCATTGTTC
GTCACAAATCTACAAAATTCGATGGAACGGCGGCGGCGATTCAATAYGGTTACGGTGGATTTGCCACTTCGGCAGATCCA
TTCTTTAGTCCAATTATTCTCACATTTTTGCAAACATACGGCGCAATCTTTGCTGTTCCTAGTATTCGAGGTGGAGGTGA
ATTCGGTGAAGAATGGCACAAGGGTGGACGAAGAGAAACCAAGGTAAATACATTCGATGATTTCATTGCCGCCGCACAGT
TTCTGGTCAAGAACAAGTATGCGGCTCCTGGCAAGGTGGCTATCAACGGCGCATCCAATGGCGGTCTTCTTGTCATGGGT
TCGATTGTTCGAGCACCGGAGGGGACCTTCGGCGCCGCGGTCCCTGAGGGTGGCGTTGCAGACCTCCTCAAGTTCCACAA
GTTCACCGGGGGCAAGCTTGGATCAGTGAATACGGAAATCCTTCCATTCCTGAAGAGTTCGACTACATCTATCCATTAT
CTCCTGTACACAATGTGCGGACCGACAAGGTTATGCCAGCTACGTTAATCACGGTCAATATTGGCGACGGCCGGGTTGTG
CCCATGCATTCCTTCAAGTTCATTGCAACACTTCAGCATAACGTGCCTCAGAACCCTCATCCATTGCTGATCAAAATTGA
CAAGTCCTGGCTTGGTCATGGTATGGGCAAACCAACGGACAAAAATGTCAAAGACGCGGCTGATAAATGGGGTTTCATCG
CACGAGCGCTCGGACTTGAATTGAAAACAGTTGAATAGGCTTTATTGCTATCGAGGACTTGGCATTGAATGTATGTACAT
ACATTTGATGGTGGCAATATACCTGCGTCATTTGA

Underlined ATGs are contemplated translational start sites

Exemplary Sequences of
prolyl oligopeptidases
Isolated from Galerina marginata.

>protein sequence of GmPOPB SEQ ID NO: 722

MSSVTWAPGNYPSTRRSDHVDTYQSASKGEVPVPDPYQWLEESTDEVDKWTTAQADLAQSYLDQNADIQKLAEKFRASEN
YAKFSAPTLLDDGSWYWFYNSGLQSQSVLYRSNEPALPDFSNGDDNVGDVFFDPNVLAYDGSAGMVLCKFSPDGKFFAYA
VSRLGGDYSTIYIRSTSSPLSQASAVQGIDGRLSDEVKWFKFSTIIWTKDSKGFLYQRYPARERHEGTRSDRNAMMCYHK
VGTTQEEDIIVYQDNEHPEWIYGADTSEDGKYLYLYQFKDTSKKNLLWVARLNEDGVKSGIQWRKVVNEYVADYNVITNH
GSLVYIKTNLNAPQYKVITIDLSKDEPEIRDFIPEEKDAKLAQVNCANEEYFVAIYKRNVKDEIYLYSKAGVQLTRLAPD
FVGAASIANRQKQTHFFLTLSGFNTPGTIARYDFTAPETQRFSILRTTKVNKLDPDDFESTQVWYESKDGTKIPMFIVRH
KSTKFDGTAAAIQYGYGGFATSADPFFSPIILTFLQTYGAIFAVPSIRGGGEFGEEWHKGGRRETKVNTFDDFIAAAQFL
VKNKYAAPGKVAINGASNGGLLVMGSIVRAPEGTFGAAVPEGGVADLLKFHKFTGGQAWISEYGNPSIPKEFDYIYPLSP
VHNVRTDKVMPATLITVNIGDGRVVPMHSFKFIATLQHNVFQNPHPLLIKIDKSWLGHGMGKPTDKNVKDAADKWGFIAR
ALGLELKTVE

*FIG. 38B*

SEQ ID NO:723

```
Sequence 1

>contig17672 length=916   numreads=17
          Length = 916

contig sequence: >gi|4017621|lcl|contig17672 length=916   numreads=17
ACCTTGTCAGGAGCTGCGTACTTATTCTTCACAAGGTATTGGCTGTGACAGGAAAGTTATTGCCGGCAGAGTAAAAAGAA
GCAAGATGCGTACGTTGCGGCGATAAAATCGTCGAAGCAATTTCCCTGCAGGACATCATGAGCAGCTGATGAAATACCAA
GAGTTAAAGGAACAAGGGACCTTCTTTTCTCTACATCCAGCCAAGTGCCAGTCCTCGCCGAATTCTCCGCCACCCCTGAT
ATTTGGAAGCGCAAACACGACGCCGTATTTTTGGAGGAATGTAAGAATTGTCGGCGCTGAAAAAGGGGTCGATGGAGATGC
TGAATCCACCATAACCTGGAGAGCGTGAGGCGTAAATACGTGTGCCATTAAAATTTTCGATCGGATATGGTCAGTCACCG
TATTGTATGACTGGGGCAGTGCCATCAAATTTCGTTGATTTGTGACGAACGATAAACATTGGGATGCTTGTGCCGTCCTT
GCTCTCATACCATACCTGCCAAGACAAGGTCAGTAAATGGACCAGCTAAGAGGTGGGCAGCAAGTACTTGGCTAGCTTCG
AAATCCTCTGTATTTAGGCCGTTGAGTTTGGTTGTTCGGTAAATGCTCCACCGCTGCTCCTCAGGATCGGTAAACTTGTA
TCTACCAATTGTGCCAGGTGAGGTAAAACCATTCAGTTCGACAAAGAAGGAGGAATGCTTTTCACGCCCAGACACATGAG
CAGCGCCCACAAAGTCCTCAGCCAGGCGAGCGAGCTGGTTTCCAGCATGCCGAATACACATATACCTCATCTTTTACCTGC
ATAAGGTGGCCGATAACGTTATTGTTATATACTTCGTATGATGGATGGGTCTTACATTGCGCTTGTAAACGAGGGCAAAG
TAGCCCTTATTTACGCTGGTAATGCTGGACAAGTAT

          Blast alignments:

          >contig17672 length=916   numreads=17
                    Length = 916

           Score =  130 bits (327), Expect(4) = 2e-64
           Identities = 64/108 (59%), Positives = 73/108 (67%), Gaps = 21/108 (19%)
           Frame = -2
```

```
SEQ ID NO: 724 (Q)   Query: 460 STQVWYKSKDGTKVPMFIVRHKSTKFDGTAPAIQNG---------------------YGG 498
                                S QVWY+SKDGT +PMFIVRHKSTKFDGTAP IQ G                     YGG
SEQ ID NO :725 (S)   Sbjct: 504 SWQVWYRSKDGTSIPMFIVRHKSTKFDGTAPVIQYGD*PYPIENFNGTRIYASRSPGYGG 325

                     Query: 499 FAITADPFFSPIMLTFMQTYGAILAVPNIRGGGEFGGEWHKAGRRETK 546
                                F+I+ DPFFS  +LTF+Q YG + A+PNIRGGGEFG +WH AG RE K
                     Sbjct: 324 FSISIDPFFSATILTFLQKYGVVFALPNIRGGGEFGEDWHLAGCREKK 181
```

*FIG. 41A-1*

```
                 Score =  110 bits (275), Expect(4) = 2e-64
                 Identities = 51/84 (60%), Positives = 65/84 (77%)
                 Frame = -1

SEQ ID NO:726  Query: 380 VKDEIYLYSKAGDQLSKLASDFIGVASITNKEKQPHSFLTFSGFNTPGTISRYDFTAPDT 439
                          VKDE+Y+YS AG+QL+KLA DF+G A ++ REK     F+  +GF +PGTI RY FT P+
SEQ ID NO: 727 Sbjct: 796 VKDEVYVYSHAGNQLARLAEDFVGAAHVSGREKHSSFFVELNGFTSPGTIGRYKFTDPES 617

               Query: 440 QRLSILKTTKLNGLNADDFESTQV 463
                          QR SI  RTTKLNGLN +DFE++QV
               Sbjct: 616 QRWSIYRTTKLNGLNTEDFEASQV 545


                 Score = 35.0 bits (79), Expect(4) = 2e-64
                 Identities = 20/42 (47%), Positives = 23/42 (54%), Gaps = 17/42 (40%)
                 Frame = -3

SEQ ID NO: 728 Query: 546 KGNTFDDFIAA-----------------AQFLVKNKYAAPGK 570
                          +GN FDDFIAA                 +Q+LVKNKYAAP K
SEQ ID NO: 729 Sbjct: 128 QGNCFDDFIAATYASCFFLLCRQ*LSCHSQYLVKNKYAAPDK 3


                 Score = 32.0 bits (71), Expect(4) = 2e-64
                 Identities = 12/21 (57%), Positives = 16/21 (76%)
                 Frame = -2

SEQ ID NO:730  Query: 361 LTQVKCVNKGYFVAIYKRNVK 381
                          L+ +  VNKGYF  +YKRNV+
SEQ ID NO: 731 Sbjct: 912 LSSITSVNKGYFALVYKRNVR 850
```

FIG. 41A-2

SEQ ID NO:732

Sequence 2

```
>contig13837 length=1036   numreads=15
          Length = 1036

>gi|4013798|lcl|contig13837 length=1036   numreads=15
TCTCTCTACAGCCGATGGCAGTGGTGGCGATTTATTCTTTGATGTGGCCAGCTTTCTGCCAATCGCATGCCTTTGCTGA
TGTTCGTGAAGCCCAATGCCCTTTCCAACGACGGAACTGCCGCTCTTTCAACCTATGCCTTCTCGGATTGTGGCAAATAT
TTTGCGTATGGGATCTCTTTCTCTGTATGTACATTGATACACTTCAAACTACTCGAGCATGTATTAACTCATCTATTTAG
GGCAGTGATTTCGTGACAATCTACGTGCGGTTGACGGATTCCCCTCTCACTAAAGATGTGGACGCGAAGAACGACAAAGG
TCGCCTTCCAGAGGAAATCAAATTTGTCAAATTTTCATCCATAGGATGGACACCTGATTCCAAGGGCTTTTTTTATCAGG
TCATTCCCTGGACCGCGTGGCATCGCTATTGGGCTAACTTCATTGTAGCGTTACCCAGATACCTCCACCGTCACCCAAGA
GAACGGGCCTATCGCGACAGAAGGTGACCTGGATGCCATGGTATATTATCATCGCCTTGGAACGCCGCAGTGTATGCACT
TTCCGTTTTTTCTGGAATCATGATTGACGGGCAGATAACTGTTTAGCGGAAGATACTCTGATCTACCAAGACAAAGAACA
TAGGGACTGGATGTTCAGCATTGATGTCACAGACGACGGCAATTACCTCCTCCTTTACATTCTCAAGGACAGCTCAAGGG
TAATGGGCTTATTATTAATTTCTTTTTATGATGTCTAAATCGCCATGTAGCAAAACTTACTTTGGATTGCTGCATTTGAT
CCTGCAAATCTTGGTCCCAATATCAAGTGGCAGAAGGTCTTCGATGAATATCACTCAGAATACGAGATGTATGGCCCTGA
TTCTTCCTTGTGTTTGGTTGATCAATGACCTTGGTACCAGTATCACAAACAAGGGCTCATTGTTCTATGTTAGAACTAAC
GAATCCGCTCCCCAGTACAGAGTCATAACGGTTGACATTGCCAAAGGGAATGAAATCAATGAACTCATCCCTGAAA

>contig13837 length=1036   numreads=15
          Length = 1036

Score = 71.2 bits (173), Expect = 2e-12
Identities = 34/97 (35%), Positives = 52/97 (53%), Gaps = 17/97 (17%)
Frame = +3
```

```
SEQ ID NO: 733   Query: 247 EDIIVQQDKENFDWTYGTDASEDGKYIYLVVYKDASK-----------------QNLLWV 289
                            ED ++ QDKE+ DW +  D ++DG Y+ L + KD+S+                 QNLLW+
SEQ ID NO: 734   Sbjct: 609 EDTLIYQDKEHRDWMFSIDVTDDGNYLLLYILKDSSRVMRLLLLISFYDV*IAM*QNLLWI 788

                 Query: 290 AEFDKDGVKPEIPWRKVINEFGADYHVITNHGSLIYV 326
                            A FD   + P I W+KV +E+ ++Y +     SL  V
                 Sbjct: 789 AAFDPANLGPNIKWQKVFDEYHSEYEMYGPDSSLCLV 899
```

FIG. 41B-1

```
                     Score = 59.7 bits (143), Expect(2) = 1e-14
                     Identities = 28/56 (50%), Positives = 38/56 (67%)
                     Frame = +1

SEQ ID NO: 735 Query: 165 GVDYFTIYVRPTSSSLSQAPEAEGGDGRLSDGVKWCKFTTIITWTKDSKGFLYQRYP 220
                          G D+ TIYVR T S L++  +A+   GRL + +K+ KF++I WT DSKGF YQ  P
SEQ ID NO: 736 Sbjct: 241 GSDFVTIYVRLTDSPLTEDVDAKNDKGRLPEEIKFVKFSSIGWTPDSEKGFFYQVIP 408

                     Score = 53.1 bits (126), Expect = 7e-07
                     Identities = 27/55 (49%), Positives = 38/55 (69%)
                     Frame = +1

SEQ ID NO: 737 Query: 301 IPWRKVINEFGADYHVITNHGSLIYVKTNVNAPQYKVVTIDLSTGEPEIRDFIPE 355
                          +P   +IN+ G     ITN GSL YV+TN +APQY+V+T+D++ G  EI + IPE
SEQ ID NO: 738 Sbjct: 883 LPCVWLINDLGTS-----ITNKGSLFYVRTNESAPQYRVITVDIAKGN-EINELIPE 1035

                     Score = 39.7 bits (91), Expect(2) = 1e-14
                     Identities = 17/33 (51%), Positives = 22/33 (66%)
                     Frame = +2

SEQ ID NO:739  Query: 130 VYFDPNVLSADGTAIMGTCRFSPSGEYFAYAVS 162
                          ++  PN LS DGTA + T  FS  G+YFAY +S
SEQ ID NO: 740 Sbjct: 80  MFVKPNALSNDGTAALSTYAFSDCGKYFAYGIS 178
```

FIG. 41B-2

SEQ ID NO:741 Sequence 3:

```
>gi|4010927|lcl|contig10958 length=1169   numreads=17
GTGGTTCAAGTTTTCAACGATAATCTGGACGAAGGACTCCAAAGGTTTTCTGTACCAAGTATGGTCCACCATTTAAGCCA
TCGTTGATCAACGCGCTGACACGATCCTTGCAGCGATATCCTGCTCGTGAACGTCATGAGGGGACACGCAGCGATAGAAA
TGCTATGATGTGTTACCACAAGGTTGGAACGACTCAAGGTAAGCTGAGATAGCATCCTGGCCTTCCCTAATTCAATTCCG
TGTGACAGAGGAGGATATTATCGTGTATCAAGATAATGAACACCCGGAATGGATTTATGGAGCAGATACGTCAGAGGATG
GGAAAATATCTCTACTTGTATCAGTTCAAGGATACCTCGAAGGTAAGGCTCTGAGATTTATTGCGCGACATCAATGAATCT
CGTACTGTCAGAAAAACCTTCTGTGGGTTGCAGAACTCGACGAAGATGGGGTCAAGTCAGGGATTCACTGGCGAAAAGTC
GTTAATGAGTATGCGGCCGACTATAACATGTGAAAATCTTTTATTATCTCCAAATCACCCTGTTTAACTTTGTATAACAC
AGTATAACGAACCACGGATCGCTGGTATACATCAAGACCAATCTCAATGCACCCCAGTATAAGGTCATCACCATCGACCT
ATCAAAAGACGAACCTGAAATCCGTGATTTTATCCCGGAAGAGAAAGATGCAAAGCTCGCTCAAGTTAATTGCGCCAACG
AAGAATACTTTGTGGCCATCTACAAGCGCAATGTAATTTCGTTCGTGACTTTCTTTGAATTTCGCTAATGTTGGTACGAC
ACCCGCAGGTCAAAGACGAAATATATCTCTACTCGAAGGCTGGAGTTCAACTGACCCGTCTTGCGCCAGACTTTGTTGGC
GCTGCGTCTATTGCGAACAGACAGAAACAAACTCATTTCTTCCTCACACTGTCCGGATTTAATACACCTGGCACCATTGC
TCGGTACGACTTCACGGCTCCAGAAACACAACGCTTCAGCATCCTTCGGACGACAAAGGTCAATGAACTGGATCCAGATG
ACTTTGAGTCCACGCAAGTCTGGTATGAGAGTAAAGATGGCACAAAAATTCCCATGTTCATTGTTCGTCAACAAATCTAC
AAAATTCGATGGAACGGCGGCGGCGATTCAATATGGTAATCCTTTTCGC
```

```
>contig10958 length=1169   numreads=17
          Length = 1169

 Score =  170 bits (431), Expect = 3e-42
 Identities = 82/105 (78%), Positives = 92/105 (87%)
 Frame = +2
```

SEQ ID NO:742
SEQ ID NO:743

```
Query: 380 VKDEIYLYSKAGDQLSRLASDFIGVASITMREKQPHSFLTFSGFNTPGTISRYDFTAPDT 439
           VKDEIYLYSKAG QL+RLA DF+G ASI NR+KQ H FLT SGFNTPGTI+RYDFTAP+T
Sbjct: 809 VKDEIYLYSKAGVQLTRLAPDFVGAASIANRQKQTHFFLTLSGFNTPGTIARYDFTAPET 988

Query: 440 QRLSIILRTTKLNGLNADDFESTQVWYKSKDGTKVPMFIVRHKSTK 484
           QR SIILRTTK+N L+ DDFESTQVWY+SKDGTK+PMFIVR +  K
Sbjct: 989 QRFSIILRTTKVNELDPDDFESTQVWYESKDGTKIPMFIVRQQIYK 1123
```

FIG. 41C-1

```
                   Score =  120 bits (301), Expect(3) = 3e-53
                   Identities = 82/200 (41%), Positives = 102/200 (51%), Gaps = 19/200 (9%)
                   Frame = +3

SEQ ID NO:744      Query: 315 HVITNNGSLIYVKSWVNAPQYKVVTIDLSTGEPKIRDFIPEQKDAKLSQVKCVNKGYFVA 374
SEQ ID NO:745                 H ITNNGSL+Y+KSW+NAPQYKV+TIDLS  EPKIRDFIPE+KDAKL QV C N+ YFVA
                   Sbjct: 598 HSITNNGSLVYIKSWLNAPQYKVITIDLSKDEPKIRDFIPEEKDAKLAQVNCANEEYFVA 737

                   Query: 375 IYKRNVKDEI--YLYSNAGDQLSRLASDFIGVASIT-NREKQPHSFLTFSGFNTPGTISR 431
                              IYKRNV   +  + +          R  + +I    +  N       + L       T
                   Sbjct: 738 IYKRNVISFVYFFEFR*CWYDTRRSKTKYISTRRLEFN*FVLRQTLLALRLLRYDRRKLI 917

                   Query: 432 YDFTAPDTQRLAIL------RYTKLNGLNADDFESTQVN---------------YKSKDGTKVPM 475
                                  FD   L+ L      R  K N   +   + +  N               + K   K P
                   Sbjct: 918 SSSHCFDLIHLAPLLGTTSKLQKHNASASFGRQRSMKHIQMTLSPKKSGRKVKMAQKFPC 109

                   Query: 476 FIVHKKSTKFDGTAPAIQNG 495
                                +  +KSTKFDGTA AIQ G
                   Sbjct: 1098SLFVKKSTKFDGTAAAIQYG 1157


                   Score = 75.1 bits (183), Expect(3) = 3e-53
                   Identities = 49/123 (39%), Positives = 58/123 (47%), Gaps = 35/123 (28%)
                   Frame = +2

SEQ ID NO:746      Query: 199 WCKFTTITWTKDSKGFLYQKYPARESLVAKDRDK---DAMVCYHRV-GTTQL------------ 246
SEQ ID NO:747                 W KF+TI WTKDSKGFLYQ +      ++V +  D     A+ C      G TQ
                   Sbjct: 2   WFKKSTIIWTKDSKGFLYQVWSTI*AIVDQRADTILAAISCS*TS*GDTQR*RCYDVLRQ 181

                   Query: 247 ----------------------------------EDIIVQQDKENPDWTYGTDASEDGKYIYLVVYKDASK 283
                                                                 EDIIV QD E+P+W YG D SEDGKY+YL  +KD SK
                   Sbjct: 182 GWNDSR*AKIASWPSLIQFRVTEKDIIVYQDNEHPEWIYGADTSEDGKYLYLYQFKDTSK 361

                   Query: 284 QNL 286
                                 L
                   Sbjct: 362 VRL 370


                   Score = 53.9 bits (128), Expect(3) = 3e-53
                   Identities = 22/34 (64%), Positives = 29/34 (85%)
                   Frame = +1

SEQ ID NO:748      Query: 283 KQNLLWVAEFDKDGVKPKIPWRKVINEFGADYHV 316
SEQ ID NO:749                 ++NLLWVAE D+DGVK  I WRKV+NE+ ADY++
                   Sbjct: 409 QKNLLWVAELDEDGVKSGIHWRKVVNEYAADYNM 510
```

*FIG. 41C-2*

SEQ ID NO:750 Sequence 4

```
>gi|4003430|lcl|contig03437 length=1306   numreads=21
TCAGGCTTATGCAGGACTCGAGTTTTCCATCCAAGAGTGGCCTCGCGAGCGTTGTTAAATGGCTTTTTGGATACTGAAGG
TTGGTGAGTCTGATTGAGTGATTATGTACACCAAGTCAATCAGGTTGGTACTTGGGACTTGGAGGACAGGACTTTCTTAG
GACTTACTCCACACGCTCATAATATCACGTCGGTATTCCATCTTCCCTGTCAGTTTTTGACCCCAAGATTGTAATAACAC
TCGTCAGGTGAGCTTCACAGAAATATATGGCAGGAGAAATGATACTGAAAAAGCAGTTGCCCTTACACATAGCGTTCATG

AAATTCGGCATGTTGCACTTCTGATAGAACAGTCATCCAAATAACTGGTTCAAGGCTTTATTTCACACCCAGTGTTGTTT
ATGGGCCCCCATGATCCATTCTTTGTCTCGATGAAACGCCCTCATCGGACGCGCGACGGAATTTGAAAATTAGGTGGACT
GAATTTGAAATGTGTTGATGGCAGAACTTTGGCTTGTCACTTACTACTTCTCCCTTTTGTCCAGAAGCCCTTTATCATAT
CTAAAATCGTGACAGTGGCACGGACCGTGGACGTTATCCCAAACCAACCCTATTGGTACCCTTAAAAAACAGGGTTTTTC
GATGTCCGTCTTCCAGCCGTATCGCTGACCCCACAATTGCGGAAAACTATTTCGTCTGTAACCTGGGCTCCTGGAAATTA
TCCCTCTACCCGTCGTTCTGACCATGTCGATACCTATCAGAGCGCGTCCAAGGGCGAAGTACCTGTGCCGGACCCCTACC
AATGGCTGGAAGAGAGCACCGATGAAGTAGACAAATGGACGACTGCTCAGGCCGATCTTGCCCAATCATATCTTGATCAG
AACGCGGATATTCAGAAACTTGCGGAGAAATTTCGTGCGAGTAGAAACTACGCAAAGGTAATTTATCGTATAAAGTCGTA
ACTTATCATCTGGCTGAAACCCGTTCTCCTAGTTTTCCGCACCGACTCTGCTCGATGACGGACATTGGTATTGGTTCTAC
AACCGAGGCCTGCAATCGCAGTCAGGTAGATATTTATTTGTCCTACGAGGGTGCAAAACTCAGACATTTTACAAGTTCTT
TACCGCTCCAAGGAACCGGCGCTTCCTGATTTCTCCAAGGGCGACGATAATGTTGGCGACGTATTCTTCGACGTAGGGGC
CTCCTTCACTGCCTCAGACGTCTTCTCTGAATGCGTTCTTAAAAGCCAAATGTACTCGCTGCTGATGGCAGCGCCGGTAT
GGTCCTCTGTAAATTCTCCCCCGATG
```

SEQ ID NO: 751 (Q)

SEQ ID NO : 752 (S)

```
>contig03437 length=1306   numreads=21
          Length = 1306

 Score =  112 bits (280), Expect(2) = 3e-25
 Identities = 67/170 (39%), Positives = 87/170 (51%), Gaps = 36/170 (21%)
 Frame = +2

Query: 23   RIMSSDQWTPNMYPSARRSDRIDTTRSETRGEVKVPDFYHWLEEYSKEEDKWTSDQEEFT 82
            + MSS  W P  YPS RASDR+DTT+S  ++GEV  VPDFY  WLEE  ++E DKWT+ Q +
Sbjct: 683 KTMSSVTWAPQWYPSTRRSDHVDTTYQSASKGEVPVVPDFYQWLEESTDEVDEWTTAQADLA 862

Query: 83   RTYLDSHPDRSKLEDAFRKAMDYRK----------------------FSAFFLNDDK--------------- 117
            ++YLD  N D +KL + FR S  +Y K                    F  D
Sbjct: 863 QSYLDQNADIQKLAEKFRASRNYAKVIYRIKS*LIIWLKPVLSVFRTDSAR*RFLVLVLQ 1042

Query: 118  -----------RNYWRYYNTGLQAQ------TVICRSKDSTLPDFSE-SDYVGKTFFD 156
                       R  +    Y +Q          V+ RSK+  LPDFS+  D VG+ FFD
Sbjct: 1043PRRPAIAVR*IFICPYRVQNSDILQVLYRSKEPALPDFSKGDDNVGDVFFD 1198

Score = 22.3 bits (46), Expect(2) = 3e-25
 Identities = 8/18 (44%), Positives = 14/18 (77%)
 Frame = +1

Query: 157  PNLLSSDGTASLSNYDFS 174
            PN+L++DG+A  +  +  FS
Sbjct: 1246 PNVLAADGSAGMVLCKFS 1299
```

FIG. 41D

USE OF GALERINA MARGINATA GENES AND PROTEINS FOR PEPTIDE PRODUCTION

This application is a continuation of U.S. patent application Ser. No. 14/933,239, filed Nov. 5, 2015, which is a continuation of U.S. patent application Ser. No. 13/362,561, filed Jan. 31, 2012, which is a continuation-in-part and claims benefit of the priority filing date of pending U.S. patent application Ser. No. 12/268,229 filed on Nov. 10, 2008 and of U.S. Provisional Patent Application Ser. No. 61/002,650, filed on Nov. 9, 2007, all of which are herein incorporated by reference in their entireties.

GOVERNMENT INTERESTS

This invention was made with government support under DE-FG02-91ER20021, awarded by the U.S. Department of Energy. The government has certain rights in the invention.

FIELD OF THE INVENTION

The present invention relates to compositions and methods comprising genes and peptides associated with cyclic peptides and cyclic peptide production in mushrooms. In particular, the present invention relates to using genes and proteins from *Galerina* species encoding peptides specifically relating to amatoxins in addition to proteins involved with processing cyclic peptide toxins. In a preferred embodiment, the present invention also relates to methods for making small peptides including small cyclic peptides including peptides similar to amanitin. Further, the present inventions relate to providing kits for making small peptides.

BACKGROUND

More than 90% of human deaths resulting from mushroom poisoning are due to peptide toxins found in *Amanita* species of mushrooms, such as *A. phalloides, A. bisporigera, A. ocreata*, and *A. virosa*. Animals, especially dogs, are frequent victims of poisoning by *Amanita* mushrooms. Two dogs died after eating toxin containing mushrooms in Michigan, See Schneider: Mushroom in backyard kills curious puppy, Lansing State Journal, Sep. 30, 2008. Besides species in the genus *Amanita*, other genera of mushrooms make similar toxins, such as phallotoxins and amatoxins. These other genera include *Galerina, Conocybe*, and *Lepiota*. Poisonings due to *Galerina* species have occurred, see FIG. 31.

High concentrations of peptide toxins are found in the above ground mushroom portion (otherwise known as carpophores or fruiting bodies) of the toxin producing mushroom species. These toxins include two major families of compounds called amatoxins (for example, α-amanitin. FIG. 1A) and phallotoxins (for example, phalloidin, phallacidin, FIG. 1B). Both classes of compounds are bicyclic peptides with a Cys-Trp cross-bridge. In general, amatoxins are 8 amino acids in length while phallotoxins are 7 amino acids in length. Amatoxins are produced by *Amanita* and some *Galerina* species of mushrooms. *Galerina* species in general do not make phallotoxins. Amatoxins survive cooking and remain intact in the intestinal tract where they are absorbed into the body where large doses irreversibly damage the liver and other organs (Enjalbert et al., (2002) J. Toxicol. Clin. Toxicol. 40:715; herein incorporated by reference).

Amatoxins and phallotoxins are used extensively for experimental research. Amatoxins are a family of bicyclic peptides that inhibit RNA polymerase II while phallotoxins bind and stabilize F-actin. However *Amanita* species do not grow well in the laboratory and harvesting from wild sources limits availability of a natural source of these peptides.

Thus it would be useful to have methods for obtaining large quantities of bicyclic amatoxins in addition to custom designed bicyclic amatoxin and phallotoxin peptides using cultivatable mushrooms.

SUMMARY OF THE INVENTION

The present invention relates to compositions and methods comprising genes and peptides associated with cyclic peptides and cyclic peptide production in mushrooms. In particular, the present invention relates to using genes and proteins from *Galerina* species encoding peptides specifically relating to amatoxins in addition to proteins involved with processing cyclic peptide toxins. In a preferred embodiment, the present invention also relates to methods for making small peptides and small cyclic peptides including peptides similar to amanitin. Further, the present inventions relate to providing kits for making small peptides.

The present invention also relates to a composition comprising a recombinant fungal prolyl oligopeptidase nucleic acid sequence selected from the group consisting of SEQ ID NO: 715 and 717.

The present invention also relates to a composition comprising a *Galerina* fungus transfected with a recombinant prepropeptide nucleic acid sequence encoding a peptide capable of forming a cyclic peptide. In one embodiment, said prepropeptide nucleic acid sequence is selected from the group consisting of nucleic acid sequences encoding SEQ ID NOs:710 and 713. In one embodiment, said cyclic peptide is a bicyclic peptide. In one embodiment, said bicyclic peptide comprises sequence SEQ ID NO:50.

The present invention also relates to a method of making a peptide from a recombinant prepropeptide sequence, comprising, a) providing, a composition comprising a *Galerina* fungus and a recombinant prepropeptide nucleic acid sequence further encoding a peptide capable of forming a cyclic peptide, and b) contacting said *Galerina* fungus with said recombinant prepropeptide nucleic acid sequence under conditions for making said peptide. In one embodiment, said contacting comprises transformation of said *Galerina* fungus with said recombinant prepropeptide sequence. In one embodiment, said peptide is selected from the group consisting of peptides at least six and up to fifteen amino acids in length. In one embodiment, said peptide is biologically active. In one embodiment, said peptide is a cyclic peptide. In one embodiment, said cyclic peptide is a bicyclic peptide. In one embodiment, said bicyclic peptide comprises sequence SEQ ID NO:50.

The present invention also relates to a method of making a synthetic cyclized peptide, comprising, a) providing, i) *Galerina* fungal cell, ii) a recombinant prepropeptide nucleic acid sequence comprising a nucleic acid sequence encoding a peptide capable of forming a cyclic peptide, and b) transforming said *Galerina* cell with said prepropeptide sequence and c) growing said *Galerina* fungal cell into a fungus under conditions for expressing said prepropeptide for making a synthetic cyclic peptide. In one embodiment, said recombinant prepropeptide encoding sequence is selected from the group consisting of nucleic acid sequences encoding SEQ ID NOs:710 and 713. In one embodiment, said cyclic peptide is selected from the group consisting of a peptide at least six and up to fifteen amino acids in length. In one embodiment, said cyclic peptide is a bicyclic peptide. In one embodiment, said bicyclic peptide comprises SEQ ID NO:50. In one embodiment, said cyclized peptide is biologically active.

The present invention provides an isolated nucleic acid sequence selected from the group consisting of SEQ ID NOs: 709-714, 715, 717, 723 and fragments thereof.

The present invention provides an isolated amino acid sequence selected from the group consisting of SEQ ID NOs: 704-708, 716, 722, 753 and fragments thereof.

The present invention provides a composition comprising a *Galerina* fungus transformed with a recombinant propeptide nucleic acid sequence encoding a peptide capable of forming a cyclic peptide.

The present invention provides a composition comprising a *Galerina* fungus transformed with a recombinant nucleic acid sequence encoding a peptide capable of forming a cyclic peptide. In one embodiment, said peptide is selected from the group consisting of peptides at least six amino acids up to fifteen amino acids in length. In one embodiment, said peptide is a bicyclic peptide. In one embodiment, said bicyclic peptide is an Amanitin peptide.

The present invention provides a composition comprising a *Galerina* fungal cell and a synthetic propeptide sequence comprising a peptide sequence capable of forming a cyclic peptide. In one embodiment, said synthetic propeptide sequence is SEQ ID NO:249. In one embodiment, said peptide sequence is SEQ ID NO:69. In one embodiment, said *Galerina* fungal cell is a lysate.

The present invention also relates to compositions and methods comprising genes and peptides associated with cyclic peptide toxins and toxin production in mushrooms. In particular, the present invention relates to using genes and proteins from *Amanita* species encoding *Amanita* peptides, specifically relating to amatoxins and phallotoxins. In a preferred embodiment, the present invention also relates to methods for detecting *Amanita* peptide toxin genes for identifying *Amanita* peptide-producing mushrooms and for diagnosing suspected cases of mushroom poisoning. Further, the present inventions relate to providing kits for diagnosing and monitoring suspected cases of mushroom poisoning in patients.

The present invention provides an isolated nucleic acid sequence comprising at least one sequence set forth in SEQ ID NOs:1-4, 55-56, 79, 81, 85-86, and 97-98. In one embodiment, the nucleic acid encodes a polypeptide comprising at least one sequence set forth in SEQ ID NOs:50, 113, 118, 121-132, and 135. In one embodiment, the nucleic acid sequence comprises a sequence at least 50% identical to any sequence set forth in SEQ ID NOs: 182, 18-22. In one embodiment, the nucleic acid sequence encodes a peptide set forth in any one of SEQ ID NOs: 136-149 and 80. In one embodiment, the nucleic acid sequence comprises SEQ ID NOs: 86. In one embodiment, the polypeptide is selected from the group consisting of IWGIGCNP (SEQ ID NO: 50) and AWLVDCP (SEQ ID NO: 69). In one embodiment, the invention provides a polypeptide encoded by the nucleic acid sequences SEQ ID NOs: 55-56, 79, 81, 85, and 86.

The present invention provides a composition comprising a nucleic acid sequence, wherein said nucleic acid sequence comprises at least one sequence set forth in SEQ ID NOs: 1-4, 55-56, 79, 81, 85-86, and 97-98.

The present invention provides a composition comprising a polypeptide, wherein said polypeptide is encoded by a nucleic acid sequence comprising at least one sequence set forth in SEQ ID NOs: 55-56, 79, 81, and 85-86.

The present invention provides a set of at least two polymerase chain reaction primer sequences, wherein said primers are capable of amplifying a mushroom nucleic acid sequence associated with encoding an *Amanita* peptide. In one embodiment, the two polymerase chain reaction primer sequences are selected from the group SEQ ID NOs: 1-4, 97-98.

The present invention provides a method of identifying a toxin producing mushroom, comprising, a) providing, i) a sample, ii) a set of at least two polymerase chain reaction primers, wherein said primers are capable of amplifying a mushroom nucleic acid sequence associated with encoding a toxin, and iii) a polymerase chain reaction, b) mixing said sample with said set of polymerase chain reaction primers, c) completing a polymerase chain reaction under conditions capable of amplifying a mushroom nucleic acid sequence associated with encoding a toxin, and d) testing for an amplified toxin associated sequence for identifying a toxin producing mushroom. In one embodiment, the testing comprises detecting the presence or absence of an amplified mushroom nucleic acid sequence. In one embodiment, the sample is selected from the group consisting of a raw sample, a cooked sample, and a digested sample. In one embodiment, the sample comprises a mushroom sample. In one embodiment, the sample is obtained from a subject. The subject may be any mammal, e.g., the subject may be a human. In one embodiment, the set of polymerase chain reaction primer sequences may identify any *Amanita* peptide. In one embodiment, the set of polymerase chain reaction primer sequences may identify an amanitin peptide. In one embodiment, the set of polymerase chain reaction primer sequences are selected from the group consisting of SEQ ID NOs: 1-4, 97-98.

The present invention provides a diagnostic kit for identifying a poisonous mushroom, providing, comprising, a set of at least two polymerase chain reaction primers, wherein said primers are capable of amplifying a mushroom nucleic acid sequence associated with producing a toxin. In one embodiment, the two polymerase chain reaction primer sequences are selected from the group consisting of SEQ ID NOs: 1-4, 97-98. In one embodiment, the kit further comprises a nucleic acid sequence associated with producing a mushroom toxin, wherein said nucleic acid sequence is capable of being amplified by said polymerase chain reaction primers. In one embodiment, the kit further comprises instructions for amplifying said mushroom nucleic acid sequence. In one embodiment, the kit further comprises instructions for detecting the presence or absence of an amplified mushroom nucleic acid sequence. In one embodiment, the kit further comprises instructions for identifying the species of an amplified mushroom nucleic acid sequence. In one embodiment, the kit further comprises instructions for identifying the presence of a mushroom toxin peptide. In one embodiment, the kit further comprises instructions for identifying the presence of a mushroom toxin nucleic acid sequence.

The present invention provides a polypeptide, wherein said polypeptide is encoded by a sequence derived from a fungal species. In one embodiment, the polypeptide is an isolated polypeptide. In one embodiment, the isolated polypeptide is isolated from a cell. In one embodiment, the cell includes but is not limited to a fungal cell and a bacterial cell. In one embodiment, the isolated polypeptide is a synthetic polypeptide. It is not meant to limit the sequence of the polypeptide. In one embodiment, the polypeptide includes but is not limited to a polypeptide comprising a toxin sequence. In one embodiment, the polypeptide includes but is not limited to a preproprotein. In one embodiment, the polypeptide comprises at least one proprotein sequence set forth in SEQ ID NOs: 23, 26-37, 107-113, 118, 249, 303-306, 308-318. In one embodiment, the polypeptide is an amino acid sequence containing MSDIN upstream of a potential toxin encoding region and downstream conserved sequences. In one embodiment, the polypeptide comprises a toxin amino acid sequence. In one embodiment, the polypeptide comprises IWGIGCNP (SEQ ID NO:50) and AWLVDCP (SEQ ID NO:69). In one embodiment, the polypeptide comprises at least one sequence set forth in SEQ ID NOs: 249, and 318. In one embodiment, the polypeptide is linear. In one embodiment, the polypeptide is cyclic. In one embodiment, the polypeptide comprises at least one sequence set forth in SEQ ID NOs: 23, 26-37, 54, 69, 107-113, 118, 249, 303-306, 308-318. In one embodiment, the polypeptide includes but is not limited to a polypeptide comprising a prolyl oligopeptidase sequence. In one embodiment, the prolyl oligopeptidase sequence comprises at least one sequence set forth in SEQ ID NOs: 236, 237, 250-256, 258-276.

A composition, comprising a polypeptide, wherein said polypeptide is encoded by a sequence derived from a fungal species.

A method, comprising a polypeptide, wherein said polypeptide is encoded by a sequence derived from a fungal species.

The present invention provides an antibody having specificity for a polypeptide comprising a toxin sequence, wherein said a polypeptide is encoded by a nucleotide sequence derived from a fungal species. In one embodiment, the polypeptide includes but is not limited to exemplary *Amanita* and *Galerina* spp. peptides, proteins, proproteins and preproproteins. SEQ ID NOs: 50, 110, 113, 118, 121-132, 135, 249, 303-306, and 308-318. In one embodiment, the toxin includes but is not limited to a cyclic toxin, a linear amino acid sequence of a cyclic toxin, a portion of a linear amino acid sequence of a cyclic toxin. In one embodiment, the toxin includes but is not limited to an amatoxin or a phallotoxin. In one embodiment, the toxin includes but is not limited to amanitin. In one embodiment, the toxin includes but is not limited to alpha, beta, gamma, etc., amanitin, Amanitin, amatoxins, etc. In one embodiment, the toxin includes but is not limited to cyclic forms of SEQ ID NOs: 50, 54, 69, 114, 117 and 135-149. In another embodiment, the invention provides an antibody having specificity for mushroom prolyl oligopeptidase including but not limited to *Amanita* and *Galerina* spp. prolyl oligopeptidase.

A composition, comprising an antibody having specificity for a preproprotein comprising a toxin sequence, wherein said preproprotein is encoded by a nucleotide sequence derived from a fungal species.

A method, comprising an antibody having specificity for a preproprotein comprising a toxin sequence, wherein said preproprotein is encoded by a nucleotide sequence derived from a fungal species.

The present invention provides an antibody having specificity for a toxin encoded by a nucleotide sequence derived from a fungal species. In one embodiment, the toxin includes but is not limited to a cyclic toxin, a linear amino acid sequence of a cyclic toxin, a portion of a linear amino acid sequence of a cyclic toxin. In one embodiment, the toxin includes but is not limited to an amanitin and a phallatoxin. In one embodiment, the toxin includes but is not limited to an alpha, beta, gamma, etc., amanitin. In one embodiment, the toxin includes but is not limited to SEQ ID NOs: 50, 54, 69, 114, 117 and 135-149. In one embodiment, the antibody includes but is not limited to a polyclonal antibody and a monoclonal antibody. In one embodiment, the antibody includes but is not limited to a rat, rabbit, mouse, chicken antibody.

A composition, comprising an antibody having specificity for a toxin encoded by a nucleotide sequence derived from a fungal species.

A method, comprising an antibody having specificity for a toxin encoded by a nucleotide sequence derived from a fungal species.

A composition, comprising an antibody having specificity for a prolyl oligopeptidase encoded by a nucleotide sequence derived from a fungal species.

A method, comprising an antibody having specificity for a prolyl oligopeptidase encoded by a nucleotide sequence derived from a fungal species.

The present invention provides an isolated prolyl oligopeptidase protein, wherein said prolyl oligopeptidase protein is encoded by nucleic acid sequence derived from a fungal species. In one embodiment, the prolyl oligopeptidase includes but is not limited to a prolyl oligopeptidase, prolyl oligopeptidase A, prolyl oligopeptidase B, and fragments thereof. In one embodiment, the prolyl oligopeptidase A comprises any one sequence set forth in SEQ ID NOs: 250-252, 254, 258, 261-269, 271-273, 275-276, 330-332, 334-336, 346. In a preferred embodiment, the prolyl oligopeptidase B comprises any one sequence set forth in SEQ ID NOs: 267, 253, 271, 273, 276, 280, 282, 286, 288, 289, 290, 293, 296-297, 332, 343, 345, 346, 336, 337, 339, 343, 302.

A composition, comprising an isolated prolyl oligopeptidase protein, wherein said prolyl oligopeptidase protein is encoded by nucleic acid sequence derived from a fungal species.

A method, comprising an isolated prolyl oligopeptidase protein, wherein said prolyl oligopeptidase protein is encoded by nucleic acid sequence derived from a fungal species.

The present invention provides an antibody having specificity to a prolyl oligopeptidase protein, wherein said prolyl oligopeptidase protein is encoded by a nucleotide sequence derived from a fungal species. In one embodiment, the prolyl oligopeptidase includes but is not limited to a prolyl oligopeptidase, prolyl oligopeptidase A prolyl oligopeptidase B, and fragments thereof. In one embodiment, the prolyl oligopeptidase A comprises any one sequence set forth in SEQ ID NOs: 250-252, 254, 258, 261-269, 271-273, 275-276, 330-332, 334-336, 346. In a preferred embodiment, the prolyl oligopeptidase B comprises any one sequence set forth in SEQ ID NOs: 267, 253, 271, 273, 276, 280, 282, 286, 288, 289, 290, 293, 296-297, 332, 343, 345, 346, 336, 337, 339, 343, 302.

A composition, comprising a mushroom P450 protein.

A method, comprising a mushroom P450 protein.

Definitions

To facilitate an understanding of the present invention, a number of terms and phrases as used herein are defined below:

The use of the article “a” or “an” is intended to include one or more.

As used herein, terms defined in the singular are intended to include those terms defined in the plural and vice versa.

As used herein, “peptide” refers to compounds containing two or more amino acids linked by the carboxyl group of one amino acid to the amino group of another, i.e. “peptide linkages” to form an amino acid sequence. It is contemplated that peptides may be purified and/or isolated from natural sources or prepared by recombinant or synthetic methods. Amino acid sequences may be encoded by naturally or non-naturally occurring nucleic acid sequences or synthesized by recombinant nucleic acid sequences or artificially synthesized. A peptide may be a linear peptide or a cyclopeptide, i.e. cyclic including bicyclic.

As used herein, "cyclic peptide" or "cyclopeptide" in general refers to a peptide comprising at least one internal bond attaching nonadjacent amino acids of the peptide, such as when the end amino acids of a linear sequence are attached to form a circular peptide. A "bicyclic peptide" may have at least two internal bonds forming a cyclopeptide of the present inventions, such as when the end amino acids of a linear sequence are attached to form a circular peptide in addition to another internal bond attaching two nonadjacent amino acids, for example, see FIG. 1, amanatoxin and pallotoxins.

As used herein, the term "*Amanita* peptide" or "*Amanita* toxin" or "*Amanita* peptide toxin" refers to any linear or cyclic peptide produced by a mushroom, not restricted to a biologically active toxin. It is not intended that the present invention be limited to a toxin or a peptide produced by an *Amanita* mushroom and includes similar peptides and toxins produced by other fungi, including but not limited to species of *Lepiota, Conocybe, Galerina*, and the like. In particular, an *Amanita* peptide toxin resembles any of the amatoxins and phallotoxins, such as similarity of amino acid sequences, matching toxin motifs as shown herein, encoded between the conserved regions (A and B) of their proproteins, encoded by hypervariable regions of their proproteins (P), and the like. The *Amanita* peptides include, but are not restricted to, amatoxins such as the amanitins, and phallotoxins such as phalloidin and phallacidin. For example, an exemplary *Amanita* peptide in one embodiment ranges from 6-15 amino acids in length. In another embodiment an *Amanita* peptide toxin ranges from 7-11 amino acids in length. In one embodiment, an *Amanita* peptide is linear. In another embodiment, an *Amanita* peptide is a bicyclic peptide. It is not meant to limit an *Amanita* peptide to a naturally produced peptide. In some embodiments, an *Amanita* peptide has a artificial sequence, in other words a nucleic acid encoding an artificial peptide sequence was not naturally found in a fungus or found encoded by a nucleic acid sequence isolated from a fungus.

As used herein, "biologically active" refers to a peptide that when contacted with a cell, tissue or organ induces a biological activity, such as stimulating a cell to divide, causing a cell to alter its function, i.e. altering T cell function, causing a cell to change expression of genes, etc.

As used herein, a "propeptide" refers to an amino acid sequence containing a smaller peptide representing the amino acid sequence found in mature amatoxins and phallotoxins in addition to new amino acid sequences in the toxin position, for example, a propeptide of GmAMA1, see FIG. 32, comprises an amanitin IWGIGCNP (SEQ ID NO: 50) while exemplary sequences coding for new peptides in the toxin position are shown in Table 10C and 11.

As used herein, a "prepropeptide" refers to an amino acid sequence containing a leader sequence, such as a signal sequence for translation, on the 5' end prior to the start site, i.e. M, in addition to a smaller peptide representing the amino acid sequence found in mature amatoxins and phallotoxins, for example, LTSHSNSNPRPLLITMSDINATRLPAWLVDCPCVGDDVNRLL shows an exemplary prepropeptide wherein the propeptide is BOLD and the peptide is underlined.

The terms "peptide," "polypeptide," "propeptide," "propolypeptide," "prepropeptide," "prepropolypeptide," and "protein" in general refer to a primary sequence of amino acids that are joined by covalent "peptide linkages." Polypeptides may encompass either peptides or proteins. In general, a peptide consists of a few amino acids, and is shorter than a protein. "Amino acid sequence" and like terms, such as "polypeptide" or "protein" are not meant to limit the amino acid sequence to the complete, native amino acid sequence associated with the recited protein molecule.

As used herein, the term "synthetic" or "artificial" in relation to a peptide sequence refers to a peptide made either artificially from covalently bonding amino acids, such as by made by a Peptide Synthesizer, (for example, Applied Biosystems) or a peptide derived from an amino acid sequence encoded by a recombinant nucleic acid sequence.

As used herein, the term "toxin" in general refers to any detrimental or harmful effects on a cell or tissue. However for the purpose of the present inventions a "toxin" or "peptide toxin" specifically refers to a peptide sequence found within a propeptide in the position of a known toxin of the present inventions, for examples, see Table 10. Therefore, a peptide found within a propeptide may have a biological activity.

As used herein, the term "toxin" in reference to a poison refers to any substance (for example, alkaloids, cyclopeptides, coumarins, and the like) that is detrimental (i.e., poisonous) to cells and/or organisms, in particular a human organism. In particularly preferred embodiments of the present inventions, the term "toxin" encompasses toxins, suspected toxins, and pharmaceutically active peptides or biologically active peptides produced by various fungal species, including, but not limited to, a cyclic peptide toxin such as an amanitin, that provides toxic activity towards cells and humans. However, it is not intended that the present invention be limited to any particular fungal toxin or frugal species. Indeed, it is intended that the term encompass fungal toxins produced by any organism. As used herein, a toxin encompasses linear sequences of cyclic pharmaceutically active peptides and linear sequences showing identity to known toxins regardless of whether these sequences are known to be toxic.

As used herein, "amatoxin" generally refers to a family of peptide compounds, related to and including the amanitins. For the purposes of the present inventions, an amatoxin refers to any small peptide, linear and cyclic, comprising an exemplary chemical structure as shown in FIG. 1 or encoded by nucleic acid sequence of the present invention, wherein the nucleic acid sequence and/or proprotein has a higher sequence homology to AMA1 than to an analogous sequence of PHA1.

As used herein, "phallotoxin" generally refers to a family of peptide compounds, related to and including phallacidin and phalloidin. For the purposes of the present inventions, a phallotoxin refers to any small peptide encoded by nucleic acid sequences where the nucleic acid sequence and/or proprotein has a higher sequence homology to PHA1 than to an analogous sequence of AMA1.

As used herein the term "microorganism" refers to microscopic organisms and taxonomically related macroscopic organisms within the categories of algae, bacteria, fungi (including lichens), protozoa, viruses, and subviral agents.

The terms "eukaryotic" and "eukaryote" are used in the broadest sense. It includes, but is not limited to, any organisms containing membrane bound nuclei and membrane bound organelles. Examples of eukaryotes include but are not limited to animals, plants, algae, diatoms, and fungi.

The terms "prokaryote" and "prokaryotic" are used in the broadest sense. It includes, but is not limited to, any organisms without a distinct nucleus. Examples of prokaryotes include but are not limited to bacteria, blue-green algae (cyanobacteria), archaebacteria, actinomycetes and *mycoplasma*. In some embodiments, a host cell is any microorganism.

As used herein, the term "fungi" is used in reference to eukaryotic organisms such as mushrooms, rusts, molds and yeasts, including dimorphic fungi. "Fungus" or "fungi" also refers to a group of lower organisms lacking chlorophyll and dependent upon other organisms for source of nutrients.

As used herein, "mushroom" refers to the fruiting body of a fungus.

As used herein, "fruiting body" refers to a reproductive structure of a fungus which produces spores, typically comprising the whole reproductive structure of a mushroom including cap, gills and stem, for example, a prominent fruiting body produced by species of Ascomycota and Basidiomycota, examples of fruiting bodies are "mushrooms," "carpophores," "toadstools," "puffballs", and the like.

As used herein, "fruiting body cell" refers to a cell of a cap or stem which may be isolated or part of the structure.

As used herein, "spore" refers to a microscopic reproductive cell or cells.

As used herein, "mycelium" refers to a mass of fungus hyphae, otherwise known as a vegetative portion of a fungus.

As used herein, "Basidiomycota" in reference to a Phylum or Division refers to a group of fungi whose sexual reproduction involves fruiting bodies comprising basidiospores formed on club-shaped cells known as basidia.

As used herein, "Basidiomycetes" in reference to a class of Phylum Basidiomycota refers to a group of fungi. Basidiomycetes include mushrooms, of which some are rich in cyclopeptides and/or toxins, and includes certain types of yeasts, rust and smut fungi, gilled-mushrooms, puffballs, polypores, jelly fungi, brackets, coral, mushrooms, boletes, puffballs, stinkhorns, etc.

As used herein, "Homobasidiomycetes" in reference to fungi refers to a recent classification of fungi, including *Amanita* spp., *Galerina* spp., and all other gilled fungi (commonly known as mushrooms), based upon cladistics rather than morphology.

As used herein, "Heterobasidiomycetes" in reference to fungi refers to those basidiomycete fungi that are not Homobasidiomycetes.

As used herein, "Ascomycota" or "ascomycetes" in reference to members of a fungal Phylum or Division refers to a "sac fungus" group. Of the Ascomycota, a class "Ascomycetes" includes *Candida albicans*, unicellular yeast, *Morchella esculentum*, the morel, and *Neurospora crassa*. Some ascomycetes cause disease, for example. *Candida albicans* causes thrush and vaginal infections; or produce chemical toxins associated with diseases, for example, *Aspergillus flavus* produces a contaminant of nuts and stored grain called aflatoxin, that acts both as a toxin and a deadly natural carcinogen.

As used herein. "*Amanita*" refer to a genus of fungus whose members comprise poisonous mushrooms, e.g., *Amanita* (*A.*) *bisporigera, A. virosa, A. ocreata, A. suballiacea*, and *A. tenuifolia* which are collectively referred to as "death angels" or "Destroying Angels" and "*Amanita phalloides*" or "*A. phalloides* var. *alba*" or "*A. phalloides* var. *verna*" or "*A. verna*", referred to as "death cap." The toxins of these mushrooms frequently cause death through liver and kidney failure in humans. Not all species of this genus are deadly, for example, *Amanita muscaria*, the fly agaric, induces gastrointestinal distress and/or hallucinations while others do not induce detectable symptoms.

As used herein, nonribosomal peptide synthetase (NRPS) is an enzyme that catalyzes the biosynthesis of a small (20 or fewer amino acids) peptide or depsipeptide, linear or circular, and is composed of one or more domains (modules) typical of this class of enzyme. Each domain is responsible for aminoacyl adenylation of one component amino acid. NRPSs can also contain auxiliary domains catalyzing, e.g., N-methylation and amino acid epimerization (Walton. et al., in Advances in Fungal Biotechnology for Industry, Agriculture, and Medicine, et al., Eds. (Kluwer Academic/Plenum, N.Y., 2004, pp. 127-162; Finking, et al., (2004) Annu Rev Microbiol 58:453-488, all of which are herein incorporated by reference). Examples are gramicidin synthetase, HC-toxin synthetase, cyclosporin synthetase, and enniatin synthetase.

As used herein, "prolyl oligopeptidase" or "POP" refers to a member of a family of enzymes classified and referred to as EC 3.4.21.26-enzymes that are capable of cleaving a peptide sequence, such that hydrolysis of Pro-|-Xaa>> Ala-|-Xaa in oligopeptides, also referred to as any one of "post-proline cleaving enzyme," "proline-specific endopeptidase," "post-proline endopeptidase," "proline endopeptidase," "endoprolyl peptidase," "prolyl endopeptidase," "post-proline cleaving enzyme," "post-proline endopeptidase," and "prolyl endopeptidase." A POPA of the present inventions refers to a mushroom sequence found in the majority of mushrooms. A POPB of the present inventions refers to a sequence which in one embodiment has approximately a 55% amino acid homology to POPA, wherein said POPB sequence is primarily found in *Amanita* peptide producing mushroom species.

As used herein, the terms "cell," "cell line," and "cell culture" may be used interchangeably. All of these terms also include their progeny, which are any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector and/or expressing a heterologous gene encoded by a vector. Several types of fungi and cultures are available for use as a host cell, such as those described for use in fungal expression systems, described below. Prokaryotes include but are not limited to gram negative or positive bacterial cells. Numerous cell lines and cultures are available for use as a host cell, and they can be obtained through the American Type Culture Collection (ATCC), an organization that serves as an archive for living cultures and genetic materials (atcc.org). An appropriate host can be determined by one of skill in the art based on the vector nucleic acid sequence and the desired result. A plasmid or cosmid, for example, can be introduced into a prokaryote host cell for replication of many vectors. Bacterial cells used as host cells for expression vector replication and/or expression include, among those listed elsewhere herein, DH5.alpha., JM109, and KC8, as well as a number of commercially available bacterial hosts such as SURE™ Competent Cells and SOLOPACK™ Gold Cells (Stratagene, La Jolla). Alternatively, bacterial cells such as *E. coli* LE392 can be used as host cells for phage viruses. In some embodiments, a host cell is used as a recipient for vectors. A host cell may be "transfected" or "transformed," which refers to a process by which exogenous nucleic acid is transferred or introduced into the host cell. For example, a host cell may be located in a transgenic mushroom. A transformed cell includes the primary subject cell and its progeny.

As used herein, "host fungus cell" refers to any fungal cell, for example, a yeast cell, a mold cell, and a mushroom cell (such as *Neurospora crassa, Aspergillus nidulans, Cochliobolus carbonum, Coprinus cinereus, Ustilago maydis*, and the like).

As used herein, the term "Fungal expression system" refers to a system using fungi to produce (express) enzymes and other proteins and peptides. Examples of filamentous fungi which are currently used or proposed for use in such processes are *Neurospora crassa, Acremonium chrysogenum, Tolypocladium geodes, Mucor circinelloides. Trichoderma reesei, Aspergillus nidulans, Aspergillus niger, Coprimns cinereus. Aspergillus oryzae*, etc. Further examples include an expression system for basidiomycete genes (for example, Gola. et al., (2003) J Basic Microbiol. 43(2): 104-12; herein incorporated by reference) and fungal expression systems using, for example, a monokaryotic laccase-deficient *Pycnoporus cinnabarinus* strain BRFM 44 (Banque de Resources Fongiques de Marseille, Marseille, France), and *Schizophyllum commune*, (for example, Alexandra, et al., (2004) Appl Environ Microbiol. 70(11):6379-638; Lugones, et al., (1999) Mol. Microbiol. 32:681-700; Schuren, et al., (1994) Curr. Genet. 26:179-183; all of which are herein incorporated by reference).

The term "transgene" as used herein refers to a foreign gene, such as a heterologous gene, that is placed into an organism by, for example, introducing the foreign gene into cells or primordial tissue. The term "foreign gene" refers to any nucleic acid (e.g., gene sequence) that is introduced into the genome of a host cell by experimental manipulations and may include gene sequences found in that cell so long as the introduced gene does not reside in the same location as does the naturally-occurring gene.

As used herein, the term "vector" is used in reference to nucleic acid molecules that transfer DNA segment(s) from one cell to another. The term "vehicle" is sometimes used interchangeably with "vector." A vector "backbone" comprises those parts of the vector which mediate its maintenance and enable its intended use (e.g., the vector backbone may contain sequences necessary for replication, genes imparting drug or antibiotic resistance, a multiple cloning site, and possibly operably linked promoter and/or enhancer elements which enable the expression of a cloned nucleic acid). The cloned nucleic acid (e.g., such as a cDNA coding sequence, or an amplified PCR product) is inserted into the vector backbone using common molecular biology techniques.

A "recombinant vector" indicates that the nucleotide sequence or arrangement of its parts is not a native configuration, and has been manipulated by molecular biological techniques. The term implies that the vector is comprised of segments of DNA that have been artificially joined.

The terms "expression vector" and "expression cassette" refer to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome-binding site, often along with other sequences. Eukaryotic cells are known to utilize promoters, enhancers, and termination and polyadenylation signals.

As used herein, "recombinant nucleic acid" or "recombinant gene" or "recombinant DNA molecule" or "recombinant nucleic acid sequence" indicates that the nucleotide sequence or arrangement of its parts is not a native configuration, and has been manipulated by molecular biological techniques. The term implies that the DNA molecule is comprised of segments of DNA that have been artificially joined together, for example, a lambda clone of the present inventions. Protocols and reagents to manipulate nucleic acids are common and routine in the art (See e.g, Maniatis et al. (eds.), Molecular Cloning: A Laboratory Manual. Cold Spring Harbor Laboratory Press, NY. [1982]; Sambrook et al. (eds.), Molecular Cloning: A Laboratory Manual, Second Edition, Volumes 1-3, Cold Spring Harbor Laboratory Press, NY, [1989]; and Ausubel et al. (eds.), Current Protocols in Molecular Biology, Vol. 1-4, John Wiley & Sons. Inc., New York [1994]; all of which are herein incorporated by reference). Similarly, a "recombinant protein" or "recombinant polypeptide" refers to a protein molecule that is expressed from a recombinant DNA molecule. Use of these terms indicates that the primary amino acid sequence, arrangement of its domains or nucleic acid elements which control its expression are not native, and have been manipulated by molecular biology techniques. As indicated above, techniques to manipulate recombinant proteins are also common and routine in the art.

As used herein, "recombinant prepropeptide nucleic acid sequence" refers to a nucleic acid sequence comprising a leader sequence which encodes a propeptide amino acid sequence. Similarly, a "recombinant propeptide nucleic acid sequence" refers to a nucleic acid sequence which encodes a propeptide amino acid sequence. Thus in general, a "recombinant peptide nucleic acid sequence" refers to a nucleic acid sequence which encodes a peptide amino acid sequence, such as a prepropeptide, a propeptide or smaller peptides, for example, peptides capable of forming cyclic peptides.

The terms "exogenous" and "heterologous" are sometimes used interchangeably with "recombinant." An "exogenous nucleic acid," "exogenous gene" and "exogenous protein" indicate a nucleic acid, gene or protein, respectively, that has come from a source other than its native source, and has been artificially supplied to the biological system. In contrast, the terms "endogenous protein," "native protein," "endogenous gene," and "native gene" refer to a protein or gene that is native to the biological system, species or chromosome under study. A "native" or "endogenous" polypeptide does not contain amino acid residues encoded by recombinant vector sequences, that is, the native protein contains only those amino acids found in the polypeptide or protein as it occurs in nature. A "native" polypeptide may be produced by recombinant means or may be isolated from a naturally occurring source. Similarly, a "native" or "endogenous" gene is a gene that does not contain nucleic acid elements encoded by sources other than the chromosome on which it is normally found in nature.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc.). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the untranslated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

As used herein, the terms "an oligonucleotide having a nucleotide sequence encoding a gene" and "polynucleotide having a nucleotide sequence encoding a gene," mean a nucleic acid sequence comprising the coding region of a gene or, in other words, the nucleic acid sequence that encodes a gene product. The coding region may be present in a cDNA, genomic DNA, or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements include splicing signals, polyadenylation signals, termination signals, etc.

The terms "in operable combination," "in operable order," "operably linked" and similar phrases when used in reference to nucleic acid herein are used to refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence (e.g., a nucleic acid sequence encoding a fusion protein of the present invention) to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," e.g., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR, in connection with the compositions disclosed herein (see U.S. Pat. Nos. 4,683,202, 5,928,906, each incorporated herein by reference). It is further contemplated that control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment (e.g., comprising nucleic acid encoding a fusion protein of the present invention) in the cell type, organelle, and organism chosen for expression. Those of skill in the art of microbiology and molecular biology generally know the use of promoters, enhancers, and cell type combinations for protein expression, for example, see Sambrook et al. (1989); herein incorporated by reference. The promoters employed may be constitutive, tissue-specific, inducible, and/or useful under the appropriate conditions to direct the desired level of expression of the introduced DNA segment comprising a target protein of the present invention (e.g., high levels of expression that are advantageous in the large-scale production of recombinant proteins and/or peptides). The promoter may be heterologous or endogenous.

Transcriptional control signals in eukaryotes comprise "promoter" and "enhancer" elements. Promoters and enhancers consist of short arrays of DNA sequences that interact specifically with cellular proteins involved in transcription (Maniatis et al., Science 236:1237 [1987]; herein incorporated by reference). Promoter and enhancer elements have been isolated from a variety of eukaryotic sources including genes in yeast, insect and mammalian cells, as well as viruses. Analogous control elements (i.e., promoters and enhancers) are also found in prokaryotes. The selection of a particular promoter and enhancer to be operably linked in a recombinant gene depends on what cell type is to be used to express the protein of interest. Some eukaryotic promoters and enhancers have a broad host range while others are functional only in a limited subset of cell types (for review, see, Voss et al., Trends Biochem. Sci., 11: 287 [1986] and Maniatis et al., Science 236:1237 [1987]; all of which are herein incorporated by reference).

The term "promoter/enhancer region" is usually used to describe this DNA region, typically but not necessarily 5' of the site of transcription initiation, sufficient to confer appropriate transcriptional regulation. The word "promoter" alone is sometimes used synonymously with "promoter/enhancer." A promoter may be constitutively active, or alternatively, conditionally active, where transcription is initialed only under certain physiological conditions or in the presence of certain drugs. The 3' flanking region may contain additional sequences for regulating transcription, especially the termination of transcription.

The term "introns" or "intervening regions" or "intervening sequences" are segments of a gene which are contained in the primary transcript (i.e., hetero-nuclear RNA, or hnRNA), but are spliced out to yield the processed mRNA form. Introns may contain transcriptional regulatory elements such as enhancers. The mRNA produced from the genomic copy of a gene is translated in the presence of ribosomes to yield the primary amino acid sequence of the polypeptide.

Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "promoter/enhancer" denotes a segment of DNA which contains sequences capable of providing both promoter and enhancer functions (i.e., the functions provided by a promoter element and an enhancer element). For example, the long terminal repeats of retroviruses contain both promoter and enhancer functions. The promoter/enhancer may be "endogenous," or "exogenous," or "heterologous." An "endogenous" promoter/enhancer is one which is naturally linked with a given gene in the genome. An "exogenous" or "heterologous" promoter/enhancer is one placed in juxtaposition to a gene by means of genetic manipulation (i.e., molecular biological techniques such as cloning and recombination) such that transcription of the gene is controlled by the linked promoter/enhancer.

As used herein, the term "subject" refers to both humans and animals.

As used herein, the term "patient" refers to a subject whose care is under the supervision of a physician/veterinarian or who has been admitted to a hospital.

The term "sample" is used in its broadest sense. In one sense it can refer to a mushroom cell or mushroom tissue. In another sense, it is meant to include a specimen or culture obtained from any source, as well as biological and environmental samples that may comprise mushroom toxins. Biological samples may be obtained from mushrooms or animals (including humans) and encompass fluids, such as gastrointestinal fluids, solids, tissues, and the like. Environmental samples include environmental material such as mushrooms, hyphae, soil, water, such as cooking water, and the like. These terms encompasses all types of samples obtained from humans and other animals, including but not limited to, body fluids such as digestive system fluid, saliva, stomach contents, intestinal contents, urine, blood, fecal matter, diarrhea, as well as solid tissue, partially and fully digested samples. These terms also refers to swabs and other sampling devices which are commonly used to obtain samples for culture of microorganisms. Biological samples may be food products and ingredients, such as a mushroom sample, a raw sample, a cooked sample, a canned sample, animal, including human, fluid or tissue and waste. Environmental samples include environmental material such as surface matter, soil, water, and industrial samples, as well as samples obtained from food processing instruments, apparatus, equipment, disposable, and non-disposable items. These examples are not to be construed as limiting the sample types applicable to the present invention.

Whether biological or environmental, a sample suspected of containing a poisonous mushroom cell or mushroom toxin, may (or may not) first be subjected to an enrichment means. By "enrichment means" or "enrichment treatment," the present invention contemplates (i) conventional techniques for isolating a particular mushroom cell or mushroom toxin or mushroom sequence of interest away from other components by means of liquid, solid, semi-solid based separation technique or any other separation technique, and (ii) novel techniques for isolating particular cells or toxins away from other components. It is not intended that the present invention be limited only to one enrichment step or type of enrichment means. For example, it is within the scope of the present invention, following subjecting a sample to a conventional enrichment means, such as HPLC, to subject the resultant preparation to further purification such that a pure sample or culture of a strain of a species of interest is produced. This pure sample or culture may then be analyzed by the compositions and methods of the present inventions.

Thus, a polynucleotide of the present invention may encode a polypeptide, a polypeptide plus a leader sequence (which may be referred to as a prepolypeptide), a precursor of a polypeptide having one or more prosequences which are not the leader sequences of a prepolypeptide, or a prepropolypeptide, which is a precursor to a propolypeptide, having a leader sequence and one or more prosequences, which generally are removed during processing steps that produce active forms of the polypeptide.

As used herein, the term "portion" when in reference to a protein (as in "a portion of a given protein") refers to fragments of that protein. The fragments may range in size from four amino acid residues to the entire amino acid sequence minus one amino acid.

As used herein, the term "target protein" or "protein of interest" when used in reference to a protein or nucleic acid refers to a protein or nucleic acid encoding a protein of interest for which structure or toxicity is to be analyzed and/or altered of the present invention, such as a gene encoding a mushroom toxin or a mushroom peptide. The term "target protein" encompasses both wild-type proteins and those that are derived from wild type proteins (e.g., variants of wild-type proteins or polypeptides, or, chimeric genes constructed with portions of target protein coding regions), and further encompasses fragments of a wild-type protein. Thus, in some embodiments, a "target protein" is a variant or mutant. The present invention is not limited by the type of target protein analyzed.

As used herein, the term "endopeptidase" refers to an enzyme that catalyzes the cleavage of peptide bonds within a polypeptide or protein. Peptidase refers to the fact that it acts on peptide bonds and endopeptidase refers to the fact that these are internal bonds. An exopeptide catalyzes the cleavage of the terminal or penultimate peptide bond, releasing a single amino acid or dipeptide from the peptide chain.

In particular, the terms "target protein gene" or "target protein genes" refer to the full-length target protein sequence, such as a prepropolypeptide. However, it is also intended that the term encompass fragments of the target protein sequences, mutants of the target protein sequences, as well as other domains within the full-length target protein nucleotide sequences. Furthermore, the terms "target protein nucleotide sequence" or "target protein polynucleotide sequence" encompasses DNA, cDNA, and RNA (e.g., mRNA) sequences.

The term "gene of interest" as used herein refers to the gene inserted into the polylinker of an expression vector whose expression in the cell is desired for the purpose of performing further studies on the transfected cell. The gene of interest may encode any protein whose expression is desired in the transfected cell at high levels. The gene of interest is not limited to the examples provided herein; the gene of interest may include cell surface proteins, secreted proteins, ion channels, cytoplasmic proteins, nuclear proteins (e.g., regulatory proteins), mitochondrial proteins, etc.

As used herein, the term "gene" refers to a DNA sequence that comprises control and coding sequences necessary for the production of a polypeptide or protein precursor. The polypeptide can be encoded by a full-length coding sequence, or by a portion of the coding sequence, as long as the desired protein activity is retained. Genes can encode a polypeptide or any portion of a polypeptide within the gene's "coding region" or "open reading frame." The polypeptide produced by the open reading frame of a gene may or may not display functional activity or properties of the full-length polypeptide product (e.g., toxin activity, enzymatic activity, ligand binding, signal transduction, etc.).

An addition to the coding region of the nucleic acid, the term "gene" also encompasses the transcribed nucleotide sequences of the full-length mRNA adjacent to the 5' and 3' ends of the coding region. These noncoding regions are variable in size, and sometimes extend for distances up to or exceeding 1 kb on both the 5' and 3' ends of the coding region. The sequences that are located 5' and 3' of the coding region and are contained on the mRNA are referred to as 5' and 3' untranslated regions (5' UTR and 3' UTR). Both the 5' and 3' UTR may serve regulatory roles, including translation initiation, post-transcriptional cleavage and polyadenylation. The term "gene" encompasses mRNA, cDNA and genomic forms of a gene.

It is contemplated that the genomic form or genomic clone of a gene may contain the sequences of the transcribed mRNA, as well as other non-coding sequences which lie outside of the mRNA. The regulatory regions which lie outside the mRNA transcription unit are sometimes called "5' or 3' flanking sequences." A functional genomic form of a gene must contain regulatory elements necessary for the regulation of transcription.

Nucleic acid molecules (e.g., DNA or RNA) are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotide or polynucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element or the coding region. Transcription termination and polyadenylation signals are located 3' or downstream of the coding region.

As used herein, the terms "nucleic acid molecule encoding," "DNA sequence encoding," and "DNA encoding" and similar phrases refer to the order or sequence of deoxyribonucleotides along a strand of deoxyribonucleic acid. The order of these deoxyribonucleotides determines the order of amino acids along the polypeptide (e.g., protein) chain. The DNA sequence thus codes for the amino acid sequence.

As used herein, the terms "an oligonucleotide having a nucleotide sequence encoding a gene," "polynucleotide having a nucleotide sequence encoding a gene," and similar phrases are meant to indicate a nucleic acid sequence comprising the coding region of a gene (i.e., the nucleic acid sequence which encodes a gene product). The coding region may be present in a cDNA, genomic DNA or RNA form. When present in a DNA form, the oligonucleotide, polynucleotide or nucleic acid may be single-stranded (i.e., the sense strand or the antisense strand) or double-stranded.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of the mRNA. Gene expression can be regulated at many stages. "Up-regulation" or "activation" refers to regulation that increases the production of gene expression products (i.e., RNA or protein), while "down-regulation" or "repression" refers to regulation that decreases mRNA or protein production. Molecules (e.g., transcription factors) that are involved in up-regulation or down-regulation are often called "activators" and "repressors," respectively.

As used herein, the term "hybridization" is used in reference to the pairing of complementary nucleic acids. Hybridization can be demonstrated using a variety of hybridization assays (Southern blot, Northern Blot, slot blot, phage plaque hybridization, and other techniques). These protocols are common in the art (See e.g., Sambrook et al. (eds.), Molecular Cloning: A Laboratory Manual, Second Edition, Volumes 1-3, Cold Spring Harbor Laboratory Press, NY, [1989]; Ausubel et al. (eds.), Current Protocols in Molecular Biology, Vol. 1-4, John Wiley & Sons, Inc., New York [1994]; all of which are herein incorporated by reference).

Hybridization is the process of one nucleic acid pairing with an antiparallel counterpart which may or may not have 100% complementarity. Two nucleic acids which contain 100% antiparallel complementarity will show strong hybridization. Two antiparallel nucleic acids which contain no antiparallel complementarity (generally considered to be less than 30/%) will not hybridize. Two nucleic acids which contain between 31-99% complementarity will show an intermediate level of hybridization. A single molecule that contains pairing of complementary nucleic acids within its structure is said to be "self-hybridized."

During hybridization of two nucleic acids under high stringency conditions, complementary base pairing will occur only between nucleic acid fragments that have a high frequency of complementary base sequences. Thus, conditions of "weak" or "low" stringency are often required with nucleic acids that are derived from organisms that are genetically diverse, as the frequency of complementary sequences is usually less. As used herein, two nucleic acids which are able to hybridize under high stringency conditions are considered "substantially homologous." Whether sequences are "substantially homologous" may be verified using hybridization competition assays. For example, a "substantially homologous" nucleotide sequence is one that at least partially inhibits a completely complementary probe sequence from hybridizing to a target nucleic acid under conditions of low stringency. This is not to say that conditions of low stringency are such that non-specific binding is permitted; low stringency conditions require that the binding of two sequences to one another be a specific (i.e., selective) interaction. The absence of non-specific binding may be verified by the use of a second target that lacks even a partial degree of complementarity (e.g., less than about 30% identity); in the absence of non-specific binding the probe will not hybridize to the second non-complementary target. When used in reference to a double-stranded nucleic acid sequence such as a cDNA or genomic clone, the term "substantially homologous" refers to any probe that can hybridize to either or both strands of the double-stranded nucleic acid sequence under conditions of high stringency.

Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "stringency" is used in reference to the conditions of temperature, ionic strength, and the presence of other compounds such as organic solvents, under which nucleic acids hybridize. "Low or weak stringency" conditions are reaction conditions which favor the complementary base pairing and annealing of two nucleic acids. "High stringency" conditions are those conditions which are less optimal for complementary base pairing and annealing. The art knows well that numerous variables affect the strength of hybridization, including the length and nature of the probe and target (DNA, RNA, base composition, present in solution or immobilized, the degree of complementary between the nucleic acids, the $T_m$ of the formed hybrid, and the G:C ratio within the nucleic acids). Conditions may be manipulated to define low or high stringency conditions: factors such as the concentration of salts and other components in the hybridization solution (e.g., the presence or absence of formamide, dextran sulfate, polyethylene glycol) as well as temperature of the hybridization and/or wash steps. Conditions of "low" or "high" stringency are specific for the particular hybridization technique used.

As used herein the term "stringency" is used in reference to the conditions of temperature, ionic strength, and the presence of other compounds such as organic solvents, under which nucleic acid hybridizations are conducted. Those skilled in the art will recognize that "stringency" conditions may be altered by varying the parameters just described either individually or in concert. With "high stringency" conditions, nucleic acid base pairing will occur only between nucleic acid fragments that have a high frequency of complementary base sequences (e.g., hybridization under "high stringency" conditions may occur between homologs with about 85-100% identity, preferably about 70-100% identity). With medium stringency conditions, nucleic acid base pairing will occur between nucleic acids with an intermediate frequency of complementary base sequences (e.g., hybridization under "medium stringency" conditions may occur between homologs with about 50-70% identity). Thus, conditions of "weak" or "low" stringency are often required with nucleic acids that are derived from organisms that are genetically diverse, as the frequency of complementary sequences is usually less. "High stringency conditions" when used in reference to nucleic acid hybridization comprise conditions equivalent to binding or hybridization at 65° C. in a solution consisting of 5.times.SSPE (43.8 g/l NaCl, 6.9 g/l $NaH_2PO_4H_2O$ and 1.85 g/l EDTA, pH adjusted to 7.4 with NaOH), 0.5% sodium dodecyl sulfate (SDS), 5×Denhardt's reagent and 100 μg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 55° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 .mu.g/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.1% SDS, 5×Denhardt's reagent (50×Denhardt's contains per 500 ml: 5 g Ficoll (Type 400, Pharamcia), 5 g BSA (Fraction V; Sigma)) and 100 μg/ml denatured salmon sperm DNA followed by washing in a solution comprising 5×SSPE, 0.1% SDS at 42° C. when a probe of about 500 nucleotides in length is employed.

As used herein, the term "$T_m$" is used in reference to the "melting temperature." The melting temperature is the temperature at which a population of double-stranded nucleic acid molecules becomes half dissociated "denatures") into single strands. The equation for calculating the $T_m$ of nucleic acids is well known in the art. As indicated by standard references, a simple estimate of the $T_m$ value may be calculated by the equation: $T_m$=81.5+0.41(% G+C), when a nucleic acid is in aqueous solution at 1 M NaCl (See e.g., Anderson and Young, Quantitative Filter Hybridization, in Nucleic Acid Hybridization (1985)). Other references include more sophisticated computations that take structural as well as sequence characteristics into account for the calculation of $T_m$.

As used herein, the terms "complementary" or "complementarity" are used in reference to polynucleotides (i.e., a sequence of nucleotides) related by the base-pairing rules. For example, the sequence 5'-A-G-T-3', is complementary to the sequence 3'-T-C-A-5'. Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in polymerase chain reaction (PCR) amplification reactions, as well as detection methods that depend upon binding between nucleic acids.

As used herein, the terms "antiparallel complementarity" and "complementarity" are synonymous. Complementarity can include the formation of base pairs between any type of nucleotides, including non-natural bases, modified bases, synthetic bases and the like.

The following definitions are the commonly accepted definitions of the terms "identity," "similarity" and "homology." Percent identity is a measure of strict amino acid conservation. Percent similarity is a measure of amino acid conservation which incorporates both strictly conserved amino acids, as well as "conservative" amino acid substitutions, where one amino acid is substituted for a different amino acid having similar chemical properties (i.e. a "conservative" substitution). The term "homology" can pertain to either proteins or nucleic acids. Two proteins can be described as "homologous" or "non-homologous," but the degree of amino acid conservation is quantitated by percent identity and percent similarity. Nucleic acid conservation is measured by the strict conservation of the bases adenine, thymine, guanine and cytosine in the primary nucleotide sequence. When describing nucleic acid conservation, conservation of the nucleic acid primary sequence is sometimes expressed as percent homology. In the same nucleic acid, one region may show a high percentage of nucleotide sequence conservation, while a different region can show no or poor conservation. Nucleotide sequence conservation can not be inferred from an amino acid similarity score. Two proteins may show domains that in one region are homologous, while other regions of the same protein are clearly non-homologous.

Numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other. When used in reference to a single-stranded nucleic acid sequence, the term "substantially homologous" refers to any probe that can hybridize (i.e., it is the exact or substantially close to the complement of) the single-stranded nucleic acid sequence under conditions of low stringency as described above.

The term "amplification" is defined as the production of additional copies of a nucleic acid sequence and is generally carried out using polymerase chain reaction technologies well known in the art (Dieffenbach and G S Dvekler, PCR Primer, a Laboratory Manual, Cold Spring Harbor Press, Plainview, N.Y. [1995]; herein incorporated by reference).

As used herein, the term "polymerase chain reaction" ("PCR") refers to the methods disclosed in U.S. Pat. Nos. 4,683,195, 4,683,202 and 4,965,188, all of which are incorporated herein by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; and/or incorporation of $^{32}$P-labeled or biotinylated deoxyribonucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications. Amplified target sequences may be used to obtain segments of DNA (e.g., genes) for the construction of targeting vectors, transgenes, etc. Reverse transcription PCR (RT-PCR) refers to amplification of RNA (preferably mRNA) to generate amplified DNA molecules (i.e. cDNA). RT-PCR may be used to quantitate mRNA levels in a sample, and to detect the presence of a given mRNA in a sample. RT-PCR may be carried out "in situ", wherein the amplification reaction amplifies mRNA, for example, present in a tissue section.

As used herein, the term "amplifiable nucleic acid" is used in reference to nucleic acids which may be amplified by any amplification method. It is contemplated that "amplifiable nucleic acid" will usually comprise "template." As used herein, the term "template" refers to nucleic acid originating from a sample that is to be used as a substrate for the generation of the amplified nucleic acid.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "primer" refers to an oligonucleotide, typically but not necessarily produced synthetically, that is capable of acting as a point of initiation of nucleic acid synthesis when placed under conditions in which synthesis of a primer extension product that is complementary to a nucleic acid strand is induced, (i.e., in the presence of nucleotides, an inducing agent such as DNA polymerase, and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "amplification reagents" refers to those reagents (e.g., deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

As used herein, the term "sample template" refers to a nucleic acid originating from a sample which is analyzed for the presence of "target," such as a positive control DNA sequence encoding a mushroom toxin. In contrast, "background template" is used in reference to nucleic acid other than sample template, which may or may not be present in a sample. Background template is most often inadvertent. It may be the result of carryover, or it may be due to the presence of nucleic acid contaminants sought to be purified away from the sample. For example, nucleic acids other than those to be detected may be present as background in a test sample.

As used herein, the term "probe" refers to a polynucleotide sequence (for example an oligonucleotide), whether occurring naturally (e.g., as in a purified restriction digest) or produced synthetically, recombinantly or by PCR amplification, which is capable of hybridizing to another nucleic acid sequence of interest, such as a nucleic acid attached to a membrane, for example, a Southern blot or a Northern blot. A probe may be single-stranded or double-stranded. Probes are useful in the detection, identification and isolation of particular gene sequences. It is contemplated that the probe used in the present invention is labeled with any "reporter molecule," so that it is detectable in a detection system, including, but not limited to enzyme (i.e., ELISA, as well as enzyme-based histochemical assays), fluorescent, radioactive, and luminescent systems. It is not intended that the present invention be limited to any particular detection system or label.

The terms "reporter molecule" and "label" are used herein interchangeably. In addition to probes, primers and deoxynucleoside triphosphates may contain labels; these labels may comprise, but are not limited to, $^{32}P$, $^{33}P$, $^{35}S$, enzymes, fluorescent molecules (e.g., fluorescent dyes) or biotin.

As used herein, the term "rapid amplification of cDNA ends" or "RACE" refers to methods such as "classical anchored" or "single-sided PCR" or "inverse PCR" or "ligation-anchored PCR" or "RNA ligase-mediated RACE" for amplifying a 5' or 3' end of a DNA sequence (Frohman et al., (1988) Proc Natl Acad Sci 85:8998-9002; herein incorporated by reference).

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. For example, a given DNA sequence (for example, a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a mushroom toxin includes, by way of example, such nucleic acid in cells ordinarily expressing a mushroom toxin, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (in other words, the oligonucleotide may be single-stranded), but may contain both the sense and anti-sense strands (in other words, the oligonucleotide may be double-stranded).

As used herein, the term "purified" or "to purify" refers to the removal of contaminants from a sample. For example, recombinant nucleotides are expressed in bacterial host cells and the nucleotides are purified by the removal of host cell nucleotides and proteins; the percent of recombinant nucleotides is thereby increased in the sample.

As used herein, the term "kit" is used in reference to a combination of reagents and other materials. It is contemplated that the kit may include reagents such as PCR primer sets, positive DNA controls, such as a DNA encoding a propolypeptide of the present inventions, diluents and other aqueous solutions, and instructions. The present invention contemplates other reagents useful for the identification and/or determination of the presence of an amplified sequence encoding a mushroom toxin, for example, a colorimetric reaction product.

BRIEF DESCRIPTION OF THE DRAWINGS

FIG. 1A shows an exemplary amatoxin structure. FIG. 1B shows an exemplary phallotoxin structure. Exemplary amino acids have the L configuration except hydroxyAsp in phallacidin and Thr in phalloidin, which have the D configuration at the alpha carbon.

FIG. 2A shows an image of an exemplary *A. bisporigera* (collected in Oakland County, Michigan).

FIG. 2B shows an image of an examplary *A. phalloides* (Alameda County, California). FIG. 2C shows an image of an exemplary non-deadly species of *Amanita*. From left to right: three specimens of *A. gemmata, A. muscaria*, and two specimens of *A. franchetii* (Mendocino County, California).

FIG. 4A-4B shows exemplary amanitin (an amatoxin) cDNA sequences, genomic DNA sequences, prepropolypeptide sequences, and polypeptide sequences coding for peptide toxins. FIG. 4A shows exemplary cDNA sequences of the α-amanitin gene (SEQ ID NOs:55 and 56) and predicted amino acid sequence, where 5' and 3' ends were determined by Rapid Amplification of cDNA Ends (RACE). * indicates a stop codon. The string of A's at the end are a poly-A tail from the cDNA. The amatoxin peptide sequence is underlined. FIG. 4B shows an exemplary sequence of genomic DNA covering the amanitin gene based on inverse PCR. The nucleotides encoding the amanitin peptide are underlined.

FIG. 5A-5B shows exemplary phallacidin cDNA, genomic DNA, propolypeptide, and polypeptide sequences encoding phallacidin peptide toxin. FIG. 5A shows exemplary cDNA sequences (SEQ ID NOs:79 and 81) and a predicted amino acid sequence (SEQ ID NO:619), where 5' and 3' ends were determined by RACE, * indicates the stop codon. The string of A's at the end are the poly-A tail and were found in the cDNA but not the genomic DNA. FIG. 5B shows exemplary genomic nucleic acid coding regions for phallacidin sequence #1, 1893 bp SacI restriction enzyme fragment (SEQ ID NO:76), and phallacidin sequence #2, 1613 nt PvuI restriction enzyme fragment (SEQ ID NO:77), where the nucleotides encoding a phallacidin peptide were underlined. These two genomic sequences encoding a phallacidin peptide were obtained by inverse PCR and confirmed by sequencing both strands.

FIGS. 6A-6C show exemplary sequence alignments. FIG. 6A shows an alignment of alpha-amanitin (AMA1) and phallacidin (PHA1) cDNA nucleotide sequences. FIG. 6B shows an alignment of the predicted amino acid sequences of alpha-amanitin (AMA1) and phallacidin (PHA1) proproteins from *A. bisporigera*, the mature toxin sequences are underlined. FIG. 6C shows a comparison of nucleic acids encoding AMA1 and PHA1 proproteins (BLAST results).

FIG. 7A-7H shows exemplary fragment genomic DNA sequences from the *A. bisporigera* genomic survey that contain conserved motifs highly similar to those found in the amanitin and phallacidin genes. Each DNA sequence is followed by the translation of the presumed correct reading frame. Conserved upstream and downstream amino acid sequences with variable known and putative toxin sequences were underlined. FIG. 7A shows SEQ ID NO: 183-189. FIG. 7B shows SEQ ID NO: 190-193. FIG. 7C shows SEQ ID NO: 194-200. FIG. 7D shows SEQ ID NO:201-203. FIG. 7E shows SEQ ID NO:204-209. FIG. 7F shows SEQ ID NO:210-211. FIG. 7G shows SEQ ID NO:212-223. FIG. 7H shows SEQ ID NO:224-227.

FIG. 9 shows an exemplary schematic of a WebLogo alignment (Crooks et al., 2004, herein incorporated by reference) showing a representation of amino acid frequency within at least 15 predicted *Amanita* peptide sequences from DNA sequences of *Amanita* species. The height of the amino acid letter indicates the degree of conservation among the *Amanita* peptide sequences, some of which are shown in FIG. 7.

FIG. 11 shows exemplary sequences found in genomic sequencing of *Galerina* (*G. marginata*, Gm) A) Nucleic Acid Sequences (GmAMA1) and B) Amino acid sequences deduced from sequences in A (GmAM1). (.=stop codon)

FIG. 12A shows an alignment of *Galerina marginata* amanitin (GmAM1) preproprotein amino acid sequence with an *Amanita* alpha-amanitin/gamma-amanitin. FIG. 12B shows a Southern blot of *Galerina marginata* (Gm) DNA probed with GmAM1 under high stringency conditions. Alpha and gamma amanitin differ in hydroxylation, which is a post-translational modification not encoded by the DNA nor produced during translation of the proprotein on the ribosome. Therefore, the genetic code for alpha and gamma amanitin are the same. Beta-amanitin, on the other hand, differs from alpha and gamma amanitin by one amino acid, and therefore the gene encoding beta-amanitin must be different from the gene encoding alpha and gamma amanitin.

FIG. 14 shows exemplary *Galerina marginata* amanitin sequences (GmAMA1). Sequences were found by genomic sequencing of *Galerina* (*G. marginata*, Gm) A) Nucleic Acid Sequences (GmAMA1); B) Amino acid sequences deduced from sequences in A (GmAMA1) (.=nonsense codon); and C) Amino acid sequence alignment of two *Galerina amanitins* GaAMA1 and GaAMA2 sequences.

FIG. 15 shows exemplary BLASTP results using human prolyl oligopeptidase (POP) as query against fungi in GenBank. The results indicate that an ortholog of human POP exists in at least some Homobasidiomycetes (*Coprinus*) and Heterobasidiomycetes (*Ustilago* and *Cryptococcus*) and few other fungal species showing various levels of significant identity and where scores and e-values of the two *Aspergillus* fungal sequences were considered statistically insignificant.

FIG. 16 shows exemplary genome survey sequences from *A. bisporigera* that align with human POP (gi:41349456) using TBLASTN. Shown are translations of *A. bisporigera* DNA sequences and the alignments of the human protein POP (query) with each predicted translation product from *A. bisporigera* (subject).

FIGS. 17A-1 to 7C show prolyl oligopeptidase sequences. FIGS. 17A-1 and 17A-2 show two exemplary prolyl oligopeptidase (POP)-like *A. bisporigera* genome sequences for POPA and POPB, respectively. FIGS. 17B-1 and 17B-2 show two exemplary cDNA sequences for POPA and POPB, respectively. FIG. 17C shows two exemplary amino acid sequences for POPA and POPB.

FIG. 18 shows exemplary Southern blots of different *Amanita* species probed with (A) POPA or (B) POPB of *A. bisporigera*. DNA was from the same species of mushroom in lanes of the same order as FIG. 8. Lanes 1-4 are *Amanita* species in sect. Phalloideae and the others are toxin non-producers. Note the presence of POPA and absence of POPB in sect. Validae (lanes 5-8), the sister group to sect. Phalloideae (lanes 1-4). The weaker hybridization of POPA to the *Amanita* species outside sect. Phalloideae (lanes 5-13) to lower DNA loading and/or lower sequence identity due to taxonomic divergence. The results show that POPB does not hybridize to any species outside sect. Phalloideae even after prolonged autoradiographic exposure.

FIG. 22A-22B show POPA and POPB sequences. FIG. 22A-1 to 22A-9 show exemplary alignment of conceptual translations of *Galerina marginata* POP DNA sequences (subject sequences) identified using *Amanita bisporigera* POPA for searching a library of *Galerina* genomic DNA sequences. FIG. 22B1-22B8 show POP sequences using POPB as a query sequence for searching a library of *Galerina* genomic DNA sequences created by the inventors for their use during the development of the present inventions. The higher scoring hits of two nonidentical contigs were strong evidence that the *Galerina* genome contains at least two POP genes (named POPA and POPB).

FIG. 23A-23C (a continuous sequence) shows an exemplary sequence found in the genomic schematic sequence shown in FIG. 10D inserted into a lambda clone; 13,254 bp lambda clone [red/underlined sequences (portions) are two copies of PHA1 encoding phallacidin in B]. The two copies are in opposite orientations, SEQ ID NO:237.

FIG. 24A-24B, a continuous table, shows an exemplary FGENESH 2.5 prediction of potential genes in the lambda clone using the *Coprinus cinereus* prediction model and sequence.

FIG. 25A-25E show P450 sequences. FIG. 25A shows an exemplary contemplated P450 gene mRNA sequence, P450-1 (OP450); SEQ ID NO:596) and the encoded amino acid sequence (OP451; SEQ ID NO:597). FIG. 25B-1 to 25B-2 show putative encoded amino acid sequences from blastp results of Predicted protein(s) P450-1 (OP451) against GenBank sequences. FIG. 25C shows BLASTP results of OP45-1 against *Coprinus cinereus* sequences at Broad. FIG. 25 shows BLASTP of OP451 against *Laccaria bicolor* genomic sequences. FIG. 25E shows results of OP451 as a query sequence for a BLASTP against nr, showing an excellent hit (SEQ ID NO:598) against a *Coprinus* protein.

FIG. 26A-26D shows P450 sequences. FIG. 26A shows an exemplary contemplated P450 mRNA sequence predicted in the lambda clone using FGEHESH and the *Coprinus* model, P450-2 (OP452) and putative encoded amino acid sequences. FIG. 26B shows blastp results of predicted protein(s): P450-2 (OP452). FIG. 26C shows results of BLASTP of P450-2 (OP452) against *Coprinus* at Broad. FIG. 26D shows BLASTP of P450-2 (OP452) against *Laccaria* genomic sequences.

FIG. 27 shows an exemplary FGENESH predicted mRNA and predicted protein number 3, which has no strong hits in any of the BLAST searches. This region overlaps with PHA1-1, which is on + strand (gene 3 is on − strand).

FIG. 28A-28D show P450 sequences. FIG. 28A-1 and FIG. 28A-2 shows an exemplary contemplated P450 predicted mRNA sequence (FIG. 28A-1) for P450-3 (OP453) and putative encoded amino acid sequence (FIG. 28A-2), blastp results of Predicted protein(s): P450-3 (OP453). FIG.

28C shows BLASTP of P450-3 (OP453) against *Coprinus* at Broad. FIG. 28D shows BLASTP of P450-3 (OP453) against *Laccaria* genomic sequences.

FIG. 29A-29B show sequences located from the genomic region shown in the schematic diagram of FIG. 10D. FIG. 29A shows exemplary PHA1-2 as described herein (5th identified sequence in the lambda clone shown in FIG. 10D).

FIG. 29B shows the nucleotide sequence of a predicted mRNA of a 6th predicted gene, and its conceptual translation, of unknown function.

FIG. 30A-30D show P450 sequences. FIG. 30A1-30A2 show exemplary alignments of a P450 genes 1,2,4 corresponding to OP451, OP452 and OP453 to each other (tree) and to genes obtained with a BLAST search as well as exemplary sequence (SEQ ID NO:611). FIG. 30B1-30B03 show the entire lambda clone reverse complement (3'-5') (SEQ ID NO:612) and SEQ ID NOs: 613 and 614 from pieces of the lambda clone translated in a particular frame to clearly show amino acids of PHA1). FIG. 30C shows SEQ ID NO:615, a FGENESH of reverse complement showing a different gene 4, which is gene 3 in the reverse complement. FIG. 30D shows a new set of exemplary gene identifications contemplated as P450 genes.

FIG. 32 shows an exemplary gene structure (introns, exons, and protein coding region) of the two variants of α-amanitin genes in *Galerina*, and comparison to AMA1 of *A. bisporigera* A. GmAMA1-1 and B. GmAMA1-2 in *Galerina marginata*. Exons are indicated by heavy lines and introns by thin lines. The predicted proprotein sequences and their location are indicated in FIG. 32.

FIGS. 33A-33F shows exemplary alignments of the predicted amino acid sequences of the proproteins of α-amanitin-encoding genes in *G. marginata* and *A. bisporigera*. FIG. 33A shows alignment of the two copies of the α-amanitin proproteins in *G. marginata* (GmAMA1-1 and GmAMA1-2), and the consensus. FIG. 33B shows alignment of AMA1 (encoding α-amanitin) and PHA1 (encoding phallacidin) from *A. bisporigera* (Ab) and the consensus. A gap was introduced in the sequence of PHA1 because phallacidin has one fewer amino acid than α-amanitin. FIG. 33C shows a consensus sequence between the proproteins of AMA1, the α-amanitin-encoding gene of *A. bisporigera*, and copy 1 (GmAMA1-1) of the α-amanitin-encoding gene of *G. marginata*, and the consensus. FIG. 33D shows a consensus sequence among the proproteins of AMA1, PHA1, GmAMA1-1, and GmAMA1-2. FIG. 33E shows a genomic DNA sequence (SEQ ID NO: 709), transcriptional start for prepropeptide nucleic acid sequence (SEQ ID NO: 710), propeptide amino acid sequence (SEQ ID NO: 711) and predicted amino acid sequence of GmAMA1-1 (SEQ ID NO: 704). FIG. 33F shows a genomic DNA sequence (SEQ ID NO: 712), transcriptional start for prepropeptide nucleic acid sequence (SEQ ID NO: 713), propeptide sequence 61 amino acids (SEQ ID NO: 690), propeptide nucleic acid sequence for 35 amino acids (SEQ ID NO: 714) and predicted 35 amino acid sequence of GmAMA1-2 (SEQ ID NO: 705).

FIGS. 38A-38B show *G. marginata* POP sequences. FIG. 38A shows exemplary sequences of isolated GmPOPA cDNA and the predicted encoded polypeptide sequence (SEQ ID NO:716). FIG. 38B shows a GmPOPB cDNA sequence (SEQ ID NO:717) with the predicted encoded polypeptide sequence (SEQ ID NO:722).

FIG. 41A-41D show exemplary contigs that were found in a *Galerina* genome survey when AbPOPA and AbPOPB sequences were used as queries. TBLASTN (protein against nucleic acid database) was used in order to obtain exemplary amino acid sequences. Note that these 4 contigs were short genomic sequences so none of them covered the entire gene. FIGS. 41A-1 and 41A-2 show contig sequence 1 (SEQ ID NO: 723) and BLAST alignments of the encoded protein. FIGS. 41B-1 and 41B-2 show contig sequence 2 (SEQ ID NO: 732) and alignments of the encoded protein. FIGS. 41C-1 and 41C-2 show contig sequence 3 (SEQ ID NO:741)

and alignments of the encoded protein. FIG. 41D shows contig sequence 4 (SEQ ID NO:750) and alignments of the encoded protein. Two *Galerina* genes (FIG. 38) were subsequently sorted out from the genes represented by the 4 contigs by PCR. Both *A. bisporigera* and *G. marginata* were found to have two POP genes. They were similar to each other, so the use of BLAST with either of the *Amanita* sequences hybridized to these contigs, which corresponded to both of the *Galerina* POP contigs.

DESCRIPTION OF THE INVENTION

The present invention relates to compositions and methods comprising genes and peptides associated with cyclic peptides and cyclic peptide production in mushrooms. In particular, the present invention relates to using genes and proteins from *Galerina* species encoding peptides specifically relating to amatoxins in addition to proteins involved with processing cyclic peptide toxins. In a preferred embodiment, the present invention also relates to methods for making small peptides and small cyclic peptides including peptides similar to amanitin. Further, the present inventions relate to providing kits for making small peptides.

The present invention also relates to compositions and methods comprising genes and peptides associated with cyclic peptide toxins and toxin production in mushrooms. In particular, the present invention relates to using genes and proteins from *Amanita* species encoding *Amanita* peptides, specifically relating to amatoxins and phallotoxins. In a preferred embodiment, the present invention also relates to methods for detecting *Amanita* peptide toxin genes for identifying *Amanita* peptide-producing mushrooms and for diagnosing suspected cases of mushroom poisoning. Further, the present inventions relate to providing kits for diagnosing and monitoring suspected cases of mushroom poisoning in patients.

The present inventions further relate to compositions and methods associated with screening a genomic library in combination with 454 pyro-sequencing for obtaining sequences of interest. In particular, the present invention relates to providing and using novel PCR primers for identifying and sequencing *Amanita* peptide genes, including methods comprising RACE PCR primers and degenerate primers for identifying *Amanita* mushroom peptides. Specifically, the present inventions relate to identifying and using sequences of interest associated with the production of small peptides, including linear peptides representing cyclic peptides, for example, compositions and methods comprising *Amanita* amanitin toxin sequences.

The present inventions further relate to compositions and methods associated with conserved genomic regions of the present inventions, in particular those conserved regions located upstream and downstream of small peptide encoding regions of the present inventions. Specifically, degenerate PCR primers based upon these conserved regions are used to identifying *Amanita* peptide-producing mushrooms.

Figure 2A:
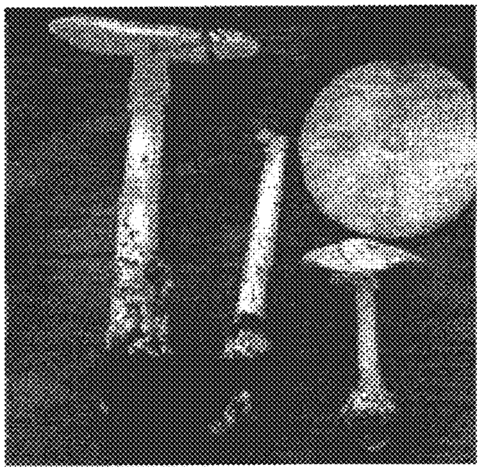
FIGS. 2A-2C show exemplary fungi of the genus *Amanita*.

Unlike genetically based disease susceptibility, every human is susceptible to lethal mushroom toxins due to the direct action of toxins, primarily amatoxins, on ubiquitous cellular organelles. Furthermore, unlike poisonous plants, poisonous mushroom species are ubiquitously found throughout the world. For example, mushrooms in the genus *Amanita* section Phalloideae are responsible for more than 90% of global (worldwide) fatal mushroom poisonings. Perspectively, there are an estimated 900-1000 species of *Amanita* wherein the majority do not produce amatoxins (or phallotoxins) of which some are actually safe for humans to eat (FIG. 2C) (Bas, (1969) Persoonia 5:285; Tulloss et al., (2000) Micologico G. Bresadola, 43:13; Wei, et al., (1998) Can J. Bot. 76:1170; all of which are herein incorporated by reference). Thus an accurate pre-ingestion determination of toxic species would prevent accidental poisoning in 100% of cases. However, there are a large number of toxin producing mushrooms commonly misidentified as an edible mushroom, see Tables 1 and 2. Therefore, accurately detecting toxic mushrooms in the wild based upon morphology in order to avoid or identify mushroom poisoning primarily depends upon expert mycological examination of an intact mushroom.

Expert identification opinions are necessary due to the large number of "look-alike" mushrooms, such as exemplary mushroom in the following Table 1. For example, the Early False Morel *Gyromitra esculenta* is easily confused with the true Morel *Morchella esculenta*, and poisonings have occurred after consumption of fresh or cooked *Gyromitra. Gyromitra* poisonings have also occurred after ingestion of commercially available "morels" contaminated with *G. esculenta*. The commercial sources for these fungi (which have not yet been successfully cultivated on a large scale) are field collection of wild morels by semi-professionals. Cultivated commercial mushrooms of whatever species are almost never implicated in poisoning outbreaks unless there are associated problems such as improper canning (which lead to bacterial food poisoning).

TABLE 1

Poisonous Mushrooms and their Edible Look-A-likes.*
Mushrooms Containing Amatoxins

| Poisonous species | Appearance | Mistaken for |
|---|---|---|
| *Amanita tenuifolia* (Slender Death Angel) | pure white | *Leucoagaricus naucina* (Smoothcap Parasol) |
| *Amanita bisporigera* (Death Angel) | pure white | *Amanita vaginata* (Grisette), *Leucoagaricus naucina* (Smoothcap Parasol), white *Agaricus* spp. (field mushrooms), *Tricholoma resplendens* (Shiny Cavalier) |
| *Amanita verna* (Fool's Mushroom) | pure white | *A vaginata*, *L. naucina*, white *Agaricus* spp. *T. resplendens* |
| *Amanita virosa* (Destroying Angel) | pure white | *A vaginata*, *L. naucina*, *Agaricus* spp., *T. resplendens* |
| *Amanita phalloides* (Deathcap) | pure white variety | *Amanita citrina* (False Deathcap), *A. vaginata*, *L. naucina*, *Agaricus* spp., *T. resplendens* |
| Buttons of *A. bisporigera*., *A. verna*, *A. virosa* | pure white | Buttons of white forms of *Agaricus* spp. Puffballs such as *Lycoperdon perlatum*, etc. |
| *Amanita phalloides* (Deathcap) | green = normal cap color | *Russula virescens* (Green Brittlegill), *Amanita calyptrodermia* (Hooded Grisette), *Amanita fulva* (Tawny Grisette), *Tricholoma flavovirens* (Cavalier Mushroom), *Tricholoma portentosum* (Sooty Head) |
| *Amanita phalloides* (Deathcap) | yellow variety | *Amanita caesarea* (Caesar's Mushroom) |
| *Amanita brunnescens* (Cleft Foot Deathcap) | na | *Amanita rubescens* (Blusher), *Amanita pantherina* (Panthercap) |
| *Galerina autumnalis* (Autumn Skullcap) | LBM | "Little Brown Mushrooms," including *Gymnopilus spectabilis* (Big Laughing Mushroom) and other *Gymnopilus* spp., *Armillaria mellea* (Honey Mushroom) |

TABLE 1-continued

| Poisonous Mushrooms and their Edible Look-A-likes.* Mushrooms Containing Amatoxins | | |
|---|---|---|
| Poisonous species | Appearance | Mistaken for |
| *Leucoagaricus brunnea* (Browning Parasol) | LBM | *Lepiota* spp., *Leucoagaricus* spp., *Gymnopilus* spp. and other Parason Mushrooms and LBM's |
| *Lepiota josserandii*, *L. helveola*, *L. subincarnata* | LBM | *Lepiota* spp., *Leucoagaricus* spp., *Gymnopilus* spp. and other Parasol Mushrooms and LBM's |

*Na = not available

Mushrooms that produce mild gastroenteritis are too numerous to list here, where exemplary examples are shown which include members of many of the most abundant genera, including *Agaricus, Boletus, Lactarius, Russula, Tricholoma, Coprinus, Pluteus*, and others. The Inky Cap Mushroom (*Coprinus atrimentarius*) is considered both edible and delicious, and only the unwary who consume alcohol after eating this mushroom need be concerned. Some other members of the genus *Coprinus* (Shaggy Mane, *C. comatus*; Glistening Inky Cap, *C. micaceus*, and others) and some of the larger members of the *Lepiota* genus such as the Parasol Mushroom (*Leucocoprinus procera*) do not contain coprine and do not cause this effect. The potentially deadly Sorrel Webcap Mushroom (*Cortinarius orellanus*) is not easily distinguished from nonpoisonous webcaps belonging to the same distinctive genus.

TABLE 2

| Mushrooms Producing Severe Gastroenteritis. Mushrooms Producing Sever Gastroenteritis | |
|---|---|
| *Chlorophyllum molybdites* (Green Gill) | *Leucocoprinus rachodes* (Shaggy Parasol), *Leucocoprinus procera* (Parasol Mushroom) |
| *Entoloma lividum* (Gray Pinkgill) | *Tricholomopsis platyphylla* (Broadgill) |
| *Tricholoma pardinum* (Tigertop Mushroom) | *Tricholoma virgatum* (Silver Streaks), *Tricholoma myomyces* (Waxygill Cavalier) |
| *Omphalotus olearius* (Jack O'Lantern Mushroom) | *Cantharellus* spp. (Chanterelles) |
| *Paxillus involutus* (Naked Brimcap) | Distinctive, but when eaten raw or undercooked, will poison some people |

*Bad Bug Book published by the U.S. Food & Drug Administration Center for Food Safety & Applied Nutrition Foodborne Pathogenic Microorganisms and Natural Toxins Handbook website at cfsan.fda.govt/~mow/table3.html herein incorporated by reference.

Individual specimens of poisonous mushrooms are characterized by individual variations in toxin content based on mushroom genetics, geographic location, and growing conditions. For example, mushroom intoxications may be more or less serious, depending not on the number of mushrooms consumed, but of the total dose of toxin delivered. In addition, although most cases of poisoning by higher plants occur in children, toxic mushrooms are consumed most often by adults. Adults who consume mushrooms are more likely to recall what was eaten and when, and are able to describe their symptoms more accurately than are children. Occasional accidental mushroom poisonings of children and pets have been reported, but adults are more likely to actively search for and consume wild mushrooms for culinary purposes.

In part because of their smaller body mass, children are usually more seriously affected by normally nonlethal mushroom toxins than are adults and are more likely to suffer very serious consequences from ingestion of relatively smaller doses. Similar to the elder population and debilitated persons who are more likely to become seriously ill from all types of mushroom poisoning, even those types of toxins which are generally considered to be mild.

Figure 31:
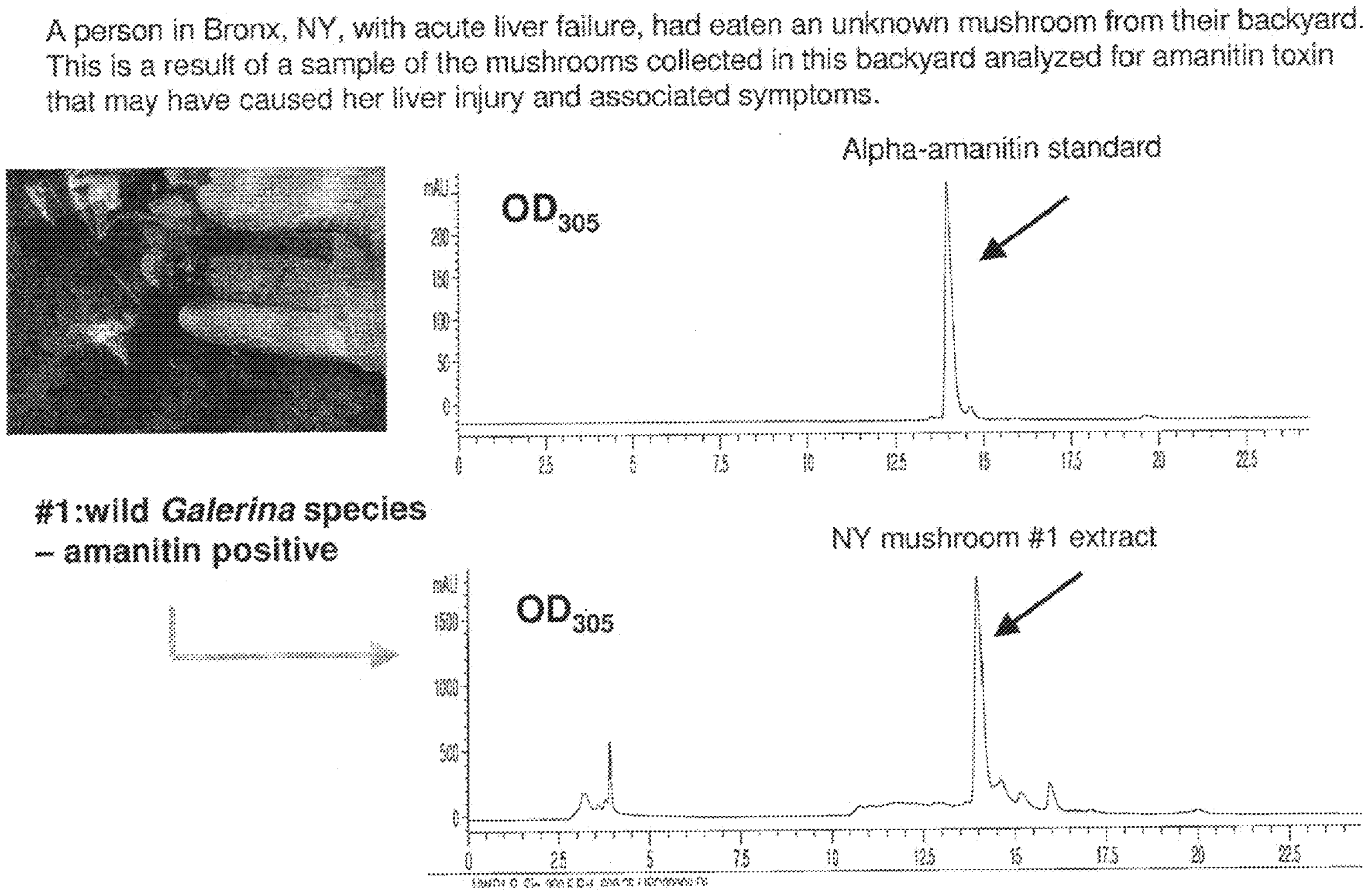
FIG. 31 shows an exemplary *Galerina* species and the result of detecting α-amanitin in samples of *Galerina* mushrooms that were implicated in the illness of a person who ate them.

Recently, in addition to humans, see, FIG. 31, dogs and other animals are becoming frequent victims of poisonous mushrooms. See Schneider: Mushroom in backyard kills curious puppy, Lansing State Journal, Sep. 30, 2008 pg. B.1 at lansingstatejournal.com.apps/pbcs.dll/article?AID=/20080930/COLUMNISTS09/-809,300 321. Body mass plays a role here in that smaller animals, such as puppies and small dogs, are likely to be more susceptible to smaller amounts of toxins. Thus in some embodiments, PCR primers of the present inventions, including PCR primers made from sequences of the present inventions, are contemplated for use in detecting toxin producing mushrooms in samples obtained from dogs or other animals, such as partially eaten material, samples obtained directly from an animals digestive system, etc. in some embodiments, antibodies of the present inventions are contemplated for use in detecting mushroom toxins in samples obtained from dogs or other animals, such as partially eaten material, samples obtained directly from an animals digestive system, etc.

I. Dangers of Mushroom Poisoning.

Mushroom poisoning in subjects, particularly humans, is caused by the consumption of raw or cooked fruiting bodies of toxin producing mushrooms, also known as toadstools (from the German Todesstuhl, death's stool) to distinguish toxic from nontoxic mushrooms. There is no general rule of thumb for distinguishing edible mushrooms from toxic mushrooms (poisonous toadstools). There are generally no easily recognizable differences between poisonous and nonpoisonous species to individuals who are not experts in mushroom identification (mycologists).

Toxins involved in and responsible for mushroom poisoning are produced naturally by the fungi, with each individual specimen within a toxic species considered equally poisonous. Most mushrooms that cause human poisoning cannot be made nontoxic by cooking, canning, freezing, or any other means of processing. Thus, the only way to completely avoid poisoning is to avoid consumption of the toxic species. Mushroom poisonings are almost always caused by ingestion of wild mushrooms that have been collected by nonspecialists (although specialists have also been poisoned). Most cases occur when toxic species are confused with edible species, and a useful question to ask of the victims or their mushroom-picking benefactors is the identity of the mushroom they thought they were picking. In the absence of a well-preserved specimen, the answer to this question could narrow the possible suspects considerably. Poisoning has also occurred when reliance was placed on some folk method of distinguishing poisonous and safe species. Outbreaks have occurred after ingestion of fresh, raw mushrooms, stir-fried mushrooms, home-canned mushrooms, mushrooms cooked in tomato sauce (which rendered the sauce itself toxic, even when no mushrooms were consumed), and mushrooms that were blanched and frozen at home. Cases of poisoning by home-canned and frozen mushrooms are especially insidious because a single outbreak may easily become a multiple outbreak when the preserved toadstools are carried to another location and consumed at another time.

Poisonings in the United States occur most commonly when hunters of wild mushrooms (especially novices) misidentify and consume a toxic species, when recent immigrants collect and consume a poisonous American species that closely resembles an edible wild mushroom from their native land, or when mushrooms that contain psychoactive compounds are intentionally consumed by persons who desire these effects.

A. Symptoms of Poisoning.

Mushroom poisonings are generally acute and are manifested by a variety of symptoms and prognoses, depending on the amount and species consumed. Because the chemistry of many of the mushroom toxins (especially the less deadly ones) is unknown and positive identification of the mushrooms is often difficult or impossible, mushroom poisonings are generally categorized by their physiological effects. There are four categories of mushroom toxins: protoplasmic poisons (poisons that result in generalized destruction of cells, followed by organ failure); neurotoxins (compounds that cause neurological symptoms such as profuse sweating, coma, convulsions, hallucinations, excitement, depression, spastic colon); gastrointestinal irritants (compounds that produce rapid, transient nausea, vomiting, abdominal cramping, and diarrhea); and disulfuram-like toxins. Mushrooms in this last category are generally nontoxic and produce no symptoms unless alcohol is consumed within 72 hours after eating them, in which case a short-lived acute toxic syndrome is produced.

In one embodiment, the inventors provide herein compositions and methods for providing molecular biology based diagnostic tests for accurately and reproducibly identifying DNA sequences encoding lethal fungal toxins. Thus accurate identification of mushroom toxins may be made from samples of uneaten mushrooms, including raw, cooked, frozen, dried, samples, and patient samples of undigested and partially digested, as in gastric contents, such as from human and dogs.

For comparison, current methods for diagnosing mushroom poisonings are briefly described below.

B. Current Diagnostic Methods.

Symptoms of potentially toxic mushroom poisoning may mimic other types of diseases, such as abnormal conditions or ingestion of other types of toxins which would trigger different and likely less drastric treatments. Exemplary differentials include, Adrenal Insufficiency and Adrenal Crisis, Alcohol and Substance Abuse Evaluation, Anorexia Nervosa, Delirium Tremens, Gastroenteritis, Hepatitis, Methemoglobinemia, Pediatrics, Dehydration, Pediatrics, Gastroenteritis, *Salmonella* Infection, Toxicity. Anticholinergic, Toxicity, Antihistamine, Disulfuram, Disulfuramlike Toxins, *Gyromitra*, Mushroom Hallucinogens, Mushroom-Orellanine, Organophosphate, and Carbamate, Theophylline, etc. In addition, an idiosyncratic reaction mimics toxin poisoning when patients with trehalase deficiency who are unable to break down trehalose, a disaccharide found in mushrooms present with diarrhea after ingestion. Further patients with an immune reaction (*Paxillus* syndrome) may develop an acquired hypersensitivity-type reaction after repeated ingestions of specific mushrooms. This may result in hemolytic crisis and most commonly involves ingestion of *Paxillus involutus. Suillus luteus* also has been implicated in a psychosomatic syndrome where some patients were reported to develop anxiety-related symptoms after learning that they ate wild mushrooms. Mushroom-drug interaction-symptoms may occur with ingestion of mushrooms contaminated with bacteria, sprayed with pesticides, or supplemented with drugs such as phencyclidine. Thus, in one embodiment, genes and proteins of the present inventions may find use in identifying the presence or lack of toxin producing mushrooms, i.e. their genes related to toxin production, for example using PCR primers for amplifying genes, peptides related to toxins, for example, using antibodies which recognize toxins, and kits comprising PCR primers or antibodies.

As described above, the protoplasmic poisons are the most likely to be fatal or to cause irreversible organ damage. In the case of poisoning by the deadly species of *Amanita* and other mushrooms that produce the *Amanita* peptides, important laboratory indicators of liver (elevated LDH, SGOT, and bilirubin levels) and kidney (elevated uric acid, creatinine, and BUN levels) damage will be present.

Unfortunately, in the absence of dietary history, these signs could be mistaken for symptoms of liver or kidney impairment as the result of other causes (e.g., viral hepatitis). It is important that this distinction be made as quickly as possible, because the delayed onset of symptoms will generally mean that the organ has already been damaged. The importance of rapid diagnosis is obvious: victims who are hospitalized and given aggressive support therapy almost immediately after ingestion have a mortality rate of only 10%, whereas those admitted 60 or more hours after ingestion have a 50-90% mortality rate.

1. Intact Mushrooms.

Ideally, once a mushroom poisoning is suspected, identification of suspect toxic mushroom, identical to the one ingested, should be made by a local medical toxicologist (certified through the American Board of Medical Toxicology or the American Board of Emergency Medicine) or at a regional poison control center.

If a pre-digested mushroom sample is available, the following information would be helpful to a mycologist or physician with mushroom poisoning experience for determining the mushroom's identity: Provide any available information, for example, size, shape, and color of the mushroom including a description of the surface and the underside of the cap, the stem, gills, veil, ring, spores and the color and texture of the flesh. It would be helpful to know the location and conditions in which the mushroom grew (e.g., wood, soil). Further, it is suggested that any mushroom samples saved for mycological examination are wrapped in foil or wax paper and stored in a paper bag in a cool dry place, pending transport to the mycologist or other professional. Moreover it is discouraged to store mushroom samples for mycological identification in a plastic bag or container where the mushroom's features may be altered due to moisture condensation and further freezing which is likely to alter or destroy any distinguishing identification features of the mushroom. Alternative methods for identifying mushrooms may be done by referring to the Poisindex or a mycology handbook.

Currently there are several research laboratory tests used for identifying *Amanita* peptides and toxins, examples of which are briefly described as follows. The Meixner test also known as the "Weiland Test" assay is qualitative assay used to detect amatoxins (eg, alpha-amanitin, beta-amanitin) in the mushroom. It is not recommended for use with stomach contents nor to determine edibility of a mushroom because false-positive and false-negative results have been described. Kuo, M. (2004, November). Meixner test for amatoxins. Retrieved from the MushroomExpert.Com Web site: mushroomexpert.com/meixner; herein incorporated by reference).

Further, an intact or partial undigested mushroom may be analyzed for actual toxic peptides, using chemical methods such as reverse-phase HPLC. In order to rule out other types of food poisoning and to conclude that the mushrooms eaten were the cause of the poisoning, it must be established that everyone who ate the suspect mushrooms became ill and that no one who did not eat the mushrooms became ill. Wild mushrooms eaten raw, cooked, or processed should always be regarded as prime suspects. After ruling out other sources of food poisoning and positively implicating mushrooms as the cause of the illness, further diagnosis is necessary to provide an early indication of the seriousness of the disease and its prognosis.

Therefore, an initial diagnosis is based entirely on symptomology and recent dietary history. Despite the fact that cases of mushroom poisoning may be broken down into a relatively small number of categories based on symptomatology, positive taxonomic identification of the mushroom species consumed remains the only means of unequivocally determining the particular type of poisoning involved, and it is still vitally important to obtain such accurate identification as quickly as possible. Cases involving ingestion of more than one toxic species in which one set of symptoms masks or mimics another set are among many reasons for needing this information.

2. Post-Ingested and Pre-Digested Mushroom Samples.

If the actual mushroom is unavailable, which is frequent in post-ingestion cases with delayed onset of symptoms, the following information may be helpful for determining the mushroom's identity. Save emesis or gastric lavage fluid for microscopic examination for spores. If mushroom fragments are available, they can be stored in a 70% solution of ethyl alcohol, methanol, or formaldehyde and placed in the refrigerator. Otherwise, emesis can be centrifuged and the heavier layer on the bottom can be examined under a microscope for the presence of spores.

Despite the availability of laboratory tests for identifying toxins, diagnosing a mushroom poisoning remains primarily limited to taxonomic identification of the mushroom that was eaten. Accurate post-ingestion analyses for specific toxins when no taxonomic identification is possible is essential for cases of suspected poisoning by toxin containing mushrooms, such as species of *Amanita*, since prompt and aggressive therapy (including lavage, activated charcoal, and plasmapheresis) can greatly reduce the mortality rate.

Samples of actual mushroom toxins may be recovered from poisonous fungi, cooking water of poisonous fungi, stomach contents with poisonous fungi, serum, and urine from poisoned patients. Procedures for extraction and quantitation of toxins are generally elaborate and time-consuming. In the case of using toxin based diagnostic procedures the patient will in most cases either have recovered or died by the time an analysis is made on the basis of toxin chemistry. However even with toxin chemistry, the exact chemical natures of many toxins, including toxins that produce milder symptoms are unknown. Lethal toxins are identified using chromatographic techniques (TLC, GLC, HPLC) for amanitins, orellanine, muscimol/ibotenic acid, psilocybin, muscarine, and the gyromitrins. Recently, amanitins were determined by commercially available .sup.3H-RIA kits. Amanitin ELA Kit from Alpco Diagnostics of American Laboratory Products Company PO Box 451 Windham, N.H. 03087 Sample Type Urine, Serum, Plasma .alpha.- and .gamma.-amanitin present in human urine, serum and plasma. A polyclonal antibody (Ab) specific for alpha- and gamma-Amanitin Diagnostic Accuracy of Urinary Amanitin in Suspected Mushroom Poisoning: A Pilot Study Butera et al., Clinical Toxicology, Volume 42, Issue 6 December 2004, pages 901-912; herein incorporated by reference).

II. Mushroom Toxins.

A large variety of toxins are produced by mushrooms, including amatoxins, phallotoxins, virotoxins, phallolysins, ibotenic acid/muscimol, alkaloids, cyclopeptides, coumarins, etc. Many of these compounds are active at extremely low concentrations and have a rapid effect including death. Milder toxins such as ibotenic acid and muscimol bind to glutamic acid and GABA receptors, respectively, and thereby interfere with CNS receptors.

Amatoxins, phallotoxins, and virotoxins are found in *A. bisporigera, A. ocreata, A. phalloides, A. phalloides* var. *alba, A. suballiacea, A. tenuifolia, A. virosa*, and some other mushrooms. The phallolysins are a recently discovered group of toxins as yet observed only in *A. phalloides*. Many of the cyclic and noncyclic peptides found in *Amanita* and other toxin producing genera are toxic to humans and other mammals, ranging from mild symptoms to death.

A. Amanitin Peptide Toxins.

Figure 1A:
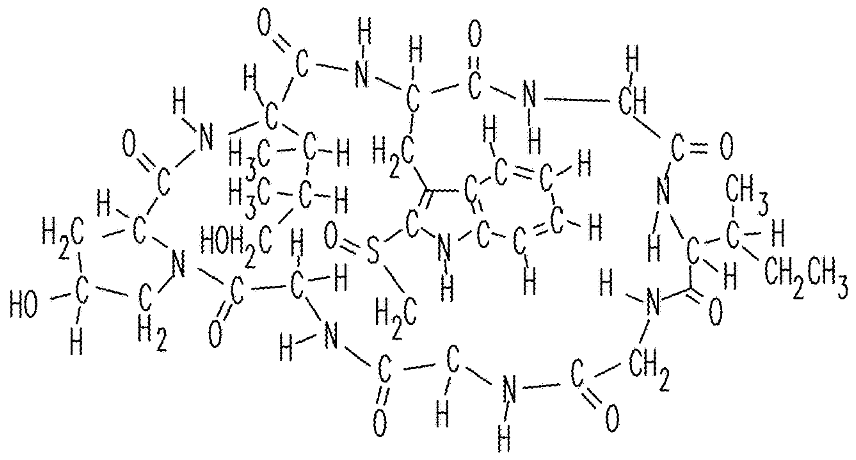
FIGS. 1A-1B show exemplary bicyclic structures.
Figure 1B:
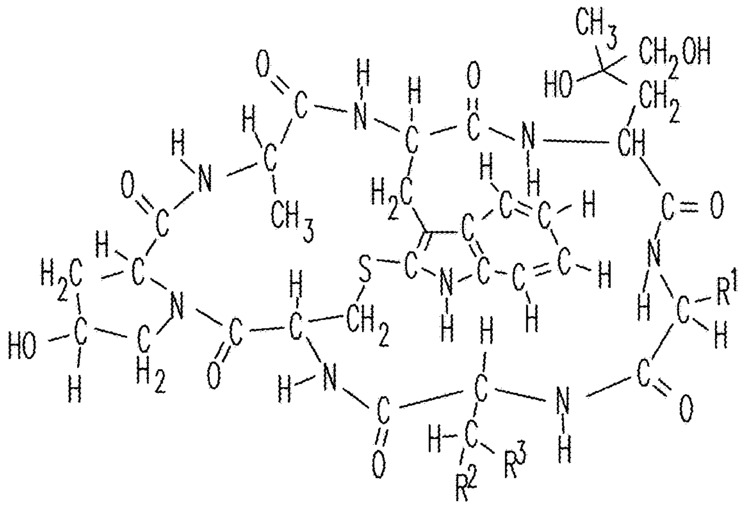
Figure 2B:
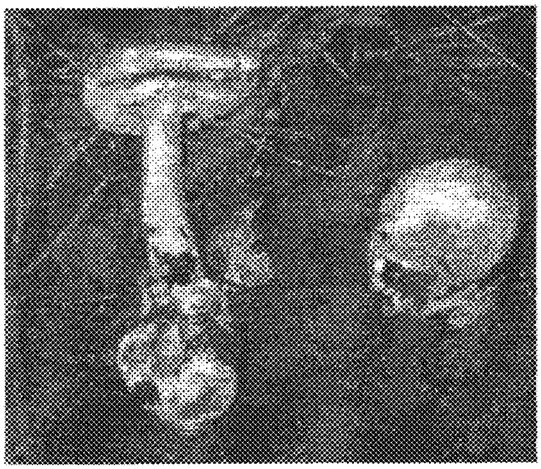
Figure 2C:
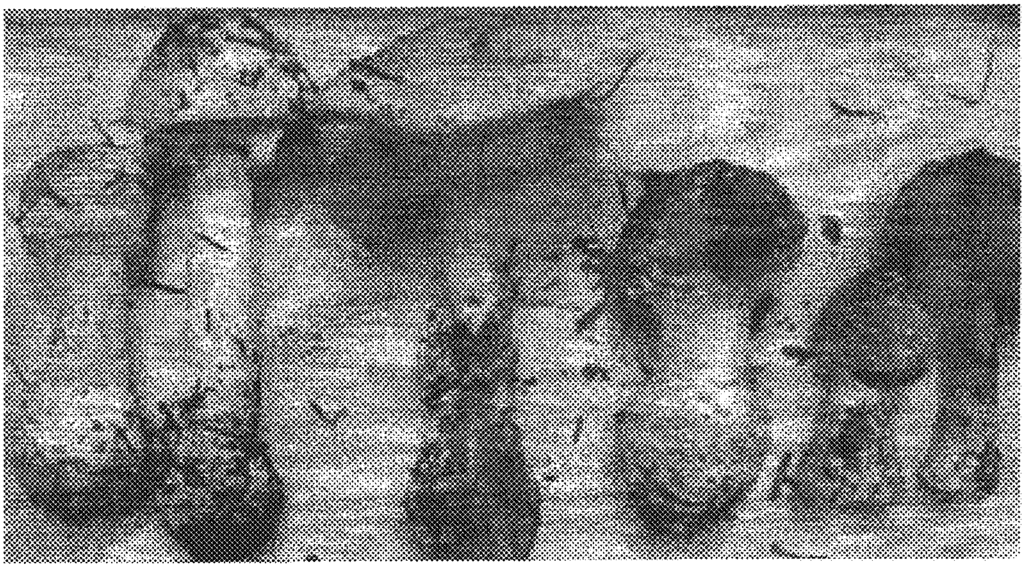

Several mushroom species, including the Death Cap or Destroying Angel (*Amanita phalloides, A. virosa*), the Fool's Mushroom (*A. verna*) and several of their relatives, along with the Autumn Skullcap (*Galerina marginata*, formerly called *Galerina autumnalis*) and some of its relatives, produce a family of cyclic octapeptides called amanitins. Because of taxonomic revisions, amanatin-producing fungi with different names might actually be the same species. *Galerina marginata*=*G. autumnalis*=*G. venenata*=*G. unicolor* (*G. beinrothii, G. sulciceps, G. fasciculata, G. helvoliceps*—may all actually be the same species as *G. marginata*). Amanitins are lethal toxins. A human $LD_{50}$ for α-amanitin is approximately 0.1 mg/kg (see, FIG. 1 for exemplary structures). Such that a fatal dose fatal for at least 50% of people weighing approximately 100-110 kgs (200-220 pounds) and around 100% for people weighing 100 or less pounds is 10-12 mg. For example, one mature destroying angel (*A. bisporigera* [FIG. 2A], *A. virosa, A. suballiacea*, and allied species) or death cap (*A. phalloides*; FIG. 2B) can contain a fatal dose of 10-12 mg of α-amanitin (Wieland, Peptides of Poisonous *Amanita* Mushrooms (Springer, N.Y., 1986); herein incorporated by reference). The news gets worse. Toxin producing mushrooms typically demonstrate a higher toxicity than these estimates. An estimated 50% of the amatoxin content of a toxin-producing mushroom is α-amanitin. Some toxin producing mushrooms can also produce other major amatoxins, such as beta-amanitin and gamma-amanitin resulting in a high death rate from mushroom poisonings.

Amatoxins are a member of a family of related molecules of which at least 9 members are known. Alpha-amanitin is one of the principal amatoxins, comprising approximately 50% of the amatoxin content of some amatoxin-producing mushrooms. Beta-amanitin and gamma-amanitin) are toxic in addition to other types of amatoxins, including but not limited to epsilon-Amanitin, Amanin, Amanin amide, Amanullin, Amanullinic acid, and Proamanullin. Members of this toxin family differ in whether they have asparagine (the position 1 amino acid) or aspartic acid, and in the degree of hydroxylation of the position 3 isoleucine and the tryptophan, and at the Cys-Trp cross-bridge.

Amatoxins can be responsible for fatal human poisonings. After ingestion, amatoxins are taken up by the liver where they begin to cause damage. They are then secreted by the bile into the blood where they are taken up by the liver again, causing a cycle of damage and excretion. In the liver, amatoxins inhibit RNA-polymerase II. The liver is slowly destroyed and is unable to repair itself due to the inactivation of the RNA-polymerase. Thus, the liver slowly dissolves with no hope of repair. Thus, one of the few effective treatments is liver transplantation (Enjalbert et al., (2002) (Treatment of Amatoxin Poisoning: 20-Year Retrospective Analysis, review of poisonings) J. Toxicol. Clin. Toxicol. 40:715; Fabrizio, et al., (2006) Transplant International 19(4):344-345; all of which are herein incorporated by reference).

Poisoning by amanitins is clinically characterized by a long latent period (range 6-48 hours, average 6-15 hours) during which the patient shows few or no symptoms. Symptoms appear at the end of the latent period in the form of sudden, severe seizures of abdominal pain, persistent vomiting and watery diarrhea, extreme thirst, and lack of urine production which lasts for about 24 hours. If this early phase is survived, the patient may appear to recover for a short time, 2-3 days, during which liver damage is ongoing. This second latent period will generally be followed by a rapid and severe loss of strength, prostration, and pain-caused restlessness. During the last stages, hepatic and renal damage becomes clinically evident typically resulting in a coma. Death usually follows a period of comatose condition and occasionally is accompanied by convulsions. If recovery occurs, it generally requires at least a month and is accompanied by enlargement of the liver. Autopsy will usually reveal fatty degeneration and necrosis of the liver and kidneys.

Amatoxins are particularly deadly because they are taken up by cells lining the gut where protein synthesis is immediately inhibited. The toxins are then released into the blood stream and transported to the liver. Once inside the liver cells, amatoxins inhibit RNA-polymerase II, which slows or stops new protein production which begins to cause cellular damage. Bushnell et al., (2002) Proc. Natl. Acad. Sci. USA 99:1218; Kroncke et al., (1986) J. Biol. Chem., 261:12562; Letschert et al., (2006) Toxicol Sci. 91:140; Lindell et al., (1970) Science 170:447; all of which are herein incorporated by reference). The liver secretes excess toxins into bile and into the blood stream where they are taken up by the liver again, causing a cycle of damage and excretion. Thus the liver is slowly destroyed and is unable to repair itself Amanitin toxins are excreted in the urine and evacuated from the body within hours of ingestion. However, if sufficient liver tissue is affected, liver failure will ensure death.

In 50-90% of the cases, death occurs from progressive and irreversible liver, kidney, cardiac, and skeletal muscle damage. The course from ingestion to death may occur in 48 hours (large dose), but effects typically lasts 6 to 8 days in adults and 4 to 6 days in children.

A dose that is likely to kill an average adult human is in the range of 6-7 mg, easily found in the cap of one mature *A. phalloides*. However, like other fungal toxins, the concentration which is fatal for individuals differs and relates to the concentration in different specimens and environment influences on concentration of toxin produced in one basidiocarp. These examples clearly show that any fungus collected from the field should be properly identified before it is consumed.

B. Phallotoxins.

In addition to bicyclic octapeptide amatoxins, mushrooms naturally produce several bicyclic heptapeptides. In particular, members of *Amanita* sect. Phalloideae produce bicyclic heptapeptides specifically called phallotoxins (FIG. 1B). Although structurally related to amatoxins, phallotoxins were found to exert a different mode of toxic action in mammalian cells, which was to stabilize F-actin (Enjalbert et al., (2002) J. Toxicol. Clin. Toxicol. 40:715, Lengsfeld et al., (1974) Proc. Natl. Acad. Sci. USA, 71:2803; Bamburg, (1999) Annu. Rev. Cell Dev. Biol. 15:185, all of which are herein incorporated by reference). Phallotoxins were found to destroy liver cells by disturbing the equilibrium of G-actin with F-actin, causing it to shift entirely to F-actin. This leads to numerous exvaginations on the liver cell's membrane which render the cell susceptible to deformity by low-pressure gradients, even those of the portal vein in vivo. This is followed by loss of potassium ions and cytoplasmic enzymes which leads to depletion of ATP and glycogen, causing the final failure of the liver.

Phallotoxins, such as phalloidin and phallacidin, are poisonous when administered parenterally, for example, when administered in a manner other than through the digestive tract, such as by inhalation, intravenous or intramuscular injection. However, because they do not appear to be absorbed by the mammalian digestive tract, they are unlikely to play a primary role in clinical mushroom poisonings.

Biochemically, there are at least seven different naturally occurring phallotoxins: phalloin, phalloidin, phallisin, prophalloin, phallacin, phallacidin, and phallisacin. There are two groups of phallotoxins, neutral and acidic. The neutral phallotoxins, such as phalloidin, contain D-threonine, while the acidic ones contain D-beta-hydroxy-Aspartic acid. Phallacidin (AWLVDCP (SEQ ID NO:69)) also includes Valine whereas phalloidin contains Alanine.

Phallotoxin was once thought to be responsible for the usual symptoms of fatal mushroom poisoning. The compound acts to inhibit F actin in the cell cytoskeleton. It acts immediately, and probably does not move beyond the lining of the gut.

C. Virotoxins.

Although they have the same toxicological effects as and appear to be derived from the phallotoxins, the virotoxins are monocyclic heptapeptides, not bicyclic peptides.

There are at least six virotoxins, viroidin desoxoviroidin, alal-viroidin, alal-desoxoviroidin, viroisin, and desoxoviroisin.

D. Other Types of Mushroom Toxins.

Phallolysins There are at least three phallolysins that are hemolytically active proteins, but, as previously stated, they are heat and acid labile and do not pose a threat to humans.

Ibotenic acid/Muscimol. Ibotenic acid is an Excitatory Amino Acid (EAA) and muscimol is its derivative. These toxins act by mimicking the natural transmitters glutamic acid and aspartic acid on neurons in the central nervous system with specialized receptors for amino acids. These toxins may also cause selective death of neurons sensitive to EAAs. However these are not known to be peptides.

III. *Amanita* Toxin Peptides in Relation to Other Peptides.

Small, modified, and biologically active peptides synthesized on ribosomes were previously identified from several sources, including bacteria, spiders, snakes, cone snails, and amphibian skin (Escoubas, 2006; Olivera, 2006; Simmaco et al., 1998). Like the *Amanita* peptide toxins, these peptides are synthesized as precursor proteins and often undergo post-translational modifications, including hydroxylation and epimerization. Circular proteins were discovered in microorganisms, plants and mammals, (for an exemplary review, see, Trabi and Craik, 2002).

Lantibiotics. Lantibiotics, such as nisin, subtilin, and cinnamycin, are produced by species of *Lactobacillus, Streptococcus*, and other bacteria. They contain 19-38 amino acids. They are characterized by the presence of lanthionine, which is formed biosynthetically by dehydration of an Ala residue followed by intramolecular addition of Cys (Willey and van der Donk, 2007). The lantibiotics are similar to the *Amanita* peptide toxins in containing a modified, cross-linked Cys residue. However, instead of Ala in the case of lantibiotics, the Cys in the *Amanita* peptides is cross-linked to a Trp residue. Furthermore, thorough BLAST searching of the genome of *Amanita* and of all other fungi whose genomes have been sequenced (available in GenBank NR or the DOE Joint Genome Institute) did not identify any orthologs of any of the known lantibiotic dehydratases or cyclases (Willey and van der Donk, 2007).

Cone snail toxins. Cone snail toxins (conotoxins) are 12-40 amino acids. They are linear peptides but are cyclized by multiple disulfide bonds (Bulaj et al., 2003). Like the *Amanita* peptides, the cone snail toxins exist as gene families, the members of which have hypervariable regions, corresponding to the amino acids present in the mature toxins, and conserved regions found in all members (Olivera, 2006; Woodward et al., 1990, all of which are herein incorporated by reference).

Conotoxins and *Amanita* peptides differ in many key respects. First, the *Amanita* peptides are smaller (7-10 amino acids vs. 12-40 for the conotoxins) (Bulaj et al., 2003). Second, the mature conotoxins are at the carboxy termini of the preproproteins and are predicted to be cleaved by a protease that cuts at basic amino acids (Arg or Lys). In contrast, the mature *Amanita* peptide toxin sequences are internal to the proprotein and are predicted to require two cleavages by one or more prolyl peptidases. Third, the conotoxins are cyclized only by multiple disulfide bonds, whereas the *Amanita* peptides are cyclized by N-terminus to C-terminus (head-to-tail) peptide bonds and do not have disulfide bonds. Fourth, the conotoxin preproproteins have signal peptides to direct secretion into the venom duct, whereas the *Amanita* peptides are not secreted (Zhang et al., 2005, herein incorporated by reference) and their proproteins lack predicted signal peptides (FIG. 4).

Amphibian, snake, and spider toxins. Like the conotoxins, these peptides are synthesized on ribosomes as preproproteins, undergo posttranslational modifications, and contain multiple disulfide bonds. None of them are truly cyclic nor and all are much bigger than the *Amanita* peptide toxins.

Cyclotides. Cyclotides such as kalata are 28-37 amino acids in size (Trabi and Craik, 2002; Craik et al., 2007, all of which are herein incorporated by reference). The precursor structure contains an N-terminal signal peptide followed by a proprotein region and a conserved "N-terminal repeat region" containing a highly conserved domain of ~20 amino acids, one to three cyclotide domains, and a short C-terminal sequence. An Asn-endopeptidase is responsible for removing the C-terminal peptide from the proprotein and cyclizing the peptide (Saska et al., 2007), but the protease that cuts the N-terminus is apparently not known. The mature cyclotides are true head-to-tail cyclic peptides but, like the conotoxins, also have multiple disulfide bonds.

Bacterial auto-inducing peptides (AIPs). Quorum sensing by certain pathogenic Gram-positive bacteria, such as species of *Staphylococcus*, involves the secretion and recognition of small (7-9 amino acid) ribosomally-encoded peptides called AIPs (Novicku and Geisinger, 2008). AIPs are post-translationally cyclized by formation of a thiolactone between the carboxyl group of the C-terminal amino acid and an internal Cys. AIP proproteins are processed at the C-terminus by agrB with simultaneous condensation to form the thiolactone ring (Lyon and Novick, 2004). The inventors determined that there are no proteins related to agrB in the genomes of *Amanita, Galerina*, or any fungus in GenBank.

Microcin and related molecules. Microcin J25 is a 21-amino acid peptide cyclized between an N-terminal Gly or Cys residue and an internal Glu or Asp residue. It is produced by *E. coli*; other enterobacteria produce related peptides. Processing of the primary translation product (58 amino acids) involves cleavage of a 37-residue leader peptide and cyclization. Cyclization requires two genes, mcjA and mcjB, which are part of the microcin operon (Duquesne et al., 2007). The maturation reaction requires ATP for amide bond formation. The inventors did not find any orthologs of mcjA or mcjB by BLAST searching of all available fungal genomes, including *Amanita bisporigera* and *Galerina marginata.*

Another example of cycle peptides are thiazolyl peptides, highly rigid trimacrocyclic compounds consisting of varying but large numbers of thiazole rings. The backbone amino acids undergo numerous posttranslational modifications while thiazolyl peptide genes are clustered into operons in bacteria. Derivatives of thiazolyl peptides are sometimes used as antibiotics. Because thiazolyl peptides were synthesized on ribosomes by bacteria such as *Streptomyces* and *Bacillus*, the inventors' searched for homologous genes. No homologs of any of the thiazolyl peptide genes were found in the genomes of *A. bisporigera, G. marginata*, or other fungi in GenBank.

In conclusion, comparison of the *Amanita* peptide toxins to other known small cyclic peptides indicates that they are unique among microbial natural products in regard to their chemistry, modes of action, and biosynthesis.

A summary of several unique characteristics of *Amanita* peptide toxins and peptides, linear and cyclic, includes but is not limited to: (1) The *Amanita* peptide toxins are true head-to-tail cyclic peptides, unlike antibiotics, cone snail toxins, microcins, or AIPs. (2) The tryptathionine moiety (Trp-Cys cross-bridge) is not found in any other natural molecule (May and Perrin, 2007, herein incorporated by reference). (3) The *Amanita* toxins are the only known ribosomally synthesized cyclic peptides from the Kingdom Mycota (Fungi), the source of many important secondary metabolites that affect human health. (4) The known *Amanita* peptide toxins have unique modes of action, which contributes to their toxicity and also makes them widely used tools for basic biomedical research. The interaction of alpha-amanitin with pol II is understood in detail (Bushnell et al., 2002, herein incorporated by reference). It is therefore possible that other linear or cyclic ribosomally-synthesized peptides known or predicted to be made by species of *Amanita, Galerina, Lepiota, Conocybe*, etc. (for example, see, might also have biologically significant modes of action that would make them useful as pharmaceutical agents or research reagents. (5) Amatoxins are not secreted (Zhang et al., 2005, herein incorporated by reference). Consistent with this the proproteins do not have predicted signal peptides. In this regard they differ from conotoxins, lantibiotics, snake and spider venoms, amphibian peptides, or microcins. (6) The *Amanita* peptide toxins are among the smallest known ribosomally synthesized peptides. Their proproteins (34 and 35 amino acids) are also very small by the standards of typical ribosomally synthesized proteins. (7) No other known peptides are predicted to be processed from their proproteins by a Pro-specific peptidase, and (8) *Galerina marginata* has advantages over other eukaryotic synthesizers of small peptides. Snakes, amphibians, cone snails, and spiders are difficult to obtain or cultivate and their peptide toxins are made only in small venom ducts.

As described herein the inventors discovered the presence of conserved and hypervariable regions in genes encoding small peptide mushroom toxins. After the inventors compared the *Amanita* peptide toxin genes of the present inventions to known conotoxin genes they discovered that genomic sequences of both organisms are characterized by the presence of conserved and hypervariable regions, however with notable significant differences in the size and structure of the coding regions. Cone snails appear to have the capacity to synthesize a large number of peptides on the same fundamental biosynthetic scaffold (Richter et al., (1990) Proc. Nat. Acad. Sci. USA 87:4836; Woodward et al. (1990), EMBO J. 9:1015; all of which are herein incorporated by reference). However, in contrast to the conotoxins (Olivera, (2006) J. Biol. Chem. 281:31173; herein incorporated by reference), the *Amanita* peptide toxin genes encode smaller peptides from shorter regions of conserved and hypervariable regions in addition to showing other significant differences, Benjamin, Denis R. 1995. Mushrooms. Poisons And Panaceas. (W.H. Freeman, New York). xxvi+422 pp; herein incorporated by reference).

IV. Contemplated Role of Prolyl Oligopeptidase Family (POP) in Mushroom Peptide Toxin Production.

Prolyl oligopeptidase family (POPs) from other organisms are known to cleave several classes of Pro-containing peptides including mammalian hormones such as vasopressin (Brandt et al., 2007; Cunningham and O'Connor, 1997; Garcia-Horsman et al., 2007; Polgar, 2002; Shan et al., 2005, all of which are incorporated by reference). Changes in human blood serum levels of POP have been associated with depression, mania, schizophrenia, and response to lithium (Williams, 2005, herein incorporated by reference). A POP inhibitor reverses scopolamine-induced amnesia in rats (Brandt et al., 2007, herein incorporated by reference). Mutation of a POP gene in *Drosophila melanogaster* results in resistance to lithium (Williams et al., 1999, herein incorporated by reference). POPs have been proposed as a treatment for celiac-sprue disease, which is caused by failure to properly digest Pro-rich peptides in gluten (Shan et al., 2002, 2005, all of which are herein incorporated by reference). Despite the demonstration that POP will cleave many small peptides, such as mammalian hormones, apparently the native, endogenous substrates of POPs are not definitively known in any biological system (Brandt et al., 2007, herein incorporated by reference).

The *Amanita* peptide toxin system is contemplated to represent the first time a native substrate of a POP was identified, as shown during the development of the present inventions (see below and FIG. 20). Specifically, alpha-amanitin and phallacidin are synthesized as proproteins of 35 and 34 amino acids, respectively, with an invariant praline residue as the last amino acid in the mature peptide and as the first immediate upstream amino acid in the upstream conserved flanking amino acids. Therefore, a praline-specific peptidase was strongly predicted by the inventors to catalyze cleavage of the proprotein to release the peptide of the mature peptide toxins.

The inventors further identified sequences distantly related to human POP (GenBank accession no. NP002717) (SEQ ID NO:150) in the genome survey sequences of *A. bisporigera*. Orthologs of human POP (POP-like genes) were also found in every other basidiomycete for which whole genome sequences were available, for example, a POP-like gene was characterized from the mushroom *Lyophyllum cinerascens*. In contrast, orthologs of human POP are rare or nonexistent in fungi outside of the basidiomycetes. Thus, it appeared that at least one component of the biochemical machinery necessary for the biosynthesis of the *Amanita* toxins is both widespread in, and restricted to, the basidiomycetes.

V. Genomic Structure of *Amanita* Peptide Encoding Genes of the Present Inventions.

The inventors discovered the genes encoding the *Amanita* peptide toxins and the translated peptides relating to *Amanita* peptide toxins during the development of the present inventions. In particular, the inventors discovered a genomic structure of *Amanita* peptide toxins, AMA1 and PHA1, relating to amatoxin and phallotoxin toxins. Both types of peptides comprise a conserved stretch (A) of about 9 homologous amino acids, followed by a hypervariable region of 6 to 10 amino acids that are specific for either the two types of toxin peptides, a-amanitin or phallacidin, in addition to longer peptides. These hypervariable regions were followed by an additional conserved stretch (B) of approximately 17 homologous amino acids. The inventors contemplate that the coding sequences of the toxins are part of a larger preproprotein, of approximately 35 amino acids, that is translated and then undergoes post-translational processing to release the active peptide, similar to processing mechanisms of neuropeptides and other small peptide toxins (e.g., conotoxins).

The genome of *A. bisporigera* contains at least 30 copies of genes coding for the first highly conserved stretch of amino acids (A), followed by a hypervariable region (P), then the second conserved region (B). The primary sequences derived from the cDNA encode peptides AWLVDCP (SEQ ID NO: 69) and IWGIGCNP (SEQ ID NO: 50), which are contemplated to be capable of cyclization into phallacidin and alpha or gamma amanitin, respectively. Neither of these peptides were found after searching the entire GenBank NR database. Therefore, by statistical coincidence they are unlikely to be present in A. bisporigera; however, experimental results shown herein demonstrate that nucleic acid sequences are present that may encode these peptides.

The *Amanita* peptide toxins differ from the other known naturally occurring small peptides in several ways. First, the animal peptides are not cyclized by peptide bonds known to be present in *Amanita* peptide toxins but acquire their essential rigidity by extensive disulfide bonds. Ribosomally synthesized cyclic peptides are known from bacteria, plants, and animals, e.g., the cyclotides and microcin J25 (Craik, (2006) Science 311:1563, Rosengren, et al., (2003), J. Am. Chem. Soc. 125:12464; all of which are herein incorporated by reference), but to the best of the inventor's knowledge all other fungal cyclic peptides are synthesized by nonribosomal peptide synthetases (Walton, et al., (2004) in Advances in Fungal Biotechnology for Industry, Agriculture, and Medicine, J. S. Tkacz, L. Lange, Eds. (Kluwer Academic/Plenum, N.Y., pp. 127-162; Finking, et al., (2004) Annu. Rev. Micro biol. 58:453; all of which are herein incorporated by reference). Second, the *Amanita* peptide toxins are not secreted, and consistent with this they lack predicted signal peptides in their sequences (FIGS. 4 and 5) (Muraoka, et al., (1999) Appl. Environ. Microbial. 65:4207, Zhang et al., (2005) FEMS Microbial. Lett. 252:223; all of which are herein incorporated by reference). Third, whereas the other known ribosomal peptides are processed from their respective proproteins by proteases that recognize basic amino acid residues (Arg or Lys) (Olivera, J. Biol. Chem. 281:31173 (2006), Richter et al., (1990) Proc. Nat. Acad. Sci. USA 87:4836; all of which are herein incorporated by reference), the peptide toxins of *Amanita* are predicted to be cleaved from their proproteins by a praline-specific protease. As shown herein, the inventors were able to begin confirming their predictions by demonstrating the cleavage of a model phalloidin peptide using an isolated POPB protein, see, FIG. 20.

Sequencing of the genome of *A. bisporigera* to 20×coverage should also yield all of the other members of the *Amanita* peptide toxin family, which is characterized by "MSDIN" as the first five amino acids of the predicted proproteins. Furthermore, other species of *Amanita* that make *Amanita* peptide toxins, such as *A. phalloides* and *A. ocreata*, should yield more members of this family. Furthermore, sequencing of additional specimens of these species of *Amanita* should yield more members. The inventors calculate that there are >30 MSDIN sequences in one isolate of *A. bisporigera* alone.

Further, the inventors contemplate that genes for *Amanita* peptide toxin biosynthesis will be clustered within the *Amanita* genome. As shown herein, an example of genomic organization of PHA1 (for phallacidin) genes in relation to adjacent genes encoding potential enzymes.

VI. Contemplated Role of P450 Homologs in Mushroom Peptide Toxin Production.

Many of the *Amanita* peptide toxins are hydroxylated at isoleucine, tryptophan, proline, and/or aspartic acid. Hydroxylation of the *Amanita* peptide toxins might be catalyzed by cytochrome P450 monooxygenases, which are known to catalyze hydroxylation of many other fungal secondary metabolites (e.g., Malonek et al., 2005; Tudzynski et al., 2003). Filamentous fungi differ widely in their numbers of P450's. Whereas some filamentous fungi have >100, the Basidiomycete *Ustilago maydis* has only about 17 (drnelson.utmem.edu/CytochromeP450.html). The inventors found three P450 genes clustered with two copies of PHA1 (FIG. 10D and in Example). These are candidates to encode one or more of the enzymes that catalyze hydroxylations of the *Amanita* peptide toxins.

In terms of identifying new P450 genes contemplated to be involved in *Amanita* peptide toxin biosynthesis, three candidates in the three P450's were found on a lambda clone clustered with two copies of PHA1 (FIG. 10D). Since secondary metabolites appear to be rare in Basidiomycetes compared to Ascomycetes, the number of P450's in *A. bisporigera* is probably closer to the Basidiomycete *Ustilago* (about 17) than the Ascomycete *Fusarium* (>100) (see website at drnelson.utmem.edu/CytochromeP450.html).

VII. *Galerina* Mushrooms for Use in the Present Inventions.

Further, the present invention relates to using genes and proteins from *Galerina* species encoding mushroom peptide toxins, specifically amatoxins. *Galerina* sequences and *Galerina* mushrooms are particularly contemplated for use in the present inventions because *Galerina*, unlike *Amanita*, is a culturable fungus that produces amanitins in the laboratory. Amatoxins are induced in cultured *Galerina*, by several methods, for example, Benedict R G, V E Tyler Jr., L R Brady, L J Weber (1966) Fermentative production of *amanita* toxins by a strain of *Galerina marginata*. J Bacteriol 91:1380-1381; and preferably using methods described in Muraoka S, T Shinozawa (2000) Effective production of amanitins by two-step cultivation of the basidiomycete, *Galerina fasciculata* GF-060. J Biosci Bioeng 89:73-76, herein incorporated by reference.

Thus the present inventions further relate to compositions and methods associated with creating and screening genomic libraries from *Galerina* for sequences of interest. In particular, the present invention relates to providing and using PCR primers for identifying and sequencing *Galerina* genes, including methods comprising RACE PCR primers. Specifically, the present inventions relate to identifying and using sequences of interest, i.e. sequences encoding proteins associated with the production of small peptides, including cyclic peptides, for example, compositions and methods comprising *Galerina* POP homologs and amatoxins.

Examples of procedures used to ligate the DNA construct of the invention, the promoter, terminator and other elements, respectively, and to insert them into suitable cloning vehicles containing the information necessary for replication, are well known to persons skilled in the art (see, e.g., Sambrook et al., 1989; herein incorporated by reference).

The polypeptide may be detected using methods known in the art that are specific for the polypeptide. These detection methods may include use of specific antibodies, formation of an enzyme product, disappearance of an enzyme substrate, or SDS-PAGE gel blotted onto membranes for immunoblotting. For example, an enzyme assay may be used to determine the activity of the polypeptide. Procedures for determining enzyme activity are known in the art for many enzymes.

A. Peptide Toxin Genes in *Galerina* Mushrooms.

The inventors' were surprised to discover that sequences of the peptide toxin genes in *Galerina marginata* is quite different compared to *A. bisporigera*. See FIGS. 12 and 33A and B for alignments of *Galerina* and *Amanita* peptide toxin proteins. For this example, approximately 73 MB of final assembled genomic DNA, as described above, was sequenced by 454 pyrosequencing. 73 MB was estimated to be approximately two times the size of the *G. marginata* genome based on the average size of known basidiomycete genomes. These sequences were put into a private database and searched using AMA1, PHA1, AbPOPA, and AbPOPB protein sequences The DNA contigs showing predicted protein sequences closely related to AbPOPB and AbPOPA were further analyzed. PCR primers were made to predicted sequences at the two ends of the proteins and used to amplify from genomic and cDNA full length genomic and mRNA copies of the two genes. Four examples of contigs are shown in FIG. 41. The results for GmAMA1 variants are described in this example while the results of screening for POP genes are described in the following example.

Using AMA1 from *A. bisporigera* as the search query, two orthologs of AMA1 were identified in the partial genome survey sequence of *G. marginata* and designated as GmAMA1-1 and GmAMA1-2.

PCR primers unique to GmAMA1- and GmAMA1-2 were designed. For GmAMA1-1, the unique primers were 5'-CTCCAATCCCCCAACCACAAA-3' (forward, SEQ ID NO:682) and 5'-GTCGAACACGGCAACAACAG-3' (reverse, SEQ ID NO:683). For GmAMA1-2, the primers were: 5'-GAAAACCGAATCTCCAATCCTC-3' (forward, SEQ ID NO:684), and 5'-AGCTCACTCGTTGCCACTAA-3' (reverse, SEQ ID NO:685). PCR primers for each gene were designed based on the partial sequences and used to amplify full-length copies. The amplicons were cloned into *E. coli* DH5α and sequenced.

The genomic DNA sequences were used for primer design to obtain full-length cDNAs by Rapid Amplification of cDNA Ends (RACE) using the GeneRacer kit (Invitrogen, Carlsbad, Calif.). A cDNA copy of GmAMA1-1 was obtained using primers 5'-CCAACGACAGGCGGGACACG-3' (5'-RACE, SEQ ID NO:686) and 5'-GACCTTTTTGCTTTAACATCTACA-3' (3'-RACE, SEQ ID NO:687), and of GmAMA1-2 with primers 5'-GTCAACAAGTCCAGGAGACATTCAAC-3' (5'-RACE, SEQ ID NO:688) and 5'-ACCGAATCTCCAATCCTCCAACCA-3' (3'-RACE, SEQ ID NO:689).

Alignments of genomic and cDNA copies were done using Spidey located at (ncbi.nlm.nih.gov/spidey/) and Splign located at ncbi.nlm.nih.gov/sutils/splign.cgi.

GmAMA1-1 contained three introns while GmAMA1-2 contained two introns (FIG. 33). The three introns of GmAMA1-1 were 53, 60, and 60 nt in length in similar locations as the three introns of AMA. The first intran in both GmAMA1-2 and GmAMA1-2 interrupted the third codon before the stop codon. GmAMA1-1 and GmAMA1-2 differed in at least eight nucleotides out of 108 nucleotides in the coding region (i.e., from the ATG through the TGA stop codon). At least two of these differences resulted in amino acid changes and six changes were silent, i.e no change in amino acid at that location (FIG. 33). There were numerous nucleotide differences between GmAMA1-1 and GmAMA1-2 in the 5' and 3' untranscribed regions in addition to having large stretches of close identity. The biggest difference between GmAMA1-1 and GmAMA1-2 was that the latter gene had a 100-bp deletion relative to GmAMA1-1, which spanned the second intron of GmAMA1-1. This deletion was in the 3' UTR (FIG. 32). This accounted for the presence of only two introns in GmAMA1-2 (FIGS. 32 and 33).

The translational start site of a gene is typically contemplated as the first in-frame ATG, SEQ ID NO:711 after the transcriptional start site, SEQ ID NO:710. When this criterion was applied to GmAMA1-1, a start site was indicated that was analogous to AMA1 of *A. bisporigera*. This start site resulted in a predicted preproprotein, SPIPQPQTHLT-KDLFALTSTMFDTNATRLPIWGIGCNPWT AEHVDQT-LASGNDIC, SEQ ID NO:690, and proprotein, SEQ ID NO: 704. However, when this criteria was applied to GmAMA1-2, there was an in-frame ATG that is 78 nucleotides upstream of the ATG, indicated in FIG. 33, i.e. atgcaagtgaaaac-cgaatctccaatcctccaaccatcaactcaaccaaagatcttcgcccttgcct-taatatctgcc, SEQ ID NO: 690, which would result in a proprotein of 61 amino acids instead of 35 as predicted for AMA1 and GmAMA1-1. Thus two translational start sites were contemplated, one, after the transcriptional start site of SEQ ID NO:713, i.e. SEQ ID NO: 690, that resulted in a 61 amino acid preproprotein, MQVKTESPILQPSTQPKIF ALALISAFDTNSTRLPIWGIGCNPWT AEHVDQTLVS-GNDIC, SEQ ID NO: 691, and the other, SEQ ID NO:714, in a 35 amino acid proprotein, MFDTNSTRLPIWGIGCN-PWTAEHVDQTLVSGNDIC, SEQ ID NO:705. However the inventors' contemplated that the 35 amino acid preproprotein was the target of the Gm POP proteins, for an example showing that prolyl oligopeptidases act on other types of peptides less than 40 amino acids see, Szeltner and Polgar, 2008, herein incorporated by reference).

GmAMA1-1 and GmAMA1-2 were both predicted to encode 35-amino acid proproteins, the same size as the proprotein of AMA1 in *A. bisporigera*. The toxin-encoding region (IWGIGCNP) was in the same relative position as it was in AMA1. There were 31 nucleotide differences between GmAMA1-1 and AMA1 in the coding region of 108 nucleotides (ATG through the stop codon). This resulted in a low level of amino acid conservation outside the toxin region and the amino acids immediately upstream of the toxin region (NATRLP, SEQ ID NO:754 (FIG. 33).

The sequenced proproteins were added to a family of genes including and related to AMA1 and PHA1 in *A. bisporigera, A. phalloides*, and *A. ocreata*, a group of genes that started with MSDIN. In contrast, when a start codon was contemplated in the same location between GmAMA1-1 and GmAMA1-2 the first five amino acids of the two *G. marginata* α-amanitin genes were MFDTN, SEQ ID NO: 675. Searching the inventors' *G. marginata* database with the upstream and downstream regions of GmAMA1-1 and GmAMA1-2 did not reveal any additional related sequences. Conversely, searching with the conserved regions of GmAMA1-1 and GmAMA1-2 did not reveal any related sequences in *A. bisporigera* beyond the known MSDIN family members described herein.

Distribution of α-amanitin Genes in the Genus *Galerina. Within the genus Amanita, AMA*1 and PHA1 are known to be present in section Phalloideae, which contains the known amatoxin- and phallotoxin-producing species in this genus. To explore the distribution of the α-amanitin genes in relation to toxin production in *Galerina*, four species of *Galerina* were compared by DNA blotting (also known as Southern blotting) and RNA blotting (also known as Northern blotting).

Figure 34:
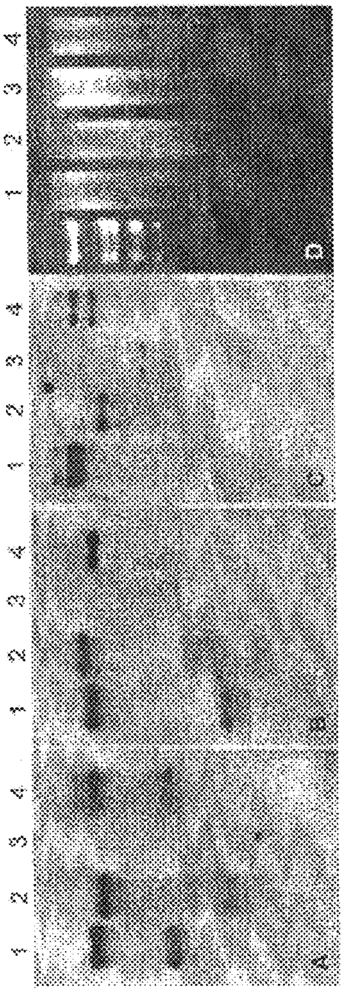
FIG. 34 shows an exemplary DNA blot of *Galerina* species. Lane 1, *G. marginata*; lane 2, *G. badipes*; lane 3, *G. hybrida*; lane 4, *G. venenata*. Panel A: Probed with GmAMA1-1; panel B probed with GmPOPB; panel C, probed with GmPOPA; panel D, gel stained with Ethidium bromide. The results showed that amanitin-producing species of *Galerina* (namely, *G. marginata, G. badipes*, and *G. venenata*) have the GmAMA1 and POPB genes, while POPA was present in all species.
Figure 35:
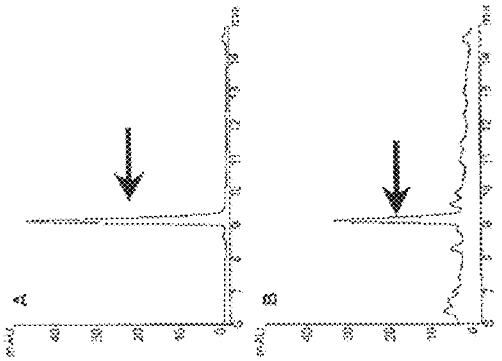
FIG. 35 shows an exemplary reverse-phase HPLC analysis of amatoxins in *Galerina marginata* strain CBS 339.88 grown on a medium containing low carbon A: α-amanitin standard (arrow). B: extract of *G. marginata*. Elution was monitored at 305 nm. The mushroom extract has a peak corresponding to the α-amanitin standard (arrow). Identify of this compound to authentic alpha-amanitin was confirmed by mass spectrometry. β-Amanitin elutes just before α-amanitin (Enjalbert et al., 1992, herein incorporated by reference) and appears to be absent in extracts of this *G. marginata* specimen.

Recent taxonomic revision of this genus indicates that *G. marginata* and *G. venenata* are synonyms, whereas *G. hybrida* and *G. badipes* are considered as separate species (Enjalbert et al., 2004; Gulden et al., 2001, 2005, all of which are herein incorporated by reference). In Southern blots, a GmAMA1-1 probe [a genomic DNA sequence made with primers (5'-ATGTTCGACACCAACTCCACT-3', SEQ ID NO:672) and (5'-CGCTACGTAACGGCATGACAGTG-3', SEQ ID NO:673) hybridized to all three α-amanitin producers (*G. marginata, G. badipes*, and *G. venenata*) but not to the toxin nonproducer, *G. hybrida* (lane 3) (FIG. 34). In contrast to *Amanita* species, which give multiple hybridizing bands when probed with AMA1 or PHA1, the pattern in *Galerina* was less complex. Instead of multiple bands, two bands were observed indicating that GmAMA1 is not part of an extended gene family in *G. marginata*. In order to determine whether there were multiple copies located on the same restriction fragment restriction digests with other enzymes were done; however, these also showed two bands. This pattern of hybridization was consistent with the genome survey sequence that indicated that *G. marginata* has two sequences closely related to GmAMA1-1. The genome survey sequence and cDNA analysis indicated that both genes encode α-amanitin (FIG. 33), and the inventors' isolate of *G. marginata* does not make other peptide toxins related to α-amanitin such as beta-amanitin. Because gamma-amanitin has the same amino acid sequence as alpha-amanitin, it is predicted to be encoded by the same gene. The sequenced isolate of *G. marginata* does not make gamma-amanitin. Further, the genome survey sequence did not contain a DNA sequence that would encode β-amanitin, which differs from α-amanitin by one amino acid (Asp instead of Asn). HPLC analysis of *G. marginata* CBS 339.88 indicated that it made, at most, a trace of β-amanitin (FIG. 35). The *G. marginata* sample contained approximately 0.3 mg α-amanitin/g dry weight.

Figure 36:
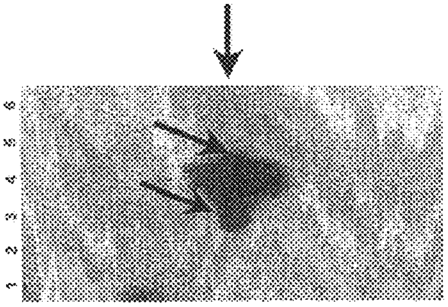
FIG. 36 shows an exemplary RNA blot of *Galerina* strains under different growth conditions. The probe was GmAMA1-1. Lane 1: *G. hybrida* grown on high carbon. Lane 2: *G. hybrida*, low carbon (note absence of hybridization signal in lanes 1 and 2). Lane 3: *G. marginata*, high carbon. Lane 4: *G. marginata*, low carbon (see RNAs corresponding to the size of AMA1 at arrows). Lane 5*: G. badipes*, high carbon, no detectable RNA signal in the region of the arrows. Lane 6*: G. badipes*, low carbon showing some RNA signal at the arrow. Each lane was loaded with 15 μg total RNA. The major band in lanes 3, 4 and 6 is approximately 300 bp. The higher molecular weight signal in lane 1 does not correspond to a specific signal. Arrows point to the presence of mushroom RNA that hybridized to the GmAMA1-1 probe.

Regulation of GmAMA1 by Low Carbon. Successful amplification of GmAMA1-1 and GmAMA1-2 by reverse transcriptase PCR with gene-specific probes indicated that both genes are transcribed in culture. Expression was further studied by RNA blotting. Muraoka and Shinozawa (2000, herein incorporated by reference) showed that α-amanitin production in *G. fasciculata* was upregulated on low glucose medium (carbon starvation). The inventors' found that expression of GmAMA1-1 and/or GmAMA1-2 were also up-regulated by carbon starvation in *G. marginata* and *G. badipes* (FIG. 36). Due to their high nucleotide similarity, this experiment did not distinguish between expression of GmAMA1-1 and GmAMA1-2. As expected from the DNA blot results, RNA from the amanitin nonproducer, *G. hybrida*, gave no signal in either high or low carbon (FIG. 36).

Discovering that *G. marginata* peptide toxin genes differed from those of *A. bisporigera* was surprising in several ways. First, the proproteins share little overall amino acid identity except in the toxin region itself (IWGIGCNP) with the exception of short regions outside of the toxin sequence. For example, whereas the *A. bisporigera* peptide toxin proproteins start with MSDIN, SEQ ID NO:674, (or with only a single amino acid difference), the two copies of AMA1 in *G. marginata* started with MFDTN, SEQ ID NO:675. Additionally, the inventors found conservations in the four amino acids after MSDIN, which were also found after MFDTN, and the start of the peptide toxin coding region (IWGIGCNP). These conserved motif sequences were found as ATRLP, SEQ ID NO:676, or STRLP, SEQ ID NO:677, in the proproteins of both the *A. bisporigera* peptide toxins and the *G. marginata* peptide toxins. The complete conservation of the Pro residue immediately upstream of the peptide toxin coding region was believed to be significant because Pro is believed to be required for processing of the proprotein by a prolyl oligopeptidase. The inventors further contemplated that upstream conserved region of amino acids in *G. marginata* peptide toxin sequences (i.e. N[A/S]TRL, SEQ ID NO:678) is important for recognition of the proproteins by Gm POPB. There was little conservation between the downstream conserved regions of the A. bisiporigera and the *G. marginata* genes. For example, MFDTNATRLP SEQ ID NO:679, was unexpectedly found in place of MSDIN.

Second, *G. marginata* was discovered to contain two nearly identical copies of the α-amanitin gene with at least one variant of each whereas one copy of the α-amanitin gene was found in *A. bisporigera*. Conversely, *A. bisporigera* has at least two copies of genes encoding phallacidin (PHA1) while none were found in the sequenced isolate of *G. marginata*, and phallacidin or other phallotoxins have not been reported from *G. marginata*.

Third, the inventors were surprised to find two sequences related to the α-amanitin genes in the genome of *G. marginata* whereas a large family of related sequences (>30 members), which encode predicted, but chemically unknown, cyclic peptides was discovered in the *A. bisporigera* genome. These predicted peptides were discovered by translating the *A. bisporigera* genes contained 7 to 10 amino acids where the majority lacked Trp and Cys predicted to be used to form tryptathionine, which was a characteristic of the amatoxins and phallotoxins of *A. bisporigera* peptides.

*G. marginata* and other species of *Galerina* were known to make α-amanitin (Enjalbert et al., 2004; Muraoka et al., 1999; Muraoka and Shinozawa, 2000, all of which are herein incorporated by reference). However phallotoxins were not found in *Galerina* species however some species were reported to make β-amanitin. β-amanitin differs from α-amanitin in having Asp in place of Asn. The difference between these two forms of amanitin was predicted to be genetically encoded and not catalyzed by, e.g., a transamidase, because the genome of *A. phalloides* contains a gene that was predicted to directly encode β-amanitin.

The inventors confirmed that the isolate of *G. marginata* prepared and used herein did not synthesize β-amanitin and the genome lacks a gene for β-amanitin. In other isolates, traces of β-amanitin from *G. marginata* grown in culture were detected i.e. Benedict et al. (1966, 1967, all of which are herein incorporated by reference). Further, β-amanitin was not detected in several wild North American specimens of *Galerina*. Therefore, some species and/or isolates of *Galerina* do make β-amanitin and others do not, therefore each isolate must be tested. Other forms of amanitin, such as γ-amanitin and ε-amanitin, differ from α-amanitin and β-amanitin in their pattern of hydroxylation. This chemical difference was not found in encoding DNA.

B. Full Length POP Gene Production.

Figure 37:
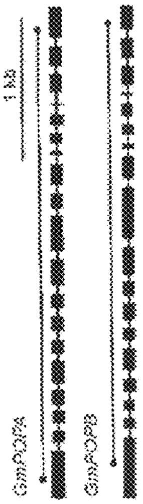
FIG. 37 shows exemplary structures of GmPOPA and GmPOPB genes encoding putative prolyl oligopeptidases from *G. marginata*. Thick bars indicate exons and thin bars indicate introns. The lines above the gene models indicate the positions of the coding regions.

The *G. marginata* partial genome survey was discovered to contain two orthologs of the POP genes of *A. bisporigera*. Genomic PCR, reverse transcriptase PCR, and RACE were used, as described herein, to isolate full-length copies of these two genes and determine their intron/exon structures (FIG. 37). GmPOPA had 18 introns, which is the same number found in AbPOPA. while GmPOPB had 17 introns, one fewer than in AbPOPB. The amino acid sequences of the predicted translational products of GmPOPA (738 amino acids) and GmPOPB (730 amino acids) are 57% identical to each other. The GmPOPA protein is 65% identical to AbPOPA and 58% identical to AbPOPB, and GmPOPB is 57% identical to AbPOPA and 75% identical to AbPOPB.

During the development of the present inventions, two orthologs were found in the *G. marginata* genome sequences corresponding to the two *A. bisporigera* prolyl oligopeptidases (AbPOPA and AbPOPB) described herein. The *G. marginata* genes with closest identity to AbPOPA or AbPOPB were designated as GmPOPA and GmPOPB, respectively.

Sequences hybridizing to AbPOPA were found to be present in amatoxin and phallotoxin-producing and non-producing species of *Amanita*, whereas AbPOPB was found present only in the toxin-producing species. By DNA blotting GmPOPA was present in all four specimens of *Galerina*, however GmPOPB was not present in the amanitin non-producing species *G. hybrida* (FIG. 34). The similarity of the hybridization pattern of *G. venenata* and *G. marginata* to GmAMA1, GmPOPA, and GmPOPB was consistent with these two isolates belonging to the same species (see, Gulden et al., 2001, herein incorporated by reference). The association of POPB with amanitin production in both *A. bisporigera* and *G. marginata*, and the higher amino acid identity of GmPOPA to AbPOPA and of GmPOPB to AmPOPB was consistent with a contemplated role for POPB in amanitin biosynthesis in both species. Other basidiomycetes in GenBank and at the DOE Joint Genome Institute (JGI) have single POP genes, which are contemplated as functional orthologs of POPA.

For isolating and cloning full-length cDNA sequences for GmPOPA and GmPOPB, PCR primers that corresponded to the amino and carboxyl termini of both genes (which were present on different contigs) were designed from the genome survey sequence. The forward primers were 5'-TTTAGGGCAGTGATTTCGTGACA-3', SEQ ID NO: 692, and 5'-AACAGGGAGGCGATTATTCAAC-3', SEQ ID NO: 693, and the reverse primers were 5'-GAACAATCGAACCCATGACAAGAA-3', SEQ ID NO: 694, and 5'-CCCCCATTGATTGTTACCTTGTC-3', SEQ ID NO: 695. The primer pairs were used in both combinations and successful amplification indicated the correct pairing of 5' and 3' primers. The resulting amplicons were cloned into *E. coli* DH5α and sequenced.

The RACE primers for GmPOPA were 5'-CGGCGTTCCAAGGCGATGATAATA-3' (5'-RACE), SEQ ID NO: 696, and 5'CATCTCCATCGACCCCTTTTTCAGC-3' (3'-RACE), SEQ ID NO: 697, and for GmPOPB 5'-AGTCTGCCGTCCGTGCCTTGG-3' (5'-RACE), SEQ ID NO: 698, and 5'-CGGTACGACTTCACGGCTCCAGA-3' (3'-RACE), SEQ ID NO: 699. Sequences generated from the RACE reactions were used to assemble full-length cDNAs of two genes, GmPOPA and GmPOPB (see FIGS. 38A and 38B).

Alignments of genomic and synthetic cDNA copies (see, FIGS. 38A and 38B) were done using Spidey available at National Center for Biotechnology Information (NCBI) at website ncbi.nlm.nih.gov/spidey/ and at Splign located at ncbi.nlm.nih.gov/sutils/splign/splign.cgi).

GmPOPA and POPB were predicted to encode exemplary polypeptides as shown in FIGS. 38A and 38B.

The inventors' contemplate that POP proteins encoded by the *G. marginata* POP sequences (known as GmPOP) of the present inventions are capable of enzymatic activity. There are three critical amino acids that constitute the active site in other POP proteins (Szeltner et al., (2008) Current Protein and Peptide Science 9:96-107, herein incorporated by reference). In a crystallized POP protein, the active site residues were Ser554, Asp641, and His680. The location of these active site residues in POPA are: Ser581, Asp665, and His 701. In POPB they are Ser571, Asp661, and His698. Thus the GmPOP genes of the present inventions are contemplated to be capable of encoding POP proteins with these active site amino acids in analogous positions for a protein capable of enzymatic activity.

The inventors showed that isolated prolyl oligpeptidase (POP) proteins of other mushroom species were capable of initial processing of the proproteins of amatoxins and phallotoxins. First, in the extended MSDIN family of *Amanita*, discovered by the inventors and now shown to correspond to an MFDTN, SEQ ID NO:675, family of α-amanitin genes of *G. marginata*, flanking Pro residues are completely conserved. One Pro remains in the mature toxin while the other is removed with the flanking sequence. Second, an enzyme that proteolytically cleaves a synthetic phalloidin proprotein, isolated from the phalloidin-producing fungus *Conocybe albipes*, was identified during the development of the presence inventions as a POP protein. The same enzyme cleaves at both Pro residues to release the mature linear peptide (AWLATC in the case of phalloidin). Third, toxin-producing species of *Amanita* have two POP genes, whereas all other sequenced basidiomycetes have one. One of the *Amanita* POP genes, AbPOPB, was found during the development of the presence inventions restricted to toxin-producing species, like AMA1 and PHA1 themselves. Fourth, the distribution of AbPOPB and α-amanitin overlap in mushroom tissues was found during the development of the presence inventions, indicating a cytological connection between α-amanitin biosynthesis and accumulation. *G. marginata* was discovered to have two POP genes, like *Amanita* but unlike other, toxin non-producing species of mushrooms. GmPOPB is absent from species such as *G. hybrida* that do not make toxins. Thus, AbPOPB and GmPOPB are believed to be involved in the biosynthesis of the amatoxins and/or phallotoxins in their respective species.

VIII. Recombinant Polypeptide Products of *Amanita* and *Galerina* Genes.

A desired end product, i.e., the polypeptide of interest, such as a POP enzyme, may be expressed by a host cell, such as a bacterium, i.e. *E. coli*, as a heterologous protein or peptide. Thus the polypeptide may be any polypeptide heterologous to the bacterial cell. The term "polypeptide" is not meant herein to refer to a specific length of the encoded product and, therefore, encompasses peptides, oligopeptides, and proteins. The heterologous polypeptide may also be an engineered variant of a polypeptide. The term "heterologous polypeptide" is defined herein as a polypeptide, which is not native to the host cell. Preferably, the host cell is modified by methods known in the art for the introduction of an appropriate cloning vehicle, i.e., a plasmid or a vector, comprising a DNA fragment encoding the desired polypeptide of interest. The cloning vehicle may be introduced into the host cell either as an autonomously replicating plasmid or integrated into the chromosome. Preferably, the cloning vehicle comprises one or more structural regions operably linked to one or more appropriate regulatory regions.

The structural regions are regions of nucleotide sequences encoding the polypeptide of interest. The regulatory regions include promoter regions comprising transcription and translation control sequences, terminator regions comprising stop signals, and polyadenylation regions. The promoter, i.e., a nucleotide sequence exhibiting a transcriptional activity in the host cell of choice, may be one derived from a gene encoding an extracellular or an intracellular protein, preferably an enzyme, such as an amylase, a glucoamylase, a protease, a lipase, a cellulase, a xylanase, an oxidoreductase, a pectinase, a cutinase, or a glycolytic enzyme.

The resulting polypeptide may be isolated by methods known in the art. For example, the polypeptide may be isolated from the nutrient medium by conventional procedures including, but not limited to, centrifugation, filtration, extraction, spray drying, evaporation, or precipitation. The isolated polypeptide may then be further purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), or extraction (see, e.g., Protein Purification, J.-C. Janson and Lars Ryden, editors, VCH Publishers, New York, 1989, herein incorporated by reference).

IV. Compositions and Methods for Expressing Small Linear Peptides and Cyclic Peptides Using Transformed *Galerina Marginata* and Lysates.

The inventors grew *G. marginata* in the laboratory and collected mycelium for use in the following transformation procedure. The inventors show herein the successful transformation of the alpha-amanitin-producing fungus *Galerina marginata* with a test construct. Thus the inventors' contemplate producing commercial levels of amanatin in addition to novel, non-natural analogs of amanitin. Further, the inventors' contemplate making novel linear and cyclic peptides from synthetic prepropeptides.

The following are exemplary methods for making buffers and reagents for us in the present inventions. *Galerina* culture methods: Vegetative mycelial stocks were prepared by culturing aseptic fragments of fruiting bodies on HSVA plates. Fungal colonies were transferred and reisolated until pure cultures were obtained. The stocks were subcultured every 6 months. HSV-2C (1 L): 1 g yeast extract, 2 g glucose, 0.1 g $NH_4Cl$, 0.1 g $CaSO_4.5H_2O$, 1 mg thiamine. HCl, and 0.1 mg biotin, pH 5.2 (Muraoka and Shinozawa, 2000, herein incorporated by reference). Agar medium (HSVA) for subculture contained 2% agar in HSV. Protoplasting Buffer: In 20 ml of 1.2 M KCl add 500 mg Driselase (Sigma), 1 mg chitinase (Sigma), and 300 mg lysing enzyme from *Aspergillus* sp. Sigma #L-3768. Stir for 30 min and filter sterilize in a 0.45 um filter. Sorbitol Tris-HCl Ca (STC) buffer: Solution a) 1.2 M sorbitol, 10 mM Tris-HCl (pH8.0), 50 mM $CaCl_2$, autoclaved. Solution b) 30% PEG Solution Mix: 300/(W/V) polyethylene glycol/STC buffer. Filter sterilize in a 0.45 um filter. Regeneration medium (RM): a) HSV-2C (1 L) and b) sucrose 273.5 g/500 ml of water. Autoclave solutions a) and b) separately and combine after autoclaving.

Figure 39:
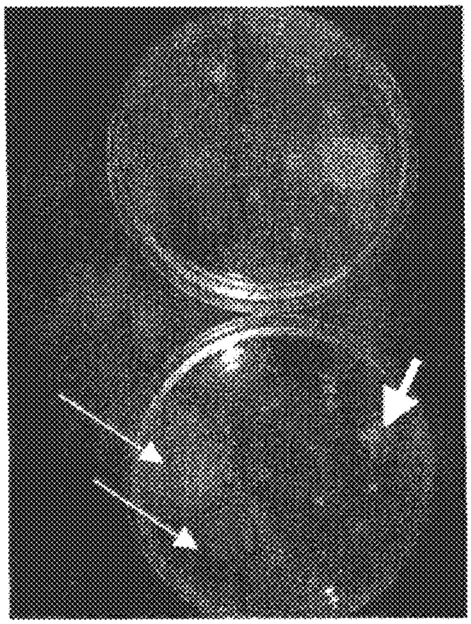
FIG. 39 shows exemplary growth of large colonies of *G. marginata* (see arrows) on hygromycin, which indicated resistance to hygromycin due to successful transformation with the hygromycin resistance gene.

The following is an exemplary *Galerina* transformation protocol for use in the present inventions. Around 20 pieces of mycelium were used to inoculate 100 ml of HSV-2C broth in a 250 ml Erlenmeyer flask. This inoculate was placed on a shaker at 150 rpm at room temperature for 9-15 days, until cloudy. The culture medium and fungus was used to begin the following steps. The cultures were: 1. Filtered through sterile Miracloth and the collected mycelia was washed thoroughly with sterile water. This fungal mycelium was placed in a sterile 250 ml Erlenmeyer flask. 20 ml Protoplasting Buffer (see recipe below) was added. 2. Digested for 8 hours on a rotary shaker at 26-30 C at 120 rpm. 3. Digestion mix was filtered through a 30 micron Nitex nylon membrane (Tetko Inc. Kansas City, Mo., U.S.A.)) into 1-2 sterile 30 ml Oakridge tubes on ice. Filtered solution was turbulent due to the presence of protoplasts when checked under the microscope. 4. This filtered solution was centrifuged in Oakridge tubes at 4 C at 2000×g for 5 min. 5. Supernatant was carefully poured off and discarded. Protoplast pellet was gently resuspended in approx. 10 ml of STC buffer and resuspended by shaking gently. Solution was spun at 2000×g for 5 min. 6. Repeat step 5 once. 7. Supernatant was discarded and the protoplast pellet was gently resuspended in 1 ml of STC buffer with a wide orifice pipette and transferred to a microcentrifuge tube and spun at room temperature at 4000×g for 6 min. 8. Supernatant was poured off and protoplasts were resuspended in 1 ml of STC in a final volume with concentration of $10^8$-$10^9$ protoplast/ml. The tube was placed on ice. 9. The following mixture was combined: 50 μl protoplasts, 50 μl STC buffer, 50 ul 30% PEG solution and 10 ul plasmid or PCR product (1 μg) depending upon the experiment. When plasmids were used they were linearized with a restriction enzyme which cut the DNA in a noncoding region. 10. 2 ml of 30% PEG solution was added and the tubes incubated for 5 min. 11. 4 ml of STC buffer was added and gently mixed by inversion. 12. The mix was added to Regeneration Media (RM) (see below) at 47° C., and mixed by inversion then poured into Petri dishes. Each solution mixture was plated in several plates. 13. Protoplasts were regenerated for up to 20 days until tiny colonies started to appear as viewed by eye. 10 ml of RM amended with 10 μg/ml Hygromycin B was overlayed onto the cultures. 14. Putative transformants were isolated from colonies that grew after the Hygromycin B overlay and eventually emerged on the surface of the overlaid agar. Examples of colonies collected for use in the present inventions are shown by arrows in FIG. 39.

Figure 40:
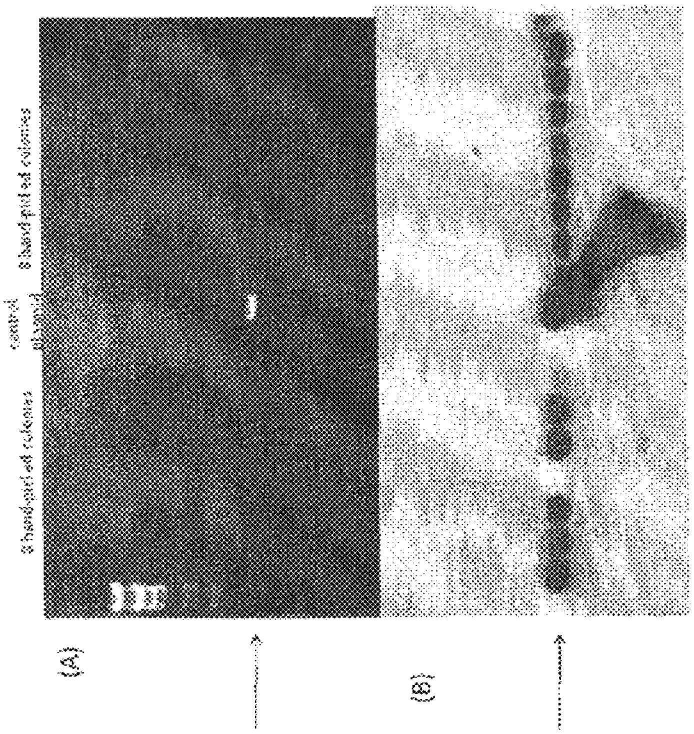
FIG. 40 shows exemplary PCR results of amplifying genes using specific primers of the hygromycin resistance transgene (see Experimental section), which indicated which colonies are transformants with the hygromycin transgene as opposed to unwanted selection of natural hygromycin resistant colonies. Panel A: Arrows indicated the hygromycin resistance gene (transgene) PCR products stained with Ethidium bromide while Panel B: shows the results of this gel blotted and probed with a copy of the hygromycin transgene in order to confirm the identity of the PCR products (arrow). The large streak crossing several lanes was an artifact.

After colonies were collected the presence of the inserted Hygromycin B transgene was tested by PCR. Primers specific to the hygromycin resistance gene used in FIG. 40 were the following: hph_forward 5'-CGTGGATATGTCCTGCGGG-3' hph_reverse, SEQ ID NO:700, 5'-CCATACAAGCCAACCACGGC-3', SEQ ID NO:701, (Kilaru et al., 2009, Curr Genet 55:543-550, herein incorporated by reference).

The inventor's contemplate that *G. marginata* can be transformed with synthetic genes, using the *G. marginata* specific contemplated cut sites, i.e. synthetic sequences comprising nucleotides encoding MDSTN, TRIPL and Prolines in conserved positions. For examples, in one embodiment, a synthetic DNA sequence encoding an amino acid sequence of alpha-amanitin may be expressed. In one embodiment, alpha-amanitin production would be increased, for example, using a high expression promoter, transforming *Galerina* with multiple copies of the alpha-amanitin gene.

In another contemplated embodiment, a synthetic, novel cyclic peptide is synthesized by transformed *Galerina* by changing specific bases of synthetic *G. marginata* alpha-amanitin sequences (including PCR copies of isolated peptide toxin genes and base by base construction of nucleic acid sequences) in order to make other types of peptide toxins and peptides. In one example, replacing the codon AAC (Asn) with GAC (Asp) will encode beta-amanitin instead of alpha-amanitin. Beta-amanitin production in *G. marginata* would be easily detected by reverse-phase HPLC because the inventor's isolate of *G. marginata* makes barely detectable levels of beta-amanitin.

The inventors further contemplate changing other amino acids to make non-natural amanitin derivatives, as one example, replacing Gly with Ala by replacing GGT with GCT. Even further, the inventor's contemplate an embodiment for making linear and cyclic peptides of at least six, seven, eight, nine, ten or more amino acids comprising the general formula XWXXXCXP, SEQ ID NO:702, where X is any amino acid. The Pro is retained in these peptides in order for correct processing by POP, and the presence of Trp (W) and Cys (C) will result in the biosynthesis of tryptathionine, a unique hallmark of the *Amanita* toxin peptides. Expression of synthetic peptides and peptide toxins would be monitored by standard assays including but not limited to PCR generated fragments (as in FIG. 40), and by HPLC methods (as in FIG. 31), and the like. Further, separation of synthetic toxins from endogenous peptide toxin and endogenous small peptides (i.e. peptides produced from genomic DNA originally contained in these *Galerina* isolates) would be done by standard techniques including but not limited to HPLC methods (as in FIG. 31). Isolated peptides produced by expression of synthetic sequences would be used in assays for assessing biological activity. For example, toxicity of synthetic amanitin toxins would be determined in assays, for one example, to measure inhibition of transcription in eukaryotic cells, such as capability to inhibit RNA Polymerase IL These toxins are contemplated for commercial levels of production.

Even further, the inventors' contemplate making new *Galerina* isolates that do not produce peptide toxins for use in the present inventions. In one embodiment, the inventors' contemplate knocking out genomic peptide toxin genes for making a new *Galerina* isolate that does not express peptide toxins. As examples for removing genomic peptide toxin genes in *Galerina*, i.e. test *Galerina* (isolates of *Galerina* used in the following methods) would be subject to homologous integration of transforming DNA that would be used for removing regions of DNA comprising the peptide toxin genes in transformed test *Galerina*, spontaneous mutants and induced mutants of test *Galerina* would be made then screened for loss of peptide toxin gene expression and more preferably loss of peptide toxin genes. Another method for eliminating endogenous toxin production is RNAi, which has been used in other basidiomycete fungi (Heneghan et al., Mol Biotechnol. 2007 35(3):283-96, 2007, herein incorporated by reference). Loss of toxin expression in test isolates would be monitored by standard assays including but not limited to genomic sequencing of test *Galerina*, PCR generated fragments of genomic sequences (as in FIG. 40), PCR generated toxin cDNA (as described herein), and by HPLC methods (as in FIG. 31), and the like. When a test *Galerina* isolate is shown to lack expression of peptide toxins this isolate would be cultured as a new *Galerina* laboratory isolate for use in the present inventions.

*G. marginata* has numerous advantages as an experimental system for use in the present inventions. First, *G. marginata* is cultured under laboratory conditions, unlike most species of *Amanita*, which do not grow well in the laboratory (Benedict et al., 1966, 1967; Muraoka and Shinozawa, 2000; Zhang et al., 2005, all of which are herein incorporated by reference). Second, *G. marginata* produced α-amanitin in culture and production was increased by carbon starvation. Third, genomic sequencing and genetic studies were facilitated by the availability of a peptide toxin-producing monokaryotic strain (isolate) of *G. margi-*

*nata*. Fourth, the panoply of peptide toxin genes, estimated greater than 30 members in species of *Amanita*, was not found in the laboratory isolate of *G. marginata*, where only two genes were found during the development of the present inventions.

EXPERIMENTAL

The following examples serve to illustrate certain embodiments and aspects of the present invention and are not to be construed as limiting the scope thereof.

In the experimental disclosures which follow, the following abbreviations apply: N (normal); M (molar); mM (millimolar); μM (micromolar); mol (moles); mmol (millimoles); μmol (micromoles); nmol (nanomoles); pmol (picomoles); g (grams); mg (milligrams); μg (micrograms); ng (nanograms); pg (picograms); L and 1 (liters): ml (milliliters); μl (microliters); cm (centimeters); mm (millimeters); μm (micrometers); nm (nanometers); U (units); min (minute); s and sec (second); deg (degree); ° C. (degrees Centigrade/Celsius).

Example I

Materials and Methods

The following is a description of exemplary materials and methods that were used in subsequent Examples during the development of the present inventions.

A. Exemplary Mushroom Species of the Present Inventions (FIG. 2 and FIG. 31).

The inventors selected the genome of *Amanita bisporigera* to provide sequences of interest because of reports on consistently high, albeit somewhat variable, levels of amatoxins and phallotoxins within individual fruiting bodies combined with the relative ease of obtaining exemplary wild growing mushrooms by merely identifying and harvesting the mushrooms.

Exemplar Basic Molecular Biology Techniques. The inventors developed and used the following exemplary materials and methods during the development of the present inventions. During the development of the present inventions the inventors were surprised to successfully clone cDNAs encoding toxin genes from mature mushrooms in addition to mushrooms in the button stage.

Genomic DNA Isolation. Although the carpophores (fruiting bodies) contain high concentrations of the toxins, like other ectomycorrhizal Basidiomycetes, species of *Amanita* grow slowly and do not form carpophores in culture (Muraoka et al., (1999) Appl. Environ. Microbial. 65:4207; Zhang et al., (2005) FEMS Microbial Lett. 252:223; all of which are herein incorporated by reference). Therefore, *A. bisporigera* mushrooms, an amatoxin and phallotoxin producing species native to North America, were harvested from the wild. Caps and undamaged stems were cleaned of soil and debris, frozen at −80° C., and lyophilized.

Genomic DNA was extracted from the lyophilized fruiting bodies using cetyl trimethyl ammonium bromide-phenol-chloroform isolation (Hallen, et al., (2003) Mycol. Res. 107:969; herein incorporated by reference). For studies requiring RNA, RNA was extracted using TRIZOL (Invitrogen) (Hallen, et al., (2007) Fung. Genet. Biol., 44:1146; herein incorporated by reference in its entirety). Specifically, DNA for genomic blotting was cut with PstI and electrophoresed in 0.7% agarose.

Probe Labeling, DNA Blotting, and Filter Hybridization. Standard protocols were followed for these and similar molecular biology procedures (see, Maniatis, et al., Molecular Cloning: A Laboratory Manual, (Cold Spring Harbor, N.Y., 1982, herein incorporated by reference) and Singh, et al., (1984) Nucl. Acids Res. 12:5627, herein incorporated by reference). In general, hybridization was done overnight at 65° C. in 4×SET (600 mM NaCl, 120 mM Tris-HCl, pH 7.4, 8 mM EDTA), 0.1% sodium pyrophosphate, 0.2% SDS, 10% dextran sulfate, 625 μg/ml heparin. Washing: twice in 2×SSPE (300 mM NaCl. 20 mM $NaH_2PO_4$, 2 mM EDTA, pH 7.4), 0.1% SDS at 21° C., then twice in 0.1.times.SSPE and 0.1% SDS at 60° Celcius.

PCR Amplification of Peptide Encoding Genes. PCR primers for amanitin and phallacidin amplification from *A. bigospora* were based on fragments within sequences shown in FIGS. 4-6. The primer sequences used are shown in Table 3.

TABLE 3

PCR primers used for making synthetic amanitin (AMA1) and phallacidin genes (PHA1)

| Sequence Name | SEQ ID NO: | SEQUENCE |
|---|---|---|
| AMA1, forward | SEQ ID NO: 1 | 5' CCATCTGGGGTATCGGTTGC 3' |
| AMA1, reverse | SEQ ID NO: 2 | 5' TTGGGATTGTGAGGTTTAGAG GTC 3' |
| PHA1, forward | SEQ ID NO: 3 | 5' CGTCAACCGTCTCCTC 3' |
| PHA1, reverse | SEQ ID NO: 4 | 5' ACGCATGGGCAGTCTA 3' |

A 551-bp fragment of the *A. bisporigera* β-tubulin gene was amplified using primers 5'-ACCTCCATCTCGTCCATACCTTCC-3' (SEQ ID NO: 5) and 5'-TGTTTGCCACGCTGCATACTA-3' (SEQ ID NO: 6) then used as a control probe on DNA blots. PCR amplification was done using REDTaq ReadyMix DNA polymerase (Sigma) and appropriate reagents under 30 cycles of denaturation (94° C., 30 sec), annealing (55° C., 30 sec), and extension (72° C., 5 min).

Target Genes for Sequencing. PCR target gene products were purified using Wizard SV Gel and PCR Clean-Up System (Promega) and then cloned into TOPO pCR 4 (Invitrogen) for obtaining sequence information.

B. Exemplary Mushroom Species of the Present Inventions (FIG. 31).

Biological Material. Four species of *Galerina* were obtained from Centraalbureau voor Schimmelcultures (CBS), Utrecht, Netherlands, including *G. marginata* (CBS 339.88), *G. badipes* (CBS 268.50), *G. venenata* (CBS 924.72), and *G. hybrida* (CBS 335.88). *G. marginata* CBS 339.88 is monokaryotic and was confirmed to make α-amanitin. *G. venenata* is considered synonymous with *G. marginata* (Gulden et al., 2001, herein incorporated by reference). The cultures were maintained on potato dextrose agar. For DNA isolation, the isolates were cultured in liquid medium for 15-30 d with rotary shaking at 120 rpm at 23° C. The medium was HSV-2C, which contains (per liter) 1 g yeast extract, 2 g glucose, 0.1 g $NH_4Cl$, 0.1 g $CaSO_4.5H_2O$, 1 mg thiamine.HCl, and 0.1 mg biotin, pH 5.2 (Muraoka and Shinozawa, 2000). For induction experiments, the media had the same formulation, except that high carbon (HSV-5C) and low carbon (HSV-1C) media contained 5 g glucose and 1 g glucose, respectively (Muraoka and Shinozawa, 2000, herein incorporated by reference).

Nucleic Acid Isolation and Genome Sequencing. Lyophilized fungal mycelia were ground in liquid nitrogen with a mortar and pestle. High molecular weight DNA was isolated using Genomic-tip 100/G (Qiagen, Germantown, Md.; catalog #10234) and RNA was extracted with TRIzol (Invitrogen, Carlsbad, Calif.), following the manufacturers' protocols.

Genomic DNA was sequenced by 454 pyrosequencing at the Research Technology Support Facility (RTSF) at Michigan State University. A general library was constructed using standard protocols and sequenced on a 454 GSFLX Titanium Sequencer (Roche manual, 20th ed., herein incorporated by reference). Raw reads were assembled with Newbler and assembled into a searchable database.

Cloning and Gene Characterization. AMA1 and PHA1 are the designations for the α-amanitin- and phallacidin-encoding genes, respectively, of *A. bisporigera*; the prefix Ab is used to designate other genes from *A. bisporigera*. The prefix Gm is used to designate all genes from *G. marginata*.

DNA and RNA Blotts. DNA for Southern blotting was digested with PstI and electrophoresed in 0.7% agarose. Probe labeling, blotting, and filter hybridization followed standard protocols (Scott-Craig et al., 1990, herein incorporated by reference). Hybridizations were performed for 15 hr at 65° C. Roughly 2 μg of DNA were loaded per lane. Probes were made by labeling genomic DNAs of GmAMA1-1, GmPOPA, and GmPOPB with [$^{32}$P]dCTP.

For the GmAMA1 induction experiment, *G. marginata* was cultured in HSV-5C media for 30 d and then transferred to HSV-5C or HSV-1C and grown for an additional 10 d. The resulting mycelia were lyophilized and stored at −80° C. prior to RNA extraction. Full-length cDNA was prepared using the GeneRacer RACE kit, following the manufacturer's protocols. Hybridization probes were amplified using a specific 5' primer (5'-ATGTTCGACACCAACTCCACT-3', SEQ ID NO:680) and GeneRacer 3' nested primer (5'-CGCTACGTAACGGCATGACAGTG-3', SEQ ID NO:681). Probe labeling, RNA gel electrophoresis, and blotting followed standard protocols (Scott-Craig et al., 1990, herein incorporated by reference). Each lane was loaded with 15 μg total RNA.

Amanitin Extraction and Analysis. *G. marginata* was cultured in HSV-5C media for 30 d and then transferred to fresh HSV-1C medium for an additional 10 d. After harvest, the mycelium was lyophilized and stored in at −80° C. A portion of dried mycelium (0.2 gm) was ground in liquid nitrogen and mixed with 2 ml methanol:water:0.01 M HCl (5:4:1) (Enjalbert et al., 1992; Hallen et al., 2003, herein incorporated by reference). The suspension was incubated at 22° C. for 30 min and then centrifuged at 10,200×g for 10 min at 4° C. The supernatant was collected and filtered through a 0.22 μ filter. Chromatographic separation was done on a C18 column (Vydac 218TP54) attached to an Agilent Model 1100 HPLC with detection at 230, 290, and 305 nm. Elution solution A was water+0.1% trifluoroacetic acid, and solution B was acetonitrile+0.075% trifluoroacetic acid. The flow rate was 1 ml/min with a gradient from 100% A to 100% B in 30 min. An α-amanitin standard (Sigma A2263) was dissolved in water at a concentration of 100 μg/ml. Loadings were 40 μl unknown or 20 μl standard.

Example II

This example describes exemplary methods for providing a fungal genomic library, specifically an *Amanita* spp., library.

The inventors initially contemplated the existence of an amatoxin synthetase gene that was a member of the class of enzyme known as nonribosomal peptide synthetases.

However after extensive unsuccessful attempts to obtain amatoxin synthetase genes or gene fragments through PCR-based techniques using isolated genomic DNA, see, Example III, and biochemical methods (such as, ATP-pyrophosphate exchange assay; amino acid feeding studies, etc.), the inventors subsequently initiated a shotgun genome sequencing project for obtaining genes of interest, such as genes associated with cyclized peptide production, toxin production, peptide encoding genes, toxin encoding genes, etc. One genomic library was generated by the Genomics Technology Support Facility at Michigan State University and one was generated by Macrogen, Inc. Each library yielded genomic fragments of approximately 2-kb in length. Random clones were end sequenced by automated dideoxy sequencing.

Approximately 5.7 Mb sequence was generated in approximately 10,000 unidirectional sequencing reads using dideoxy sequencing using an ABI 3730 Genetic Analyzer and an ABI Prism 3700 DNA Analyzer (sequencing performed at the Research Technologies Support Facility at Michigan State University, and by Macrogen, Inc.).

The inventors originally began a public *Amanita* sequence database; however, after a brief posting of the above-described sequencing results, the inventors removed those sequences from public access (see, Examining amatoxins: The *Amanita* Genome Project. Hallen, Walton, 159. The utility of the incomplete genome: the *Amanita bisporigera* genome project. Mar. 15-20, 2005 Asilomar Conference Center, Pacific Grove Calif. Fungal Genetics Newsletter, Volume 52-Supplement XXIII FUNGAL GENETICS CONFERENCE; herein incorporated by reference). Moreover, to the inventors' knowledge, sequences of the present inventions were never publicly available.

The inventors subsequently also completed at least four runs on a Genome Sequencer 20 from 454 Life Sciences (Margulies et al., (2005) Nature 437:376; herein incorporated by reference). This generated approximately 70 MB of sequence data, which is approximately 2× coverage of the genome of *A. bisporigera*, based on the known size of other Homobasidiomycetes, (Le Quere et al., Fung. Genet. Biol. 36, 234 (2002); *Coprinus cinereus* Sequencing Project. Broad Institute of MIT and Harvard (broad.mitedu/annotation/genome/coprincis_cinereus/Hom-e.html); all of which are herein incorporated by reference).

The inventors structured and maintained the sequenced DNA in a password-protected, private BLAST-searchable format. The sequences were compared to GenBank's non-redundant database.

BLASTX (translated query against protein database) was used in searching the non-redundant database (NR) at GenBank, and TBLASTX (translated query against translated database) and BLASTN (nucleotide query against nucleotide database) were used in searching the genomes of *Coprinopsis cinereus* (also known as *Coprinus cinereus*) and *Phanerochaete chrysosporium*, the two closest relatives to *Amanita bisporigera* for which complete genome sequences were available at that time. In some embodiments, BLAST results were examined, catalogued, and automatically annotated.

Example III

This example describes the failure of the inventors to obtain a gene homologous to a fungal nonribosomal peptide synthetases (NRPSs) in *Amanita bisporigera*, which produces amatoxins, phallotoxins, and other putative *Amanita* peptide toxins. Details are shown in a poster entitled "Examining amatoxins: The *Amanita* Genome Project" Hallen Walton 159. The utility of the incomplete genome: the *Amanita bisporigera* genome project. Mar. 15-20, 2005 Asilomar Conference Center Pacific Grove Calif. Fungal Genetics Newsletter, Volume 52—Supplement XXIII FUNGAL GENETICS CONFERENCE; herein incorporated by reference.

Because known fungal cyclic peptides are biosynthesized by methods comprising nonribosomal peptide synthetases (NRPSs) (Walton, et al., in Advances in Fungal Biotechnology for Industry, Agriculture, and Medicine, et al., Eds. (Kluwer Academic/Plenum, N.Y., 2004, pp. 127-162; Finking, et al., (2004) Arum Rev Microbiol 58:453-488, all of which are herein incorporated by reference), the inventors initiated an attempt to identify by PCR in the total genomic DNA of *Amanita bisporigera* sequences encoding an NRPS using PCR primers based on known bacterial and fungal NRPSs and total *A. bisporigera* DNA as template. The inventors contemplated that any NRPS genes sequences within the *Amanita bisporigera* genome should have been readily amplified using two or more of PCR primers. Then, from sequencing genomic DNA outward from the PCR products, they should have ultimately identified an NRPS with 8 adenylating domains containing other conserved regions present in all known NRPS-encoding sequences.

TABLE 4

Figure 3:
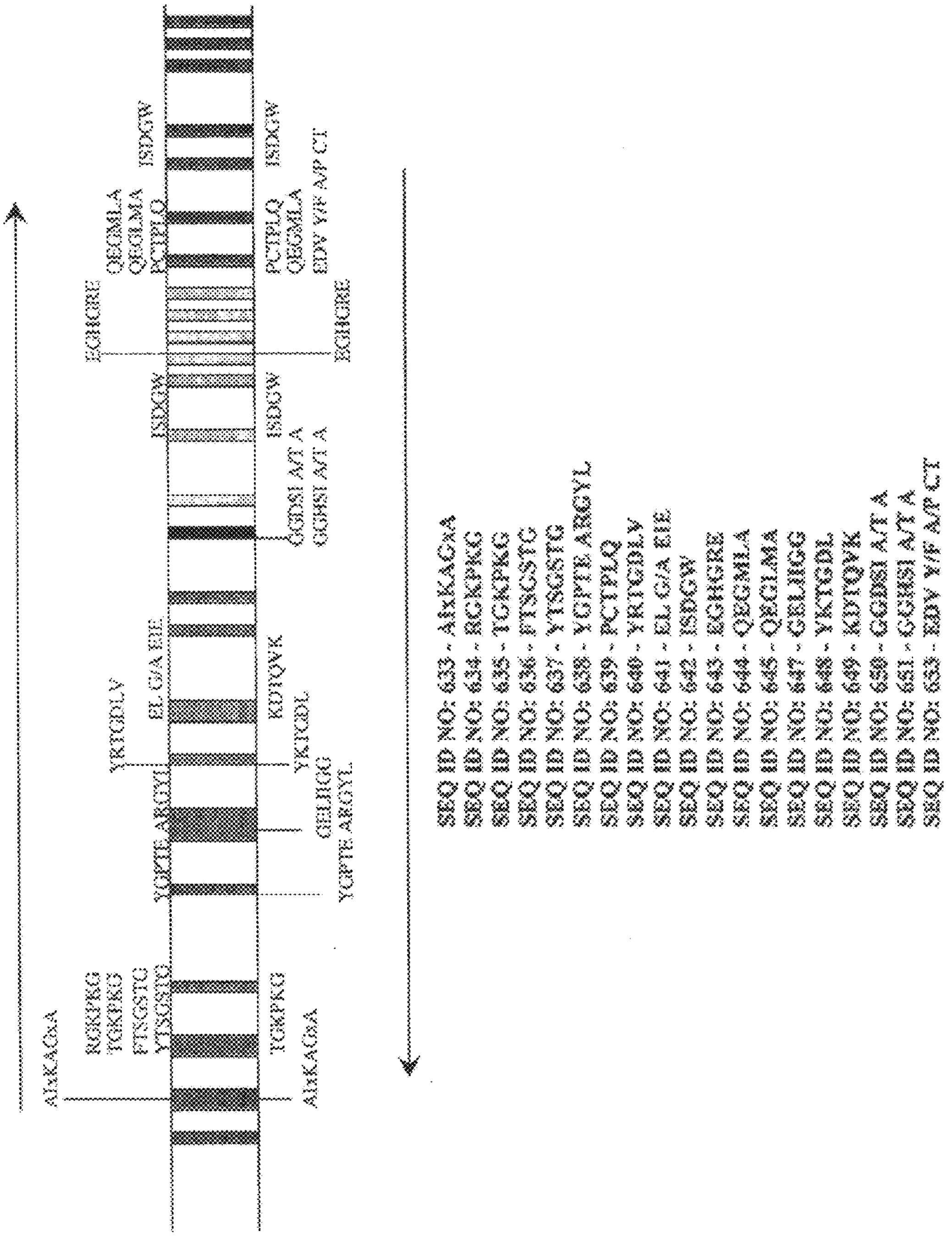
FIG. 3 shows an exemplary hypothetical nonribosomal peptide synthetase showing conserved motifs found in many NRPS proteins that served as the basis for the design of PCR primers (see Table 4).

PCR primers used that failed to obtain a NRPS sequence (See FIG. 3).

| Forward Primers 5'-3' | | Reverse Primers 5'-3' | |
|---|---|---|---|
| AIxKAGxA: SEQ ID NO: 5 | GCN ATH TNN AAR GCN GGN NCN GC | AIxKAGx SEQ ID NO: 6 | GCN GNN CCN GCY TTN NAD ATN GC |
| FTSGSTG (JA4F): SEQ ID NO: 7 | TTY ACI TCI GGI TCI ACI GG[1] | na | na |
| YTSGSTGI: SEQ ID NO: 8 | TAY ACN AGY GGN AGY ACN GG | na | na |
| YTSGSTG2: SEQ ID NO: 9 | TAY ACN AGY GGN TCN ACN GG | na | na |
| YTSGSTG3: SEQ ID NO: 10 | TAY ACN TCN GGN TCN ACN GG | na | na |
| YTSGSTG4: SEQ ID NO: 11 | TAY ACN TCN GGN AGY ACN GG | na | na |
| SRGKPKG: SEQ ID NO: 12 | TCT AGA GGN AAR CCN AAR GG[2] | na | na |
| TGKPKG: SEQ ID NO: 13 | ACN GGN AAR CCN AAR GG[4] | TGKPKG: SEQ ID NO: 14 | CCY TTN GGY TTN CCN GT |
| YGPTE: SEQ ID NO: 15 | TAY GGN CCN ACN GA[4] | YGPTE: SEQ ID NO: 16 | TTC NGT NGG NCC RTA |
| YGPTE2: SEQ ID NO: 17 | TAC GGN CCN ACN GAN | na | na |
| na | na | GELIIGG: SEQ ID NO: 18 | CCN CCN ATN ATN AGY TCN CC |
| ARGY X: SEQ ID NO: 19 | TBG CNC GNG GNT ACN | ARGY: SEQ ID NO: 20 | GTA NCC NCG NGC GAN |
| Y K/R TGDL: SEQ ID NO: 21 | TAC ARR ACN GGN GAY CT | YKTGDL: SEQ ID NO: 22 | ARR TCN CCN GTN TTR TAT CTA $GA_2$ |
| YRTGDLV: SEQ ID NO: 23 | TAY MGI ACI GGI GAY YTI GT | na | na |
| Y/F RTGD L/R G/V R(TGD): SEQ ID NO: 24 | TWY GCI ACI GGI GAY YKI GKI CG[3] | na | na |

TABLE 4-continued

| PCR primers used that failed to obtain a NRPS sequence (See FIG. 3). | | | |
|---|---|---|---|
| Forward Primers 5'-3' | | Reverse Primers 5'-3' | |
| ELGEIE: SEQ ID NO: 25 | GAR YTN GSN GAR ATH GA | KDTQVK (JA5): SEQ ID NO: 26 | GGI ACY TGI TGR TCY TT[1] |
| na | na | LLXLGGXS (LGG): SEQ ID NO: 27 | AWI GAR KSI CCI CCI RRS IMR AAR AA[3] |
| GGDSI A/T: SEQ ID NO: 28 | GGN GGN GAAY TCN ATY RCN | GGDSI A/T A: SEQ ID NO: 29 | GCN GYD ATN SWR TCN CCN CC |
| na | na | GGHSI A/T A: SEQ ID NO: XX | GCN GYR ATN GAR TGN CCN CC |
| na | na | GDSITA *Cochliobolus victoriae*: SEQ ID NO: 30 | CGC CGT GAT CGA ATC CCC |
| ISGDW: SEQ ID NO: 31 | CAY CAY NNN ATH WSN GAY GGN TGG | ISGDW: SEQ ID NO: 32 | CCT NCC RTC NSW NAT NNN RTG RTG |
| EGHGRE: SEQ ID NO: 33 | GAR GGN CAY GGN MGN GA | EGHGRE: SEQ ID NO: 34 | TCN CKN CCR TGN CCY TC |
| DAYPCS *C. victoriae*: SEQ ID NO: 35 | GAT GCC TAC CCA TGC TCG | DVYPCTP: SEQ ID NO: 36 | GTK CAN GSR WAN ACR TCY TC |
| PCTPLQ: SEQ ID NO: 37 | CCN TGY ACN CCN YTN CA | PCTPLQ: SEQ ID NO: 38 | TGN ARN GGN GTR CAN GG |
| na | na | PCTPLQ2: SEQ ID NO: 39 | TGI ARI GGI GTR CAI GG |
| QEGLMA (JA1): SEQ ID NO: 40 | CAR GAR GGI YTI ATG GC[1] | QEGLMA: SEQ ID NO: 41 | CGC ATN AGN CCY TCC TG |
| QEGLMA: SEQ ID NO: 42 | KAR GGN ATG AWN GC | QEGLMA: SEQ ID NO: 43 | GCN WTC ATN CCY TMY TG |

[1]Primer sequences that the inventors obtained from Dr. Aric Weist
[2]Primers referenced in Panaccione, (1996) Mycological Research 100:429-436; herein incorporated by reference.
[3]Primers referenced in Turgay & Marahiel (1994), Peptide Research 7:238-241; herein incorporated by reference.
[4]Primers references in Nikolskaya et al. (1995) Gene 165:207-211
Abbreviations: A, adenine; T, thymine; G, guanine; C, cytosine; I, inosine, K, G or T; R, A or G; M, A or C; W, A or T; Y, C or T.
Na = not available In order to find an NRPS in *A. bisporigera*, the inventors first contemplated that amatoxins were synthesized via a non-ribosomal peptide synthetase (NRPS) as found in other types of fungi (see, example in FIG. 3). Specifically, the inventors further contemplated that an NRPS responsible for biosynthesizing amatoxins would be encoded by a gene of approximately 30 kb in size. Because amatoxins contain eight amino acids, and in NRPS enzymes one domain activates by adenylation one amino acid, the enzyme should be approximately one MDa. Such a protein was predicted to be encoded by a 30-kb gene. The inventors further contemplated random (shotgun) sequencing of the genome and an average read size of 600 by and calculated a >99% probability of hitting a 30 kb target in a 40 Mb genome in 7,000 random, independent sequences.

The inventors generated more than 70 MB of DNA sequence and searched using BLAST and more than 20 known NRPS genes and proteins from prokaryotes and eukaryotes for evidence for an NRPS in the genome of *A. bisporigera*. However, the inventors did not find evidence for any NRPS-like sequence in *A. bisporigera*. In contrast, the inventors discovered that the most closely related sequences to NRPSs were orthologs of aminoadipate reductase and acyl-CoA synthase, which, like bacterial and fungal NRPSs, are classified within the aminoacyl-adenylating superfamily (Finking et al., (2004) Annu. Rev. Microbiol. 58:453; herein incorporated by reference).

Approximately 59% of the *Amanita bisporigera* sequences of the present inventions did not show a hit to the GenBank NR database. This is consistent with results from other fungal genome projects (see, e.g. Schulte, U (2004) Genomics of filamentous fungi. In Advances in Fungal Biotechnology for Industry, Agriculture, and Medicine (J S Tkacz & L Lange, eds.):15-29. Kluwyer Academic/Plenum Publishers, New York; herein incorporated by reference). Little annotation is yet available for fungal genomes, so the proportion of unidentified sequences is high. Three thousand eight sequences that produced no hits to GenBank NR did yield hits to the *Phanerochaete chrysosporium* and/or *Coprinopsis cinereus* genomes. The following known genes were identified using BLAST comparisons of the novel *Amanita* fragments of the present inventions. The inventors found matches contemplated to be *Amanita* homologs to members of the aminoacyl-adenylating superfamily (Finking et al., (2004) Annu Rev Microbiol 58:453-488; herein incorporated by reference) which includes but is not limited to exemplary sequences of L-aminoadipate-semialdehyde dehydrogenase. In particular, L-aminoadipate-semialdehyde dehydrogenase is related to but is not a non-ribosomal peptide synthetase (NRPS), an enzyme originally contemplated to be responsible for *Amanita* peptide toxin biosynthesis. The inventors ruled out a NRPS identity of this match after they sequenced the remainder of the clone 16_c01KoreaM13Rrc, then extended the sequence by approximately 700 by using inverse PCR.

Cap64 is a capsule formation protein first identified in the pathogenic basidiomycete *Filobasidiella neoformans* with a known homolog in the saprophytic basidiomycete *Pleurotus ostreatus*, of which the later does not form capsules associated with mammalian pathogenicity. The discovery of an AmanitaCap64 homologous sequence was not expected because like *Pleurotus, Amanita* species are not known to form capsules associated with mammalian pathogenicity.

Laccases, like Cap64, were not expected even though they were previously found to be widespread in saprophytic fungi (*Coprinopsis, Melanocarpus*, and the white rot fungus *Trametes*), and in both asco- and basidiomycetes. Their role in an ectomycorrhizal fungus such as *Amanita*, which is expected to obtain most of its nutrients in the form of photosynthate and would therefore lack the need to degrade plant tissue, is unknown.

Therefore, despite predictions to the contrary, the inventors did not find evidence of an NRPS gene that would likely be involved with synthesizing amatoxins and phallotoxins (Walton et al. (2004) Peptide synthesis without ribosomes. In: Advances in Fungal Biotechnology for Industry, Agriculture, and Medicine. J Tkacz, L Lange, eds. Kluwer Academic, New York, pp. 127-162; herein incorporated by reference). Yet on the other hand, surprisingly, the inventors discovered other types of genes.

Example IV

This example describes exemplary compositions and methods for identifying amatoxin-encoding genes. The inventors initially focused on amatoxins, in particular amanitins, bicyclic octapeptides which are more potent toxins to humans than any of the other mushroom toxins and are directly responsible for the majority of fatal human mushroom poisonings. Specifically, this example describes the discovery of an *A. bisporigera* gene sequence contemplated to encode alpha amanitin.

An exemplary structure of α-amanitin is cyclic(L-asparaginyl-4-hydroxy-L-prolyl-(R)-4,5-dihydroxy-L-isoleucyl-6-hydroxy-2-mercapto-L-tryptophylglycyl-L-isoleucylglycyl-L-cysteinyl), cyclic (4-8)-sulfide, (R)—S-oxide (ChemIDplus), wherein the amino acids have the L configuration and several amino acids are modified by hydroxylation. When simplified to the 20 proteogenic amino acids, the chemical name became cyclic(NPIWGIGC) (SEQ ID NO:46) (ChemIDplus). However because this is a cyclized peptide, the order in which the amino acids are assembled biosynthetically was unknown. Moreover, the structure of β-amanitin, RN: 21150-22-1 was based upon the known chemical structure of α-amanitin RN: 23109-05-9 and named in a similar manner. See chem.sis.nlm.nih.gov/chemidplus/ProxyServlet?objectHandle=DBMaint&actionH-andle=default&nextPage-jsp/chemidheavy/ResultScreen.jsp&ROW_NUM=0&TX TSUPER-LISTID=023109059.

Therefore, the inventors searched the DNA sequences from their *A. bisporigera* genome seeking DNA fragments capable of encoding amino acid sequences of amanitins, such as predicted sequences comprising a predicted sequence of NPIWGIGC (SEQ ID NO:46). Thus the inventors discovered an exemplary sequence encoding α-amanitin, ECIMO1V02FKY4Z S CCCAACTAAATCCCATTCGAACCTAACTCCAAGACCTCTAAACCTCACA ATCCCAATGTCTGACATCAATGCTACCCGTCTCCCATCTGGGGTATCGG TTGCAACCCGTGCG, length=113 (SEQ ID NO:48) encoding prepropetide PTKSHSNLTPRPLNLTIPMSDINATRLPIWGIGCNPC (SEQ ID NO:49), propeptide in BOLD, underlined peptide, SEQ ID NO: 50. The inventors' exemplary sequence translated into a IWGIGCNP, SEQ ID NO: 50, which the inventors contemplate would be capable of forming a, cyclo(IWGIGCNP), SEQ ID NO: 51, wherein the inventors further contemplated several posttranslational hydroxylations and a sulfoxide crossbridge between the Trp and the Cys in order to form the bicyclic peptide known as alpha-amanitin. The inventors used the amino acid sequence and the nucleic acid sequences encoding IWGIGCNP (SEQ ID NO: 50) for searching known sequences in GenBank's non-redundant database. There was no evidence of any gene encoding or protein with IWGIGCNP (α- and γ-amanitins) (SEQ ID NO: 50). Therefore, the inventors contemplated that these sequences are unique for *A. bisporigera* and further these sequence orders were unlikely to be present in an *Amanita* genome by statistical coincidence.

The inventors also obtained a second and longer sequence comprising nucleotides encoding IWGIGCNP (SEQ ID NO: 50) using inverse PCR (AMA1 forward and reverse primers, see above) and obtained a genomic sequence contig 49252 AATCTCAGCGTTCAGTACCCAACTCCCATTCGAACCTAACTCCAAGACCT CTAAACCTCACAATCCCAATGTCTGACATCAATGCTACCCGTCTCCCCAT CTGGGGTATCGGTTGCAACCCGTGCGTCGGTGACGACGTCACTACG, length=146 (SEQ ID NO:52) encoding SQRSVPNSHSNLTPRPLNLTIPMSDINATRLP IWGIGCNPCVGDDVTT (SEQ ID NO:53), propeptide in BOLD, underlined peptide, SEQ ID NO: 50.

Therefore the inventors found nucleotide sequences that encode the amino acid sequence of .alpha.-amanitin with the sequence order of IWGIGCNP, in single letter code, and further identified two larger genomic sequences encoding an IWGIGCNP amanitin peptide in the genome of *A. bisporigera*. The inventors contemplated that amanitins would be a cyclic permutation of linear peptides of IWGIGCNP (α- and γ-amanitins) and IWGIGCDP (SEQ ID NO:54) (β- and ε-amanitins).

Example V

This example demonstrates using amino acid and nucleic acid information of the present inventions, inverse PCR and RACE methods to identify a cDNA and a large genomic fragment that comprises an amanitin gene as indicated in FIG. 4.

The inventors initiated a genomic survey using nucleic acid coding regions encoding the AMA1 gene, as described in the previous Example. SEQ ID NOs: 48, 49, 52, and 53, encoding an AMA1 polypeptide, were used to design AMA1 forward and reverse primers that were used in an inverse PCR reaction to obtain a larger genomic fragment of the AMA1 gene. Specifically, inverse PCR, using circularized PvuI generated genomic fragments as target (template) DNA resulted in the isolation of a 2.5-kb fragment of flanking genomic DNA.

RACE (Rapid Amplification of cDNA Ends) (for example, see, Frohman et al., (1988) Proc Natl Acad Sci 85:8998-9002; herein incorporated by reference), was used to obtain a full-length cDNA copy of AMA1, SEQ ID NO:55, encoding an AMA1 polypeptide, SEQ ID NO:56. When compared to the AMA1 genomic sequence, SEQ ID NO:57, the cDNA indicated that AMA1 contains three introns (53, 59, and 58 nt in length), with canonical GT/AG boundaries. Two of the introns were in the 3' untranslated region, while the first intron was in the third codon from the end of the coding region (FIG. 4A). The inventors contemplated that translation started at the first ATG downstream of the transcriptional start site thus encoding a proprotein of 35 amino acids (FIG. 4A). The string of A's at the end represents the poly-A tail typical of eukaryotic mRNAs and their corresponding cDNAs (though not encoded within the genomic sequence). The amatoxin prepropeptide and propeptide encoding sequences are shown in relation to the encoded amino acid sequence for an amanitin peptide (underlined), FIG. 4A. The amatoxin prepropeptide and propeptide encoding sequences are shown where the amanitin peptide encoding sequence is underlined, FIG. 4B.

TABLE 5

Examples of RACE primers used herein.

| SEQUENCE Name | SEQUENCE | SEQ ID NO: XX |
|---|---|---|
| GeneRace ™ 5' Primer | 5'-GCACGAGGACACUGACAUGGACUGA-3' | SEQ ID NO: 6 |
| GeneRacer ™ 5' Nested Primer | 5'-GGACACTGACATGGACTGAAGGAGTA-3' | SEQ ID NO: 58 |
| GeneRacer ™ 3' Primer | 5'-GCTGTCAACGKFACGCTACGTAACG-3' | SEQ ID NO: 8 |
| 3' AMA1 RACE initial primer | 5' CCCATTCGAACCTAACTCCAAGAC 3' | SEQ ID NO: 9 |
| 3' AMA1 RACE primer, nested primer | 5' CCTCTAAACCTCACAATCCCAATG 3' | SEQ ID NO: 10 |
| 5' AMA1 RACE cDNA, primer | 5' GCCCAAGCCTGATAACGTCCACAACT 3' | SEQ ID NO: 11 |
| 5' AMA1 RACE cDNA, nested primer | 5' TATCGCCCACTACTTCGTGTCATA 3' | SEQ ID NO: 12 |
| 3' PHA1, initial primer | 5' GACCTCTGCTCTAAATCACAATG 3' | SEQ ID NO: 13 |
| 3' PHA1, nested primer | 5' ATCAATGCCACCCGTCTTCCTG 3' | SEQ ID NO: 14 |
| 5' PHA% initial primer | 5' CGGATCATTTACGTGGGTTTTA 3' | SEQ ID NO: 15 |
| 5' nested primer | 5' AACTTGCCTTGACTAGTGGATGAGAC 3' | SEQ ID NO: 16 |

Thus an exemplary amino acid sequence of the proprotein of AMA1 is MSDINATRLPIWGIGCNPCIGDDVTTLLTRGEALC, SEQ ID NO:617, underlined peptide, SEQ ID NO: 50. The inventors further contemplated an exemplary structure of β-amanitin, wherein Asn is replaced by Asp to provide IWGIGCDP, SEQ ID NO:54. Indeed, further investigations described below, did result in the finding of an *Amanita* PCR product encoding a β-amanitin, sequence.

An RNA blot of total RNA extracted from mushrooms of *Amanita bisporigera* probed with DNA fragment SEQ ID NO: 48 showed an approximately 400 nt band contemplated as an AMA1 mRNA. Minor discrepancies between the genomic and cDNA sequences are likely due to natural variation among the amatoxin genes.

Example VI

This example describes the discovery of an *A. bisporigera* gene sequence contemplated to encode a phallotoxin, specifically a phallacidin toxin sequence.

An exemplary structure of phallacidin is a cyclic(L-alanyl-2-mercapto-L-tryptophyl-4,5-di hydroxy-L-leucyl-L-valyl-er-ythro-3-hydroxy-D-alpha-aspartyl-L-cysteinyl-cis-4-hydroxy-L-prolyl)cyclic (2-6)-sulfide, RN: 26645-35-2, with predicted amino acid sequences simplified to the 20 proteogenic amino acids comprising cyclo(ATCPAWL), SEQ ID NO:70. Another phallotoxin, phalloidin, RN: 17466-45-4, is a cyclic(L-alanyl-D-threonyl-L-cysteinyl-cis-4-hydroxy-L-prolyl-L-alanyl-2-mercapto-L-tryptophyl-4,5-dihydroxy-L-leucyl), cyclic (3,6)-sulfide, which translates into the sequence cyclo(ATCPAWL), SEQ ID NO:70. Several of the phallacidin and phalloidin amino acids are hydroxylated. The Asp residue (which is replaced by Thr in phalloidin) has the D configuration at the alpha carbon.

A genomic survey of *A. bisporigera* sequences yielded at least 2 nucleic acid sequences encoding a predicted sequence comprising a linear AWLVDCP, SEQ ID NO:69, which would encode cyclicphallacidin (SEQ ID NO:71), for example, SEQ ID NO:72, ECGK9LO01B8L63 S TGAGGAGACGGTTGACGTCGTCACCGACGCATGGGCAGTCTACAAGCCA AGCAGGAAGACGGGTGGCATTGATGTCAGACATTGTGATTTAGAGTAG, length=97 encoding LLITMSDINATRLPCVGDDVNRLL, SEQ ID NO:73, and SEQ ID NO:74, contig73170, TGAGGAGACGGTTGACGTCGTCACCGACGCATGGGCAGTCTACAAGCCA AGCAGGAAGACGGGTGGCATTGATGTCAGACATTGTGATTTAGAGTAGA GGTCTTGGGTTCGAGTTCGAATGGGAGGTAAG, length 130, encoding a prepropeptide LTSHSNSNPRPLLITMSDINATRLP<u>AWLVDCP</u>CVGDDVNRLL, showing the propeptide in BOLD and underlined peptide SEQ ID NO:69.

Inverse PCR following PvuI and SacI digestion of whole genomic DNA and ligation was used to isolate genomic fragments of 1.6 kb and 1.9 kb, respectively, named phallacidin sequence PHA1#1-1893 bp. SacI, SEQ ID NO:76, and phallacidin-sequence PHA1#2-1613 nt. PvuI, SEQ ID NO:77, collectively named PHA1, comprising phallacidin amino acid sequences. These were two different classes of sequences, identical in the region of phallacidin, SEQ ID NO:78, but diverged approximately 135 nt upstream. These two sequences showed that *A. bisporigera* genome has at least two copies of the PHA1 gene, both of which encode a phallacidin toxin sequence, FIG. 5. Furthermore, a cDNA for PHA1, SEQ ID NO:44, was isolated by 5' and 3' RACE (FIG. 5) using methods similar to those used in Example IV in combination with PHA1 RACE primers listed above.

Nucleotide sequences of a cDNA for PHA1 are shown in FIG. 5A. When the genomic sequence (FIG. 5, #2) was compared to a cDNA sequence, the inventors found three introns (50-69 nt). Two of the introns were in the 3' untranslated region, while the first intron was in the third codon from the end of the coding region. Carats marked within the sequence indicate the positions of introns. The c DNA sequence, SEQ ID NO:79, is predicted to encode an amino acid sequence as a proprotein of PHA1 that is 34 amino acids in length, SEQ ID NO: 80, translating into MSDINATRLP<u>AWLVDCP</u>CVGDDVNRLLTRSLC (phallacidin sequence, SEQ ID NO: 69 in BOLD), whose coding sequence was underlined in FIG. 5A.

Because two different phallacidin genomic sequences were obtained, the inventors contemplate that *A. bisporigera* has at least two copies of PHA1. Further, the inventors concluded that these two PHA1 sequences represent natural variants of the phallacidin gene because both are present in the same isolate of *A. bisporigera*. The inventors further contemplate that these two PHA1 genes arose as a gene duplication event.

Example VII

This example describes methods and results from exemplary comparisons of AMA1 and PHA1 for obtaining exemplary consensus sequences.

Based on the cDNA sequence, the inventors chose the first ATG sequence downstream of the transcriptional start site as the translational start site of the proprotein polypeptides and the first in-frame stop codon as the translational stop. AMA1 and PHA1 nucleic acid and predicted amino acid sequences were compared by alignment of each set of two target sequences using a BLAST engine for local alignment through the NCBI website, (world wide web.ncbi.nlm.nih.gov/blast/b12 seq/wblast2.cgi).

Alignment of the predicted proproteins, amanitin to phallacidin sequences, is shown in FIG. 6A. Proproteins of amanitin and phallacidin were 35 and 34 amino acids in length, respectively. Sequences corresponding to amanitin and phallacidin are underlined, and for clarity are separated by spaces from the upstream and downstream amino acid sequences.

When the inventors compared the sequences of genomic and cDNA copies of AMA1 and PHA1, the inventors observed that both comprise 3 introns (approximately 57, 70, and 51 nt in length), in approximately the same positions. Furthermore, AMA1 and PHA1 gene sequences and their translation products were found to be similar in overall size and sequence, except strikingly in the region encoding the peptide toxins themselves (FIG. 6 and Table 6).

Within amino acid encoding regions (the proproteins), nucleic acid sequence regions upstream of IWGIGCNP (amatoxin) and AWLVDCP (phallotoxin (SEQ ID NO:69)) comprise 28 of 30 identical nt (93%), while regions downstream of IWGIGCNP and AWLVDCP comprise 41 of 50 identical nt (82%). However, these findings were in contrast to the amatoxin and phallotoxin-encoding regions themselves (IWGIGCNP and AWLVDCP) where merely 12 of 24 nt were identical (50%). Thus the inventors designated these proprotein areas of .alpha.-amanitin and phallacidin as being composed of three domains, one conserved upstream region (A), one conserved downstream region (B), and a hypervariable peptide region (P) encoding amatoxin and phallotoxin. In other words, proprotein sequences of the present inventions consist of an upstream conserved region (A), a downstream conserved region (B) in relation to a variable region (P), such that the variable *Amanita* cyclic peptide toxin region is flanked by two conserved regions, (FIG. 6B).

Because amatoxins contain 8 amino acids and phallotoxins contain 7 amino acids, the inventors inserted a 3-nucleotide gap (---) in the cDNA sequence and a one-amino acid space (-) in the proprotein sequence in order to emphasize the alignment of the conserved sequences downstream of the amatoxin and phallotoxin-encoding regions (FIG. 7A).

TABLE 6

| Exemplary comparisons between AMA1 and PHA1 using BLASTN. | | |
|---|---|---|
| SEQ ID NO: | Sequence | Comparison and Identity No. aa/No. aa (percent identity) |
| AMA1 A. SEQ ID NO: 182 | atg tct gac atc aat gct acc cgt ctt ccc (30 aa) | |
| PHA1 A, SEQ ID NO: 18 | atg tct gac atc aat gcc acc cgt ctt ccc (30 aa) | AMA1A v. PHA1 A 29/30 (96%), |
| AMA1 B. SEQ ID NO: 19 | tgc atc ggt gac gac gtc act aca ctc ctc act cgt ggc gag gcc ctt tgt (51 aa) | |
| PHA1 B, SEQ ID NO: 20 | tgc gtc ggt gac gat gtc aac cgt ctc ctc act cgt ggc gag agc ctt tgg (48 aa) | AMA1 B v. PHA1 B 41/50 (82%) |
| AMA1 toxin, SEQ ID NO: 21 | atc tgg ggt atc ggt tgc aac ccg (24 aa) | |
| PHA1 toxin, SEQ ID NO: 22 | gct tgg ctt gta gat tgc --- cca (21 aa) (50%) | AMA1 toxin v. PHA1 toxin 12/24 |

TABLE 7A

| Exemplary BLAST searches for AMA1 and PHA1 using BLAST. | | | |
|---|---|---|---|
| Query SEQ | Hit | Comparison and Identity No. na/No. na | percent identity |
| Alpha-Amanitin | *Rhodococcus* sp. gb\|CP000431.1\| CGGGTACAACACGTGCATCGGTGACGC CGTCA | 28/32 | 87% |
| | Zebrafish DNA sequence emb\|CR385042.30\| CGACACTACCCTCACCACTCGTGCCCTT AGTTA | 28/33 | 84% |
| Phallacidin | *Agrobacterium tumefaciens* gb\|AE009415.1.\| TCTGTGACGATGTCATCCAGTCTC-TCACTCGTA | 31/35 | 88% |
| | CP000479.1 *Mycobacterium avium* 104 CGTCGGTGACGATGTACACCGTCGCCA CGCTCG | 28/33 | 84% |
| | AC112739.5 *Rattus norvegicus* 7 BAC CH230-108A12 TGTCAACCGTCTCCTCTGTCGTTTCCTTT G | 26/30 | 86% |
| | XM_382946.1 *Gibberella zeae* PH-1 chromosone 1 conserved hypothetical protein (FG02770.1) partial mRNA CGTCGGTGACGATGTCCTCCGTCTCTTC | 25/28 | 89% |
| | AM444890.2 *Vitis vinifera* contig TTGTAGACTGCCCATGCGTCTGT | 22/23 | 95% |
| | gb\|AAQY01001277.1\| *Phytophthora sojae* strain P6497 CGGTGACGATGTCAACCGTCT | 21/21 | 100% |
| | gb\|AAQR01490933.1\| *Otolemur garnettii* cont1.490932 TGTCTGACATCAATGCCACCC | 21/21 | 100% |

TABLE 7B

Exemplary BLAST searches for AMA1 and PHA1 using BLASTN.

| SEQ ID NO: | Query SEQ | Hit | Compatison and Identity No. na/No. na | percent identity |
|---|---|---|---|---|
| 524 | Amanitin A | ATGTCTGACATCAATGCTACCCGTCTCCCC | 30/30 | 100% |
| 563 | | ref\|XM__01182437.1\| PREDICTED: *Strongylocentrotus purpuratus* similar to ESP-1 (LOC574923), purple sea urchin TGTCTGACATCAATGGTACC | 19/20 | 95% |
| 530 | | dbj\|AK173931.1\| *Ciona intestinalis* cDNA, ATGTCTGACATCAATGCT | 18/18 | 100% |
| 564 | | ref\|XM_001365250.1\| *Monodelphis domestica* similar to transducin beta-3-subunit mRNA short-tailed opossums, GTCTGACATCAATGCTA | 17/17 | 100% |
| 568 | | ref\|XM_814507.1\| *Trypanosoma cruzi* strain CL Brener kinesin AATGCTACCCGTCTCC | 16/16 | 100% |
| 565 | | ref\|XM_652576.1\| *Aspergillus nidulans* FGSC A4 hypothetical protein (AN0064.2 TGTCTGACATCAATGC | 16/16 | 100% |
| 537 | | emb\|BX842594.1\| *Neurospora crassa* DNA linkage group II BAC clone B18P7 TGTCTGACATCAATGC | 16/16 | 100% |
| 532 | | dbj\|AP007162.1\| *Aspergillus oryzae* RIB40 genomic DNA, SC102 CTGACATCAATGCTAC | 16/16 | 100% |
| 82 | Phallacidin A | ATGTCTGACATCAATGCCACCCGTCTTCCC | 30/30 | 100% |
| 567 | | ref\|XM_753671.1\| Corn smut is of maize caused by the pathogenic plant fungus *Ustilago maydis* CATCAATGCCACCCGCCTTCC | 20/21 | 95% |
| 542 | | gb\|AC122231,2\| *Mus musculus* BAC clone RP23-135M3ATGTCTGACATCAATGCCA | 19/19 | 100% |
| 536 | | emb\|AL031736.16\| Human DNA sequence from clone RP4-738P11ATGTCTGACATCAATGCCA | 19/19 | 100% |
| 562 | | ref\|NM_ 202010.2\| *Arabidopsis thaliana* FUS5 (FUSCA 5); MAP kinase kinase (FUS5) CAATGCCACCCGTCTTCC | 18/18 | 100% |
| 566 | | ref\|XM_652576.1\| *Aspergillus nidulans* FGSC A4 hypothetical protein (AN0064.2) TGTCTGACATCAATGCCA | 18/18 | 100% |
| 533 | | dbj\|AP008214.1\| *Oryza sativa (japonica cultivar-group)* genomic TCTGACATCAATGCCACC | 18/18 | 100% |
| 543 | | gb\|EF469872.1\| *Helianthus annuus* RFLP probe ZVG13 mRNA sequence AATGCCACCCGTCTTCC | 17/17 | 100% |
| 538 | | emb\|CR619305.1\| B cells (Ramos cell line) GTCTGACATCAATGCCA | 17/17 | 100% |
| 538 | | emb\|CR595196.1\| T cells (Jurkat cell line) GTCTGACATCAATGCCA | 17/17 | 100% |
| 538 | | emb\|CR592893.1\| Neuroblastoma of *Homo sapiens* (human) GTCTGACATCAATGCCA | 17/17 | 100% |
| 531 | | dbj\|AK173931.1\| *Ciona intestinalis* or Sea squirt. ATGTCTGACATCAATGC | 17/17 | 100% |
| 525 | Amanitin B | TGCATCGGTGACGACGTCACTACT CTCCTCACTCGTGCCCTTTGT | 45 | 100% |
| 573 | | *Strongylocentrotus purpuratus* CATCGGTGACGACGTCACT | 19/19 | 100% |
| 548 | | *Ostrococcus lucimarinus* unicellular coccoid green alga CGATCGGTGACGACGTCA | 18/18 | 100% |
| 529 | | *Chaetomium globosum dematiaceous filamentous* fungus infectous in humus CTCCTCACTCGTGCCCTT | 18/18 | 100% |
| 546 | | Human DNA sequence from clone XXyac-60D10 TCACTACTCTCCTCACTC | 18/18 | 100% |
| 561 | | *Rattus norvegicus* LEA_4 domain containing protein ACGTCACTACTCTCCTC | 17/17 | 100% |
| 526 | | Atlantic Salmon CTCCTCACTCGTGCCCT | 17/17 | 100% |

TABLE 7B-continued

Exemplary BLAST searches for AMA1 and PHA1 using BLASTN.

| SEQ ID NO: | Query SEQ | Hit | Compatison and Identity No. na/No. na | percent identity |
|---|---|---|---|---|
| 527 | | *Burkholderia cenocepacia* Gram-negative bacteria Pathogen ATCGTGACGACGTCAC | 17/17 | 100% |
| 547 | | *Omithorhynchus anatinus* Platypus ACGTCACTACTCTCCTC | 17/17 | 100% |
| 82 | Phallacidin B | TGCGTCGGTGACGATGTCAACCGT CTCCTCACTCGTAGCCTTTGG | 45 | 100% |
| 528 | | *Chaetomium globosum* CBS 148.51 GGTGACGATGACAACCGCCTCCTCAG | 24/26 | 92% |
| 545 | | *Giberella zeae* CGTCGGTGACGATGTCCTCCGTCTC | 23/25 | 92% |
| 571 | | *Rhizobium leguminosarum* bv. viciae chromosome CGTCGGTGACGAGGTCAACCG | 20/21 | 95% |
| 574 | | *Tetraodon nigroviridis* GATGTCAACCGTCTCCTCA | 19/19 | 100% |

The conserved amino acid regions encoded by conserved domains A and B and consensus region B were used as query sequences for BLAST searching the GenBank public NR database. These sequences per se were not found within the database, however somewhat similar sequences were discovered, with exemplary sequences shown below.

TABLE 8

Exemplary homology comparisons using Consensus MSDINATRLP, XWXXXCXP, and CVGDDVXXLLTRALC as query sequences using BLASTP (MSDINATRLPXWXXXCXPCVGDDVXXLILTRALC, SEQ ID NO: 45).

| SEQUENCE | Identity No. aa/matching No. aa | GenBank sequence hit |
|---|---|---|
| AMA1 Conserved A MSDINATRLP SEQ ID NO: 46 | 7/10 (70%), | gb\|EDN21666.1\| predicted protein [*Botryotinia fuckeliana* B05.10] |
| | 7/8 (87%), | gb\|EAT86097.1\| hypothetical protein SNOG_06266 [*Phaeosphaeria nodorum* SN15] |
| | 7/9 (77%), | gb\|EAK82279.1\| hypothetical protein UM01662.1 [*Ustilago maydis* 521] |
| | 6/9 (66%) | gb\|EAU90435.1\| predicted protein [*Coprinopsis cinerea okayama*7#130] |
| | MREINSTRLP 7/10 (70%) | predicted protein [*Botryotinia fuckeliana* B05.10]. Pathogenic fungus (aka *Botrytis cinerea*) that causes gray mold rot in plants |
| | MSNIAAPRLP 7/10 (70%) | gb\|ABD10583.1\| *Endopeptidase* Clp [*Frankia* sp. CcI3] |
| | MSDIAWIIPDNATR 8/13 (61%) | hypothetical protein CC1G_09232 [*Coprinopsis cinerea okayama*7#130] |
| | SDVNAPRLP 7/9 (77%) | hypothetical protein UM01662.1 [*Ustilago maydis* 521] |
| | SDI-ATRLP 8/9 (88%) | non-ribosomal peptide synthetase [*Saccharopolyspora erythraea* NRRL 2338] |

TABLE 8-continued

Exemplary homology comparisons using Consensus MSDINATRLP, XWXXXCXP, and CVGDDVXXLLTRALC as query sequences using BLASTP (MSDINATRLPXWXXXCXPCVGDDVXXLILTRALC, SEQ ID NO: 45).

| SEQUENCE | Identity No. aa/matching No. aa | GenBank sequence hit |
|---|---|---|
| AMA1 Conserved Region B CIGDDVTTLL TRGEALC SEQ ID NO: 618 | 8/11 (72%) | gb\|ABF87913.1\|ATP-binding protein, ClpX family [*Myxococcus xanthus* DK 1622] |
| | 8/10 (80%) | emb\|CAG61741.1\|unnamed protein product [*Candida glabrata* CBS 138] |
| | 10/16 (62%) | gb\|EAK84527.1\|hypothetical protein UM03624.1 [*Ustilago maydis* 521] |
| | 11/16 (68%) | gb\|EAU39589.1\|conserved hypothetical protein [*Aspergillus terreus* NIH2624] |
| | 8/8 (100%) | dbj\|BAE56937.1\|unnamed protein product [*Aspergillus oryzae*] |
| PHA1 Conserved Region B CVGDDVNRL LTRGESLC SEQ ID NO: 89 | 14/21 (66%) | gb\|AAZ10451.1\|hypothetical protein Tb927.3.4180 [*Trypanosoma brucei*] |
| | 11/18 (61%) | gb\|EAQ84320.1\|hypothtical protein CHGG_10724 [Chaetomium globosum CBS 148.51] |
| | 9/11 (81%) | gb\|ABE92653.1\|Peptidase, cysteine peptidase active site; Aromatic-ring hydroxylase [*Medicago truncatula*] |
| | 9/14 (64%) | gb\|EDN63642.1\|conserved protein [*Saccharomyces cerevisiae* YJM789] |
| Consensus B CXGDDVXXL LTRXLC SEQ ID NO: 91 | 9/14 (64%) GDDVAALLSRRVLC | ref\|XP_760134.1\|hypothetical protein UM03987.1 [*Ustilago maydis* 521] |
| | 8/12 (66%) | ref\|ZP_00591779.1\|ClpX, ATPase regulatory subunit [*Prosthecochloris aestuarii* DSM 271] green sulfur bacterium |

Example VIII

This example describes materials and methods for determining whether the amatoxin and phallotoxin-encoding nucleic acids are specific for *Amanita* mushroom species that produce amatoxins and phallotoxins.

Many secondary metabolites such as mushroom peptide toxins are limited in their taxonomic distribution; for example, most species of *Amanita* do not make amatoxins or phallotoxins. Thus the inventors contemplated whether the lack of amatoxin and phallotoxin production among other species of *Amanita* was due to absence of the encoding genes or due to the absence of productive translation of the genes. The inventors tested for the presence of amatoxins such as alpha-amanitin and phallotoxins such as phallacidin and in the same mushrooms tested for the presence of DNA encoding alpha amanitin (AMA1) and phallacidin (PHA1). The inventors tested for the presence of AMA1 and PHA1 in the genomes of known amatoxin and phallotoxin-producing mushroom species and non-producing mushroom species in order to associate the AMA1 and PBA1 sequences with amatoxin and phallotoxin production.

Preparation and Isolation of *Amanita* Genomic Sequences. DNA was extracted from a variety of species of *Amanita* that were either known as amatoxin and phallotoxin-producers (*A. bisporigera, A. ocreata, A.* aff. *suballiacea* and *A. phalloides*) or were known to not produce amatoxins (*A. novinupta, A. franchetti, A. porphyria, A. velosa, A. gemmata, A. muscaria, A. flavoconia, A. section* Vaginatae, and *A. hemibapha*). DNA was extracted from lyophilized fruiting bodies using cetyl trimethyl ammonium bromide-phenol-chloroform isolation (Hallen, (2003) Mycol. Res. 107:969; herein incorporated by reference). Following the usual preparation methods, sequences were separated by gel electrophoresis and then transferred to blotting media for subsequent probe hybridization.

Southern blots of DNA were probed with AMA1 and PBA1 as described. As shown in FIG. 8A, a blot was probed with an amanitin gene AMA1 (nt 1710-2175 as numbered in FIG. 5) while the blot shown in FIG. 8B was probed with a phallacidin gene PBA1 (nt 635-1115 in phallacidin #2, see, FIG. 6). For references on amatoxin and phallotoxin production in relation to *Amanita* taxonomy, see website pluto.njcc.com/.about.ret/amanita/mainaman.html; Hallen (2002) Studies in amatoxin-producing genera of fungi: phylogenetics and toxin distribution. Ph.D. dissertation, East Lansing, Mich.: Michigan State University. 192 pp.; and Arora D (1986) Mushrooms Demystified, Second Edition. Ten Speed Press, Berkeley; (Bas, Persoonia 5, 285 (1969); Tulloss et al., Boll Gruppo Micologico G Bresadola, 43, 13 (2000); WeiB et al., Can J. Bot. 76, 1170 (1998); all of which are herein incorporated by reference).

The results showed that AMA1 and PHA1 sequences hybridized to DNA from known amatoxin and phallotoxin-producing species but did not hybridize to the species known to not produce these compounds. The inventors concluded that these genes were present in amatoxin and phallotoxin-producing species and absent in non-producers, thus providing additional evidence that the genes described herein encode amatoxins and phallotoxins.

Extraction and analysis of amatoxins and phallotoxins. Variability in toxin content is known even within species of *Amanita* that normally produce amatoxins and phallotoxins (Beutler, et al., (1981) J. Nat. Prod. 44:422 and Tyler, et al., (1966) J. Pharm. Sci. 55:590; all of which are herein incorporated by reference in its entirety). Therefore in order to confirm that the presence of AMA1 and PHA1-encoding sequences correlates with actual production of amatoxins and phallotoxins, the inventors tested the same mushrooms that were used for extraction of DNA and Southern blotting (FIG. 8) for the presence of amatoxins and phallotoxins. Thus amatoxins and phallotoxins were extracted from these mushrooms, then analyzed by established HPLC methods (Hallen, et al., Mycol. Res. 107:969 (2003), Enjalbert, (1992) J. Chromatogr. 598:227; all of which are herein incorporated by reference in its entirety). Standards of α-amanitin, β-amanitin, phalloidin, and phallacidin were purchased from Sigma.

Each of the tested mushrooms that contain amatoxins and phallotoxins, but none of the nonproducers, hybridizes to AMA1 and PHA1. This is consistent with AMA1 and PHA1 as being responsible for alpha-amanitin and phallacidin biosynthesis and provides a molecular explanation for why *Amanita* species outside of sect. Phalloideae are not deadly poisonous. Some of the species of *Amanita* that do not make amatoxins or phallotoxins are edible, but others make toxic compounds chemically unrelated to the *Amanita* cyclic peptide toxins.

Example IX

This Example demonstrates PCR amplification of an α-amanitin gene in mushroom species known to produce α-amanitin while failing to amplify DNA from species that do not produce alpha-amanatin (FIG. 10C).

PCR amplification of the gene for α-amanitin. Primers were based on the sequences in FIGS. 4, 5 and 6. The primer sequences used were: forward primer: 5'-AGCATCTGCCCGCACCTTACG-3', SEQ ID NO:92; Reverse primer: 5'ACTGCCTTGTATCACCGTTATG-3', SEQ ID NO:93. PCR mixtures and running conditions were REDTaq ReadyMix DNA polymerase (Sigma), 30 cycles of denaturation (94° C., 30 sec), annealing (55° C., 30 sec), and extension (72° C., 5 min).

Figure 10:
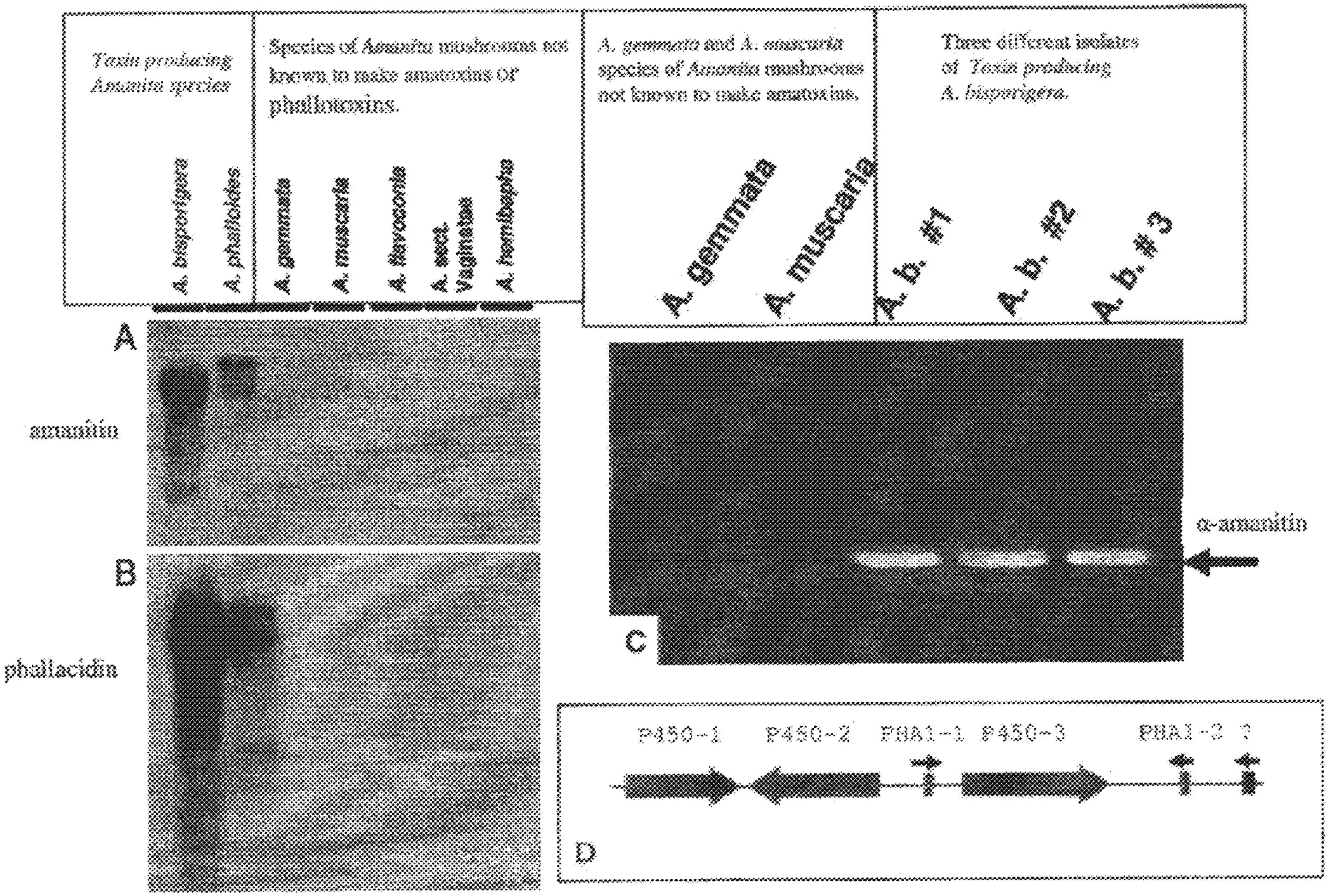
FIG. 10 shows an exemplary correlation of toxin genes and expression with toxin producing species of mushrooms in addition to a schematic of types of genes discovered near toxin producing genes in at least one lambda clone from a toxin producing mushroom. Panels A and B show a Southern blot of DNA from species of *Amanita* that does (*A. bisporigera* and *A. phalloides*) or does not (*A. gemmata, A. muscaria, A. flavoconia*, A section Vaginatae, and *A. hemibapha*) make amatoxin (probe used in Panel A) and phallotoxin (probe used in panel B). Panel C shows PCR amplification products of the gene for alpha-amanitin. Primers were based on the sequences in FIG. 4. *A. gemmata* and *A. muscaria* are species of *Amanita* that do not make amatoxins (or phallotoxins). *A. bisporigera* #'s 1-3 are three different specimens of *A. bisporigera* collected in the wild. Panel D shows an exemplary schematic map of *Amanita bisporigera* genes predicted in a single lambda clone (13.4 kb) isolated using PHA1 as probe: showing two copies of PHA1 clustered with each other and with three P450 genes, NOTE: P450 genes were predicted using FGENESH and the *Coprinus cinereus* model; however, *Coprinus* does not have a PHA1 gene.

*A. gemmata* and *A. muscaria* are species of *Amanita* that do not make amatoxins (or phallotoxins) and did not yield a PCR product using these primers (FIG. 10C). A. b. numbers 1-3 in FIG. 10C indicate three different isolates of *A. bisporigera*, all of which produced alpha-amanitin, and all of which yielded PCR products, indicating the presence of the gene for alpha-amanitin (FIG. 10).

Example X

This Example shows the development of conserved regions upstream and downstream of *Amanita* peptide encoding regions.

Figure 8:
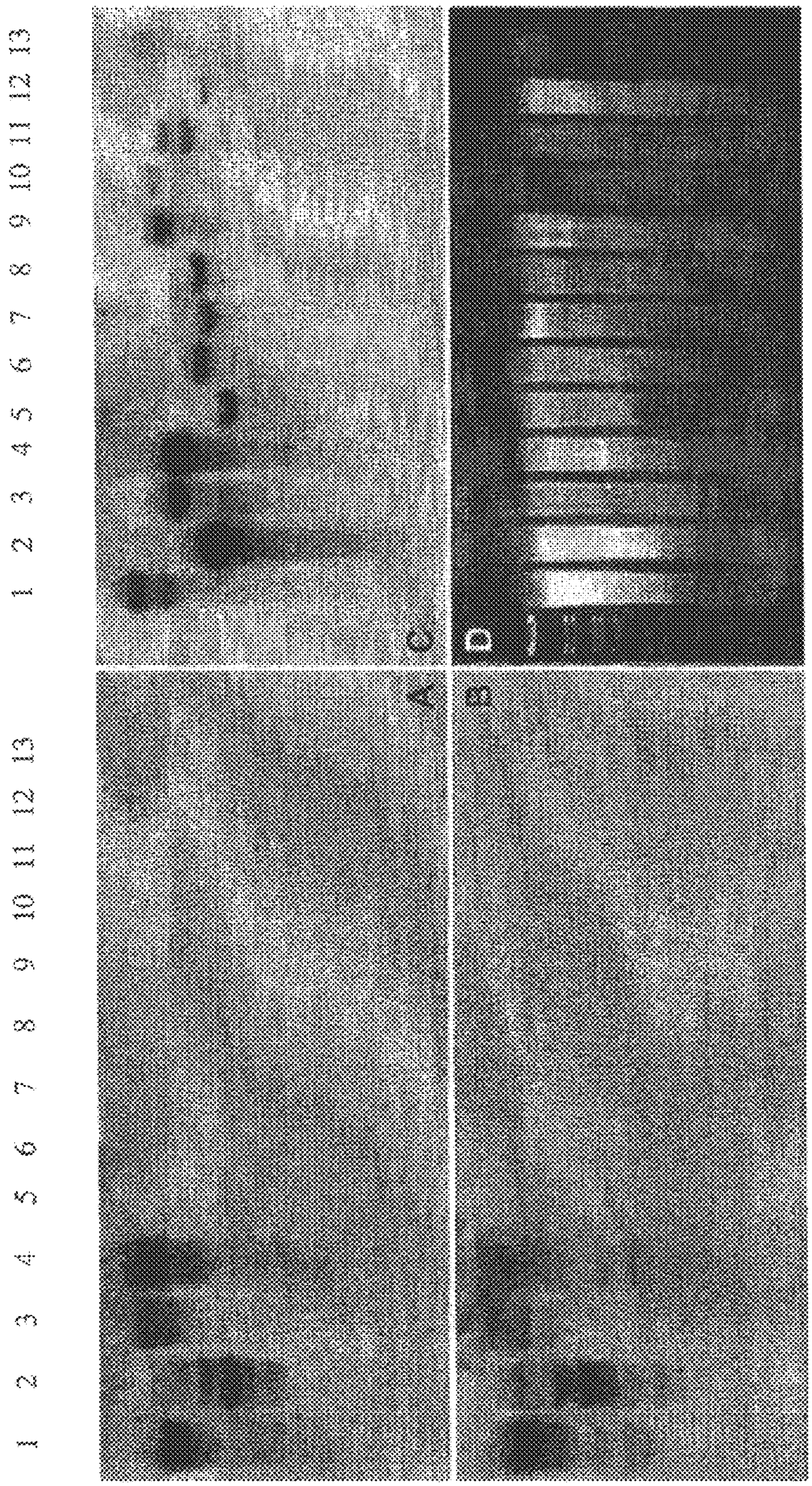
FIG. 8 shows exemplary DNA blots of different species of *Amanita*. Panel A shows a blot of *Amanita* DNA probed with AMA1 cDNA. Panel B shows a blot of *Amanita* DNA probed with PHA1 cDNA. Panel C shows a blot of *Amanita* DNA probed with a fragment of the β-tubulin gene isolated from *A. bisporigera* as a control. Panel D is an ethidium-stained gel showing relative lane loading. Markers are lambda cut with BstEII. Species and provenances: Lane 1, *A.* aff *suballiacea* (Ingham County, Michigan); lane 2, *A. bisporigera* (Ingham County); lane 3, *A. phalloides* (Alameda County, California); lane 4, *A. ocreata* (Sonoma County, California); lane 5, *A. novimipta* (Sonoma County); lane 6, *A. franchetii* (Mendocino County, California); lane 7, (Sonoma County); lane 8, a second isolate of *A. franchetii* (Sonoma County); lane 9, *A. muscaria* (Monterey County, California); lane 10, *A. gemmata* (Mendocino County); lane 11, *A. hemibapha* (Mendocino County); lane 12, *A. velosa* (Napa County, California); lane 13, A. sect. Vaginatae (Mendocino County). Mushrooms represent sect. Phalloideae (#'s 1-4), sect. Validae (#'s 5-8), sect. *Amanita* (#'s 9-10), sect. Caesarea (#11), sect. Vaginatae (#'s 12-13). Four separate gels were run; the lanes are in the same order on each gel and approximately the same amount of DNA was loaded per lane. The blots shown in panels A and B are to the same scale, and the blots shown in panels C and D are to the same scale.

The unexpected complex hybridization patterns shown in FIG. 8 led the inventors to contemplate that AMA1 and PHA1 are members of gene families such that additional short peptides related to AMA1 and PHA1 should be encoded by genes in *A. bisporigera.*

The conserved upstream and downstream amino acid sequences of AMA1 and PHA1 were used as queries using BLASTP to search for additional related sequences in the *A. bisporigera* genome sequence database. The inventors thereby found at least 12 new related DNA sequences that could encode proproteins as long or longer than the proproteins of AMA1 and PHA1 and another 10-15 partial sequences (missing the upstream or the downstream conserved sequences) see exemplary sequences, including partial sequences in FIG. 7). These new sequences comprise an upstream conserved sequence MSDINTARLP. MSDIN, R, and P were invariant yielding an exemplary consensus sequence MSDINXXRXP, SEQ ID NO: 94), and a downstream conserved sequence CVGDDV, wherein the first D is invariant, for a consensus sequence CVGDXV, SEQ ID NO: 95, and a consensus sequence CVGDDVXXXDXX, SEQ ID NO: 96. The regions capable of comprising interesting peptides are those in the same positions relative to the upstream and downstream conserved regions in AMA1 and PHA1, namely, starting immediately downstream of the first invariant Pro residue and ending just after a second invariant Pro residue. These regions between these two absolutely conserved Pro residues are much more variable ("hypervariable") in predicted amino acid sequence compared to the upstream and downstream conserved sequences. The "hypervariable regions" between the two invariant Pro residues are predicted to contain from seven to ten amino acids. Among the described putative new hypervariable regions (FIGS. 7 and 9) all twenty proteinogenic amino acids are represented in at least one. These new hypervariable sequences might represent previously unknown linear and cyclic peptides made by *A. bisporigera.*

Example XI

This example describes methods and results of using conserved regions of AMA1 and PHA1 for obtaining additional regions encoding potentially biologically active linear or cyclic peptides from *A. bisporigera, A. phalloides*, and other species of *Amanita*. In particular, a DNA sequence encoding amino acid sequences was found that was highly similar to α-amanitin and comprising the amino acid sequence found in .beta.-amanitin, and a DNA that was highly similar to phallacidin and comprising the amino acid sequence found in phalloidin.

During the course of developing the present inventions, the inventors discovered regions of conserved sequence whose use resulted in the discovery of additional sequences contemplated to encode proproteins related to amatoxin and phallotoxin proproteins, which could encode novel small linear or cyclic peptides. Degenerate primers were designed against the conserved sequences of AMA1 and PHA1. DNA extracted from *A. phalloides* and *A. ocreata* was used as template. This also shows that the AMA1 and PHA1 genes and related genes are conserved in other species of amatoxin and phallotoxin-producing *Amanita* species, and that PCR primers designed against one species (*A. bisporigera*) function to identify amatoxin and phallotoxin genes in other species of *Amanita*.

New degenerate PCR primer sequences that the inventors developed and used on genomic DNA as a template were 5'-ATGTCNGAYATYAAYGCNACNCG (forward), SEQ ID NO: 97, and 5'-AAGGSYCTCGCCACGAGTGAGGAGWSKRKTGAC (reverse), SEQ ID NO: 98, W indicates A or T, S indicates C or G, K indicates G or T, R indicates A or G, and Y indicates T or C. The resulting PCR products (approximately 100 nt) were cloned and sequenced. Exemplary sequences of three amplicons are: number 1: ATGTCTGATATTAATGCAACGCGTCTTCCCTTCAATATTCTGCCATTCAT GCTTCCCCCGTGCGTCAGTGACGATGTCAATATACTCCTCACTCGTGGCG AG, SEQ ID NO: 99, translation: MSDINATRLP <u>FNILPFMLPP</u>CVSDDVNILLTRGE, SEQ ID NO: 110, [predicted to encode a unique linear and cyclic peptide, underlined, SEQ ID NO: 114]; number 2: ATGTCAGATATCAATGCGACGCGTCTTCCCATATGGGGAATAGGTTGCG ACCCGTGCATCGGTGACGACGTCACCATACTCCTCACTCGTGGCGAG translation, SEQ ID NO: 101, MSDINATRLP<u>IWGIGCDP</u>CIGDDVTILLTRGE, SEQ ID NO: 102, [predicted to encode beta-amanitin SEQ ID NO:54]; number 3: ATGTCGGATATTAATGCTACACGTCTTCCAATTATTGGGATCTTACTTCC CCCGTGCATCGGTGACGATGTCACCCTACTCCTCACTCGTGGCGAG, SEQ ID NO: 103, [translation: MSDINATRLP<u>IIGILLPP</u>CIGDDVTLLLTRGE, SEQ ID NO: 47, [predicted to encode a unique linear or cyclic peptide, underlined SEQ ID NO: 117]; and number 4: ATGTCAGACA TTAACGCGAC CCGTCTTCCCGCCTGGCTCGCCACCTGCCCGTGCGCCGGTGACGACGTCA ACCCTCTCCT CACTCGTGGC GAG, SEQ ID NO: 105, translation: MSDINATRLP<u>AWLATCP</u>CAGDDVNPLLTRGE, SEQ ID NO: 106, [predicted to encode phalloidin, underlined (SEQ ID NO:136].

TABLE 9

Exemplary comparisons of *Amanita* peptide sequences.

| Preprotprotein nucleic acid | Identity No. na/ matching No. na | Percent Identity |
|---|---|---|
| Alpha-Amanitin vs. new peptide 1 SEQ ID NO: 114 | 35/41 | 85% |
| Alpha-Amanitin vs. new peptide 2, beta-Amanitin | 79/91 | 86% |
| Alpha-Amanitin vs. new peptide 3 SEQ ID NO: 117 | 36/41 | 87% |
| Phallacidin vs. new peptide 1 SEQ ID NO: 114 | 34/40 | 85% |
| Phallacidin vs. new peptide 2, beta-Amanitin | 33/40 | 82% |
| Phallacidin vs. new peptide 3 SEQ ID NO: 117 | 35/40 | 87% |

The inventors then initiated a BLASTN and TBLASTN search of the *Amanita bisporigera* genome DNA sequences using conserved region A for identifying homologous sequences. The inventors discovered numerous nucleic acid sequences encoding MSDINVTRLP SEQ ID NO:88 or versions thereof, followed by variable short regions that were in turn followed by regions homologous to regions B of AMA1 and PHA1, see, FIG. 9, and the Table below. The inventors contemplated that these sequences encode additional proproteins and biologically active linear or cyclic peptides, such as toxins or enzyme inhibitors.

TABLE 10A

Exemplary comparisons to AMA1 and PHA1.

| Name | Proprotein | Identity |
|---|---|---|
| [amanitin] peptide, SEQ ID NO: 48 | MSDINATRLP **<u>IWGIGCNP</u>** CVGDDVITLLTRGE SEQ ID NO: 107 | 100% |
| [phallacidin], SEQ ID NO: 49 | MSDINATRLP **<u>AWLVDCP</u>** CVGDDVNRLLTRGE SEQ ID NO: 108 | 25/32 (78.1%) |
| [consensus], SEQ ID NO: 50 | MSDINATRLP <u>XWXXXCAP</u> CVGDDVXXLLTRGE SEQ ID NO: 109 | |
| new potential peptide 1, SEQ ID NO: 51 | MSDINATRLP <u>FNILPFMLPP</u> CVSDDVNILLTRGE SEQ ID NO: 110 | AMA1 23/34 (67%) PHA1 22/34 (64%) |
| new potential peptide 2, SEQ ID NO: 52 | MSDINATRLP <u>IWGIGCDP</u> CIGDDVTILLTRGE SEQ ID NO: 111 | AMA1 29/32 (90%) PHA1 24/32 (75%) |

TABLE 10A-continued

| Exemplary comparisons to AMA1 and PHA1. | | |
|---|---|---|
| Name | Proprotein | Identity |
| new potential peptide 3, SEQ ID NO: 53 | MSDINATRLP IIGILLPP CIGDDVTLLLTRGE SEQ ID NO: 112. | AMA1 26/32 (81%) PHA1 22/32 (68%) |
| new potential peptide 4, SEQ ID NO: 54 | MSDINATRLP AWLATCPC AGDDVNPUTRGE SEQ ID NO: 113 | AMA1 26/32 (81%) PHA1 22/32 (68%) |

TABLE 10B

| Exemplary comparisons using Amanita peptide sequences as query sequences in GenBank (BLASTP). | | | |
|---|---|---|---|
| Alpha-amanitin (AMA1) | IWGIGCNP (8) (SEQ ID NO: 50) | 6/8 (75%) IWGIGCVL (SEQ ID NO: 655) (6/8 (75%) | gb\|AAZ19981.1\| conserved hypothetical protein [*Psychrobacter arcticus* 273-4] gv\|EAU82808.1\| hypothetical protein CC1G_11325 [*Coprinopsis cinera okayama*7#130] |
| Alpha-amanitin (AMA1) | IWGIGCNP (8) (SEQ ID NO: 50) | 5/8 (40.0%) | AWLVDCP (pha1) (SEQ ID NO: 69) |
| phallacidin (PHA1) | AWLVDCP (7) (SEQ ID NO: 69) | AWLVDC (SEQ ID NO: 656) 6/7 (85.5%) AWVVDCP (SEQ ID NO: 657) 6/7 (85.5%) | gb\|EAV54171.1\| simgma54 specific transcriptional regulator, Fis family [*Burkholderia ambifaria* MC40-6] gb\|AAG04585.1\| AE004550_1 probable transcriptional regulator [*Pseudomonas aeruginosa* PAO1] gb\|EAL84365.1\| conserved hypothetical protein [*Aspergillus fumigatus* Af293] |
| Peptide 1 SEQ ID NO: 114 | FNILPFMLPP (10) | 2/10 (20%) 2/10 (20%) 8/10 (80%) | AMA1 PHA1 ref\|ZP_01047917.1\| hypothetical protein NB311A_09386 [*Nitrobacter* sp. Nb-311A] |
| beta-amanitin SEQ ID NO: 54 | IWGIGCDP (8) | 7/8 (87%) 5/8 (40.0%) 7/8 (87%) | AMA1 PHA1 ref\|YP_265415.1\| hypothetical protein Psyc_2134 [*Psychrobacter arcticus* 273-4] |
| Peptide 3 SEQ ID NO: 117 | IIGILLPP (8) | 4/8 (50%) 1/8 (12.5%) 7/8 (87%) IIGILLP 7/7 (100%) | AMA1 PHA1 gb\|ABR79950.1\| hypothetical protein [*Klebsiella pneumoniae* subsp. pneumoniae MGH 78578] ref\|YP_001292803.1 hypothetical protein [*Haemophilus influenzae* PittGG] ref\|XP_001139896.1\| PREDICTED: prolyl 4-hydroxylase, alpha I subunit isoform 2 [*Pan troglodytes*] |

TABLE 10C

Exemplary sequences related to AMA1 and PHA1. Predicted amino acid sequences encoded by genomic survey sequences of A. bisporigera (FIG. 7). Spaces were sometimes inserted before and after the peptide/toxin regions (underlined), when the peptide/toxin reigon had fewer than 10 predicted amino acids, in oreder to emphasize the conservation of the upstream and downstream sequences. *indicates stop codon. These are genomic survey sequences. Based on the cDNA sequences of AMA1 and PHA1, an introl in contemplated near the C-terminus of the indicated proproteins.

| SEQ ID NO: | Exemplary Amanita peptides |
|---|---|
| SEQ ID NO: 23 | MSDINATRLP HPFPLGLQP CAGDVDNLTTKGEG |
| SEQ ID NO: 111 | MSDINATRLP IWGIGCDP CIGDDVTILLTRGE |
| SEQ ID NO: 113 | MSDINATRLP AWLATCP CAGDDVNPLLTRGE |
| SEQ ID NO: 26 | MSDINATRLP GFVPILFP CVGDDVNTALT |
| SEQ ID NO: 27 | MSDINATRLP FYQFPDFKYP CVGDDIEMVLARGER* |
| SEQ ID NO: 28 | MSDINATRLP FFQPPEFRPP CVGDDIEMVLTRG* |
| SEQ ID NO: 29 | MSDINATRLP LFLPPVRMPP CVGDDIEMVLTRGER* |
| SEQ ID NO: 30 | MSDINATRLP LFLPPVRLPP CVGDDIEMVLTR |
| SEQ ID NO: 31 | MSDINATRLP YVVFMSFIPP CVNDDIQVVLTRGEE* |
| SEQ ID NO: 32 | MSDINATRLP CIGFLGIP SVGDDIEMVLRH |
| SEQ ID NO: 44 | MSDINATRLP LSSPMLLP CVGDDILMV |
| SEQ ID NO: 34 | MSDINATRLP ILMLAILP CVGDDIEVLRRGEG* |
| SEQ ID NO: 35 | MSDINATRLP IPGLIPLGIP CVSDDVNPTLTRGER* |
| SEQ ID NO: 36 | MSDINATRLP GAYPPVPMP CVGDADNFTLTRGEK* |
| SEQ ID NO: 37 | MSDINATRLP GMEPPSPMP CVGDADNFTLTRGN |
| SEQ ID NO: 118 | MSDINATRLP HPFPLGLQP CAGVDNLTLTKGEG* |

In particular, the inventors analyzed three sequences encoding short peptides and potential toxins including comparing sequence homology to α-amanitin and phallacidin.

TABLE 11

Exemplary Amanita Petides.

| Peptide sequence | SEQ ID Number. |
|---|---|
| IWGIGCNP | SEQ ID NO: 50 |
| AWLVDCP | SEQ ID NO: 69 |
| XWXXXCXP | SEQ ID NO: 135 |
| FNILPFMLPP | SEQ ID NO: 114 |
| IWGIGCDP | SEQ ID NO: 54 |
| IIGILLPP | SEQ ID NO: 117 |
| AWLATCP | SEQ ID NO: 136 |
| GFVPILFP | SEQ ID NO: 137 |
| FYQFPDFKYP | SEQ ID NO: 138 |

TABLE 11-continued

Exemplary Amanita Petides.

| Peptide sequence | SEQ ID Number. |
|---|---|
| FFQPPEFRPP | SEQ ID NO: 139 |
| LFLPPVRMPP | SEQ ID NO: 140 |
| LFLPPVRLPP | SEQ ID NO: 141 |
| YVVFMSFIPP | SEQ ID NO: 142 |
| CIGFLGIP | SEQ ID NO: 143 |
| LSSMLAILP | SEQ ID NO: 144 |
| ILMLAILP | SEQ ID NO: 145 |
| IPGLIPLGIP | SEQ ID NO: 146 |
| GAYPPVPMP | SEQ ID NO: 147 |
| GMEPPSPMP | SEQ ID NO: 148 |
| HPFPLGLQP | SEQ ID NO: 149 |

Example XII

This example shows the complex hybridization patterns of Example VIII, FIG. 8, that indicated that AMA1 and PHA1 are members of gene families.

Using the conserved upstream and downstream amino acid sequences of AMA1 and PHA1 as queries, the inventors found at least 15 new related sequences (Table 11B) and another 10-15 partial sequences in the genome survey sequence of *A. bisporigera*. Each of them had an upstream conserved consensus sequence MSDINATRLP (MSD, N, R, and Pare invariant), and a downstream conserved consensus CVGDDXXXXLTRGE (D is invariant). The putative peptide toxin regions, which start immediately downstream of an invariant Pro residue and end just after an invariant Pro residue, are more variable compared to the upstream and downstream sequences. The hypervariable regions contain seven to ten amino acids, while all of the twenty proteinogenic amino acids are represented at least once (FIGS. 7 and 9). With specific 5' PCR primers and oligo-dT, the inventors demonstrated that at least two of the sequences starting with "MSDIN" or closely similar sequence (FIG. 7) are expressed at the mRNA level.

TABLE 11B

AMA1 and PHA1 related sequences.

| Fifteen additional AMA1 and PHA1 related sequences found in a genome survey of *A. bisporigera* using conserved upstream and downstream amino acid sequences of AMA1 and PHA1 as queries. | SEQ ID NO: XX |
|---|---|
| MSDINATRLPIWGIGCN--PCVGDDVTTLLTRGE | SEQ ID NO: 303 |
| MSDINATRLPAWLVDC---PCVGDDVNRLLTRGE | SEQ ID NO: 304 |
| MSDINATRLPIWGIGCD--PCIGDDVTILLTRGE | SEQ ID NO: 305 |
| MSDINATRLPIIGILLP--PCIGDDVTLLLTRGE | SEQ ID NO: 306 |
| MSDINATRLPFNILPFMLPPCVSDDVNILLTRGE | SEQ ID NO: 110 |
| MSDINTARLPFYQFPDFKYPCVGDDIEMVLARGE | SEQ ID NO: 308 |
| MSDINTARLPFFQPPEFRPPCVGDDIEMVLTRGE | SEQ ID NO: 309 |
| MSDVNDTRLPFNFFRFPY-PCIGDDSGSVLRLGE | SEQ ID NO: 310 |
| SMDINTARLPLFLPPVRMPPCVGDDIEMVLTRGE | SEQ ID NO: 311 |
| MSDINTARLPYVVFMSFIPPCVNDDIQVVLTRGE | SEQ ID NO: 312 |
| MSDINAIRAPILMLAIL--PCVGDDIEVLRRGEG | SEQ ID NO: 313 |
| MSDINGTRLPIPGLIPLGIPCVSDDVNPTLTRGE | SEQ ID NO: 314 |
| MSDINATRLPGAYPPVPM-PCVGDADNFTLTRGE | SEQ ID NO: 315 |
| MSDINATRLPHPFPLGLQ-PVAGDVDNLTLTKGE | SEQ ID NO: 316 |
| MSDINATRLPAWLATC---PCAGDDVNPLLTRGE | SEQ ID NO: 317 |

Fifteen sequences listed in Table 11B were used for constructing a WebLogo graphic (Crooks et al., 2004, herein incorporated by reference) showing the relative conservation by letter size representing amino acids, such that highly conserved amino acids are represented by large letters (for example, MSDIN; positions 1-5, and P; positions 10 and 20) while less conserved amino acids have smaller letters (for example A/T, G/S; positions 6 and 23, respectively) and low areas of conserved amino acids have small letters (for example, in regions 11-18). These results showed upstream MSDINATRLP (SEQ ID NO: 88) (MSD, N, R, and P are invariant, consensus was MSDXNXXRXP) and downstream conserved consensus CVGDDXXXXLTRGE (SEQ ID NO: 239) (D is invariant). FIG. 9. Because WebLogo requires that all sequences have the same length, therefore the spaces were replaced with one, two, or three X's within the toxin region before the second conserved Pro residue for toxin peptides of nine, eight, or seven amino acids, respectively.

Example XIII

This example shows exemplary sequences for amanitin produced by *G. marginata* mushrooms.

*Galerina marginata* (a synonym for *G. autumnalis*) produces amatoxins but not phallotoxins (Benedict et al., 1966). This fungus is contemplated as a potentially valuable experimental system for elucidating the biosynthesis and regulation of amatoxin biosynthesis because, unlike *Amanita*, it is saprophytic and grows and produces amatoxins in culture (Muraoka and Shinozawa, 2000). *Galerina* spp. are relatively small and rare, but they nonetheless sometimes cause mushroom poisonings (e.g., Kaneko et al, 2001, herein incorporated by reference, and FIG. 31).

Figures 12A, 12B:
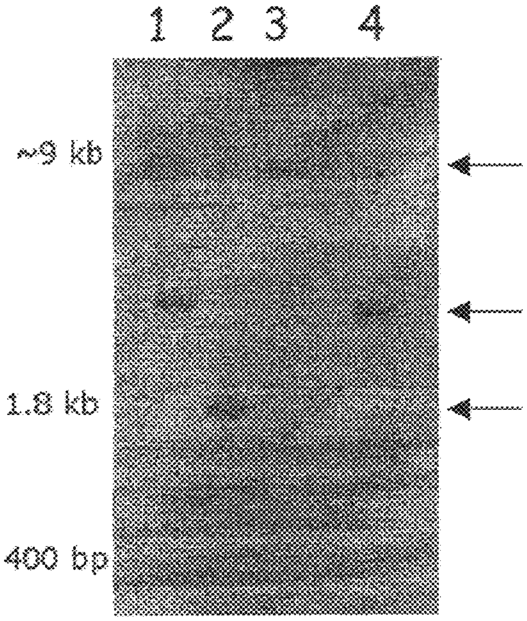
FIG. 12A-12B shows an exemplary *Galerina marginata* amanitin (GmAM1) preproprotein amino acid sequence as well as a Southern blot of *Galerina marginata* (Gm) DNA probed with GmAM1.

Therefore, the inventors sequenced about 40 MB of *G. marginata* and identified two genomic sequences that could encode alpha-amanitin (GmAMA1) (FIGS. 11 and 12). Comparison of the DNA and amino acid sequences of AMA1 and GmAMA1 (FIG. 12A) indicated that amatoxins are also made on ribosomes in *Galerina* and probably processed similarly. DNA probed with GmAM1 under high stringency conditions showed at least 2 sequences, a Southern blot of *G. autumnalis* FIG. 12B. Lanes 1-4 are samples of total genomic DNA cut with PstI, HindUII, EcoRV, and BamHI. The blot shows that there are two copies of GmAMA1. This corresponds to the two copies of GmAM1. One was identified by 454 sequencing and the other by inverse PCR (see herein). However, the upstream and downstream sequences are much less well conserved when compared to the *Amanita* alpha amanitin sequence. The four amino acids immediately upstream of the toxin region (TRLP) are conserved in *Amanita* and *Galerina* (FIG. 11). This might be an indication that these amino acids are important for processing of the proproteins by prolyl oligopeptidase (see below).

An RNA blot of the *Galerina marginata* amanitin gene (GmAMA1) showed that the gene is expressed in two known amanitin-producing species of *Galerina* (*G. marginata* and *G. badipes*) and not in a nonproducer (*G. hybrida*), and that the gene is induced by low carbon. Lane 1: *G. hybrida*, high carbon. Lane 2: *G. hybrida*, low carbon. Lane 3: *G. marginata*, high carbon. Lane 4: *G. marginata*, low carbon. Lane 5: *G. badipes*, high carbon. Lane 6: *G. badipes*, low carbon. Each lane was loaded with 15 ug total RNA. The agarose gel was blotted to nitrocellulose by standard methods and probed with the *G. marginata* AMA1 gene (GmAMA1) predicted to encode alpha-amanitin. Fungi were grown in liquid culture for 30 d on 0.5% glucose (high carbon) then switched to fresh culture of 0.5% glucose or 0.1% glucose (low carbon) for 10 d before harvest. The major band in lanes 3-6 is about 300 bp. The high MW signal in lane 1 is spurious.

Figure 13:
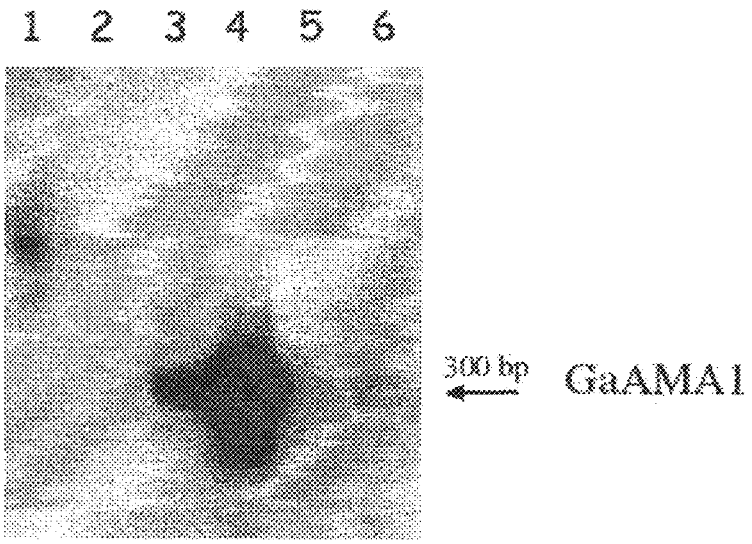
FIG. 13 shows an exemplary RNA blot of the *Galerina marginata* amanitin gene (GmAMA1). The results show that the gene is expressed in two known amanitin-producing species of *Galerina* (*G. marginata* and *G. badipes*) but not in a species that is a nonproducer of toxin (*G. hybrida*). Induction of gene expression was triggered by low carbon growth conditions. Lane 1: *G. hybrida*, high carbon. Lane 2: *G. hybrida*, low carbon. Lane 3: *G. marginata*, high carbon. Lane 4: *G. marginata*, low carbon. Lane 5: *G. badipes*, high carbon. Lane 6: *G. badipes*, low carbon. The probe was *G. marginata* AMA1 gene (GmAMA1) predicted to encode alpha-amanitin (FIG. 4). Each lane was loaded with 15 ug total RNA. Fungi were grown in liquid culture for 30 d on 0.5% glucose (high carbon) then switched to fresh culture of 0.5% glucose or 0.1% glucose (low carbon) for 10 d before harvest. The major band in lanes 3-6 is approximately 300 bp. The high MW signal in lane 1 is spurious.

Therefore, by RNA blotting, the inventors found that GmAMA1 is expressed in culture and is induced by carbon starvation, as has been reported for the toxin itself (Muraoka and Shinozawa, 2000, herein incorporated by reference) (FIG. 13).

Genomic DNA Isolation. *Galerina marginata*, an amatoxin producing species of circumboreal distribution, was harvested from the wild. Caps and undamaged stems were cleaned of soil and debris, frozen at −80° C., and lyophilized.

Genomic DNA was extracted from the lyophilized fruiting bodies using cetyl trimethyl ammonium bromide-phenol-chloroform isolation (Hallen, et al., (2003) Mycol. Res. 107:969; herein incorporated by reference). For studies requiring RNA, RNA was extracted using TRIZOL (Invitrogen) (Hallen, et al., (2007) Fung. Genet. Biol., 44:1146; herein incorporated by reference in its entirety). The inventors used a Genome Sequencer FLX from 454 Life Sciences (Margulies, et al., (2005) Nature 437:376; herein incorporated by reference) for generating sequences from *Galerina* species genomic DNA. There was no subcloning necessary. The inventors structured and maintained the sequenced DNA in a password-protected, private BLAST-searchable format.

Therefore, the inventors searched the DNA sequences from their *Galerina marginata* genome seeking DNA fragments capable of encoding amino acid sequences of amanitins, such as predicted sequences comprising a known predicted sequence of IWGIGCNP. Thus the inventors discovered an exemplary DNA sequence encoding either or both α-amanitin and/or γ-amanatin (these two forms of amanitin have the same amino acid sequence because they differ only in hydroxylation, which is a posttranslational modification). The sequences were compared (BLAST) to *Amanita* sequences previously discovered by the inventor and disclosed in a Provisional U.S. Patent Application Ser. No. 61/002,650 (FIG. 12A and FIG. 14). Therefore the inventors found nucleotide sequences that encode the amino acid sequence of α-amanitin or γ-amanatin with the sequence order of IWGIGCNP, in single letter code, in the genome of *G. marginata*. The inventors contemplate that IWGIGCNP would form a cyclic α-amanitin and/or γ-amanatin, which is also known to be present in *G. marginata*.

Specifically, PCR primers were designed based on the full-length (248 bp) Genome Sequencer 454 FLX read encoding IWGIGCNP and were used successfully to amplify the predicted amanitin coding region from *G. marginata* genomic DNA for use as probes in Southern and Northern blots. Primers were also designed for inverse PCR, in order to isolate and sequence DNA upstream and downstream of the amanitin-encoding region. Primers are as follows: A) Gal 454 start F: CCA GTG AAA ACC GAG TCT CCA; SEQ ID NO: 319, B) Gal before MFD F: CAA AGA TCT TCG CCC TTG CCT; SEQ ID NO: 320; C) Gal CDS MFD F: ATG TTC GAC ACC AAC TCC ACT, SEQ ID NO: 321; D) Gal end 454 R: ACA CAT TCA ACA AAT ACT AAC; SEQ ID NO: 322; E) Gal inverse->: GCT GAA CAC GTC GAT CAA ACT; SEQ ID NO: 323; F) Gal inverse<-: TCC ATG GGT TGC AGC CAA TAC; SEQ ID NO: 324. Primer combinations A:D, B:D, and C:D amplify unique PCR products from *G. marginata* of sizes 244, 201 and 169 bp, respectively; when cloned and sequenced, these PCR products are perfect matches to the Genome Technologies 454 FLX sequence. FIG. 14. Unlike GmAMA1, GmAMA2 (MFD2) was obtained by inverse PCR on genomic DNA of *Galerina* using primers GCT GAA CAC GTC GAT CAA ACT; SEQ ID NO: 323 and TCC ATG GGT TGC AGC CAA TAC; SEQ ID NO: 324. This yielded one PCR product (MFD2). Thus the inventors showed that *Galerina* has at least two genes encoding for amanitin.

Example XIV

This Example describes identifying potential prolyl oligopeptidase (POP)—like genes in fungal species.

The inventors discovered during the development of the present inventions, that both sequences of the present inventions and the structurally resolved *Amanita* cyclic peptides (amatoxins and phallotoxins) contained conserved Prolines. In particular, the inventors found in each predicted peptide sequence a Proline was located downstream of a N-terminal conserved region where proline (Pro) was the last amino acid of the sequence, while the last amino acid in the peptide toxin region itself was always a conserved Pro (for examples, FIGS. 5, 7). Thus the inventors contemplated that during processing of the propeptides of AMA1 and PHA1 to smaller peptides representing the amino acids found in the final mature amatoxins and phallotoxins, there would be a role for a proline-specific peptidase, for example a prolyl oligopeptidase enzyme, which is a peptidase or protease that cuts peptide bonds specifically after Pro residues. It was contemplated that such an enzyme also processes the other proproteins related to AMA1 and PHA1, resulting in the release of a small (7-10 amino acid) peptide that could be subsequently modified by, e.g., cyclization, hydroxylation, epimerization, and other posttranslational modifications.

Based on the conservation of a Pro residue immediately upstream of the peptide toxin region, and of a Pro as the last amino acid in the toxin region of all *Amanita* peptide toxin family members the inventors contemplated that an enzyme that recognizes and cleaves peptides at the carboxy side of Pro residues catalyzes the first post-translational step in *Amanita* toxin biosynthesis. Further, Based on the properties of the known proline-specific peptidases (Cunningham, et al., (1997) Biochim Biophys Acta 1343:160, Polgar, (2002) Cell. Mol. Life Sci. 59:349; all of which are herein incorporated by reference), the inventors contemplated that a member of the prolyl oligopeptidase family (POP) (EC 3.4.21.26) family was the most likely to be involved in the processing of the proproteins encoded by AMA1 and PHA1.

POPs are known to be widespread in animals, plants, and bacteria. However, none of the other known Pro-recognizing proteases specifically cleave at internal Pro residues of small peptides (Cunningham and O'Connor, 1997; Gass and Khosla, 2007).

Thus, the inventors used a human POP sequence (GenBank NP_002717, SEQ ID NO: 150) as a query sequence to search GenBank and known fungal genomes in order to identify a candidate fungal POP (see Table 12 below). A TBLASTN search was conducted using human POP (GenBank NP_002717) as query. BLASTP (default parameters) identified no orthologs of human POP with a score >53 and E value <e-06 in any fungus outside the Basidiomycetes, except perhaps *Phaeosphaeria nodorum* (SNOG_1288; score=166; E value=3e-40) (FIG. 15).

Orthologs of human POP are were present in other Basidiomycetes including *Coprinopsis cinereus* (GenBank CC1G_09936), *Ustilago maydis* (UM05288), *Cryptococcus neoformans* (SNOG_11288 and XP_567292), *Laccaria bicolor* (Lacbi1|303722) hypertext transfer protocol site: genome.jgi-psf.org/Lacbi1/Lacbi1.home.html), *Phanerochaete chrysosporium* (Phchr1|1293) hypertext transfer protocol site:genome.jgi-psf.org/Phchr1/Phchr1.home.html), and *Sporobolomyces roseus* (Sporo1|33368) hypertext transfer protocol site:genome.jgi-psf.org/Sporo1/Sporo1.home.html). A POP enzyme has been previously purified from the mushroom *Lyophyllum cinerascens* (Yoshimoto, et al., (1988) *J Biochem.* 104:622; herein incorporated by reference). Surprisingly, POP orthologs (POP-like genes and proteins) are rare or nonexistent in fungi outside of the Basidiomycetes, a possible exception being one in the Ascomycete *Phaeosphaeria* (*Septoria*) *nodorum* (SNOG_11288). However, this single potential Ascomycete POP-like gene is much less similar to human POP than any of the POP-like genes found in Basidiomycetes.

TABLE 12

Exemplary results using human prolyl oligopeptidase (POP; (GenBank NP_002717, SEQ ID NO: 150) as a query sequence for fungal sequences (BLAST of GenBank unless otherwise noted).

| Fungal sequences related to human POP found in public databanks | Sequence Reference No. | SEQ ID NO: XX |
|---|---|---|
| human prolyl oligopeptidase (POP). | (GenBank NP_002717) | SEQ ID NO: 150 |
| *Coprinopsis* (*Coprinus*) *cinereus* | (GenBank CC1G_09936) | SEQ ID NO: 151 |
| *Ustilago maydis* | (GenBank UM05288) | SEQ ID NO: 152 |
| *Cryptococcus neoformans* | (GenBank XP_567311) | SEQ ID NO: 153 |
| *Cryptococcus neoformans* | (GenBank XP_567292) | SEQ ID NO: 154 |
| *Laccaria bicolor** | (The DOE Joint Genome Institute (JGI) Lacbi1|303722) | SEQ ID NO: 155 |
| *Phanerochaete chrysosporium* * | (The DOE Joint Genome Institute (JGI) Phchr1|1293) | SEQ ID NO: 156 |
| *Puccinia graminis* | PGTG_14822.2 | na |
| *Sporobolomyces roseus** | (The DOE Joint Genome Institute (JGI) 1|33368, Sporo1|33368) | SEQ ID NO: 157 |
| mushroom *Lyophyllum cinerascens* | Yoshimoto, et al., (1988) *J. Biochem.* 104: 622; herein incorporated by reference | na |
| Ascomycete *Phaeosphaeria* (*Septoria*) *nodorum* | (GenBank SNOG_11288) | SEQ ID NO: 158 |

Based upon these discoveries the inventors contemplated that a POP-like protease was rare or nonexistent in the Ascomycota yet found widespread within the Basidiomycota.

Example XV

This example describes the identification and isolation of an *Amanita bisporigera* orthologous to human prolyl oligopeptidase (POP). The inventors used the sequence for human POP (GenBank NP_002717) for screening their *A. bisporigera* genomic DNA sequence database.

Genome survey sequences were identified in the *A. bisporigera* genome (subject) by TBLASTN using human POP (GenBank accession no. NP_002717, SEQ ID NO:150) as a query sequence (FIG. 16 and Table 13).

TABLE 13

Exemplary homology results using human prolyl oligopeptidase (POP) as a query sequence (BLAST of *A. bisporigera* genome).

| Sequences related to human POP found in the Amanita genome of the present inventions | SEQUENCE | SEQ ID NO: |
|---|---|---|
| ECGK9LO02JKSHRR | TTGAGAGCACACAAGTCTGGTATGAGAGC AAAGACGGAACGAAAGTTCCAATGTTCAT CGTTCGTCACAAATCAACGAAATTTGACG GAACGGCGCCGGCGATTCAAAACGG | SEQ ID NO: 159 |
| ECGK9LO02JKSHRR | ESTQVWYESKDGTKVPMFIVRHKSTKFDGT APA | SEQ ID NO: 160 |

TABLE 13-continued

Exemplary homology results using human prolyl oligopeptidase
(POP) as a query sequence (BLAST of A. bisporigera genome).

| Sequences related to human POP found in the Amanita genome of the present inventions | SEQUENCE | SEQ ID NO: |
|---|---|---|
| contig26093 | CGTATATCGAACTGCCAAGGTCAAGGGTT TAAATCCGAACGATTTCGAGGCTCGACAG GTGACTAGTTGGTTTTATATTGCATGAAA AGTGCGTCTCATGCGGTCTAGGTGTGGTA TGACAGCTACGACGGAACAAAGATTCCA ATGTTCATCGTCCGTCACAAGAATACCAA ATTTAATGGGACGGCGCCAGCTATACAAT ATGG | SEQ ID NO: 161 |
| contig26093 | VWYDSYDGTKIPMFIVRHKNTKFNGTAPAI QY | SEQ ID NO: 162 |
| ECIM01V02I2IO5 A | CGACAAACAAGTAACACCTACGCGCGAA AAACTCGCGATCTCCGGCGGCAGCAACGG CGGACTCCTCGTCGGCGCAAGCCGATTGA CCCAGCGCCCCGACCTCTTCG | SEQ ID NO: 163 |
| ECIM01V02I2IO5 A | EKLAISGGSNGGLLVGASRLTQRPDLF | SEQ ID NO: 164 |
| ECIM01V01CKHE5R | ATCCTCGGATGGCACAGCCTCGCTCTCCA TGTATGATTTCTCACACTGTGGCAAATAC TTCGCATATGGTATTTCTCTTTCCGTATGT AATTTT | SEQ ID NO: 165 |
| ECIM01V01CKHE5R | SSDGTASLSMYDFSHCGKYFAYGISLS | SEQ ID NO: 166 |
| EEISCGG02IHTSVR | GGGATAATTAATTGCAGCGAGTTATGACA ACGGAAAAACCCACCTCTTCTCAGTAGAT TTTCCTCCGCCATGCCCCCGCTTTCTTGTCT ACACGTAGCAGAAGTGGA | SEQ ID NO: 167 |
| EEISCGG02IHTSVR | PLLLRVDKKAGHGGGKSTEK | SEQ ID NO: 168 |
| ECIM01V02H2WNRS | DGTKVPMFIVRHKSTK | SEQ ID NO: 169 |

After identifying homologous fragments, the inventors used PCR to amplify two Amanita prolyl oligopeptidase (POP)-like genes, with primers shown in Tables 14A and 14B. The full genomic sequences of prolyl oligopeptidas-likeA (POPA), SEQ ID NO: 170 and prolyl oligopeptidas-likeB (POPB), SEQ ID NO: 171 are shown in FIG. 17. Based on 5' and 3' RACE, using primers shown in Tables 14A and 14B, cDNA clones were obtained and sequenced, SEQ ID NOs: 234 and 235. Comparison of full length genomic and cDNA sequences (FIG. 17A -17B) indicated that POPA and POPB each have 19 introns. The cDNA sequences of POPA and POPB are shown (FIG. 14B). The amino acid sequences of POPA and POPB are shown in (FIG. 17C), SEQ ID NOs: 236 and 237.

TABLE 14A

PCR primers used to amplify prolyl oligopeptidase-likeA (POPA)
genomic sequences and for 5' and 3' RACE to identify full-length
cDNA clones of POPA.

| Primer | Sequence | SEQ ID NO: |
|---|---|---|
| PopA genomic forward primer | 5' GAAACGAGAGGCGAAGTCAAGGTG 3' | SEQ ID NO: 172 |
| PopA genomic reverse primer | 5' AAGTGGATGACGATTATGCGGCAG 3' | SEQ ID NO: 173 |
| PopA gene-specific primer for 3' RACE (used with GeneRacer 3' primer) | 5' GATTGGGTATTTGGCGCAGAAGTCACG 3' | SEQ ID NO: 174 |

TABLE 14A-continued

PCR primers used to amplify prolyl oligopeptidase-likeA (POPA) genomic sequences and for 5' and 3' RACE to identify full-length cDNA clones of POPA.

| Primer | Sequence | SEQ ID NO: |
|---|---|---|
| PopA gene-specific primer for 5' RACE (used with GeneRacer 5' primer) | 5' ATGTCTCGCCGAACTCGCCGCCTCCTC 3' | SEQ ID NO: 175 |

TABLE 14B

PCR primers used to amplify prolyl oligopeptidase-like B (POPB) genomic sequences and for 5' and 3' RACE to identify full-length cDNA clones of POPA.

| Primer | Sequence | SEQ ID NO: |
|---|---|---|
| PopB genomic forward primer | 5' TCAAATGAAGTAGACGAATGGAC 3' | SEQ ID NO: 176 |
| PopB genomic reverse primer | 5' CACACGGATGAGCAATGGATGAG 3' | SEQ ID NO: 177 |
| PopB gene-specific primer for 3' RACE (used with GeneRacer 3' primer) | 5' AAAGTTCCAATGTTCATCGTTCGTCA 3' | SEQ ID NO: 178 |
| PopB gene-specific primer for 5' RACE (used with GeneRacer 5' primer) | 5' TGGGACTAAAGAATGGATCGGCTGTAAT 3' | SEQ ID NO: 179 |

The finding of a second POP gene was unexpected. Furthermore, the inventors found at least two POP genes in *A. bisporigera*, while the majority of other mushrooms whose genomes were examined by BLAST had only one POP (i.e., *Coprinus cinerea, Laccaria bicolor, Phanerochaete chrysosporium*, and *Agaricus bisporus*). Based on genome survey sequences, *Galerina* species are contemplated to contain genes for the two types of POPs (see above). By Southern blotting, POPA is present in all *Amanita* species (FIG. 18A). POPB, on the other hand, is present only in peptide toxin-producing species, corresponding to the discovery of genes encoding its putative substrates, AMA1 and PHA1 (FIG. 18B). In these experiments, the Southern blot of different *Amanita* species probed with (A) POPA or (B) POPB of *A. bisporigera*. Lanes 1-4 are *Amanita* species in sect. Phalloideae and the others are peptide toxin non-producers. Note the presence of POPA and absence of POPB in sect. Validae (lanes 5-8), the sister group (i.e., the section most closely related) to sect. Phalloideae (lanes 1-4). We attribute the weaker hybridization of POPA to the *Amanita* species outside sect. Phalloideae (lanes 5-13) to lower DNA loading and/or lower sequence identity due to taxonomic divergence.

POPB fragments were not observed to hybridize to any species tested outside of sect. Phalloideae even after prolonged autoradiographic exposure. Therefore, the inventors contemplated that while POPA appears to be present in the genomes of peptide toxin producing and peptide nontoxin producing mushrooms, the presence of POPB appears to be limited to peptide toxin producing mushroom species and thus identifies an amanitin-toxin producing mushroom from a nontoxin (at least for amanitin) producing mushroom.

Example XVI

This example describes the expression and isolation of prolyl oligopeptidase (POP) of the present inventions.

The inventors first tried to express POP genes from *A. bisporigera* in a heterologous system, which has been successful with porcine and bacterial POPs (Szeltner et al., 2000; Shan et al., 2005). Exhaustive attempts were made to express these fungal proteins in *E. coli* or *Pichia pastoris* in a soluble, active form but were unsuccessful. However the inventors were able to use the inclusion bodies to raise antibodies; see below.

Therefore, the inventors purified POP from the mushroom *Conocybe lactea* (also known as *C. albipes* or *C. apala*). *Conocybe lactea* was chosen as a source of POP because (1) it produces phalloidin, one of the phallotoxins; (2) it grows abundantly in the lawns of Michigan State University while *Amanita* mushrooms themselves are less common and more restricted in their fruiting season. Proteins isolated from

*Conocybe* were assayed for POP activity with a standard colorimetric substrate (Z-Gly-Pro-pNA) and was inhibited by a specific POP inhibitor, Z-Pro-Prolinal.

The inventors synthesized model peptides, ATRLPIWGIGCNPCVGDD (SEQ ID NO:318), MSDINATRLPAWLATCPCAGDD, and ATRLPAWLVDCPCVGDD (SEQ ID NO:249), i.e., the mature toxin peptides flanked by five amino acids on each end. Based on other successful synthetic POP substrates (e.g., Shan et al., 2005; Szeltner et al., 2000), these were contemplated as test mimics of the proproteins. The peptides IWGIGCNP (SEQ ID NO:50), AWLATCP (SEQ ID NO: 136), and AWLVDCP (SEQ ID NO:69) were also synthesized as standards.

Figure 19:
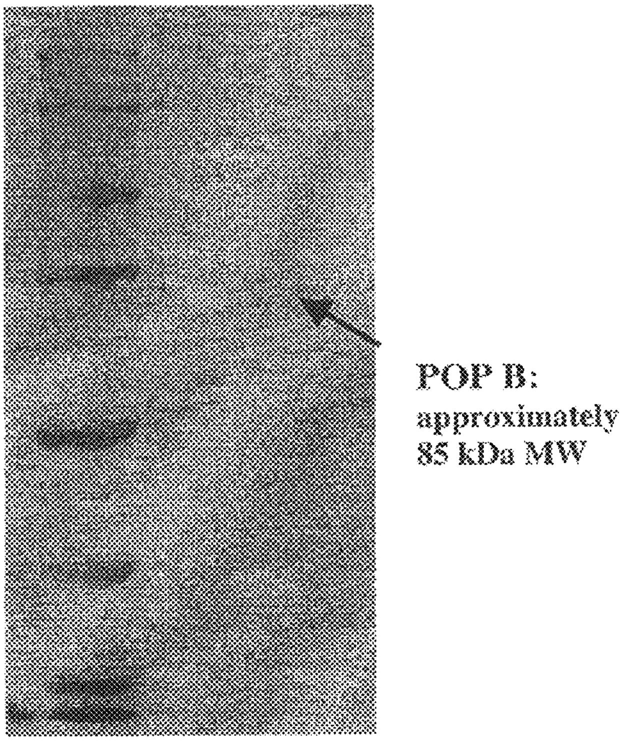
FIG. 19 shows exemplary purified POPB protein isolated from *Conocybe albipes*, also known as *C. lactea* and *C. apala*, which produces phallotoxins, separated by standard SDS-PAGE gel electrophoresis and Coomassie Blue dye stained to show the location of protein.

Extracts of *Conocybe* mushrooms catalyze the cleavage of a model phalloidin peptide to the mature heptamer. The responsible enzyme was purified. Specifically, *Conocybe* mushrooms were freeze-dried, ground in buffer, and the extracts concentrated by ammonium sulfate precipitation. After desalting, the proteins were fractionated by anion exchange high-performance liquid chromatography (or high pressure liquid chromatography, HPLC). FIG. 19.

Fractions containing peptides were assayed using Z-Gly-Pro-pNA and the model phallacidin substrate. Reaction products were separated by reverse phase HPLC (FIG. 20). In some experiments the HPLC eluant was analyzed by MS, while in other cases the peaks of UV absorption were collected and analyzed by MS in the inventors' lab and the central LC/MS facility, in particular for long HPLC run times. The Michigan State University Proteomics and Mass Spectrometry facilities are equipped with several suitable mass spectrometers, including a Waters Quattro Premier XE LC MS/MS (for simultaneous separation and identification), vMALDI MS/MS, and a Shimadzu MALDI TOF MS/MS (for analysis of collected HPLC fractions). PepSeq within the MassLynx program was used to determine peptide sequences. The peptides eluting from HPLC were monitored at 280 nm.

The inventors purified the enzyme responsible for cleaving synthetic model compounds to the linear, mature forms to a single band on an SDS-PAGE gel. Sequencing of this protein showed high sequence similarity to POPA and POPB from *A. bisporigera* and POP proteins from other organisms including pig and human. After incubation of the test propeptide and the isolated POPB, the inventors consistently observed the production of a mature seven-amino acid product (FIG. 20B), whose identity was confirmed by the high resolution mass of the parent compound and the deduced amino acid sequence derived from MS/MS fragmentation. The inventors also detected one of the two possible intermediate products (i.e., (MSDINATRLPAWLATCP)) transiently, but not a compound of the right mass to be the cyclized product. Thus, the same enzyme cuts the phalloidin precursor at both Pro residues, and cuts first at the second (C-terminal) Pro. The cleavage activity was sensitive to boiling of the mushroom extract (FIG. 20A) indicating that the reaction is catalyzed by a labile protein, and was inhibited by Z-Pro-Prolinal, a specific POP inhibitor, which is further evidence that a POP catalyzes this reaction. The same fractions showed activity against the colorimetric generic POP substrate Z-Gly-Pro-pNA and against the synthetic peptide. Confirmation of reaction product structures was accomplished by MS/MS.

The results showed that purified POP cuts a synthetic phalloidin peptide precisely at the expected flanking Pro residues. The purified POP also cut a synthetic amanitin precursor and a synthetic phallacidin precursor.

Further contemplated products (shown in Table 15) for alpha-amanitin; phalloidin precursors where natural or synthetic propeptide sequences will be the substrates for *Conocybe* POPB protein.

TABLE 15

Peptides and their corresponding molecular mass for use in the present inventions.

| SEQ ID NO: | Peptide No. | AMA1 peptides | Mr (molecular mass) |
|---|---|---|---|
| 549 | 1 | TRLPIWGIGCNPCIGD (substrate) | 1714.99 |
| 549 | 2 | TRLPIWGIGCNPCIGD (substrate, Cys oxidized to disulfide) | 1712.99 |
| 551 | 3 | TRLPIWGIGCNP (cut on C side) | 1326.55 |
| 552 | 4 | IWGIGCNPCIGD (cut at N side) | 1247.42 |
| 552 | 5 | IWGIGCNPCIGD (cut at N side, oxidized) | 1245.42 |
| 50 | 6 | IWGIGCNP (final product, cut both sides) | 858.98 |
| 51 | 7 | IWGIGCNP (cyclized) | 840.97 |

Figure 20:
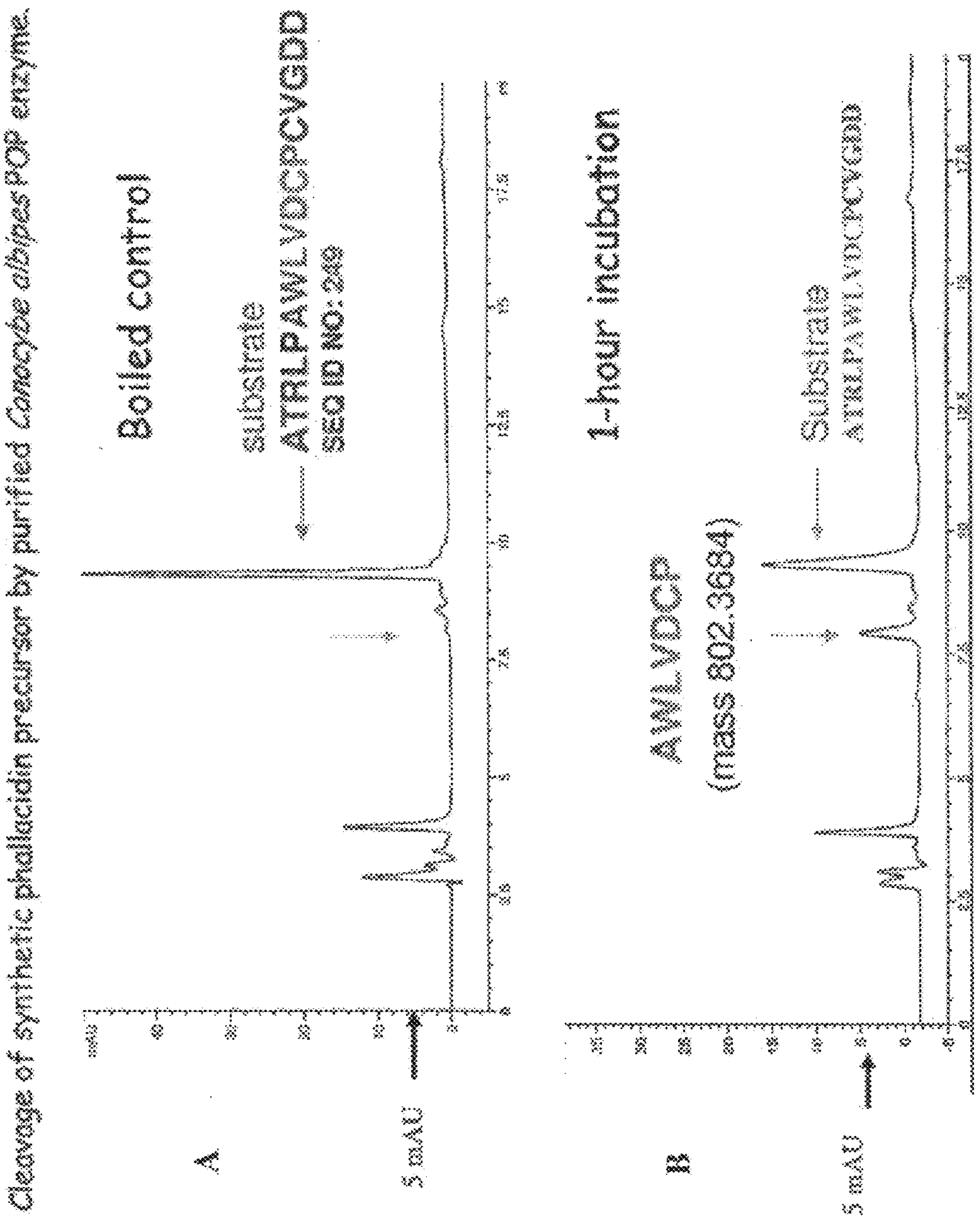
FIG. 20 shows an exemplary experiment demonstrated that POPB of *C. albipes* processed a synthetic phallacidin propeptide to the mature linear heptapeptide A) HPLC analysis of an enzymatic reaction of a synthetic phallacidin propeptide with a boiled sample of POPB showing no cleavage product at the vertical arrow where a AWLVDCP (SEQ ID NO: 69) should be found and B) cleavage of a synthetic phallacidin precursor by purified *Conocybe albipes* POPB enzyme (see, FIG. 19) showing a cleavage product matching AWLVDCP (SEQ ID NO: 69) at the vertical arrow. The identity of the cleavage product was confirmed by Mass Spectrometry. The results show that purified POPB cuts a synthetic phallacidin peptide precisely at the flanking Pro residues.

Thus, the inventors found production of the mature heptapeptide of phalloidin by extracts of *Conocybe*, i.e. isolated POPB extracts (FIG. 20). Thus purified POPs from *Amanita* and *Galerina* are contemplated to release peptides 3, 4, and/or 6 from an amanitin precursor (prepropeptide or portion thereof).

*Amanita* species in sect. Phalloideae, and *Galerina*, have two predicted POP genes (FIG. 17).

Example XVII

In this Example, POPA and POPB of *A. bisporigera* were expressed in inclusion bodies, purified and used to provide rat anti-POPA and POPB antibodies for use in the present inventions.

*E. coli* were engineered for expressing POPA and POPB (in separate bacterium). Expression of recombinant POP was done by the procedures outlined in the pET handbook (Novagen). Briefly, a pET vector engineered to comprise a POP coding sequence of the present inventions was transformed into *Escherichia coli* AD494 cells, and cultures were grown according to the manufacturer's instructions in Luria-Bertani medium and then induced with isopropyl-D-thiogalactoside (final concentration of 1 mM) for 3 h. Pelleted cells were lysed with a French press (16,000 p.s.i.) and recentrifuged, and the pellet was extracted with B-Per II reagent (Pierce, Rockford, Ill.). The resulting purified inclusion bodies were solubilized and refolded using the Protein Refolding Kit (Novagen) according to the manufacturer's instructions.

Figure 21:
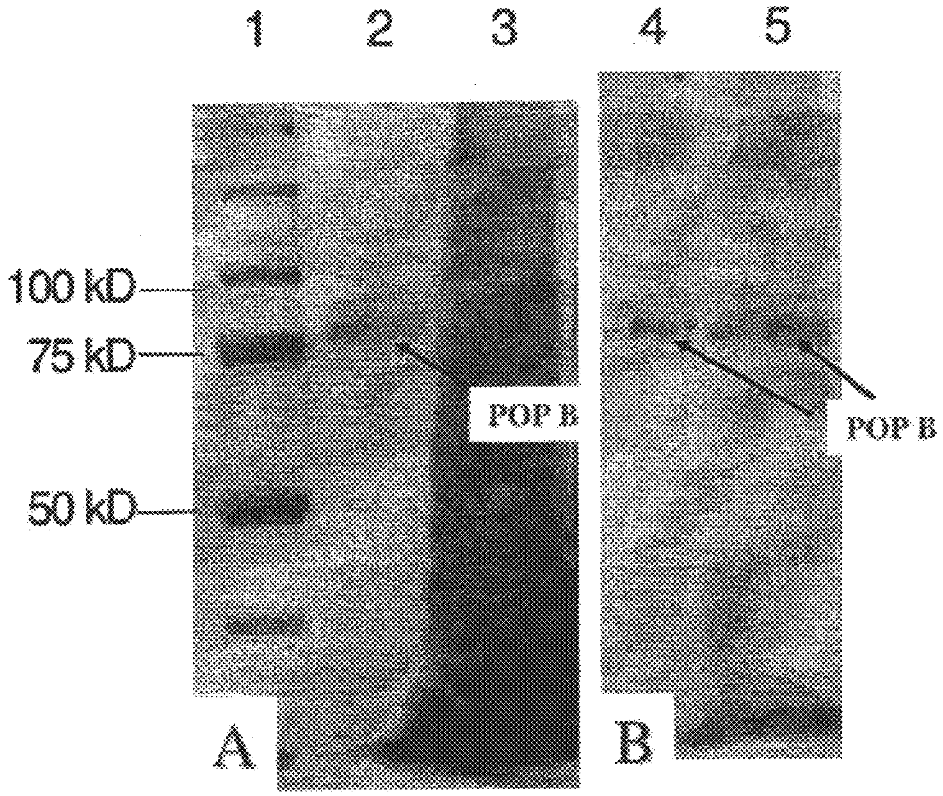
FIG. 21 shows exemplary expression of POPB in *E. coli* and production of anti-POPB antibodies. Lane 1: Markers; Lane 2: recombinant POPB expressed by *E. coli* purified from inclusion bodies; Lane 3: Soluble extract of *Amanita bisporigera*; Lane 4: Immunoblot of POPB inclusion body; Lane 5: Immunoblot of *Amanita bisporigera* extract with antibody raised against purified POPB; where the crude antiserum (as drawn from rats) was used at 1:5000 dilution and a reaction product was observed with an anti-rat antibody using well known visualization methods, arrows point to the bands corresponding to single band of POPB protein. A) Lanes 1-3: stained with Coomassie Blue. B) Lanes 4-5 antibody binding visualized by enhanced chemiluminescence.

The inventors raised antibodies against POPA and POPB of *A. bisporigera* (POPB shown in FIG. 21A) showing immunoreactivity to a band of the same molecular weight as POPB (arrows) (FIG. 21B). The inventors observed that anti-POPB antibodies did not cross-react with POPA. Cross-reactivity between POPB and POPA was not contemplated to be a concern because POPA and POPB are merely 55% identical at the amino acid level, and the immunoblot showed a single band (FIG. 21; Lane 1: Markers. Lane 2: POPB purified from inclusion bodies. Lane 3: Total soluble extract of *Amanita bisporigera*. Lanes 1-3 were stained with Coomassie blue. Lane 4: immunoblot of POPB inclusion body. Lane 5: immunoblot of *Amanita bisporigera* extract. Crude antiserum was used at 1:5000 dilutions.

Example XVIII

In this example, exemplary *Galerina* POP sequences identified using *Amanita bisporigera* POPA and POPB were used as query sequences for searching a library of *Galerina* sequences created by the inventors for their use during the development of the present inventions, and additional mushroom libraries. These *Galerina* sequences were obtained by the inventors from 454 sequencing (45 Mb total), see above. Not every sequence with identity to these genes are shown, merely what are considered the best examples.

*Galerina marginata* POP sequences were identified using *Amanita bisporigera* POPA (FIG. 22A) and POPB (FIG. 22B) as query sequences. The specific regions of identity and corresponding sequences are listed. The higher scoring hits (areas of identity) were strong evidence that the *Galerina* genome contains at least two POP genes. The inventors contemplate using these fragments for isolating full-length sequences for use in the present inventions.

Example XIX

Genes for fungal secondary metabolites are typically clustered (Walton, 2000; Keller et al., 2005). Examples include aflatoxin, penicillin, HC-toxin, fumonisin, sirodesmin, and gibberellins (Ahn et al., 2002; Gardiner et al., 2004; Tudzynski and Holter, 1998). From Basidiomycetes, an example of clustering are the genes for ferrichrome (Welzel et al., 2005).

To test clustering of *Amanita* toxin genes, the inventors constructed a partial lambda genomic library of *A. bisporigera* (insert size about 15 kb) and screened it with PHA1. One exemplary lambda clone was found to contain two copies of PHA1 and three putative cytochrome P450 genes (FIG. 10D). (Based on inverse PCR results, the inventors also discovered two copies of PHA1 in *A. bisporigera* on a single lambda clone. Thus, at least two *Amanita* peptide toxin genes are clustered in the genome of *A. bisporigera*. Furthermore, because *Amanita* peptide toxins undergo three to five hydroxylations (FIG. 1), which reactions are often catalyzed by P450's in fungi and other organisms (e.g., Malonek et al., 2005; Tudzynski et al., 2003), one or all of these three P450 genes also has a plausible role in the biosynthesis of the *Amanita* peptide toxins. Therefore, on both theoretical and experimental grounds the inventors contemplated finding additional *Amanita* peptide toxin biosynthetic genes by examining regions of DNA adjacent to the known *Amanita* peptide toxin genes.

In this example, a software program and system, FGENESH, Salamov and Solovyev, Genome Res. 2000. 10:516-522, at softberry.com, //linux 1.softberry.com/berry.phtml?topic=fgenesh& group=programs&subgroup=-gfind. was used to identify and predict novel sequences adjacent to PHA genes of a 13,254 bp lambda clone (SEQ ID NO:327). This software predicts genes (by which we mean predicting where the gene starts and stops and where intron and exons are) when the gene is pasted in as genomic sequence. In recent rice genome sequencing projects, this software was cited "the most successful (gene finding) program (Yu et al. (2002) Science 296:79) and was used to produce 87% of all high-evidence predicted genes (Goff et al. (2002) Science 296:79).

However, gene prediction is an inexact science, so the FGENESH software is "trained" with known gene structures from different organisms. That is, different organisms have different (and poorly understood) rules for gene structure. Gene structure in humans isn't the same as plants, etc. To get the best prediction, an organism on which the software has been trained that is taxonomically closest to the source of the DNA was used. Therefore, the inventors used a known *Coprinus* (*Coprinopsis*) *cinerea* model for their *Amanita* genes.

Using this type of analysis as shown in FIGS. 24-30, the inventors found in an adjacent piece of genomic DNA, two PHA1 genes (one by FGENESH) and 3 P450's, P450-1 (OP451), P450-2 (OP452) and P450-3 (OP453). For comparison, an estimated number of P450 genes in other organisms are provided as follows: Human 50, *Arabidopsis* 273, *Phanerochaete* 149, *Fusarium* 110, *Ustilago* 17, while there are 282 families of fungal P450's. For each contemplated gene, a BLASTp search was made in the inventors' mushroom libraries and publically available libraries including NCBI GENBANK and *Coprinus cinereus* genome annotations (Broad contigs) at //genome.semo.edu/cgi-bin/gbrowse/cc/?reset=l, Genomic sequence data from the Broad Institute (broad.mit.edu/annotation/genome/coprinus_cinereus/Home.html, herein incorporated by reference in it's entirety). The predictions may not find every sequence, however the inventors at this time show that the lambda clone analyzed herein contains at least three P450 genes, genes 1, 2, and 4, at least one PHA gene, gene 5, and at least one unidentified gene that is not PHA1-2, Gene 6, Gene 6 has no significant match to any protein in NCBI GenBank. In addition to the genes listed in the Figures, a PHA1-2 was found (where the software analysis showed a start, stop, and introns correctly) but FGENESH did not predict PHA1-1, which, however, is clearly present by manual annotation.

This example shows that two copies of PHA1 are clustered with each other and with three P450 genes. A map of predicted genes in this lambda clone (13.4 kb), isolated using PHA1 as probe is shown in FIG. 10D.

Example XX

This example shows identification of exemplary variants of two α-amanitin genes identified in laboratory isolates of *Galerina marginata*.

The inventors' were surprised to discover that sequences of the peptide toxin genes in *Galerina marginata* are quite different compared to *A. bisporigera*. See FIGS. 12 and 33A and B for alignments of *Galerina* and *Amanita* peptide toxin proteins. For this example, approximately 73 MB of final assembled genomic DNA, as described above, was sequenced by 454 pyrosequencing. 73 MB was estimated to be approximately two times the size of the *G. marginata* genome based on the average size of known basidiomycete genomes. These sequences were put into a private database and searched using AMA1, PHA1, AbPOPA, and AbPOPB protein sequences The DNA contigs showing predicted protein sequences closely related to AbPOPB and AbPOPA were further analyzed. PCR primers were made to predicted sequences at the two ends of the proteins and used to amplify from genomic and cDNA full length genomic and mRNA copies of the two genes. Four examples of contigs are shown in FIG. 41. The results for GmAMA1 variants are described in this example while the results of screening for POP genes are described in the following example.

Using AMA1 from *A. bisporigera* as the search query, two orthologs of AMA1 were identified in the partial genome survey sequence of *G. marginata* and designated as GmAMA1-1 and GmAMA1-2.

PCR primers unique to GmAMA1-1 and GmAMA1-2 were designed. For GmAMA1-1, the unique primers were 5'-CTCCAATCCCCCAACCACAAA-3' (forward, SEQ ID NO:682) and 5'-GTCGAACACGGCAACAACAG-3' (reverse, SEQ ID NO:683). For GmAMA1-2, the primers were: 5'-GAAAACCGAATCTCCAATCCTC-3' (forward, SEQ ID NO:684), and 5'-AGCTCACTCGTTGCCACTAA-3' (reverse, SEQ ID NO:685). PCR primers for each gene were designed based on the partial sequences and used to amplify full-length copies. The amplicons were cloned into *E. coli* DH5α and sequenced.

The genomic DNA sequences were used for primer design to obtain full-length cDNAs by Rapid Amplification of cDNA Ends (RACE) using the GeneRacer kit (Invitrogen, Carlsbad, Calif.). A cDNA copy of GmAMA1-1 was obtained using primers 5'-CCAACGACAGGCGGGA-CACG-3' (5'-RACE, SEQ ID NO:686) and 5'-GAC-CTTTTTGCTTTAACATCTACA-3' (3'-RACE, SEQ ID NO:687), and of GmAMA1-2 with primers 5'-GT-CAACAAGTCCAGGAGACATTCAAC-3' (5'-RACE, SEQ ID NO:688) and 5'-ACCGAATCTCCAATCCTC-CAACCA-3' (3'-RACE, SEQ ID NO:689).

Alignments of genomic and cDNA copies were done using Spidey located at (ncbi.nlm.nih.gov/spidey/) and Splign (ncbi.nlm.nih.gov/sutils/splign/splign.cgi).

GmAMA1-1 contains three introns while GmAMA1-2 contains two introns (FIG. 33). The three introns of GmAMA1-1 are 53, 60, and 60 nt in length in similar locations as the three introns of AMA1. The first intron in both GmAMA1-2 and GmAMA1-2 interrupts the third codon before the stop codon. GmAMA1-1 and GmAMA1-2 differ in at least eight nucleotides out of 108 nucleotides in the coding region (i.e., from the ATG through the TGA stop codon). At least two of these differences result in amino acid changes and six changes are silent, i.e no change in amino acid at that location (FIG. 33). There are numerous nucleotide differences between GmAMA1-1 and GmAMA1-2 in the 5' and 3' untranscribed regions in addition to having large stretches of close identity. The biggest difference between GmAMA1-1 and GmAMA1-2 is that the latter gene has a 100-bp deletion relative to GmAMA1-1, which spans the second intron of GmAMA1-1. This deletion is in the 3' UTR (FIG. 32). This accounts for the presence of only two introns in GmAMA1-2 (FIGS. 32 and 33).

The translational start site of a gene is typically contemplated as the first in-frame ATG after the transcriptional start site. When this criterion was applied to GmAMA1-1, a start site was indicated that was analogous to AMA1 of *A. bisporigera*. However, when this criteria was applied to GmAMA1-2, there was an in-frame ATG that is 78 nucleotides upstream of the ATG indicated in FIG. 33, which would result in a proprotein of 61 amino acids instead of 35 as predicted for AMA1 and GmAM1-1. Thus two start sites are contemplated, one that results in a 61 amino acid preproprotein, SEQ ID NO:690, and the other in a 35 amino acid proprotein, SEQ ID NO:691. However the inventors' contemplate that the 35 amino acid preproprotein is the target of the Gm POP proteins, for an example showing that prolyl oligopeptidases act on other types of peptides less than 40 amino acids see, Szeltner and Polgar, 2008, herein incorporated by reference).

GmAMA1-1 and GmAMA1-2 were both predicted to encode 35-amino acid proproteins, the same size as the proprotein of AMA1 in *A. bisporigera*. The toxin-encoding region (IWGIGCNP) was in the same relative position as it was in AMA1. There were 31 nucleotide differences between GmAMA1-1 and AMA1 in the coding region of 108 nucleotides (ATG through the stop codon). This results in a low level of amino acid conservation outside the toxin region and the amino acids immediately upstream of the toxin region (NATRLP, SEQ ID NO:754 (FIG. 33).

The sequenced proproteins were added by the inventors to form a group of a family of genes including and related to AMA1 and PHA1 in *A. bisporigera, A. phalloides*, and *A. ocreata* start with MSDIN. In contrast, when a start codon is contemplated in the same location between GmAMA1-1 and GmAMA1-2 the first five amino acids of the two *G. marginata* α-amanitin genes are MFDTN, SEQ ID NO: 675. Searching of the *G. marginata* database with the upstream and downstream regions of GmAMA1-1 and GmAMA1-2 did not reveal any additional related sequences. Conversely, searching with the conserved regions of GmAMA1-1 and GmAMA1-2 did not reveal any related sequences in *A. bisporigera* beyond the known MSDIN family members described herein.

Example XXI

This example shows identification of two exemplary full-length genes encoding orthologs of Prolyl oligopeptidase genes, i.e. POPA and POPB proteins, isolated from *G. marginata*.

During the development of the present inventions, using a *G. marginata* partial genome survey, the inventors' discovered two orthologs of the POP genes of *A. bisporigera*. These two orthologs corresponded to the two *A. bisporigera* prolyl oligopeptidases (AbPOPA and AbPOPB) described herein. The *G. marginata* genes with closest identity to AbPOPA or AbPOPB were designated as GmPOPA and GmPOPB, respectively. Genomic PCR, reverse transcriptase PCR, and RACE were used, as described herein, to isolate full-length copies of these two genes and determine their intron/exon structures (FIG. 37). GmPOPA had 18 introns, which is the same number found in AbPOPA, while GmPOPB had 17 introns, one fewer than in AbPOPB. The amino acid sequences of the predicted translational products of GmPOPA (738 amino acids) and GmPOPB (730 amino acids) are 57% identical to each other. The GmPOPA protein is 65% identical to AbPOPA and 58% identical to AbPOPB, and GmPOPB is 57% identical to AbPOPA and 75% identical to AbPOPB.

Sequences hybridizing to AbPOPA were found to be present in amatoxin and phallotoxin-producing and non-producing species of *Amanita*, whereas AbPOPB was found present only in the toxin-producing species. By DNA blotting GmPOPA was present in all four specimens of *Galerina*, however GmPOPB was not present in the amanitin non-producing species *G. hybrida* (FIG. 34). The similarity of the hybridization pattern of *G. venenata* and *G. marginata* to GmAMA1, GmPOPA, and GmPOPB was consistent with these two isolates belonging to the same species (see, Gulden et al., 2001, herein incorporated by reference). The association of POPB with amanitin production in both *A. bisporigera* and *G. marginata*, and the higher amino acid identity of GmPOPA to AbPOPA and of GmPOPB to AmPOPB was consistent with a contemplated role for POPB in amanitin biosynthesis in both species. Other basidiomycetes in GenBank and at the DOE Joint Genome Institute (JGI) have single POP genes, which are contemplated as functional orthologs of POPA.

For isolating and cloning full-length cDNA sequences for GmPOPA (SEQ ID NO: 715) and GmPOPB (SEQ ID NO: 717), PCR primers that corresponded to the amino and carboxyl termini of both genes (which were present on different contigs) were designed from the genome survey sequence. The forward primers were 5'-TTTAGGGCAGTGATTTCGTGACA-3', SEQ ID NO: 692, and 5'-AACAGGGAGGCGATTATTCAAC-3', SEQ ID NO: 693, and the reverse primers were 5'-GAACAATCGAACCCATGACAAGAA-3', SEQ ID NO: 694, and 5'-CCCCCATTGATTGTTACCTTGTC-3', SEQ ID NO: 695. The primer pairs were used in both combinations and successful amplification indicated the correct pairing of 5' and 3' primers. The resulting amplicons were cloned into *E. coli* DH5α and sequenced.

The RACE primers for GmPOPA were 5'-CGGCGTTCCAAGGCGATGATAATA-3' (5'-RACE), SEQ ID NO: 696, and 5'-CATCTCCATCGACCCCTTTTTCAGC-3' (3'-RACE), SEQ ID NO: 697, and for GmPOPB 5'-AGTCTGCCGTCCGTGCCTTGG-3' (5'-RACE), SEQ ID NO: 698, and 5'-CGGTACGACTTCACGGCTCCAGA-3' (3'-RACE), SEQ ID NO: 699. Sequences generated from the RACE reactions were used to assemble full-length cDNAs of two genes, GmPOPA and GmPOPB (see FIGS. 38A and 38B).

Alignments of genomic and synthetic cDNA copies (see, FIGS. 38A and 38B) were done using Spidey available at National Center for Biotechnology Information (NCBI) at websites www.ncbi.nlm.nih.gov/spidey/ and Splign www.ncbi.nlm.nih.gov/sutils/splign/splign.cgi).

GmPOPA and POPB were predicted to encode exemplary polypeptides as shown in FIG. 38A (SEQ ID NO: 716) and 38B (SEQ ID NO: 722), respectively.

Example XXII

This example shows an exemplary successful transformation of *G. marginata*.

The inventors grew *G. marginata* in the laboratory and collected mycelium for use in the following transformation procedure. The inventors show herein the successful transformation of the alpha-amanitin-producing fungus *Galerina marginata* with a test construct. Thus the inventors' contemplate producing commercial levels of amanatin in addition to novel, non-natural analogs of amanitin. Further, the inventors' contemplate making novel linear and cyclic peptides from synthetic prepropeptides.

The following are exemplary methods for making buffers and reagents for us in the present inventions. *Galerina* culture methods: Vegetative mycelial stocks were prepared by culturing aseptic fragments of fruiting bodies on HSVA plates. Fungal colonies were transferred and reisolated until pure cultures were obtained. The stocks were subcultured every 6 months. HSV-2C (1 L): 1 g yeast extract, 2 g glucose, 0.1 g $NH_4Cl$, 0.1 g $CaSO_4.5H_2O$, 1 mg thiamine. HCl, and 0.1 mg biotin, pH 5.2 (Muraoka and Shinozawa, 2000, herein incorporated by reference). Agar medium (HSVA) for subculture contained 2% agar in HSV. Protoplasting Buffer: In 20 ml of 1.2 M KCl add 500 mg Driselase (Sigma), 1 mg chitinase (Sigma), and 300 mg lysing enzyme from *Aspergillus* sp. Sigma #L-3768. Stir for 30 min and filter sterilize in a 0.45 um filter. Sorbitol Tris-HCl Ca (STC) buffer: Solution a) 1.2 M sorbitol, 10 mM Tris-HCl (pH8.0), 50 mM $CaCl_2$, autoclaved. Solution b) 30, PEG Solution Mix: 30% (W/V) polyethylene glycol/STC buffer. Filter sterilize in a 0.45 um filter. Regeneration medium (RM): a) HSV-2C (1 L) and b) sucrose 273.5 g/500 ml of water. Autoclave solutions a) and b) separately and combine after autoclaving.

The following is an exemplary *Galerina* transformation protocol for use in the present inventions. Around 20 pieces of mycelium were used to inoculate 100 ml of HSV-2C broth in a 250 ml Erlenmeyer flask. This inoculate was placed on a shaker at 150 rpm at room temperature for 9-15 days, until cloudy. The culture medium and fungus was used to begin the following steps. The cultures were: 1. Filtered through sterile Miracloth and the collected mycelia was washed thoroughly with sterile water. This fungal mycelium was placed in a sterile 250 ml Erlenmeyer flask. 20 ml Protoplasting Buffer (see recipe below) was added. 2. Digested for 8 hours on a rotary shaker at 26-30 C at 120 rpm. 3. Digestion mix was filtered through a 30 micron Nitex nylon membrane (Tetko Inc. Kansas City, Mo., U.S.A.)) into 1-2 sterile 30 ml Oakridge tubes on ice. Filtered solution was turbulent due to the presence of protoplasts when checked under the microscope. 4. This filtered solution was centrifuged in Oakridge tubes at 4 C at 2000×g for 5 min. 5. Supernatant was carefully poured off and discarded. Protoplast pellet was gently resuspended in approx. 10 ml of STC buffer and resuspended by shaking gently. Solution was spun at 2000×g for 5 min. 6. Repeat step 5 once. 7. Supernatant was discarded and the protoplast pellet was gently resuspended in 1 ml of STC buffer with a wide orifice pipette and transferred to a microcentrifuge tube and spun at room temperature at 4000×g for 6 min. 8. Supernatant was poured off and protoplasts were resuspended in 1 ml of STC in a final volume with concentration of $10^8$-$10^9$ protoplast/ml. The tube was placed on ice. 9. The following mixture was combined: 50 μl protoplasts, 50 μl STC buffer, 50 ul 30% PEG solution and 10 ul plasmid or PCR product (1 μg) depending upon the experiment. When plasmids were used they were linearized with a restriction enzyme which cut the DNA in a noncoding region. 10. 2 ml of 30% PEG solution was added and the tubes incubated for 5 min. 11. 4 ml of STC buffer was added and gently mixed by inversion. 12. The mix was added to Regeneration Media (RM) (see below) at 47° C., and mixed by inversion then poured into Petri dishes. Each solution mixture was plated in several plates. 13. Protoplasts were regenerated for up to 20 days until tiny colonies started to appear as viewed by eye. 10 ml of RM amended with 10 μg/ml Hygromycin B was overlayed onto the cultures. 14. Putative transformants were isolated from colonies that grew after the Hygromycin B overlay and eventually emerged on the surface of the overlaid agar. Examples of colonies collected for use in the present inventions are shown by arrows in FIG. 39.

After colonies were collected the presence of the inserted Hygromycin B transgene was tested by PCR. Primers specific to the hygromycin resistance gene used in FIG. 40 were the following: hph_forward 5'-CGTGGATATGTCCTGCGGG-3' hph_reverse, SEQ ID NO:700, 5'-CCATACAAGCCAACCACGGC-3', SEQ ID NO: 701, (Kilaru et al., 2009, Curr Genet 55:543-550, herein incorporated by reference).

The inventor's contemplate that *G. marginata* can be transformed with synthetic genes, using the *G. marginata* specific contemplated cut sites, i.e. synthetic sequences comprising nucleotides encoding MDSTN, TRIPL and Prolines in conserved positions. For examples, in one embodiment, a synthetic DNA sequence encoding an amino acid sequence of alpha-amanitin may be expressed. In one embodiment, alpha-amanitin production would be increased, for example, using a high expression promoter, transforming *Galerina* with multiple copies of the alpha-amanitin gene.

In another contemplated embodiment, a synthetic, novel cyclic peptide is synthesized by transformed *Galerina* by changing specific bases of synthetic *G. marginata* alpha-amanitin sequences (including PCR copies of isolated peptide toxin genes and base by base construction of nucleic acid sequences) in order to make other types of peptide toxins and peptides. In one example, replacing the codon AAC (Asn) with GAC (Asp) will encode beta-amanitin instead of alpha-amanitin. Beta-amanitin production in *G. marginata* would be easily detected by reverse-phase HPLC because the inventor's isolate of *G. marginata* makes barely detectable levels of beta-amanitin.

The inventors further contemplate changing other amino acids to make non-natural amanitin derivatives, as one example, replacing Gly with Ala by replacing GGT with GCT. Even further, the inventor's contemplate an embodiment for making linear and cyclic peptides of at least six, seven, eight, nine, ten or more amino acids comprising the general formula XWXXXCXP, SEQ ID NO:702, where X is any amino acid. The Pro is retained in these peptides in order for correct processing by POP, and the presence of Trp (W) and Cys (C) will result in the biosynthesis of tryptathionine, a unique hallmark of the *Amanita* toxin peptides. Expression of synthetic peptides and peptide toxins would be monitored by standard assays including but not limited to PCR generated fragments (as in FIG. 40), and by HPLC methods (as in FIG. 31), and the like. Further, separation of synthetic toxins from endogenous peptide toxin and endogenous small peptides (i.e. peptides produced from genomic DNA originally contained in these *Galerina* isolates) would be done by standard techniques including but not limited to HPLC methods (as in FIG. 31). Isolated peptides produced by expression of synthetic sequences would be used in assays for assessing biological activity. For example, toxicity of synthetic amanitin toxins would be determined in assays, for one example, to measure inhibition of transcription in eukaryotic cells, such as capability to inhibit RNA Polymerase II. These toxins are contemplated for commercial levels of production.

Even further, the inventors' contemplate making new *Galerina* isolates that do not produce peptide toxins for use in the present inventions. In one embodiment, the inventors' contemplate knocking out genomic peptide toxin genes for making a new *Galerina* isolate that does not express peptide toxins. As examples for removing genomic peptide toxin genes in *Galerina*, i.e. test *Galerina* (isolates of *Galerina* used in the following methods) would be subject to homologous integration of transforming DNA that would be used for removing regions of DNA comprising the peptide toxin genes in transformed test *Galerina*, spontaneous mutants and induced mutants of test *Galerina* would be made then screened for loss of peptide toxin gene expression and more preferably loss of peptide toxin genes. Another method for eliminating endogenous toxin production is RNAi, which has been used in other basidiomycete fungi (Heneghan et al., Mol Biotechnol. 2007 35(3):283-96, 2007, herein incorporated by reference). Loss of toxin expression in test isolates would be monitored by standard assays including but not limited to genomic sequencing of test *Galerina*, PCR generated fragments of genomic sequences (as in FIG. 40), PCR generated toxin cDNA (as described herein), and by HPLC methods (as in FIG. 31), and the like. When a test *Galerina* isolate is shown to lack expression of peptide toxins this isolate would be cultured as a new *Galerina* laboratory isolate for use in the present inventions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in mycology, molecular biology, biochemistry, chemistry, botany, and medicine, or related fields are intended to be within the scope of the following claims.

The invention claimed is:

1. A cell comprising a recombinant prepropeptide nucleic acid encoding a proline-containing peptide operably linked to a promoter, and a heterologous fungal prolyl oligopeptidase nucleic acid encoding an amino acid sequence selected from the group consisting of SEQ ID NO: 236, 237, 348, 716, and 722.

2. The cell of claim 1, which is a prokaryotic cell.

3. The cell of claim 1, which is a eukaryotic cell.

4. The cell of claim 1, which is an insect cell.

5. The cell of claim 1, which is a mammalian cell.

6. A bacterial, fungal, or algal organism comprising a cell comprising a recombinant prepropeptide nucleic acid encoding a proline-containing peptide operably linked to a promoter, and a heterologous fungal prolyl oligopeptidase nucleic acid encoding an amino acid sequence selected from the group consisting of SEQ ID NO: 236, 237, 348, 716, and 722.

7. The organism of claim 6, which is a eukaryotic organism.

8. The organism of claim 6, which is a fungus.

9. A method of making a synthetic cyclized peptide, comprising:

a) providing, i) a cell comprising a fungal prolyl oligopeptidase with an amino acid sequence selected from the group consisting of SEQ ID NOs: 236, 237, 348, 716, and 722;

ii) a recombinant prepropeptide nucleic acid comprising a nucleic acid sequence encoding a proline-containing prepropeptide, and iii) amino acids for making the synthetic cyclized peptide; and b) growing the cell under conditions for expressing said prepropeptide and thereby making the synthetic cyclized peptide.

10. The method of claim 9, wherein the amino acids for making the synthetic cyclized peptide comprise D-amino acids.

11. The method of claim 9, wherein the peptide is at least six amino acids in length.

12. The method of claim 9, wherein the peptide is up to fifteen amino acids in length.

13. The method of claim 9, wherein the peptide is a bicyclic peptide.

14. A method of making a peptide from a recombinant prepropeptide sequence, comprising:

(a) providing a fungal prolyl oligopeptidase comprising an amino acid sequence selected from SEQ ID NO: 236, 237, 348, 716, and 722, and a proline-containing prepropeptide; and (b) amino acids for making the synthetic cyclized peptide comprising D-amino acids; and (c) contacting the fungal prolyl oligopeptidase with the prepropeptide and the amino acids to make the peptide.

15. The method of claim 14, wherein the peptide is at least six amino acids in length.

16. The method of claim 14, wherein the peptide is up to fifteen amino acids in length.

17. The method of claim 14, wherein the peptide is a bicyclic peptide.

18. A composition comprising a proline-containing prepropeptide, amino acids for making a synthetic cyclized peptide comprising D-amino acids, and a fungal prolyl oligopeptidase comprising an amino acid sequence with in a sequence selected from amino acid SEQ ID NO: 236, 237, 348, 716, and 722, or optionally a fungal prolyl oligopeptidase comprising an amino acid sequence with a sequence selected from amino acid SEQ ID NO: 236, 237, 348, 716, and 722 with one amino acid change.

* * * * *

SEQUENCE LISTING

```
<160> NUMBER OF SEQ ID NOS: 756

<210> SEQ ID NO 1
<211> LENGTH: 20
<212> TYPE: DNA
<213> ORGANISM: Amanita bisporigera

<400> SEQUENCE: 1

ccatctgggg tatcggttgc                                                  20


<210> SEQ ID NO 2
<211> LENGTH: 24
<212> TYPE: DNA
<213> ORGANISM: Amanita bisporigera

<400> SEQUENCE: 2

ttgggattgt gaggtttaga ggtc                                             24


<210> SEQ ID NO 3
<211> LENGTH: 16
```

<212> TYPE: DNA
<213> ORGANISM: Amanita bisporigera

<400> SEQUENCE: 3
cgtcaaccgt ctcctc 16

<210> SEQ ID NO 4
<211> LENGTH: 17
<212> TYPE: DNA
<213> ORGANISM: Amanita bisporigera

<400> SEQUENCE: 4
acgcatgggc agtctac 17

<210> SEQ ID NO 5
<211> LENGTH: 24
<212> TYPE: DNA
<213> ORGANISM: Amanita bisporigera

<400> SEQUENCE: 5
acctccatct cgtccatacc ttcc 24

<210> SEQ ID NO 6
<211> LENGTH: 21
<212> TYPE: DNA
<213> ORGANISM: Amanita bisporigera

<400> SEQUENCE: 6
tgtttgccac gctgcatact a 21

<210> SEQ ID NO 7
<211> LENGTH: 23
<212> TYPE: PRT
<213> ORGANISM: Artificial sequence
<220> FEATURE:
<223> OTHER INFORMATION: A synthetic peptide

<400> SEQUENCE: 7

Gly Cys Asn Ala Thr His Thr Asn Asn Ala Ala Arg Gly Cys Asn Gly
1 5 10 15

Gly Asn Asn Cys Asn Gly Cys
20

<210> SEQ ID NO 8
<211> LENGTH: 23
<212> TYPE: PRT
<213> ORGANISM: Artificial sequence
<220> FEATURE:
<223> OTHER INFORMATION: A synthetic peptide

<400> SEQUENCE: 8

Gly Cys Asn Gly Asn Asn Cys Cys Asn Gly Cys Tyr Thr Thr Asn Asn
1 5 10 15

Ala Asp Ala Thr Asn Gly Cys
20

<210> SEQ ID NO 9
<211> LENGTH: 20
<212> TYPE: PRT
<213> ORGANISM: Artificial sequence
<220> FEATURE:
<223> OTHER INFORMATION: A synthetic peptide

<400> SEQUENCE: 9

```
Thr Thr Tyr Ala Cys Ile Thr Cys Ile Gly Gly Ile Thr Cys Ile Ala
1               5                   10                  15

Cys Ile Gly Gly
            20


<210> SEQ ID NO 10
<211> LENGTH: 20
<212> TYPE: PRT
<213> ORGANISM: Artificial sequence
<220> FEATURE:
<223> OTHER INFORMATION: A synthetic peptide

<400> SEQUENCE: 10

Thr Ala Tyr Ala Cys Asn Ala Gly Tyr Gly Gly Asn Ala Gly Tyr Ala
1               5                   10                  15

Cys Asn Gly Gly
            20


<210> SEQ ID NO 11
<211> LENGTH: 20
<212> TYPE: PRT
<213> ORGANISM: Artificial sequence
<220> FEATURE:
<223> OTHER INFORMATION: A synthetic peptide

<400> SEQUENCE: 11

Thr Ala Tyr Ala Cys Asn Ala Gly Tyr Gly Gly Asn Thr Cys Asn Ala
1               5                   10                  15

Cys Asn Gly Gly
            20


<210> SEQ ID NO 12
<211> LENGTH: 20
<212> TYPE: PRT
<213> ORGANISM: Artificial sequence
<220> FEATURE:
<223> OTHER INFORMATION: A synthetic peptide

<400> SEQUENCE: 12

Thr Ala Tyr Ala Cys Asn Thr Cys Asn Gly Gly Asn Thr Cys Asn Ala
1               5                   10                  15

Cys Asn Gly Gly
            20


<210> SEQ ID NO 13
<211> LENGTH: 20
<212> TYPE: PRT
<213> ORGANISM: Artificial sequence
<220> FEATURE:
<223> OTHER INFORMATION: A synthetic peptide

<400> SEQUENCE: 13

Thr Ala Tyr Ala Cys Asn Thr Cys Asn Gly Gly Asn Ala Gly Tyr Ala
1               5                   10                  15

Cys Asn Gly Gly
            20


<210> SEQ ID NO 14
<211> LENGTH: 20
<212> TYPE: PRT
<213> ORGANISM: Artificial sequence
<220> FEATURE:
<223> OTHER INFORMATION: A synthetic peptide

<400> SEQUENCE: 14
```

Thr Cys Thr Ala Gly Ala Gly Gly Asn Ala Ala Arg Cys Cys Asn Ala
1 5 10 15

Ala Arg Gly Gly
20

<210> SEQ ID NO 15
<211> LENGTH: 17
<212> TYPE: PRT
<213> ORGANISM: Artificial sequence
<220> FEATURE:
<223> OTHER INFORMATION: A synthetic peptide

<400> SEQUENCE: 15

Ala Cys Asn Gly Gly Asn Ala Ala Arg Cys Cys Asn Ala Ala Arg Gly
1 5 10 15

Gly

<210> SEQ ID NO 16
<211> LENGTH: 17
<212> TYPE: PRT
<213> ORGANISM: Artificial sequence
<220> FEATURE:
<223> OTHER INFORMATION: A synthetic peptide

<400> SEQUENCE: 16

Cys Cys Tyr Thr Thr Asn Gly Gly Tyr Thr Thr Asn Cys Cys Asn Gly
1 5 10 15

Thr

<210> SEQ ID NO 17
<211> LENGTH: 14
<212> TYPE: PRT
<213> ORGANISM: Artificial sequence
<220> FEATURE:
<223> OTHER INFORMATION: A synthetic peptide

<400> SEQUENCE: 17

Thr Ala Tyr Gly Gly Asn Cys Cys Asn Ala Cys Asn Gly Ala
1 5 10

<210> SEQ ID NO 18
<211> LENGTH: 15
<212> TYPE: PRT
<213> ORGANISM: Artificial sequence
<220> FEATURE:
<223> OTHER INFORMATION: A synthetic peptide

<400> SEQUENCE: 18

Thr Thr Cys Asn Gly Thr Asn Gly Gly Asn Cys Cys Arg Thr Ala
1 5 10 15

<210> SEQ ID NO 19
<211> LENGTH: 15
<212> TYPE: PRT
<213> ORGANISM: Artificial sequence
<220> FEATURE:
<223> OTHER INFORMATION: A synthetic peptide

<400> SEQUENCE: 19

Thr Ala Cys Gly Gly Asn Cys Cys Asn Ala Cys Asn Gly Ala Asn
1 5 10 15

<210> SEQ ID NO 20
<211> LENGTH: 20

<212> TYPE: PRT
<213> ORGANISM: Artificial sequence
<220> FEATURE:
<223> OTHER INFORMATION: A synthetic peptide

<400> SEQUENCE: 20

```
Cys Cys Asn Cys Cys Asn Ala Thr Asn Ala Thr Asn Ala Gly Tyr Thr
1               5                   10                  15

Cys Asn Cys Cys
            20
```

<210> SEQ ID NO 21
<211> LENGTH: 15
<212> TYPE: PRT
<213> ORGANISM: Artificial sequence
<220> FEATURE:
<223> OTHER INFORMATION: A synthetic peptide

<400> SEQUENCE: 21

```
Gly Thr Ala Asn Cys Cys Asn Cys Gly Asn Gly Cys Gly Ala Asn
1               5                   10                  15
```

<210> SEQ ID NO 22

<400> SEQUENCE: 22

000

<210> SEQ ID NO 23
<211> LENGTH: 17
<212> TYPE: PRT
<213> ORGANISM: Artificial sequence
<220> FEATURE:
<223> OTHER INFORMATION: A synthetic peptide

<400> SEQUENCE: 23

```
Thr Ala Cys Ala Arg Arg Ala Cys Asn Gly Gly Asn Gly Ala Tyr Cys
1               5                   10                  15

Thr
```

<210> SEQ ID NO 24
<211> LENGTH: 23
<212> TYPE: PRT
<213> ORGANISM: Artificial sequence
<220> FEATURE:
<223> OTHER INFORMATION: A synthetic peptide

<400> SEQUENCE: 24

```
Ala Arg Arg Thr Cys Asn Cys Cys Asn Gly Thr Tyr Thr Thr Arg Thr
1               5                   10                  15

Ala Thr Cys Thr Ala Gly Ala
            20
```

<210> SEQ ID NO 25
<211> LENGTH: 20
<212> TYPE: PRT
<213> ORGANISM: Artificial sequence
<220> FEATURE:
<223> OTHER INFORMATION: A synthetic peptide

<400> SEQUENCE: 25

```
Thr Ala Tyr Met Gly Ile Ala Cys Ile Gly Gly Ile Gly Ala Tyr Tyr
1               5                   10                  15

Thr Ile Gly Thr
            20
```

<210> SEQ ID NO 26
<211> LENGTH: 23
<212> TYPE: PRT
<213> ORGANISM: Artificial sequence
<220> FEATURE:
<223> OTHER INFORMATION: A synthetic peptide

<400> SEQUENCE: 26

```
Thr Trp Tyr Gly Cys Ile Ala Cys Ile Gly Gly Ile Gly Ala Tyr Tyr
1               5                   10                  15

Lys Ile Gly Lys Ile Cys Gly
            20
```

<210> SEQ ID NO 27
<211> LENGTH: 17
<212> TYPE: PRT
<213> ORGANISM: Artificial sequence
<220> FEATURE:
<223> OTHER INFORMATION: A synthetic peptide

<400> SEQUENCE: 27

```
Gly Ala Arg Tyr Thr Asn Gly Ser Asn Gly Ala Arg Ala Thr His Gly
1               5                   10                  15

Ala
```

<210> SEQ ID NO 28
<211> LENGTH: 17
<212> TYPE: PRT
<213> ORGANISM: Artificial sequence
<220> FEATURE:
<223> OTHER INFORMATION: A synthetic peptide

<400> SEQUENCE: 28

```
Gly Gly Ile Ala Cys Tyr Thr Gly Ile Thr Gly Arg Thr Cys Tyr Thr
1               5                   10                  15

Thr
```

<210> SEQ ID NO 29
<211> LENGTH: 26
<212> TYPE: PRT
<213> ORGANISM: Artificial sequence
<220> FEATURE:
<223> OTHER INFORMATION: A synthetic peptide

<400> SEQUENCE: 29

```
Ala Trp Ile Gly Ala Arg Lys Ser Ile Cys Cys Ile Cys Cys Ile Arg
1               5                   10                  15

Arg Ser Ile Met Arg Ala Ala Arg Ala Ala
            20                  25
```

<210> SEQ ID NO 30
<211> LENGTH: 18
<212> TYPE: PRT
<213> ORGANISM: Artificial sequence
<220> FEATURE:
<223> OTHER INFORMATION: A synthetic peptide

<400> SEQUENCE: 30

```
Gly Gly Asn Gly Gly Asn Gly Ala Tyr Thr Cys Asn Ala Thr Tyr Arg
1               5                   10                  15

Cys Asn
```

<210> SEQ ID NO 31
<211> LENGTH: 20
<212> TYPE: PRT
<213> ORGANISM: Artificial sequence
<220> FEATURE:
<223> OTHER INFORMATION: A synthetic peptide

<400> SEQUENCE: 31

```
Gly Cys Asn Gly Tyr Asp Ala Thr Asn Ser Trp Arg Thr Cys Asn Cys
1               5                   10                  15

Cys Asn Cys Cys
            20
```

<210> SEQ ID NO 32
<211> LENGTH: 18
<212> TYPE: PRT
<213> ORGANISM: Cochliobolus victoriae

<400> SEQUENCE: 32

```
Cys Gly Cys Cys Gly Thr Gly Ala Thr Cys Gly Ala Ala Thr Cys Cys
1               5                   10                  15

Cys Cys
```

<210> SEQ ID NO 33
<211> LENGTH: 24
<212> TYPE: PRT
<213> ORGANISM: Artificial sequence
<220> FEATURE:
<223> OTHER INFORMATION: A synthetic peptide

<400> SEQUENCE: 33

```
Cys Ala Tyr Cys Ala Tyr Asn Asn Asn Ala Thr His Trp Ser Asn Gly
1               5                   10                  15

Ala Tyr Gly Gly Asn Thr Gly Gly
            20
```

<210> SEQ ID NO 34
<211> LENGTH: 24
<212> TYPE: PRT
<213> ORGANISM: Artificial sequence
<220> FEATURE:
<223> OTHER INFORMATION: A synthetic peptide

<400> SEQUENCE: 34

```
Cys Cys Thr Asn Cys Cys Arg Thr Cys Asn Ser Trp Asn Ala Thr Asn
1               5                   10                  15

Asn Asn Arg Thr Gly Arg Thr Gly
            20
```

<210> SEQ ID NO 35
<211> LENGTH: 17
<212> TYPE: PRT
<213> ORGANISM: Artificial sequence
<220> FEATURE:
<223> OTHER INFORMATION: A synthetic peptide

<400> SEQUENCE: 35

```
Gly Ala Arg Gly Gly Asn Cys Ala Tyr Gly Gly Asn Met Gly Asn Gly
1               5                   10                  15

Ala
```

<210> SEQ ID NO 36
<211> LENGTH: 17
<212> TYPE: PRT

<213> ORGANISM: Artificial sequence
<220> FEATURE:
<223> OTHER INFORMATION: A synthetic peptide

<400> SEQUENCE: 36

Thr Cys Asn Cys Lys Asn Cys Cys Arg Thr Gly Asn Cys Cys Tyr Thr
1 5 10 15

Cys

<210> SEQ ID NO 37
<211> LENGTH: 18
<212> TYPE: PRT
<213> ORGANISM: Cochliobolus victoriae

<400> SEQUENCE: 37

Gly Ala Thr Gly Cys Cys Thr Ala Cys Cys Cys Ala Thr Gly Cys Thr
1 5 10 15

Cys Gly

<210> SEQ ID NO 38
<211> LENGTH: 20
<212> TYPE: PRT
<213> ORGANISM: Artificial sequence
<220> FEATURE:
<223> OTHER INFORMATION: A synthetic peptide

<400> SEQUENCE: 38

Gly Thr Lys Cys Ala Asn Gly Ser Arg Trp Ala Asn Ala Cys Arg Thr
1 5 10 15

Cys Tyr Thr Cys
20

<210> SEQ ID NO 39
<211> LENGTH: 17
<212> TYPE: PRT
<213> ORGANISM: Artificial sequence
<220> FEATURE:
<223> OTHER INFORMATION: A synthetic peptide

<400> SEQUENCE: 39

Cys Cys Asn Thr Gly Tyr Ala Cys Asn Cys Cys Asn Tyr Thr Asn Cys
1 5 10 15

Ala

<210> SEQ ID NO 40
<211> LENGTH: 17
<212> TYPE: PRT
<213> ORGANISM: Artificial sequence
<220> FEATURE:
<223> OTHER INFORMATION: A synthetic peptide

<400> SEQUENCE: 40

Thr Gly Asn Ala Arg Asn Gly Gly Asn Gly Thr Arg Cys Ala Asn Gly
1 5 10 15

Gly

<210> SEQ ID NO 41
<211> LENGTH: 17
<212> TYPE: PRT
<213> ORGANISM: Artificial sequence
<220> FEATURE:
<223> OTHER INFORMATION: A synthetic peptide

<400> SEQUENCE: 41

```
Thr Gly Ile Ala Arg Ile Gly Gly Ile Gly Thr Arg Cys Ala Ile Gly
1               5                   10                  15

Gly


<210> SEQ ID NO 42
<211> LENGTH: 17
<212> TYPE: PRT
<213> ORGANISM: Artificial sequence
<220> FEATURE:
<223> OTHER INFORMATION: A synthetic peptide

<400> SEQUENCE: 42

Cys Ala Arg Gly Ala Arg Gly Gly Ile Tyr Thr Ile Ala Thr Gly Gly
1               5                   10                  15

Cys


<210> SEQ ID NO 43
<211> LENGTH: 17
<212> TYPE: PRT
<213> ORGANISM: Artificial sequence
<220> FEATURE:
<223> OTHER INFORMATION: A synthetic peptide

<400> SEQUENCE: 43

Cys Gly Cys Ala Thr Asn Ala Gly Asn Cys Cys Tyr Thr Cys Cys Thr
1               5                   10                  15

Gly


<210> SEQ ID NO 44
<211> LENGTH: 14
<212> TYPE: PRT
<213> ORGANISM: Artificial sequence
<220> FEATURE:
<223> OTHER INFORMATION: A synthetic peptide

<400> SEQUENCE: 44

Lys Ala Arg Gly Gly Asn Ala Thr Gly Ala Trp Asn Gly Cys
1               5                   10


<210> SEQ ID NO 45
<211> LENGTH: 17
<212> TYPE: PRT
<213> ORGANISM: Artificial sequence
<220> FEATURE:
<223> OTHER INFORMATION: A synthetic peptide

<400> SEQUENCE: 45

Gly Cys Asn Trp Thr Cys Ala Thr Asn Cys Cys Tyr Thr Met Tyr Thr
1               5                   10                  15

Gly


<210> SEQ ID NO 46
<211> LENGTH: 8
<212> TYPE: PRT
<213> ORGANISM: Amanita bisporigera
<220> FEATURE:
<221> NAME/KEY: MISC_FEATURE
<222> LOCATION: (1)..(8)
<223> OTHER INFORMATION: Cyclic Peptide.
<220> FEATURE:
<221> NAME/KEY: MISC_FEATURE
<222> LOCATION: (2)..(2)
<223> OTHER INFORMATION: 4-hydroxy-L-prolyl
<220> FEATURE:
<221> NAME/KEY: MISC_FEATURE
```

```
<222> LOCATION: (3)..(3)
<223> OTHER INFORMATION: (R)-4,5-dihydroxy-L-isoleucyl
<220> FEATURE:
<221> NAME/KEY: MISC_FEATURE
<222> LOCATION: (4)..(4)
<223> OTHER INFORMATION: 6-hydroxy-2-mercapto-L-tryptophyl

<400> SEQUENCE: 46

Asn Pro Ile Trp Gly Ile Gly Cys
1               5

<210> SEQ ID NO 47

<400> SEQUENCE: 47

000

<210> SEQ ID NO 48
<211> LENGTH: 113
<212> TYPE: DNA
<213> ORGANISM: Amanita bisporigera

<400> SEQUENCE: 48

cccaactaaa tcccattcga acctaactcc aagacctcta aacctcacaa tcccaatgtc      60

tgacatcaat gctacccgtc tccccatctg gggtatcggt tgcaacccgt gcg           113

<210> SEQ ID NO 49
<211> LENGTH: 37
<212> TYPE: PRT
<213> ORGANISM: Amanita bisporigera

<400> SEQUENCE: 49

Pro Thr Lys Ser His Ser Asn Leu Thr Pro Arg Pro Leu Asn Leu Thr
1               5                   10                  15

Ile Pro Met Ser Asp Ile Asn Ala Thr Arg Leu Pro Ile Trp Gly Ile
            20                  25                  30

Gly Cys Asn Pro Cys
        35

<210> SEQ ID NO 50
<211> LENGTH: 8
<212> TYPE: PRT
<213> ORGANISM: Amanita bisporigera

<400> SEQUENCE: 50

Ile Trp Gly Ile Gly Cys Asn Pro
1               5

<210> SEQ ID NO 51
<211> LENGTH: 8
<212> TYPE: PRT
<213> ORGANISM: Amanita bisporigera
<220> FEATURE:
<221> NAME/KEY: MISC_FEATURE
<222> LOCATION: (1)..(8)
<223> OTHER INFORMATION: This sequence is a cyclic peptide with a
      sulfoxide crossbridge between the Trp (position 2) and the Cys
      (position 6).

<400> SEQUENCE: 51

Ile Trp Gly Ile Gly Cys Asn Pro
1               5

<210> SEQ ID NO 52
<211> LENGTH: 146
```

<212> TYPE: DNA
<213> ORGANISM: Amanita bisporigera

<400> SEQUENCE: 52
aatctcagcg ttcagtaccc aactcccatt cgaacctaac tccaagacct ctaaacctca 60
caatcccaat gtctgacatc aatgctaccc gtctccccat ctggggtatc ggttgcaacc 120
cgtgcgtcgg tgacgacgtc actacg 146

<210> SEQ ID NO 53
<211> LENGTH: 48
<212> TYPE: PRT
<213> ORGANISM: Amanita bisporigera

<400> SEQUENCE: 53

Ser Gln Arg Ser Val Pro Asn Ser His Ser Asn Leu Thr Pro Arg Pro
1 5 10 15

Leu Asn Leu Thr Ile Pro Met Ser Asp Ile Asn Ala Thr Arg Leu Pro
20 25 30

Ile Trp Gly Ile Gly Cys Asn Pro Cys Val Gly Asp Asp Val Thr Thr
35 40 45

<210> SEQ ID NO 54
<211> LENGTH: 8
<212> TYPE: PRT
<213> ORGANISM: Amanita bisporigera

<400> SEQUENCE: 54

Ile Trp Gly Ile Gly Cys Asp Pro
1 5

<210> SEQ ID NO 55
<211> LENGTH: 381
<212> TYPE: DNA
<213> ORGANISM: Amanita bisporigera

<400> SEQUENCE: 55
acccaactcc cattcgaacc taactccaag acctctaaac ctcacaatcc caatgtctga 60
catcaatgct acccgtcttc ccatctgggg tatcggttgc aacccgtgca tcggtgacga 120
cgtcactaca ctcctcactc gtggcgaggc cctttgttaa attccccatc catttgtccg 180
ctgctatgac acgaagtagt gggcgataca agttgtggac gttatcaggc ttgggccgtt 240
gagcctgcat cggaaacaac ttatgttcct tcttttttct gttttcattt gttaaaatac 300
agaacccatg tcgatgatct gtgttgtagt caatataaag ttgtactgtg tttcttgtca 360
aaaaaaaaaa aaaaaaaaaa a 381

<210> SEQ ID NO 56
<211> LENGTH: 105
<212> TYPE: DNA
<213> ORGANISM: Amanita bisporigera

<400> SEQUENCE: 56
atgtctgaca tcaatgctac ccgtcttccc atctggggta tcggttgcaa cccgtgcatc 60
ggtgacgacg tcactacact cctcactcgt ggcgaggccc tttgt 105

<210> SEQ ID NO 57
<211> LENGTH: 2532
<212> TYPE: DNA
<213> ORGANISM: Amanita bisporigera -continued

<400> SEQUENCE: 57

```
cgatcgaaaa cagaaatcac acactcggct agatgtccat taagtatggg agcggaagtc     60
tgttgccaaa tatggacgac cagacgtttt ttaaaattat gagtcgcgtg actcgaccat    120
taaagtacga atactcagca ttgtataggt cccgaatatc atccgcagta gccgccattg    180
ttggcggcca cgagaagttg gtaatcgccg ctcaaactat caaacgtcgt gcacgtcgca    240
ctattggctg tgctatgtat atacagttca tactgacatc actgtgacct cgtcactttc    300
cacctgtcga acaagccaag gaagcttaag acggccgacg atagccgaaa gtacaaccta    360
gaggtatggc agtagataag tcggacgaac caaagtcaaa ctactgacag gaacttcacc    420
ctgaactgtt gccgcgcgat ggttcaacag gggttgtcat aagtttagcc tgacacgtaa    480
tggtcgccca accgggcatg gatatatgga gagcgagagg tgtgtgaatg gacaactacc    540
gccgaaaaag gataaccagg ctcccttgac cgaacagcgg cgggatcgca gttcgtatca    600
ccgcaccatc ttgtcgcgtt tcactctgtc agaacattca tgtaatgagc tagtgtgaat    660
ggaaatattt tcgctatgtc gaaaaaggat gaacttcgga tagagaaagc caacgaatgc    720
ttgaccgaac aacggtagta ccgcagtacc accgcaccaa cttggtgcaa ttcgctctgt    780
cagaagattc atatcaactc cgccgaggaa atgagttggc aagatgaaaa attcgcagat    840
cccatatgag agcgtgagga gacgctcaga aacttccagc ttgaagcgct tagcccagca    900
ggcggacaag acgtggtggt ccttaagatt ccgagggaga atgaaatgag cctcggtctt    960
atcttcgtcg agccgtgtgg ggaatttaag agtacggaaa tattcttata gcctcaaaac   1020
actcatctcc ggcaaaaagt gaccacctac ccagggcacg taacgatgtc cttgttcaca   1080
ggcctctgat cgtgccgtgc gcagcagcgg tccataccat agaagtcatg ctgcgagcct   1140
ttggattggc atggttgtcg tcgccgatgg ggcataggta aacgtgacca attttaatcg   1200
ataatcatcg gatcaaagtc gttgaaactt gaagaggatg agccgtttta actgtgacgt   1260
cagtttagga aaataaggaa ctagccaaca cgatggtcga gtaaatcatg aatggagaaa   1320
atatttcact atcaccaaga aagaatgact aggcgtgcat gggaagggct ggctgatggt   1380
ttgacgaatg gggggtcaac caccgtaacg aagtggtccc agtccccgtt tctcaaggtg   1440
actatagcaa aaccctacgg attttgcagg tagtccaaca agataagggt gagatgtgtc   1500
tgttgccgaa aaaaggaatc cgctcaaatg ctcacaaaat gtgttggact cctatcaaga   1560
taacatactt gatgtcaagt tactccgaga atggggtctt ctattagttc cttttgattc   1620
tctcatttcg attgggcgaa ctggtgcgaa tggcgacaag tacttcgtta ctacccccat   1680
ggaataacca aatttctgtg gaaaaagaag catctgcccg caccttacgg tatactactt   1740
ttgttccgca ttcgcgcact gattcttcta tctattrtgt ttctcaggct attataccaa   1800
tttctgcgac tcataggatt gattttacct ccaaccaact aggcaatgay gtataaaagg   1860
gaytgtgaat ctcagcgttc agtacccaac taaatcccat tcgaacctaa ctccaagacc   1920
tctaaacctc acaatcccaa tgtctgacat caatgctacc cgtctcccca tctggggtat   1980
cggttgcaac ccgtgcgtcg gtgacgacgt cactacrcty ctcactcgtg gcgaggcgta   2040
agcacgattt ctctccacta atgtactagt gcacttatgt gtgtatcagc ctttgttaaa   2100
ttccccwtcc atttgtccgc tgctatgaca cgaaggtatc accatctcac ttcataacgg   2160
tgatacaagg cagttgtcct gactcaagac gtagtagtgg gcgatacaag ttgtggacgt   2220
tatcaggctt ggaccgttga gcctgcatcg gaagtaaggc cttcaagtta ttatttgtgg   2280
caaaccacga ggctaaattg tcttttgcca gacaacttac gttctttcat tttttctgtt   2340
```

ctcatttgta aaaatacaaa acccatgtcg atgatctgtg ttgtagtcaa tataaagttg 2400
tactgtgttt cttgtcagca ggagtgcatt aacttgttca ggaaacgtca ccctccgagt 2460
ctgctcacga ttcatagcaa tacaaactgt ttttttaag cagatgcgtc actctgagaa 2520
caactccgat cg 2532

<210> SEQ ID NO 58
<211> LENGTH: 25
<212> TYPE: DNA
<213> ORGANISM: Artificial Sequence
<220> FEATURE:
<223> OTHER INFORMATION: A synthetic oligonucleotide

<400> SEQUENCE: 58
gcacgaggac acugacaugg acuga 25

<210> SEQ ID NO 59

<400> SEQUENCE: 59

000

<210> SEQ ID NO 60
<211> LENGTH: 25
<212> TYPE: DNA
<213> ORGANISM: Artificial Sequence
<220> FEATURE:
<223> OTHER INFORMATION: A synthetic oligonucleotide

<400> SEQUENCE: 60
gctgtcaacg atacgctacg taacg 25

<210> SEQ ID NO 61
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 61
cccattcgaa cctaactcca agac 24

<210> SEQ ID NO 62
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 62
cctctaaacc tcacaatccc aatg 24

<210> SEQ ID NO 63
<211> LENGTH: 26
<212> TYPE: DNA
<213> ORGANISM: Artificial Sequence
<220> FEATURE:
<223> OTHER INFORMATION: A synthetic oligonucleotide

<400> SEQUENCE: 63
gcccaagcct gataacgtcc acaact 26

<210> SEQ ID NO 64
<211> LENGTH: 24

<212> TYPE: DNA
<213> ORGANISM: Artificial Sequence
<220> FEATURE:
<223> OTHER INFORMATION: A synthetic oligonucleotide

<400> SEQUENCE: 64
tatcgcccac tacttcgtgt cata 24

<210> SEQ ID NO 65
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 65
tatcgcccac tacttcgtgt cata 24

<210> SEQ ID NO 66
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 66
atcaatgcca cccgtcttcc tg 22

<210> SEQ ID NO 67
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 67
cggatcattt acgtgggttt ta 22

<210> SEQ ID NO 68
<211> LENGTH: 26
<212> TYPE: DNA
<213> ORGANISM: Artificial Sequence
<220> FEATURE:
<223> OTHER INFORMATION: A synthetic oligonucleotide

<400> SEQUENCE: 68
aacttgcctt gactagtgga tgagac 26

<210> SEQ ID NO 69
<211> LENGTH: 7
<212> TYPE: PRT
<213> ORGANISM: Amanita bisporigera
<220> FEATURE:
<221> NAME/KEY: MISC_FEATURE
<222> LOCATION: (1)..(7)
<223> OTHER INFORMATION: Cyclic Peptide.
<220> FEATURE:
<221> NAME/KEY: MISC_FEATURE
<222> LOCATION: (2)..(2)
<223> OTHER INFORMATION: 2-mercapto-L-tryptophyl
<220> FEATURE:
<221> NAME/KEY: MISC_FEATURE
<222> LOCATION: (3)..(3)
<223> OTHER INFORMATION: 4,5-dihydroxy-L-leucyl
<220> FEATURE:
<221> NAME/KEY: MISC_FEATURE
<222> LOCATION: (5)..(5)
<223> OTHER INFORMATION: erythro-3-hydroxy-D-alpha-aspartyl
<220> FEATURE:

-continued

```
<221> NAME/KEY: MISC_FEATURE
<222> LOCATION: (7)..(7)
<223> OTHER INFORMATION: cis-4-hydroxy-L-prolyl

<400> SEQUENCE: 69

Ala Trp Leu Val Asp Cys Pro
1               5


<210> SEQ ID NO 70
<211> LENGTH: 7
<212> TYPE: PRT
<213> ORGANISM: Amanita bisporigera
<220> FEATURE:
<221> NAME/KEY: MISC_FEATURE
<222> LOCATION: (1)..(8)
<223> OTHER INFORMATION: Cyclic Peptide.
<220> FEATURE:
<221> NAME/KEY: MISC_FEATURE
<222> LOCATION: (4)..(4)
<223> OTHER INFORMATION: cis-4-hydroxy-L-prolyl
<220> FEATURE:
<221> NAME/KEY: MISC_FEATURE
<222> LOCATION: (6)..(6)
<223> OTHER INFORMATION: 2-mercapto-L-tryptophyl
<220> FEATURE:
<221> NAME/KEY: MISC_FEATURE
<222> LOCATION: (7)..(7)
<223> OTHER INFORMATION: 4,5-dihydroxy-L-leucyl

<400> SEQUENCE: 70

Ala Thr Cys Pro Ala Trp Leu
1               5


<210> SEQ ID NO 71
<211> LENGTH: 7
<212> TYPE: PRT
<213> ORGANISM: Amanita bisporigera

<400> SEQUENCE: 71

Ala Trp Leu Val Asp Cys Pro
1               5


<210> SEQ ID NO 72
<211> LENGTH: 97
<212> TYPE: DNA
<213> ORGANISM: Amanita bisporigera

<400> SEQUENCE: 72

tgaggagacg gttgacgtcg tcaccgacgc atgggcagtc tacaagccaa gcaggaagac     60

gggtggcatt gatgtcagac attgtgattt agagtag                              97


<210> SEQ ID NO 73
<211> LENGTH: 31
<212> TYPE: PRT
<213> ORGANISM: Amanita bisporigera

<400> SEQUENCE: 73

Leu Leu Ile Thr Met Ser Asp Ile Asn Ala Thr Arg Leu Pro Ala Trp
1               5                   10                  15

Leu Val Asp Cys Pro Cys Val Gly Asp Asp Val Asn Arg Leu Leu
            20                  25                  30


<210> SEQ ID NO 74
<211> LENGTH: 130
<212> TYPE: DNA
<213> ORGANISM: Amanita bisporigera
```

<400> SEQUENCE: 74
tgaggagacg gttgacgtcg tcaccgacgc atgggcagtc tacaagccaa gcaggaagac 60
gggtggcatt gatgtcagac attgtgattt agagtagagg tcttgggttc gagttcgaat 120
gggaggtaag 130

<210> SEQ ID NO 75
<211> LENGTH: 42
<212> TYPE: PRT
<213> ORGANISM: Amanita bisporigera

<400> SEQUENCE: 75

Leu Thr Ser His Ser Asn Ser Asn Pro Arg Pro Leu Leu Ile Thr Met
1 5 10 15

Ser Asp Ile Asn Ala Thr Arg Leu Pro Ala Trp Leu Val Asp Cys Pro
20 25 30

Cys Val Gly Asp Asp Val Asn Arg Leu Leu
35 40

<210> SEQ ID NO 76
<211> LENGTH: 1893
<212> TYPE: DNA
<213> ORGANISM: Amanita bisporigera

<400> SEQUENCE: 76
gagctcagca cggagggtct cttggatttc tggccggcgt gcaagttcaa tgagagacca 60
ctgagtgaag gctcagtgat agaacagctt gaacactcgt aggcgaagat taccgttagg 120
gtgactatga gcagcaccat ttcactacat cggttatgac ggggttgttt gatcgctctg 180
atgacggaga acatgaatcc catgctggcc gattgttttg agactgaaac cgttctaacc 240
tgatgggcag aattcaagca cacgggagtg agattgcgaa ttgctgaaac cgacagtgga 300
gaagacagtc tccgtagtct gcgatcatgt taagtttatg ccctaatcgt tgagcgataa 360
agagcgacca accgcttgtg agtctcgcgc tcagaaatag atataacatc accatactgg 420
aacgacaatg aggctggcag ctgaaaaatg gtgcaaaaca aagactcgcc aacctggctc 480
aaagcggttg tccctgcgag ccgaggatat gtggtggtat cctcggaata tatgtgtgtg 540
agccttggga tcgctcaata caacatggct gtagccgatg ccagtgggta tctcgtaagg 600
cccatacatt cgttcccaat cccgatatac caccgtactg aggttcgcgg aagggaagat 660
cttggtgtta ctgaatctga agctctcgct gcgtggtcct tgtagtctgg gcgttctgat 720
acctcggcat ctccaataga tagaaatgac gacgagcaat gtcagaggtc acaatcctta 780
tcgaattacc tttgagatac tctgccacat caggccagag gccgttggag ttgaggttca 840
acatcacggg tgacggagtg gacgagccgt tatgcaagga aggaaggcca tcgcggataa 900
gtactagtat agcgaccaac ccaaccagac gtggaaatgc cattgaaggg tgggagttgc 960
gcgaatacga ggaaaacgtt tctgaggagc cgaaaccgta accaggcgcg agaacttgac 1020
ctatctatct ccgggaacgg tgttgggggt ccatgttacc gtgaaggtgg atagggggcgg 1080 attcgattcc aggaaagtta gagccacata gtcataagtg atgcaacacg cctgtgcgcg 1140
atggagataa tgcgtctttg ttgcatcggc aaaccgggtc acacggacga aaatcattac 1200
tacatggtcc atttcaggac aaaaccccta tctattgatc ctacaaactg cttgactgtt 1260
caatctgtga ccaccgggac agagaaaggc tgtgctcagt ggggtgttta atccagcgag 1320
aaacgcgtta ggcccagtcg ccgatcagga tacgacgaaa aagtgtaagg tcaagactcc 1380

-continued

```
cttgatgcga ttcaactatt cttgacgggg ggttgccatt gtattgcacc gtcttgcccg   1440

actggctgtg cccgcaaaga cagaacgtcc caaaaacagg aaagaacaaa gaagttttgt   1500

ggagcctgcc aagaatgtgt gatgaacagt gactgacagc atgaatgggg gatgaatatt   1560

gaataccgaa aaaggatgat cagacaactg tttatggaga ttttgcgcca actcgtcttc   1620

atctccgtgt caggacaaga ttctcttatc tatcgtcctt tccgcggttt ttgcaaccat   1680

gcgaattcgt gactgagaca gataaaaggc gttggattca gcttagcatt caatattcaa   1740

tacttacctc ccattcgaac tcgagcccaa gacctctgct ctaaatcaca atgtctgaca   1800

tcaatgccac ccgtcttccy gcttggcttg tagactgccc atgcgtcggt gacgatgtca   1860

accgtctcct cactcgtggc gagaggtgag ctc                                1893
```

```
<210> SEQ ID NO 77
<211> LENGTH: 1613
<212> TYPE: DNA
<213> ORGANISM: Amanita bisporigera

<400> SEQUENCE: 77

cgatcgggtg gtatgagcga cgttgatgca tggattagat aaaaaactca tttttgcctt     60

gacattgtaa catgcgaata agagagcaag gaccccatca gagcaaaaaa ggaatcacgg    120

atttgatatc gacctgaccc aagtcggcaa cggtaatagg ggctagagcc acatatgagt    180

gatgagcgat ggagataatg ttgcatcggg aaaccgggtc acacggccga taatcattct    240

catacatgtc catttctatc tattggtctg taggactgct taacggttta aatctgtgac    300

caccaggaca gacaaagaaa ggctgtgctg ttcgaaacgc gttactaatt aggcccagtt    360

cggcataaat cgccgacacg caggatacga cgaaaagtgt aagcttaagg tcaagactcc    420

tctgatgtga ttcaacaact tttgacgggg ggttgccatt gtatgcaccg tcttgcccgg    480

ctggccatgt ccgcagaacc gaacgcccct aacgacagga aagaagaaag aagttcacgg    540

attccatata gtaagcgtgg agcctgtgtg ataaacagtc atgaatgatt catgggaatg    600

aagaccgatc agacaaacgc ttatggagat tttgtgccaa tttgtctttc catctacgat    660

tctcttatct atcgtccttt ctgcggtttt tgcaaccatg cgaagtcgtg actgaaacag    720

ataaaaggcg ttggatgtgg ctcagtagtc aatattcaat acttacctcc cattcgaact    780

cgaacccaag acctctgctc taaatcacaa tgtctgacat caatgccacc cgtcttcctg    840

cttggcttgt agactgccca tgcgtcggtg acgacgtcaa ccgtctcctc actcgtggtg    900

agaggtgagc tcaaaattcc atttaataat gtagcaatgt actcatgtgt cgtgtatcag    960

cctttgttaa atgtctcatc cactagtcaa ggtatccgcc tctgatttct tgatgacaat   1020

gcatggtcat ggtacttact ttgatgtagt agtggacgac gcaagttgtt gacaatgtta   1080

ggcttggagc gttgagcctg catcggaagt aaggccttca aatttttctg tgataagcag   1140

cgagctaact tgggttagac gactcacatt ctttctcatt ctttctcatt ctcatataaa   1200

acccacgtaa atgatccgag ctgtactatg gaatgcaatg tacgcgtgta tatgtgtgtg   1260

ttgtcagtaa gagagcattt agcaatccga gcttgcatgc cgctgtcgcc agagctgtct   1320

acttgtcagc aacatatcgc atatcacata ggcagctgtt gtaccattga aaagccgtgg   1380

ggcgtataac ctggaggaat ttcaaagaag ggtcttttat gatgagtttg atagctcgca   1440

tagttgtgaa agtcggcaag ttcacaaaaa acagtgattt tatgttacat gtgacgagga   1500

gcatgagaca caactttgaa ctgcacccgg gagaaagcag gcttagcaac accgatgacg   1560

agggggagga gaaatacggg gagaatgccg atgatgtagg cataatgcga tcg          1613
```

<210> SEQ ID NO 78
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 78
gcttggcttg tagactgccc a 21

<210> SEQ ID NO 79
<211> LENGTH: 319
<212> TYPE: DNA
<213> ORGANISM: Amanita bisporigera

<400> SEQUENCE: 79
gacctctgct ctaaatcaca atgtctgaca tcaatgccac ccgtcttccc gcttggcttg 60
tagattgccc atgcgtcggt gacgatgtca accgtctcct cactcgtggc gagagccttt 120
ggtaaatgtc tcatccacta gtcaaggcaa gttgttgaca atgtcaggct tgcggaccgt 180
tgagcctgca tcggaaacga ctcacgttct ttctcattct ttctgattct catttgtaaa 240
catataaaac ccacgtaaat gatccgttgt gctatggaat gcaatatact tgtgaaaaaa 300
aaaaaaaaaa aaaaaaaaa 319

<210> SEQ ID NO 80
<211> LENGTH: 32
<212> TYPE: PRT
<213> ORGANISM: Amanita bisporigera

<400> SEQUENCE: 80

Met Ser Asp Ile Asn Ala Thr Arg Leu Pro Ala Trp Leu Val Asp Cys
1 5 10 15

Pro Cys Val Gly Asp Asp Val Asn Arg Leu Leu Thr Arg Ser Leu Cys
20 25 30

<210> SEQ ID NO 81
<211> LENGTH: 102
<212> TYPE: DNA
<213> ORGANISM: Amanita bisporigera

<400> SEQUENCE: 81
atgtctgaca tcaatgccac ccgtcttccc gcttggcttg tagattgccc atgcgtcggt 60
gacgatgtca accgtctcct cactcgtggc gagagccttt gg 102

<210> SEQ ID NO 82
<211> LENGTH: 30
<212> TYPE: DNA
<213> ORGANISM: Amanita bisporigera

<400> SEQUENCE: 82
atgtctgaca tcaatgccac ccgtcttccc 30

<210> SEQ ID NO 83
<211> LENGTH: 51
<212> TYPE: DNA
<213> ORGANISM: Amanita bisporigera

<400> SEQUENCE: 83
tgcatcggtg acgacgtcac tacactcctc actcgtggcg aggccctttg t 51

<210> SEQ ID NO 84
<211> LENGTH: 51
<212> TYPE: DNA
<213> ORGANISM: Amanita bisporigera

<400> SEQUENCE: 84
tgcgtcggtg acgatgtcaa ccgtctcctc actcgtggcg agagcctttg g 51

<210> SEQ ID NO 85
<211> LENGTH: 24
<212> TYPE: DNA
<213> ORGANISM: Amanita bisporigera

<400> SEQUENCE: 85
atctggggta tcggttgcaa cccg 24

<210> SEQ ID NO 86
<211> LENGTH: 21
<212> TYPE: DNA
<213> ORGANISM: Amanita bisporigera

<400> SEQUENCE: 86
gcttggcttg tagattgccc a 21

<210> SEQ ID NO 87
<211> LENGTH: 33
<212> TYPE: PRT
<213> ORGANISM: Amanita bisporigera
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(15)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (25)..(26)
<223> OTHER INFORMATION: Xaa can be any naturally occurring amino acid

<400> SEQUENCE: 87

```
Met Ser Asp Ile Asn Ala Thr Arg Leu Pro Xaa Trp Xaa Xaa Xaa Cys
1               5                   10                  15

Xaa Pro Cys Val Gly Asp Asp Val Xaa Xaa Leu Leu Thr Arg Ala Leu
            20                  25                  30

Cys
```

<210> SEQ ID NO 88
<211> LENGTH: 10
<212> TYPE: PRT
<213> ORGANISM: Amanita bisporigera

<400> SEQUENCE: 88

```
Met Ser Asp Ile Asn Ala Thr Arg Leu Pro
1               5                   10
```

<210> SEQ ID NO 89

<400> SEQUENCE: 89

000

<210> SEQ ID NO 90
<211> LENGTH: 17
<212> TYPE: PRT
<213> ORGANISM: Amanita bisporigera

<400> SEQUENCE: 90

Cys Val Gly Asp Asp Val Asn Arg Leu Leu Thr Arg Gly Glu Ser Leu
1               5                   10                  15

Cys

<210> SEQ ID NO 91
<211> LENGTH: 15
<212> TYPE: PRT
<213> ORGANISM: Amanita bisporigera
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 91

Cys Xaa Gly Asp Asp Val Xaa Xaa Leu Leu Thr Arg Xaa Leu Cys
1               5                   10                  15

<210> SEQ ID NO 92
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 92
agcatctgcc cgcaccttac g                                                21

<210> SEQ ID NO 93
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 93
actgccttgt atcaccgtta tg                                               22

<210> SEQ ID NO 94
<211> LENGTH: 10
<212> TYPE: PRT
<213> ORGANISM: Amanita bisporigera
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 94

Met Ser Asp Ile Asn Xaa Xaa Arg Xaa Pro
1               5                   10

<210> SEQ ID NO 95
<211> LENGTH: 6
<212> TYPE: PRT
<213> ORGANISM: Amanita bisporigera
<220> FEATURE:
<221> NAME/KEY: misc_feature
<222> LOCATION: (5)..(5)
<223> OTHER INFORMATION: Xaa can be any naturally occurring amino acid

<400> SEQUENCE: 95

Cys Val Gly Asp Xaa Val
1               5

<210> SEQ ID NO 96
<211> LENGTH: 12
<212> TYPE: PRT
<213> ORGANISM: Amanita bisporigera
<220> FEATURE:
<221> NAME/KEY: misc_feature
<222> LOCATION: (7)..(9)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid

<400> SEQUENCE: 96

Cys Val Gly Asp Asp Val Xaa Xaa Xaa Asp Xaa Xaa
1               5                   10

<210> SEQ ID NO 97
<211> LENGTH: 23
<212> TYPE: DNA
<213> ORGANISM: Artificial Sequence
<220> FEATURE:
<223> OTHER INFORMATION: A synthetic oligonucleotide
<220> FEATURE:
<221> NAME/KEY: N
<222> LOCATION: (6)..(6)
<223> OTHER INFORMATION: N can be any nucleic acid
<220> FEATURE:
<221> NAME/KEY: misc_feature
<222> LOCATION: (6)..(6)
<223> OTHER INFORMATION: n is a, c, g, t or u
<220> FEATURE:
<221> NAME/KEY: N
<222> LOCATION: (18)..(18)
<223> OTHER INFORMATION: N can be any nucleic acid
<220> FEATURE:
<221> NAME/KEY: misc_feature
<222> LOCATION: (18)..(18)
<223> OTHER INFORMATION: n is a, c, g, t or u
<220> FEATURE:
<221> NAME/KEY: N
<222> LOCATION: (21)..(21)
<223> OTHER INFORMATION: N can be any nucleic acid
<220> FEATURE:
<221> NAME/KEY: misc_feature
<222> LOCATION: (21)..(21)
<223> OTHER INFORMATION: n is a, c, g, t or u

<400> SEQUENCE: 97
atgtcngaya tyaaygcnac ncg                                          23

<210> SEQ ID NO 98
<211> LENGTH: 33
<212> TYPE: DNA
<213> ORGANISM: Artificial Sequence
<220> FEATURE:
<223> OTHER INFORMATION: A synthetic oligonucleotide

<400> SEQUENCE: 98
aaggsyctcg ccacgagtga ggagwskrkt gac 33

<210> SEQ ID NO 99
<211> LENGTH: 102
<212> TYPE: DNA
<213> ORGANISM: Artificial Sequence
<220> FEATURE:
<223> OTHER INFORMATION: A synthetic oligonucleotide

<400> SEQUENCE: 99
atgtctgata ttaatgcaac gcgtcttccc ttcaatattc tgccattcat gcttccccg 60 tgcgtcagtg acgatgtcaa tatactcctc actcgtggcg ag 102

<210> SEQ ID NO 100
<211> LENGTH: 34
<212> TYPE: PRT
<213> ORGANISM: Artificial Sequence
<220> FEATURE:
<223> OTHER INFORMATION: A synthetic peptide

<400> SEQUENCE: 100

Met Ser Asp Ile Asn Ala Thr Arg Leu Pro Phe Asn Ile Leu Pro Phe
1 5 10 15

Met Leu Pro Pro Cys Val Ser Asp Asp Val Asn Ile Leu Leu Thr Arg
20 25 30

Gly Glu

<210> SEQ ID NO 101
<211> LENGTH: 96
<212> TYPE: DNA
<213> ORGANISM: Artificial Sequence
<220> FEATURE:
<223> OTHER INFORMATION: A synthetic oligonucleotide

<400> SEQUENCE: 101
atgtcagata tcaatgcgac gcgtcttccc atatggggaa taggttgcga cccgtgcatc 60
ggtgacgacg tcaccatact cctcactcgt ggcgag 96

<210> SEQ ID NO 102
<211> LENGTH: 32
<212> TYPE: PRT
<213> ORGANISM: Artificial Sequence
<220> FEATURE:
<223> OTHER INFORMATION: A synthetic peptide

<400> SEQUENCE: 102

Met Ser Asp Ile Asn Ala Thr Arg Leu Pro Ile Trp Gly Ile Gly Cys
1 5 10 15

Asp Pro Cys Ile Gly Asp Asp Val Thr Ile Leu Leu Thr Arg Gly Glu
20 25 30

<210> SEQ ID NO 103
<211> LENGTH: 96
<212> TYPE: DNA
<213> ORGANISM: Artificial Sequence
<220> FEATURE:
<223> OTHER INFORMATION: A synthetic oligonucleotide

<400> SEQUENCE: 103
atgtcggata ttaatgctac acgtcttcca attattggga tcttacttcc cccgtgcatc 60
ggtgacgatg tcaccctact cctcactcgt ggcgag 96

<210> SEQ ID NO 104
<211> LENGTH: 32
<212> TYPE: PRT
<213> ORGANISM: Artificial Sequence
<220> FEATURE:
<223> OTHER INFORMATION: A synthetic peptide

<400> SEQUENCE: 104

Met Ser Asp Ile Asn Ala Thr Arg Leu Pro Ile Ile Gly Ile Leu Leu
1 5 10 15

Pro Pro Cys Ile Gly Asp Asp Val Thr Leu Leu Leu Thr Arg Gly Glu
20 25 30

<210> SEQ ID NO 105
<211> LENGTH: 93
<212> TYPE: DNA
<213> ORGANISM: Artificial Sequence
<220> FEATURE:
<223> OTHER INFORMATION: A synthetic oligonucleotide

<400> SEQUENCE: 105
atgtcagaca ttaacgcgac ccgtcttccc gcctggctcg ccacctgccc gtgcgccggt 60
gacgacgtca accctctcct cactcgtggc gag 93

<210> SEQ ID NO 106
<211> LENGTH: 31
<212> TYPE: PRT
<213> ORGANISM: Artificial Sequence
<220> FEATURE:
<223> OTHER INFORMATION: A synthetic peptide

<400> SEQUENCE: 106

Met Ser Asp Ile Asn Ala Thr Arg Leu Pro Ala Trp Leu Ala Thr Cys
1 5 10 15

Pro Cys Ala Gly Asp Asp Val Asn Pro Leu Leu Thr Arg Gly Glu
20 25 30

<210> SEQ ID NO 107
<211> LENGTH: 32
<212> TYPE: PRT
<213> ORGANISM: Amanita bisporigera

<400> SEQUENCE: 107

Met Ser Asp Ile Asn Ala Thr Arg Leu Pro Ile Trp Gly Ile Gly Cys
1 5 10 15

Asn Pro Cys Val Gly Asp Asp Val Thr Thr Leu Leu Thr Arg Gly Glu
20 25 30

<210> SEQ ID NO 108
<211> LENGTH: 31
<212> TYPE: PRT
<213> ORGANISM: Amanita bisporigera

<400> SEQUENCE: 108

Met Ser Asp Ile Asn Ala Thr Arg Leu Pro Ala Trp Leu Val Asp Cys
1 5 10 15

Pro Cys Val Gly Asp Asp Val Asn Arg Leu Leu Thr Arg Gly Glu
20 25 30

<210> SEQ ID NO 109
<211> LENGTH: 32
<212> TYPE: PRT

<213> ORGANISM: Amanita bisporigera
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(15)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (25)..(26)
<223> OTHER INFORMATION: Xaa can be any naturally occurring amino acid

<400> SEQUENCE: 109

```
Met Ser Asp Ile Asn Ala Thr Arg Leu Pro Xaa Trp Xaa Xaa Xaa Cys
1               5                   10                  15

Xaa Pro Cys Val Gly Asp Asp Val Xaa Xaa Leu Leu Thr Arg Gly Glu
            20                  25                  30
```

<210> SEQ ID NO 110
<211> LENGTH: 34
<212> TYPE: PRT
<213> ORGANISM: Amanita bisporigera

<400> SEQUENCE: 110

```
Met Ser Asp Ile Asn Ala Thr Arg Leu Pro Phe Asn Ile Leu Pro Phe
1               5                   10                  15

Met Leu Pro Pro Cys Val Ser Asp Asp Val Asn Ile Leu Leu Thr Arg
            20                  25                  30

Gly Glu
```

<210> SEQ ID NO 111
<211> LENGTH: 32
<212> TYPE: PRT
<213> ORGANISM: Amanita bisporigera

<400> SEQUENCE: 111

```
Met Ser Asp Ile Asn Ala Thr Arg Leu Pro Ile Trp Gly Ile Gly Cys
1               5                   10                  15

Asp Pro Cys Ile Gly Asp Asp Val Thr Ile Leu Leu Thr Arg Gly Glu
            20                  25                  30
```

<210> SEQ ID NO 112
<211> LENGTH: 32
<212> TYPE: PRT
<213> ORGANISM: Amanita bisporigera

<400> SEQUENCE: 112

```
Met Ser Asp Ile Asn Ala Thr Arg Leu Pro Ile Ile Gly Ile Leu Leu
1               5                   10                  15

Pro Pro Cys Ile Gly Asp Asp Val Thr Leu Leu Leu Thr Arg Gly Glu
            20                  25                  30
```

<210> SEQ ID NO 113
<211> LENGTH: 31
<212> TYPE: PRT
<213> ORGANISM: Amanita bisporigera

<400> SEQUENCE: 113

```
Met Ser Asp Ile Asn Ala Thr Arg Leu Pro Ala Trp Leu Ala Thr Cys
```

-continued

```
1               5                   10                  15

Pro Cys Ala Gly Asp Asp Val Asn Pro Leu Leu Thr Arg Gly Glu
            20                  25                  30


<210> SEQ ID NO 114
<211> LENGTH: 10
<212> TYPE: PRT
<213> ORGANISM: Amanita bisporigera

<400> SEQUENCE: 114

Phe Asn Ile Leu Pro Phe Met Leu Pro Pro
1               5                   10


<210> SEQ ID NO 115

<400> SEQUENCE: 115

000


<210> SEQ ID NO 116

<400> SEQUENCE: 116

000


<210> SEQ ID NO 117
<211> LENGTH: 8
<212> TYPE: PRT
<213> ORGANISM: Amanita bisporigera

<400> SEQUENCE: 117

Ile Ile Gly Ile Leu Leu Pro Pro
1               5


<210> SEQ ID NO 118
<211> LENGTH: 34
<212> TYPE: PRT
<213> ORGANISM: Amanita bisporigera

<400> SEQUENCE: 118

Met Ser Asp Ile Asn Ala Thr Arg Leu Pro His Pro Phe Pro Leu Gly
1               5                   10                  15

Leu Gln Pro Cys Ala Gly Asp Val Asp Asn Leu Thr Leu Thr Lys Gly
            20                  25                  30

Glu Gly


<210> SEQ ID NO 119

<400> SEQUENCE: 119

000


<210> SEQ ID NO 120

<400> SEQUENCE: 120

000


<210> SEQ ID NO 121
<211> LENGTH: 29
<212> TYPE: PRT
<213> ORGANISM: Amanita bisporigera

<400> SEQUENCE: 121
```

-continued

Met Ser Asp Ile Asn Val Thr Arg Leu Pro Gly Phe Val Pro Ile Leu
1 5 10 15

Phe Pro Cys Val Gly Asp Asp Val Asn Thr Ala Leu Thr
20 25

<210> SEQ ID NO 122
<211> LENGTH: 35
<212> TYPE: PRT
<213> ORGANISM: Amanita bisporigera

<400> SEQUENCE: 122

Met Ser Asp Ile Asn Thr Ala Arg Leu Pro Phe Tyr Gln Phe Pro Asp
1 5 10 15

Phe Lys Tyr Pro Cys Val Gly Asp Asp Ile Glu Met Val Leu Ala Arg
20 25 30

Gly Glu Arg
35

<210> SEQ ID NO 123
<211> LENGTH: 33
<212> TYPE: PRT
<213> ORGANISM: Amanita bisporigera

<400> SEQUENCE: 123

Met Ser Asp Ile Asn Thr Ala Arg Leu Pro Phe Phe Gln Pro Pro Glu
1 5 10 15

Phe Arg Pro Pro Cys Val Gly Asp Asp Ile Glu Met Val Leu Thr Arg
20 25 30

Gly

<210> SEQ ID NO 124
<211> LENGTH: 35
<212> TYPE: PRT
<213> ORGANISM: Amanita bisporigera

<400> SEQUENCE: 124

Met Ser Asp Ile Asn Thr Ala Arg Leu Pro Leu Phe Leu Pro Pro Val
1 5 10 15

Arg Met Pro Pro Cys Val Gly Asp Asp Ile Glu Met Val Leu Thr Arg
20 25 30

Gly Glu Arg
35

<210> SEQ ID NO 125
<211> LENGTH: 32
<212> TYPE: PRT
<213> ORGANISM: Amanita bisporigera

<400> SEQUENCE: 125

Met Ser Asp Ile Asn Thr Ala Arg Leu Pro Leu Phe Leu Pro Pro Val
1 5 10 15

Arg Leu Pro Pro Cys Val Gly Asp Asp Ile Glu Met Val Leu Thr Arg
20 25 30

<210> SEQ ID NO 126
<211> LENGTH: 35
<212> TYPE: PRT
<213> ORGANISM: Amanita bisporigera

<400> SEQUENCE: 126

Met Ser Asp Ile Asn Thr Ala Arg Leu Pro Tyr Val Val Phe Met Ser

-continued

```
1               5                   10                  15

Phe Ile Pro Pro Cys Val Asn Asp Asp Ile Gln Val Val Leu Thr Arg
            20                  25                  30

Gly Glu Glu
        35


<210> SEQ ID NO 127
<211> LENGTH: 30
<212> TYPE: PRT
<213> ORGANISM: Amanita bisporigera

<400> SEQUENCE: 127

Met Ser Asp Ile Asn Thr Ala Arg Leu Pro Cys Ile Gly Phe Leu Gly
1               5                   10                  15

Ile Pro Ser Val Gly Asp Asp Ile Glu Met Val Leu Arg His
            20                  25                  30


<210> SEQ ID NO 128
<211> LENGTH: 27
<212> TYPE: PRT
<213> ORGANISM: Amanita bisporigera

<400> SEQUENCE: 128

Met Ser Asp Ile Asn Thr Ala Arg Leu Pro Leu Ser Ser Pro Met Leu
1               5                   10                  15

Leu Pro Cys Val Gly Asp Asp Ile Leu Met Val
            20                  25


<210> SEQ ID NO 129
<211> LENGTH: 32
<212> TYPE: PRT
<213> ORGANISM: Amanita bisporigera

<400> SEQUENCE: 129

Met Ser Asp Ile Asn Ala Ile Arg Ala Pro Ile Leu Met Leu Ala Ile
1               5                   10                  15

Leu Pro Cys Val Gly Asp Asp Ile Glu Val Leu Arg Arg Gly Glu Gly
            20                  25                  30


<210> SEQ ID NO 130
<211> LENGTH: 35
<212> TYPE: PRT
<213> ORGANISM: Amanita bisporigera

<400> SEQUENCE: 130

Met Ser Asp Ile Asn Gly Thr Arg Leu Pro Ile Pro Gly Leu Ile Pro
1               5                   10                  15

Leu Gly Ile Pro Cys Val Ser Asp Asp Val Asn Pro Thr Leu Thr Arg
            20                  25                  30

Gly Glu Arg
        35


<210> SEQ ID NO 131
<211> LENGTH: 34
<212> TYPE: PRT
<213> ORGANISM: Amanita bisporigera

<400> SEQUENCE: 131

Met Ser Asp Ile Asn Ala Thr Arg Leu Pro Gly Ala Tyr Pro Pro Val
1               5                   10                  15

Pro Met Pro Cys Val Gly Asp Ala Asp Asn Phe Thr Leu Thr Arg Gly
```

```
            20                  25                  30

Glu Lys


<210> SEQ ID NO 132
<211> LENGTH: 33
<212> TYPE: PRT
<213> ORGANISM: Amanita bisporigera

<400> SEQUENCE: 132

Met Ser Asp Ile Asn Ala Thr Arg Leu Pro Gly Met Glu Pro Pro Ser
1               5                   10                  15

Pro Met Pro Cys Val Gly Asp Ala Asp Asn Phe Thr Leu Thr Arg Gly
            20                  25                  30

Asn


<210> SEQ ID NO 133

<400> SEQUENCE: 133

000


<210> SEQ ID NO 134

<400> SEQUENCE: 134

000


<210> SEQ ID NO 135
<211> LENGTH: 8
<212> TYPE: PRT
<213> ORGANISM: Amanita bisporigera
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 135

Xaa Trp Xaa Xaa Xaa Cys Xaa Pro
1               5


<210> SEQ ID NO 136
<211> LENGTH: 7
<212> TYPE: PRT
<213> ORGANISM: Amanita bisporigera

<400> SEQUENCE: 136

Ala Trp Leu Ala Thr Cys Pro
1               5


<210> SEQ ID NO 137
<211> LENGTH: 8
<212> TYPE: PRT
<213> ORGANISM: Amanita bisporigera

<400> SEQUENCE: 137

Gly Phe Val Pro Ile Leu Phe Pro
1               5
```

-continued

<210> SEQ ID NO 138
<211> LENGTH: 10
<212> TYPE: PRT
<213> ORGANISM: Amanita bisporigera

<400> SEQUENCE: 138

Phe Tyr Gln Phe Pro Asp Phe Lys Tyr Pro
1 5 10

<210> SEQ ID NO 139
<211> LENGTH: 10
<212> TYPE: PRT
<213> ORGANISM: Amanita bisporigera

<400> SEQUENCE: 139

Phe Phe Gln Pro Pro Glu Phe Arg Pro Pro
1 5 10

<210> SEQ ID NO 140
<211> LENGTH: 10
<212> TYPE: PRT
<213> ORGANISM: Amanita bisporigera

<400> SEQUENCE: 140

Leu Phe Leu Pro Pro Val Arg Met Pro Pro
1 5 10

<210> SEQ ID NO 141
<211> LENGTH: 10
<212> TYPE: PRT
<213> ORGANISM: Amanita bisporigera

<400> SEQUENCE: 141

Leu Phe Leu Pro Pro Val Arg Leu Pro Pro
1 5 10

<210> SEQ ID NO 142
<211> LENGTH: 10
<212> TYPE: PRT
<213> ORGANISM: Amanita bisporigera

<400> SEQUENCE: 142

Tyr Val Val Phe Met Ser Phe Ile Pro Pro
1 5 10

<210> SEQ ID NO 143
<211> LENGTH: 8
<212> TYPE: PRT
<213> ORGANISM: Amanita bisporigera

<400> SEQUENCE: 143

Cys Ile Gly Phe Leu Gly Ile Pro
1 5

<210> SEQ ID NO 144
<211> LENGTH: 8
<212> TYPE: PRT
<213> ORGANISM: Amanita bisporigera

<400> SEQUENCE: 144

Leu Ser Ser Pro Met Leu Leu Pro
1 5

<210> SEQ ID NO 145

<211> LENGTH: 8
<212> TYPE: PRT
<213> ORGANISM: Amanita bisporigera

<400> SEQUENCE: 145

Ile Leu Met Leu Ala Ile Leu Pro
1 5

<210> SEQ ID NO 146
<211> LENGTH: 10
<212> TYPE: PRT
<213> ORGANISM: Amanita bisporigera

<400> SEQUENCE: 146

Ile Pro Gly Leu Ile Pro Leu Gly Ile Pro
1 5 10

<210> SEQ ID NO 147
<211> LENGTH: 9
<212> TYPE: PRT
<213> ORGANISM: Amanita bisporigera

<400> SEQUENCE: 147

Gly Ala Tyr Pro Pro Val Pro Met Pro
1 5

<210> SEQ ID NO 148
<211> LENGTH: 9
<212> TYPE: PRT
<213> ORGANISM: Amanita bisporigera

<400> SEQUENCE: 148

Gly Met Glu Pro Pro Ser Pro Met Pro
1 5

<210> SEQ ID NO 149
<211> LENGTH: 9
<212> TYPE: PRT
<213> ORGANISM: Amanita bisporigera

<400> SEQUENCE: 149

His Pro Phe Pro Leu Gly Leu Gln Pro
1 5

<210> SEQ ID NO 150
<211> LENGTH: 710
<212> TYPE: PRT
<213> ORGANISM: Homo sapiens

<400> SEQUENCE: 150

Met Leu Ser Leu Gln Tyr Pro Asp Val Tyr Arg Asp Glu Thr Ala Val
1 5 10 15

Gln Asp Tyr His Gly His Lys Ile Cys Asp Pro Tyr Ala Trp Leu Glu
20 25 30

Asp Pro Asp Ser Glu Gln Thr Lys Ala Phe Val Glu Ala Gln Asn Lys
35 40 45

Ile Thr Val Pro Phe Leu Glu Gln Cys Pro Ile Arg Gly Leu Tyr Lys
50 55 60

Glu Arg Met Thr Glu Leu Tyr Asp Tyr Pro Lys Tyr Ser Cys His Phe
65 70 75 80

Lys Lys Gly Lys Arg Tyr Phe Tyr Phe Tyr Asn Thr Gly Leu Gln Asn
85 90 95

```
Gln Arg Val Leu Tyr Val Gln Asp Ser Leu Glu Gly Glu Ala Arg Val
            100                 105                 110

Phe Leu Asp Pro Asn Ile Leu Ser Asp Asp Gly Thr Val Ala Leu Arg
        115                 120                 125

Gly Tyr Ala Phe Ser Glu Asp Gly Glu Tyr Phe Ala Tyr Gly Leu Ser
    130                 135                 140

Ala Ser Gly Ser Asp Trp Val Thr Ile Lys Phe Met Lys Val Asp Gly
145                 150                 155                 160

Ala Lys Glu Leu Pro Asp Val Leu Glu Arg Val Lys Phe Ser Cys Met
                165                 170                 175

Ala Trp Thr His Asp Gly Lys Gly Met Phe Tyr Asn Ser Tyr Pro Gln
            180                 185                 190

Gln Asp Gly Lys Ser Asp Gly Thr Glu Thr Ser Thr Asn Leu His Gln
        195                 200                 205

Lys Leu Tyr Tyr His Val Leu Gly Thr Asp Gln Ser Glu Asp Ile Leu
    210                 215                 220

Cys Ala Glu Phe Pro Asp Glu Pro Lys Trp Met Gly Gly Ala Glu Leu
225                 230                 235                 240

Ser Asp Asp Gly Arg Tyr Val Leu Leu Ser Ile Arg Glu Gly Cys Asp
                245                 250                 255

Pro Val Asn Arg Leu Trp Tyr Cys Asp Leu Gln Gln Glu Ser Ser Gly
            260                 265                 270

Ile Ala Gly Ile Leu Lys Trp Val Lys Leu Ile Asp Asn Phe Glu Gly
        275                 280                 285

Glu Tyr Asp Tyr Val Thr Asn Glu Gly Thr Val Phe Thr Phe Lys Thr
    290                 295                 300

Asn Arg Gln Ser Pro Asn Tyr Arg Val Ile Asn Ile Asp Phe Arg Asp
305                 310                 315                 320

Pro Glu Glu Ser Lys Trp Lys Val Leu Val Pro Glu His Glu Lys Asp
                325                 330                 335

Val Leu Glu Trp Ile Ala Cys Val Arg Ser Asn Phe Leu Val Leu Cys
            340                 345                 350

Tyr Leu His Asp Val Lys Asn Ile Leu Gln Leu His Asp Leu Thr Thr
        355                 360                 365

Gly Ala Leu Leu Lys Thr Phe Pro Leu Asp Val Gly Ser Ile Val Gly
    370                 375                 380

Tyr Ser Gly Gln Lys Lys Asp Thr Glu Ile Phe Tyr Gln Phe Thr Ser
385                 390                 395                 400

Phe Leu Ser Pro Gly Ile Ile Tyr His Cys Asp Leu Thr Lys Glu Glu
                405                 410                 415

Leu Glu Pro Arg Val Phe Arg Glu Val Thr Val Lys Gly Ile Asp Ala
            420                 425                 430

Ser Asp Tyr Gln Thr Val Gln Ile Phe Tyr Pro Ser Lys Asp Gly Thr
        435                 440                 445

Lys Ile Pro Met Phe Ile Val His Lys Lys Gly Ile Lys Leu Asp Gly
    450                 455                 460

Ser His Pro Ala Phe Leu Tyr Gly Tyr Gly Gly Phe Asn Ile Ser Ile
465                 470                 475                 480

Thr Pro Asn Tyr Ser Val Ser Arg Leu Ile Phe Val Arg His Met Gly
                485                 490                 495

Gly Ile Leu Ala Val Ala Asn Ile Arg Gly Gly Gly Glu Tyr Gly Glu
            500                 505                 510

Thr Trp His Lys Gly Gly Ile Leu Ala Asn Lys Gln Asn Cys Phe Asp
```

```
        515                 520                 525

Asp Phe Gln Cys Ala Ala Glu Tyr Leu Ile Lys Glu Gly Tyr Thr Ser
    530                 535                 540

Pro Lys Arg Leu Thr Ile Asn Gly Gly Ser Asn Gly Gly Leu Leu Val
545                 550                 555                 560

Ala Ala Cys Ala Asn Gln Arg Pro Asp Leu Phe Gly Cys Val Ile Ala
                565                 570                 575

Gln Val Gly Val Met Asp Met Leu Lys Phe His Lys Tyr Thr Ile Gly
            580                 585                 590

His Ala Trp Thr Thr Asp Tyr Gly Cys Ser Asp Ser Lys Gln His Phe
        595                 600                 605

Glu Trp Leu Val Lys Tyr Ser Pro Leu His Asn Val Lys Leu Pro Glu
    610                 615                 620

Ala Asp Asp Ile Gln Tyr Pro Ser Met Leu Leu Leu Thr Ala Asp His
625                 630                 635                 640

Asp Asp Arg Val Val Pro Leu His Ser Leu Lys Phe Ile Ala Thr Leu
                645                 650                 655

Gln Tyr Ile Val Gly Arg Ser Arg Lys Gln Ser Asn Pro Leu Leu Ile
            660                 665                 670

His Val Asp Thr Lys Ala Gly His Gly Ala Gly Lys Pro Thr Ala Lys
        675                 680                 685

Val Ile Glu Glu Val Ser Asp Met Phe Ala Phe Ile Ala Arg Cys Leu
    690                 695                 700

Asn Val Asp Trp Ile Pro
705                 710


<210> SEQ ID NO 151
<211> LENGTH: 737
<212> TYPE: PRT
<213> ORGANISM: Coprinus cinereus

<400> SEQUENCE: 151

Met Ala Ala Lys Ala Trp Thr Pro Asn Thr Tyr Pro Pro Ala Arg Arg
1               5                   10                  15

Ser Asp His Val Asp Thr Tyr Lys Ser Ala Ser Lys Gly Glu Val Lys
            20                  25                  30

Val Pro Asp Pro Tyr Arg Trp Met Glu Glu Tyr Thr Glu Glu Thr Asp
        35                  40                  45

Lys Trp Thr Thr Ala Gln Glu Ala Tyr Thr Arg Ala Tyr Ile Asp Glu
    50                  55                  60

Tyr Pro His Arg Lys Arg Leu Glu Asp Ala Phe Leu Ala Ser Gln Asp
65                  70                  75                  80

Tyr Ala Arg Ala Gly Ala Pro Ile Leu Arg Asp Asp Lys Arg Trp Tyr
                85                  90                  95

Trp Phe His Asn Thr Gly Leu Gln Pro Gln Asp Val Met Phe Arg Ser
            100                 105                 110

Lys Asp Ser Gln Leu Pro Asp Arg Ser Lys Gly Ala Asp Asn Gly Glu
        115                 120                 125

Val Phe Leu Asp Gln Asn Leu Leu Ser Asp Asp Gly Thr Ala Ser Ile
    130                 135                 140

Ser Thr His Ala Phe Ser Asp Ser Gly Glu Tyr Tyr Ala Tyr Gly Ile
145                 150                 155                 160

Ser Tyr Ser Gly Ser Asp Phe Thr Thr Val Tyr Val Arg Arg Thr Asp
                165                 170                 175
```

-continued

```
Ser Pro Leu Ala Ser Lys Glu Gln Ala Ala Asn Asp Asn Gly Arg Leu
            180                 185                 190

Pro Glu Val Leu Lys Phe Val Lys Phe Ser Ser Leu Lys Trp Thr Pro
        195                 200                 205

Asp Ser Lys Gly Phe Phe Tyr Gln Arg Met Pro Asp Arg Ser Lys Gly
    210                 215                 220

Glu Lys Val Asn Gly Ser Gly Ile Glu Thr Gly Gly Asp Arg Asp Ala
225                 230                 235                 240

Met Leu Tyr Tyr His Arg Val Asn Thr Pro Gln Ser Glu Asp Val Leu
                245                 250                 255

Val Tyr His Asn Lys Asp Glu Pro Glu Trp Met Tyr Gly Ile Glu Ile
            260                 265                 270

Thr Asp Asp Asp Lys Tyr Ala Val Leu Thr Val Val Ala Asp Thr Ser
        275                 280                 285

Arg Lys Asn Leu Phe Trp Ile Ala Glu Leu Lys Glu Asp Ser Ile Glu
    290                 295                 300

Lys Gly Phe Lys Trp Asn Lys Val Val Asn Glu Tyr Glu Ala Glu Tyr
305                 310                 315                 320

Glu Tyr Val Thr Asn Tyr Gly Pro Val Phe Val Val Arg Thr Asn Asp
                325                 330                 335

Lys Ala Pro Lys Tyr Lys Ala Ile Thr Ile Asp Ile Ser Lys Gly Asn
            340                 345                 350

Glu Arg Lys Asp Phe Val Pro Glu Thr Asp Gly Phe Leu Asn Ser Ile
        355                 360                 365

Asp Ala Val Asn Lys Gly Glu Asn Phe Val Val Ser Tyr Lys Arg Asn
    370                 375                 380

Val Lys Asp Glu Ala Tyr Val Tyr Ser Lys Glu Gly Lys Glu Leu Glu
385                 390                 395                 400

Arg Leu Leu Pro Asp Phe Ile Gly Ala Leu Thr Ile Thr Ala Arg Tyr
                405                 410                 415

Arg Asp Ser Trp Phe Phe Ile Asn Ala Val Gly Phe Thr Thr Pro Gly
            420                 425                 430

Thr Leu Gly Arg Tyr Asp Phe Thr Ala Pro Glu Gly Gln Arg Trp Ser
        435                 440                 445

Ile Tyr Ser Gln Thr Lys Val Lys Gly Leu Asn Pro Glu Glu Phe Ser
    450                 455                 460

Ala Glu Gln Val Trp Tyr Glu Ser Lys Asp Gly Thr Lys Ile Pro Met
465                 470                 475                 480

Phe Ile Val Arg His Lys Ser Thr Pro Ile Asp Gly Thr Ala Pro Ala
                485                 490                 495

Ile Gln Tyr Gly Tyr Gly Gly Phe Ser Ile Ser Ile Asn Pro Ser Phe
            500                 505                 510

Ser Pro Thr Ile Leu Thr Phe Leu Lys Thr Tyr Gly Gly Val Tyr Ala
        515                 520                 525

Ile Ala Asn Ile Arg Gly Gly Gly Glu Phe Gly Glu Glu Trp His Glu
    530                 535                 540

Gly Gly Tyr Arg Asp Lys Lys His Asn Cys Phe Asp Asp Phe Ile Ala
545                 550                 555                 560

Ala Thr Glu Tyr Leu His Lys Asn Lys Ile Ala Ala Pro Gly Lys Val
                565                 570                 575

Thr Ile Asn Gly Gly Ser Asn Gly Gly Leu Leu Val Ser Ala Cys Val
            580                 585                 590

Asn Arg Ala Pro Glu Gly Thr Phe Gly Ala Ala Val Ala Glu Val Gly
```

595 600 605

Val His Asp Leu Leu Arg Phe His Lys Phe Thr Ile Gly Arg Ala Trp
610 615 620

Ile Ser Asp Tyr Gly Asp Pro Asp Asp Pro Lys Asp Phe Asp Phe Ile
625 630 635 640

His Pro Ile Ser Pro Leu His Asn Val Ser Pro Thr Lys Ile Leu Pro
645 650 655

Pro Phe Met Leu Ile Thr Ala Asp His Asp Asp Arg Val Val Pro Ser
660 665 670

His Ser Phe Lys Leu Ala Ala Thr Leu Gln His Leu Arg Ala Asp Asn
675 680 685

Pro Asn Pro Ile Leu Leu Arg Val Asp Lys Lys Ala Gly His Gly Ala
690 695 700

Gly Lys Ser Thr Thr Lys Arg Met Gln Glu Ala Ala Asp Lys Trp Gly
705 710 715 720

Phe Val Ala Lys Thr Leu Gly Leu Glu Trp Lys Asp Thr Ala Thr Lys
725 730 735

Leu

<210> SEQ ID NO 152
<211> LENGTH: 923
<212> TYPE: PRT
<213> ORGANISM: Ustilago maydis

<400> SEQUENCE: 152

Met Asn Asn Leu Ile Ala His Thr Leu Leu Val Ala Pro Gln Arg Ala
1 5 10 15

Arg Ser Pro Pro Ala Thr Glu Arg Met Tyr Ala Leu Gly Tyr Thr Lys
20 25 30

Pro Ile Ala Arg Leu Arg Gly Val Val Asp Thr Asn Asn Asp Asp Lys
35 40 45

His Glu Ala His Thr Asn Val Gly Lys Ala Asn Arg Gly Ser Leu Cys
50 55 60

Gln Arg Arg Ser Phe Ile Leu Pro Ser Thr Ile Thr Ala Val Phe Val
65 70 75 80

Ser Pro His Leu Met Leu Ser Arg Phe Ala Arg Leu Arg Tyr Leu Asp
85 90 95

Pro Ser Tyr Arg Ser Pro Leu Val Ser Ser Phe Arg Ser Cys Ser Asn
100 105 110

Lys Ala Arg Ala His Ser Tyr Arg Ser Phe Ala Ser Thr Ala Thr Ala
115 120 125

Met Thr Val Gln Asn Ala Pro Gly Trp Thr Thr Gln Pro Asn Pro Tyr
130 135 140

Pro Gln Ala Arg Arg Asp Asp Gln Ala Ser Leu Thr Tyr Lys Ser Ala
145 150 155 160

Ala Asn Gly Ser Val Thr Val Pro Glu Pro Tyr Ile Trp Leu Glu Gln
165 170 175

Pro Pro Ser Gln Ser Gln Glu Thr Lys Asp Trp Val His Ala Gln Ala
180 185 190

Lys Leu Thr Gln Ser Tyr Leu Asp Gly Cys Gln Pro Asp Leu Asp Ile
195 200 205

Leu Lys Ser Arg Ile Glu Lys Asn Phe Asp Phe Ala Arg Phe Ser Cys
210 215 220

Pro Ser Leu Lys Gly Asn Gly Lys Tyr Tyr Tyr Ser Phe Asn Ser Gly

-continued

```
225                 230                 235                 240

Leu Ser Pro Gln Ser Leu Ile Tyr Ser Ala Thr Lys Gln Gln Val Asp
                245                 250                 255

Ala Asn Ala Gly Lys Asn Gln Arg Asp Pro Ile Gly Glu Ile Phe Phe
            260                 265                 270

Asp Ser Asn Leu Leu Ser Ala Asp Gly Thr Val Ala Leu Ser Phe Thr
        275                 280                 285

Thr Phe Ser His Ser Gly Lys Tyr Leu Ala Tyr Gly Ile Ser Lys Ser
    290                 295                 300

Gly Ser Asp Trp Val Glu Ile Phe Ile Arg Glu Thr Ser Lys Pro Phe
305                 310                 315                 320

Lys Leu Asp Asp Ala His Tyr Asn Ser Asn Gly Thr Ile Lys Leu Ser
                325                 330                 335

Lys Asp Glu Leu Ala Lys Phe Val Asp Ala Thr Gly Gly Lys Glu Arg
            340                 345                 350

Leu Asn Asp Arg Leu Glu His Val Lys Phe Ser Gly Ala Ala Phe Thr
        355                 360                 365

His Asp Asp Lys Gly Leu Phe Tyr Gln Thr Tyr Pro Ser Ala Ser Val
    370                 375                 380

Ser Asp Lys Gly Thr Glu Thr Asp Ala Asn Lys Asp Ala Gln Leu Trp
385                 390                 395                 400

Tyr His Arg Ile Gly Thr Asp Gln Ser Glu Asp Val Leu Val Val Ser
                405                 410                 415

Lys Asp Ile Lys Val Pro Glu Ser Met Trp Ser Thr Asn Val Ser His
            420                 425                 430

Asp Gly Asn Phe Leu Met Leu Tyr Asn Ser Lys Asp Thr Asp Ser Lys
        435                 440                 445

Glu Arg Val Tyr Val Leu Pro Leu Gln Asp His Gly Phe Ser Ala Ser
    450                 455                 460

Lys Gln Leu Lys Trp Ile Pro Leu Ala Leu Ser Phe Lys Tyr Val Leu
465                 470                 475                 480

Asn Tyr Val Thr Asn Lys Gly Asn Arg Phe Tyr Phe Met Thr Asn Lys
                485                 490                 495

Asp Ala Pro Asn Tyr Arg Leu Val Ser Val Asp Leu Asp Pro Ala Lys
            500                 505                 510

Gln Ala Gln Pro Thr Asp Asn Val Trp Glu Leu Thr Gly Gln Asp Val
        515                 520                 525

Glu Leu Thr Asp Val Ile Ala Glu Glu Lys Glu Ala Leu Leu Ser Ser
    530                 535                 540

Val Gln Val Ile Asp Asn Asn Lys Leu Leu Val Val Tyr Ser Arg Asp
545                 550                 555                 560

Val Lys Asp Glu Leu Tyr Gln Tyr Glu Leu Glu Ser Gly Lys Arg Val
                565                 570                 575

Glu Arg Leu Leu Pro His Leu Val Gly Thr Ile Glu Gln Ile Ala Ala
            580                 585                 590

Arg His Thr Asp Asp His Ala Phe Val Lys Phe Gly Ser Phe Val Asn
        595                 600                 605

Pro Gly Gln Val Val Arg Leu Asp Trp Gln Thr Asn Ser Glu Pro Asn
    610                 615                 620

Ala Thr Lys Val Lys Lys Val Ala Tyr Tyr Asp Thr Gln Val Asp Gly
625                 630                 635                 640

Ile Lys Ala Asp Asp Phe Val Ser Glu Gln Val Phe Ile Lys Ser Lys
                645                 650                 655
```

```
Asp Gly Thr Arg Val Pro Met Phe Val Thr His Pro Lys Thr Val Thr
            660                 665                 670

Lys Asp Gly Ser Ala Pro Ala Ile Leu Tyr Phe Tyr Gly Gly Phe Asn
        675                 680                 685

Ile Ser Ile Thr Pro Val Phe Ser Pro Ser Met Met Ser Trp Ile Ser
    690                 695                 700

Ser Tyr Asn Gly Val Leu Ala Phe Val Asn Cys Arg Gly Gly Gly Glu
705                 710                 715                 720

Tyr Gly Asp Lys Trp His Glu Ala Gly Thr Leu Leu Asn Lys Gln Asn
                725                 730                 735

Val Phe Asp Asp Ala Leu Ser Ala Ala Lys Phe Leu His Glu Ser Gly
            740                 745                 750

Tyr Ala Ala Lys Gly Lys Ile Ile Leu Ser Gly Gly Ser Asn Gly Gly
        755                 760                 765

Leu Gly Val Ala Ala Cys Ile Asn Gln Gln Leu Pro Glu His Gly Ile
    770                 775                 780

Gly Ala Gly Ile Ala Asp Val Gly Val Met Asp Met Leu Lys Phe His
785                 790                 795                 800

Thr Trp Thr Ile Gly Lys Ala Trp Thr Ala Asp Tyr Gly Asn Pro Ser
                805                 810                 815

Glu Asp Pro His Ile Phe Asp Tyr Val Tyr Lys Tyr Ser Pro Leu His
            820                 825                 830

Asn Val Asp Ser Asn Lys Val Tyr Pro Thr Thr Val Leu Ala Cys Ala
        835                 840                 845

Asp His Asp Asp Arg Val Val Pro Ala His Ser Phe Lys Leu Ile Ala
    850                 855                 860

Glu Met Gln His Lys Leu Ala Thr Asn Pro Asn Pro Leu Leu Leu Arg
865                 870                 875                 880

Val Glu Ile Asp Ala Gly His Gly Ala Gly Lys Ser Thr Gln Lys Arg
                885                 890                 895

Ile Gln Glu Ala Ala Glu Lys Tyr Ala Ile Val Gly Arg Ala Leu Arg
            900                 905                 910

Leu Lys Ile Thr Asp Asp Ala Ala Ser Arg Leu
        915                 920


<210> SEQ ID NO 153
<211> LENGTH: 803
<212> TYPE: PRT
<213> ORGANISM: Cryptococcus neoformans

<400> SEQUENCE: 153

Met Ser Gly Gln Gln Ala Ser His Ser Phe Ser Thr Asp Lys Thr Gly
1               5                   10                  15

His Gly Thr Leu Lys Asn Val His Ala Ser Asp Phe Thr Ile Ser Pro
            20                  25                  30

Gly Gln Trp Lys Lys Asn Val Asn Phe Ser Pro Tyr Pro Val Pro Pro
        35                  40                  45

Gln His Gly Gly Ile Thr Glu Ile Ile His Gly Ile Glu Ile Glu Asp
    50                  55                  60

Pro Trp Arg Ala Leu Glu Asp Pro Asp Ser Glu Val Thr Lys Lys Phe
65                  70                  75                  80

Val Lys Glu Gln Asn Asp Phe Ser Val Pro Arg Leu Thr Asn His Pro
                85                  90                  95

Leu Arg Lys Glu Leu Glu Ala Ala Val Glu Gln Cys Tyr Asn His Glu
```

-continued

```
            100                 105                 110

Arg Met Thr Ser Pro Glu Leu Gln Gly Asp Gly Tyr Tyr Tyr Trp Lys
        115                 120                 125

Phe Asn Pro Gly Thr Ser Pro Arg Asp Val Ile Val Arg Ser Lys Asp
    130                 135                 140

Leu Lys Arg Asp Phe Gly Lys Ala Pro Gly Gly Ser Gly Pro Glu Ile
145                 150                 155                 160

Phe Tyr Asp Leu Asn Lys Glu Glu Asn Ile Ser Leu Tyr Ala His Ser
                165                 170                 175

Phe Ser Pro Ser Gly Lys Leu Trp Cys Ala Val Leu Gln Tyr Ala Gly
            180                 185                 190

Ser Asp Trp Gln Arg Ile Arg Val Ile Asp Thr Glu Ser Lys Ala Val
        195                 200                 205

Leu Glu Lys Asp Leu Gly Gly Ser Lys Phe Thr Phe Gly Val Thr Trp
    210                 215                 220

Gly Phe Ile Tyr Lys Arg Ser Ile Asp Tyr Asp Ala Thr Ser Asp Gly
225                 230                 235                 240

Tyr Asp Gly Ile Asp Gly Ser Phe Gly Met Phe Tyr His Ala Val Gly
                245                 250                 255

Gln His Gln Ser Thr Asp Val Ile Val Trp Ser Pro Pro Pro Gly Glu
            260                 265                 270

Phe Gln Phe Ile Gly Lys Ala Lys Val Val Ala Val Asp Glu Lys Glu
        275                 280                 285

Glu Asn Asn Lys Arg Ala Phe Leu Ala Leu Asp Ile Tyr Lys Asn Thr
    290                 295                 300

Ser Pro Glu Thr Glu Leu Leu Leu Val Glu Leu Pro Gly Gly Thr Ala
305                 310                 315                 320

Gly Pro Ala Gly Val Leu Leu Pro Glu Leu Val Thr Lys Glu Met Lys
                325                 330                 335

Trp Val Ser Arg Gly Phe Thr Gly Glu Thr His Tyr Ile Gly Ser Ser
            340                 345                 350

Ser Ala Glu Arg His Phe Phe Thr Ser Phe Thr Asp Gly Val Ser Thr
        355                 360                 365

Gly Arg Ile Ile Ala Phe Asp Ser Ala Asp Trp Asp Ala Thr Asp Ile
    370                 375                 380

Asp Ser Pro Leu Pro Met Gln Glu Ile Val Pro Ala Asp Pro Glu Gly
385                 390                 395                 400

His Gln Leu Gln Ser Ala Tyr Phe Ile Gly Asp Arg Leu Leu Ala Leu
                405                 410                 415

Ile Tyr Leu Lys His Ala Cys Ala Ser Val Val Phe Ile Asp Ala Arg
            420                 425                 430

Thr Gly Lys Pro Leu Gly Ser Ala Asp Ala Gln Gly Thr His Gly Asn
        435                 440                 445

Val Ala Ala Asp Pro Glu Thr Gln Val Pro Val Pro Glu Glu Glu Val
    450                 455                 460

Gln His Ala Lys Glu Gly Gln Val Val Ile Pro Glu His Gly Ala Ile
465                 470                 475                 480

Thr Ser Ile Ser Cys Arg Pro Asp Ala Asn Asp Phe Tyr Phe Thr Val
                485                 490                 495

Asp Thr Trp Val Ala Pro Ser Tyr Val Leu Lys Gly Glu Leu Ile Lys
            500                 505                 510

Asn Lys Ala Gly Arg Tyr Glu Val Asp Ile Ser Ser Val Asn Ser Ser
        515                 520                 525
```

```
Glu Thr Ala Ala Gln Glu Thr Leu Val Cys Ser Gln Val Phe Tyr Thr
    530                 535                 540

Ser His Asp Gly Thr Arg Ile Pro Met Phe Ile Cys His Pro His Asp
545                 550                 555                 560

Leu Asp Leu Thr Arg Pro His Pro Leu Leu Leu His Ala Tyr Gly Gly
                565                 570                 575

Phe Cys Ser Pro Leu Ile Pro His Phe Asp Pro Met Phe Ala Val Phe
            580                 585                 590

Met Arg Asn Leu Arg Gly Val Val Ala Ile Ala Gly Ile Arg Gly Gly
        595                 600                 605

Gly Glu Tyr Gly Lys Ala Trp His Glu Ala Ala Ile Gly Ile Lys Arg
    610                 615                 620

Ser Val Gly Trp Asp Asp Phe Ala Ala Ala Ala Arg Tyr Val Gln Ser
625                 630                 635                 640

Arg Gly Leu Thr Thr Pro Ser Leu Thr Ala Ile Tyr Gly Ser Ser Asn
                645                 650                 655

Gly Gly Leu Leu Val Ser Ala Ala Thr Val Arg Asn Pro Glu Leu Tyr
            660                 665                 670

Ser Val Val Phe Ala Asp Val Ala Ile Thr Asp Leu Ile Arg Tyr His
        675                 680                 685

Lys Phe Thr Leu Gly Arg Met Trp Met Thr Glu Tyr Gly Ser Pro Glu
    690                 695                 700

Glu Pro Glu Thr Leu Ala Val Leu Arg Ala Asn Ser Pro Leu His Asn
705                 710                 715                 720

Ile Ser Arg Asp Pro Ser Val Gln Tyr Pro Ala Met Leu Leu Thr Thr
                725                 730                 735

Gly Asp His Asp Thr Arg Val Val Pro Gly His Ser Leu Lys Leu Leu
            740                 745                 750

Ala Glu Leu Gln Thr Leu Lys Ala Lys Asn His Gly Ala Ile Leu Gly
        755                 760                 765

Arg Val Tyr Ile Asn Ala Gly His Glu Gln Ser Thr Lys Ser Thr Glu
    770                 775                 780

Lys Lys Val Glu Glu Ala Val Asp Arg Leu Val Phe Ala Leu Asp Asn
785                 790                 795                 800

Ile Lys Ile


<210> SEQ ID NO 154
<211> LENGTH: 811
<212> TYPE: PRT
<213> ORGANISM: Cryptococcus neoformans

<400> SEQUENCE: 154

Met Ala Ile Glu Thr Ser Ala Ala His Asp Val Asp Ser Ala Pro His
1               5                   10                  15

Gly Leu Leu Lys Asn Ala Pro Thr Asp Asp Leu Thr Leu Glu Asp Glu
            20                  25                  30

Ser Trp Gln His Ser Val Cys Val His Ser Tyr Pro Ser Pro Pro Leu
        35                  40                  45

Asn Gly Gly Val Thr Glu Ile Ile Phe Asp Ile Glu Val Lys Asp Pro
    50                  55                  60

Trp Arg Ala Leu Glu Asp Gln Gly Ser Glu Val Thr Lys Lys Phe Ile
65                  70                  75                  80

Glu Glu Gln Asn His Leu Ser Val Pro Arg Leu Ser Asn His Pro Leu
                85                  90                  95
```

-continued

```
Arg Thr Glu Leu Glu Ile Ala Val Glu Gln Cys Tyr Asn His Glu Arg
            100                 105                 110

Met Thr Cys Pro Glu Leu Gln Ala Ser Gly Tyr Tyr Tyr Trp Lys Tyr
        115                 120                 125

Asn Gln Gly Thr Ser Pro Arg Asp Val Ile Leu Arg Ser Lys Asn Leu
    130                 135                 140

Glu Ser Asp Phe Gly Lys Phe Ala Ser Glu Asp Gly Lys Gly Pro Glu
145                 150                 155                 160

Leu Phe Phe Asp Leu Asn Thr Glu Glu Asn Ile Ser Leu Tyr Ala His
                165                 170                 175

Ser Phe Ser Pro Ser Gly Lys Leu Trp Cys Ala Ile Leu Gln Gln Ser
            180                 185                 190

Gly Gly Asp Trp Leu Arg Leu Arg Val Tyr Asp Thr Gln Thr Lys Lys
        195                 200                 205

Ala Ile Glu Arg Ser Val Gly Gly Ala Lys Phe Thr Phe Gly Ala Thr
    210                 215                 220

Trp Val Gly Glu Lys Gly Phe Ile Tyr Lys Arg Val Ile Asp Tyr Asp
225                 230                 235                 240

Thr Thr Asp Gly Asn Tyr Gln Ala Lys Glu Gly Gln Phe Gly Leu Phe
                245                 250                 255

Tyr His Gln Ile Gly Thr Pro Gln Ser Glu Asp Val Leu Val Trp Lys
            260                 265                 270

Ala Pro Glu Gly Val Phe Gln Tyr Ile Gly Lys Pro Leu Ile Ile Thr
        275                 280                 285

Ser Asp Ala Lys Glu Glu Asn Lys Lys Arg Ala Trp Phe Met Leu Asp
    290                 295                 300

Ile Tyr Arg Asn Thr Ser Pro Glu Thr Glu Val Leu Met Val Glu Leu
305                 310                 315                 320

Pro Gly Gly Thr Ala Gly Pro Val Gly His Thr Leu Pro Ser Leu Val
                325                 330                 335

Leu His Gly Lys Lys Trp Val Ser Lys Gly Phe Thr Gly Met Thr Asn
            340                 345                 350

Tyr Ile Gly Ser Leu Ser Asp Asp Thr His Leu Phe Thr Ser Phe Thr
        355                 360                 365

Asp Gly Ile Ser Thr Gly Arg Ile Ile Ser Val Ser Ala Ala Asp Tyr
    370                 375                 380

Asp Ala Cys Gly Val Asn Glu Ala Ile Lys Phe Asn Thr Val Val Pro
385                 390                 395                 400

Ala Asn Ser Glu Gly His Gln Leu Arg His Ala Tyr Leu Ile Gly Asp
                405                 410                 415

Gln Val Ile Val Leu Asp Tyr Leu Lys His Gly Cys Ser Phe Leu Val
            420                 425                 430

Phe Leu Asp Ala Arg Thr Gly Lys Ser Val Gly Ser Ser Asp Ser Arg
        435                 440                 445

Gly Thr Arg Gly Asp Ala Ala Ile Asp Pro Asp Val Glu Val Pro Val
    450                 455                 460

Pro Glu Glu Glu Val Ala Glu Gln Ser Pro Thr Glu Asp Gln Val Ile
465                 470                 475                 480

Ile Pro Gln His Ala Ser Ile Asn Glu Leu Gln Ser Arg Pro Asp Ser
                485                 490                 495

Asn Asp Phe Tyr Phe Ser Val Asn Thr Phe Val Ala Pro Pro Tyr Val
            500                 505                 510
```

```
Leu Arg Gly Glu Leu Ile Lys Asn His Lys Val Glu Lys Gly Ile Lys
        515                 520                 525

Ile Ser Gly Ile Ser Lys Ser His Thr Met Pro Gln Glu Thr Leu Val
    530                 535                 540

Cys Ser Gln Leu Phe Tyr Glu Ser His Asp Gly Val Lys Ile Pro Met
545                 550                 555                 560

Phe Ile Cys His Ala His Asp Leu Asp Leu Thr Lys Pro Asn Pro Ala
                565                 570                 575

Leu Val His Ala Tyr Gly Gly Phe Cys Ser Pro Ser Leu Pro Arg Phe
            580                 585                 590

Asp Pro Met Phe Val Ala Phe Met Arg Asn Leu Arg Gly Ile Val Ala
        595                 600                 605

Val Ala Gly Ile Arg Gly Gly Gly Glu Tyr Gly Pro Glu Trp His Glu
    610                 615                 620

Ala Ala Leu Gly Ile Lys Arg Trp Val Gly Trp Asp Asp Phe Ala Trp
625                 630                 635                 640

Ala Ala Lys Tyr Leu Gln Gly Lys Gly Leu Thr Thr Pro Ala Leu Thr
                645                 650                 655

Ala Thr Tyr Gly Thr Ser Asn Gly Gly Leu Leu Val Ser Ala Ala Met
            660                 665                 670

Val Arg Asn Pro Ser Leu Tyr Ser Val Val Phe Pro Asp Val Ala Ile
        675                 680                 685

Thr Asp Leu Leu Arg Tyr His Lys Phe Thr Leu Gly Arg Ile Trp Met
    690                 695                 700

Asp Glu Tyr Gly Ser Pro Glu Lys Ala Glu Asp Phe Pro Ile Leu His
705                 710                 715                 720

Ser Thr Ser Pro Leu His Ser Val Asp Gly Asp Pro Ala Val Gln Tyr
                725                 730                 735

Pro Ala Val Leu Ile Thr Thr Ala Asp His Asp Thr Arg Val Val Pro
            740                 745                 750

Ser His Ser Leu Lys Phe Leu Ala Glu Leu Gln Ala Arg Lys Ser Glu
        755                 760                 765

Asn Lys Gly Val Phe Leu Gly Arg Ile Tyr Glu Asn Ala Gly His Glu
    770                 775                 780

Leu Gly Ser Lys Pro Thr Lys Lys Lys Val Glu Glu Ala Val Asp Arg
785                 790                 795                 800

Leu Val Phe Val Leu Tyr Asn Leu Lys Glu Gln
                805                 810
```

<210> SEQ ID NO 155
<211> LENGTH: 669
<212> TYPE: DNA
<213> ORGANISM: Homo sapiens

<400> SEQUENCE: 155

```
cacttacgat gacaaattaa gaaatatctt actcagtaag gaagtatctt ttcctttctt      60

ccactaaggt acaagccata tatatagaag gtggaataat gaggaaactc ctgtcgaaat     120

tcaaaacatt acaggcaagc tttctcatgc acaaaatgct gcttttaatt ggttcttaac     180

taaattaatt aagctggtat gactcactct ccagtcacaa ctcaacttga aaaacacaaa     240

ggaatatggc tgggataaca aaagctaaga tccctgaatt actcctgatt ttcatattaa     300

caagagagtt cagcctatag agaaaaggtt aatttgtttt ttaataggct tttgaaagac     360

gtgatcaggt ctagtgtgat aatttatggt taatcatatg tttagaggca aaagggatta     420
```

atcttttaat attagagcaa ttttttctgt aatataaaac aaagttcttt tcatagtaac 480
attaaaagtc agatcaaact tcctttttga gcaaagttgg caaattgaca agaaggaaga 540
agaaaatctg tctgaacagc agcatagtaa gaagatcaga ccagcatggt aactccctgc 600
aaaagcctct ttcccaatct gtctcctttt ttattttacc ataagtggtg taaaccaaaa 660
attaaattc 669

<210> SEQ ID NO 156
<211> LENGTH: 2253
<212> TYPE: DNA
<213> ORGANISM: Phanerochaete chrysosporium

<400> SEQUENCE: 156
atgcgtacac cgtggacacc gaaccgctat cctccagcac gtcgctctga tcactatgat 60
gaatacaaga gcgagaagaa cggcgtggtc agagtacacg atccgtacaa ctggctggaa 120
cacaatacac aggaaactga gtcgtggacg tccgctcaag tcgcattcac caaagaatat 180
ctggaccaga atccagacag acagaagctc gaggacgaaa tcaggaggaa cactgactat 240
gccaagttct ccgcgccgag cctaaaggac gacggccgct ggtactggta ctataacagc 300
ggcctacagc cacagtcagg tgtgcatgca tttgtactac tcttgtgcca ctctgatatt 360
gatgtaccga cctcagtgat ataccgttcc cgagatagga acctacctac tatgagcaat 420
gaagagggac ctggcggaga ggtgttcttc gaccccaatc tcctctctaa cgatggcaca 480
gctgctctcg cggctactgc attctcgcgt gatggcaaat actttgcata tggtatatcc 540
cgctctggaa gcgactttta caccgtctat gtccgcccaa cttcggcacc gctcgcgtct 600
caaggcgagt cacgggtttc ccatgatgac gaacgtctgc aggacgaggt caggttcgtg 660
aagttctcga gcatctcctg gtcgcacgac tccaaaggat tcttctacca gcgatatcct 720
gagcgaaagt ctcatggatc tgcagacgag gacaaagctg gtacagagac ggaaagcgac 780
aagcatgcta tgctctacta tcaccgtgta ggaacctcac agcttgagga cgtccttgtc 840
tataaggatg acgcgaatcc agaatggttc tggggtgcag agatctctga agaggatggc 900
cgttacctca ttctatctgt gtccagggac acttcaagaa aaaacctcct atggattgcg 960
gacctcgaga gcaatgcaat tggtcaggat atgcagtgga acaaattgat tgacgaattc 1020
gatgcctcat atgactacat cgcaaacaac ggcaacaagt tctacttcca gacgaacaaa 1080
gacgctccac aatacaagct agtcagcgtc gatatatctg cccctccggc acagcgcacc 1140
ttcgaggatg tcatacctga ggataagaat gctcatttgg aggacgtcct cgccatcgcc 1200
gacgacaagt ttgcggtcgt gtacaagcgc aatgtcaaag atgagatcta catttacgac 1260
atgaatggca agcagttgga gcgcgtggcg cccgactttg tcggagcagc cagtatcgct 1320
gggcgcaggt cacaaccgtg gttctttgcc acactcactg gctttacaaa ccccggcatc 1380
gtctcacggt acgacttcac tcagcaagat ccagcgaaga gatggagtac atatcgtacc 1440
acgctcttga agggcttgaa ggcggaggat ttcgaagcgc agcaggtttg gtaccatagc 1500
aaggacggca cgaagattcc catgttcatt gtccgccaca ggaataccaa atttgatgga 1560
acagcgccag ccatccaata tggctacggc ggattcacca tctcaatcaa tccgttcttc 1620
agcgcatctt tcttgacttt cctccaacgt tatggcgccg tgctcgccgt gccaaatatc 1680
cggggaggtg gtgagttcgg tgaagagtgg cacctggctg gcactcgaga gcgcaaggtc 1740
aactgcttcg acgattttat tgccgccaca caatttttga ttgacaacaa gtacgctgcg 1800
ccgggctgcg gtaattccga ttatgcgcca gactcaagag ttacaacagg tctcctggtc 1860

```
gctgcctgtg tgaatcgtgc tcccgagggg ctacttggcg ctgctgtcgc ggaggtcggt   1920

gtccttgatc tcctcaagtt cgcggacttc accatcggtc gggcgtggac gtcagattac   1980

ggtaatccac acgatccaca tgacttcgac ttcatctacc caatctctcc gctgcacaac   2040

gtgccgaagg acaaagatct tcctccaacc atcttgttga cggctgaccc aagcatagac   2100

gacgacaggg ttgtaccatt gcattcttac aagcatgctg ctacgctgca atacaccttg   2160

tcgcacaaca cgcatcccct tctcatccgc atagacaaga aggcgggcca tggtgctgga   2220

aagtccacgg accagaggca cgccattctc tga                                2253
```

<210> SEQ ID NO 157
<211> LENGTH: 2207
<212> TYPE: DNA
<213> ORGANISM: Sporobolomyces roseus

<400> SEQUENCE: 157

```
atgtcgtccg cccgcaccgc gtgggatccg aaatcgactc cgtacccttc ggtacaccgc     60

tccgacactg tcgaagagtt caaatctgcc aaacacggta ccgtcaaggt cgcagatccg    120

tacgactggc tcgcgttccc agattcgaaa gagactcaac acttcgtcca gcagcaaggc    180

gacttcacca agaagtacct cgaccagtac caggacaagg agaagttctc gaaagagctc    240

gaaaagaact ggaactatgc gaggttctct tgcccttctc tcaaagggga tggatactac    300

tacttcacct acaactctgg actagccgct ccgaacctcc tcagcaccga cgggtccgtc    360

tctcgttcaa catcttcttt ctcggaagac ggaaagtact acgcgtatgc gctctcgcgt    420

tccggatccg actggaacac gatttacgtt cgagaaacgt cttcacctca cctctcgacc    480

caagccgtcg gatccgacga aggacgtctt ccgaacgacg ttctccgatt cgtcaagttt    540

tctggaatcg gttggacggc ggattcgaaa ggtttcttct accaaaggtt ccccgagcgc    600

aaagagcacg gaggagaaga ggatgacaag gctggtaccg agacggacaa agacttgaac    660

gcgagtctct actatcaccg agtcggtact cctcaaagtg aggacgtctt gattcaccaa    720

gacaaggaac accccgaatg gatgtttggc gccggagcta ccgaagatgg tcgataccte    780

gtcatgactt cgtcgcgaga cactgctcgc tcgaacctcc tctggattgc cgatttgcaa    840

gaccctcaaa actcggaaat cggtcccaac ctcaagtgga acaaactcat caacgagtgg    900

ggtacctact ggtccgagtt gacgaacgac gggtccaagt tctactttta caccaacgcc    960

gaagacagtc cgaattacaa gatcgtcact ttcgacttgg agaaaccgga acaaggattc   1020

aaagacttga tcgctcacaa cccgaaatcg cctctcactt cggctcacct cgccgcaaac   1080

gaccaactga tcctcctcta ctcgaacgac gtcaaggacg aactctacct tcactctctc   1140

gagacgggag aacgagtcaa gcgactcgcg tcagacttga tcggcacggt cgagcaattc   1200

agtggaaggc gagaacacaa ggagatgtgg ttctcgatga gcggattcac ttcacccggt   1260

actgtgtacc gttacgaatt cgagggagag aacgctggcg tcgagcagga gtacaggaaa   1320

gcgactgtcg aagggatcaa ggcggaagac tttgaaagct cgcaagtctt ttacgagagc   1380

aaggatggaa ccaaagtccc catgttcatc acgagaccga aaggagtcga gaaaggaccg   1440

gttctcttat atgcctacgg tggattcagt cacgccatca ctcccttctt ctcaccctcg   1500

ctcatgacgt ggatcaagca ctacaaagct gcgttatgta ttgccaacat tcgaggtgga   1560

gacgagtacg gcgagaaatg gcatgaggct ggaacgaagg agcggaagca aaactgtttc   1620

gacgatttcc aatgggcagc gaagtacttg tacaaagagg gaatcgcaga agaaggcaag   1680
```

```
atcgcaatct cgggaggttc gaatggaggt ctgcttgtcg gagcgtgcgt gaatcaagcg   1740

cctgagttgt acggtgccgc gattgcagat gtcggagtac ttgacatgct ccgctttcat   1800

cgctacacga tcggtcgagc gtggtcctcg gactatggat gttcggacga gcccgaagga   1860

ttcgactatc tctacgctta ttcacctttg caaaacgtcg acccgagcaa gaagccgttc   1920

ccgccgacga tgctcttgac cgcggatcac gacgatcgtg tcgttcccct tcattcgttc   1980

aagcacatct cggaactgca gcacaaactt cccgacaacc ctcaccctct cctgttacga   2040

gtcgacacga aatcaggtca cggtgccgga aagagtacgg cgaagaagat cgaggaagca   2100

tgcgagaagt atgggttcgt atctcagtcc atgggattac gatggcacga ctagatgtag   2160

cgatgtgacg gaccttggct ggaaaatgct tattctcttt tcgcgag                 2207


<210> SEQ ID NO 158
<211> LENGTH: 723
<212> TYPE: PRT
<213> ORGANISM: Phaeosphaeria nodorum

<400> SEQUENCE: 158

Met Ala Glu Gln Asn Ser Ala Leu Ile Ala Gly Leu Gly Cys Gln Pro
1               5                   10                  15

Val Glu Ser Ser Ser Glu Ala Asp Ala Gly Ile Asn Trp Gln Trp Leu
            20                  25                  30

Glu Glu Pro Gln Gly Ala Thr Gly Leu Glu Trp Ala Lys His Glu Thr
        35                  40                  45

Glu Ile Thr Gln Glu His Leu Asp Arg Leu Pro Arg Ala His Lys Leu
    50                  55                  60

His Glu Lys Leu Glu Lys Met Ile Glu Gln Asn Ala Ala Pro Pro Thr
65                  70                  75                  80

Tyr Ala Leu Cys Gly Arg Leu Phe Arg Leu Arg Arg Asp Ala Val Arg
                85                  90                  95

Lys Ser Gly Ile Ile Glu Val Ala Ala Leu Glu Thr Pro Asp Glu Trp
            100                 105                 110

Thr Thr Val Ile Asp Ile Asp Asp Leu Arg Glu Arg Glu Gly Lys Pro
        115                 120                 125

Trp Gln Leu Ser Gln Thr Val Leu Pro Cys Phe Ser Ser Val Tyr Leu
    130                 135                 140

Gly Gly Gln Ser Ser Arg Leu Leu Leu Gly Leu Ser Glu Gly Gly Ser
145                 150                 155                 160

Asp Glu Thr Thr Ile Arg Glu Phe Asp Val Asp Gln Ala Ala Trp Val
                165                 170                 175

Thr Asp Gly Phe Ala Ala Gly Pro Gly Arg Phe Ser Ala Ala Trp Leu
            180                 185                 190

Asp Leu Asp His Val Met Ile Thr His Ala Leu Asn Gly Gly Pro Thr
        195                 200                 205

Cys Asn Thr Gly Trp Pro Leu Asn Thr Tyr Ile Trp Ala Arg Gly Thr
    210                 215                 220

Glu Leu Ala Asp Ala Lys Leu Val His Ser Gly Asp Pro Gly Asp Ala
225                 230                 235                 240

Ile Leu Tyr Cys Ser Ala Val Gly Thr Gly Arg Thr Arg Arg Gly Leu
                245                 250                 255

Ile Gly Gln Ala Ala Thr Phe Ala Asp Leu Lys Phe His Thr Val Ser
            260                 265                 270

Ile Asp Gly Thr Val Glu Arg Ala Ser Leu Pro Gln Gly Leu Ser Leu
        275                 280                 285
```

-continued

```
Ala Met Phe Leu Pro Ser Thr Ser Thr His Leu Phe Val Thr Thr Thr
    290                 295                 300

Glu Glu Ser Thr Ile Gly Asn Lys Lys Ile Arg Lys Asp Ala Leu Leu
305                 310                 315                 320

Ala Trp Lys Tyr Thr His Gly Gln Thr Arg Thr Ser Val Val Tyr Val
                325                 330                 335

Pro Glu Ser Gly Glu Ala Ile Leu Asp Ala Val Thr Gly Gly Ile Ser
            340                 345                 350

Ala Gly Pro Ser Lys Val Tyr Phe Thr Leu Leu Lys Arg Asn Thr Glu
        355                 360                 365

Arg Arg Met Val Met Glu Tyr Val Asn Asp Glu Trp Lys Leu Cys Gln
    370                 375                 380

Ala Ile Pro Thr Pro Thr Gly Ala Ser Ala Lys Val Gln Thr Ala Asp
385                 390                 395                 400

Pro Tyr Ser Asp Ser Ile Ile Val Glu Thr Ser Gly Leu Leu Asn Pro
                405                 410                 415

Lys His Val Cys Leu Glu Asn Ala Gly Gly Ser Arg Lys Thr Asp Leu
            420                 425                 430

Tyr Ser Gln Lys Ala Ala Phe Asp His Ser Asn Cys Ala Val Glu Thr
        435                 440                 445

Gln Val Ala Thr Ser Lys Asp Gly Thr Glu Ile Asp Tyr Phe Ile Met
    450                 455                 460

Ala Pro Lys Gln Gly Arg Glu Lys Leu Pro Val Leu Ile Thr Gly Tyr
465                 470                 475                 480

Gly Ala Phe Gly Met Asn Phe Asp Leu Ser Tyr Val Gly Pro Met Leu
                485                 490                 495

Gly Gly Leu Ser Leu Ala Leu Trp Leu Glu Leu Gly Gly Ala Leu Val
            500                 505                 510

Val Pro Leu Ile Arg Gly Gly Gly Glu Arg Gly Glu Asp Trp His Gln
        515                 520                 525

Ala Ala Leu Arg Glu Asn Arg Gln Arg Ser Tyr Asp Asp Phe Ala Ala
    530                 535                 540

Val Ala Glu Ala Ile Ile Ser Asn Gly Leu Thr Ser Pro Gln Lys Leu
545                 550                 555                 560

Gly Val Phe Gly Phe Ser Asn Gly Gly Leu Leu Ala Ala Val Met Gly
                565                 570                 575

Thr Gln Arg Pro Asp Leu Phe Gly Ala Val Val Ser Asp Val Pro Leu
            580                 585                 590

Thr Asp Met Leu Arg Phe Pro Glu Leu Ala Met Gly Ser Ala Trp Leu
        595                 600                 605

Asn Glu Tyr Gly Asp Pro Lys Val Pro Glu Gln Ala Lys Ala Leu Arg
    610                 615                 620

Ala Tyr Ser Pro Phe His Asn Val Lys Gln Gly Thr Ala Tyr Pro Pro
625                 630                 635                 640

Met Leu Ile Thr Cys Ser Thr Leu Asp Asp Arg Val Gly Val Gly His
                645                 650                 655

Ser Arg Lys Leu Val Ala Arg Leu Lys Glu Val Glu Ser Pro Lys Thr
            660                 665                 670

Phe Leu Tyr Glu Glu Thr Glu Gly Gly His Ser Ser Tyr Arg Asp Leu
        675                 680                 685

Thr Thr Asn His Leu His His Leu Phe Arg Asp Met Asp Asp Ser Pro
    690                 695                 700
```

Val Asn Ile Glu Ser Lys Val Gly Thr Ala Gly His Ile Lys Ile Ser
705 710 715 720

Met Ser Gly

<210> SEQ ID NO 159
<211> LENGTH: 112
<212> TYPE: DNA
<213> ORGANISM: Amanita bisporigera

<400> SEQUENCE: 159
ttgagagcac acaagtctgg tatgagagca aagacggaac gaaagttcca atgttcatcg 60
ttcgtcacaa atcaacgaaa tttgacggaa cggcgccggc gattcaaaac gg 112

<210> SEQ ID NO 160
<211> LENGTH: 33
<212> TYPE: PRT
<213> ORGANISM: Amanita bisporigera

<400> SEQUENCE: 160

Glu Ser Thr Gln Val Trp Tyr Glu Ser Lys Asp Gly Thr Lys Val Pro
1 5 10 15

Met Phe Ile Val Arg His Lys Ser Thr Lys Phe Asp Gly Thr Ala Pro
20 25 30

Ala

<210> SEQ ID NO 161
<211> LENGTH: 206
<212> TYPE: DNA
<213> ORGANISM: Amanita bisporigera

<400> SEQUENCE: 161
cgtatatcga actgccaagg tcaagggttt aaatccgaac gatttcgagg ctcgacaggt 60
gactagttgg ttttatattg catgaaaagt gcgtctcatg cggtctaggt gtggtatgac 120
agctacgacg gaacaaagat tccaatgttc atcgtccgtc acaagaatac caaatttaat 180
gggacggcgc cagctataca atatgg 206

<210> SEQ ID NO 162
<211> LENGTH: 32
<212> TYPE: PRT
<213> ORGANISM: Amanita bisporigera

<400> SEQUENCE: 162

Val Trp Tyr Asp Ser Tyr Asp Gly Thr Lys Ile Pro Met Phe Ile Val
1 5 10 15

Arg His Lys Asn Thr Lys Phe Asn Gly Thr Ala Pro Ala Ile Gln Tyr
20 25 30

<210> SEQ ID NO 163
<211> LENGTH: 107
<212> TYPE: DNA
<213> ORGANISM: Amanita bisporigera

<400> SEQUENCE: 163
cgacaaacaa gtaacaccta cgcgcgaaaa actcgcgatc tccggcggca gcaacggcgg 60
actcctcgtc ggcgcaagcc gattgaccca gcgccccgac ctcttcg 107

<210> SEQ ID NO 164
<211> LENGTH: 27
<212> TYPE: PRT

<213> ORGANISM: Amanita bisporigera

<400> SEQUENCE: 164

Glu Lys Leu Ala Ile Ser Gly Gly Ser Asn Gly Gly Leu Leu Val Gly
1 5 10 15

Ala Ser Arg Leu Thr Gln Arg Pro Asp Leu Phe
20 25

<210> SEQ ID NO 165
<211> LENGTH: 94
<212> TYPE: DNA
<213> ORGANISM: Amanita bisporigera

<400> SEQUENCE: 165
atcctcggat ggcacagcct cgctctccat gtatgatttc tcacactgtg gcaaatactt 60
cgcatatggt atttctcttt ccgtatgtaa tttt 94

<210> SEQ ID NO 166
<211> LENGTH: 27
<212> TYPE: PRT
<213> ORGANISM: Amanita bisporigera

<400> SEQUENCE: 166

Ser Ser Asp Gly Thr Ala Ser Leu Ser Met Tyr Asp Phe Ser His Cys
1 5 10 15

Gly Lys Tyr Phe Ala Tyr Gly Ile Ser Leu Ser
20 25

<210> SEQ ID NO 167
<211> LENGTH: 106
<212> TYPE: DNA
<213> ORGANISM: Amanita bisporigera

<400> SEQUENCE: 167
gggataatta attgcagcga gttatgacaa cggaaaaacc cacctcttct cagtagattt 60
tcctccgcca tgccccgctt tcttgtctac acgtagcaga agtgga 106

<210> SEQ ID NO 168
<211> LENGTH: 20
<212> TYPE: PRT
<213> ORGANISM: Amanita bisporigera

<400> SEQUENCE: 168

Pro Leu Leu Leu Arg Val Asp Lys Lys Ala Gly His Gly Gly Gly Lys
1 5 10 15

Ser Thr Glu Lys
20

<210> SEQ ID NO 169
<211> LENGTH: 16
<212> TYPE: PRT
<213> ORGANISM: Amanita bisporigera

<400> SEQUENCE: 169

Asp Gly Thr Lys Val Pro Met Phe Ile Val Arg His Lys Ser Thr Lys
1 5 10 15

<210> SEQ ID NO 170
<211> LENGTH: 3054
<212> TYPE: DNA
<213> ORGANISM: Amanita bisporigera

<400> SEQUENCE: 170

```
ggacacccca accatgtacc cttctgctcg ccgttcagac catatagaca catacaggag     60
cgaaacgaga ggcgaagtca aggtgccgga cccataccac tggctagagg aatattcaga    120
agagacggac aagtggacgt ccgaccagga ggagttcacg aggacatatt tggacagcaa    180
ccctgatcga aagaagctag aagacgcatt cagaaagagt atggattatc ccaaggtttc    240
ttcggcattc tattcattct gatggaatgg aatcgttgat ggctgccaat cttctttcct    300
tttatatagt tctccgctcc ttttttgaat gatgacaagc gatggtattg gttttacaat    360
accggccttc aagcacaaac aggtaaacac atcaagctct gtcgtgcgaa atatttacaa    420
cttttggtag tcatctgcag atcaaaggat gagactcttc ccgacttctc agagagtgac    480
tacgtcgggg aaacattttt tgatgtaagt gtagtttgtc gctggcggtg ttcgatatca    540
atgatagcgt tttcgcagcc gaacctatta tcctcggatg gcacagcctc gctctccatg    600
tatgatttct cacactgtgg caaatacttc gcatatggta tttctctttc cgtatgtaat    660
tttcaacgag caaccatccc ttccgatgag atgaacttct ttttcgtcac aggggagcga    720
tttttcaact atatacgttc ggtcaacttc ctctccactg gcccctggca acgacagcat    780
tagaaatgac gacggtagac ttccagacga gcttagatat gtcaaatttt cctccatcag    840
ctggacaaag gactcccaag gatttttcta tcaggtacta cactatggaa agatctgcgg    900
acttgactaa attacttgca gcgctatccc ggtacaggca ctgtgaatgg acagaatggc    960
atccaaactc aaggcgatcg tgatgctatg atttactatc accggatagg gacatcacaa   1020
tgtatacccc gctcttttgt ccaatcctct catttcaatt cgctcttcta gccgatgata   1080
ttcttgtgca tgaagaccag gaacatcctg attgggtatt tggcgcagaa gtcacggaag   1140
atggtaaata tgtggccctg tacacaatga aggacacatc aagggtatgc tttaagtggt   1200
cccacctgcg ttgctaaccg gttcttgtag aaaaatctat tgtggattgc tgatcttgga   1260
caaaacgaag ttggacgaaa catgaaatgg aacaagattt gcaacgtttt tgactcagaa   1320
tacgacctgt aagtccctga acggtaatac ggttgttttt ttgcttattt gcgacagaat   1380
tggcaacgac ggttcattac tatacatcag aactaataaa gctgcacctc aatacaagat   1440
tgtcacctta gatatagaga aaccagaatt agggtttaag gaattcatac cggaagatcc   1500
caaagcatat ctctctcaag tcaaaatttt taataaggat agactagcac tagtatacaa   1560
gcgtaacgtg agtccagaac acggcaatat atcgcaggag agcaaattga tggaaaaaat   1620
aggttatagg cgaactctac gtctacaata acactgggtc acgactaatg cgcctagccc   1680
gggactttgt tggctccatg acggtgaccg ctcgagaaac ggagccatgg tttttttgcca   1740
ctctcacggg cttcaatacc cctggaatcg tatgcaggta caatatccag cgaccggaag   1800
aacagcgttg gagcgtatat cgaactgcca aggtcaaggg tttaaatccg aacgatttcg   1860
aggctcgaca ggtgactagt tggttttata ttgcatgaaa agtgcgtctc atgcggtcta   1920
ggtgtggtat gacagctacg atggaacaaa gattccaatg ttcatcgtcc gtcacaagaa   1980
taccaaattt aatgggacgg cgccagctat acaatatggt aggctaaaga cagtgaattt   2040
attaccggat gacatgtcta attcactctg gcaaggttac ggtggcttta atatatctat   2100
aaatcccttc tttagtccaa cgattttgac gttcttgcaa aagtatggag caattctagc   2160
tgtacctaat atccgaggag gcggcgagtt cggcgagaca tggcatgatg ctggtatacg   2220
agagaaacga gtataacgca cgccttctcc acggtgatag ctctgacatt atttccaggc   2280
taatgtttac gatgatttca ttgcggcaac gtacgtgtca gttgtccttg aattctacat   2340
```

tgccatttac ttggtaccag tcagttcttg gtaaaaaaca agtatgccgc gggcggcaaa 2400
gtggccatca acggggggtc caatggaggt ctgttggcat gtctttatcc accctcagtc 2460
tcttatatta gccttaggac ttttggtcgc ggcctgtgtc aatcgtgcac ctgaaggaac 2520
ctttggagct gccattgctg aagttggggt cctagacttg ctcaaggttt gtccgatcgt 2580
gtcttacaga gatatatgct ccaactcata acctttgatt ttagttctcc aaatttacca 2640
taggtatatg atcaacactg ctcatgactt ttgttcttaa gtcgatatca ggcaaagctt 2700
ggactagcga ctacggcgat ccagaagatc cgcgcgattt tgatttcatt tacacacatt 2760
caccacttca taatatacca aagaacatgg tcttacctcc gacgatgctt ctgacagctg 2820
atcgtgagtt ggctcccatg gtataattgc taggttcctg acgcgaccta gatgatgacc 2880
gtgtcgtccc aatgcattca tttaagtatg ctgcaatgct acaatacacc ctgccgcata 2940
atcgtcatcc acttctgcta cgtgtagaca agaaaggcgg ggcatggcgg aggaaaatct 3000
actgagaaga ggtgggtttt tccgttgtca taactcgctg caattaatta tccc 3054

<210> SEQ ID NO 171
<211> LENGTH: 3110
<212> TYPE: DNA
<213> ORGANISM: Amanita bisporigera

<400> SEQUENCE: 171
accaatggct ggaggagaat tcaaatgaag tagacgaatg gacgacggcg cagacagctt 60
tcacgcaagr ctatcttgat aagaatgcgg atagacagaa gctcgaggag aaatttcgtg 120
caagcaagga ctacgtcaag gtaatcgatg atcgatatag cgttgtgtct gtgctgaaga 180
ccttgcccat agttttctgc gccaactctg cttgatagtg gacactggta ttggttctac 240
aatagcggcg tacaatcgca agcaggtatg tacccatctg tctctggcga tgccgaattc 300
agacagtgtt cagtcctcta ccgctccaag aaacccgttc ttcctgattt ctcaaagagg 360
gacgaggaag tcggcgaagt atacttcgat gtagggatct ccacgacgtt tgaatacttc 420
tttgacttca ctcttgaaag ccaaacgtac tctctgctga tggcaccgca attatgggca 480
cgtgccgatt ctcccctagt ggcgagtatt tcgcatatgc agtgtcccac ttggtgagta 540
accacgttcc tacatgggcc aactccttgg tcttattttt tgcacaggga gttgattatt 600
ttactatcta tgttcgccct acgagttcat cattgtctca agctccggaa gctgaaggtg 660
gggatggtcg attgtcggat gaagtgaaat ggtgcaagtt tacgactata acgtggacaa 720
aggactccaa aggatttctt taccaggtat gatacatcca gccacccaac catccgttcg 780
ttaacctgtg tcatacagcg gtaccctgct cgggaatctc ttgtggcgaa agatcgtgat 840
aaagatgcta tggtatgcta tcatagggtt ggaacgactc aatgtaggga ttacttggcg 900
tcttgacttt ccccaaactg atccagtagt acagtggaag atatcattgt ccaacaagac 960
aaggagaacc cagactggac atatggaaca gatgcgtcag aggacggcaa atatatctac 1020
ttagtggtat acaaggatgc ctcgaaggca agagtttaag ttctatcgcc cgacatcaat 1080
aaccttcata ctaccagcaa aatcttctgt gggttgcaga attcgacaag gacggggtca 1140
agccggaaat tccctggcga aaagtcatca atgagtttgg ggcggattac catgtgtgag 1200
tcctcccctc cttcacgtcc ccttcacgtc cccttttttaa ctcggcatgg tatagtatca 1260
cgaaccacgg atctttgatc tatgtcaaga ctaacgtgaa tgcgccccaa tataaagttg 1320
tcactatcga cctttcgaca ggagaacccg aaattcgtga tttcatcccg gaacagaaag 1380
atgcgaagct cactcaagtc aaatgcgtca acaaggaata tttcgtcgcg atctacaagc 1440
gcaatgtatt ttcattgaca atttgatttc gaatttccct aacgtcgatt ttgcatccac 1500
aggtcaaaga tgaaatatat ctttactcca aagcaggcga tcaactcagt cgtctggcgt 1560
cggacttcat tggcgttgca tctataacta acagagagaa acaacctcat ttcttcctca 1620
ctttctctgg atttaacacg ccgggcacca tttctcgcta cgattttaca gctccagaga 1680
cacaacgtct cagcatcctt agaacgacga agctaaatgg tctgaatgca gatgactttg 1740
agagcacaca agtctggtat gagagcaaag acggaacgaa agttccaatg ttcatcgttc 1800
gtcacaaatc aacgaaattt gacggaacgg cgccggcgat tcaaaacggt aatcctttct 1860
catccatcac aaccagtagg aatctctgac aacctgtctt gcttcgcaca ggttatggtg 1920
gtttcgcgat tacagccgat ccattcttta gtcccatcat gctcaccttt atgcagacat 1980
atggcgcaat cctggctgtc ccgaacatca gaggtggagg tgaattcggc ggagaatggc 2040
acaaggcagg gagacgagaa accaaggttt gtgcccattg ccttatattt ctgttgcatg 2100
cagcctggac ctccgtaata gggaaatact tttgatgatt tcatcgctgc cgcgtatgtc 2160
cgccgctatt cgaattttcg tgatttcaca ggctcacgga ggtcttttgt tgctacagtc 2220
aatttcttgt caaaaacaag tacgcggctc caggcaaagg tggccatcac tggtgcatcc 2280
aatggcggta aagtgaccct cgttcttgtt ttcatcccgg tactcacctc gcgatggtgg 2340
aataggtttt cttgtctgtg gttccgtagt tcgggcacca gaggggacat tcggcgctgc 2400
tgtttccgaa ggtggtgtcg cggacctcct aaaggtattt tggttgtcca cgatatccgt 2460
gctcgttctc taatttctgt atttgagttt aataaattta ccgggggtga gttgacattg 2520
gtcttgtgtc caccgctgat ttgattaatt acatcgtcag ggatggcgtg gacgagtgaa 2580
tatggaaacc cttttattaa ggaggacttc gactttgtcc aagcattgtc tcctgtgcat 2640
aacgtaccca aggatagggt tcttcctgcc acattactta tgaccaatgc gggtgggtga 2700
ctctctggag cccagattta ccagtacctg acgctcgact ctcatcaggt gacgatcgtg 2760
tagttccaat gcattcgctt aagttcgtcg caaaccttca gtacaatgtg cctcaaaatc 2820
ctcatccatt gctcatccgt gtggataaat cttggcttgg tcattggttt tggcaagaca 2880
acagacaagc agtaaattgc cctcctttc tacgttccat tgcttatatt ttacagtact 2940
aaagatgctg cggacaagtg gagtttcgta gcgcaatcgt tagggctaga atggaaaacg 3000
gttgactagg ctgtcaaatt aacagatgcg ggctcaaaat accgtccacg ttagatgtat 3060
tcaatgtact ctgtttcctg taaccctgcg tacggcccaa tacagccatg 3110

<210> SEQ ID NO 172
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 172
gaaacgagag gcgaagtcaa ggtg 24

<210> SEQ ID NO 173
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 173
aagtggatga cgattatgcg gcag 24

<210> SEQ ID NO 174
<211> LENGTH: 27
<212> TYPE: DNA
<213> ORGANISM: Artificial Sequence
<220> FEATURE:
<223> OTHER INFORMATION: A synthetic oligonucleotide

<400> SEQUENCE: 174
gattgggtat ttggcgcaga agtcacg 27

<210> SEQ ID NO 175
<211> LENGTH: 27
<212> TYPE: DNA
<213> ORGANISM: Artificial Sequence
<220> FEATURE:
<223> OTHER INFORMATION: A synthetic oligonucleotide

<400> SEQUENCE: 175
atgtctcgcc gaactcgccg cctcctc 27

<210> SEQ ID NO 176
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 176
tcaaatgaag tagacgaatg gac 23

<210> SEQ ID NO 177
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 177
cacacggatg agcaatggat gag 23

<210> SEQ ID NO 178
<211> LENGTH: 26
<212> TYPE: DNA
<213> ORGANISM: Artificial Sequence
<220> FEATURE:
<223> OTHER INFORMATION: A synthetic oligonucleotide

<400> SEQUENCE: 178
aaagttccaa tgttcatcgt tcgtca 26

<210> SEQ ID NO 179
<211> LENGTH: 28
<212> TYPE: DNA
<213> ORGANISM: Artificial Sequence
<220> FEATURE:
<223> OTHER INFORMATION: A synthetic oligonucleotide

<400> SEQUENCE: 179
tgggactaaa gaatggatcg gctgtaat 28

<210> SEQ ID NO 180
<211> LENGTH: 101
<212> TYPE: DNA

<213> ORGANISM: Amanita bisporigera

<400> SEQUENCE: 180
atgtctgaca tcaatgctac ccgtctcccc atctggggta tcggttgcaa cccgtgcatc 60
ggtgacgacg tcactactct cctcactcgt gccctttgta a 101

<210> SEQ ID NO 181

<400> SEQUENCE: 181

000

<210> SEQ ID NO 182
<211> LENGTH: 30
<212> TYPE: DNA
<213> ORGANISM: Amanita bisporigera

<400> SEQUENCE: 182
atgtctgaca tcaatgctac ccgtcttccc 30

<210> SEQ ID NO 183
<211> LENGTH: 115
<212> TYPE: DNA
<213> ORGANISM: Amanita bisporigera

<400> SEQUENCE: 183
ttggggtttg gcagtcggtt agtacccagt cctcttcgaa ctcggaaaac ctttactctc 60
aataaaccat gtctgacatc aatgccaccc gtcttcctat ctggtggtac atata 115

<210> SEQ ID NO 184
<211> LENGTH: 36
<212> TYPE: PRT
<213> ORGANISM: Amanita bisporigera

<400> SEQUENCE: 184

Gly Val Trp Gln Ser Val Ser Thr Gln Ser Ser Ser Asn Ser Glu Asn
1               5                   10                  15

Leu Tyr Ser Gln Thr Met Ser Asp Ile Asn Ala Thr Arg Leu Pro Ile
            20                  25                  30

Trp Trp Tyr Ile
        35

<210> SEQ ID NO 185
<211> LENGTH: 98
<212> TYPE: DNA
<213> ORGANISM: Amanita bisporigera

<400> SEQUENCE: 185
gtgggtacgc gccggggaga cgggtggcat tgatgtccga cattgcgatt gagagtagag 60
gatgctgtag gtttctgagg ggtcttgtga gtattgaa 98

<210> SEQ ID NO 186
<211> LENGTH: 32
<212> TYPE: PRT
<213> ORGANISM: Amanita bisporigera

<400> SEQUENCE: 186

Ser Ile Leu Thr Arg Pro Leu Arg Asn Leu Gln His Pro Leu Leu Ser
1               5                   10                  15

Ile Ala Met Ser Asp Ile Asn Ala Thr Arg Leu Pro Gly Ala Tyr Pro
            20                  25                  30

<210> SEQ ID NO 187
<211> LENGTH: 106
<212> TYPE: DNA
<213> ORGANISM: Amanita bisporigera

<400> SEQUENCE: 187
ctcacaagac cctcacgaaa cctacagcat cctctacttc tcaatcgcaa tgtcggacat 60
caatgccacc cgtctccccg gcgcgtaccc acctgttcct tggccg 106

<210> SEQ ID NO 188
<211> LENGTH: 35
<212> TYPE: PRT
<213> ORGANISM: Amanita bisporigera

<400> SEQUENCE: 188

Ser Gln Asp Pro His Glu Thr Tyr Ser Ile Leu Tyr Phe Ser Ile Ala
1 5 10 15

Met Ser Asp Ile Asn Ala Thr Arg Leu Pro Gly Ala Tyr Pro Pro Val
20 25 30

Pro Trp Pro
35

<210> SEQ ID NO 189
<211> LENGTH: 1266
<212> TYPE: DNA
<213> ORGANISM: Amanita bisporigera

<400> SEQUENCE: 189
tgaggcacgg gaagtatatg aaccagaaga taggaagact ggtgacattg atgtcagaca 60
tggttatcag taaagagttt gacgaggact gggtactaat tgccaaaccc cagaaccttt 120
atgtgattcg acaagagcaa atataattgc agaacttgac ccaatgtttc aggtgttggc 180
gctgtctcag gcaatggtag cgccgccttg tgggtggctc tagggtgtaa cgtgtaacag 240
ttagcaatta ggctatatgc tgctctgcga aacaggcttg cgacgcctgt caccttgccg 300
accgtactat ctagcaccat tcaacgccat gtgattatga tagcgtcggc attccgtgcc 360
agttgcatgt gctttgagtt ttccatgttt agtaaccgcg agccgcgagc gttcagaatc 420
atagtggtgg cggtgctaga gttacaacat gtatgtaaca tacgagtcag gaataaatta 480
ccataggaat ctagttctga tgtccattgg tcaactcgac ccagtacctt tcctccctct 540
ccttccaccg ccttcgtctc cttcattgtc cccaccactg gtatacaacg ccgacgtcga 600
ccgctgcgcc gtcctctcaa caatagacgt cccgtctcta aatcttgccc taaacagcac 660
atttgcgttc gtaaacagcc cttccttcag tgacaccact ataaattgcg acccccttgaa 720 ccgcgtccgg aacagctgtc caatatgctg cgtgtgcgat agatccaggg cagcgtcgat 780
ctcgtcgagg atgtacattg gcgctggttt gaattggagg agcgccatga tgagcgagag 840
cgcgatgaga gatctgcagc ataccgtcag acgaagcaac ttgggtgttc aaacgacata 900
cctctggccc ccacttaact cagtcaagct ctccttccaa acggtgccga gttgaacttt 960
gacttctaga ccgtccataa gatcttggcc ttcgggcggt accagtttgg caaaattgcc 1020
aggcaagagt tctgcaaaga tcccgccaaa gtcgctttac cacatgcctt caatcccctt 1080
gtcatacaaa tggtgacaaa gtgactcacc cgtcaacctt ttcccaagtt ttttgaagcg 1140
catccctctt gtaccggtct agttcttcga tagtctcttc aatcttttct ttatctttca 1200
gcacctgact aagcatcttt ttaagatgtg cctctctgct cacgacgcta gacacgtggc 1260
aggaaa 1266

<210> SEQ ID NO 190
<211> LENGTH: 403
<212> TYPE: PRT
<213> ORGANISM: Amanita bisporigera

<400> SEQUENCE: 190

Ser Cys His Val Ser Ser Val Val Ser Arg Glu Ala His Leu Lys Lys
1 5 10 15

Met Leu Ser Gln Val Leu Lys Asp Lys Glu Lys Ile Glu Glu Thr Ile
20 25 30

Glu Glu Leu Asp Arg Tyr Lys Arg Asp Ala Leu Gln Lys Thr Trp Glu
35 40 45

Lys Val Asp Gly Val Thr Leu Ser Pro Phe Val Gln Gly Asp Arg His
50 55 60

Val Val Lys Arg Leu Trp Arg Asp Leu Cys Arg Thr Leu Ala Trp Gln
65 70 75 80

Phe Cys Gln Thr Gly Thr Ala Arg Arg Pro Arg Ser Tyr Gly Arg Ser
85 90 95

Arg Ser Gln Ser Ser Thr Arg His Arg Leu Glu Gly Glu Leu Asp Val
100 105 110

Lys Trp Gly Pro Glu Val Cys Arg Leu Asn Thr Gln Val Ala Ser Ser
115 120 125

Asp Gly Met Leu Gln Ile Ser His Arg Ala Leu Ala His His Gly Ala
130 135 140

Pro Pro Ile Gln Thr Ser Ala Asn Val His Pro Arg Arg Asp Arg Arg
145 150 155 160

Cys Pro Gly Ser Ile Ala His Ala Ala Tyr Trp Thr Ala Val Pro Asp
165 170 175

Ala Val Gln Gly Val Ala Ile Tyr Ser Gly Val Thr Glu Gly Arg Ala
180 185 190

Val Tyr Glu Arg Lys Cys Ala Val Gly Lys Ile Arg Arg Asp Val Tyr
195 200 205

Cys Glu Asp Gly Ala Ala Val Asp Val Gly Val Val Tyr Gln Trp Trp
210 215 220

Gly Gln Arg Arg Arg Arg Arg Trp Lys Glu Arg Glu Glu Arg Tyr Trp
225 230 235 240

Val Glu Leu Thr Asn Gly His Gln Asn Ile Pro Met Val Ile Tyr Ser
245 250 255

Leu Val Cys Tyr Ile His Val Val Thr Leu Ala Pro Pro Pro Leu Phe
260 265 270

Thr Leu Ala Ala Arg Gly Tyr Thr Trp Lys Thr Gln Ser Thr Cys Asn
275 280 285

Trp His Gly Met Pro Thr Leu Ser Ser His Gly Val Glu Trp Cys Ile
290 295 300

Val Arg Ser Ala Arg Gln Ala Ser Gln Ala Cys Phe Ala Glu Gln His
305 310 315 320

Ile Ala Leu Leu Thr Val Thr Arg Tyr Thr Leu Glu Pro Pro Thr Arg
325 330 335

Arg Arg Tyr His Cys Leu Arg Gln Arg Gln His Leu Lys His Trp Val
340 345 350

Lys Phe Cys Asn Tyr Ile Cys Ser Cys Arg Ile Thr Arg Phe Trp Gly
355 360 365

```
Leu Ala Ile Ser Thr Gln Ser Ser Ser Asn Ser Leu Leu Ile Thr Met
    370                 375                 380

Ser Asp Ile Asn Val Thr Ser Leu Pro Ile Phe Trp Phe Ile Tyr Phe
385                 390                 395                 400

Pro Cys Leu


<210> SEQ ID NO 191
<211> LENGTH: 554
<212> TYPE: DNA
<213> ORGANISM: Amanita bisporigera

<400> SEQUENCE: 191

tatgctttta gtccaagctt ttacttcacc tggacgttgg gatacgtcag gaatatgtac      60

tgacaataaa tatcaccgca gcggcgccga aactcaccaa tctttacttc acctggacgt     120

tgggatagat gacgtattca ctggaaaagg gttagcggat aacatgggtc gcatgtcatc     180

atgaatatag ttagtgcgtc tccactcaca attgtccaag ttatttcgct tccgtcattc     240

gcggacagtt gaggtttgcc cctgcccaac tcggcaatgg gtcatgactg agacagataa     300

aagatgctgg gggcgcaagc attcaatact cagttcccct ccaaatttga atcgttcaga     360

aacctactac ttcatttact ctctcacaat gtctgacatc aatactgctc gtcttccttt     420

ctaccagttt cccgatttta agtatccctg cgttggtgac gacatcgaga tggtcctcgc     480

gcgtggcgag aggtgaatac aacatccggc caaggctgta tcaaacgact tacgtgctac     540

gtatcagcct ttgc                                                       554


<210> SEQ ID NO 192
<211> LENGTH: 181
<212> TYPE: PRT
<213> ORGANISM: Amanita bisporigera

<400> SEQUENCE: 192

Met Leu Leu Val Gln Ala Phe Thr Ser Pro Gly Arg Trp Asp Thr Ser
1               5                   10                  15

Gly Ile Cys Thr Asp Asn Lys Tyr His Arg Ser Gly Ala Glu Thr His
            20                  25                  30

Gln Ser Leu Leu His Leu Asp Val Gly Ile Asp Asp Val Phe Thr Gly
        35                  40                  45

Lys Gly Leu Ala Asp Asn Met Gly Arg Met Ser Ser Ile Leu Val Arg
    50                  55                  60

Leu His Ser Gln Leu Ser Lys Leu Phe Arg Phe Arg His Ser Arg Thr
65                  70                  75                  80

Val Glu Val Cys Pro Cys Pro Thr Arg Gln Trp Val Met Thr Glu Thr
                85                  90                  95

Asp Lys Arg Cys Trp Gly Arg Lys His Ser Ile Leu Ser Ser Pro Pro
            100                 105                 110

Asn Leu Asn Arg Ser Glu Thr Tyr Tyr Phe Ile Tyr Ser Leu Thr Met
        115                 120                 125

Ser Asp Ile Asn Thr Ala Arg Leu Pro Phe Tyr Gln Phe Pro Asp Phe
    130                 135                 140

Lys Tyr Pro Cys Val Gly Asp Asp Ile Glu Met Val Leu Ala Arg Gly
145                 150                 155                 160

Glu Arg Ile Gln His Pro Ala Lys Ala Val Ser Asn Asp Leu Arg Ala
                165                 170                 175

Thr Tyr Gln Pro Leu
```

180

<210> SEQ ID NO 193
<211> LENGTH: 684
<212> TYPE: DNA
<213> ORGANISM: Amanita bisporigera

<400> SEQUENCE: 193
aatttgaatc tctcagaaac ctacttactc tctcacaatg tctgacatca atactgctcg 60
tcttcctttc ttccagcctc ccgaatttag gcctccctgc gtcggtgacg acatcgagat 120
ggtcctcacg cgtggtgaga ggtgagtaca catccggcca aggatgtatc aaaccactca 180
cgtgctacgt atcagccttt gctaaatgca cggcctatcg gtccactcct atggcatgaa 240
ggtgtcgccg tcgcatttca actacaacgt aaggcaattg tactgacttg aatgtagtag 300
tggtcattat gttgttgacg atatcaggct tggaccgttg agcctgcatc agaagtatga 360
ctttgcttgt ggtgaagaag cactggattt aacccatctt ttttcctaga taactcgctt 420
tctttttcaa gtttatgtcg aatccgtttt gtagtaaaca tataaaaccc acgtcaacga 480
tcccgtgtta cttgttactt gttctttgtt cttgaaaccc tcgtcaatga tccgcgttat 540
agtcaataaa cttgttcttt gttcttgtca gtgtgagggc attttgtacg cgagtggttt 600
caagaaatca gtcaaaaggt gtctttccaa catatctgtt gagcctgtcc ggtcctgaag 660
cctgattgga gaatcaatca gtat 684

<210> SEQ ID NO 194
<211> LENGTH: 438
<212> TYPE: PRT
<213> ORGANISM: Amanita bisporigera

<400> SEQUENCE: 194

Ile Ile Ser Gln Lys Pro Thr Tyr Ser Leu Thr Met Ser Asp Ile Asn
1               5                   10                  15

Thr Ala Arg Leu Pro Phe Phe Gln Pro Pro Glu Phe Arg Pro Pro Cys
            20                  25                  30

Val Gly Asp Asp Ile Glu Met Val Leu Thr Arg Gly Glu Arg Val His
        35                  40                  45

Ile Arg Pro Arg Met Tyr Gln Thr Thr His Val Leu Arg Ile Ser Leu
    50                  55                  60

Cys Met His Gly Leu Ser Val His Ser Tyr Gly Met Lys Val Ser Pro
65                  70                  75                  80

Ser His Phe Asn Tyr Asn Val Arg Gln Leu Tyr Leu Glu Cys Ser Ser
                85                  90                  95

Gly His Tyr Val Val Asp Asp Ile Arg Leu Gly Pro Leu Ser Leu His
            100                 105                 110

Gln Lys Tyr Asp Phe Ala Cys Gly Glu Glu Ala Leu Asp Leu Thr His
        115                 120                 125

Leu Phe Ser Ile Thr Arg Phe Leu Phe Gln Val Tyr Val Glu Ser Val
    130                 135                 140

Leu Thr Tyr Lys Thr His Val Asn Asp Pro Val Leu Leu Val Thr Cys
145                 150                 155                 160

Ser Leu Phe Leu Lys Pro Ser Ser Met Ile Arg Val Ile Val Asn Lys
                165                 170                 175

Leu Val Leu Cys Ser Cys Gln Cys Glu Gly Ile Leu Tyr Ala Ser Gly
            180                 185                 190

Phe Lys Lys Ser Val Lys Arg Cys Leu Ser Asn Ile Ser Val Glu Pro

```
        195                 200                 205

Val Arg Ser Ser Leu Ile Gly Glu Ser Ile Ser Ile Ile Ser Gln Lys
    210                 215                 220

Pro Thr Tyr Ser Leu Thr Met Ser Asp Ile Asn Thr Ala Arg Leu Pro
225                 230                 235                 240

Phe Phe Gln Pro Pro Glu Phe Arg Pro Pro Cys Val Gly Asp Asp Ile
                245                 250                 255

Glu Met Val Leu Thr Arg Gly Glu Arg Val His Ile Arg Pro Arg Met
            260                 265                 270

Tyr Gln Thr Thr His Val Leu Arg Ile Ser Leu Cys Met His Gly Leu
        275                 280                 285

Ser Val His Ser Tyr Gly Met Lys Val Ser Pro Ser His Phe Asn Tyr
    290                 295                 300

Asn Val Arg Gln Leu Tyr Leu Glu Cys Ser Ser Gly His Tyr Val Val
305                 310                 315                 320

Asp Asp Ile Arg Leu Gly Pro Leu Ser Leu His Gln Lys Tyr Asp Phe
                325                 330                 335

Ala Cys Gly Glu Glu Ala Leu Asp Leu Thr His Leu Phe Ser Ile Thr
            340                 345                 350

Arg Phe Leu Phe Gln Val Tyr Val Glu Ser Val Leu Thr Tyr Lys Thr
        355                 360                 365

His Val Asn Asp Pro Val Leu Leu Val Thr Cys Ser Leu Phe Leu Lys
    370                 375                 380

Pro Ser Ser Met Ile Arg Val Ile Val Asn Lys Leu Val Leu Cys Ser
385                 390                 395                 400

Cys Gln Cys Glu Gly Ile Leu Tyr Ala Ser Gly Phe Lys Lys Ser Val
                405                 410                 415

Lys Arg Cys Leu Ser Asn Ile Ser Val Glu Pro Val Arg Ser Ser Leu
            420                 425                 430

Ile Gly Glu Ser Ile Ser
        435


<210> SEQ ID NO 195
<211> LENGTH: 96
<212> TYPE: DNA
<213> ORGANISM: Amanita bisporigera

<400> SEQUENCE: 195

cacaatgtct gatatcaata ccgctcgtct tccttgcatc gggttccttg gcattccctc     60

cgtcggtgac gacatcgaga tggtcctcag gcatgg                               96


<210> SEQ ID NO 196
<211> LENGTH: 31
<212> TYPE: PRT
<213> ORGANISM: Amanita bisporigera

<400> SEQUENCE: 196

Thr Met Ser Asp Ile Asn Thr Ala Arg Leu Pro Cys Ile Gly Phe Leu
1               5                   10                  15

Gly Ile Pro Ser Val Gly Asp Asp Ile Glu Met Val Leu Arg His
            20                  25                  30


<210> SEQ ID NO 197
<211> LENGTH: 36
<212> TYPE: PRT
<213> ORGANISM: Amanita bisporigera
```

<400> SEQUENCE: 197

Pro Ser Ala Met Ser Asp Val Asn Asp Thr Arg Leu Pro Phe Asn Phe
1 5 10 15

Phe Arg Phe Pro Tyr Pro Cys Ile Gly Asp Asp Ser Gly Ser Val Leu
20 25 30

Arg Leu Gly Glu
35

<210> SEQ ID NO 198
<211> LENGTH: 93
<212> TYPE: DNA
<213> ORGANISM: Amanita bisporigera

<400> SEQUENCE: 198
ccttccgaac caagaaccta cagatacctt tgcactctca caatgtctga catcaatgcc 60
atccgtgctc ccatcctgat gctcgcaatt ttg 93

<210> SEQ ID NO 199
<211> LENGTH: 31
<212> TYPE: PRT
<213> ORGANISM: Amanita bisporigera

<400> SEQUENCE: 199

Pro Ser Glu Pro Arg Thr Tyr Arg Tyr Leu Cys Thr Leu Thr Met Ser
1 5 10 15

Asp Ile Asn Ala Ile Arg Ala Pro Ile Leu Met Leu Ala Ile Leu
20 25 30

<210> SEQ ID NO 200
<211> LENGTH: 816
<212> TYPE: DNA
<213> ORGANISM: Amanita bisporigera

<400> SEQUENCE: 200
ttcaatttaa tgccccccctg cgtcggtgac gacatcaaca tggtcctcac gcgtggcgag 60
aggtgagtac aaattccggc caacaatgta tcaaaccact tacgtgctac gtattagcct 120
ttgctagatg cattctatcg gtccactcct gtggcatgaa ggtgtcgccg tctcacttaa 180
attacaacgt aaagcaattg tactgacttg gatgtagtag tggacactgt tgttgacgat 240
atcaggctcg gaccattgag cctgcatcag aagtatgact ttggttgtgg taaagtactg 300
ggttaactcg tcttttcttc ctagataact cacgttcgtt ttcatttgaa tctgctttgt 360
aaacatataa aacccacgtc tacgatccgt gccatacttg ttctttgttc ttgtcagatt 420
tcgaaattgc caacgatatg ccagttttcc tgtgtctgca agcttggaac tgtgtgcgtc 480
ggatactgga tactggcgtt tcctcgtcct aaaggtagca aagtgcgcat gcgggtgcta 540
acggttgcat gataaatcat cgcaagcatc aatgggtttc gttggcaacg atccaaatga 600
acgactgagg gcttcgaaat gtgtagatgg ttgcaaaaac aaaacaaaaa aaccattaga 660
ccgtgaatat cgaatctctt agttactatt gatttcgact tggagtatca gccgcgatca 720
tttcgtcctc ggccctagta tcacaacata tgtaatatca tcctcaggat tacatgtatt 780
cttcaggtag cgtgactgtg atacctacct cccttc 816

<210> SEQ ID NO 201
<211> LENGTH: 258
<212> TYPE: PRT
<213> ORGANISM: Amanita bisporigera

<400> SEQUENCE: 201

Phe Asn Leu Met Pro Pro Cys Val Gly Asp Asp Ile Asn Met Val Leu
1               5                   10                  15

Thr Arg Gly Glu Arg Val Gln Ile Pro Ala Asn Asn Val Ser Asn His
            20                  25                  30

Leu Arg Ala Thr Tyr Pro Leu Leu Asp Ala Phe Tyr Arg Ser Thr Pro
        35                  40                  45

Val Ala Arg Cys Arg Arg Leu Thr Ile Thr Thr Ser Asn Cys Thr Asp
    50                  55                  60

Leu Asp Val Val Val Asp Thr Val Val Asp Asp Ile Arg Leu Gly Pro
65                  70                  75                  80

Leu Ser Leu His Gln Lys Tyr Asp Phe Gly Cys Gly Lys Val Leu Gly
                85                  90                  95

Leu Val Phe Ser Ser Ile Thr His Val Arg Phe His Leu Asn Leu Leu
            100                 105                 110

Cys Lys His Ile Lys Pro Thr Ser Thr Ile Arg Ala Ile Leu Val Leu
        115                 120                 125

Cys Ser Cys Gln Ile Ser Lys Leu Pro Thr Ile Cys Gln Phe Ser Cys
    130                 135                 140

Val Cys Lys Leu Gly Thr Val Cys Val Gly Tyr Trp Ile Leu Ala Phe
145                 150                 155                 160

Pro Arg Pro Lys Gly Ser Lys Val Arg Met Arg Val Leu Thr Val Ala
                165                 170                 175

Ile Ile Ala Ser Ile Asn Gly Phe Arg Trp Gln Arg Ser Lys Thr Thr
            180                 185                 190

Glu Gly Phe Glu Met Cys Arg Trp Leu Gln Lys Gln Asn Lys Lys Thr
        195                 200                 205

Ile Arg Pro Ile Ser Asn Leu Leu Val Thr Ile Asp Phe Asp Leu Glu
    210                 215                 220

Tyr Gln Pro Arg Ser Phe Arg Pro Arg Pro Tyr His Asn Ile Cys Asn
225                 230                 235                 240

Ile Ile Leu Arg Ile Thr Cys Ile Leu Gln Val Ala Leu Tyr Leu Pro
                245                 250                 255

Pro Phe

<210> SEQ ID NO 202
<211> LENGTH: 882
<212> TYPE: DNA
<213> ORGANISM: Amanita bisporigera

<400> SEQUENCE: 202
tctggtaaag gatgagttaa cccaatgctt caccacaagg aaactcatac ttctgatgca 60
ggctcaacgg tccaagcctg atatcgtcaa caacagtgtc cactactacg tccaagtcag 120
tacaattgcc ttcaatgcgt tgaagttgaa aagagacggc gacaccttca tgccatagga 180
gtggatcgat atactgtgca tttaggaaag gctaataata cgtagcacgt aagtcatttg 240
atacatcgtt ggccagatgt tgtactcacc tctcgccacg cgtgaggacc atctcgatgt 300
cgtcaccgac gcagggggc atccgaacgg gagggaggaa gagaggaaga cgagcagtat 360
tgatgtcaga catcgtaaaa ggaagctgta ggtttctgaa agattgaagt ttggagggga 420
actgagtttt gaacgctccg cccccagcat cttttatctg tcccagtcat ggcctattgc 480
tgatttgggc agaggcaaac ctcaatccgc cgacgacgga agcgaataac ttggataagc 540
gacggtgatt ctttttttat ttatttagag gaacttcggc atcaatcatg ttgatatctt 600
gcagaagtcg tatatcattg tgatatcatt gtgacaaatg tcacccacta tctctttcct 660
tgtgaatgtg ccatgtatcc aacgtccagg tgaagtaaac cttggtgatt ctcgccgccg 720
ctgcggtgat attgacagca taatgatctg aaaacgtact gatggaagcg tacttgacgg 780
cccgtccaaa ctgacatggg agtaatcgca cagtattact atgctatttg tattcagatt 840
ccacaattcc attacagtca cccgtgagtt ttccatatct gc 882

<210> SEQ ID NO 203
<211> LENGTH: 285
<212> TYPE: PRT
<213> ORGANISM: Amanita bisporigera

<400> SEQUENCE: 203

```
Arg Tyr Gly Lys Leu Thr Gly Asp Cys Asn Gly Ile Val Glu Ser Glu
1               5                   10                  15

Tyr Lys His Ser Asn Thr Val Arg Leu Leu Pro Cys Gln Phe Gly Arg
            20                  25                  30

Ala Val Lys Tyr Ala Ser Ile Ser Thr Phe Ser Asp His Tyr Ala Val
        35                  40                  45

Asn Ile Thr Ala Ala Ala Ala Arg Ile Thr Lys Val Tyr Phe Thr Trp
    50                  55                  60

Thr Leu Asp Thr Trp His Ile His Lys Glu Arg Asp Ser Gly His Leu
65                  70                  75                  80

Ser Gln Tyr His Asn Asp Ile Arg Leu Leu Gln Asp Ile Asn Met Ile
                85                  90                  95

Asp Ala Glu Val Pro Leu Asn Lys Lys Lys Asn His Arg Arg Leu Ser
            100                 105                 110

Lys Leu Phe Ala Ser Val Val Gly Gly Leu Arg Phe Ala Ser Ala Gln
        115                 120                 125

Ile Ser Asn Arg Pro Leu Gly Gln Ile Lys Asp Ala Gly Gly Gly Ala
    130                 135                 140

Phe Lys Thr Gln Phe Pro Ser Lys Leu Gln Ser Phe Arg Asn Leu Gln
145                 150                 155                 160

Leu Pro Phe Thr Met Ser Asp Ile Asn Thr Ala Arg Leu Pro Leu Phe
                165                 170                 175

Leu Pro Pro Val Arg Met Pro Pro Cys Val Gly Asp Asp Ile Glu Met
            180                 185                 190

Val Leu Thr Arg Gly Glu Arg Val Gln His Leu Ala Asn Asp Val Ser
        195                 200                 205

Asn Asp Leu Arg Ala Thr Tyr Tyr Pro Phe Leu Asn Ala Gln Tyr Ile
    210                 215                 220

Asp Pro Leu Leu Trp His Glu Gly Val Ala Val Ser Phe Gln Leu Gln
225                 230                 235                 240

Arg Ile Glu Gly Asn Cys Thr Asp Leu Asp Val Val Val Asp Thr Val
                245                 250                 255

Val Asp Asp Ile Arg Leu Gly Pro Leu Ser Leu His Gln Lys Tyr Glu
            260                 265                 270

Phe Pro Cys Gly Glu Ala Leu Gly Leu Ile Leu Tyr Gln
        275                 280                 285
```

<210> SEQ ID NO 204
<211> LENGTH: 881
<212> TYPE: DNA
<213> ORGANISM: Amanita bisporigera

<400> SEQUENCE: 204

```
cctctgaaac ttgctgcgac ggcacgatct gactgggaga tcttcgttgc atctctaggt     60
tgagtgaatt cacaattcca gtattcagtt cggaggagca tgttggatcg attaccgtac    120
gttctggctc ttcatcgact ggctttagga acgaacctta ccaaacttgt atatcgtatt    180
gcaggtgaat cgagaaaaca ccttttacgt cgagtgttgt aacctggctc aaagattcaa    240
aaactctcaa cgacaagcag tttattgact ataacaccga tcgtcgacgt gggatttgtg    300
tttacagaac aaattcgaca gagaacgaga aagaatgtaa gttatctggg agacaaatta    360
gaccagtgct tcgtgacgaa caaagtcata cttctgatgc aggctcagcg gtccaagcct    420
ggtatcgtca acagcagagt ccactactac atgcatttag caaaggctat acgtagcatg    480
taagtgattt gatacatcat tggtcagttg ttgtactcac tcctcgccac gcgtgaggac    540
cacctggatg tcgtcattga cacatggggg gatgaagctc atgaagacga cgtaaggaag    600
acgagcggta ttgatgtcag acattgtgag agttggaggg gaactgagta ttgaatattg    660
gatattgaac gctgcgtccc aagcaccttt tatctgtccc agccatggcc caggcccatt    720
cctagttgag gctcgatcta ttgcaaaatt tgacagcctg cgtggtatgg aagacgaagg    780
actgacgatg atgcttagtt gacatgtgtc aagcccacgt acgatatcga agccagagat    840
agatcgcgta ttcgtatatc gtacgaggga tgcttacttg g                        881
```

<210> SEQ ID NO 205
<211> LENGTH: 280
<212> TYPE: PRT
<213> ORGANISM: Amanita bisporigera

<400> SEQUENCE: 205

```
Lys Ala Ser Leu Val Arg Tyr Thr Asn Thr Arg Ser Ile Ser Gly Phe
1               5                   10                  15

Asp Ile Val Arg Gly Leu Asp Thr Cys Gln Leu Ser Ile Ile Val Ser
            20                  25                  30

Pro Ser Ser Ser Ile Pro Arg Arg Leu Ser Asn Phe Ala Ile Asp Arg
        35                  40                  45

Ala Ser Thr Arg Asn Gly Pro Gly Pro Trp Leu Gly Gln Ile Lys Gly
    50                  55                  60

Ala Trp Asp Ala Ala Phe Asn Ile Gln Tyr Ser Ile Leu Ser Ser Pro
65                  70                  75                  80

Pro Thr Leu Thr Met Ser Asp Ile Asn Thr Ala Arg Leu Pro Tyr Val
                85                  90                  95

Val Phe Met Ser Phe Ile Pro Pro Cys Val Asn Asp Asp Ile Gln Val
            100                 105                 110

Val Leu Thr Arg Gly Glu Glu Val Gln Gln Leu Thr Asn Asp Val Ser
        115                 120                 125

Asn His Leu His Ala Thr Tyr Ser Leu Cys Met His Val Val Val Asp
    130                 135                 140

Ser Ala Val Asp Asp Thr Arg Leu Gly Pro Leu Ser Leu His Gln Lys
145                 150                 155                 160

Tyr Asp Phe Val Arg His Glu Ala Leu Val Phe Val Ser Gln Ile Thr
                165                 170                 175

Tyr Ile Leu Ser Arg Ser Leu Ser Asn Leu Phe Cys Lys His Lys Ser
            180                 185                 190

His Val Asp Asp Arg Cys Tyr Ser Gln Thr Ala Cys Arg Glu Phe Leu
        195                 200                 205
```

```
Asn Leu Ala Arg Leu Gln His Ser Thr Lys Val Phe Ser Arg Phe Thr
    210                 215                 220

Cys Asn Thr Ile Tyr Lys Phe Gly Lys Val Arg Ser Ser Gln Ser Met
225                 230                 235                 240

Lys Ser Gln Asn Val Arg Ser Ile Gln His Ala Pro Pro Asn Ile Leu
                245                 250                 255

Glu Leu Ile His Ser Thr Arg Cys Asn Glu Asp Leu Pro Val Arg Ser
            260                 265                 270

Cys Arg Arg Ser Lys Phe Gln Arg
        275                 280


<210> SEQ ID NO 206
<211> LENGTH: 172
<212> TYPE: DNA
<213> ORGANISM: Amanita bisporigera

<400> SEQUENCE: 206

ggaccatcag gatgtcgtca ccgacgcaag ggaggagcat tggcgaggag aggggaagac      60

gagcggtatt gatgtcagac attgtgagag agtaaaggaa gttgtaggtt tctgaaagat     120

tcaagtttgg aggggaggtg agtattgaac gctgcgcccc cagcacctcc ag             172


<210> SEQ ID NO 207
<211> LENGTH: 57
<212> TYPE: PRT
<213> ORGANISM: Amanita bisporigera

<400> SEQUENCE: 207

Leu Glu Val Leu Gly Ala Gln Arg Ser Ile Leu Thr Ser Pro Pro Asn
1               5                   10                  15

Leu Asn Leu Ser Glu Thr Tyr Asn Phe Leu Tyr Ser Leu Thr Met Ser
            20                  25                  30

Asp Ile Asn Thr Ala Arg Leu Pro Leu Ser Ser Pro Met Leu Leu Pro
        35                  40                  45

Cys Val Gly Asp Asp Ile Leu Met Val
    50                  55


<210> SEQ ID NO 208
<211> LENGTH: 234
<212> TYPE: DNA
<213> ORGANISM: Amanita bisporigera

<400> SEQUENCE: 208

ccttccgaac caagaaccta cagatacctt tgcactctca caatgtctga catcaatgcc      60

atccgtgctc ccatcctgat gctcgcaatt ttgccctgcg tcggcgacga catcgaggtc     120

ctcaggcgtg gcgaggggtg agcctaacat ccgtcaacgg cgtacaaatg tacttatgcg     180

ctgcgtatca gcctttccta aatacccggt tcatcagctc gctcctatgg catg           234


<210> SEQ ID NO 209
<211> LENGTH: 75
<212> TYPE: PRT
<213> ORGANISM: Amanita bisporigera

<400> SEQUENCE: 209

Pro Ser Glu Pro Arg Thr Tyr Arg Tyr Leu Cys Thr Leu Thr Met Ser
1               5                   10                  15

Asp Ile Asn Ala Ile Arg Ala Pro Ile Leu Met Leu Ala Ile Leu Pro
            20                  25                  30
```

Cys Val Gly Asp Asp Ile Glu Val Leu Arg Arg Gly Glu Gly Ala His
35 40 45

Pro Ser Thr Ala Tyr Lys Cys Thr Tyr Ala Leu Arg Ile Ser Leu Ser
50 55 60

Ile Pro Gly Ser Ser Ala Arg Ser Tyr Gly Met
65 70 75

<210> SEQ ID NO 210
<211> LENGTH: 1706
<212> TYPE: DNA
<213> ORGANISM: Amanita bisporigera

<400> SEQUENCE: 210
cttctaacgt gggctttacg tgtttataaa tgtgaaaaac cttaaaagaa aaaaatcaga 60
gttgtccccc acagacaaaa taaggactta ctccgatgta ggctcaacgg tccaagcctc 120
atatcgtgaa caactttgaa aatttatcac tacataatac atacgagtca gaacggttgc 180
cttgtattat acgaggatgg cgacaccttt aatggcaccg agttctcagc agagactaac 240
gcacgcgaca taagtgtaca tcattgggta gatgatattg ctcacctctc gccacgagtg 300
agggtagggt tgacgtcgtc actgacgcac ggaattccga ggggtatcaa accagggatg 360
ggaagacgag tgccattgat atcagacatt gcgaatgaga gtaaaggagg ctctgagagg 420
tcttggattc aagttgggag aggaactggg tattgtacgc cctgcccgat gcctttttat 480
ctgtctcagc caaggccaat tgcctagttg ggcataggga aacccaagag gcgcttcgag 540
ttcgtccgtg gtcattcaag ctcttttagg agagctggaa ccatgatggg cctaatgtag 600
ctcaaccagg tatggaatgg cgcaagaatt ccggccagaa cggatgatat gagtggttct 660
catcacgctg ttcgctgact tccaacgtcc aacgtctttg ggtacatgaa gtacggcatg 720
tcctcttaga aaaaaaggcc ggtggacgat ggacagtagc gaacatcgtg gtgcctatag 780
gctatggcgt agccggatgt gggtagaaca aaggagcggt gcatgttgga cagtagtgaa 840
cagcgtggcg tcctcgtttc gcacgaggta ccgccgcact gactcgttgt gcgctgataa 900
aggatatcgg ccctcgatcg cgcaccgccc catcatgcgc tccattgcca ccacgaggat 960
gtgcatacag tgcaaccccc cgaggactgc acgacccagt tgatccgcga caagtactcc 1020
gcgcagaacg tggtcgggag gtactggcgc atacatcacc cggcccaagc gcaagcatcc 1080
gcggctgatc cgagcttgca caagctggtc gaagacgtag ctctcccaaa catgtctgtc 1140
cgccctttcg caaactggtc gctcgacagc cctaaaatct gctccgcctt cgagtgcaga 1200
tccgtcccag cagccttagt ccaagtgtca tccaccccag tgtcgtcgcg tgatgcatcc 1260
caaattgcgc atccccatac agcttgaaat ctacacttcc tcagggtcca tgtccgcatc 1320
gactatcgcg tgcccaggcg gcacgcacca tcacggttct gcttcacatt caaccacgtc 1380
ttttcgatcg cgcgccgcat gatggcgcct atcgtgatcg atgatcacct ggggaagcct 1440
gaagatcatc ccccacgtag agaagcaaga atccacttca tcgtgacatc gcaccaccaa 1500
ccgcaagcgg aagaagcttc ctccaccagt cccaaccaat gccaaacatt ctcttgtctc 1560
tattccgctt gttgtcgtcg tcaccctcgt cgtcgcagag agcaggacta tttgactcgg 1620
gcgacccgcc caatccttcg atgctgacga tcttatgaca ttgcccgctt gccttctcac 1680
attaatttga ggacgaactg gattcg 1706

<210> SEQ ID NO 211
<211> LENGTH: 542
<212> TYPE: PRT

<213> ORGANISM: Amanita bisporigera

<400> SEQUENCE: 211

```
Arg Ile Gln Phe Val Leu Lys Leu Met Glu Gly Lys Arg Ala Met Ser
1               5                   10                  15

Asp Arg Gln His Arg Arg Ile Gly Arg Val Ala Arg Val Lys Ser Cys
            20                  25                  30

Ser Leu Arg Arg Arg Gly Arg Arg Gln Gln Ala Glu Arg Gln Glu Asn
        35                  40                  45

Val Trp His Trp Leu Gly Leu Val Glu Glu Ala Ser Ser Ala Cys Gly
    50                  55                  60

Trp Trp Cys Asp Val Thr Met Lys Trp Ile Leu Ala Ser Leu Arg Gly
65                  70                  75                  80

Gly Ser Ser Gly Phe Pro Arg Ser Ser Ile Thr Ile Gly Ala Ile Met
                85                  90                  95

Arg Arg Ala Ile Glu Lys Thr Trp Leu Asn Val Lys Gln Asn Arg Asp
            100                 105                 110

Gly Ala Cys Arg Leu Gly Thr Arg Ser Met Arg Thr Trp Thr Leu Arg
        115                 120                 125

Lys Cys Arg Phe Gln Ala Val Trp Gly Cys Ala Ile Trp Asp Ala Ser
    130                 135                 140

Arg Asp Asp Thr Gly Val Asp Asp Thr Trp Thr Lys Ala Ala Gly Thr
145                 150                 155                 160

Asp Leu His Ser Lys Ala Glu Gln Ile Leu Gly Leu Ser Ser Asp Gln
                165                 170                 175

Phe Ala Lys Gly Arg Thr Asp Met Phe Gly Arg Ala Thr Ser Ser Thr
            180                 185                 190

Ser Leu Cys Lys Leu Gly Ser Ala Ala Asp Ala Cys Ala Trp Ala Gly
        195                 200                 205

Cys Met Arg Gln Tyr Leu Pro Thr Thr Phe Cys Ala Glu Tyr Leu Ser
    210                 215                 220

Arg Ile Asn Trp Val Val Gln Ser Ser Gly Gly Cys Thr Val Cys Thr
225                 230                 235                 240

Ser Ser Trp Trp Gln Trp Ser Ala Trp Gly Gly Ala Arg Ser Arg Ala
                245                 250                 255

Asp Ile Leu Tyr Gln Arg Thr Thr Ser Gln Cys Gly Gly Thr Ser Cys
            260                 265                 270

Glu Thr Arg Thr Pro Arg Cys Ser Leu Leu Ser Asn Met His Arg Ser
        275                 280                 285

Phe Val Leu Pro Thr Ser Gly Tyr Ala Ile Ala Tyr Arg His His Asp
    290                 295                 300

Val Arg Tyr Cys Pro Ser Ser Thr Gly Leu Phe Phe Glu Asp Met Pro
305                 310                 315                 320

Tyr Phe Met Tyr Pro Lys Thr Leu Asp Val Gly Ser Gln Arg Thr Ala
                325                 330                 335

Glu Pro Leu Ile Ser Ser Val Leu Ala Gly Ile Leu Ala Pro Phe His
            340                 345                 350

Thr Trp Leu Ser Tyr Ile Arg Pro Ile Met Val Pro Ala Leu Leu Lys
        355                 360                 365

Glu Leu Glu Pro Arg Thr Asn Ser Lys Arg Leu Leu Gly Phe Pro Met
    370                 375                 380

Pro Asn Ala Ile Gly Leu Gly Asp Arg Lys Gly Ile Gly Gln Gly Val
385                 390                 395                 400
```

```
Gln Tyr Pro Val Pro Leu Pro Thr Ile Gln Asp Leu Ser Glu Pro Pro
                405                 410                 415

Leu Leu Ser Phe Ala Met Ser Asp Ile Asn Gly Thr Arg Leu Pro Ile
            420                 425                 430

Pro Gly Leu Ile Pro Leu Gly Ile Pro Cys Val Ser Asp Asp Val Asn
        435                 440                 445

Pro Thr Leu Thr Arg Gly Glu Arg Ala Ile Ser Ser Thr Gln Cys Thr
    450                 455                 460

Leu Met Ser Arg Ala Leu Val Ser Ala Glu Asn Ser Val Pro Leu Lys
465                 470                 475                 480

Val Ser Pro Ser Ser Tyr Asn Thr Arg Gln Pro Phe Leu Val Cys Ile
                485                 490                 495

Met Ile Phe Lys Val Val His Asp Met Arg Leu Gly Pro Leu Ser Leu
            500                 505                 510

His Arg Ser Lys Ser Leu Phe Cys Leu Trp Gly Thr Thr Leu Ile Phe
        515                 520                 525

Phe Phe Gly Phe Ser His Leu Thr Arg Lys Ala His Val Arg
    530                 535                 540


<210> SEQ ID NO 212

<400> SEQUENCE: 212

000


<210> SEQ ID NO 213

<400> SEQUENCE: 213

000


<210> SEQ ID NO 214
<211> LENGTH: 103
<212> TYPE: DNA
<213> ORGANISM: Amanita bisporigera

<400> SEQUENCE: 214

gtccgacatc aacgccactc gtcttcccat gatccaacgc cccttctacc cgtgcgccag      60

tgacgacgtc acctccaccc tcactcgtgg cgagaggtga gcg                       103


<210> SEQ ID NO 215
<211> LENGTH: 33
<212> TYPE: PRT
<213> ORGANISM: Amanita bisporigera

<400> SEQUENCE: 215

Ser Asp Ile Asn Ala Thr Arg Leu Pro Met Ile Gln Arg Pro Phe Tyr
1               5                   10                  15

Pro Cys Ala Ser Asp Asp Val Thr Ser Thr Leu Thr Arg Gly Glu Arg
            20                  25                  30

Ala


<210> SEQ ID NO 216
<211> LENGTH: 103
<212> TYPE: DNA
<213> ORGANISM: Amanita bisporigera

<400> SEQUENCE: 216

ccgaacttaa atcccagacc tcacaaagcc tctttattct tgaatcgcaa tgtctgatat      60
```

-continued

```
caatgccgct cgtcttccca tcatttttga accaatcatc ccg                    103


<210> SEQ ID NO 217
<211> LENGTH: 32
<212> TYPE: PRT
<213> ORGANISM: Amanita bisporigera

<400> SEQUENCE: 217

Arg Thr Ile Pro Asp Leu Thr Lys Pro Leu Tyr Ser Ile Ala Met Ser
1               5                   10                  15

Asp Ile Asn Ala Ala Arg Leu Pro Ile Ile Phe Glu Pro Ile Ile Pro
            20                  25                  30


<210> SEQ ID NO 218
<211> LENGTH: 168
<212> TYPE: DNA
<213> ORGANISM: Amanita bisporigera

<400> SEQUENCE: 218

tgctgggctc acttctcgcc cctagtgagg gtgaaattgt ccgcgtcacc gacgcacggc     60

ataggaacag gtgggtacgc gccggggaga cgggtggcat tgatgtccga cattgcgatt    120

gagagtagag gatgctgtag gtttctgagg ggtcttgtga gtattgaa                 168


<210> SEQ ID NO 219
<211> LENGTH: 54
<212> TYPE: PRT
<213> ORGANISM: Amanita bisporigera

<400> SEQUENCE: 219

Ser Ile Leu Thr Arg Pro Leu Arg Asn Leu Gln His Pro Leu Leu Ser
1               5                   10                  15

Ile Ala Met Ser Asp Ile Asn Ala Thr Arg Leu Pro Gly Ala Tyr Pro
            20                  25                  30

Pro Val Pro Met Pro Cys Val Gly Asp Ala Asp Asn Phe Thr Leu Thr
        35                  40                  45

Arg Gly Glu Lys Ala Gln
    50


<210> SEQ ID NO 220
<211> LENGTH: 105
<212> TYPE: DNA
<213> ORGANISM: Amanita bisporigera

<400> SEQUENCE: 220

atgtctgaca tcaatgccac ccgtctcccc catccgtttc cattaggatt gcaaccgtgt     60

gccggtgacg tggacaattt gaccctcact aaaggcgaag ggtga                    105


<210> SEQ ID NO 221

<400> SEQUENCE: 221

000


<210> SEQ ID NO 222

<400> SEQUENCE: 222

000


<210> SEQ ID NO 223
```

<400> SEQUENCE: 223

000

<210> SEQ ID NO 224
<211> LENGTH: 96
<212> TYPE: DNA
<213> ORGANISM: Amanita phalloides

<400> SEQUENCE: 224
atgtcagata tcaatgcgac gcgtcttccc atatggggaa taggttgcga cccgtgcatc 60
ggtgacgacg tcaccatact cctcactcgt ggcgag 96

<210> SEQ ID NO 225
<211> LENGTH: 32
<212> TYPE: PRT
<213> ORGANISM: Amanita phalloides

<400> SEQUENCE: 225

Met Ser Asp Ile Asn Ala Thr Arg Leu Pro Ile Trp Gly Ile Gly Cys
1 5 10 15

Asp Pro Cys Ile Gly Asp Asp Val Thr Ile Leu Leu Thr Arg Gly Glu
20 25 30

<210> SEQ ID NO 226
<211> LENGTH: 93
<212> TYPE: DNA
<213> ORGANISM: Amanita ocreata

<400> SEQUENCE: 226
atgtcagaca ttaacgcgac ccgtcttccc gcctggctcg ccacctgccc gtgcgccggt 60
gacgacgtca accctctcct cactcgtggc gag 93

<210> SEQ ID NO 227
<211> LENGTH: 31
<212> TYPE: PRT
<213> ORGANISM: Amanita ocreata

<400> SEQUENCE: 227

Met Ser Asp Ile Asn Ala Thr Arg Leu Pro Ala Trp Leu Ala Thr Cys
1 5 10 15

Pro Cys Ala Gly Asp Asp Val Asn Pro Leu Leu Thr Arg Gly Glu
20 25 30

<210> SEQ ID NO 228
<211> LENGTH: 33
<212> TYPE: PRT
<213> ORGANISM: Amanita bisporigera

<400> SEQUENCE: 228

Gln Thr Val Gln Ile Phe Tyr Pro Ser Lys Asp Gly Thr Lys Ile Pro
1 5 10 15

Met Phe Ile Val His Lys Lys Ser Ile Lys Leu Asp Gly Ser His Pro
20 25 30

Ala

<210> SEQ ID NO 229
<211> LENGTH: 32
<212> TYPE: PRT
<213> ORGANISM: Amanita bisporigera

<400> SEQUENCE: 229

```
Ile Phe Tyr Pro Ser Lys Asp Gly Thr Lys Ile Pro Met Phe Ile Val
1               5                   10                  15

His Lys Lys Ser Ile Lys Leu Asp Gly Ser His Pro Ala Phe Leu Tyr
            20                  25                  30


<210> SEQ ID NO 230
<211> LENGTH: 26
<212> TYPE: PRT
<213> ORGANISM: Amanita bisporigera

<400> SEQUENCE: 230

Lys Arg Leu Thr Ile Asn Gly Gly Ser Asn Gly Gly Leu Leu Val Ala
1               5                   10                  15

Ala Cys Ala Asn Gln Arg Pro Asp Leu Phe
            20                  25


<210> SEQ ID NO 231
<211> LENGTH: 27
<212> TYPE: PRT
<213> ORGANISM: Amanita bisporigera

<400> SEQUENCE: 231

Ser Asp Asp Gly Thr Val Ala Leu Arg Gly Tyr Ala Phe Ser Glu Asp
1               5                   10                  15

Gly Glu Tyr Phe Ala Tyr Gly Leu Ser Ala Ser
            20                  25


<210> SEQ ID NO 232
<211> LENGTH: 20
<212> TYPE: PRT
<213> ORGANISM: Amanita bisporigera

<400> SEQUENCE: 232

Pro Leu Leu Ile His Val Asp Thr Lys Ala Gly His Gly Ala Gly Lys
1               5                   10                  15

Pro Thr Ala Lys
            20


<210> SEQ ID NO 233
<211> LENGTH: 16
<212> TYPE: PRT
<213> ORGANISM: Amanita bisporigera

<400> SEQUENCE: 233

Asp Gly Thr Lys Ile Pro Met Phe Ile Val His Lys Lys Ser Ile Lys
1               5                   10                  15


<210> SEQ ID NO 234
<211> LENGTH: 2444
<212> TYPE: DNA
<213> ORGANISM: Amanita bisporigera

<400> SEQUENCE: 234

acaccgtctc aaattcaagc catgcaccgt tttttgcagc ccgtaagaga acgccttcgc      60

tctgctctcg cccgctactt tggttcgcgg atcatgtctt ctacacagtg gacacccaac     120

atgtaccctt ctgctcgccg ttcagaccat atagacacat acaggagcga aacgagaggc     180

gaagtcaagg tgccggaccc gtaccactgg ctagaggaat attcagaaga gacggacaag     240

tggacgtccg accaggagga gttcacgagg acatatttgg acagcaaccc tgatcgaaag     300

aagctagaag acgcattcag aaagagtatg gattatccca agttctccgc tcctttttg      360
```

```
aatgatgaca agcgatggta ttggttttac aataccggcc ttcaagcaca aacagtcatc    420
tgcagatcaa aggatgagac tcttcccgac ttctcagaga gtgactacgt cggggaaaca    480
ttttttgatc cgaacctatt atcctcggat ggcacagcct cgctctccat gtatgatttc    540
tcacactgtg gcaaatactt cgcatatggt atttctcttt ccgggagcga tttttcaact    600
atatacgtac ggtcaacttc ctctccactg gcccctggca acaacagcat tagaaatgac    660
gacggtagac ttccagacga gcttagatat gtcaaatttt cctccatcag ctggacaaag    720
gactccaaag gatttttcta tcagcgctat cccggtacag gcactgtgaa tggacagaat    780
ggcatccaaa ctcaaggcga tcgtgatgct atgatttact atcaccggat agggacatca    840
caatccgatg atattcttgt gcatgaagac caggaacatc ctgattgggt atttggcgca    900
gaagtcacgg aagatggtaa atatgtggcc ctgtacacaa tgaaggacac atcaaggaaa    960
aatctattgt ggattgctga tcttggacaa aacgaagttg gacgaaacat gaaatggaac   1020
aagatttgca acgtttttga ctcagaatac gacctaattg gcaacgacgg ttcattacta   1080
tacatcagaa ctaataaagc tgcacctcaa tacaagattg tcaccttaga tatagagaaa   1140
ccagaattag ggtttaagga attcataccg gaagatccca aagcatatct ctctcaagtc   1200
aaaattttta ataaggatag actagcacta gtatacaagc gtaacgttat aggcgaactc   1260
tacgtctaca ataacactgg gtcacgacta atgcgcctag cccgggactt tgttggctcc   1320
atgacggtga ccgctcgaga aacggagcca tggtttttttg ccactctcac gggcttcaat   1380
acccctggaa tcgtatgcag gtacaatatc cagcgaccgg aagaacagcg ttggagcgta   1440
tatcgaactg ccaaggtcaa gggtttaaat ccgaacgatt tcgaggctcg acaggtgtgg   1500
tatgacagct acgatggaac aaagattcca atgttcatcg tccgtcacaa gaatacccaa   1560
tttaatggga cggcgccagc tatacaatat ggttacggtg gctttaatat atctataaat   1620
cccttcttta gtccaacgat tttgacgttc ttgcaaaagt atggagcaat tctagctgta   1680
cctaatatcc gaggaggcgg cgagttcggc gagacatggc atgatgctgg tatacgagag   1740
aaacgagcta atgtttacga tgatttcatt gcggcaactc agttcttggt aaaaaacaag   1800
tatgccgcgg gcggcaaagt ggccatcaac ggggggtcca atggaggact tttggtcgcg   1860
gcctgtgtca atcgtgcacg tgaaggaacc tttggagctg ccattgctga agttggggtc   1920
ctagacttgc tcaagttccc caaatttacc ataggcaaag cttggattag cgactacggc   1980
gatccagaag atccgcgtga ttttgattac atttacacac attcaccact tcataatata   2040
ccaaagaaca tggtcttacc tccgacgatg cttctgacag ctgatcatga tgaccgtgtc   2100
gtcccaatgc attcatttaa gtatgctgca atgctacaat acaccctgcc gcataatcgt   2160
catccacttc tgctacgtgt agacaagaaa gcggggcatg gcggaggaaa atctactgag   2220
aagaggttac aggaggctgc cgacaaatgg ggttttgccg cgcagtccat gggtcttgcg   2280
tggaaggata gacaagctaa tctgtgatga gtttcggcat gcattcagca tttagacatc   2340
tgttttactg tttgggctac attttacgac actcacgatt ccaggtatat tatttaacgc   2400
attgcacttg tgcaggctaa aaaaaaaaaa aaaaaaaaaa aaaa                    2444
```

<210> SEQ ID NO 235
<211> LENGTH: 2189
<212> TYPE: DNA
<213> ORGANISM: Amanita bisporigera

<400> SEQUENCE: 235

```
atgcccccta caccatgggc tcctcacagt tatcctccta cccgtcgttc tgaccacgtt      60
gatgtatatc agagcgcatc cagaggcgaa gtaccagtac cggacccgta ccaatggctg     120
gaggagaatt caaatgaagt cgacgaatgg acgacggcgc agacagcttt cacgcaaggc     180
tatcttgata agaatgcgga tagacagaag ctcgaggaga aatttcgtgc aagcaaggac     240
tacgtcaagt tttctgcgcc aactctgctt gatagtggac actggtattg gttctacaat     300
agcggcgtac aatcgcaagc agtcctctac cgctccaaga aacccgttct tcctgatttc     360
tcaaagaggg acgaggaaat cggcgaagta tacttcgatc caaacgtact ctctgctgat     420
ggcaccgcaa ttatgggcac gtgccgattc tcccctagtg gcgagtattt cgcatatgca     480
gtgtcccact tgggagttga ttattttact atctatgttc gccctacgag ttcatcattg     540
tctcaagctc cggaagctga aggtggggat ggtcgattgt cggatgaagt gaaatggtgc     600
aagtttacga ctataacgtg gacaaaggac tccaaaggat ttctttacca gcggtaccct     660
gctcgggaat ctcttgtggc gaaagatcgt gataaagatg ctatggtatg ctatcatagg     720
gttggaacga ctcaattgga agatatcatt gtccaacaag acaaggagaa cccagactgg     780
acatatggga cagatgcgtc agaggacggc aaatatatct acttagtggt atacaaggat     840
gcctcgaagc aaaatcttct gtgggttgca gaattcgaca aggacggggt caagccggaa     900
attccctggc gaaaagtcat caatgagttt ggggcggatt accatgttat cacgaaccac     960
ggatctttga tctatgtcaa gactaacgtg aatgcgcccc aatataaagt tgtcactatc    1020
gacctttcga caggagaacc cgaaattcgt gatttcatcc cggaacagaa agatgcgaag    1080
ctcactcaag tcaaatgcgt caacaaggaa tatttcgtcg cgatctacaa gcgcaatgtc    1140
aaagatgaaa tatatcttta ctccaaagca ggcgatcaac tcagtcgtct ggcgtcggac    1200
ttcattggcg ttgcatctat aactaacaga gagaaacaac ctcatttctt cctcactttc    1260
tctggattta acacgccggg caccatttct cgctacgatt ttacagctcc agacacacaa    1320
cgtctcagca tccttaggac tacgaagcta aatggtctga atgcagatga ctttgagagc    1380
acacaagtct ggtataagag caaagacgga acgaaagttc caatgttcat cgttcgtcac    1440
aaatcaacaa aatttgacgg aacggcgccg gcgattcaaa acggttatgg tggtttcgct    1500
attacagccg atccattctt tagtcccatc atgctcacct ttatgcagac atatggcgca    1560
atcctggctg tcccgaacat cagaggtgga ggtgaattcg gcggagaatg gcacaaggca    1620
gggagacgag aaaccaaggg aaatactttt gatgatttca tcgctgccgc tcaatttctt    1680
gtcaaaaaca agtacgcggc tccaggcaag gtggccatca ctggtgcatc caatggcggt    1740
tttcttgtct gtggttccgt agttcggaca ccagagggaa cattcggcgc tgctgtttcc    1800
gaaggtggtg tcgcggacct cctaaagttt aataaattca ccgggggggat ggcgtggacg    1860
agtgaatatg gaaacccttt tattaaggag gacttcgact ttgtccaagc attgtctcct    1920
gtgcataacg tacccaagga tagggttctt cctgccacat tacttatgac caatgcgggt    1980
gacgatcgtg tagttccaat gcattcgctc aagttcgtcg caaaccttca gtacaatgtg    2040
cctcaaaatc ctcatccatt gctcatccgt gtggataaat cttggcttgg tcatggtttt    2100
ggcaagacaa cagacaagca tactaaagat gctgcggaca agtggagttt cgtagcgcaa    2160
tcgttagggc tagaatggaa aacggttga                                     2189
```

<210> SEQ ID NO 236
<211> LENGTH: 761
<212> TYPE: PRT
<213> ORGANISM: Amanita bisporigera

<400> SEQUENCE: 236

```
Met His Arg Phe Leu Gln Pro Val Arg Glu Arg Leu Arg Ser Ala Leu
1               5                   10                  15

Ala Arg Tyr Phe Gly Ser Arg Ile Met Ser Ser Thr Gln Trp Thr Pro
            20                  25                  30

Asn Met Tyr Pro Ser Ala Arg Arg Ser Asp His Ile Asp Thr Tyr Arg
        35                  40                  45

Ser Glu Thr Arg Gly Glu Val Lys Val Pro Asp Pro Tyr His Trp Leu
    50                  55                  60

Glu Glu Tyr Ser Glu Glu Thr Asp Lys Trp Thr Ser Asp Gln Glu Glu
65                  70                  75                  80

Phe Thr Arg Thr Tyr Leu Asp Ser Asn Pro Asp Arg Lys Lys Leu Glu
                85                  90                  95

Asp Ala Phe Arg Lys Ser Met Asp Tyr Pro Lys Phe Ser Ala Pro Phe
            100                 105                 110

Leu Asn Asp Asp Lys Arg Trp Tyr Trp Phe Tyr Asn Thr Gly Leu Gln
        115                 120                 125

Ala Gln Thr Val Ile Cys Arg Ser Lys Asp Glu Thr Leu Pro Asp Phe
    130                 135                 140

Ser Glu Ser Asp Tyr Val Gly Glu Thr Phe Phe Asp Pro Asn Leu Leu
145                 150                 155                 160

Ser Ser Asp Gly Thr Ala Ser Leu Ser Met Tyr Asp Phe Ser His Cys
                165                 170                 175

Gly Lys Tyr Phe Ala Tyr Gly Ile Ser Leu Ser Gly Ser Asp Phe Ser
            180                 185                 190

Thr Ile Tyr Val Arg Ser Thr Ser Ser Pro Leu Ala Pro Gly Asn Asn
        195                 200                 205

Ser Ile Arg Asn Asp Asp Gly Arg Leu Pro Asp Glu Leu Arg Tyr Val
    210                 215                 220

Lys Phe Ser Ser Ile Ser Trp Thr Lys Asp Ser Lys Gly Phe Phe Tyr
225                 230                 235                 240

Gln Arg Tyr Pro Gly Thr Gly Thr Val Asn Gly Gln Asn Gly Ile Gln
                245                 250                 255

Thr Gln Gly Asp Arg Asp Ala Met Ile Tyr Tyr His Arg Ile Gly Thr
            260                 265                 270

Ser Gln Ser Asp Asp Ile Leu Val His Glu Asp Gln Glu His Pro Asp
        275                 280                 285

Trp Val Phe Gly Ala Glu Val Thr Glu Asp Gly Lys Tyr Val Ala Leu
    290                 295                 300

Tyr Thr Met Lys Asp Thr Ser Arg Lys Asn Leu Leu Trp Ile Ala Asp
305                 310                 315                 320

Leu Gly Gln Asn Glu Val Gly Arg Asn Met Lys Trp Asn Lys Ile Cys
                325                 330                 335

Asn Val Phe Asp Ser Glu Tyr Asp Leu Ile Gly Asn Asp Gly Ser Leu
            340                 345                 350

Leu Tyr Ile Arg Thr Asn Lys Ala Ala Pro Gln Tyr Lys Ile Val Thr
        355                 360                 365

Leu Asp Ile Glu Lys Pro Glu Leu Gly Phe Lys Glu Phe Ile Pro Glu
    370                 375                 380

Asp Pro Lys Ala Tyr Leu Ser Gln Val Lys Ile Phe Asn Lys Asp Arg
385                 390                 395                 400

Leu Ala Leu Val Tyr Lys Arg Asn Val Ile Gly Glu Leu Tyr Val Tyr
```

```
                405                 410                 415

Asn Asn Thr Gly Ser Arg Leu Met Arg Leu Ala Arg Asp Phe Val Gly
            420                 425                 430

Ser Met Thr Val Thr Ala Arg Glu Thr Glu Pro Trp Phe Phe Ala Thr
        435                 440                 445

Leu Thr Gly Phe Asn Thr Pro Gly Ile Val Cys Arg Tyr Asn Ile Gln
    450                 455                 460

Arg Pro Glu Glu Gln Arg Trp Ser Val Tyr Arg Thr Ala Lys Val Lys
465                 470                 475                 480

Gly Leu Asn Pro Asn Asp Phe Glu Ala Arg Gln Val Trp Tyr Asp Ser
                485                 490                 495

Tyr Asp Gly Thr Lys Ile Pro Met Phe Ile Val Arg His Lys Asn Thr
            500                 505                 510

Gln Phe Asn Gly Thr Ala Pro Ala Ile Gln Tyr Gly Tyr Gly Gly Phe
        515                 520                 525

Asn Ile Ser Ile Asn Pro Phe Phe Ser Pro Thr Ile Leu Thr Phe Leu
    530                 535                 540

Gln Lys Tyr Gly Ala Ile Leu Ala Val Pro Asn Ile Arg Gly Gly Gly
545                 550                 555                 560

Glu Phe Gly Glu Thr Trp His Asp Ala Gly Ile Arg Glu Lys Arg Ala
                565                 570                 575

Asn Val Tyr Asp Asp Phe Ile Ala Ala Thr Gln Phe Leu Val Lys Asn
            580                 585                 590

Lys Tyr Ala Ala Gly Gly Lys Val Ala Ile Asn Gly Gly Ser Asn Gly
        595                 600                 605

Gly Leu Leu Val Ala Ala Cys Val Asn Arg Ala Arg Glu Gly Thr Phe
    610                 615                 620

Gly Ala Ala Ile Ala Glu Val Gly Val Leu Asp Leu Leu Lys Phe Pro
625                 630                 635                 640

Lys Phe Thr Ile Gly Lys Ala Trp Ile Ser Asp Tyr Gly Asp Pro Glu
                645                 650                 655

Asp Pro Arg Asp Phe Asp Tyr Ile Tyr Thr His Ser Pro Leu His Asn
            660                 665                 670

Ile Pro Lys Asn Met Val Leu Pro Pro Thr Met Leu Leu Thr Ala Asp
        675                 680                 685

His Asp Asp Arg Val Val Pro Met His Ser Phe Lys Tyr Ala Ala Met
    690                 695                 700

Leu Gln Tyr Thr Leu Pro His Asn Arg His Pro Leu Leu Leu Arg Val
705                 710                 715                 720

Asp Lys Lys Ala Gly His Gly Gly Gly Lys Ser Thr Glu Lys Arg Leu
                725                 730                 735

Gln Glu Ala Ala Asp Lys Trp Gly Phe Ala Ala Gln Ser Met Gly Leu
            740                 745                 750

Ala Trp Lys Asp Arg Gln Ala Asn Leu
        755                 760


<210> SEQ ID NO 237
<211> LENGTH: 730
<212> TYPE: PRT
<213> ORGANISM: Amanita bisporigera

<400> SEQUENCE: 237

Met Pro Pro Thr Pro Trp Ala Pro His Ser Tyr Pro Pro Thr Arg Arg
1               5                   10                  15
```

-continued

```
Ser Asp His Val Asp Val Tyr Gln Ser Ala Ser Arg Gly Glu Val Pro
            20                  25                  30

Val Pro Asp Pro Tyr Gln Trp Leu Glu Glu Asn Ser Asn Glu Val Asp
        35                  40                  45

Glu Trp Thr Thr Ala Gln Thr Ala Phe Thr Gln Gly Tyr Leu Asp Lys
    50                  55                  60

Asn Ala Asp Arg Gln Lys Leu Glu Glu Lys Phe Arg Ala Ser Lys Asp
65                  70                  75                  80

Tyr Val Lys Phe Ser Ala Pro Thr Leu Leu Asp Ser Gly His Trp Tyr
                85                  90                  95

Trp Phe Tyr Asn Ser Gly Val Gln Ser Gln Ala Val Leu Tyr Arg Ser
            100                 105                 110

Lys Lys Pro Val Leu Pro Asp Phe Gln Arg Gly Thr Arg Lys Val Gly
        115                 120                 125

Glu Val Tyr Phe Asp Pro Asn Val Leu Ser Ala Asp Gly Thr Ala Ile
    130                 135                 140

Met Gly Thr Cys Arg Phe Ser Pro Ser Gly Glu Tyr Phe Ala Tyr Ala
145                 150                 155                 160

Val Ser His Leu Gly Val Asp Tyr Phe Thr Ile Tyr Val Arg Pro Thr
                165                 170                 175

Ser Ser Ser Leu Ser Gln Ala Pro Glu Ala Glu Gly Gly Asp Gly Arg
            180                 185                 190

Leu Ser Asp Gly Val Lys Trp Cys Lys Phe Thr Thr Ile Thr Trp Thr
        195                 200                 205

Lys Asp Ser Lys Gly Phe Leu Tyr Gln Arg Tyr Pro Ala Arg Glu Ser
    210                 215                 220

Leu Val Ala Lys Asp Arg Asp Lys Asp Ala Met Val Cys Tyr His Arg
225                 230                 235                 240

Val Gly Thr Thr Gln Leu Glu Asp Ile Ile Val Gln Gln Asp Lys Glu
                245                 250                 255

Asn Pro Asp Trp Thr Tyr Gly Thr Asp Ala Ser Glu Asp Gly Lys Tyr
            260                 265                 270

Ile Tyr Leu Val Val Tyr Lys Asp Ala Ser Lys Gln Asn Leu Leu Trp
        275                 280                 285

Val Ala Glu Phe Asp Lys Asp Gly Val Lys Pro Glu Ile Pro Trp Arg
    290                 295                 300

Lys Val Ile Asn Glu Phe Gly Ala Asp Tyr His Val Ile Thr Asn His
305                 310                 315                 320

Gly Ser Leu Ile Tyr Val Lys Thr Asn Val Asn Ala Pro Gln Tyr Lys
                325                 330                 335

Val Val Thr Ile Asp Leu Ser Thr Gly Glu Pro Glu Ile Arg Asp Phe
            340                 345                 350

Ile Pro Glu Gln Lys Asp Ala Lys Leu Thr Gln Val Lys Cys Val Asn
        355                 360                 365

Lys Gly Tyr Phe Val Ala Ile Tyr Lys Arg Asn Val Lys Asp Glu Ile
    370                 375                 380

Tyr Leu Tyr Ser Lys Ala Gly Asp Gln Leu Ser Arg Leu Ala Ser Asp
385                 390                 395                 400

Phe Ile Gly Val Ala Ser Ile Thr Asn Arg Glu Lys Gln Pro His Ser
                405                 410                 415

Phe Leu Thr Phe Ser Gly Phe Asn Thr Pro Gly Thr Ile Ser Arg Tyr
            420                 425                 430

Asp Phe Thr Ala Pro Asp Thr Gln Arg Leu Ser Ile Leu Arg Thr Thr
```

```
        435                 440                 445

Lys Leu Asn Gly Leu Asn Ala Asp Asp Phe Glu Ser Thr Gln Val Trp
    450                 455                 460

Tyr Lys Ser Lys Asp Gly Thr Lys Val Pro Met Phe Ile Val Arg His
465                 470                 475                 480

Lys Ser Thr Lys Phe Asp Gly Thr Ala Pro Ala Ile Gln Asn Gly Tyr
                485                 490                 495

Gly Gly Phe Ala Ile Thr Ala Asp Pro Phe Phe Ser Pro Ile Met Leu
            500                 505                 510

Thr Phe Met Gln Thr Tyr Gly Ala Ile Leu Ala Val Pro Asn Ile Arg
        515                 520                 525

Gly Gly Gly Glu Phe Gly Gly Glu Trp His Lys Ala Gly Arg Arg Glu
    530                 535                 540

Thr Lys Gly Asn Thr Phe Asp Asp Phe Ile Ala Ala Ala Gln Phe Leu
545                 550                 555                 560

Val Lys Asn Lys Tyr Ala Ala Pro Gly Lys Val Ala Ile Thr Gly Ala
                565                 570                 575

Ser Asn Gly Gly Phe Leu Val Cys Gly Ser Val Val Arg Ala Pro Glu
            580                 585                 590

Gly Thr Phe Gly Ala Ala Val Ser Glu Gly Gly Val Ala Asp Leu Leu
        595                 600                 605

Lys Phe Asn Lys Phe Thr Gly Gly Met Ala Trp Thr Ser Glu Tyr Gly
    610                 615                 620

Asn Pro Phe Ile Lys Glu Asp Phe Asp Phe Val Gln Ala Leu Ser Pro
625                 630                 635                 640

Val His Asn Val Pro Lys Asp Arg Val Leu Pro Ala Thr Leu Leu Met
                645                 650                 655

Thr Asn Ala Gly Asp Asp Arg Val Val Pro Met His Ser Leu Lys Phe
            660                 665                 670

Val Ala Asn Leu Gln Tyr Asn Val Pro Gln Asn Pro His Pro Leu Leu
        675                 680                 685

Ile Arg Val Asp Lys Ser Trp Leu Gly His Gly Phe Gly Lys Thr Thr
    690                 695                 700

Asp Lys His Thr Lys Asp Ala Ala Asp Lys Trp Ser Phe Val Ala Gln
705                 710                 715                 720

Ser Leu Gly Leu Glu Trp Lys Thr Val Asp
                725                 730


<210> SEQ ID NO 238

<400> SEQUENCE: 238

000


<210> SEQ ID NO 239
<211> LENGTH: 14
<212> TYPE: PRT
<213> ORGANISM: Homo sapiens
<220> FEATURE:
<221> NAME/KEY: misc_feature
<222> LOCATION: (6)..(9)
<223> OTHER INFORMATION: Xaa can be any naturally occurring amino acid

<400> SEQUENCE: 239

Cys Val Gly Asp Asp Xaa Xaa Xaa Xaa Leu Thr Arg Gly Glu
1               5                   10
```

<210> SEQ ID NO 240
<211> LENGTH: 248
<212> TYPE: DNA
<213> ORGANISM: Galerina marginata

<400> SEQUENCE: 240
acacattcaa caaatactaa cgcacaacgc atgagtacgt cgaacaagtc aacaacagaa 60
attgagctca ctcgttgcca ctaacgagag tttgatcgac gtgttcagca gtccatgggt 120
tgcagccaat accccagatt ggaagacgag tggagttggt gtcgaacatg gtagatatta 180
aggcaagggc gaagatcttt ggctgattga gttgacggtc ggaagattgg agactcggtt 240
ttcactgg 248

<210> SEQ ID NO 241
<211> LENGTH: 99
<212> TYPE: DNA
<213> ORGANISM: Galerina marginata

<400> SEQUENCE: 241
atgttcgaca ccaactccac tcgtcttcca atctggggta ttggctgcaa cccatggact 60
gctgaacacg tcgatcaaac tctcgttagt ggcaacgag 99

<210> SEQ ID NO 242
<211> LENGTH: 24
<212> TYPE: DNA
<213> ORGANISM: Galerina marginata

<400> SEQUENCE: 242
atctggggta ttggctgcaa ccca 24

<210> SEQ ID NO 243
<211> LENGTH: 73
<212> TYPE: PRT
<213> ORGANISM: Galerina marginata

<400> SEQUENCE: 243

Lys Pro Ser Leu Gln Ser Ser Asp Arg Gln Leu Asn Gln Pro Lys Ile
1               5                   10                  15

Phe Ala Leu Ala Leu Ile Ser Thr Met Phe Asp Thr Asn Ser Thr Arg
            20                  25                  30

Leu Pro Ile Trp Gly Ile Gly Cys Asn Pro Trp Thr Ala Glu His Val
        35                  40                  45

Asp Gln Thr Leu Val Ser Gly Asn Glu Ala Gln Phe Leu Leu Leu Thr
    50                  55                  60

Cys Ser Thr Tyr Ser Cys Val Val Arg
65                  70

<210> SEQ ID NO 244
<211> LENGTH: 33
<212> TYPE: PRT
<213> ORGANISM: Galerina marginata
<220> FEATURE:
<221> NAME/KEY: MISC_FEATURE
<222> LOCATION: (11)..(18)
<223> OTHER INFORMATION: Predicted sequence of a-amanitin.

<400> SEQUENCE: 244

Met Phe Asp Thr Asn Ser Thr Arg Leu Pro Ile Trp Gly Ile Gly Cys
1               5                   10                  15

Asn Pro Trp Thr Ala Glu His Val Asp Gln Thr Leu Val Ser Gly Asn
            20                  25                  30

Glu

<210> SEQ ID NO 245

<400> SEQUENCE: 245

000

<210> SEQ ID NO 246
<211> LENGTH: 614
<212> TYPE: DNA
<213> ORGANISM: Galerina amanitins

<400> SEQUENCE: 246
agcttacgtc tggcgacatt tgacccatga tagactaact ttggtagtcg aatcggtaca 60
atcacgactc cacggctttt tgccactgtt cggtgaatca ggttatctct ttataggagc 120
ctcttttctg ttatctgaaa actccaagcc atgtgaggat cgccgcgacc accttaggta 180
ctccttcgtg ccgtctgtca aagtggacaa agatacacct cggcgcgagt tttacttgac 240
ttaccaccga tctggaactt ccccatgggc tggtcagatg ccctcagatc acagaactcc 300
accaatgaag acagctcctc gtaatggcgt cgaaaatgtc ttggaccttt attctagaag 360
ttcacagtcc tgcggagtcg ttgctatttc ctaactcatc agctctattc ggtcctcgaa 420
agagataaaa ggcggtcgtc agtgcaggct gatctccaat cccccaacgc aaactcactt 480
aaccaaagat tctttttgc tctaacatct acaatgttcg acaccaacgc cactcgyctc 540
ccaatctggg gtattggctg caacccatgg actgctgagc acgtcgacca gactctcgct 600
agtgcaacga gtaa 614

<210> SEQ ID NO 247
<211> LENGTH: 9
<212> TYPE: PRT
<213> ORGANISM: Galerina amanitins

<400> SEQUENCE: 247

Ser Leu Arg Leu Ala Thr Phe Asp Pro
1 5

<210> SEQ ID NO 248
<211> LENGTH: 85
<212> TYPE: PRT
<213> ORGANISM: Galerina amanitins
<220> FEATURE:
<221> NAME/KEY: MISC_FEATURE
<222> LOCATION: (53)..(85)
<223> OTHER INFORMATION: Putative preproprotein.
<220> FEATURE:
<221> NAME/KEY: MISC_FEATURE
<222> LOCATION: (63)..(70)
<223> OTHER INFORMATION: Toxin sequence.

<400> SEQUENCE: 248

Lys Phe Thr Val Leu Arg Ser Arg Cys Tyr Phe Leu Thr His Gln Leu
1 5 10 15

Tyr Ser Val Leu Glu Arg Asp Lys Arg Arg Ser Ser Val Gln Ala Asp
20 25 30

Leu Gln Ser Pro Asn Ala Asn Ser Leu Asn Gln Arg Phe Phe Phe Ala
35 40 45

Leu Thr Ser Thr Met Phe Asp Thr Asn Ala Thr Arg Leu Pro Ile Trp
50 55 60

```
Gly Ile Gly Cys Asn Pro Trp Thr Ala Glu His Val Asp Gln Thr Leu
65                  70                  75                  80

Ala Ser Gly Asn Glu
                85


<210> SEQ ID NO 249
<211> LENGTH: 17
<212> TYPE: PRT
<213> ORGANISM: Artificial Sequence
<220> FEATURE:
<223> OTHER INFORMATION: A synthetic peptide

<400> SEQUENCE: 249

Ala Thr Arg Leu Pro Ala Trp Leu Val Asp Cys Pro Cys Val Gly Asp
1               5                   10                  15

Asp


<210> SEQ ID NO 250
<211> LENGTH: 77
<212> TYPE: PRT
<213> ORGANISM: Amanita bisporigera

<400> SEQUENCE: 250

Ser Ser Ile Ala Trp Ala Pro Gly Asn Tyr Pro Ser Thr Arg Arg Ser
1               5                   10                  15

Asp His Val Asp Ser Tyr Gln Ser Ala Ser Lys Gly Glu Val Pro Val
            20                  25                  30

Pro Asp Pro Tyr Gln Trp Leu Glu Glu Ser Thr Asp Glu Val Asp Lys
        35                  40                  45

Trp Thr Thr Ala Gln Ala Asp Leu Ala Gln Ala Tyr Leu Asp Gln Asn
    50                  55                  60

Ala Asp Ile Gln Lys Leu Ala Asp Lys Phe Arg Ala Ser
65                  70                  75


<210> SEQ ID NO 251
<211> LENGTH: 64
<212> TYPE: PRT
<213> ORGANISM: Amanita bisporigera

<400> SEQUENCE: 251

Val Asp Ile Tyr Lys Ser Ala Leu Arg Gly Asp Val His Val Gln Asp
1               5                   10                  15

Pro Tyr Gln Trp Leu Glu Glu Tyr Thr Asp Glu Thr Asp Lys Trp Thr
            20                  25                  30

Thr Ala Gln Glu Val Phe Thr Arg Thr Tyr Leu Asp Lys Asn Pro Asp
        35                  40                  45

Leu Pro Arg Leu Glu Lys Ala Phe Gln Ala Cys Asn Asp Tyr Pro Lys
    50                  55                  60


<210> SEQ ID NO 252
<211> LENGTH: 70
<212> TYPE: PRT
<213> ORGANISM: Amanita bisporigera

<400> SEQUENCE: 252

Gly Ala Ala Ser Ile Ala Asn Arg Gln Lys Gln Thr His Phe Phe Leu
1               5                   10                  15

Thr Leu Ser Gly Phe Asn Thr Pro Gly Thr Ile Ala Arg Tyr Asp Phe
            20                  25                  30

Thr Ala Pro Glu Thr Gln Arg Phe Ser Ile Leu Arg Thr Thr Lys Val
```

```
        35                  40                  45

Asn Glu Leu Asp Pro Asp Asp Phe Glu Ser Thr Gln Val Trp Tyr Glu
    50                  55                  60

Ser Lys Asp Gly Asn Lys
65                  70


<210> SEQ ID NO 253
<211> LENGTH: 50
<212> TYPE: PRT
<213> ORGANISM: Amanita bisporigera

<400> SEQUENCE: 253

Gly Gly Phe Ser Ile Ser Ile Asp Pro Phe Phe Ser Ala Thr Ile Leu
1               5                   10                  15

Thr Phe Leu Gln Lys Tyr Gly Val Val Phe Ala Leu Pro Asn Ile Arg
            20                  25                  30

Gly Gly Gly Glu Phe Gly Glu Asp Trp His Leu Ala Gly Cys Arg Glu
        35                  40                  45

Lys Lys
    50


<210> SEQ ID NO 254
<211> LENGTH: 46
<212> TYPE: PRT
<213> ORGANISM: Amanita bisporigera

<400> SEQUENCE: 254

Asp Asp Arg Val Val Pro Met His Ser Phe Lys Leu Ala Ala Glu Leu
1               5                   10                  15

Gln Tyr Ser Leu Pro His Asn Pro Asn Pro Leu Leu Ile Arg Ile Asp
            20                  25                  30

Lys Lys Ala Gly His Gly Ala Gly Lys Ser Thr Gln Gln Lys
        35                  40                  45


<210> SEQ ID NO 255
<211> LENGTH: 34
<212> TYPE: PRT
<213> ORGANISM: Amanita bisporigera

<400> SEQUENCE: 255

Ala Ala Glu Leu Gln Tyr Ser Leu Pro His Asn Pro Asn Pro Leu Leu
1               5                   10                  15

Ile Arg Ile Asp Lys Lys Thr Gly His Gly Ala Gly Lys Ser Thr Gln
            20                  25                  30

Gln Arg


<210> SEQ ID NO 256
<211> LENGTH: 34
<212> TYPE: PRT
<213> ORGANISM: Amanita bisporigera

<400> SEQUENCE: 256

Gln Val Trp Tyr Glu Ser Lys Asp Gly Thr Ser Ile Pro Met Phe Ile
1               5                   10                  15

Val Arg His Lys Ser Thr Lys Phe Asp Gly Thr Ala Pro Val Ile Gln
            20                  25                  30

Tyr Gly


<210> SEQ ID NO 257
```

<400> SEQUENCE: 257

000

<210> SEQ ID NO 258
<211> LENGTH: 59
<212> TYPE: PRT
<213> ORGANISM: Amanita bisporigera

<400> SEQUENCE: 258

Ser Asp Phe Val Thr Ile Tyr Val Trp Ser Thr Asp Ser Pro Leu Thr
1               5                   10                  15

Asn Asp Val Asp Ser Lys Asn Asp Lys Gly Arg Leu Pro Glu Glu Ile
            20                  25                  30

Lys Phe Val Lys Phe Ser Ser Ile Gly Trp Thr Pro Asp Ser Lys Gly
        35                  40                  45

Phe Phe Ile Arg Ser Ile Pro Trp Thr Ala Ser
    50                  55

<210> SEQ ID NO 259
<211> LENGTH: 35
<212> TYPE: PRT
<213> ORGANISM: Amanita bisporigera

<400> SEQUENCE: 259

Lys Asn Asp Lys Gly Arg Leu Pro Glu Glu Ile Lys Phe Val Lys Phe
1               5                   10                  15

Ser Ser Ile Gly Trp Thr Pro Asp Ser Lys Gly Phe Phe Ile Arg Ser
            20                  25                  30

Phe Pro Gly
        35

<210> SEQ ID NO 260
<211> LENGTH: 47
<212> TYPE: PRT
<213> ORGANISM: Amanita bisporigera

<400> SEQUENCE: 260

Asp Asp Arg Val Val Pro Met His Ser Phe Lys Phe Ile Ala Thr Leu
1               5                   10                  15

Gln His Asn Val Pro Gln Asn Pro His Pro Leu Leu Ile Lys Ile Asp
            20                  25                  30

Lys Ser Trp Leu Gly His Gly Met Gly Lys Pro Thr Asp Lys Lys
        35                  40                  45

<210> SEQ ID NO 261
<211> LENGTH: 53
<212> TYPE: PRT
<213> ORGANISM: Amanita bisporigera

<400> SEQUENCE: 261

Gly Gly Asp Tyr Ser Thr Ile Tyr Val Arg Ser Thr Ser Ser Pro Leu
1               5                   10                  15

Ser Gln Ser Ser Val Ala Gln Gly Val Asp Gly Arg Leu Ser Asp Glu
            20                  25                  30

Val Lys Trp Phe Lys Phe Ser Thr Ile Ile Trp Thr Lys Asp Phe Lys
        35                  40                  45

Gly Phe Leu Tyr Gln
    50

<210> SEQ ID NO 262
<211> LENGTH: 71
<212> TYPE: PRT
<213> ORGANISM: Amanita bisporigera

<400> SEQUENCE: 262

```
Val Phe Asp Ser Met Thr Phe Thr Ser Ile Thr Asn Lys Gly Ser Leu
1               5                   10                  15

Phe Tyr Val Arg Thr Asn Glu Ser Ala Pro Gln Tyr Arg Val Ile Thr
            20                  25                  30

Val Asp Ile Ala Lys Arg Asn Glu Ile Lys Glu Leu Ile Pro Glu Thr
        35                  40                  45

Asp Ala Tyr Leu Ser Ser Ile Thr Ser Val Asn Lys Gly Tyr Phe Ala
    50                  55                  60

Leu Val Tyr Lys Arg Asn Val
65                  70
```

<210> SEQ ID NO 263
<211> LENGTH: 62
<212> TYPE: PRT
<213> ORGANISM: Amanita bisporigera

<400> SEQUENCE: 263

```
Ile Thr Asn Lys Gly Ser Leu Phe Tyr Val Arg Thr Asn Glu Ser Ala
1               5                   10                  15

Pro Gln Tyr Arg Val Ile Thr Val Asp Ile Ala Lys Arg Asn Glu Ile
            20                  25                  30

Lys Glu Leu Ile Pro Glu Thr Asp Ala Tyr Leu Ser Ser Ile Thr Ser
        35                  40                  45

Val Asn Lys Gly Tyr Phe Ala Leu Val Tyr Lys Arg Asn Val
    50                  55                  60
```

<210> SEQ ID NO 264
<211> LENGTH: 73
<212> TYPE: PRT
<213> ORGANISM: Amanita bisporigera

<400> SEQUENCE: 264

```
Ser Leu Gly Gln Ala Trp Ile Ser Glu Tyr Gly Asn Pro Ser Ile Pro
1               5                   10                  15

Glu Glu Phe Asp Tyr Ile Tyr Pro Leu Ser Pro Val His Asn Val Gln
            20                  25                  30

Thr Asp Lys Val Met Pro Ala Met Leu Ile Thr Val Asn Ile Gly Glu
        35                  40                  45

Gln Leu Thr Ser Ser Asn Leu Ile Met Pro His Thr Arg Pro Ser Pro
    50                  55                  60

Gly Asp Asp Arg Val Val Pro Met His
65                  70
```

<210> SEQ ID NO 265
<211> LENGTH: 34
<212> TYPE: PRT
<213> ORGANISM: Amanita bisporigera

<400> SEQUENCE: 265

```
Ala Ala Glu Leu Gln Tyr Ser Leu Pro His Asn Pro Asn Pro Leu Leu
1               5                   10                  15

Ile Arg Ile Asp Lys Lys Ala Gly His Gly Ala Gly Lys Ser Thr Gln
            20                  25                  30
```

Gln Lys

<210> SEQ ID NO 266
<211> LENGTH: 85
<212> TYPE: PRT
<213> ORGANISM: Amanita bisporigera

<400> SEQUENCE: 266

```
Ala Val Thr His Ile Arg Gly Gly Ser Glu Lys Gly Trp Gly Trp Phe
1               5                   10                  15

Leu Asp Gly Arg Lys Asp Lys Lys Pro Asn Ser Phe Thr Asp Phe Ile
            20                  25                  30

Ala Cys Ala Glu Ala Leu Ile Ala Glu Gly Tyr Gly Thr Ala Gly Arg
        35                  40                  45

Ile Val Ala Glu Gly Arg Ser Ala Gly Gly Met Leu Met Gly Ala Val
    50                  55                  60

Ala Asn Leu Arg Pro Asp Leu Trp Ala Gly Val Ile Gly Gly Val Pro
65                  70                  75                  80

Phe Val Asp Val Leu
                85
```

<210> SEQ ID NO 267
<211> LENGTH: 77
<212> TYPE: PRT
<213> ORGANISM: Amanita bisporigera

<400> SEQUENCE: 267

```
Gln Tyr Tyr Ala Pro Tyr Leu His Asp Asp Asn Arg Trp Tyr Trp Tyr
1               5                   10                  15

Tyr Asn Ser Gly Leu Glu Pro Gln Thr Gly Glu Arg Phe Lys Gln Pro
            20                  25                  30

Phe Arg Pro Arg Trp Leu Thr Ser Val Pro Ala Lys Ala Leu Tyr Arg
        35                  40                  45

Ser Lys Asp Ser Asn Leu Pro Asp Leu Ser Thr Ala Asp Gly Ser Gly
    50                  55                  60

Gly Asp Leu Phe Phe Asp Val Gly Pro Leu Ser Ala Asn
65                  70                  75
```

<210> SEQ ID NO 268
<211> LENGTH: 38
<212> TYPE: PRT
<213> ORGANISM: Amanita bisporigera

<400> SEQUENCE: 268

```
Ala Glu Asp Ser Leu Ile Tyr Gln Asp Arg Glu His Arg Asp Trp Met
1               5                   10                  15

Phe Ser Ile Asp Val Thr Asp Asp Gly Asn Tyr Leu Leu Leu Tyr Ile
            20                  25                  30

Leu Lys Asp Ser Ser Arg
        35
```

<210> SEQ ID NO 269
<211> LENGTH: 30
<212> TYPE: PRT
<213> ORGANISM: Amanita bisporigera

<400> SEQUENCE: 269

```
Gly Leu Leu Val Ser Ala Cys Val Asn Arg Ala Pro Glu Gly Thr Phe
1               5                   10                  15
```

Gly Cys Ala Val Ala Asp Val Gly Val His Asp Leu Leu Lys
20 25 30

<210> SEQ ID NO 270
<211> LENGTH: 27
<212> TYPE: PRT
<213> ORGANISM: Amanita bisporigera

<400> SEQUENCE: 270

Glu Asp Ile Ile Val Tyr Gln Asp Asn Glu His Pro Glu Trp Ile Tyr
1 5 10 15

Gly Ala Asp Thr Ser Glu Asp Gly Lys Tyr Leu
20 25

<210> SEQ ID NO 271
<211> LENGTH: 30
<212> TYPE: PRT
<213> ORGANISM: Amanita bisporigera

<400> SEQUENCE: 271

Met Ser Ser Ile Ala Trp Ala Pro Gly Asn Tyr Pro Ser Thr Arg Arg
1 5 10 15

Ser Asp His Val Asp Ser Tyr Gln Ser Ala Ser Lys Gly Glu
20 25 30

<210> SEQ ID NO 272
<211> LENGTH: 95
<212> TYPE: PRT
<213> ORGANISM: Amanita bisporigera

<400> SEQUENCE: 272

Phe Ser Ser Asp His Ile Arg Leu Arg Tyr Glu Ala Leu Asn Arg Pro
1 5 10 15

Ala Gln Ile Arg Arg Leu Ala Leu Ala Asp Gly Ala Gln Gln Val Leu
20 25 30

Lys Glu Thr Pro Val Leu Gly Val Phe Asn Ala Asp Asp Tyr Val Ser
35 40 45

Gln Arg Leu Trp Ala Thr Ser Val Asp Gly Thr Gln Val Pro Ile Ser
50 55 60

Leu Val Val Arg His Asp Gln Leu Gly Gln Pro Thr Pro Leu Tyr Leu
65 70 75 80

Tyr Gly Tyr Gly Ala Tyr Gly His Ser Leu Asp Pro Trp Phe Ser
85 90 95

<210> SEQ ID NO 273
<211> LENGTH: 23
<212> TYPE: PRT
<213> ORGANISM: Amanita bisporigera

<400> SEQUENCE: 273

Gln Phe Leu Val Lys Asn Lys Tyr Ala Ala Pro Gly Lys Val Ala Ile
1 5 10 15

Asn Gly Ala Ser Asn Gly Gly
20

<210> SEQ ID NO 274
<211> LENGTH: 38
<212> TYPE: PRT
<213> ORGANISM: Amanita bisporigera

<400> SEQUENCE: 274

Phe Ser Ala Pro Thr Leu Leu Asp Asp Gly His Trp Tyr Trp Phe Tyr
1 5 10 15

Asn Arg Gly Leu Gln Ser Gln Ser Gly Arg Tyr Leu Phe Ile Leu Arg
20 25 30

Arg Cys Lys Thr Gln Thr
35

<210> SEQ ID NO 275
<211> LENGTH: 62
<212> TYPE: PRT
<213> ORGANISM: Amanita bisporigera

<400> SEQUENCE: 275

Asn Asp Ser Arg Val Gln Tyr Trp Glu Ala Ala Lys Trp Val Ala Lys
1 5 10 15

Leu Arg Asp Thr Lys Thr Asp Asp His Pro Leu Leu Leu Lys Thr Glu
20 25 30

Leu Gly Ala Gly His Gly Gly Met Ser Gly Arg Tyr Gln Gly Leu Arg
35 40 45

Asp Val Ala Leu Glu Tyr Ala Phe Cys Phe Gln Gly Thr Gly
50 55 60

<210> SEQ ID NO 276
<211> LENGTH: 34
<212> TYPE: PRT
<213> ORGANISM: Amanita bisporigera

<400> SEQUENCE: 276

Gln Lys Asn Leu Leu Trp Val Ala Glu Leu Asn Glu Asp Gly Val Lys
1 5 10 15

Ser Gly Ile Gln Trp Arg Lys Val Val Asn Glu Tyr Val Ala Asp Tyr
20 25 30

Asn Val

<210> SEQ ID NO 277

<400> SEQUENCE: 277

000

<210> SEQ ID NO 278

<400> SEQUENCE: 278

000

<210> SEQ ID NO 279

<400> SEQUENCE: 279

000

<210> SEQ ID NO 280
<211> LENGTH: 75
<212> TYPE: PRT
<213> ORGANISM: Amanita bisporigera

<400> SEQUENCE: 280

Trp Ala Pro Gly Asn Tyr Pro Ser Thr Arg Arg Ser Asp His Val Asp
1 5 10 15

Ser Tyr Gln Ser Ala Ser Lys Gly Glu Val Pro Val Pro Asp Pro Tyr 20 25 30

Gln Trp Leu Glu Glu Ser Thr Asp Glu Val Asp Lys Trp Thr Thr Ala
35 40 45

Gln Ala Asp Leu Ala Gln Ala Tyr Leu Asp Gln Asn Ala Asp Ile Gln
50 55 60

Lys Leu Ala Asp Lys Phe Arg Ala Ser Arg Asn
65 70 75

<210> SEQ ID NO 281
<211> LENGTH: 47
<212> TYPE: PRT
<213> ORGANISM: Amanita bisporigera

<400> SEQUENCE: 281

Gly Asp Asp Arg Val Val Pro Met His Ser Phe Lys Phe Ile Ala Thr
1 5 10 15

Leu Gln His Asn Val Pro Gln Asn Pro His Pro Leu Leu Ile Lys Ile
20 25 30

Asp Lys Ser Trp Leu Gly His Gly Met Gly Lys Pro Thr Asp Lys
35 40 45

<210> SEQ ID NO 282
<211> LENGTH: 70
<212> TYPE: PRT
<213> ORGANISM: Amanita bisporigera

<400> SEQUENCE: 282

Val Asp Ile Tyr Lys Ser Ala Leu Arg Gly Asp Val His Val Gln Asp
1 5 10 15

Pro Tyr Gln Trp Leu Glu Glu Tyr Thr Asp Glu Thr Asp Lys Trp Thr
20 25 30

Thr Ala Gln Glu Val Phe Thr Arg Thr Tyr Leu Asp Lys Asn Pro Asp
35 40 45

Leu Pro Arg Leu Glu Lys Ala Phe Gln Ala Cys Asn Asp Tyr Pro Lys
50 55 60

Val Leu Ser Ala Thr Ile
65 70

<210> SEQ ID NO 283

<400> SEQUENCE: 283

000

<210> SEQ ID NO 284

<400> SEQUENCE: 284

000

<210> SEQ ID NO 285

<400> SEQUENCE: 285

000

<210> SEQ ID NO 286
<211> LENGTH: 63
<212> TYPE: PRT
<213> ORGANISM: Amanita bisporigera

<400> SEQUENCE: 286

```
Ile Thr Asn Lys Gly Ser Leu Phe Tyr Val Arg Thr Asn Glu Ser Ala
1               5                   10                  15

Pro Gln Tyr Arg Val Ile Thr Val Asp Ile Ala Lys Arg Asn Glu Ile
            20                  25                  30

Lys Glu Leu Ile Pro Glu Thr Asp Ala Tyr Leu Ser Ser Ile Thr Ser
        35                  40                  45

Val Asn Lys Gly Tyr Phe Ala Leu Val Tyr Lys Arg Asn Val Arg
    50                  55                  60


<210> SEQ ID NO 287

<400> SEQUENCE: 287

000


<210> SEQ ID NO 288
<211> LENGTH: 71
<212> TYPE: PRT
<213> ORGANISM: Amanita bisporigera

<400> SEQUENCE: 288

Gly Gln Ala Trp Ile Ser Glu Tyr Gly Asn Pro Ser Ile Pro Glu Glu
1               5                   10                  15

Phe Asp Tyr Ile Tyr Pro Leu Ser Pro Val His Asn Val Gln Thr Asp
            20                  25                  30

Lys Val Met Pro Ala Met Leu Ile Thr Val Asn Ile Gly Glu Gln Leu
        35                  40                  45

Thr Ser Ser Asn Leu Ile Met Pro His Thr Arg Pro Ser Pro Gly Asp
    50                  55                  60

Asp Arg Val Val Pro Met His
65                  70


<210> SEQ ID NO 289
<211> LENGTH: 48
<212> TYPE: PRT
<213> ORGANISM: Amanita bisporigera

<400> SEQUENCE: 289

Asn Leu Asp Asp Asp Arg Val Val Pro Met His Ser Phe Lys Leu Ala
1               5                   10                  15

Ala Glu Leu Gln Tyr Ser Leu Pro His Asn Pro Asn Pro Leu Leu Ile
            20                  25                  30

Arg Ile Asp Lys Lys Ala Gly His Gly Ala Gly Lys Ser Thr Gln Gln
        35                  40                  45


<210> SEQ ID NO 290
<211> LENGTH: 32
<212> TYPE: PRT
<213> ORGANISM: Amanita bisporigera

<400> SEQUENCE: 290

Ala Glu Leu Gln Tyr Ser Leu Pro His Asn Pro Asn Pro Leu Leu Ile
1               5                   10                  15

Arg Ile Asp Lys Lys Thr Gly His Gly Ala Gly Lys Ser Thr Gln Gln
            20                  25                  30


<210> SEQ ID NO 291
<211> LENGTH: 27
<212> TYPE: PRT
<213> ORGANISM: Amanita bisporigera
```

```
<400> SEQUENCE: 291

Phe Ser Ala Pro Thr Leu Leu Asp Asp Gly His Trp Tyr Trp Phe Tyr
1               5                   10                  15

Asn Arg Gly Leu Gln Ser Gln Ser Gly Arg Tyr
            20                  25


<210> SEQ ID NO 292
<211> LENGTH: 46
<212> TYPE: PRT
<213> ORGANISM: Amanita bisporigera

<400> SEQUENCE: 292

Arg Ala Pro Glu Gly Thr Phe Gly Ala Ala Val Pro Glu Gly Gly Val
1               5                   10                  15

Ala Asp Leu Leu Lys Val Val Phe Val Phe Gln Leu Cys Asn Ser Gln
            20                  25                  30

Ser Leu Ile Leu Thr Leu Gln Phe His Lys Phe Thr Gly Gly
        35                  40                  45


<210> SEQ ID NO 293
<211> LENGTH: 61
<212> TYPE: PRT
<213> ORGANISM: Amanita bisporigera

<400> SEQUENCE: 293

Ala Val Thr His Ile Arg Gly Gly Ser Glu Lys Gly Trp Gly Trp Phe
1               5                   10                  15

Leu Asp Gly Arg Lys Asp Lys Lys Pro Asn Ser Phe Thr Asp Phe Ile
            20                  25                  30

Ala Cys Ala Glu Ala Leu Ile Ala Glu Gly Tyr Gly Thr Ala Gly Arg
        35                  40                  45

Ile Val Ala Glu Gly Arg Ser Ala Gly Gly Met Leu Met
    50                  55                  60


<210> SEQ ID NO 294

<400> SEQUENCE: 294

000


<210> SEQ ID NO 295

<400> SEQUENCE: 295

000


<210> SEQ ID NO 296
<211> LENGTH: 54
<212> TYPE: PRT
<213> ORGANISM: Amanita bisporigera

<400> SEQUENCE: 296

Asp Phe Val Thr Ile Tyr Val Trp Ser Thr Asp Ser Pro Leu Thr Asn
1               5                   10                  15

Asp Val Asp Ser Lys Asn Asp Lys Gly Arg Leu Pro Glu Glu Ile Lys
            20                  25                  30

Phe Val Lys Phe Ser Ser Ile Gly Trp Thr Pro Asp Ser Lys Gly Phe
        35                  40                  45

Phe Ile Arg Ser Ile Pro
    50
```

<210> SEQ ID NO 297
<211> LENGTH: 91
<212> TYPE: PRT
<213> ORGANISM: Amanita bisporigera

<400> SEQUENCE: 297

```
His Ile Arg Leu Arg Tyr Glu Ala Leu Asn Arg Pro Ala Gln Ile Arg
1               5                   10                  15

Arg Leu Ala Leu Ala Asp Gly Ala Gln Gln Val Leu Lys Glu Thr Pro
            20                  25                  30

Val Leu Gly Val Phe Asn Ala Asp Asp Tyr Val Ser Gln Arg Leu Trp
        35                  40                  45

Ala Thr Ser Val Asp Gly Thr Gln Val Pro Ile Ser Leu Val Val Arg
    50                  55                  60

His Asp Gln Leu Gly Gln Pro Thr Pro Leu Tyr Leu Tyr Gly Tyr Gly
65                  70                  75                  80

Ala Tyr Gly His Ser Leu Asp Pro Trp Phe Ser
                85                  90
```

<210> SEQ ID NO 298

<400> SEQUENCE: 298

000

<210> SEQ ID NO 299

<400> SEQUENCE: 299

000

<210> SEQ ID NO 300

<400> SEQUENCE: 300

000

<210> SEQ ID NO 301

<400> SEQUENCE: 301

000

<210> SEQ ID NO 302
<211> LENGTH: 37
<212> TYPE: PRT
<213> ORGANISM: Amanita bisporigera

<400> SEQUENCE: 302

```
Glu Asp Ser Leu Ile Tyr Gln Asp Arg Glu His Arg Asp Trp Met Phe
1               5                   10                  15

Ser Ile Asp Val Thr Asp Asp Gly Asn Tyr Leu Leu Leu Tyr Ile Leu
            20                  25                  30

Lys Asp Ser Ser Arg
        35
```

<210> SEQ ID NO 303
<211> LENGTH: 34
<212> TYPE: PRT
<213> ORGANISM: Amanita bisporigera
<220> FEATURE:
<221> NAME/KEY: misc_feature
<222> LOCATION: (18)..(19)
<223> OTHER INFORMATION: Xaa can be any naturally occurring amino acid

<400> SEQUENCE: 303

Met Ser Asp Ile Asn Ala Thr Arg Leu Pro Ile Trp Gly Ile Gly Cys
1 5 10 15

Asn Xaa Xaa Pro Cys Val Gly Asp Asp Val Thr Thr Leu Leu Thr Arg
20 25 30

Gly Glu

<210> SEQ ID NO 304
<211> LENGTH: 34
<212> TYPE: PRT
<213> ORGANISM: Amanita bisporigera
<220> FEATURE:
<221> NAME/KEY: misc_feature
<222> LOCATION: (17)..(19)
<223> OTHER INFORMATION: Xaa can be any naturally occurring amino acid

<400> SEQUENCE: 304

Met Ser Asp Ile Asn Ala Thr Arg Leu Pro Ala Trp Leu Val Asp Cys
1 5 10 15

Xaa Xaa Xaa Pro Cys Val Gly Asp Asp Val Asn Arg Leu Leu Thr Arg
20 25 30

Gly Glu

<210> SEQ ID NO 305
<211> LENGTH: 34
<212> TYPE: PRT
<213> ORGANISM: Amanita bisporigera
<220> FEATURE:
<221> NAME/KEY: misc_feature
<222> LOCATION: (18)..(19)
<223> OTHER INFORMATION: Xaa can be any naturally occurring amino acid

<400> SEQUENCE: 305

Met Ser Asp Ile Asn Ala Thr Arg Leu Pro Ile Trp Gly Ile Gly Cys
1 5 10 15

Asp Xaa Xaa Pro Cys Ile Gly Asp Asp Val Thr Ile Leu Leu Thr Arg
20 25 30

Gly Glu

<210> SEQ ID NO 306
<211> LENGTH: 34
<212> TYPE: PRT
<213> ORGANISM: Amanita bisporigera
<220> FEATURE:
<221> NAME/KEY: misc_feature
<222> LOCATION: (18)..(19)
<223> OTHER INFORMATION: Xaa can be any naturally occurring amino acid

<400> SEQUENCE: 306

Met Ser Asp Ile Asn Ala Thr Arg Leu Pro Ile Ile Gly Ile Leu Leu
1 5 10 15

Pro Xaa Xaa Pro Cys Ile Gly Asp Asp Val Thr Leu Leu Leu Thr Arg
20 25 30

Gly Glu

<210> SEQ ID NO 307

<400> SEQUENCE: 307

000

<210> SEQ ID NO 308
<211> LENGTH: 34
<212> TYPE: PRT
<213> ORGANISM: Amanita bisporigera

<400> SEQUENCE: 308

Met Ser Asp Ile Asn Thr Ala Arg Leu Pro Phe Tyr Gln Phe Pro Asp
1 5 10 15

Phe Lys Tyr Pro Cys Val Gly Asp Asp Ile Glu Met Val Leu Ala Arg
20 25 30

Gly Glu

<210> SEQ ID NO 309
<211> LENGTH: 34
<212> TYPE: PRT
<213> ORGANISM: Amanita bisporigera

<400> SEQUENCE: 309

Met Ser Asp Ile Asn Thr Ala Arg Leu Pro Phe Phe Gln Pro Pro Glu
1 5 10 15

Phe Arg Pro Pro Cys Val Gly Asp Asp Ile Glu Met Val Leu Thr Arg
20 25 30

Gly Glu

<210> SEQ ID NO 310
<211> LENGTH: 34
<212> TYPE: PRT
<213> ORGANISM: Amanita bisporigera
<220> FEATURE:
<221> NAME/KEY: misc_feature
<222> LOCATION: (19)..(19)
<223> OTHER INFORMATION: Xaa can be any naturally occurring amino acid

<400> SEQUENCE: 310

Met Ser Asp Val Asn Asp Thr Arg Leu Pro Phe Asn Phe Phe Arg Phe
1 5 10 15

Pro Tyr Xaa Pro Cys Ile Gly Asp Asp Ser Gly Ser Val Leu Arg Leu
20 25 30

Gly Glu

<210> SEQ ID NO 311
<211> LENGTH: 34
<212> TYPE: PRT
<213> ORGANISM: Amanita bisporigera

<400> SEQUENCE: 311

Met Ser Asp Ile Asn Thr Ala Arg Leu Pro Leu Phe Leu Pro Pro Val
1 5 10 15

Arg Met Pro Pro Cys Val Gly Asp Asp Ile Glu Met Val Leu Thr Arg
20 25 30

Gly Glu

<210> SEQ ID NO 312
<211> LENGTH: 34
<212> TYPE: PRT
<213> ORGANISM: Amanita bisporigera

<400> SEQUENCE: 312

Met Ser Asp Ile Asn Thr Ala Arg Leu Pro Tyr Val Val Phe Met Ser
1 5 10 15

Phe Ile Pro Pro Cys Val Asn Asp Asp Ile Gln Val Val Leu Thr Arg
20 25 30

Gly Glu

<210> SEQ ID NO 313
<211> LENGTH: 34
<212> TYPE: PRT
<213> ORGANISM: Amanita bisporigera
<220> FEATURE:
<221> NAME/KEY: misc_feature
<222> LOCATION: (18)..(19)
<223> OTHER INFORMATION: Xaa can be any naturally occurring amino acid

<400> SEQUENCE: 313

Met Ser Asp Ile Asn Ala Ile Arg Ala Pro Ile Leu Met Leu Ala Ile
1 5 10 15

Leu Xaa Xaa Pro Cys Val Gly Asp Asp Ile Glu Val Leu Arg Arg Gly
20 25 30

Glu Gly

<210> SEQ ID NO 314
<211> LENGTH: 34
<212> TYPE: PRT
<213> ORGANISM: Amanita bisporigera

<400> SEQUENCE: 314

Met Ser Asp Ile Asn Gly Thr Arg Leu Pro Ile Pro Gly Leu Ile Pro
1 5 10 15

Leu Gly Ile Pro Cys Val Ser Asp Asp Val Asn Pro Thr Leu Thr Arg
20 25 30

Gly Glu

<210> SEQ ID NO 315
<211> LENGTH: 34
<212> TYPE: PRT
<213> ORGANISM: Amanita bisporigera
<220> FEATURE:
<221> NAME/KEY: misc_feature
<222> LOCATION: (19)..(19)
<223> OTHER INFORMATION: Xaa can be any naturally occurring amino acid

<400> SEQUENCE: 315

Met Ser Asp Ile Asn Ala Thr Arg Leu Pro Gly Ala Tyr Pro Pro Val
1 5 10 15

Pro Met Xaa Pro Cys Val Gly Asp Ala Asp Asn Phe Thr Leu Thr Arg
20 25 30

Gly Glu

<210> SEQ ID NO 316
<211> LENGTH: 34
<212> TYPE: PRT
<213> ORGANISM: Amanita bisporigera
<220> FEATURE:
<221> NAME/KEY: misc_feature
<222> LOCATION: (19)..(19)
<223> OTHER INFORMATION: Xaa can be any naturally occurring amino acid

<400> SEQUENCE: 316

Met Ser Asp Ile Asn Ala Thr Arg Leu Pro His Pro Phe Pro Leu Gly
1 5 10 15

Leu Gln Xaa Pro Val Ala Gly Asp Val Asp Asn Leu Thr Leu Thr Lys
20 25 30

Gly Glu

<210> SEQ ID NO 317
<211> LENGTH: 34
<212> TYPE: PRT
<213> ORGANISM: Amanita bisporigera
<220> FEATURE:
<221> NAME/KEY: misc_feature
<222> LOCATION: (17)..(19)
<223> OTHER INFORMATION: Xaa can be any naturally occurring amino acid

<400> SEQUENCE: 317

Met Ser Asp Ile Asn Ala Thr Arg Leu Pro Ala Trp Leu Ala Thr Cys
1 5 10 15

Xaa Xaa Xaa Pro Cys Ala Gly Asp Asp Val Asn Pro Leu Leu Thr Arg
20 25 30

Gly Glu

<210> SEQ ID NO 318
<211> LENGTH: 18
<212> TYPE: PRT
<213> ORGANISM: Artificial sequence
<220> FEATURE:
<223> OTHER INFORMATION: A synthetic peptide

<400> SEQUENCE: 318

Ala Thr Arg Leu Pro Ile Trp Gly Ile Gly Cys Asn Pro Cys Val Gly
1 5 10 15

Asp Asp

<210> SEQ ID NO 319
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 319
ccagtgaaaa ccgagtctcc a 21

<210> SEQ ID NO 320
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 320
caaagatctt cgcccttgcc t 21

<210> SEQ ID NO 321
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 321
atgttcgaca ccaactccac t 21

<210> SEQ ID NO 322
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 322
acacattcaa caaatactaa c 21

<210> SEQ ID NO 323
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 323
gctgaacacg tcgatcaaac t 21

<210> SEQ ID NO 324
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 324
tccatgggtt gcagccaata c 21

<210> SEQ ID NO 325

<400> SEQUENCE: 325

000

<210> SEQ ID NO 326

<400> SEQUENCE: 326

000

<210> SEQ ID NO 327
<211> LENGTH: 13254
<212> TYPE: DNA
<213> ORGANISM: Artificial Sequence
<220> FEATURE:
<223> OTHER INFORMATION: A synthetic oligonucleotide

<400> SEQUENCE: 327
gatcggagag aagtcagaga agtttcacta ttttcagcac atcgcagccg aagggcggcg 60
atgtccatga tgggagcgta gcataaccag aaatggatag aatcgataat cgatgatgga 120
aagtggagac ggtgacaggg gggagctagt aaatccaaaa gatacagtaa tgaagataat 180
gtgtctctca ccgaaaaaaa gggacgaatc ggaaccatca gtgcaaccta cgaaactcag 240
catcatcttc aatcggagat ttaaccgatc cacctacaag tttgaaacgt ttgcccgtta 300
ccaagttaat aacaatggtc gacttgcaca ccatctcgta ttcagctctc gtcactttca 360
ggcttatatt ccaattcctc aagctatctg cagctgcatt gactatctat ggactttaca 420
gagtcactcg tgtaatttat gttgagctga cttctccaat acgccatctc cccggtccag 480
caaacgccaa tatatttctt ggtaatctca aacagctctg gacagatgta agtacaaaat 540
cacccaccta cccacccatt gttaaccact attaccacag acatatcatt ggcattcaca 600
atatgggccg atgataagac taaatggatt tctcggtgta agaaccaatc catttattct 660
gatatagata acaatcaagt ttagctttcg catttatatg tgacggatcc gcaggccttg 720

-continued

```
aaccacattt tgacgaatgg ttacgtttac accaaaccat cgtttactcg ccgccagatc    780
ggcaagttgt ggggtccagg tgctttttca cctaccatac ttaagaggcg atgatccaac    840
catacgtcag gtctcccttt tgtcgaaggg gatcaacata aaaagcaggt gcgtacttcc    900
gttgcctcaa cctagttcgt attatgatat attacgttta acagcggaag attttggtga    960
ctatctatcc attccaaatc gtggtccatc agtgtctcaa tcacaaccag aatcctgcct   1020
ttggtccggt ccgcattcgc gaattcacag attgcttcgt aaaaaaatca aaacgggtcg   1080
gtttttacta ctcatccatg ctaccagtga tgaacttcgc ctagctccaa gactcttggg   1140
ctactgaatg ctcgaaacaa ggtggtactt gccgcttaga cattatggta ggccttggta   1200
aggtggtgat ggacatcatc agctcaacag gtatgtctga tgttgccagc atacttatta   1260
gtgtttaccg atgccattcg atggaaaggc ttccgttacg agcttgattc cctggatcgt   1320
gaaagtgact ttagccgtgt ggctacaatt ttatctcaat tgaacctgat tcgttggcaa   1380
ctccgaagat tcatcccact tctatggttc atagtatgga aattccaaat cactgtaacg   1440
gagttctcat cgcgttgtct agcctgatcc tgtagagaca caactagacg atatcaagca   1500
gaccctttct cggattacga gtcggcttct gaacgagagc aagggatccg tacgtacgaa   1560
taatgacaat tccggcagtc gagatctcct atcgcttttg gttcgcacca atatgtcccc   1620
cgatgtgcca gagcaccgtc gtctatccga tgacgaagtc aaagcgcgtg aggctgatgt   1680
atttgtcact gcgagtatac ctgatctttt tatttagagg ttatctcatt tgtaattgct   1740
ggacgtgaaa gtccgatgta agtctgagtc tgtttatctg tttaaggact attctcgaat   1800
atttgattgg tagtaacgta atggcgtggg ctttattttc tctggcaaaa aaccgtgaaa   1860
tccaggctaa gctgcgtaga gagctgctca cggtcgatac ctgtcagcca acgacggacc   1920
agctcaatgc actttcatat ttggatatgg taattaggga gacgctacgt ctgtatcctt   1980
catctaggcc actcgagggt gtgtgccaag gacgacattt tacctttggc taagccgatc   2040
accgaccgga gaggaaacct attctccagt attaggtgag gattcggtcg ttcccatatt   2100
tctttttagc gttcaccggt cttatagtat caaaagaggg caagtagtca taattcccat   2160
ttctgccatc cacaaggaca agtcgatatg gggtgaagat gctttagact tcaggtaaat   2220
attgcacgtc gctgttggct cctgagtcat tcagttttga tagaccagaa cgatgggaat   2280
gtctacctga aggcgtcaat accatcccag gcgtctggag ccatttgctc agtttttggg   2340
gtggtccacg ttcgtgtatc ggattcagat ttgctatcgc cgagtgagca agtttctct    2400
agcatttcga agatatagtg ctgacactgg taacgacaag aatgaaagct ctactcttca   2460
cactagtccg tgccctcgaa tttgacttgg ctgtgccagc ggagcaaatt tctgtggaaa   2520
gtggactaag taaccgaccg atttgacca cggacccggg ccgttatcag ctcccgctgc    2580
tcatcaagcc atataaagct cgaagttaac gcgcctcgtg gttcattata cctagaggtc   2640
tagggaccac tgtgtggagt ttgtactggc atctatgata ttacatagca gtcaattacg   2700
aactgagttc ggggctgaga aatgatgaga gtaaaatgtg gaggatggaa aagagcttga   2760
gcatgcgagc tgccgccgaa gtttagttca taaccagggt tctagcccgt caaagaaccg   2820
gttagcgatt gaatttgaca gaagcttctt gccactacta aatgcgttct gacggtgcag   2880
gcactgcgga tgacgcagca ttggaacgcg gcgttaatgg cgggagactt tagcgcaagc   2940
ctcgagatgt cggttggttg aatgacatca gtggggccaa ctgttgcgac atgccatgac   3000
ttcccaagca aaaatttaca atacgactcg tatgagtcac caccgacttc atcgccccaa   3060
tgtcgtggtc tcttatgccc gtcatcgatt gacatggtgt ttcgcacgag tctgcttatc   3120
```

```
aagtaggcga gcaccaccac catgttttct accctagtac aaaaacagtg gtacggggaa   3180
cgcctatgtt aactttcgca caagaagagg aacttttgta ccatcctcgc cagctacctt   3240
ggggcgcgta aaatgccaac tcagttccgt cgatggccca ttggggagct caaaggcaaa   3300
atatctgacc agaaccgaca gcacagccta gagattgtgc agtcaaacaa ccaaaccgct   3360
gacatggggt tcaatcgtac cttcacctcc agtacggcga ggtctctgcc tggacacatc   3420
ctgggaccag caccgaaagt taagagaccc cggtagccag ctagttctcc cttgtttcct   3480
ttcttatgac cctcagcgtc cagccatctg cttggatcga acatgcccgc gtctggcccc   3540
cacaacgctt ccgacatatt cactcccccc aagggtatac ggacgaccat acctttcttc   3600
aaaaacaagc tatcgatcgt cgctccagat gcaatacgta tgggatttgt caacggtatc   3660
acatcgtctt cggctgcctg ccaagataat agggggatgc gggaaggaat taaacaatga   3720
agacgaacca cacggattga ttgcatttcg ggggcatgga gtctcagtat ctcggctata   3780
aaagcatcga ggtatttcag atcctttgtt agctggtcgt atgtaggacg ttctcccttt   3840
gccaaacatt ctgagagctc agcacggagg ctctcttgga tttctggccg gcgtgcaagt   3900
tcaatgagag accactgagt gaaggctcag taatagaaca gcttgaacac tcgtaggcga   3960
agattaccgt taaggtgact atgagcagca cgggtcatag tttatgagat ctttgataaa   4020
caaggacaac cgttcgcaga acttacttgc tgttgtttca tatgcagcca tgaaaaggaa   4080
actcttcggt tatattaact tacagagaat atcagaggag tggcaaaggt acgtacggcc   4140
tacaaagtat gttgattagg catcaagccg atgtgcactt gggctacata cctgggccgt   4200
gatctcggag agtgacaaac ggctgttggg atttgcgttt tctgacttga ctatacaggg   4260
aagcgtaggc acgaagaaac atcacctcat atattggtga catacccaga atcccaagga   4320
ctgattcgtt gacagtatct tccggttcct tacatgcctt gttcaggctg ttagttgtaa   4380
gcctattcaa gtgtgctact gattgtgcga gcttctcttc tctgacgctc atgagggtaa   4440
ctttaaacag ggcatagagt atcggtgaca gaaagtgaat aagccttata aagggggaag   4500
gcttgactgt gtggatagag tcaaaggcgg ccatcatcaa ggacgtgcgg ccccttagag   4560
ttccaaagtc atgcgacaat atagctttcc ctatagtgtc caatctagga acatttcagg   4620
gcaagggcgg aatgaaggct gcgcaacgta cgtgacagaa ttcatccttg ggcacagaga   4680
acaaggttaa ctaacaatgg gggagataga tacagcaact tgccatttca cgacatcaat   4740
tatgacgggg ttgtttgagt gctctgatga cggagaacat gaatcccatg ctgctttgag   4800
ctgtcattta tgttggtcaa tcggccgatt gttttaagaa tggaaccatt ctaacctgat   4860
aggcagaatc caagcacacg ggagtgagat tgcgaattgc tgagaccgac agtggagaag   4920
acaggcctct ccgtagtctg cgatcatgtt aagtttatgc cctgatcgtt gagcgataaa   4980
gagtgaccga ccgcttgtga gtctcgccct cagaaataga tacaacatca ccatactgga   5040
acgtaaataa ggctggcagc taagaaaaat ggtgcaaaac agatactcgc caacttccgg   5100
ctcaaagcgg ttgtccctgc gagccgacaa tatgtggtgg tatccttgga atatatgtgt   5160
gtgagagcct tgggatcgct taatacaaca tggctggagc cgatgccagt gggtatctcg   5220
taaacgggcc catacattcg ttcccaatcc cgatatacca cactgaggtt cgccgaaggg   5280
aagatcttct tggtgttacc gaagatgaag ctctcgctgc gtggtccttg cagtctgggc   5340
gttctgatac ctcggcgtct tcgatagata gaaatgacga cgagcaacgt aaaggcagag   5400
gtcacaatcc tcatcgaatc gcctttgaaa tactctgcta catcaggcca gaggccgttg   5460
```

```
aagttgaggt tcaacatcac gaagtggacg agccgtggaa ggcgatcaag ttgcgcgaat   5520
gcgaggaaaa tgtttctgag gacccgaaac cgtaaccagg cgcgataaat gcttgaccta   5580
tctatctccg gggacggtgt tgggggtcca tcttaccgtg aaggtggata gggacagatc   5640
cgattccggg aaagaacaga cgaaacgttc gtatgatgca acacaagtgt gagcgcaaga   5700
tggagccgaa tgatcgggaa ctcggccgaa gggattctta aatacacacg cccgataatc   5760
attctcatac atgtccattt tgggacaaaa cacctatcta tcggtctgta ggactgccac   5820
ttaactgttt aatctgtgac caccaggaca gacaaagaga ggctgtgcta agtggtgttc   5880
gaaacgcgtt atgcccagtt cggcataaat cgccaacacg caggatacga tgaaaagtgt   5940
aagcttaagg tcaagactcc cttgatgtga ttcaacaact tttgacgggg ttgccattgt   6000
attgcaccgt cttgcccggc tgaatgtccg cagaaaccga acgcccctaa aaacaaagaa   6060
gttcacggat tccatatagt aagcgtggag cctgtgtgat aaagagtggg ggacagcatg   6120
aatgattcat gggaagaccg atcagacaaa cgcttatgga gattttgcgc caatttgtct   6180
tctcatctcc gtgtcaggac aagattctct tatctatcgt actttctgcg gttttccaat   6240
cttgcgaatt cgtgactgaa acagataaaa ggcgttggat gcggctcagc tgtcaatatt   6300
acttacctcc cattcgaact cgaacccaag acctctactc taaatcacaa tgtctgacat   6360
caatgccacc cgtcttcctg cttggcttgt agactgccca tgcgtcggtg acgacgtcaa   6420
ccgtctcctc actcgtggtg agaggtgagc tcaaaattcc atttaataat gtagcaatgt   6480
acttatgtgt cgtgtaccag cctttgctaa atgtctcatc cactagtcaa ggtatccgcc   6540
tctgatttct tgatgacaat gcatggtcat ggtacttact tcgatgtagt agtggacgac   6600
gcaagttgtt gacaatgtta ggcttggagc gttgagcctg catcggaagt aaggccttca   6660
agtttttctg tgataagcag cgagccaact tggattagac gactcacgtt atttctcatt   6720
ctttctcatt ctcatataaa acccacgtaa atgatccgag ctgtactatg gaatgcaata   6780
tacttgtgtg tgtatgtgtg tgtgttgtca gtaagagagc gtttagcaat ccgagcgcat   6840
gctgctgtcg ccagagcttg accgtcctga ctgtccttat cattgctact tgtcagcaac   6900
atatcacata tcacataggc agctgttgta ccattgaaaa gccgtggggc gtataacctg   6960
gaggaatttc aaagaagggt cttttatgat gagtttgata gctcgcatag ttgtggaagt   7020
cggcaagttc acaaaaacag tgaatttatg ttacattgcg tgacgaggag catgagacga   7080
gcaatttgca actttgaact acacccggga aaaagcaggc tcagcaaccc cgatgacgag   7140
ggggaggaga gaatggcgat gatgtaggca taatgcgatc gcatgtgtgt aggcgaacac   7200
gggcgacgat tggagagata gacacgctac gcgattacta cgccagtctc tcaagggccg   7260
ttcattaaag ttggctaaag tcgcggggga agggctggtg atgaggtatc ttgtgtcgac   7320
gcgggcacaa tggaccatgg gaggcagtcg ccgcatatct gaaaagctgg gctcccgacg   7380
tgaagtgagg aatcacgaaa atcatatttg cttggaagga aagcccatgc agctcagcaa   7440
actctagtaa gacaacggaa cgaaatcact ggcgatgttt gcgacatcag atctctggta   7500
tgaagtcagc ctgaaacctg ccctgtcaag gacatgcggc cgcaaccgcg actggttgat   7560
ggtaaatcca aatgcgacgc ccagttcgaa agatgagaca tacctgcgcc aaacagtgat   7620
taccacagcc acctacgagg cctcgtgagt tggcctcaat attcattagc tatcagtaga   7680
tgagcaccga agtagggctt ctgcgtgtag ttagggtgcg tgaatccgca gtgacgctca   7740
tttgtttggc tcagcgtggc cagtcgcgcc tcgggattta ccggcgcgat acaaacggaa   7800
agttctttcg cagcgttccc acccgcgcgg ccgtaagcgt gcaaaccgtc acccatagga   7860
```

aataaaccgt cggcaagaat agaatgtgat cccttcggcc gaatcgtcga aagcaatctg 7920
atcatagatc atcagtgacc tttcatcctt tttcagcgac agatcttgca ttcatgctgt 7980
ccgccactca tcatcttctt cttcacaata ttatactatt caccccacac tatccatatc 8040
cagttgggcc aatagtaaat cccgctgagg ctgtccgccc ttgatggaaa tgacttggag 8100
actcgccagt ttggcatcct tttttggtga ggaccccatt ttctatcttg agtcgtatcc 8160
atatctggat ggcctactgg tggtctcacc tctgtaacgg cccgcgatcg ctctcttcgc 8220
gatgttgaac ctcaatttca gcagcctttg gccttatgtc gcggagtacc tcaaagtcaa 8280
ttcgatgagg ataatagcct ctggcatatc cttgctcgtc gttgtttcca tttaccgaag 8340
ccgtcgaggt cctagaacgc cgagactgca aggaccacac atggagagct tcatcctcgg 8400
caatgctagg aagatcttcc cttcagccaa cctcagtttg gtgtatcaag gtttggagca 8460
gacttacggg cccgtctatg aaatagcctc tggctttggc tccaaccacg tcgtattgaa 8520
cgatcccaag gctctcacac acttattttc caaggacact gtcacatatt ctcagcctgc 8580
taggcagaaa gacatggggc ggaagttggt gagcgtttgt tccagcgttt tcccgagctg 8640
tcagacttaa cttgttccag tttggtgata ttttggtgct cacggaaggg gagacccaca 8700
agaggttggt cgctcttgac tgcttgaaaa catggcataa atttaatatt gaacggatta 8760
tagaatacgg agggtcttgt cttctcccct gtcggtctcg gcaatccgca atttcactcc 8820
tatgtgtttg gattccgcct atcaggtcag gacggttcca gctttgagag tcagtcgatt 8880
gaacagcaca aatgatagct caaagcatca tgggattcat gtttccagtt gtcaaacaat 8940
tcgaaccgtg ctatcgtgct tgatgcagag aaatggtgag ttgctttcct tctagccttc 9000
atttaattgg ttcattatgt gcccaaggat gaactgttac acgtatgact cgcaaccttt 9060
actctgcccc attcttctca cctgcaatat attcctagca tggataatat tggaaaagct 9120
gtattgtcgt atgacttcgg caacatgagg ggccatacgt gttcgatctt agctgacttg 9180
gatgctttcc acgcagtcag cccttcaggc ctttacataa ggtttattgt gtttacccgc 9240
gagatacttt ataacctctt caagattacc ttaccgaatg ccaaagaaaa gcagtttgag 9300
gaactggcag cgcactttaa agtactcgcg actggctttc tgcgggaagc acgtgaggcg 9360
cctgaagata gcgccgttca ccaatcaatc cttggggtta tgcgtatgtt acctctatcc 9420
tgaccacgtg taaggagatt tcagctttcc tatatatagt caagtccaaa aatgaaaatg 9480
ctaacgtccg tttatcactt cccgagatca cggcccaggt aagttgcttc acacatcggc 9540
gtcggtgctc gatcaacatc ctttgtaggc tgtatgtccc tatgcaatct cttttgtatc 9600
cactctgacc tgatataacc gaagggtggt cttgtcttgg ccgggtatga aactacggca 9660
agtaagttct atgactagca gtccgatgat ctcataatcc actaactatg ctgttcacag 9720
ttgccatgac ggtaatgtta tttatctaca agagatccat cgccgagctt tccctcagtg 9780
gtccctcatt gagcttgctc gccgggcaga aattcaagag actctccgtg ccgaactcaa 9840
ggagtgcttg gcagacggag aacgccctac atacgaccag ctgacaaagg atctgaaata 9900
cctcgatgct tttatatccg agatactgag gttacatccc tcagaaatgg tactaacccg 9960
cgtggttcgt cccttccttt catccctatc tttttatgat gacgatcttt tcgactaggc 10020
agccgaagac gatgtgatac cgctgacgga tcccatacga actgcatctg gagcgatgat 10080
cgacagcttg ttcgtgagga aaggcaccgt ctccgcatcc ctttaggagg aatgaatata 10140
tcagagacgt tgtggggacc ggatgcggcg acattcgatc caagcaggtg gctggaagtt 10200
gatggtcata agaaaggaag aagggagaaa gtacccggct accgaaatct attgactttc 10260
ggtgctggcc aaaggctgtg tccgggaaga gacctcgcct tgctggagat gaaggtatgg 10320
cgaaactcct gccggttttt attcattttt gacttgacaa ttgccaggct gcgcttgtga 10380
ttctggtcct ccatttcagt tttgagttcc ccaatggacc atcgacggaa ctgagttggc 10440
agttcgggcg gcccaaggta gccggcgagg atggtccgaa agtgcctatg ctgtgcgaga 10500
ctgacatagg atctcatgtg caacatcgtt cgtttcgtgt cttagtagag tttactgagt 10560
cgcatgggct ttccttccaa gcaaaaatga ctttcatgat tcctcacttc acgtggagga 10620
ccagcttttc agatgtgtgg cgatgaggct tagcatcgtg acgtaaatgg taggttggat 10680
gactggcata cccacatatt tcacatcatc cttatagacc tactagtacg ccaaacttgc 10740
ctcccatagt ccatcgtgcc acgcaccgac acaagatgca tcatcaccag cccactctaa 10800
ccaactttga tgaacgatca ttacagcctg agagggctgg cgtagtaatc acgtagcgtg 10860
tctatctctc ctcgagcacg cctgcagcct gcagtgtttt cccgccccaa gcgacccttc 10920
cgcctcttcc caatcgtcgc cagcacatgc catcgcatgc ctatacatac atcatcacca 10980
tgattcttcc tcatcggcgt tgcatctttc tctcaggtgc tcggcccagt tcaaggttgc 11040
aaaatgctcg tctcatgctc tcattacctc ctcgtcacgc aatgtaacat aaaatcgctg 11100
tttttgtgga cttgccgctt ttacaactat gcgagctgtc aaactcatca ggaaggaccc 11160
ctgctggaaa ttcttccagg ctacacgccg caggactctt aaacggtaca aaagctgcca 11220
atgttgtatg tgatatgttc aagtaggcaa gtagcaatga cacggtcggt caggtcggtc 11280
tgctgtggat cgcggcatac aagctggcat tgataaatgt tgagatgcta tctctcacac 11340
ctcccccccc ttctctagtg cattgcattg cacagctcag agcatcattg aggggggtat 11400
tagagattga caaaggagaa tcagtaagaa gggtaatgta cttcagtcgt gttagccaag 11460
tgtccccgat gattatcacg acaatcttta agacgctggt tcagcggcac gatcatcgct 11520
ttgcaagcaa gacgtgttct acaatttgcc ttcgtcatag tcagcacaat cacccttcgt 11580
tatcatgaaa tccgaggcgg gtaccttgac tagtggatga gacatttagc aaaggctgat 11640
acacgacaca tgagtccatt gctacattat taaatggaat tttgagctca cctctcgcca 11700
cgagtgagga gacggttgac atcgtcaccg acgcatgggc aatctacaag ccaagcggga 11760
agacgggtgg cattgatgtc agacattgtg atttagagca gaggtcttgg gctcgagttc 11820
gaatgggagg taagtattga atattgaatg ctaagctgaa tccaacgcct tttatctgtc 11880
tcagtcacga attcgcatgg ttgcaaaaac cgcggaaagg acgatagata agagaatctt 11940
gtcctgacac ggagatgaag acgagttggc gcaaaatctc cataaacagt tgtctgatca 12000
tccttttttcg gtattcaata ttcatccccc attcatgctg tcagtcactg ttcatcacac 12060
attcttggca ggctccacaa aacttctttg ttctttcctg tttttgggac gttctgtctt 12120
tgcgggcaca gccagtcggg caagacggtg caatacaatg gcaacccccc gtcaagaata 12180
gttgaatcgc atcaagggag tcttgaccct acacttttttc gtcgtatcct gatcggcgac 12240
tgggcctaac gcgtttctcg ctggattaaa caccccactg agcacagcct ttctctgtcc 12300
cggtggtcac agattgaaca gtcaagcagt ttgtaggatc aatagatagg ggttttgtcc 12360
tgaaatggac catgtagtaa tgattttcgt ccgtgtgacc cggtttgccg atgcaacaaa 12420
gacgcattat ctccatcgcg cacaggcgtg ttgcatcact tatgactatg tggctctaac 12480
tttcctggaa tcgaatccgc ccctatccac cttcacggta acatggaccc ccaacaccgt 12540
tcccggagat agataggtca agttctcgcg cctggttacg gtttcggctc ctcagaaacg 12600

```
ttttcctcgt attcgcgcaa ctcccaccct tcaatggcat ttccacgtct ggttgggttg  12660

gttgctatac tagtacttat ccgcgatggc cttccttcct tgcataacgg ctcgtccact  12720

ccgtcacccg tgatgttgaa cctcaactcc aacggcctct ggcctgatgt ggcagagtat  12780

ctcaaaggta attcgataag gattgtgacc tctgacattg ctcgtcgtca tttctatcta  12840

tcggagatgc cgaggtatca gaacgcccag actacaagga ccacgcagcg agagcttcag  12900

attcagtaac accaagatct tcccttccgc gaacctcagt acggtggtat atcgggattg  12960

ggaacgaatg tatgggcctt acgagatacc cactggcatc ggctacagcc atgttgtatt  13020

gagcgatccc aaggctcaca cacatatatt ccgaggatac caccacatat cctcggctcg  13080

cagggacaac cgctttgagc caggttggcg agtctttgtt ttgcaccatt tttcagctgc  13140

cagcctcatt gtcgttccag tatggtgatg ttatatctat ttctgagcgc gagactcaca  13200

aggggttggt cgctctttat cgctcaacga ttagggcata aacttaacat gatc        13254
```

```
<210> SEQ ID NO 328

<400> SEQUENCE: 328

000


<210> SEQ ID NO 329

<400> SEQUENCE: 329

000


<210> SEQ ID NO 330
<211> LENGTH: 10
<212> TYPE: PRT
<213> ORGANISM: Amanita bisporigera

<400> SEQUENCE: 330

Asn Cys Phe Asp Asp Phe Ile Ala Ala Thr
1               5                   10


<210> SEQ ID NO 331
<211> LENGTH: 22
<212> TYPE: PRT
<213> ORGANISM: Amanita bisporigera

<400> SEQUENCE: 331

Arg Ile Lys Glu Ser Ala Asp Lys Trp Gly Phe Val Ala Gln Ser Leu
1               5                   10                  15

Gly Leu Val Trp Lys Asp
            20


<210> SEQ ID NO 332
<211> LENGTH: 20
<212> TYPE: PRT
<213> ORGANISM: Amanita bisporigera

<400> SEQUENCE: 332

Ile Tyr Arg Thr Thr Lys Leu Asn Gly Leu Asn Thr Glu Asp Phe Lys
1               5                   10                  15

Ala Ser Gln Val
            20


<210> SEQ ID NO 333
```

<400> SEQUENCE: 333

000

<210> SEQ ID NO 334
<211> LENGTH: 26
<212> TYPE: PRT
<213> ORGANISM: Amanita bisporigera

<400> SEQUENCE: 334

Arg Tyr Pro Asp Thr Ser Thr Ala Thr Gln Glu Asn Gly Pro Ile Ala
1 5 10 15

Thr Glu Gly Asp Leu Asp Ala Met Val Tyr
20 25

<210> SEQ ID NO 335
<211> LENGTH: 12
<212> TYPE: PRT
<213> ORGANISM: Amanita bisporigera

<400> SEQUENCE: 335

Val Lys Asp Ala Ala Asp Lys Trp Gly Phe Ile Ala
1 5 10

<210> SEQ ID NO 336
<211> LENGTH: 13
<212> TYPE: PRT
<213> ORGANISM: Amanita bisporigera

<400> SEQUENCE: 336

Met Met Cys Tyr His Lys Val Gly Thr Thr Gln Gly Glu
1 5 10

<210> SEQ ID NO 337
<211> LENGTH: 13
<212> TYPE: PRT
<213> ORGANISM: Amanita bisporigera

<400> SEQUENCE: 337

Val Leu Tyr Arg Ser Lys Glu Pro Ala Leu Pro Asp Phe
1 5 10

<210> SEQ ID NO 338
<211> LENGTH: 15
<212> TYPE: PRT
<213> ORGANISM: Amanita bisporigera

<400> SEQUENCE: 338

Lys Met Ala Thr Lys Ile Pro Met Phe Ile Val Arg His Lys Ser
1 5 10 15

<210> SEQ ID NO 339
<211> LENGTH: 11
<212> TYPE: PRT
<213> ORGANISM: Amanita bisporigera

<400> SEQUENCE: 339

Lys Asp Ala Ala Asp Lys Trp Gly Phe Ile Ala
1 5 10

<210> SEQ ID NO 340

<400> SEQUENCE: 340

000

<210> SEQ ID NO 341

<400> SEQUENCE: 341

000

<210> SEQ ID NO 342

<400> SEQUENCE: 342

000

<210> SEQ ID NO 343
<211> LENGTH: 9
<212> TYPE: PRT
<213> ORGANISM: Amanita bisporigera

<400> SEQUENCE: 343

Asn Cys Phe Asp Asp Phe Ile Ala Ala
1               5

<210> SEQ ID NO 344
<211> LENGTH: 19
<212> TYPE: PRT
<213> ORGANISM: Amanita bisporigera

<400> SEQUENCE: 344

Lys Glu Ser Ala Asp Lys Trp Gly Phe Val Ala Gln Ser Leu Gly Leu
1               5                   10                  15

Val Trp Lys

<210> SEQ ID NO 345

<400> SEQUENCE: 345

000

<210> SEQ ID NO 346
<211> LENGTH: 19
<212> TYPE: PRT
<213> ORGANISM: Amanita bisporigera

<400> SEQUENCE: 346

Ser Ser Gly Gln Ala Trp Ile Ser Glu Tyr Gly Asn Pro Ser Ile Pro
1               5                   10                  15

Glu Glu Phe

<210> SEQ ID NO 347

<400> SEQUENCE: 347

000

<210> SEQ ID NO 348
<211> LENGTH: 750
<212> TYPE: PRT
<213> ORGANISM: Amanita bisporigera

<400> SEQUENCE: 348

Met Arg Thr Pro Trp Thr Pro Asn Arg Tyr Pro Pro Ala Arg Arg Ser
1               5                   10                  15

Asp His Tyr Asp Glu Tyr Lys Ser Glu Lys Asn Gly Val Val Arg Val
            20                  25                  30

-continued

```
His Asp Pro Tyr Asn Trp Leu Glu His Asn Thr Gln Glu Thr Glu Ser
        35                  40                  45

Trp Thr Ser Ala Gln Val Ala Phe Thr Lys Glu Tyr Leu Asp Gln Asn
    50                  55                  60

Pro Asp Arg Gln Lys Leu Glu Asp Glu Ile Arg Arg Asn Thr Asp Tyr
65                  70                  75                  80

Ala Lys Phe Ser Ala Pro Ser Leu Lys Asp Asp Gly Arg Trp Tyr Trp
                85                  90                  95

Tyr Tyr Asn Ser Gly Leu Gln Pro Gln Ser Gly Val His Ala Phe Val
            100                 105                 110

Leu Leu Leu Cys His Ser Asp Ile Asp Val Pro Thr Ser Val Ile Tyr
        115                 120                 125

Arg Ser Arg Asp Arg Asn Leu Pro Thr Met Ser Asn Glu Glu Gly Pro
    130                 135                 140

Gly Gly Glu Val Phe Phe Asp Pro Asn Leu Leu Ser Asn Asp Gly Thr
145                 150                 155                 160

Ala Ala Leu Ala Ala Thr Ala Phe Ser Arg Asp Gly Lys Tyr Phe Ala
                165                 170                 175

Tyr Gly Ile Ser Arg Ser Gly Ser Asp Phe Tyr Thr Val Tyr Val Arg
            180                 185                 190

Pro Thr Ser Ala Pro Leu Ala Ser Gln Gly Glu Ser Arg Val Ser His
        195                 200                 205

Asp Asp Glu Arg Leu Gln Asp Glu Val Arg Phe Val Lys Phe Ser Ser
    210                 215                 220

Ile Ser Trp Ser His Asp Ser Lys Gly Phe Phe Tyr Gln Arg Tyr Pro
225                 230                 235                 240

Glu Arg Lys Ser His Gly Ser Ala Asp Glu Asp Lys Ala Gly Thr Glu
                245                 250                 255

Thr Glu Ser Asp Lys His Ala Met Leu Tyr Tyr His Arg Val Gly Thr
            260                 265                 270

Ser Gln Leu Glu Asp Val Leu Val Tyr Lys Asp Asp Ala Asn Pro Glu
        275                 280                 285

Trp Phe Trp Gly Ala Glu Ile Ser Glu Glu Asp Gly Arg Tyr Leu Ile
    290                 295                 300

Leu Ser Val Ser Arg Asp Thr Ser Arg Lys Asn Leu Leu Trp Ile Ala
305                 310                 315                 320

Asp Leu Glu Ser Asn Ala Ile Gly Gln Asp Met Gln Trp Asn Lys Leu
                325                 330                 335

Ile Asp Glu Phe Asp Ala Ser Tyr Asp Tyr Ile Ala Asn Asn Gly Asn
            340                 345                 350

Lys Phe Tyr Phe Gln Thr Asn Lys Asp Ala Pro Gln Tyr Lys Leu Val
        355                 360                 365

Ser Val Asp Ile Ser Ala Pro Pro Ala Gln Arg Thr Phe Glu Asp Val
    370                 375                 380

Ile Pro Glu Asp Lys Asn Ala His Leu Glu Asp Val Leu Ala Ile Ala
385                 390                 395                 400

Asp Asp Lys Phe Ala Val Val Tyr Lys Arg Asn Val Lys Asp Glu Ile
                405                 410                 415

Tyr Ile Tyr Asp Met Asn Gly Lys Gln Leu Glu Arg Val Ala Pro Asp
            420                 425                 430

Phe Val Gly Ala Ala Ser Ile Ala Gly Arg Arg Ser Gln Pro Trp Phe
        435                 440                 445
```

Phe Ala Thr Leu Thr Gly Phe Thr Asn Pro Gly Ile Val Ser Arg Tyr
450 455 460

Asp Phe Thr Gln Gln Asp Pro Ala Lys Arg Trp Ser Thr Tyr Arg Thr
465 470 475 480

Thr Leu Leu Lys Gly Leu Lys Ala Glu Asp Phe Glu Ala Gln Gln Val
485 490 495

Trp Tyr His Ser Lys Asp Gly Thr Lys Ile Pro Met Phe Ile Val Arg
500 505 510

His Arg Asn Thr Lys Phe Asp Gly Thr Ala Pro Ala Ile Gln Tyr Gly
515 520 525

Tyr Gly Gly Phe Thr Ile Ser Ile Asn Pro Phe Phe Ser Ala Ser Phe
530 535 540

Leu Thr Phe Leu Gln Arg Tyr Gly Ala Val Leu Ala Val Pro Asn Ile
545 550 555 560

Arg Gly Gly Gly Glu Phe Gly Glu Glu Trp His Leu Ala Gly Thr Arg
565 570 575

Glu Arg Lys Val Asn Cys Phe Asp Asp Phe Ile Ala Ala Thr Gln Phe
580 585 590

Leu Ile Asp Asn Lys Tyr Ala Ala Pro Gly Cys Gly Asn Ser Asp Tyr
595 600 605

Ala Pro Asp Ser Arg Val Thr Thr Gly Leu Leu Val Ala Ala Cys Val
610 615 620

Asn Arg Ala Pro Glu Gly Leu Leu Gly Ala Ala Val Ala Glu Val Gly
625 630 635 640

Val Leu Asp Leu Leu Lys Phe Ala Asp Phe Thr Ile Gly Arg Ala Trp
645 650 655

Thr Ser Asp Tyr Gly Asn Pro His Asp Pro His Asp Phe Asp Phe Ile
660 665 670

Tyr Pro Ile Ser Pro Leu His Asn Val Pro Lys Asp Lys Asp Leu Pro
675 680 685

Pro Thr Ile Leu Leu Thr Ala Asp Pro Ser Ile Asp Asp Asp Arg Val
690 695 700

Val Pro Leu His Ser Tyr Lys His Ala Ala Thr Leu Gln Tyr Thr Leu
705 710 715 720

Ser His Asn Thr His Pro Leu Leu Ile Arg Ile Asp Lys Lys Ala Gly
725 730 735

His Gly Ala Gly Lys Ser Thr Asp Gln Arg His Ala Ile Leu
740 745 750

<210> SEQ ID NO 349
<211> LENGTH: 2151
<212> TYPE: PRT
<213> ORGANISM: Amanita bisporigera

<400> SEQUENCE: 349

Met Ser Ser Ala Arg Thr Ala Trp Asp Pro Lys Ser Thr Pro Tyr Pro
1 5 10 15

Ser Val His Arg Ser Asp Thr Val Glu Glu Phe Lys Ser Ala Lys His
20 25 30

Gly Thr Val Lys Val Ala Asp Pro Tyr Asp Trp Leu Ala Phe Pro Asp
35 40 45

Ser Lys Glu Thr Gln His Phe Val Gln Gln Gln Gly Asp Phe Thr Lys
50 55 60

Lys Tyr Leu Asp Gln Tyr Gln Asp Lys Glu Lys Phe Ser Lys Glu Leu
65 70 75 80

-continued

```
Glu Lys Asn Trp Asn Tyr Ala Arg Phe Ser Cys Pro Ser Leu Lys Gly
                85                  90                  95

Asp Gly Tyr Tyr Tyr Phe Thr Tyr Asn Ser Gly Leu Ala Ala Pro Asn
            100                 105                 110

Leu Leu Ser Thr Asp Gly Ser Val Ser Arg Ser Thr Ser Ser Phe Ser
        115                 120                 125

Glu Asp Gly Lys Tyr Tyr Ala Tyr Ala Leu Ser Arg Ser Gly Ser Asp
    130                 135                 140

Trp Asn Thr Ile Tyr Val Arg Glu Thr Ser Ser Pro His Leu Ser Thr
145                 150                 155                 160

Gln Ala Val Gly Ser Asp Glu Gly Arg Leu Pro Asn Asp Val Leu Arg
                165                 170                 175

Phe Val Lys Phe Ser Gly Ile Gly Trp Thr Ala Asp Ser Lys Gly Phe
            180                 185                 190

Phe Tyr Gln Arg Phe Pro Glu Arg Lys Glu His Gly Gly Glu Glu Asp
        195                 200                 205

Asp Lys Ala Gly Thr Glu Thr Asp Lys Asp Leu Asn Ala Ser Leu Tyr
    210                 215                 220

Tyr His Arg Val Gly Thr Pro Gln Ser Glu Asp Val Leu Ile His Gln
225                 230                 235                 240

Asp Lys Glu His Pro Glu Trp Met Phe Gly Ala Gly Ala Thr Glu Asp
                245                 250                 255

Gly Arg Tyr Leu Val Met Thr Ser Ser Arg Asp Thr Ala Arg Ser Asn
            260                 265                 270

Leu Leu Trp Ile Ala Asp Leu Gln Asp Pro Gln Asn Ser Glu Ile Gly
        275                 280                 285

Pro Asn Leu Lys Trp Asn Lys Leu Ile Asn Glu Trp Gly Thr Tyr Trp
    290                 295                 300

Ser Glu Leu Thr Asn Asp Gly Ser Lys Phe Tyr Phe Tyr Thr Asn Ala
305                 310                 315                 320

Glu Asp Ser Pro Asn Tyr Lys Ile Val Thr Phe Asp Leu Glu Lys Pro
                325                 330                 335

Glu Gln Gly Phe Lys Asp Leu Ile Ala His Asn Pro Lys Ser Pro Leu
            340                 345                 350

Thr Ser Ala His Leu Ala Ala Asn Asp Gln Leu Ile Leu Leu Tyr Ser
        355                 360                 365

Asn Asp Val Lys Asp Glu Leu Tyr Leu His Ser Leu Glu Thr Gly Glu
    370                 375                 380

Arg Val Lys Arg Leu Ala Ser Asp Leu Ile Gly Thr Val Glu Gln Phe
385                 390                 395                 400

Ser Gly Arg Arg Glu His Lys Glu Met Trp Phe Ser Met Ser Gly Phe
                405                 410                 415

Thr Ser Pro Gly Thr Val Tyr Arg Tyr Glu Phe Glu Gly Glu Asn Ala
            420                 425                 430

Gly Val Glu Gln Glu Tyr Arg Lys Ala Thr Val Glu Gly Ile Lys Ala
        435                 440                 445

Glu Asp Phe Glu Ser Ser Gln Val Phe Tyr Glu Ser Lys Asp Gly Thr
    450                 455                 460

Lys Val Pro Met Phe Ile Thr Arg Pro Lys Gly Val Glu Lys Gly Pro
465                 470                 475                 480

Val Leu Leu Tyr Ala Tyr Gly Gly Phe Ser His Ala Ile Thr Pro Phe
                485                 490                 495
```

```
Phe Ser Pro Ser Leu Met Thr Trp Ile Lys His Tyr Lys Ala Ala Leu
            500                 505                 510

Cys Ile Ala Asn Ile Arg Gly Gly Asp Glu Tyr Gly Glu Lys Trp His
        515                 520                 525

Glu Ala Gly Thr Lys Glu Arg Lys Gln Asn Cys Phe Asp Asp Phe Gln
    530                 535                 540

Trp Ala Ala Lys Tyr Leu Tyr Lys Glu Gly Ile Ala Glu Glu Gly Lys
545                 550                 555                 560

Ile Ala Ile Ser Gly Gly Ser Asn Gly Gly Leu Leu Val Gly Ala Cys
                565                 570                 575

Val Asn Gln Ala Pro Glu Leu Tyr Gly Ala Ala Ile Ala Asp Val Gly
            580                 585                 590

Val Leu Asp Met Leu Arg Phe His Arg Tyr Thr Ile Gly Arg Ala Trp
        595                 600                 605

Ser Ser Asp Tyr Gly Cys Ser Asp Glu Pro Glu Gly Phe Asp Tyr Leu
    610                 615                 620

Tyr Ala Tyr Ser Pro Leu Gln Asn Val Asp Pro Ser Lys Lys Pro Phe
625                 630                 635                 640

Pro Pro Thr Met Leu Leu Thr Ala Asp His Asp Asp Arg Val Val Pro
                645                 650                 655

Leu His Ser Phe Lys His Ile Ser Glu Leu Gln His Lys Leu Pro Asp
            660                 665                 670

Asn Pro His Pro Leu Leu Leu Arg Val Asp Thr Lys Ser Gly His Gly
        675                 680                 685

Ala Gly Lys Ser Thr Ala Lys Lys Ile Glu Glu Ala Cys Glu Lys Tyr
    690                 695                 700

Gly Phe Val Ser Gln Ser Met Gly Leu Arg Trp His Asp Met Ser Ser
705                 710                 715                 720

Ala Arg Thr Ala Trp Asp Pro Lys Ser Thr Pro Tyr Pro Ser Val His
                725                 730                 735

Arg Ser Asp Thr Val Glu Glu Phe Lys Ser Ala Lys His Gly Thr Val
            740                 745                 750

Lys Val Ala Asp Pro Tyr Asp Trp Leu Ala Phe Pro Asp Ser Lys Glu
        755                 760                 765

Thr Gln His Phe Val Gln Gln Gln Gly Asp Phe Thr Lys Lys Tyr Leu
    770                 775                 780

Asp Gln Tyr Gln Asp Lys Glu Lys Phe Ser Lys Glu Leu Glu Lys Asn
785                 790                 795                 800

Trp Asn Tyr Ala Arg Phe Ser Cys Pro Ser Leu Lys Gly Asp Gly Tyr
                805                 810                 815

Tyr Tyr Phe Thr Tyr Asn Ser Gly Leu Ala Ala Pro Asn Leu Leu Ser
            820                 825                 830

Thr Asp Gly Ser Val Ser Arg Ser Thr Ser Ser Phe Ser Glu Asp Gly
        835                 840                 845

Lys Tyr Tyr Ala Tyr Ala Leu Ser Arg Ser Gly Ser Asp Trp Asn Thr
    850                 855                 860

Ile Tyr Val Arg Glu Thr Ser Ser Pro His Leu Ser Thr Gln Ala Val
865                 870                 875                 880

Gly Ser Asp Glu Gly Arg Leu Pro Asn Asp Val Leu Arg Phe Val Lys
                885                 890                 895

Phe Ser Gly Ile Gly Trp Thr Ala Asp Ser Lys Gly Phe Phe Tyr Gln
            900                 905                 910

Arg Phe Pro Glu Arg Lys Glu His Gly Gly Glu Glu Asp Asp Lys Ala
```

```
        915                 920                 925

Gly Thr Glu Thr Asp Lys Asp Leu Asn Ala Ser Leu Tyr Tyr His Arg
    930                 935                 940

Val Gly Thr Pro Gln Ser Glu Asp Val Leu Ile His Gln Asp Lys Glu
945                 950                 955                 960

His Pro Glu Trp Met Phe Gly Ala Gly Ala Thr Glu Asp Gly Arg Tyr
                965                 970                 975

Leu Val Met Thr Ser Ser Arg Asp Thr Ala Arg Ser Asn Leu Leu Trp
            980                 985                 990

Ile Ala Asp Leu Gln Asp Pro Gln  Asn Ser Glu Ile Gly  Pro Asn Leu
        995                 1000                1005

Lys Trp  Asn Lys Leu Ile Asn  Glu Trp Gly Thr Tyr  Trp Ser Glu
    1010                 1015                 1020

Leu Thr  Asn Asp Gly Ser Lys  Phe Tyr Phe Tyr Thr  Asn Ala Glu
    1025                 1030                 1035

Asp Ser  Pro Asn Tyr Lys Ile  Val Thr Phe Asp Leu  Glu Lys Pro
    1040                 1045                 1050

Glu Gln  Gly Phe Lys Asp Leu  Ile Ala His Asn Pro  Lys Ser Pro
    1055                 1060                 1065

Leu Thr  Ser Ala His Leu Ala  Ala Asn Asp Gln Leu  Ile Leu Leu
    1070                 1075                 1080

Tyr Ser  Asn Asp Val Lys Asp  Glu Leu Tyr Leu His  Ser Leu Glu
    1085                 1090                 1095

Thr Gly  Glu Arg Val Lys Arg  Leu Ala Ser Asp Leu  Ile Gly Thr
    1100                 1105                 1110

Val Glu  Gln Phe Ser Gly Arg  Arg Glu His Lys Glu  Met Trp Phe
    1115                 1120                 1125

Ser Met  Ser Gly Phe Thr Ser  Pro Gly Thr Val Tyr  Arg Tyr Glu
    1130                 1135                 1140

Phe Glu  Gly Glu Asn Ala Gly  Val Glu Gln Glu Tyr  Arg Lys Ala
    1145                 1150                 1155

Thr Val  Glu Gly Ile Lys Ala  Glu Asp Phe Glu Ser  Ser Gln Val
    1160                 1165                 1170

Phe Tyr  Glu Ser Lys Asp Gly  Thr Lys Val Pro Met  Phe Ile Thr
    1175                 1180                 1185

Arg Pro  Lys Gly Val Glu Lys  Gly Pro Val Leu Leu  Tyr Ala Tyr
    1190                 1195                 1200

Gly Gly  Phe Ser His Ala Ile  Thr Pro Phe Phe Ser  Pro Ser Leu
    1205                 1210                 1215

Met Thr  Trp Ile Lys His Tyr  Lys Ala Ala Leu Cys  Ile Ala Asn
    1220                 1225                 1230

Ile Arg  Gly Gly Asp Glu Tyr  Gly Glu Lys Trp His  Glu Ala Gly
    1235                 1240                 1245

Thr Lys  Glu Arg Lys Gln Asn  Cys Phe Asp Asp Phe  Gln Trp Ala
    1250                 1255                 1260

Ala Lys  Tyr Leu Tyr Lys Glu  Gly Ile Ala Glu Glu  Gly Lys Ile
    1265                 1270                 1275

Ala Ile  Ser Gly Gly Ser Asn  Gly Gly Leu Leu Val  Gly Ala Cys
    1280                 1285                 1290

Val Asn  Gln Ala Pro Glu Leu  Tyr Gly Ala Ala Ile  Ala Asp Val
    1295                 1300                 1305

Gly Val  Leu Asp Met Leu Arg  Phe His Arg Tyr Thr  Ile Gly Arg
    1310                 1315                 1320
```

```
Ala Trp  Ser Ser Asp Tyr Gly  Cys Ser Asp Glu Pro  Glu Gly Phe
    1325                 1330                 1335

Asp Tyr  Leu Tyr Ala Tyr Ser  Pro Leu Gln Asn Val  Asp Pro Ser
    1340                 1345                 1350

Lys Lys  Pro Phe Pro Pro Thr  Met Leu Leu Thr Ala  Asp His Asp
    1355                 1360                 1365

Asp Arg  Val Val Pro Leu His  Ser Phe Lys His Ile  Ser Glu Leu
    1370                 1375                 1380

Gln His  Lys Leu Pro Asp Asn  Pro His Pro Leu Leu  Leu Arg Val
    1385                 1390                 1395

Asp Thr  Lys Ser Gly His Gly  Ala Gly Lys Ser Thr  Ala Lys Lys
    1400                 1405                 1410

Ile Glu  Glu Ala Cys Glu Lys  Tyr Gly Phe Val Ser  Gln Ser Met
    1415                 1420                 1425

Gly Leu  Arg Trp His Asp Met  Ser Ser Ala Arg Thr  Ala Trp Asp
    1430                 1435                 1440

Pro Lys  Ser Thr Pro Tyr Pro  Ser Val His Arg Ser  Asp Thr Val
    1445                 1450                 1455

Glu Glu  Phe Lys Ser Ala Lys  His Gly Thr Val Lys  Val Ala Asp
    1460                 1465                 1470

Pro Tyr  Asp Trp Leu Ala Phe  Pro Asp Ser Lys Glu  Thr Gln His
    1475                 1480                 1485

Phe Val  Gln Gln Gln Gly Asp  Phe Thr Lys Lys Tyr  Leu Asp Gln
    1490                 1495                 1500

Tyr Gln  Asp Lys Glu Lys Phe  Ser Lys Glu Leu Glu  Lys Asn Trp
    1505                 1510                 1515

Asn Tyr  Ala Arg Phe Ser Cys  Pro Ser Leu Lys Gly  Asp Gly Tyr
    1520                 1525                 1530

Tyr Tyr  Phe Thr Tyr Asn Ser  Gly Leu Ala Ala Pro  Asn Leu Leu
    1535                 1540                 1545

Ser Thr  Asp Gly Ser Val Ser  Arg Ser Thr Ser Ser  Phe Ser Glu
    1550                 1555                 1560

Asp Gly  Lys Tyr Tyr Ala Tyr  Ala Leu Ser Arg Ser  Gly Ser Asp
    1565                 1570                 1575

Trp Asn  Thr Ile Tyr Val Arg  Glu Thr Ser Ser Pro  His Leu Ser
    1580                 1585                 1590

Thr Gln  Ala Val Gly Ser Asp  Glu Gly Arg Leu Pro  Asn Asp Val
    1595                 1600                 1605

Leu Arg  Phe Val Lys Phe Ser  Gly Ile Gly Trp Thr  Ala Asp Ser
    1610                 1615                 1620

Lys Gly  Phe Phe Tyr Gln Arg  Phe Pro Glu Arg Lys  Glu His Gly
    1625                 1630                 1635

Gly Glu  Glu Asp Asp Lys Ala  Gly Thr Glu Thr Asp  Lys Asp Leu
    1640                 1645                 1650

Asn Ala  Ser Leu Tyr Tyr His  Arg Val Gly Thr Pro  Gln Ser Glu
    1655                 1660                 1665

Asp Val  Leu Ile His Gln Asp  Lys Glu His Pro Glu  Trp Met Phe
    1670                 1675                 1680

Gly Ala  Gly Ala Thr Glu Asp  Gly Arg Tyr Leu Val  Met Thr Ser
    1685                 1690                 1695

Ser Arg  Asp Thr Ala Arg Ser  Asn Leu Leu Trp Ile  Ala Asp Leu
    1700                 1705                 1710
```

Gln Asp Pro Gln Asn Ser Glu Ile Gly Pro Asn Leu Lys Trp Asn
1715 1720 1725

Lys Leu Ile Asn Glu Trp Gly Thr Tyr Trp Ser Glu Leu Thr Asn
1730 1735 1740

Asp Gly Ser Lys Phe Tyr Phe Tyr Thr Asn Ala Glu Asp Ser Pro
1745 1750 1755

Asn Tyr Lys Ile Val Thr Phe Asp Leu Glu Lys Pro Glu Gln Gly
1760 1765 1770

Phe Lys Asp Leu Ile Ala His Asn Pro Lys Ser Pro Leu Thr Ser
1775 1780 1785

Ala His Leu Ala Ala Asn Asp Gln Leu Ile Leu Leu Tyr Ser Asn
1790 1795 1800

Asp Val Lys Asp Glu Leu Tyr Leu His Ser Leu Glu Thr Gly Glu
1805 1810 1815

Arg Val Lys Arg Leu Ala Ser Asp Leu Ile Gly Thr Val Glu Gln
1820 1825 1830

Phe Ser Gly Arg Arg Glu His Lys Glu Met Trp Phe Ser Met Ser
1835 1840 1845

Gly Phe Thr Ser Pro Gly Thr Val Tyr Arg Tyr Glu Phe Glu Gly
1850 1855 1860

Glu Asn Ala Gly Val Glu Gln Glu Tyr Arg Lys Ala Thr Val Glu
1865 1870 1875

Gly Ile Lys Ala Glu Asp Phe Glu Ser Ser Gln Val Phe Tyr Glu
1880 1885 1890

Ser Lys Asp Gly Thr Lys Val Pro Met Phe Ile Thr Arg Pro Lys
1895 1900 1905

Gly Val Glu Lys Gly Pro Val Leu Leu Tyr Ala Tyr Gly Gly Phe
1910 1915 1920

Ser His Ala Ile Thr Pro Phe Phe Ser Pro Ser Leu Met Thr Trp
1925 1930 1935

Ile Lys His Tyr Lys Ala Ala Leu Cys Ile Ala Asn Ile Arg Gly
1940 1945 1950

Gly Asp Glu Tyr Gly Glu Lys Trp His Glu Ala Gly Thr Lys Glu
1955 1960 1965

Arg Lys Gln Asn Cys Phe Asp Asp Phe Gln Trp Ala Ala Lys Tyr
1970 1975 1980

Leu Tyr Lys Glu Gly Ile Ala Glu Glu Gly Lys Ile Ala Ile Ser
1985 1990 1995

Gly Gly Ser Asn Gly Gly Leu Leu Val Gly Ala Cys Val Asn Gln
2000 2005 2010

Ala Pro Glu Leu Tyr Gly Ala Ala Ile Ala Asp Val Gly Val Leu
2015 2020 2025

Asp Met Leu Arg Phe His Arg Tyr Thr Ile Gly Arg Ala Trp Ser
2030 2035 2040

Ser Asp Tyr Gly Cys Ser Asp Glu Pro Glu Gly Phe Asp Tyr Leu
2045 2050 2055

Tyr Ala Tyr Ser Pro Leu Gln Asn Val Asp Pro Ser Lys Lys Pro
2060 2065 2070

Phe Pro Pro Thr Met Leu Leu Thr Ala Asp His Asp Asp Arg Val
2075 2080 2085

Val Pro Leu His Ser Phe Lys His Ile Ser Glu Leu Gln His Lys
2090 2095 2100

Leu Pro Asp Asn Pro His Pro Leu Leu Leu Arg Val Asp Thr Lys 2105 2110 2115

Ser Gly His Gly Ala Gly Lys Ser Thr Ala Lys Lys Ile Glu Glu
2120 2125 2130

Ala Cys Glu Lys Tyr Gly Phe Val Ser Gln Ser Met Gly Leu Arg
2135 2140 2145

Trp His Asp
2150

<210> SEQ ID NO 350
<211> LENGTH: 12
<212> TYPE: PRT
<213> ORGANISM: Amanita bisporigera

<400> SEQUENCE: 350

Ala Trp Leu Val Asp Cys Pro Cys Val Gly Asp Asp
1 5 10

<210> SEQ ID NO 351
<211> LENGTH: 12
<212> TYPE: PRT
<213> ORGANISM: Amanita bisporigera

<400> SEQUENCE: 351

Ala Thr Arg Leu Pro Ala Trp Leu Val Asp Cys Pro
1 5 10

<210> SEQ ID NO 352
<211> LENGTH: 60
<212> TYPE: PRT
<213> ORGANISM: Amanita bisporigera

<400> SEQUENCE: 352

Trp Ala Pro His Ser Tyr Pro Pro Thr Arg Arg Ser Asp His Val Asp
1 5 10 15

Val Tyr Gln Ser Ala Ser Arg Gly Glu Val Pro Val Pro Asp Pro Tyr
20 25 30

Gln Trp Leu Glu Glu Asn Ser Asn Glu Val Asp Glu Trp Thr Thr Ala
35 40 45

Gln Thr Ala Phe Thr Gln Gly Tyr Leu Asp Lys Asn
50 55 60

<210> SEQ ID NO 353
<211> LENGTH: 60
<212> TYPE: PRT
<213> ORGANISM: Galerina marginata

<400> SEQUENCE: 353

Trp Ala Pro Gly Asn Tyr Pro Ser Thr Arg Arg Ser Asp His Val Asp
1 5 10 15

Ser Tyr Gln Ser Ala Ser Lys Gly Glu Val Pro Val Pro Asp Pro Tyr
20 25 30

Gln Trp Leu Glu Glu Ser Thr Asp Glu Val Asp Lys Trp Thr Thr Ala
35 40 45

Gln Ala Asp Leu Ala Gln Ala Tyr Leu Asp Gln Asn
50 55 60

<210> SEQ ID NO 354
<211> LENGTH: 60
<212> TYPE: PRT
<213> ORGANISM: Amanita bisporigera

<400> SEQUENCE: 354

```
Ser Ser Thr Gln Trp Thr Pro Asn Met Tyr Pro Ser Ala Arg Arg Ser
1               5                   10                  15

Asp His Ile Asp Thr Tyr Arg Ser Glu Thr Arg Gly Glu Val Lys Val
            20                  25                  30

Pro Asp Pro Tyr His Trp Leu Glu Glu Tyr Ser Glu Glu Thr Asp Lys
        35                  40                  45

Trp Thr Ser Asp Gln Glu Glu Phe Thr Arg Thr Tyr
    50                  55                  60
```

<210> SEQ ID NO 355
<211> LENGTH: 17
<212> TYPE: PRT
<213> ORGANISM: Amanita bisporigera

<400> SEQUENCE: 355

```
Leu Asp Ser Asn Pro Asp Arg Lys Lys Leu Glu Asp Ala Phe Arg Lys
1               5                   10                  15

Ser
```

<210> SEQ ID NO 356
<211> LENGTH: 60
<212> TYPE: PRT
<213> ORGANISM: Galerina marginata

<400> SEQUENCE: 356

```
Ser Ser Ile Ala Trp Ala Pro Gly Asn Tyr Pro Ser Thr Arg Arg Ser
1               5                   10                  15

Asp His Val Asp Ser Tyr Gln Ser Ala Ser Lys Gly Glu Val Pro Val
            20                  25                  30

Pro Asp Pro Tyr Gln Trp Leu Glu Glu Ser Thr Asp Glu Val Asp Lys
        35                  40                  45

Trp Thr Thr Ala Gln Ala Asp Leu Ala Gln Ala Tyr
    50                  55                  60
```

<210> SEQ ID NO 357
<211> LENGTH: 17
<212> TYPE: PRT
<213> ORGANISM: Galerina marginata

<400> SEQUENCE: 357

```
Leu Asp Gln Asn Ala Asp Ile Gln Lys Leu Ala Asp Lys Phe Arg Ala
1               5                   10                  15

Ser
```

<210> SEQ ID NO 358
<211> LENGTH: 4
<212> TYPE: PRT
<213> ORGANISM: Amanita bisporigera

<400> SEQUENCE: 358

```
Asp Tyr Pro Lys
1
```

<210> SEQ ID NO 359
<211> LENGTH: 60
<212> TYPE: PRT
<213> ORGANISM: Amanita bisporigera

<400> SEQUENCE: 359

Ile Asp Thr Tyr Arg Ser Glu Thr Arg Gly Glu Val Lys Val Pro Asp
1 5 10 15

Pro Tyr His Trp Leu Glu Glu Tyr Ser Glu Glu Thr Asp Lys Trp Thr
20 25 30

Ser Asp Gln Glu Glu Phe Thr Arg Thr Tyr Leu Asp Ser Asn Pro Asp
35 40 45

Arg Lys Lys Leu Glu Asp Ala Phe Arg Lys Ser Met
50 55 60

<210> SEQ ID NO 360
<211> LENGTH: 60
<212> TYPE: PRT
<213> ORGANISM: Galerina marginata

<400> SEQUENCE: 360

Val Asp Ile Tyr Lys Ser Ala Leu Arg Gly Asp Val His Val Gln Asp
1 5 10 15

Pro Tyr Gln Trp Leu Glu Glu Tyr Thr Asp Glu Thr Asp Lys Trp Thr
20 25 30

Thr Ala Gln Glu Val Phe Thr Arg Thr Tyr Leu Asp Lys Asn Pro Asp
35 40 45

Leu Pro Arg Leu Glu Lys Ala Phe Gln Ala Cys Asn
50 55 60

<210> SEQ ID NO 361
<211> LENGTH: 60
<212> TYPE: PRT
<213> ORGANISM: Amanita bisporigera

<400> SEQUENCE: 361

Gly Ser Met Thr Val Thr Ala Arg Glu Thr Glu Pro Trp Phe Phe Ala
1 5 10 15

Thr Leu Thr Gly Phe Asn Thr Pro Gly Ile Val Cys Arg Tyr Asn Ile
20 25 30

Gln Arg Pro Glu Glu Gln Arg Trp Ser Val Tyr Arg Thr Ala Lys Val
35 40 45

Lys Gly Leu Asn Pro Asn Asp Phe Glu Ala Arg Gln
50 55 60

<210> SEQ ID NO 362
<211> LENGTH: 10
<212> TYPE: PRT
<213> ORGANISM: Amanita bisporigera

<400> SEQUENCE: 362

Val Trp Tyr Asp Ser Tyr Asp Gly Thr Lys
1 5 10

<210> SEQ ID NO 363
<211> LENGTH: 12
<212> TYPE: PRT
<213> ORGANISM: Amanita bisporigera

<400> SEQUENCE: 363

Thr Lys Ile Pro Met Phe Ile Val Arg His Lys Asn
1 5 10

<210> SEQ ID NO 364
<211> LENGTH: 60
<212> TYPE: PRT
<213> ORGANISM: Galerina marginata

<400> SEQUENCE: 364

Gly Ala Ala Ser Ile Ala Asn Arg Gln Lys Gln Thr His Phe Phe Leu
1 5 10 15

Thr Leu Ser Gly Phe Asn Thr Pro Gly Thr Ile Ala Arg Tyr Asp Phe
20 25 30

Thr Ala Pro Glu Thr Gln Arg Phe Ser Ile Leu Arg Thr Thr Lys Val
35 40 45

Asn Glu Leu Asp Pro Asp Asp Phe Glu Ser Thr Gln
50 55 60

<210> SEQ ID NO 365
<211> LENGTH: 12
<212> TYPE: PRT
<213> ORGANISM: Galerina marginata

<400> SEQUENCE: 365

Thr Lys Ile Pro Met Phe Ile Val Arg His Lys Ser
1 5 10

<210> SEQ ID NO 366
<211> LENGTH: 10
<212> TYPE: PRT
<213> ORGANISM: Galerina marginata

<400> SEQUENCE: 366

Val Trp Tyr Glu Ser Lys Asp Gly Asn Lys
1 5 10

<210> SEQ ID NO 367
<211> LENGTH: 50
<212> TYPE: PRT
<213> ORGANISM: Amanita bisporigera

<400> SEQUENCE: 367

Gly Gly Phe Asn Ile Ser Ile Asn Pro Phe Phe Ser Pro Thr Ile Leu
1 5 10 15

Thr Phe Leu Gln Lys Tyr Gly Ala Ile Leu Ala Val Pro Asn Ile Arg
20 25 30

Gly Gly Gly Glu Phe Gly Glu Thr Trp His Asp Ala Gly Ile Arg Glu
35 40 45

Lys Arg
50

<210> SEQ ID NO 368
<211> LENGTH: 50
<212> TYPE: PRT
<213> ORGANISM: Galerina marginata

<400> SEQUENCE: 368

Gly Gly Phe Ser Ile Ser Ile Asp Pro Phe Phe Ser Ala Thr Ile Leu
1 5 10 15

Thr Phe Leu Gln Lys Tyr Gly Val Val Phe Ala Leu Pro Asn Ile Arg
20 25 30

Gly Gly Gly Glu Phe Gly Glu Asp Trp His Leu Ala Gly Cys Arg Glu
35 40 45

Lys Lys
50

<210> SEQ ID NO 369

<211> LENGTH: 10
<212> TYPE: PRT
<213> ORGANISM: Amanita bisporigera

<400> SEQUENCE: 369

Asn Val Tyr Asp Asp Phe Ile Ala Ala Thr
1 5 10

<210> SEQ ID NO 370
<211> LENGTH: 10
<212> TYPE: PRT
<213> ORGANISM: Galerina marginata

<400> SEQUENCE: 370

Asn Cys Phe Asp Asp Phe Ile Ala Ala Thr
1 5 10

<210> SEQ ID NO 371
<211> LENGTH: 46
<212> TYPE: PRT
<213> ORGANISM: Amanita bisporigera

<400> SEQUENCE: 371

Asp Asp Arg Val Val Pro Met His Ser Phe Lys Tyr Ala Ala Met Leu
1 5 10 15

Gln Tyr Thr Leu Pro His Asn Arg His Pro Leu Leu Leu Arg Val Asp
20 25 30

Lys Lys Ala Gly His Gly Gly Gly Lys Ser Thr Glu Lys Arg
35 40 45

<210> SEQ ID NO 372
<211> LENGTH: 46
<212> TYPE: PRT
<213> ORGANISM: Galerina marginata

<400> SEQUENCE: 372

Asp Asp Arg Val Val Pro Met His Ser Phe Lys Leu Ala Ala Glu Leu
1 5 10 15

Gln Tyr Ser Leu Pro His Asn Pro Asn Pro Leu Leu Ile Arg Ile Asp
20 25 30

Lys Lys Ala Gly His Gly Ala Gly Lys Ser Thr Gln Gln Lys
35 40 45

<210> SEQ ID NO 373
<211> LENGTH: 34
<212> TYPE: PRT
<213> ORGANISM: Amanita bisporigera

<400> SEQUENCE: 373

Ala Ala Met Leu Gln Tyr Thr Leu Pro His Asn Arg His Pro Leu Leu
1 5 10 15

Leu Arg Val Asp Lys Lys Ala Gly His Gly Gly Gly Lys Ser Thr Glu
20 25 30

Lys Arg

<210> SEQ ID NO 374
<211> LENGTH: 34
<212> TYPE: PRT
<213> ORGANISM: Galerina marginata

<400> SEQUENCE: 374

Ala Ala Glu Leu Gln Tyr Ser Leu Pro His Asn Pro Asn Pro Leu Leu

-continued

```
1               5                   10                  15

Ile Arg Ile Asp Lys Lys Thr Gly His Gly Ala Gly Lys Ser Thr Gln
            20                  25                  30

Gln Arg


<210> SEQ ID NO 375
<211> LENGTH: 22
<212> TYPE: PRT
<213> ORGANISM: Amanita bisporigera

<400> SEQUENCE: 375

Arg Leu Gln Glu Ala Ala Asp Lys Trp Gly Phe Ala Ala Gln Ser Met
1               5                   10                  15

Gly Leu Ala Trp Lys Asp
            20


<210> SEQ ID NO 376
<211> LENGTH: 22
<212> TYPE: PRT
<213> ORGANISM: Galerina marginata

<400> SEQUENCE: 376

Arg Ile Lys Glu Ser Ala Asp Lys Trp Gly Phe Val Ala Gln Ser Leu
1               5                   10                  15

Gly Leu Val Trp Lys Asp
            20


<210> SEQ ID NO 377
<211> LENGTH: 34
<212> TYPE: PRT
<213> ORGANISM: Amanita bisporigera

<400> SEQUENCE: 377

Gln Val Trp Tyr Asp Ser Tyr Asp Gly Thr Lys Ile Pro Met Phe Ile
1               5                   10                  15

Val Arg His Lys Asn Thr Gln Phe Asn Gly Thr Ala Pro Ala Ile Gln
            20                  25                  30

Tyr Gly


<210> SEQ ID NO 378
<211> LENGTH: 34
<212> TYPE: PRT
<213> ORGANISM: Galerina marginata

<400> SEQUENCE: 378

Gln Val Trp Tyr Glu Ser Lys Asp Gly Thr Ser Ile Pro Met Phe Ile
1               5                   10                  15

Val Arg His Lys Ser Thr Lys Phe Asp Gly Thr Ala Pro Val Ile Gln
            20                  25                  30

Tyr Gly


<210> SEQ ID NO 379
<211> LENGTH: 20
<212> TYPE: PRT
<213> ORGANISM: Amanita bisporigera

<400> SEQUENCE: 379

Val Tyr Arg Thr Ala Lys Val Lys Gly Leu Asn Pro Asn Asp Phe Glu
1               5                   10                  15

Ala Arg Gln Val
```

20

<210> SEQ ID NO 380
<211> LENGTH: 20
<212> TYPE: PRT
<213> ORGANISM: Galerina marginata

<400> SEQUENCE: 380

```
Ile Tyr Arg Thr Thr Lys Leu Asn Gly Leu Asn Thr Glu Asp Phe Lys
1               5                   10                  15

Ala Ser Gln Val
            20
```

<210> SEQ ID NO 381

<400> SEQUENCE: 381

000

<210> SEQ ID NO 382
<211> LENGTH: 20
<212> TYPE: PRT
<213> ORGANISM: Galerina marginata

<400> SEQUENCE: 382

```
Val Tyr Arg Thr Ala Lys Val Lys Gly Leu Asn Pro Asn Asp Phe Glu
1               5                   10                  15

Ala Arg Gln Val
            20
```

<210> SEQ ID NO 383

<400> SEQUENCE: 383

000

<210> SEQ ID NO 384

<400> SEQUENCE: 384

000

<210> SEQ ID NO 385
<211> LENGTH: 60
<212> TYPE: PRT
<213> ORGANISM: Amanita bisporigera

<400> SEQUENCE: 385

```
Ser Asp Phe Ser Thr Ile Tyr Val Arg Ser Thr Ser Ser Pro Leu Ala
1               5                   10                  15

Pro Gly Asn Asn Ser Ile Arg Asn Asp Asp Gly Arg Leu Pro Asp Glu
            20                  25                  30

Leu Arg Tyr Val Lys Phe Ser Ser Ile Ser Trp Thr Lys Asp Ser Lys
        35                  40                  45

Gly Phe Phe Tyr Gln Arg Tyr Pro Gly Thr Gly Thr
    50                  55                  60
```

<210> SEQ ID NO 386
<211> LENGTH: 59
<212> TYPE: PRT
<213> ORGANISM: Galerina marginata

<400> SEQUENCE: 386

Ser Asp Phe Val Thr Ile Tyr Val Trp Ser Thr Asp Ser Pro Leu Thr
1               5                   10                  15

Asn Asp Val Asp Ser Lys Asn Asp Lys Gly Arg Leu Pro Glu Glu Ile
            20                  25                  30

Lys Phe Val Lys Phe Ser Ser Ile Gly Trp Thr Pro Asp Ser Lys Gly
        35                  40                  45

Phe Phe Ile Arg Ser Ile Pro Trp Thr Ala Ser
    50                  55

<210> SEQ ID NO 387
<211> LENGTH: 35
<212> TYPE: PRT
<213> ORGANISM: Amanita bisporigera

<400> SEQUENCE: 387

Arg Asn Asp Asp Gly Arg Leu Pro Asp Glu Leu Arg Tyr Val Lys Phe
1               5                   10                  15

Ser Ser Ile Ser Trp Thr Lys Asp Ser Lys Gly Phe Phe Tyr Gln Arg
            20                  25                  30

Tyr Pro Gly
        35

<210> SEQ ID NO 388
<211> LENGTH: 35
<212> TYPE: PRT
<213> ORGANISM: Galerina marginata

<400> SEQUENCE: 388

Lys Asn Asp Lys Gly Arg Leu Pro Glu Glu Ile Lys Phe Val Lys Phe
1               5                   10                  15

Ser Ser Ile Gly Trp Thr Pro Asp Ser Lys Gly Phe Phe Ile Arg Ser
            20                  25                  30

Phe Pro Gly
        35

<210> SEQ ID NO 389
<211> LENGTH: 25
<212> TYPE: PRT
<213> ORGANISM: Amanita bisporigera

<400> SEQUENCE: 389

Arg Tyr Pro Gly Thr Gly Thr Val Asn Gly Gln Asn Gly Ile Gln Thr
1               5                   10                  15

Gln Gly Asp Arg Asp Ala Met Ile Tyr
            20                  25

<210> SEQ ID NO 390
<211> LENGTH: 26
<212> TYPE: PRT
<213> ORGANISM: Galerina marginata

<400> SEQUENCE: 390

Arg Tyr Pro Asp Thr Ser Thr Ala Thr Gln Glu Asn Gly Pro Ile Ala
1               5                   10                  15

Thr Glu Gly Asp Leu Asp Ala Met Val Tyr
            20                  25

<210> SEQ ID NO 391
<211> LENGTH: 43
<212> TYPE: PRT
<213> ORGANISM: Amanita bisporigera

<400> SEQUENCE: 391

Ser Ser Leu Ser Gln Ala Pro Glu Ala Glu Gly Gly Asp Gly Arg Leu
1               5                   10                  15

Ser Asp Gly Val Lys Trp Cys Lys Phe Thr Thr Ile Thr Trp Thr Lys
            20                  25                  30

Asp Ser Lys Gly Phe Leu Tyr Gln Arg Tyr Pro
        35                  40

<210> SEQ ID NO 392
<211> LENGTH: 43
<212> TYPE: PRT
<213> ORGANISM: Galerina marginata

<400> SEQUENCE: 392

Ser Pro Leu Thr Lys Asp Val Asp Ala Lys Asn Asp Lys Gly Arg Leu
1               5                   10                  15

Pro Glu Glu Ile Lys Phe Val Lys Phe Ser Ser Ile Gly Trp Thr Pro
            20                  25                  30

Asp Ser Lys Gly Phe Phe Ile Arg Ser Phe Pro
        35                  40

<210> SEQ ID NO 393

<400> SEQUENCE: 393

000

<210> SEQ ID NO 394
<211> LENGTH: 47
<212> TYPE: PRT
<213> ORGANISM: Galerina marginata

<400> SEQUENCE: 394

Asp Asp Arg Val Val Pro Met His Ser Phe Lys Phe Ile Ala Thr Leu
1               5                   10                  15

Gln His Asn Val Pro Gln Asn Pro His Pro Leu Leu Ile Lys Ile Asp
            20                  25                  30

Lys Ser Trp Leu Gly His Gly Met Gly Lys Pro Thr Asp Lys Lys
        35                  40                  45

<210> SEQ ID NO 395

<400> SEQUENCE: 395

000

<210> SEQ ID NO 396
<211> LENGTH: 12
<212> TYPE: PRT
<213> ORGANISM: Galerina marginata

<400> SEQUENCE: 396

Leu Gln Glu Ala Ala Asp Lys Trp Gly Phe Ala Ala
1               5                   10

<210> SEQ ID NO 397
<211> LENGTH: 54
<212> TYPE: PRT
<213> ORGANISM: Amanita bisporigera

<400> SEQUENCE: 397

```
Gly Ser Asp Phe Ser Thr Ile Tyr Val Arg Ser Thr Ser Ser Pro Leu
1               5                   10                  15

Ala Pro Gly Asn Asn Ser Ile Arg Asn Asp Asp Gly Arg Leu Pro Asp
            20                  25                  30

Glu Leu Arg Tyr Val Lys Phe Ser Ser Ile Ser Trp Thr Lys Asp Ser
        35                  40                  45

Lys Gly Phe Phe Tyr Gln
    50


<210> SEQ ID NO 398
<211> LENGTH: 53
<212> TYPE: PRT
<213> ORGANISM: Galerina marginata

<400> SEQUENCE: 398

Gly Gly Asp Tyr Ser Thr Ile Tyr Val Arg Ser Thr Ser Ser Pro Leu
1               5                   10                  15

Ser Gln Ser Ser Val Ala Gln Gly Val Asp Gly Arg Leu Ser Asp Glu
            20                  25                  30

Val Lys Trp Phe Lys Phe Ser Thr Ile Ile Trp Thr Lys Asp Phe Lys
        35                  40                  45

Gly Phe Leu Tyr Gln
    50


<210> SEQ ID NO 399
<211> LENGTH: 58
<212> TYPE: PRT
<213> ORGANISM: Amanita bisporigera

<400> SEQUENCE: 399

Val Phe Asp Ser Glu Tyr Asp Leu Ile Gly Asn Asp Gly Ser Leu Leu
1               5                   10                  15

Tyr Ile Arg Thr Asn Lys Ala Ala Pro Gln Tyr Lys Ile Val Thr Leu
            20                  25                  30

Asp Ile Glu Lys Pro Glu Leu Gly Phe Lys Glu Phe Ile Pro Glu Asp
        35                  40                  45

Pro Lys Ala Tyr Leu Ser Gln Val Lys Ile
    50                  55


<210> SEQ ID NO 400
<211> LENGTH: 57
<212> TYPE: PRT
<213> ORGANISM: Galerina marginata

<400> SEQUENCE: 400

Val Phe Asp Ser Met Thr Phe Thr Ser Ile Thr Asn Lys Gly Ser Leu
1               5                   10                  15

Phe Tyr Val Arg Thr Asn Glu Ser Ala Pro Gln Tyr Arg Val Ile Thr
            20                  25                  30

Val Asp Ile Ala Lys Arg Asn Glu Ile Lys Glu Leu Ile Pro Glu Thr
        35                  40                  45

Asp Ala Tyr Leu Ser Ser Ile Thr Ser
    50                  55


<210> SEQ ID NO 401
<211> LENGTH: 14
<212> TYPE: PRT
<213> ORGANISM: Amanita bisporigera

<400> SEQUENCE: 401
```

```
Val Asn Lys Gly Tyr Phe Ala Leu Val Tyr Lys Arg Asn Val
1               5                   10


<210> SEQ ID NO 402
<211> LENGTH: 14
<212> TYPE: PRT
<213> ORGANISM: Galerina marginata

<400> SEQUENCE: 402

Val Asn Lys Gly Tyr Phe Ala Leu Val Tyr Lys Arg Asn Val
1               5                   10


<210> SEQ ID NO 403
<211> LENGTH: 60
<212> TYPE: PRT
<213> ORGANISM: Amanita bisporigera

<400> SEQUENCE: 403

Ile Gly Asn Asp Gly Ser Leu Leu Tyr Ile Arg Thr Asn Lys Ala Ala
1               5                   10                  15

Pro Gln Tyr Lys Ile Val Thr Leu Asp Ile Glu Lys Pro Glu Leu Gly
            20                  25                  30

Phe Lys Glu Phe Ile Pro Glu Asp Pro Lys Ala Tyr Leu Ser Gln Val
        35                  40                  45

Lys Ile Phe Asn Lys Asp Arg Leu Ala Leu Val Tyr
    50                  55                  60


<210> SEQ ID NO 404
<211> LENGTH: 58
<212> TYPE: PRT
<213> ORGANISM: Galerina marginata

<400> SEQUENCE: 404

Ile Thr Asn Lys Gly Ser Leu Phe Tyr Val Arg Thr Asn Glu Ser Ala
1               5                   10                  15

Pro Gln Tyr Arg Val Ile Thr Val Asp Ile Ala Lys Arg Asn Glu Ile
            20                  25                  30

Lys Glu Leu Ile Pro Glu Thr Asp Ala Tyr Leu Ser Ser Ile Thr Ser
        35                  40                  45

Val Asn Lys Gly Tyr Phe Ala Leu Val Tyr
    50                  55


<210> SEQ ID NO 405
<211> LENGTH: 4
<212> TYPE: PRT
<213> ORGANISM: Amanita bisporigera

<400> SEQUENCE: 405

Lys Arg Asn Val
1


<210> SEQ ID NO 406
<211> LENGTH: 4
<212> TYPE: PRT
<213> ORGANISM: Galerina marginata

<400> SEQUENCE: 406

Lys Arg Asn Val
1


<210> SEQ ID NO 407
```

<211> LENGTH: 46
<212> TYPE: PRT
<213> ORGANISM: Amanita bisporigera

<400> SEQUENCE: 407

Thr Ile Gly Lys Ala Trp Ile Ser Asp Tyr Gly Asp Pro Glu Asp Pro
1 5 10 15

Arg Asp Phe Asp Tyr Ile Tyr Thr His Ser Pro Leu His Asn Ile Pro
20 25 30

Lys Asn Met Val Leu Pro Pro Thr Met Leu Leu Thr Ala Asp
35 40 45

<210> SEQ ID NO 408
<211> LENGTH: 59
<212> TYPE: PRT
<213> ORGANISM: Galerina marginata

<400> SEQUENCE: 408

Ser Leu Gly Gln Ala Trp Ile Ser Glu Tyr Gly Asn Pro Ser Ile Pro
1 5 10 15

Glu Glu Phe Asp Tyr Ile Tyr Pro Leu Ser Pro Val His Asn Val Gln
20 25 30

Thr Asp Lys Val Met Pro Ala Met Leu Ile Thr Val Asn Ile Gly Glu
35 40 45

Gln Leu Thr Ser Ser Asn Leu Ile Met Pro His
50 55

<210> SEQ ID NO 409
<211> LENGTH: 9
<212> TYPE: PRT
<213> ORGANISM: Amanita bisporigera

<400> SEQUENCE: 409

His Asp Asp Arg Val Val Pro Met His
1 5

<210> SEQ ID NO 410
<211> LENGTH: 14
<212> TYPE: PRT
<213> ORGANISM: Galerina marginata

<400> SEQUENCE: 410

Thr Arg Pro Ser Pro Gly Asp Asp Arg Val Val Pro Met His
1 5 10

<210> SEQ ID NO 411

<400> SEQUENCE: 411

000

<210> SEQ ID NO 412
<211> LENGTH: 34
<212> TYPE: PRT
<213> ORGANISM: Galerina marginata

<400> SEQUENCE: 412

Ala Ala Glu Leu Gln Tyr Ser Leu Pro His Asn Pro Asn Pro Leu Leu
1 5 10 15

Ile Arg Ile Asp Lys Lys Ala Gly His Gly Ala Gly Lys Ser Thr Gln
20 25 30

Gln Lys

<210> SEQ ID NO 413
<211> LENGTH: 60
<212> TYPE: PRT
<213> ORGANISM: Amanita bisporigera

<400> SEQUENCE: 413

Ala Val Pro Asn Ile Arg Gly Gly Gly Glu Phe Gly Glu Thr Trp His
1               5                   10                  15

Asp Ala Gly Ile Arg Glu Lys Arg Ala Asn Val Tyr Asp Asp Phe Ile
            20                  25                  30

Ala Ala Thr Gln Phe Leu Val Lys Asn Lys Tyr Ala Ala Gly Gly Lys
        35                  40                  45

Val Ala Ile Asn Gly Gly Ser Asn Gly Gly Leu Leu
    50                  55                  60

<210> SEQ ID NO 414
<211> LENGTH: 60
<212> TYPE: PRT
<213> ORGANISM: Galerina marginata

<400> SEQUENCE: 414

Ala Val Thr His Ile Arg Gly Gly Ser Glu Lys Gly Trp Gly Trp Phe
1               5                   10                  15

Leu Asp Gly Arg Lys Asp Lys Lys Pro Asn Ser Phe Thr Asp Phe Ile
            20                  25                  30

Ala Cys Ala Glu Ala Leu Ile Ala Glu Gly Tyr Gly Thr Ala Gly Arg
        35                  40                  45

Ile Val Ala Glu Gly Arg Ser Ala Gly Gly Met Leu
    50                  55                  60

<210> SEQ ID NO 415
<211> LENGTH: 26
<212> TYPE: PRT
<213> ORGANISM: Amanita bisporigera

<400> SEQUENCE: 415

Val Ala Ala Cys Val Asn Arg Ala Arg Glu Gly Thr Phe Gly Ala Ala
1               5                   10                  15

Ile Ala Glu Val Gly Val Leu Asp Leu Leu
            20                  25

<210> SEQ ID NO 416
<211> LENGTH: 25
<212> TYPE: PRT
<213> ORGANISM: Galerina marginata

<400> SEQUENCE: 416

Met Gly Ala Val Ala Asn Leu Arg Pro Asp Leu Trp Ala Gly Val Ile
1               5                   10                  15

Gly Gly Val Pro Phe Val Asp Val Leu
            20                  25

<210> SEQ ID NO 417
<211> LENGTH: 41
<212> TYPE: PRT
<213> ORGANISM: Amanita bisporigera

<400> SEQUENCE: 417

Lys Phe Ser Ala Pro Phe Leu Asn Asp Asp Lys Arg Trp Tyr Trp Phe
1               5                   10                  15

```
Tyr Asn Thr Gly Leu Gln Ala Gln Thr Val Ile Cys Arg Ser Lys Asp
            20                  25                  30

Glu Thr Leu Pro Asp Phe Ser Glu Ser
        35                  40


<210> SEQ ID NO 418
<211> LENGTH: 60
<212> TYPE: PRT
<213> ORGANISM: Galerina marginata

<400> SEQUENCE: 418

Gln Tyr Tyr Ala Pro Tyr Leu His Asp Asp Asn Arg Trp Tyr Trp Tyr
1               5                   10                  15

Tyr Asn Ser Gly Leu Glu Pro Gln Thr Gly Glu Arg Phe Lys Gln Pro
            20                  25                  30

Phe Arg Pro Arg Trp Leu Thr Ser Val Pro Ala Lys Ala Leu Tyr Arg
        35                  40                  45

Ser Lys Asp Ser Asn Leu Pro Asp Leu Ser Thr Ala
    50                  55                  60


<210> SEQ ID NO 419
<211> LENGTH: 16
<212> TYPE: PRT
<213> ORGANISM: Amanita bisporigera

<400> SEQUENCE: 419

Asp Tyr Val Gly Glu Thr Phe Phe Asp Pro Asn Leu Leu Ser Ser Asp
1               5                   10                  15


<210> SEQ ID NO 420
<211> LENGTH: 17
<212> TYPE: PRT
<213> ORGANISM: Galerina marginata

<400> SEQUENCE: 420

Asp Gly Ser Gly Gly Asp Leu Phe Phe Asp Val Gly Pro Leu Ser Ala
1               5                   10                  15

Asn


<210> SEQ ID NO 421
<211> LENGTH: 38
<212> TYPE: PRT
<213> ORGANISM: Amanita bisporigera

<400> SEQUENCE: 421

Ser Asp Asp Ile Leu Val His Glu Asp Gln Glu His Pro Asp Trp Val
1               5                   10                  15

Phe Gly Ala Glu Val Thr Glu Asp Gly Lys Tyr Val Ala Leu Tyr Thr
            20                  25                  30

Met Lys Asp Thr Ser Arg
        35


<210> SEQ ID NO 422
<211> LENGTH: 38
<212> TYPE: PRT
<213> ORGANISM: Galerina marginata

<400> SEQUENCE: 422

Ala Glu Asp Ser Leu Ile Tyr Gln Asp Arg Glu His Arg Asp Trp Met
1               5                   10                  15
```

```
Phe Ser Ile Asp Val Thr Asp Asp Gly Asn Tyr Leu Leu Leu Tyr Ile
            20                  25                  30

Leu Lys Asp Ser Ser Arg
        35


<210> SEQ ID NO 423
<211> LENGTH: 30
<212> TYPE: PRT
<213> ORGANISM: Amanita bisporigera

<400> SEQUENCE: 423

Gly Leu Leu Val Ala Ala Cys Val Asn Arg Ala Arg Glu Gly Thr Phe
1               5                   10                  15

Gly Ala Ala Ile Ala Glu Val Gly Val Leu Asp Leu Leu Lys
            20                  25                  30


<210> SEQ ID NO 424
<211> LENGTH: 30
<212> TYPE: PRT
<213> ORGANISM: Galerina marginata

<400> SEQUENCE: 424

Gly Leu Leu Val Ser Ala Cys Val Asn Arg Ala Pro Glu Gly Thr Phe
1               5                   10                  15

Gly Cys Ala Val Ala Asp Val Gly Val His Asp Leu Leu Lys
            20                  25                  30


<210> SEQ ID NO 425
<211> LENGTH: 30
<212> TYPE: PRT
<213> ORGANISM: Amanita bisporigera

<400> SEQUENCE: 425

Gly Phe Leu Val Cys Gly Ser Val Val Arg Ala Pro Glu Gly Thr Phe
1               5                   10                  15

Gly Ala Ala Val Ser Glu Gly Gly Val Ala Asp Leu Leu Lys
            20                  25                  30


<210> SEQ ID NO 426

<400> SEQUENCE: 426

000


<210> SEQ ID NO 427
<211> LENGTH: 27
<212> TYPE: PRT
<213> ORGANISM: Amanita bisporigera

<400> SEQUENCE: 427

Asp Asp Ile Leu Val His Glu Asp Gln Glu His Pro Asp Trp Val Phe
1               5                   10                  15

Gly Ala Glu Val Thr Glu Asp Gly Lys Tyr Val
            20                  25


<210> SEQ ID NO 428
<211> LENGTH: 27
<212> TYPE: PRT
<213> ORGANISM: Galerina marginata

<400> SEQUENCE: 428

Glu Asp Ile Ile Val Tyr Gln Asp Asn Glu His Pro Glu Trp Ile Tyr
1               5                   10                  15
```

Gly Ala Asp Thr Ser Glu Asp Gly Lys Tyr Leu
20 25

<210> SEQ ID NO 429
<211> LENGTH: 13
<212> TYPE: PRT
<213> ORGANISM: Amanita bisporigera

<400> SEQUENCE: 429

Met Ile Tyr Tyr His Arg Ile Gly Thr Ser Gln Ser Asp
1 5 10

<210> SEQ ID NO 430
<211> LENGTH: 13
<212> TYPE: PRT
<213> ORGANISM: Galerina marginata

<400> SEQUENCE: 430

Met Met Cys Tyr His Lys Val Gly Thr Thr Gln Gly Glu
1 5 10

<210> SEQ ID NO 431
<211> LENGTH: 30
<212> TYPE: PRT
<213> ORGANISM: Amanita bisporigera

<400> SEQUENCE: 431

Met Ser Ser Thr Gln Trp Thr Pro Asn Met Tyr Pro Ser Ala Arg Arg
1 5 10 15

Ser Asp His Ile Asp Thr Tyr Arg Ser Glu Thr Arg Gly Glu
20 25 30

<210> SEQ ID NO 432
<211> LENGTH: 30
<212> TYPE: PRT
<213> ORGANISM: Galerina marginata

<400> SEQUENCE: 432

Met Ser Ser Ile Ala Trp Ala Pro Gly Asn Tyr Pro Ser Thr Arg Arg
1 5 10 15

Ser Asp His Val Asp Ser Tyr Gln Ser Ala Ser Lys Gly Glu
20 25 30

<210> SEQ ID NO 433
<211> LENGTH: 50
<212> TYPE: PRT
<213> ORGANISM: Amanita bisporigera

<400> SEQUENCE: 433

Phe Asn Thr Pro Gly Ile Val Cys Arg Tyr Asn Ile Gln Arg Pro Glu
1 5 10 15

Glu Gln Arg Trp Ser Val Tyr Arg Thr Ala Lys Val Lys Gly Leu Asn
20 25 30

Pro Asn Asp Phe Glu Ala Arg Gln Val Trp Tyr Asp Ser Tyr Asp Gly
35 40 45

Thr Lys
50

<210> SEQ ID NO 434
<211> LENGTH: 60
<212> TYPE: PRT
<213> ORGANISM: Galerina marginata

<400> SEQUENCE: 434

```
Phe Ser Ser Asp His Ile Arg Leu Arg Tyr Glu Ala Leu Asn Arg Pro
1               5                   10                  15

Ala Gln Ile Arg Arg Leu Ala Leu Ala Asp Gly Ala Gln Gln Val Leu
            20                  25                  30

Lys Glu Thr Pro Val Leu Gly Val Phe Asn Ala Asp Asp Tyr Val Ser
        35                  40                  45

Gln Arg Leu Trp Ala Thr Ser Val Asp Gly Thr Gln
    50                  55                  60
```

<210> SEQ ID NO 435
<211> LENGTH: 36
<212> TYPE: PRT
<213> ORGANISM: Amanita bisporigera

<400> SEQUENCE: 435

```
Ile Pro Met Phe Ile Val Arg His Lys Asn Thr Gln Phe Asn Gly Thr
1               5                   10                  15

Ala Pro Ala Ile Gln Tyr Gly Tyr Gly Gly Phe Asn Ile Ser Ile Asn
            20                  25                  30

Pro Phe Phe Ser
        35
```

<210> SEQ ID NO 436
<211> LENGTH: 35
<212> TYPE: PRT
<213> ORGANISM: Galerina marginata

<400> SEQUENCE: 436

```
Val Pro Ile Ser Leu Val Val Arg His Asp Gln Leu Gly Gln Pro Thr
1               5                   10                  15

Pro Leu Tyr Leu Tyr Gly Tyr Gly Ala Tyr Gly His Ser Leu Asp Pro
            20                  25                  30

Trp Phe Ser
        35
```

<210> SEQ ID NO 437
<211> LENGTH: 23
<212> TYPE: PRT
<213> ORGANISM: Amanita bisporigera

<400> SEQUENCE: 437

```
Gln Phe Leu Val Lys Asn Lys Tyr Ala Ala Gly Gly Lys Val Ala Ile
1               5                   10                  15

Asn Gly Gly Ser Asn Gly Gly
            20
```

<210> SEQ ID NO 438
<211> LENGTH: 23
<212> TYPE: PRT
<213> ORGANISM: Galerina marginata

<400> SEQUENCE: 438

```
Gln Phe Leu Val Lys Asn Lys Tyr Ala Ala Pro Gly Lys Val Ala Ile
1               5                   10                  15

Asn Gly Ala Ser Asn Gly Gly
            20
```

<210> SEQ ID NO 439

<211> LENGTH: 33
<212> TYPE: PRT
<213> ORGANISM: Amanita bisporigera

<400> SEQUENCE: 439

Phe Ser Ala Pro Phe Leu Asn Asp Asp Lys Arg Trp Tyr Trp Phe Tyr
1 5 10 15

Asn Thr Gly Leu Gln Ala Gln Thr Val Ile Cys Arg Ser Lys Asp Glu
20 25 30

Thr

<210> SEQ ID NO 440
<211> LENGTH: 38
<212> TYPE: PRT
<213> ORGANISM: Galerina marginata

<400> SEQUENCE: 440

Phe Ser Ala Pro Thr Leu Leu Asp Asp Gly His Trp Tyr Trp Phe Tyr
1 5 10 15

Asn Arg Gly Leu Gln Ser Gln Ser Gly Arg Tyr Leu Phe Ile Leu Arg
20 25 30

Arg Cys Lys Thr Gln Thr
35

<210> SEQ ID NO 441
<211> LENGTH: 13
<212> TYPE: PRT
<213> ORGANISM: Amanita bisporigera

<400> SEQUENCE: 441

Val Ile Cys Arg Ser Lys Asp Glu Thr Leu Pro Asp Phe
1 5 10

<210> SEQ ID NO 442
<211> LENGTH: 13
<212> TYPE: PRT
<213> ORGANISM: Galerina marginata

<400> SEQUENCE: 442

Val Leu Tyr Arg Ser Lys Glu Pro Ala Leu Pro Asp Phe
1 5 10

<210> SEQ ID NO 443
<211> LENGTH: 60
<212> TYPE: PRT
<213> ORGANISM: Amanita bisporigera

<400> SEQUENCE: 443

His Asp Asp Arg Val Val Pro Met His Ser Phe Lys Tyr Ala Ala Met
1 5 10 15

Leu Gln Tyr Thr Leu Pro His Asn Arg His Pro Leu Leu Leu Arg Val
20 25 30

Asp Lys Lys Ala Gly His Gly Gly Gly Lys Ser Thr Glu Lys Arg Leu
35 40 45

Gln Glu Ala Ala Asp Lys Trp Gly Phe Ala Ala Gln
50 55 60

<210> SEQ ID NO 444
<211> LENGTH: 59
<212> TYPE: PRT
<213> ORGANISM: Galerina marginata

<400> SEQUENCE: 444

Asn Asp Ser Arg Val Gln Tyr Trp Glu Ala Ala Lys Trp Val Ala Lys
1 5 10 15

Leu Arg Asp Thr Lys Thr Asp Asp His Pro Leu Leu Leu Lys Thr Glu
20 25 30

Leu Gly Ala Gly His Gly Gly Met Ser Gly Arg Tyr Gln Gly Leu Arg
35 40 45

Asp Val Ala Leu Glu Tyr Ala Phe Cys Phe Gln
50 55

<210> SEQ ID NO 445
<211> LENGTH: 4
<212> TYPE: PRT
<213> ORGANISM: Amanita bisporigera

<400> SEQUENCE: 445

Gln Ser Met Gly
1

<210> SEQ ID NO 446
<211> LENGTH: 4
<212> TYPE: PRT
<213> ORGANISM: Galerina marginata

<400> SEQUENCE: 446

Gln Gly Thr Gly
1

<210> SEQ ID NO 447
<211> LENGTH: 34
<212> TYPE: PRT
<213> ORGANISM: Amanita bisporigera

<400> SEQUENCE: 447

Arg Lys Asn Leu Leu Trp Ile Ala Asp Leu Gly Gln Asn Glu Val Gly
1 5 10 15

Arg Asn Met Lys Trp Asn Lys Ile Cys Asn Val Phe Asp Ser Glu Tyr
20 25 30

Asp Leu

<210> SEQ ID NO 448
<211> LENGTH: 34
<212> TYPE: PRT
<213> ORGANISM: Galerina marginata

<400> SEQUENCE: 448

Gln Lys Asn Leu Leu Trp Val Ala Glu Leu Asn Glu Asp Gly Val Lys
1 5 10 15

Ser Gly Ile Gln Trp Arg Lys Val Val Asn Glu Tyr Val Ala Asp Tyr
20 25 30

Asn Val

<210> SEQ ID NO 449
<211> LENGTH: 47
<212> TYPE: PRT
<213> ORGANISM: Amanita bisporigera

<400> SEQUENCE: 449

Gly Asp Asp Arg Val Val Pro Met His Ser Leu Lys Phe Val Ala Asn
1 5 10 15

Leu Gln Tyr Asn Val Pro Gln Asn Pro His Pro Leu Leu Ile Arg Val
20 25 30

Asp Lys Ser Trp Leu Gly His Gly Phe Gly Lys Thr Thr Asp Lys
35 40 45

<210> SEQ ID NO 450
<211> LENGTH: 47
<212> TYPE: PRT
<213> ORGANISM: Galerina marginata

<400> SEQUENCE: 450

Gly Asp Asp Arg Val Val Pro Met His Ser Phe Lys Phe Ile Ala Thr
1 5 10 15

Leu Gln His Asn Val Pro Gln Asn Pro His Pro Leu Leu Ile Lys Ile
20 25 30

Asp Lys Ser Trp Leu Gly His Gly Met Gly Lys Pro Thr Asp Lys
35 40 45

<210> SEQ ID NO 451
<211> LENGTH: 11
<212> TYPE: PRT
<213> ORGANISM: Amanita bisporigera

<400> SEQUENCE: 451

Lys Asp Ala Ala Asp Lys Trp Ser Phe Val Ala
1 5 10

<210> SEQ ID NO 452
<211> LENGTH: 11
<212> TYPE: PRT
<213> ORGANISM: Galerina marginata

<400> SEQUENCE: 452

Lys Asp Ala Ala Asp Lys Trp Gly Phe Ile Ala
1 5 10

<210> SEQ ID NO 453
<211> LENGTH: 34
<212> TYPE: PRT
<213> ORGANISM: Amanita bisporigera

<400> SEQUENCE: 453

Gln Val Trp Tyr Lys Ser Lys Asp Gly Thr Lys Val Pro Met Phe Ile
1 5 10 15

Val Arg His Lys Ser Thr Lys Phe Asp Gly Thr Ala Pro Ala Ile Gln
20 25 30

Asn Gly

<210> SEQ ID NO 454

<400> SEQUENCE: 454

000

<210> SEQ ID NO 455
<211> LENGTH: 20
<212> TYPE: PRT
<213> ORGANISM: Amanita bisporigera

<400> SEQUENCE: 455

Ile Leu Arg Thr Thr Lys Leu Asn Gly Leu Asn Ala Asp Asp Phe Glu
1 5 10 15

```
Ser Thr Gln Val
            20


<210> SEQ ID NO 456

<400> SEQUENCE: 456

000


<210> SEQ ID NO 457

<400> SEQUENCE: 457

000


<210> SEQ ID NO 458

<400> SEQUENCE: 458

000


<210> SEQ ID NO 459

<400> SEQUENCE: 459

000


<210> SEQ ID NO 460

<400> SEQUENCE: 460

000


<210> SEQ ID NO 461
<211> LENGTH: 53
<212> TYPE: PRT
<213> ORGANISM: Amanita bisporigera

<400> SEQUENCE: 461

Gly Val Asp Tyr Phe Thr Ile Tyr Val Arg Pro Thr Ser Ser Ser Leu
1               5                   10                  15

Ser Gln Ala Pro Glu Ala Glu Gly Gly Asp Gly Arg Leu Ser Asp Gly
            20                  25                  30

Val Lys Trp Cys Lys Phe Thr Thr Ile Thr Trp Thr Lys Asp Ser Lys
        35                  40                  45

Gly Phe Leu Tyr Gln
    50


<210> SEQ ID NO 462
<211> LENGTH: 50
<212> TYPE: PRT
<213> ORGANISM: Amanita bisporigera

<400> SEQUENCE: 462

Gly Gly Phe Ala Ile Thr Ala Asp Pro Phe Phe Ser Pro Ile Met Leu
1               5                   10                  15

Thr Phe Met Gln Thr Tyr Gly Ala Ile Leu Ala Val Pro Asn Ile Arg
            20                  25                  30

Gly Gly Gly Glu Phe Gly Gly Glu Trp His Lys Ala Gly Arg Arg Glu
        35                  40                  45

Thr Lys
    50
```

<210> SEQ ID NO 463

<400> SEQUENCE: 463

000

<210> SEQ ID NO 464

<400> SEQUENCE: 464

000

<210> SEQ ID NO 465
<211> LENGTH: 9
<212> TYPE: PRT
<213> ORGANISM: Amanita bisporigera

<400> SEQUENCE: 465

Asn Thr Phe Asp Asp Phe Ile Ala Ala
1               5

<210> SEQ ID NO 466
<211> LENGTH: 9
<212> TYPE: PRT
<213> ORGANISM: Galerina marginata

<400> SEQUENCE: 466

Asn Cys Phe Asp Asp Phe Ile Ala Ala
1               5

<210> SEQ ID NO 467
<211> LENGTH: 60
<212> TYPE: PRT
<213> ORGANISM: Amanita bisporigera

<400> SEQUENCE: 467

Ile Thr Asn His Gly Ser Leu Ile Tyr Val Lys Thr Asn Val Asn Ala
1               5                   10                  15

Pro Gln Tyr Lys Val Val Thr Ile Asp Leu Ser Thr Gly Glu Pro Glu
            20                  25                  30

Ile Arg Asp Phe Ile Pro Glu Gln Lys Asp Ala Lys Leu Thr Gln Val
        35                  40                  45

Lys Cys Val Asn Lys Gly Tyr Phe Val Ala Ile Tyr
    50                  55                  60

<210> SEQ ID NO 468

<400> SEQUENCE: 468

000

<210> SEQ ID NO 469
<211> LENGTH: 5
<212> TYPE: PRT
<213> ORGANISM: Amanita bisporigera

<400> SEQUENCE: 469

Lys Arg Asn Val Lys
1               5

<210> SEQ ID NO 470
<211> LENGTH: 5
<212> TYPE: PRT
<213> ORGANISM: Galerina marginata

<400> SEQUENCE: 470

Lys Arg Asn Val Arg
1 5

<210> SEQ ID NO 471

<400> SEQUENCE: 471

000

<210> SEQ ID NO 472

<400> SEQUENCE: 472

000

<210> SEQ ID NO 473

<400> SEQUENCE: 473

000

<210> SEQ ID NO 474

<400> SEQUENCE: 474

000

<210> SEQ ID NO 475
<211> LENGTH: 43
<212> TYPE: PRT
<213> ORGANISM: Amanita bisporigera

<400> SEQUENCE: 475

Gly Met Ala Trp Thr Ser Glu Tyr Gly Asn Pro Phe Ile Lys Glu Asp
1 5 10 15

Phe Asp Phe Val Gln Ala Leu Ser Pro Val His Asn Val Pro Lys Asp
20 25 30

Arg Val Leu Pro Ala Thr Leu Leu Met Thr Asn
35 40

<210> SEQ ID NO 476
<211> LENGTH: 60
<212> TYPE: PRT
<213> ORGANISM: Galerina marginata

<400> SEQUENCE: 476

Gly Gln Ala Trp Ile Ser Glu Tyr Gly Asn Pro Ser Ile Pro Glu Glu
1 5 10 15

Phe Asp Tyr Ile Tyr Pro Leu Ser Pro Val His Asn Val Gln Thr Asp
20 25 30

Lys Val Met Pro Ala Met Leu Ile Thr Val Asn Ile Gly Glu Gln Leu
35 40 45

Thr Ser Ser Asn Leu Ile Met Pro His Thr Arg Pro
50 55 60

<210> SEQ ID NO 477
<211> LENGTH: 10
<212> TYPE: PRT
<213> ORGANISM: Amanita bisporigera

<400> SEQUENCE: 477

Ala Gly Asp Asp Arg Val Val Pro Met His 1 5 10

<210> SEQ ID NO 478
<211> LENGTH: 11
<212> TYPE: PRT
<213> ORGANISM: Galerina marginata

<400> SEQUENCE: 478

Ser Pro Gly Asp Asp Arg Val Val Pro Met His
1 5 10

<210> SEQ ID NO 479
<211> LENGTH: 49
<212> TYPE: PRT
<213> ORGANISM: Amanita bisporigera

<400> SEQUENCE: 479

Asn Ala Gly Asp Asp Arg Val Val Pro Met His Ser Leu Lys Phe Val
1 5 10 15

Ala Asn Leu Gln Tyr Asn Val Pro Gln Asn Pro His Pro Leu Leu Ile
20 25 30

Arg Val Asp Lys Ser Trp Leu Gly His Gly Phe Gly Lys Thr Thr Asp
35 40 45

Lys

<210> SEQ ID NO 480
<211> LENGTH: 48
<212> TYPE: PRT
<213> ORGANISM: Galerina marginata

<400> SEQUENCE: 480

Asn Leu Asp Asp Asp Arg Val Val Pro Met His Ser Phe Lys Leu Ala
1 5 10 15

Ala Glu Leu Gln Tyr Ser Leu Pro His Asn Pro Asn Pro Leu Leu Ile
20 25 30

Arg Ile Asp Lys Lys Ala Gly His Gly Ala Gly Lys Ser Thr Gln Gln
35 40 45

<210> SEQ ID NO 481
<211> LENGTH: 33
<212> TYPE: PRT
<213> ORGANISM: Amanita bisporigera

<400> SEQUENCE: 481

Ala Asn Leu Gln Tyr Asn Val Pro Gln Asn Pro His Pro Leu Leu Ile
1 5 10 15

Arg Val Asp Lys Ser Trp Leu Gly His Gly Phe Gly Lys Thr Thr Asp
20 25 30

Lys

<210> SEQ ID NO 482
<211> LENGTH: 32
<212> TYPE: PRT
<213> ORGANISM: Galerina marginata

<400> SEQUENCE: 482

Ala Glu Leu Gln Tyr Ser Leu Pro His Asn Pro Asn Pro Leu Leu Ile
1 5 10 15

Arg Ile Asp Lys Lys Thr Gly His Gly Ala Gly Lys Ser Thr Gln Gln
20 25 30

<210> SEQ ID NO 483
<211> LENGTH: 19
<212> TYPE: PRT
<213> ORGANISM: Amanita bisporigera

<400> SEQUENCE: 483

Lys Asp Ala Ala Asp Lys Trp Ser Phe Val Ala Gln Ser Leu Gly Leu
1 5 10 15

Glu Trp Lys

<210> SEQ ID NO 484
<211> LENGTH: 19
<212> TYPE: PRT
<213> ORGANISM: Galerina marginata

<400> SEQUENCE: 484

Lys Glu Ser Ala Asp Lys Trp Gly Phe Val Ala Gln Ser Leu Gly Leu
1 5 10 15

Val Trp Lys

<210> SEQ ID NO 485
<211> LENGTH: 27
<212> TYPE: PRT
<213> ORGANISM: Amanita bisporigera

<400> SEQUENCE: 485

Phe Ser Ala Pro Thr Leu Leu Asp Ser Gly His Trp Tyr Trp Phe Tyr
1 5 10 15

Asn Ser Gly Val Gln Ser Gln Ala Val Leu Tyr
20 25

<210> SEQ ID NO 486
<211> LENGTH: 27
<212> TYPE: PRT
<213> ORGANISM: Galerina marginata

<400> SEQUENCE: 486

Phe Ser Ala Pro Thr Leu Leu Asp Asp Gly His Trp Tyr Trp Phe Tyr
1 5 10 15

Asn Arg Gly Leu Gln Ser Gln Ser Gly Arg Tyr
20 25

<210> SEQ ID NO 487
<211> LENGTH: 13
<212> TYPE: PRT
<213> ORGANISM: Amanita bisporigera

<400> SEQUENCE: 487

Val Leu Tyr Arg Ser Lys Lys Pro Val Leu Pro Asp Phe
1 5 10

<210> SEQ ID NO 488

<400> SEQUENCE: 488

000

<210> SEQ ID NO 489
<211> LENGTH: 28
<212> TYPE: PRT
<213> ORGANISM: Amanita bisporigera

<400> SEQUENCE: 489

```
Arg Ala Pro Glu Gly Thr Phe Gly Ala Ala Val Ser Glu Gly Gly Val
1               5                   10                  15

Ala Asp Leu Leu Lys Phe Asn Lys Phe Thr Gly Gly
            20                  25
```

<210> SEQ ID NO 490
<211> LENGTH: 46
<212> TYPE: PRT
<213> ORGANISM: Galerina marginata

<400> SEQUENCE: 490

```
Arg Ala Pro Glu Gly Thr Phe Gly Ala Ala Val Pro Glu Gly Gly Val
1               5                   10                  15

Ala Asp Leu Leu Lys Val Val Phe Val Phe Gln Leu Cys Asn Ser Gln
            20                  25                  30

Ser Leu Ile Leu Thr Leu Gln Phe His Lys Phe Thr Gly Gly
        35                  40                  45
```

<210> SEQ ID NO 491
<211> LENGTH: 19
<212> TYPE: PRT
<213> ORGANISM: Amanita bisporigera

<400> SEQUENCE: 491

```
Thr Gly Gly Met Ala Trp Thr Ser Glu Tyr Gly Asn Pro Phe Ile Lys
1               5                   10                  15

Glu Asp Phe
```

<210> SEQ ID NO 492
<211> LENGTH: 19
<212> TYPE: PRT
<213> ORGANISM: Galerina marginata

<400> SEQUENCE: 492

```
Ser Ser Gly Gln Ala Trp Ile Ser Glu Tyr Gly Asn Pro Ser Ile Pro
1               5                   10                  15

Glu Glu Phe
```

<210> SEQ ID NO 493
<211> LENGTH: 60
<212> TYPE: PRT
<213> ORGANISM: Amanita bisporigera

<400> SEQUENCE: 493

```
Ala Val Pro Asn Ile Arg Gly Gly Gly Glu Phe Gly Gly Glu Trp His
1               5                   10                  15

Lys Ala Gly Arg Arg Glu Thr Lys Gly Asn Thr Phe Asp Asp Phe Ile
            20                  25                  30

Ala Ala Ala Gln Phe Leu Val Lys Asn Lys Tyr Ala Ala Pro Gly Lys
        35                  40                  45

Val Ala Ile Thr Gly Ala Ser Asn Gly Gly Phe Leu
    50                  55                  60
```

<210> SEQ ID NO 494

<400> SEQUENCE: 494

000

<210> SEQ ID NO 495

<211> LENGTH: 5
<212> TYPE: PRT
<213> ORGANISM: Amanita bisporigera

<400> SEQUENCE: 495

Gly Gly Phe Leu Val
1               5

<210> SEQ ID NO 496
<211> LENGTH: 5
<212> TYPE: PRT
<213> ORGANISM: Galerina marginata

<400> SEQUENCE: 496

Gly Gly Met Leu Met
1               5

<210> SEQ ID NO 497
<211> LENGTH: 27
<212> TYPE: PRT
<213> ORGANISM: Amanita bisporigera

<400> SEQUENCE: 497

Glu Asp Ile Ile Val Gln Gln Asp Lys Glu Asn Pro Asp Trp Thr Tyr
1               5                   10                  15

Gly Thr Asp Ala Ser Glu Asp Gly Lys Tyr Ile
            20                  25

<210> SEQ ID NO 498

<400> SEQUENCE: 498

000

<210> SEQ ID NO 499
<211> LENGTH: 13
<212> TYPE: PRT
<213> ORGANISM: Amanita bisporigera

<400> SEQUENCE: 499

Met Val Cys Tyr His Arg Val Gly Thr Thr Gln Leu Glu
1               5                   10

<210> SEQ ID NO 500

<400> SEQUENCE: 500

000

<210> SEQ ID NO 501
<211> LENGTH: 34
<212> TYPE: PRT
<213> ORGANISM: Amanita bisporigera

<400> SEQUENCE: 501

Lys Gln Asn Leu Leu Trp Val Ala Glu Phe Asp Lys Asp Gly Val Lys
1               5                   10                  15

Pro Glu Ile Pro Trp Arg Lys Val Ile Asn Glu Phe Gly Ala Asp Tyr
            20                  25                  30

His Val

<210> SEQ ID NO 502

<400> SEQUENCE: 502

000

<210> SEQ ID NO 503
<211> LENGTH: 54
<212> TYPE: PRT
<213> ORGANISM: Amanita bisporigera

<400> SEQUENCE: 503

Asp Tyr Phe Thr Ile Tyr Val Arg Pro Thr Ser Ser Ser Leu Ser Gln
1 5 10 15

Ala Pro Glu Ala Glu Gly Gly Asp Gly Arg Leu Ser Asp Gly Val Lys
20 25 30

Trp Cys Lys Phe Thr Thr Ile Thr Trp Thr Lys Asp Ser Lys Gly Phe
35 40 45

Leu Tyr Gln Arg Tyr Pro
50

<210> SEQ ID NO 504
<211> LENGTH: 54
<212> TYPE: PRT
<213> ORGANISM: Galerina marginata

<400> SEQUENCE: 504

Asp Phe Val Thr Ile Tyr Val Trp Ser Thr Asp Ser Pro Leu Thr Asn
1 5 10 15

Asp Val Asp Ser Lys Asn Asp Lys Gly Arg Leu Pro Glu Glu Ile Lys
20 25 30

Phe Val Lys Phe Ser Ser Ile Gly Trp Thr Pro Asp Ser Lys Gly Phe
35 40 45

Phe Ile Arg Ser Ile Pro
50

<210> SEQ ID NO 505
<211> LENGTH: 60
<212> TYPE: PRT
<213> ORGANISM: Amanita bisporigera

<400> SEQUENCE: 505

His Ser Phe Leu Thr Phe Ser Gly Phe Asn Thr Pro Gly Thr Ile Ser
1 5 10 15

Arg Tyr Asp Phe Thr Ala Pro Asp Thr Gln Arg Leu Ser Ile Leu Arg
20 25 30

Thr Thr Lys Leu Asn Gly Leu Asn Ala Asp Asp Phe Glu Ser Thr Gln
35 40 45

Val Trp Tyr Lys Ser Lys Asp Gly Thr Lys Val Pro
50 55 60

<210> SEQ ID NO 506
<211> LENGTH: 58
<212> TYPE: PRT
<213> ORGANISM: Galerina marginata

<400> SEQUENCE: 506

His Ile Arg Leu Arg Tyr Glu Ala Leu Asn Arg Pro Ala Gln Ile Arg
1 5 10 15

Arg Leu Ala Leu Ala Asp Gly Ala Gln Gln Val Leu Lys Glu Thr Pro
20 25 30

Val Leu Gly Val Phe Asn Ala Asp Asp Tyr Val Ser Gln Arg Leu Trp
35 40 45

```
Ala Thr Ser Val Asp Gly Thr Gln Val Pro
    50                  55


<210> SEQ ID NO 507
<211> LENGTH: 33
<212> TYPE: PRT
<213> ORGANISM: Amanita bisporigera

<400> SEQUENCE: 507

Ile Ser Leu Val Val Arg His Asp Gln Leu Gly Gln Pro Thr Pro Leu
1               5                   10                  15

Tyr Leu Tyr Gly Tyr Gly Ala Tyr Gly His Ser Leu Asp Pro Trp Phe
            20                  25                  30

Ser


<210> SEQ ID NO 508
<211> LENGTH: 34
<212> TYPE: PRT
<213> ORGANISM: Galerina marginata

<400> SEQUENCE: 508

Met Phe Ile Val Arg His Lys Ser Thr Lys Phe Asp Gly Thr Ala Pro
1               5                   10                  15

Ala Ile Gln Asn Gly Tyr Gly Gly Phe Ala Ile Thr Ala Asp Pro Phe
            20                  25                  30

Phe Ser


<210> SEQ ID NO 509
<211> LENGTH: 30
<212> TYPE: PRT
<213> ORGANISM: Amanita bisporigera

<400> SEQUENCE: 509

Met Pro Pro Thr Pro Trp Ala Pro His Ser Tyr Pro Pro Thr Arg Arg
1               5                   10                  15

Ser Asp His Val Asp Val Tyr Gln Ser Ala Ser Arg Gly Glu
            20                  25                  30


<210> SEQ ID NO 510

<400> SEQUENCE: 510

000


<210> SEQ ID NO 511
<211> LENGTH: 41
<212> TYPE: PRT
<213> ORGANISM: Amanita bisporigera

<400> SEQUENCE: 511

Lys Phe Ser Ala Pro Thr Leu Leu Asp Ser Gly His Trp Tyr Trp Phe
1               5                   10                  15

Tyr Asn Ser Gly Val Gln Ser Gln Ala Val Leu Tyr Arg Ser Lys Lys
            20                  25                  30

Pro Val Leu Pro Asp Phe Gln Arg Gly
        35                  40


<210> SEQ ID NO 512

<400> SEQUENCE: 512
```

000

<210> SEQ ID NO 513
<211> LENGTH: 17
<212> TYPE: PRT
<213> ORGANISM: Amanita bisporigera

<400> SEQUENCE: 513

Thr Arg Lys Val Gly Glu Val Tyr Phe Asp Pro Asn Val Leu Ser Ala
1 5 10 15

Asp

<210> SEQ ID NO 514

<400> SEQUENCE: 514

000

<210> SEQ ID NO 515
<211> LENGTH: 23
<212> TYPE: PRT
<213> ORGANISM: Amanita bisporigera

<400> SEQUENCE: 515

Gln Phe Leu Val Lys Asn Lys Tyr Ala Ala Pro Gly Lys Val Ala Ile
1 5 10 15

Thr Gly Ala Ser Asn Gly Gly
20

<210> SEQ ID NO 516

<400> SEQUENCE: 516

000

<210> SEQ ID NO 517

<400> SEQUENCE: 517

000

<210> SEQ ID NO 518

<400> SEQUENCE: 518

000

<210> SEQ ID NO 519
<211> LENGTH: 37
<212> TYPE: PRT
<213> ORGANISM: Amanita bisporigera

<400> SEQUENCE: 519

Glu Asp Ile Ile Val Gln Gln Asp Lys Glu Asn Pro Asp Trp Thr Tyr
1 5 10 15

Gly Thr Asp Ala Ser Glu Asp Gly Lys Tyr Ile Tyr Leu Val Val Tyr
20 25 30

Lys Asp Ala Ser Lys
35

<210> SEQ ID NO 520
<211> LENGTH: 37
<212> TYPE: PRT
<213> ORGANISM: Galerina marginata

<400> SEQUENCE: 520

Glu Asp Ser Leu Ile Tyr Gln Asp Arg Glu His Arg Asp Trp Met Phe
1 5 10 15

Ser Ile Asp Val Thr Asp Asp Gly Asn Tyr Leu Leu Leu Tyr Ile Leu
20 25 30

Lys Asp Ser Ser Arg
35

<210> SEQ ID NO 521
<211> LENGTH: 30
<212> TYPE: DNA
<213> ORGANISM: Rattus norvegicus

<400> SEQUENCE: 521
tgtcaaccgt ctcctctgtc gtttcctttg 30

<210> SEQ ID NO 522
<211> LENGTH: 33
<212> TYPE: PRT
<213> ORGANISM: Agrobacterium tumefaciens

<400> SEQUENCE: 522

Thr Cys Thr Gly Thr Gly Ala Cys Gly Ala Thr Gly Thr Cys Ala Thr
1 5 10 15

Cys Cys Ala Gly Thr Cys Thr Cys Thr Cys Ala Cys Thr Cys Gly Thr
20 25 30

Ala

<210> SEQ ID NO 523
<211> LENGTH: 23
<212> TYPE: DNA
<213> ORGANISM: Vitis vinifera

<400> SEQUENCE: 523
ttgtagactg cccatgcgtc tgt 23

<210> SEQ ID NO 524
<211> LENGTH: 30
<212> TYPE: DNA
<213> ORGANISM: Amanita bisporigera

<400> SEQUENCE: 524
atgtctgaca tcaatgctac ccgtctcccc 30

<210> SEQ ID NO 525
<211> LENGTH: 45
<212> TYPE: DNA
<213> ORGANISM: Amanita bisporigera

<400> SEQUENCE: 525
tgcatcggtg acgacgtcac tactctcctc actcgtgccc tttgt 45

<210> SEQ ID NO 526
<211> LENGTH: 17
<212> TYPE: PRT
<213> ORGANISM: Salmo salar

<400> SEQUENCE: 526

Ala Thr Cys Gly Gly Thr Gly Ala Cys Gly Ala Cys Gly Thr Cys Ala
1 5 10 15

Cys

<210> SEQ ID NO 527
<211> LENGTH: 17
<212> TYPE: DNA
<213> ORGANISM: Burkholderia cenocepacia

<400> SEQUENCE: 527
atcggtgacg acgtcac 17

<210> SEQ ID NO 528
<211> LENGTH: 26
<212> TYPE: DNA
<213> ORGANISM: Chaetomium globosum

<400> SEQUENCE: 528
ggtgacgatg acaaccgcct cctcac 26

<210> SEQ ID NO 529
<211> LENGTH: 18
<212> TYPE: DNA
<213> ORGANISM: Chaetomium globosum

<400> SEQUENCE: 529
ctcctcactc gtgccctt 18

<210> SEQ ID NO 530
<211> LENGTH: 18
<212> TYPE: DNA
<213> ORGANISM: Ciona intestinalis

<400> SEQUENCE: 530
atgtctgaca tcaatgct 18

<210> SEQ ID NO 531
<211> LENGTH: 17
<212> TYPE: DNA
<213> ORGANISM: Ciona intestinalis

<400> SEQUENCE: 531
atgtctgaca tcaatgc 17

<210> SEQ ID NO 532
<211> LENGTH: 16
<212> TYPE: DNA
<213> ORGANISM: Aspergillus oryzae

<400> SEQUENCE: 532
ctgacatcaa tgctac 16

<210> SEQ ID NO 533
<211> LENGTH: 18
<212> TYPE: DNA
<213> ORGANISM: Oryza sativa

<400> SEQUENCE: 533
tctgacatca atgccacc 18

<210> SEQ ID NO 534
<211> LENGTH: 6
<212> TYPE: PRT
<213> ORGANISM: Amanita bisporigera

<400> SEQUENCE: 534

Cys Val Gly Asp Asp Val
1 5

<210> SEQ ID NO 535

<400> SEQUENCE: 535

000

<210> SEQ ID NO 536
<211> LENGTH: 19
<212> TYPE: DNA
<213> ORGANISM: Homo sapiens

<400> SEQUENCE: 536
atgtctgaca tcaatgcca 19

<210> SEQ ID NO 537
<211> LENGTH: 16
<212> TYPE: DNA
<213> ORGANISM: Neurospora crassa

<400> SEQUENCE: 537
tgtctgacat caatgc 16

<210> SEQ ID NO 538
<211> LENGTH: 17
<212> TYPE: DNA
<213> ORGANISM: Homo sapiens

<400> SEQUENCE: 538
gtctgacatc aatgcca 17

<210> SEQ ID NO 539

<400> SEQUENCE: 539

000

<210> SEQ ID NO 540
<211> LENGTH: 21
<212> TYPE: DNA
<213> ORGANISM: Otolemur garnettii

<400> SEQUENCE: 540
tgtctgacat caatgccacc c 21

<210> SEQ ID NO 541
<211> LENGTH: 21
<212> TYPE: DNA
<213> ORGANISM: Phytophthora sojae

<400> SEQUENCE: 541
cggtgacgat gtcaaccgtc t 21

<210> SEQ ID NO 542
<211> LENGTH: 19
<212> TYPE: DNA
<213> ORGANISM: Mus musculus

<400> SEQUENCE: 542
atgtctgaca tcaatgcca 19

<210> SEQ ID NO 543
<211> LENGTH: 17
<212> TYPE: DNA
<213> ORGANISM: Helianthus annuus

<400> SEQUENCE: 543
aatgccaccc gtcttcc 17

<210> SEQ ID NO 544
<211> LENGTH: 20
<212> TYPE: PRT
<213> ORGANISM: Amanita bisporigera

<400> SEQUENCE: 544

Gly Cys Asn Gly Tyr Arg Ala Thr Asn Gly Ala Arg Thr Gly Asn Cys
1 5 10 15

Cys Asn Cys Cys
20

<210> SEQ ID NO 545
<211> LENGTH: 25
<212> TYPE: DNA
<213> ORGANISM: Gibberella zeae

<400> SEQUENCE: 545
cgtcggtgac gatgtcctcc gtctc 25

<210> SEQ ID NO 546
<211> LENGTH: 18
<212> TYPE: DNA
<213> ORGANISM: Homo sapiens

<400> SEQUENCE: 546
tcactactct cctcactc 18

<210> SEQ ID NO 547
<211> LENGTH: 17
<212> TYPE: DNA
<213> ORGANISM: Ornithorhynchus anatinus

<400> SEQUENCE: 547
acgtcactac tctcctc 17

<210> SEQ ID NO 548
<211> LENGTH: 18
<212> TYPE: DNA
<213> ORGANISM: Ostreococcus lucimarinus

<400> SEQUENCE: 548
gcatcggtga cgacgtca 18

<210> SEQ ID NO 549
<211> LENGTH: 16
<212> TYPE: PRT
<213> ORGANISM: Amanita bisporigera

<400> SEQUENCE: 549

Thr Arg Leu Pro Ile Trp Gly Ile Gly Cys Asn Pro Cys Ile Gly Asp
1 5 10 15

<210> SEQ ID NO 550

<400> SEQUENCE: 550

000

<210> SEQ ID NO 551
<211> LENGTH: 12
<212> TYPE: PRT
<213> ORGANISM: Amanita bisporigera

<400> SEQUENCE: 551

Thr Arg Leu Pro Ile Trp Gly Ile Gly Cys Asn Pro
1               5                   10

<210> SEQ ID NO 552
<211> LENGTH: 12
<212> TYPE: PRT
<213> ORGANISM: Amanita bisporigera

<400> SEQUENCE: 552

Ile Trp Gly Ile Gly Cys Asn Pro Cys Ile Gly Asp
1               5                   10

<210> SEQ ID NO 553

<400> SEQUENCE: 553

000

<210> SEQ ID NO 554

<400> SEQUENCE: 554

000

<210> SEQ ID NO 555

<400> SEQUENCE: 555

000

<210> SEQ ID NO 556

<400> SEQUENCE: 556

000

<210> SEQ ID NO 557

<400> SEQUENCE: 557

000

<210> SEQ ID NO 558
<211> LENGTH: 45
<212> TYPE: DNA
<213> ORGANISM: Amanita bisporigera

<400> SEQUENCE: 558
tgcgtcggtg acgatgtcaa ccgtctcctc actcgtagcc tttgg                     45

<210> SEQ ID NO 559
<211> LENGTH: 35
<212> TYPE: PRT
<213> ORGANISM: Amanita bisporigera

<400> SEQUENCE: 559

Met Ser Asp Ile Asn Ala Thr Arg Leu Pro Ile Trp Gly Ile Gly Cys
1               5                   10                  15

Asn Pro Cys Ile Gly Asp Asp Val Thr Thr Leu Leu Thr Arg Gly Glu
20 25 30

Ala Leu Cys
35

<210> SEQ ID NO 560
<211> LENGTH: 17
<212> TYPE: PRT
<213> ORGANISM: Amanita bisporigera

<400> SEQUENCE: 560

Ala Thr Arg Leu Pro Ala Trp Leu Val Asp Cys Pro Cys Val Gly Asp
1 5 10 15

Asp

<210> SEQ ID NO 561
<211> LENGTH: 17
<212> TYPE: DNA
<213> ORGANISM: Rattus norvegicus

<400> SEQUENCE: 561
acgtcactac tctcctc 17

<210> SEQ ID NO 562
<211> LENGTH: 18
<212> TYPE: DNA
<213> ORGANISM: Amanita bisporigera

<400> SEQUENCE: 562
caatgccacc cgtcttcc 18

<210> SEQ ID NO 563
<211> LENGTH: 20
<212> TYPE: DNA
<213> ORGANISM: Strongylocentrotus purpuratus

<400> SEQUENCE: 563
tgtctgacat caatggtacc 20

<210> SEQ ID NO 564
<211> LENGTH: 17
<212> TYPE: DNA
<213> ORGANISM: Monodelphis domestica

<400> SEQUENCE: 564
gtctgacatc aatgcta 17

<210> SEQ ID NO 565
<211> LENGTH: 16
<212> TYPE: DNA
<213> ORGANISM: Aspergillus nidulans

<400> SEQUENCE: 565
tgtctgacat caatgc 16

<210> SEQ ID NO 566
<211> LENGTH: 18
<212> TYPE: DNA
<213> ORGANISM: Aspergillus nidulans

<400> SEQUENCE: 566
tgtctgacat caatgcca 18

<210> SEQ ID NO 567
<211> LENGTH: 21
<212> TYPE: DNA
<213> ORGANISM: Ustilago maydis

<400> SEQUENCE: 567
catcaatgcc acccgccttc c 21

<210> SEQ ID NO 568
<211> LENGTH: 16
<212> TYPE: DNA
<213> ORGANISM: Amanita bisporigera

<400> SEQUENCE: 568
aatgctaccc gtctcc 16

<210> SEQ ID NO 569
<211> LENGTH: 14
<212> TYPE: PRT
<213> ORGANISM: Ustilago maydis

<400> SEQUENCE: 569

Gly Asp Asp Val Ala Ala Leu Leu Ser Arg Arg Val Leu Cys
1 5 10

<210> SEQ ID NO 570
<211> LENGTH: 12
<212> TYPE: PRT
<213> ORGANISM: Prosthecochloris aestuarii

<400> SEQUENCE: 570

Gly Asp Asp Val Glu Thr Ile Leu Thr Arg Leu Leu
1 5 10

<210> SEQ ID NO 571
<211> LENGTH: 21
<212> TYPE: DNA
<213> ORGANISM: Rhizobium leguminosarum

<400> SEQUENCE: 571
cgtcggtgac gaggtcaacc g 21

<210> SEQ ID NO 572
<211> LENGTH: 32
<212> TYPE: DNA
<213> ORGANISM: Rhodococcus

<400> SEQUENCE: 572
cgggtacaac acgtgcatcg gtgacgccgt ca 32

<210> SEQ ID NO 573
<211> LENGTH: 19
<212> TYPE: DNA
<213> ORGANISM: Strongylocentrotus purpuratus

<400> SEQUENCE: 573
catcggtgac gacgtcact 19

<210> SEQ ID NO 574
<211> LENGTH: 19
<212> TYPE: DNA
<213> ORGANISM: Amanita bisporigera

<400> SEQUENCE: 574
gatgtcaacc gtctcctca 19

<210> SEQ ID NO 575
<211> LENGTH: 10
<212> TYPE: PRT
<213> ORGANISM: Amanita bisporigera

<400> SEQUENCE: 575

Met Ser Asp Ile Asn Thr Ala Arg Leu Pro
1 5 10

<210> SEQ ID NO 576

<400> SEQUENCE: 576

000

<210> SEQ ID NO 577

<400> SEQUENCE: 577

000

<210> SEQ ID NO 578
<211> LENGTH: 28
<212> TYPE: DNA
<213> ORGANISM: Gibberella zeae

<400> SEQUENCE: 578
cgtcggtgac gatgtcctcc gtctcttc 28

<210> SEQ ID NO 579
<211> LENGTH: 33
<212> TYPE: DNA
<213> ORGANISM: Danio rerio

<400> SEQUENCE: 579
cgacactacc ctcaccactc gtgcccttag tta 33

<210> SEQ ID NO 580
<211> LENGTH: 33
<212> TYPE: DNA
<213> ORGANISM: Mycobacterium avium

<400> SEQUENCE: 580
cgtcggtgac gatgtacacc gtcgccacgc tcg 33

<210> SEQ ID NO 581
<211> LENGTH: 15
<212> TYPE: PRT
<213> ORGANISM: Amanita bisporigera
<220> FEATURE:
<221> NAME/KEY: misc_feature
<222> LOCATION: (7)..(8)
<223> OTHER INFORMATION: Xaa can be any naturally occurring amino acid

<400> SEQUENCE: 581

Cys Val Gly Asp Asp Val Xaa Xaa Leu Leu Thr Arg Ala Leu Cys
1 5 10 15

<210> SEQ ID NO 582
<211> LENGTH: 10
<212> TYPE: PRT
<213> ORGANISM: Botryotinia fuckeliana

<400> SEQUENCE: 582

Met Arg Glu Ile Asn Ser Thr Arg Leu Pro
1 5 10

<210> SEQ ID NO 583
<211> LENGTH: 10
<212> TYPE: PRT
<213> ORGANISM: Frankia

<400> SEQUENCE: 583

Met Ser Asn Ile Ala Ala Pro Arg Leu Pro
1 5 10

<210> SEQ ID NO 584
<211> LENGTH: 13
<212> TYPE: PRT
<213> ORGANISM: Coprinopsis cinerea

<400> SEQUENCE: 584

Met Ser Asp Ile Ala Trp His Pro Asp Asn Ala Thr Arg
1 5 10

<210> SEQ ID NO 585
<211> LENGTH: 9
<212> TYPE: PRT
<213> ORGANISM: Ustilago maydis

<400> SEQUENCE: 585

Ser Asp Val Asn Ala Pro Arg Leu Pro
1 5

<210> SEQ ID NO 586
<211> LENGTH: 8
<212> TYPE: PRT
<213> ORGANISM: Saccharopolyspora erythraea

<400> SEQUENCE: 586

Ser Asp Ile Ala Thr Arg Leu Pro
1 5

<210> SEQ ID NO 587
<211> LENGTH: 5
<212> TYPE: PRT
<213> ORGANISM: Amanita bisporigera

<400> SEQUENCE: 587

Met Ser Asp Ile Asn
1 5

<210> SEQ ID NO 588
<211> LENGTH: 60
<212> TYPE: PRT
<213> ORGANISM: Amanita bisporigera

<400> SEQUENCE: 588

Gly Val Ala Ser Ile Thr Asn Arg Glu Lys Gln Pro His Ser Phe Leu
1 5 10 15

Thr Phe Ser Gly Phe Asn Thr Pro Gly Thr Ile Ser Arg Tyr Asp Phe
20 25 30

Thr Ala Pro Asp Thr Gln Arg Leu Ser Ile Leu Arg Thr Thr Lys Leu
35 40 45

Asn Gly Leu Asn Ala Asp Asp Phe Glu Ser Thr Gln 50 55 60

<210> SEQ ID NO 589
<211> LENGTH: 10
<212> TYPE: PRT
<213> ORGANISM: Amanita bisporigera

<400> SEQUENCE: 589

Val Trp Tyr Lys Ser Lys Asp Gly Thr Lys
1 5 10

<210> SEQ ID NO 590
<211> LENGTH: 15
<212> TYPE: PRT
<213> ORGANISM: Amanita bisporigera

<400> SEQUENCE: 590

Lys Asp Gly Thr Lys Val Pro Met Phe Ile Val Arg His Lys Ser
1 5 10 15

<210> SEQ ID NO 591
<211> LENGTH: 15
<212> TYPE: PRT
<213> ORGANISM: Amanita bisporigera

<400> SEQUENCE: 591

Ala Asp Arg Gln Lys Leu Glu Glu Lys Phe Arg Ala Ser Lys Asp
1 5 10 15

<210> SEQ ID NO 592
<211> LENGTH: 15
<212> TYPE: PRT
<213> ORGANISM: Galerina marginata

<400> SEQUENCE: 592

Ala Asp Ile Gln Lys Leu Ala Asp Lys Phe Arg Ala Ser Arg Asn
1 5 10 15

<210> SEQ ID NO 593
<211> LENGTH: 60
<212> TYPE: PRT
<213> ORGANISM: Amanita bisporigera

<400> SEQUENCE: 593

Val Asp Val Tyr Gln Ser Ala Ser Arg Gly Glu Val Pro Val Pro Asp
1 5 10 15

Pro Tyr Gln Trp Leu Glu Glu Asn Ser Asn Glu Val Asp Glu Trp Thr
20 25 30

Thr Ala Gln Thr Ala Phe Thr Gln Gly Tyr Leu Asp Lys Asn Ala Asp
35 40 45

Arg Gln Lys Leu Glu Glu Lys Phe Arg Ala Ser Lys
50 55 60

<210> SEQ ID NO 594
<211> LENGTH: 10
<212> TYPE: PRT
<213> ORGANISM: Amanita bisporigera

<400> SEQUENCE: 594

Asp Tyr Val Lys Phe Ser Ala Pro Thr Leu
1 5 10

<210> SEQ ID NO 595

<211> LENGTH: 10
<212> TYPE: PRT
<213> ORGANISM: Galerina marginata

<400> SEQUENCE: 595

Asp Tyr Pro Lys Val Leu Ser Ala Thr Ile
1 5 10

<210> SEQ ID NO 596
<211> LENGTH: 1572
<212> TYPE: DNA
<213> ORGANISM: Galerina marginata

<400> SEQUENCE: 596
atggtcgact tgcacaccat ctcgtattca gctctcgtca ctttcaggct tatattccaa 60
ttcctcaagc tatctgcagc tgcattgact atctatggac tttacagagt cactcgtgta 120
atttatgttg agctgacttc tccaatacgc catctccccg gtccagcaaa cgccaatata 180
tttcttggta atctcaaaca gctctggaca gatctttcgc atttatatgt gacggatccg 240
caggccttga accacatttt gacgaatggt tacgtttaca ccaaaccatc gtttactcgc 300
cgccagatcg gcaagttgtg gggtccaggt ctcccttttg tcgaagggga tcaacataaa 360
aagcagcgga agattttggt gactatctat ccattccaaa tcgtggtcca tcagtgtctc 420
aatcacaacc agaatcctgc ctttggtccg ctccaagact cttgggctac tgaatgctcg 480
aaacaaggtg gtacttgccg cttagacatt atggtaggcc ttggtaaggt ggtgatggac 540
atcatcagct caacagtgtt taccgatgcc attcgatgga aaggcttccg ttacgagctt 600
gattccctgg atcgtgaaag tgactttagc cgtgtggcta caattttatc tcaattgaac 660
ctgattcgtt ggcaactccg aagattcatc ccacttctat ggttcatacc tgatcctgta 720
gagacacaac tagacgatat caagcagacc ctttctcgga ttacgagtcg gcttctgaac 780
gagagcaagg gatccgtacg tacgaataat gacaattccg gcagtcgaga tctcctatcg 840
cttttggttc gcaccaatat gtcccccgat gtgccagagc accgtcgtct atccgatgac 900
gaagtcaaag cgcaggttat ctcatttgta attgctggac gtgaaagtcc gattaacgta 960
atggcgtggg ctttatttc tctggcaaaa aaccgtgaaa tccaggctaa gctgcgtaga 1020
gagctgctca cggtcgatac ctgtcagcca acgacggacc agctcaatgc actttcatat 1080
ttggatatgg taattaggga gacgctacgc cactcgaggg tgtgtgccaa ggacgacatt 1140
ttacctttgg ctaagccgat caccgaccgg agaggaaacc tattctccag tattagtatc 1200
aaaagagggc aagtagtcat aattcccatt tctgccatcc acaaggacaa gtcgatatgg 1260
ggtgaagatg ctttagactt cagaccagaa cgatgggaat gtctacctga aggcgtcaat 1320
accatcccag gcgtctggag ccatttgctc agtttttggg gtggtccacg ttcgtgtatc 1380
ggattcagat ttgctatcgc cgaaatgaaa gctctactct tcacactagt ccgtgccctc 1440
gaatttgact tggctgtgcc agcggagcaa atttctgtgg aaagtggact aagtaaccga 1500
ccgattttga ccacggaccc gggccgttat cagctcccgc tgctcatcaa gccatataaa 1560
gctcgaagtt aa 1572

<210> SEQ ID NO 597
<211> LENGTH: 523
<212> TYPE: PRT
<213> ORGANISM: Galerina marginata

<400> SEQUENCE: 597

```
Met Val Asp Leu His Thr Ile Ser Tyr Ser Ala Leu Val Thr Phe Arg
1               5                   10                  15

Leu Ile Phe Gln Phe Leu Lys Leu Ser Ala Ala Ala Leu Thr Ile Tyr
            20                  25                  30

Gly Leu Tyr Arg Val Thr Arg Val Ile Tyr Val Glu Leu Thr Ser Pro
        35                  40                  45

Ile Arg His Leu Pro Gly Pro Ala Asn Ala Asn Ile Phe Leu Gly Asn
    50                  55                  60

Leu Lys Gln Leu Trp Thr Asp Leu Ser His Leu Tyr Val Thr Asp Pro
65                  70                  75                  80

Gln Ala Leu Asn His Ile Leu Thr Asn Gly Tyr Val Tyr Thr Lys Pro
                85                  90                  95

Ser Phe Thr Arg Arg Gln Ile Gly Lys Leu Trp Gly Pro Gly Leu Pro
            100                 105                 110

Phe Val Glu Gly Asp Gln His Lys Lys Gln Arg Lys Ile Leu Val Thr
        115                 120                 125

Ile Tyr Pro Phe Gln Ile Val Val His Gln Cys Leu Asn His Asn Gln
    130                 135                 140

Asn Pro Ala Phe Gly Pro Leu Gln Asp Ser Trp Ala Thr Glu Cys Ser
145                 150                 155                 160

Lys Gln Gly Gly Thr Cys Arg Leu Asp Ile Met Val Gly Leu Gly Lys
                165                 170                 175

Val Val Met Asp Ile Ile Ser Ser Thr Val Phe Thr Asp Ala Ile Arg
            180                 185                 190

Trp Lys Gly Phe Arg Tyr Glu Leu Asp Ser Leu Asp Arg Glu Ser Asp
        195                 200                 205

Phe Ser Arg Val Ala Thr Ile Leu Ser Gln Leu Asn Leu Ile Arg Trp
    210                 215                 220

Gln Leu Arg Arg Phe Ile Pro Leu Leu Trp Phe Ile Pro Asp Pro Val
225                 230                 235                 240

Glu Thr Gln Leu Asp Asp Ile Lys Gln Thr Leu Ser Arg Ile Thr Ser
                245                 250                 255

Arg Leu Leu Asn Glu Ser Lys Gly Ser Val Arg Thr Asn Asn Asp Asn
            260                 265                 270

Ser Gly Ser Arg Asp Leu Leu Ser Leu Leu Val Arg Thr Asn Met Ser
        275                 280                 285

Pro Asp Val Pro Glu His Arg Arg Leu Ser Asp Asp Glu Val Lys Ala
    290                 295                 300

Gln Val Ile Ser Phe Val Ile Ala Gly Arg Glu Ser Pro Ile Asn Val
305                 310                 315                 320

Met Ala Trp Ala Leu Phe Ser Leu Ala Lys Asn Arg Glu Ile Gln Ala
                325                 330                 335

Lys Leu Arg Arg Glu Leu Leu Thr Val Asp Thr Cys Gln Pro Thr Thr
            340                 345                 350

Asp Gln Leu Asn Ala Leu Ser Tyr Leu Asp Met Val Ile Arg Glu Thr
        355                 360                 365

Leu Arg His Ser Arg Val Cys Ala Lys Asp Asp Ile Leu Pro Leu Ala
    370                 375                 380

Lys Pro Ile Thr Asp Arg Arg Gly Asn Leu Phe Ser Ser Ile Ser Ile
385                 390                 395                 400

Lys Arg Gly Gln Val Val Ile Ile Pro Ile Ser Ala Ile His Lys Asp
                405                 410                 415

Lys Ser Ile Trp Gly Glu Asp Ala Leu Asp Phe Arg Pro Glu Arg Trp
```

```
            420                 425                 430

Glu Cys Leu Pro Glu Gly Val Asn Thr Ile Pro Gly Val Trp Ser His
        435                 440                 445

Leu Leu Ser Phe Trp Gly Gly Pro Arg Ser Cys Ile Gly Phe Arg Phe
    450                 455                 460

Ala Ile Ala Glu Met Lys Ala Leu Leu Phe Thr Leu Val Arg Ala Leu
465                 470                 475                 480

Glu Phe Asp Leu Ala Val Pro Ala Glu Gln Ile Ser Val Glu Ser Gly
                485                 490                 495

Leu Ser Asn Arg Pro Ile Leu Thr Thr Asp Pro Gly Arg Tyr Gln Leu
            500                 505                 510

Pro Leu Leu Ile Lys Pro Tyr Lys Ala Arg Ser
        515                 520


<210> SEQ ID NO 598
<211> LENGTH: 545
<212> TYPE: PRT
<213> ORGANISM: Galerina marginata

<400> SEQUENCE: 598

Met Gly Arg Thr Cys Leu Leu Val Val Ser Ala Thr Ala Thr Leu Gly
1               5                   10                  15

Val Tyr Gly Leu Tyr Lys Ile Ala Gly Ile Val Tyr Arg Glu Trp Leu
            20                  25                  30

Ser Pro Leu Arg Val Leu Pro Gly Thr Lys Ser Pro Ser Phe Leu Tyr
        35                  40                  45

Gly Asp Leu Lys Glu Leu Trp Glu Glu Glu Asp Thr Gly Thr Ser Gly
    50                  55                  60

Ile Leu Val Glu Lys Tyr Gly Thr Thr Phe Arg Tyr Lys Ser Leu Leu
65                  70                  75                  80

Gly Ile Ser Arg Leu Tyr Thr Ala Asp Thr Arg Ala Leu Asn His Ile
                85                  90                  95

Leu Met Asn Ser Tyr Asp Tyr Glu Lys Leu Pro Glu Ser Arg Ala Ala
            100                 105                 110

Leu Thr Asn Ile Leu Gly Ala Gly Leu Leu Val Val Glu Gly Asp Lys
        115                 120                 125

His Lys Gln Gln Arg Lys Ile Met Asn Pro Ala Phe Gly Pro Ala Gln
    130                 135                 140

Ile Arg Glu Leu Thr Asp Ile Phe Val Arg Lys Ser Ile Gln Leu Arg
145                 150                 155                 160

Asp Leu Trp Ala Glu Glu Cys Thr Lys Gln Gly Gly Gln Gly Arg Ile
                165                 170                 175

Glu Ile Leu Ser Trp Leu Thr Trp Thr Thr Leu Asp Val Ile Gly Leu
            180                 185                 190

Ala Gly Phe Asn Tyr Lys Phe Asn Ala Leu Met Arg Asp Ser Lys Ala
        195                 200                 205

Asn Glu Leu Ser Glu Ala Phe Asn Thr Ile Phe Gln Ala Gly Thr Ser
    210                 215                 220

Val Asn Val Met Leu Ile Leu Arg Ala Phe Ile Pro Ala Leu Ser Trp
225                 230                 235                 240

Ile Leu Pro Glu Ala Gly Asp Val Glu Ala Lys Lys Ala Ser Ser Thr
                245                 250                 255

Met Ser Arg Ile Gly Lys Glu Leu Leu Ser Asn Ser Lys Ala Ala Val
            260                 265                 270
```

Ser Gln Gln Glu Ser Leu Glu Lys Asp Thr Trp Lys Thr Arg Asp Leu
275 280 285

Leu Ser Leu Leu Val Arg Ala Asn Val Ala Thr Asp Leu Thr Glu Ser
290 295 300

Gln Arg Met Leu Asp Glu Asp Val Leu Ala Gln Ile Pro Thr Phe Ile
305 310 315 320

Val Ala Gly His Glu Thr Thr Ser Asn Ala Thr Thr Trp Ala Leu Phe
325 330 335

Ala Leu Asn Ser Gln Asn Pro Asp Ala Gln Ile Lys Leu Arg Asn Glu
340 345 350

Leu Leu Thr Val Ser Thr Asp Asn Pro Thr Met Asp Glu Leu Asn Ala
355 360 365

Leu Pro Tyr Leu Asp Ala Val Val Arg Glu Thr Leu Arg Leu His Ala
370 375 380

Pro Val Ser Met Thr Ser Arg Val Ala Met Lys Asp Asp Val Leu Pro
385 390 395 400

Leu Ala Ile Pro Phe Thr Asp Ser Lys Gly Val Ile His His Glu Ile
405 410 415

Arg Ile Arg Lys Gly Glu Pro Leu Leu Ile Pro Ile Leu Ala Leu Asn
420 425 430

Arg Asp Lys Ser Ile Trp Gly Glu Asp Ala His Glu Phe Arg Pro Glu
435 440 445

Arg Trp Glu Ser Ile Pro Asp Ala Ala Ser Ser Ile Pro Gly Val Trp
450 455 460

Gly His Met Leu Thr Phe Leu Gly Gly Pro His Ser Cys Ile Gly Tyr
465 470 475 480

Arg Phe Ala Leu Val Glu Met Lys Ala Leu Leu Phe Thr Leu Ile Arg
485 490 495

Ser Phe Glu Phe Glu Leu Ala Val Pro Ala Ser Asp Ile Gly Lys Lys
500 505 510

Ala Gly Ile Val His Arg Pro Ile Leu Leu Ser Asn Pro Glu Gly Gly
515 520 525

Ser Gln Met Pro Leu Phe Val Lys Ala Tyr Gln Pro Pro Leu Glu Glu
530 535 540

Ala
545

<210> SEQ ID NO 599
<211> LENGTH: 514
<212> TYPE: PRT
<213> ORGANISM: Galerina marginata

<400> SEQUENCE: 599

Met Gly Leu Val Trp Met Val Ala Ala Ala Val Ala Ala Val Leu Ala
1 5 10 15

Ser Trp Ala Phe Asp Ala Leu Val Tyr Leu Val Trp Arg Pro Arg Ala
20 25 30

Ile Thr Arg Gln Leu Arg Ala Gln Gly Val Gly Gly Pro Gly Tyr Arg
35 40 45

Phe Phe Ala Gly Asn Leu Ala Glu Ile Lys Gln Leu Arg Ala Asp Ser
50 55 60

Ala Gly Ala Ala Leu Asp Ile Gly Asp His Asp Phe Val Pro Arg Val
65 70 75 80

Gln Pro His Phe Arg Lys Trp Ile Pro Ile His Gly Arg Thr Phe Leu
85 90 95

```
Tyr Trp Phe Gly Ala Lys Pro Thr Leu Cys Ile Ala Asp Val Asn Val
            100                 105                 110

Val Lys Gln Val Leu Ser Asp Arg Gly Gly Leu Tyr Pro Lys Ser Ile
        115                 120                 125

Gly Asn Pro His Ile Ala Arg Leu Leu Gly Lys Gly Leu Val Leu Thr
    130                 135                 140

Asp Gly Asp Asp Trp Lys Arg His Arg Lys Val Val His Pro Ala Phe
145                 150                 155                 160

Asn Met Asp Lys Leu Lys Met Met Thr Val Thr Met Ser Asp Cys Ala
                165                 170                 175

Gly Ser Met Met Ser Glu Trp Lys Ala Lys Met Asp Lys Gly Gly Ser
            180                 185                 190

Val Glu Ile Asp Leu Ser Ser Gln Phe Glu Glu Leu Thr Ala Asp Val
        195                 200                 205

Ile Ser His Thr Ala Phe Gly Ser Ser Tyr Glu Gln Gly Lys Lys Val
    210                 215                 220

Phe Leu Ala Gln Arg Glu Leu Gln Phe Leu Ala Phe Ser Thr Val Phe
225                 230                 235                 240

Asn Val Gln Ile Pro Ser Phe Arg Tyr Leu Pro Thr Glu Lys Asn Leu
                245                 250                 255

Lys Ile Trp Lys Leu Asp Lys Glu Val Arg Thr Met Leu Met Asn Ile
            260                 265                 270

Ile Lys Gly Arg Leu Ala Thr Lys Asp Thr Met Gly Tyr Gly Asn Asp
        275                 280                 285

Leu Leu Gly Leu Met Leu Glu Ala Cys Ala Pro Glu Asp Gly Gln Asn
    290                 295                 300

Pro Leu Leu Ser Met Asp Glu Ile Ile Asp Glu Cys Lys Thr Phe Phe
305                 310                 315                 320

Phe Ala Gly His Asp Thr Ser Ser His Leu Leu Thr Trp Thr Met Phe
                325                 330                 335

Leu Leu Ser Thr His Pro Glu Trp Gln Glu Lys Leu Arg Glu Glu Val
            340                 345                 350

Leu Arg Glu Cys Gly Asn Gly Ile Pro Thr Gly Asp Met Leu Asn Lys
        355                 360                 365

Leu Gln Leu Val Asn Met Phe Leu Leu Glu Thr Leu Arg Leu Tyr Ala
    370                 375                 380

Pro Val Ser Ala Ile Gln Arg Lys Ala Gly Ser Asp Leu Glu Val Gly
385                 390                 395                 400

Gly Ile Lys Val Thr Glu Gly Thr Phe Leu Thr Ile Pro Ile Ala Thr
                405                 410                 415

Ile His Arg Asp Lys Glu Val Trp Gly Glu Asp Ala Asn Lys Phe Lys
            420                 425                 430

Pro Met Arg Phe Glu Asn Gly Val Thr Arg Ala Gly Lys His Pro Asn
        435                 440                 445

Ala Leu Leu Ser Phe Ser Ser Gly Pro Arg Ser Cys Ile Gly Gln Asn
    450                 455                 460

Phe Ala Met Ile Glu Ala Lys Ala Val Ile Ala Val Ile Leu Gln Arg
465                 470                 475                 480

Phe Ser Phe Ser Leu Ser Pro Lys Tyr Val His Ala Pro Met Asp Val
                485                 490                 495

Ile Thr Leu Arg Pro Lys Phe Gly Leu Pro Met Ile Leu Lys Ser Leu
            500                 505                 510
```

Glu Met

<210> SEQ ID NO 600
<211> LENGTH: 1875
<212> TYPE: DNA
<213> ORGANISM: Amanita bisporigera

<400> SEQUENCE: 600
atgttgaacc tcaacttcaa cggcctctgg cctgatgtag cagagtattt caaaggcgat 60
tcgatgagga ttgtgacctc tgcctttacg ttgctcgtcg tcatttctat ctatcgaaga 120
cgccgaggta tcagaacgcc cagactgcaa ggaccacgca gcgagagctt catcttcggt 180
aacaccaaga agatcttccc ttcggcgaac ctcagtgtgg tatatcggga ttgggaacga 240
atgtatgggc ccgtttacga gatacccact ggcatcggct ccagccatgt tgtattaagc 300
gatcccaagg ctctcacaca catatattcc aaggatacca ccacatattg tcggctcgca 360
gggacaaccg ctttgagccg gaagttggcg agtatctgtt ttgcaccatt tttcttagct 420
gccagcctta tttacgttcc aactacggag aggcctgtct tctccactgt cggtctcagc 480
aattcgcaat ctcactcccg tgtgcttgga ttctgcctat cagggaaagc tatattgtcg 540
catgactttg gaactctaag ggccgcacg tccttgatga tggccgcctt tgactctatc 600
cacacagtca agccttcccc ctttataagg cttattcact ttctgtcacc gatactctat 660
gccctgttta aagttaccct catgagcgtc agagaagaga agctcgcaca atcagtagca 720
cacttgaata ggcttacaac taacagcctg aacaaggcat gtaaggaacc ggaagatact 780
gtcaacgaat cagtccttgg gattctggtc aagtcagaaa acgcaaatcc caacagccgt 840
ttgtcactct ccgagatcac ggcccaggcc gtacgtacct ttgccactcc tctgatattc 900
tctcaatggt ctctcattga acttgcacgc cggccagaaa tccaagagag cctccgtgct 960
gagctctcag aatgtttggc aaagggagaa cgtcctacat acgaccagct aacaaaggat 1020
ctgaaatacc tcgatgcttt tatagccgag atactgagac tccatgcccc cgaaatgcaa 1080
tcaatccgtg tggcagccga agacgatgtg ataccgttga caaatcccat acgtattgca 1140
tctggagcga cgatcgatag cttgtttttg aagaaaggta tggtcgtccg tatacccttg 1200
gggggagtga atatgtcgga agcgttgtgg gggccagacg cgggcatgtt cgatccaagc 1260
agatggctgg acgctgaggg tcataagaaa ggaaacaagg gagaactagc tggctaccgg 1320
ggtctcttaa ctttcggtgc tggtcccagg atgtgtccag gcagagacct cgccgtactg 1380
gaggtgaagg ctgtgctgtc ggttctggtc agatattttg cctttgagct ccccaatggg 1440
ccatcgacgg aactgagttg gcattttacg cgccccaagg tagctggcga ggatggtaca 1500
aaagttcctc ttcttgtgcg aaaggtagaa aacatggtgg tggtgctcgc ctacttgata 1560
agcagactcg tgcgaaacac catgtcaatc gatgacgggc ataagagacc acgacattgg 1620
ggcgatgaag tcggtggtga ctcatacgag tcgtattgta aatttttgct tgggaagtca 1680
tggcatgtcg caacagttgg ccccactgat gtcattcaac caaccgacat ctcgaggctt 1740
gcgctaaagt ctcccgccat taacgccgcg ttccaatgct gcgtcatccg cagtgcctgc 1800
accgtcagaa cgcatttagt agtggcaaga agcttctgtc aaattcaatc gctaaccggt 1860
tctttgacgg gctag 1875

<210> SEQ ID NO 601
<211> LENGTH: 624
<212> TYPE: PRT
<213> ORGANISM: Galerina marginata

<400> SEQUENCE: 601

Met Leu Asn Leu Asn Phe Asn Gly Leu Trp Pro Asp Val Ala Glu Tyr
1               5                   10                  15

Phe Lys Gly Asp Ser Met Arg Ile Val Thr Ser Ala Phe Thr Leu Leu
            20                  25                  30

Val Val Ile Ser Ile Tyr Arg Arg Arg Arg Gly Ile Arg Thr Pro Arg
        35                  40                  45

Leu Gln Gly Pro Arg Ser Glu Ser Phe Ile Phe Gly Asn Thr Lys Lys
    50                  55                  60

Ile Phe Pro Ser Ala Asn Leu Ser Val Val Tyr Arg Asp Trp Glu Arg
65                  70                  75                  80

Met Tyr Gly Pro Val Tyr Glu Ile Pro Thr Gly Ile Gly Ser Ser His
                85                  90                  95

Val Val Leu Ser Asp Pro Lys Ala Leu Thr His Ile Tyr Ser Lys Asp
            100                 105                 110

Thr Thr Thr Tyr Cys Arg Leu Ala Gly Thr Thr Ala Leu Ser Arg Lys
        115                 120                 125

Leu Ala Ser Ile Cys Phe Ala Pro Phe Phe Leu Ala Ala Ser Leu Ile
    130                 135                 140

Tyr Val Pro Thr Thr Glu Arg Pro Val Phe Ser Thr Val Gly Leu Ser
145                 150                 155                 160

Asn Ser Gln Ser His Ser Arg Val Leu Gly Phe Cys Leu Ser Gly Lys
                165                 170                 175

Ala Ile Leu Ser His Asp Phe Gly Thr Leu Arg Gly Arg Thr Ser Leu
            180                 185                 190

Met Met Ala Ala Phe Asp Ser Ile His Thr Val Lys Pro Ser Pro Phe
        195                 200                 205

Ile Arg Leu Ile His Phe Leu Ser Pro Ile Leu Tyr Ala Leu Phe Lys
    210                 215                 220

Val Thr Leu Met Ser Val Arg Glu Glu Lys Leu Ala Gln Ser Val Ala
225                 230                 235                 240

His Leu Asn Arg Leu Thr Thr Asn Ser Leu Asn Lys Ala Cys Lys Glu
                245                 250                 255

Pro Glu Asp Thr Val Asn Glu Ser Val Leu Gly Ile Leu Val Lys Ser
            260                 265                 270

Glu Asn Ala Asn Pro Asn Ser Arg Leu Ser Leu Ser Glu Ile Thr Ala
        275                 280                 285

Gln Ala Val Arg Thr Phe Ala Thr Pro Leu Ile Phe Ser Gln Trp Ser
    290                 295                 300

Leu Ile Glu Leu Ala Arg Arg Pro Glu Ile Gln Glu Ser Leu Arg Ala
305                 310                 315                 320

Glu Leu Ser Glu Cys Leu Ala Lys Gly Glu Arg Pro Thr Tyr Asp Gln
                325                 330                 335

Leu Thr Lys Asp Leu Lys Tyr Leu Asp Ala Phe Ile Ala Glu Ile Leu
            340                 345                 350

Arg Leu His Ala Pro Glu Met Gln Ser Ile Arg Val Ala Ala Glu Asp
        355                 360                 365

Asp Val Ile Pro Leu Thr Asn Pro Ile Arg Ile Ala Ser Gly Ala Thr
    370                 375                 380

Ile Asp Ser Leu Phe Leu Lys Lys Gly Met Val Val Arg Ile Pro Leu
385                 390                 395                 400

Gly Gly Val Asn Met Ser Glu Ala Leu Trp Gly Pro Asp Ala Gly Met

-continued

```
                405                 410                 415

Phe Asp Pro Ser Arg Trp Leu Asp Ala Glu Gly His Lys Lys Gly Asn
            420                 425                 430

Lys Gly Glu Leu Ala Gly Tyr Arg Gly Leu Leu Thr Phe Gly Ala Gly
        435                 440                 445

Pro Arg Met Cys Pro Gly Arg Asp Leu Ala Val Leu Glu Val Lys Ala
    450                 455                 460

Val Leu Ser Val Leu Val Arg Tyr Phe Ala Phe Glu Leu Pro Asn Gly
465                 470                 475                 480

Pro Ser Thr Glu Leu Ser Trp His Phe Thr Arg Pro Lys Val Ala Gly
                485                 490                 495

Glu Asp Gly Thr Lys Val Pro Leu Leu Val Arg Lys Val Glu Asn Met
            500                 505                 510

Val Val Val Leu Ala Tyr Leu Ile Ser Arg Leu Val Arg Asn Thr Met
        515                 520                 525

Ser Ile Asp Asp Gly His Lys Arg Pro Arg His Trp Gly Asp Glu Val
    530                 535                 540

Gly Gly Asp Ser Tyr Glu Ser Tyr Cys Lys Phe Leu Leu Gly Lys Ser
545                 550                 555                 560

Trp His Val Ala Thr Val Gly Pro Thr Asp Val Ile Gln Pro Thr Asp
                565                 570                 575

Ile Ser Arg Leu Ala Leu Lys Ser Pro Ala Ile Asn Ala Ala Phe Gln
            580                 585                 590

Cys Cys Val Ile Arg Ser Ala Cys Thr Val Arg Thr His Leu Val Val
        595                 600                 605

Ala Arg Ser Phe Cys Gln Ile Gln Ser Leu Thr Gly Ser Leu Thr Gly
    610                 615                 620


<210> SEQ ID NO 602
<211> LENGTH: 405
<212> TYPE: DNA
<213> ORGANISM: Galerina marginata

<400> SEQUENCE: 602

atgagaaata acaaaaactt gaaggcctta cttccgatgc aggctcaacg ctccaagcct      60

aacattgtca acaacttgcg tcgtccacta ctacatcgaa tggatgagac atttagcaaa     120

ggctggtaca cgacacataa gtacattgct acattattaa atggaatttt gagctcacct     180

ctcaccacga gtgaggagac ggttgacgtc gtcaccgacg catgggcagt ctacaagcca     240

agcaggaaga cgggtggcat tgatagtaga ggtcttgggt tcgagttcga atgggagtca     300

cgaattcgca agattggaaa accgcagaaa gggcgttcgg tttctgcgga cattcagccg     360

ggcaagacgg tgcaatacaa tggcaacccc gtcaaaagtt gttga                     405


<210> SEQ ID NO 603
<211> LENGTH: 134
<212> TYPE: PRT
<213> ORGANISM: Galerina marginata

<400> SEQUENCE: 603

Met Arg Asn Asn Lys Asn Leu Lys Ala Leu Leu Pro Met Gln Ala Gln
1               5                   10                  15

Arg Ser Lys Pro Asn Ile Val Asn Asn Leu Arg Arg Pro Leu Leu His
            20                  25                  30

Arg Met Asp Glu Thr Phe Ser Lys Gly Trp Tyr Thr Thr His Lys Tyr
        35                  40                  45
```

```
Ile Ala Thr Leu Leu Asn Gly Ile Leu Ser Ser Pro Leu Thr Thr Ser
    50                  55                  60

Glu Glu Thr Val Asp Val Val Thr Asp Ala Trp Ala Val Tyr Lys Pro
65                  70                  75                  80

Ser Arg Lys Thr Gly Gly Ile Asp Ser Arg Gly Leu Gly Phe Glu Phe
                85                  90                  95

Glu Trp Glu Ser Arg Ile Arg Lys Ile Gly Lys Pro Gln Lys Gly Arg
            100                 105                 110

Ser Val Ser Ala Asp Ile Gln Pro Gly Lys Thr Val Gln Tyr Asn Gly
        115                 120                 125

Asn Pro Val Lys Ser Cys
    130


<210> SEQ ID NO 604
<211> LENGTH: 1689
<212> TYPE: DNA
<213> ORGANISM: Galerina marginata

<400> SEQUENCE: 604

atgcgatcgc attctctcaa gggccgttca ttaaagttgg ctaaagtcgc gggggaaggg      60

ctggtgatga ggtatcttgt gtcgacgcgg gcacaatgga ccatgggagg cagtcgccgc     120

atatctgaaa agctgggctc ccgacgtgaa gtgaggaatc acgaaaatca tatttgcttg     180

gaaggaaagc ccatgcagct cagcaaactc tacctgaaac ctgccctgtc aaggacatgc     240

ggccgcaacc gcgactggtt gatggtaaat ccaaatgcga cgcccagttc gaaagatgag     300

acatacctgc gccaaacagt gattaccaca gccacctacg aggcctccgt ggccagtcgc     360

gcctcgggat ttaccggcgc gatacaaacg gaaagttctt tcgcagcgtt cccacccgcg     420

cggcccettt ggccttatgt cgcggagtac ctcaaagtca attcgatgag gataatagcc     480

tctggcatat ccttgctcgt cgttgtttcc atttaccgaa gccgtcgagg tcctagaacg     540

ccgagactgc aaggaccaca catggagagc ttcatcctcg gcaatgctag gaagatcttc     600

ccttcagcca acctcagttt ggtgtatcaa ggtttggagc agacttacgg gcccgtctat     660

gaaatagcct ctggctttgg ctccaaccac gtcgtattga acgatcccaa ggctctcaca     720

cacttatttt ccaaggacac tgtcacatat tctcagcctg ctaggcagaa agacatgggg     780

cggaagttga atacggaggg tcttgtcttc tcccctgtcg gtctcggcaa tccgcaattt     840

cactcctatg tgtttggatt ccgcctatca ggtcaggacg gttccagctt tgagacatca     900

tgggattcat gtttccagtt gtcaaacaat tcgaaccgtg ctatcgtgct tgatgcagag     960

aaatgcatgg ataatattgg aaaagctgta ttgtcgtatg acttcggcaa catgaggggc    1020

catacgtgtt cgatcttagc tgacttggat gctttccacg cagtcagccc ttcaggcctt    1080

tacataaggt ttattgtgtt tacccgcgag atactttata acctcttcaa gattacctta    1140

ccgaatgcca aagaaaagca gtttgaggaa ctggcagcgc actttaaagt actcgcgact    1200

ggctttctgc gggaagcacg tgaggcgcct gaagatagcg ccgttcacca atcaatcctt    1260

ggggttatgc tcaagtccaa aaatgaaaat gctaacgtcc gtttatcact tcccgagatc    1320

acggcccagg ctggtggtct tgtcttggcc gggtatgaaa ctacggcaaa gatccatcgc    1380

cgagctttcc ctcagtggtc cctcattgag cttgctcgcc gggcagaaat tcaagagact    1440

ctccgtgccg aactcaagga gtgcttggca gacggagaac gccctacata cgaccagctg    1500

acaaaggatc tgaaatacct cgatgctttt atatccgaga tactgaggtt acatccctca    1560
```

```
gaaatggtac taacccgcgt ggcagccgaa gacgatgtga taccgctgac ggatcccata   1620

cgaactgcat ctggagcgat gatcgacagc ttgttcgtga ggaaaggcac cgtctccgca   1680

tccctttag                                                           1689


<210> SEQ ID NO 605
<211> LENGTH: 562
<212> TYPE: PRT
<213> ORGANISM: Galerina marginata

<400> SEQUENCE: 605

Met Arg Ser His Ser Leu Lys Gly Arg Ser Leu Lys Leu Ala Lys Val
1               5                   10                  15

Ala Gly Glu Gly Leu Val Met Arg Tyr Leu Val Ser Thr Arg Ala Gln
            20                  25                  30

Trp Thr Met Gly Gly Ser Arg Arg Ile Ser Glu Lys Leu Gly Ser Arg
        35                  40                  45

Arg Glu Val Arg Asn His Glu Asn His Ile Cys Leu Glu Gly Lys Pro
    50                  55                  60

Met Gln Leu Ser Lys Leu Tyr Leu Lys Pro Ala Leu Ser Arg Thr Cys
65                  70                  75                  80

Gly Arg Asn Arg Asp Trp Leu Met Val Asn Pro Asn Ala Thr Pro Ser
                85                  90                  95

Ser Lys Asp Glu Thr Tyr Leu Arg Gln Thr Val Ile Thr Thr Ala Thr
            100                 105                 110

Tyr Glu Ala Ser Val Ala Ser Arg Ala Ser Gly Phe Thr Gly Ala Ile
        115                 120                 125

Gln Thr Glu Ser Ser Phe Ala Ala Phe Pro Pro Ala Arg Pro Leu Trp
    130                 135                 140

Pro Tyr Val Ala Glu Tyr Leu Lys Val Asn Ser Met Arg Ile Ile Ala
145                 150                 155                 160

Ser Gly Ile Ser Leu Leu Val Val Val Ser Ile Tyr Arg Ser Arg Arg
                165                 170                 175

Gly Pro Arg Thr Pro Arg Leu Gln Gly Pro His Met Glu Ser Phe Ile
            180                 185                 190

Leu Gly Asn Ala Arg Lys Ile Phe Pro Ser Ala Asn Leu Ser Leu Val
        195                 200                 205

Tyr Gln Gly Leu Glu Gln Thr Tyr Gly Pro Val Tyr Glu Ile Ala Ser
    210                 215                 220

Gly Phe Gly Ser Asn His Val Val Leu Asn Asp Pro Lys Ala Leu Thr
225                 230                 235                 240

His Leu Phe Ser Lys Asp Thr Val Thr Tyr Ser Gln Pro Ala Arg Gln
                245                 250                 255

Lys Asp Met Gly Arg Lys Leu Asn Thr Glu Gly Leu Val Phe Ser Pro
            260                 265                 270

Val Gly Leu Gly Asn Pro Gln Phe His Ser Tyr Val Phe Gly Phe Arg
        275                 280                 285

Leu Ser Gly Gln Asp Gly Ser Ser Phe Glu Thr Ser Trp Asp Ser Cys
    290                 295                 300

Phe Gln Leu Ser Asn Asn Ser Asn Arg Ala Ile Val Leu Asp Ala Glu
305                 310                 315                 320

Lys Cys Met Asp Asn Ile Gly Lys Ala Val Leu Ser Tyr Asp Phe Gly
                325                 330                 335

Asn Met Arg Gly His Thr Cys Ser Ile Leu Ala Asp Leu Asp Ala Phe
            340                 345                 350
```

His Ala Val Ser Pro Ser Gly Leu Tyr Ile Arg Phe Ile Val Phe Thr
355 360 365

Arg Glu Ile Leu Tyr Asn Leu Phe Lys Ile Thr Leu Pro Asn Ala Lys
370 375 380

Glu Lys Gln Phe Glu Glu Leu Ala Ala His Phe Lys Val Leu Ala Thr
385 390 395 400

Gly Phe Leu Arg Glu Ala Arg Glu Ala Pro Glu Asp Ser Ala Val His
405 410 415

Gln Ser Ile Leu Gly Val Met Leu Lys Ser Lys Asn Glu Asn Ala Asn
420 425 430

Val Arg Leu Ser Leu Pro Glu Ile Thr Ala Gln Ala Gly Gly Leu Val
435 440 445

Leu Ala Gly Tyr Glu Thr Thr Ala Lys Ile His Arg Arg Ala Phe Pro
450 455 460

Gln Trp Ser Leu Ile Glu Leu Ala Arg Arg Ala Glu Ile Gln Glu Thr
465 470 475 480

Leu Arg Ala Glu Leu Lys Glu Cys Leu Ala Asp Gly Glu Arg Pro Thr
485 490 495

Tyr Asp Gln Leu Thr Lys Asp Leu Lys Tyr Leu Asp Ala Phe Ile Ser
500 505 510

Glu Ile Leu Arg Leu His Pro Ser Glu Met Val Leu Thr Arg Val Ala
515 520 525

Ala Glu Asp Asp Val Ile Pro Leu Thr Asp Pro Ile Arg Thr Ala Ser
530 535 540

Gly Ala Met Ile Asp Ser Leu Phe Val Arg Lys Gly Thr Val Ser Ala
545 550 555 560

Ser Leu

<210> SEQ ID NO 606
<211> LENGTH: 105
<212> TYPE: DNA
<213> ORGANISM: Galerina marginata

<400> SEQUENCE: 606
atgtctgaca tcaatgccac ccgtcttccc gcttggcttg tagattgccc atgcgtcggt 60
gacgatgtca accgtctcct cactcgtggc gagagccttt gctaa 105

<210> SEQ ID NO 607
<211> LENGTH: 34
<212> TYPE: PRT
<213> ORGANISM: Galerina marginata

<400> SEQUENCE: 607

Met Ser Asp Ile Asn Ala Thr Arg Leu Pro Ala Trp Leu Val Asp Cys
1 5 10 15

Pro Cys Val Gly Asp Asp Val Asn Arg Leu Leu Thr Arg Gly Glu Ser
20 25 30

Leu Cys

<210> SEQ ID NO 608
<211> LENGTH: 105
<212> TYPE: DNA
<213> ORGANISM: Galerina marginata

<400> SEQUENCE: 608
ttagcaaagg ctctcgccac gagtgaggag acggttgaca tcgtcaccga cgcatgggca 60
atctacaagc caagcgggaa gacgggtggc attgatgtca gacat 105

<210> SEQ ID NO 609
<211> LENGTH: 258
<212> TYPE: DNA
<213> ORGANISM: Galerina marginata

<400> SEQUENCE: 609
atggtgcaaa acaaagactc gccaacctgg ctcaaagcgg ttgtccctgc gagccgagga 60
tatgtggtgg tatcctcgga atatatgtgt gtgagccttg ggatcgctca atacaacatg 120
gctgtagccg atgccagtgg gtatctcgta aggcccatac attcgttccc aatcccgata 180
taccaccgta ctgaggttcg cggaagggaa gatcttggtg ttactgaatc tgaagctctc 240
gctgcgtggt ccttgtag 258

<210> SEQ ID NO 610
<211> LENGTH: 85
<212> TYPE: PRT
<213> ORGANISM: Galerina marginata

<400> SEQUENCE: 610

Met Val Gln Asn Lys Asp Ser Pro Thr Trp Leu Lys Ala Val Val Pro
1 5 10 15

Ala Ser Arg Gly Tyr Val Val Val Ser Ser Glu Tyr Met Cys Val Ser
20 25 30

Leu Gly Ile Ala Gln Tyr Asn Met Ala Val Ala Asp Ala Ser Gly Tyr
35 40 45

Leu Val Arg Pro Ile His Ser Phe Pro Ile Pro Ile Tyr His Arg Thr
50 55 60

Glu Val Arg Gly Arg Glu Asp Leu Gly Val Thr Glu Ser Glu Ala Leu
65 70 75 80

Ala Ala Trp Ser Leu
85

<210> SEQ ID NO 611
<211> LENGTH: 582
<212> TYPE: PRT
<213> ORGANISM: Cryptococcus

<400> SEQUENCE: 611

Met Thr Met Glu Leu Leu Lys Val Leu His His Glu Ala Ser Gln Leu
1 5 10 15

Phe Pro Asn Cys Ile Arg Ser Ser Pro Val Ala Cys Ile Val Leu Tyr
20 25 30

Ser Phe Gly Gly Ile Ala Ile Leu Leu Phe Ser Val Tyr Leu Trp Leu
35 40 45

Trp Pro Phe Gln Tyr Ala Lys Leu Tyr Phe Arg Asn Leu Pro Gly Pro
50 55 60

Pro Ser Asp Ser Trp Phe Trp Gly Val Val Pro Thr Leu Ile Lys Ser
65 70 75 80

Pro Pro Ser Val Pro His Ser Met Trp Thr Asp Glu Tyr Gly Pro Thr
85 90 95

Val Arg Tyr Arg Val Ala Leu Gly Ala Gln Arg Phe Leu Thr Ile Asp
100 105 110

Pro Thr Ala Leu Asn Tyr Ile Leu Ser His Ala Asp Leu Phe Pro Lys
115 120 125

```
Pro Ser Arg Val Arg Lys Ala Leu Ser Asp Leu Leu Gly Asn Gly Leu
    130                 135                 140

Leu Thr Ala Glu Gly His Thr His Lys Lys Gln Arg Lys Ala Leu Asn
145                 150                 155                 160

Pro Ser Phe Ser Pro Ala Ala Val Arg Gly Met Ile Pro Val Phe Tyr
                165                 170                 175

Asp Lys Ala Tyr Glu Leu Lys Ala Lys Leu Leu Gly Ile Ile Glu Gly
            180                 185                 190

Asp Glu Thr Glu Gln Ala Ser Pro Thr Pro Cys Lys Glu Glu Asp Glu
        195                 200                 205

Val Glu Gly Gly Lys Lys Ile Asp Val Met Lys Tyr Leu Gly Lys Thr
    210                 215                 220

Thr Leu Asp Val Ile Gly Ile Val Gly Phe Ser Tyr Asp Phe Lys Ala
225                 230                 235                 240

Leu Ser Glu Pro Arg Asn Glu Leu Ser Glu Ala Tyr Ser Lys Met Phe
                245                 250                 255

Gln Ala Gly Met Asp Ala Asn Phe Trp Asp Phe Leu Arg Gly Ala Ile
            260                 265                 270

Pro Leu Val Asn Lys Leu Pro Asn Lys Arg Ala Thr Glu Ile Ala Ala
        275                 280                 285

Arg Lys Ala Val Thr Leu Arg Ile Ser Lys Lys Ile Val Glu Asp Lys
    290                 295                 300

Lys Arg Glu Val Met Ser Ala His Ser Glu Gly Leu Glu Lys Arg Glu
305                 310                 315                 320

Asp Ile Gly Asp Asp Leu Leu Ser Ile Leu Ile Lys Ala Asn Met Ala
                325                 330                 335

Ser Asp Val Lys Pro Glu Gln Lys Leu Ser Asp Glu Glu Val Leu Asp
            340                 345                 350

Gln Ile Thr Thr Phe Met Leu Ala Gly Asn Glu Thr Ser Ser Thr Ala
        355                 360                 365

Leu Thr Trp Ile Leu Tyr Ser Leu Thr Gln His Pro Glu Cys Gln Thr
    370                 375                 380

Arg Leu Arg Glu Glu Val Leu Ala Val Pro Asp Asp Arg Pro Ser Leu
385                 390                 395                 400

Glu Thr Leu Asn Asn Leu Pro Tyr Met Asp Ala Val Ile Arg Glu Ala
                405                 410                 415

Leu Arg Leu His Ala Pro Ala Pro Gly Thr Met Arg Glu Ala Lys Glu
            420                 425                 430

Asp Thr Val Ile Pro Leu Ser Met Pro Val Ile Gly Arg Asp Gly Lys
        435                 440                 445

Gln Ile Asp Ser Val Lys Ile Asn Lys Gly Thr Met Val Phe Ile Pro
    450                 455                 460

Ile Ile Thr Val Asn Thr Ser Pro Ala Ile Trp Gly Pro Asp Ala Arg
465                 470                 475                 480

Val Phe Asn Pro Asp Arg His Leu Lys Thr Ser Ser Asp Ser Phe Gly
                485                 490                 495

Gly Ala Asn Met His Val Pro Gly Val Trp Gly Asn Met Leu Ser Phe
            500                 505                 510

Leu Gly Gly Ala Arg Asn Cys Ile Gly Tyr Lys Leu Ala Leu Ala Glu
        515                 520                 525

Ile Ser Thr Ile Leu Phe Val Leu Ile Arg Ser Phe Glu Phe Gln Glu
    530                 535                 540

Leu Lys Ser Lys Pro Glu Val Glu Lys Lys Ala Ser Val Val Met Arg
```

```
545                 550                 555                 560

Pro Arg Ile Lys Gly Glu Glu Ser Ala Gly Leu Gln Met Pro Leu Met
                565                 570                 575

Val Lys Pro Leu Leu Met
            580
```

<210> SEQ ID NO 612
<211> LENGTH: 13254
<212> TYPE: DNA
<213> ORGANISM: Amanita bisporigera

<400> SEQUENCE: 612

```
gatcatgtta agtttatgcc ctaatcgttg agcgataaag agcgaccaac cccttgtgag     60

tctcgcgctc agaaatagat ataacatcac catactggaa cgacaatgag gctggcagct    120

gaaaaatggt gcaaaacaaa gactcgccaa cctggctcaa agcggttgtc cctgcgagcc    180

gaggatatgt ggtggtatcc tcggaatata tgtgtgtgag ccttgggatc gctcaataca    240

acatggctgt agccgatgcc agtgggtatc tcgtaaggcc catacattcg ttcccaatcc    300

cgatatacca ccgtactgag gttcgcggaa gggaagatct tggtgttact gaatctgaag    360

ctctcgctgc gtggtccttg tagtctgggc gttctgatac ctcggcatct ccgatagata    420

gaaatgacga cgagcaatgt cagaggtcac aatccttatc gaattacctt tgagatactc    480

tgccacatca ggccagaggc cgttggagtt gaggttcaac atcacgggtg acggagtgga    540

cgagccgtta tgcaaggaag gaaggccatc gcggataagt actagtatag caaccaaccc    600

aaccagacgt ggaaatgcca ttgaagggtg ggagttgcgc gaatacgagg aaaacgtttc    660

tgaggagccg aaaccgtaac caggcgcgag aacttgacct atctatctcc gggaacggtg    720

ttgggggtcc atgttaccgt gaaggtggat aggggcggat tcgattccag gaaagttaga    780

gccacatagt cataagtgat gcaacacgcc tgtgcgcgat ggagataatg cgtctttgtt    840

gcatcggcaa accgggtcac acggacgaaa atcattacta catggtccat ttcaggacaa    900

aacccctatc tattgatcct acaaactgct tgactgttca atctgtgacc accgggacag    960

agaaaggctg tgctcagtgg ggtgtttaat ccagcgagaa acgcgttagg cccagtcgcc   1020

gatcaggata cgacgaaaaa gtgtagggtc aagactccct tgatgcgatt caactattct   1080

tgacgggggg ttgccattgt attgcaccgt cttgcccgac tggctgtgcc cgcaaagaca   1140

gaacgtccca aaaacaggaa agaacaaaga agttttgtgg agcctgccaa gaatgtgtga   1200

tgaacagtga ctgacagcat gaatggggga tgaatattga ataccgaaaa aggatgatca   1260

gacaactgtt tatggagatt ttgcgccaac tcgtcttcat ctccgtgtca ggacaagatt   1320

ctcttatcta tcgtcctttc cgcggttttt gcaaccatgc gaattcgtga ctgagacaga   1380

taaaaggcgt tggattcagc ttagcattca atattcaata cttacctccc attcgaactc   1440

gagcccaaga cctctgctct aaatcacaat gtctgacatc aatgccaccc gtcttcccgc   1500

ttggcttgta gattgcccat gcgtcggtga cgatgtcaac cgtctcctca ctcgtggcga   1560

gaggtgagct caaaattcca tttaataatg tagcaatgga ctcatgtgtc gtgtatcagc   1620

ctttgctaaa tgtctcatcc actagtcaag gtacccgcct cggatttcat gataacgaag   1680

ggtgattgtg ctgactatga cgaaggcaaa ttgtagaaca cgtcttgctt gcaaagcgat   1740

gatcgtgccg ctgaaccagc gtcttaaaga ttgtcgtgat aatcatcggg gacacttggc   1800

taacacgact gaagtacatt acccttctta ctgattctcc tttgtcaatc tctaataccc   1860

ccctcaatga tgctctgagc tgtgcaatgc aatgcactag agaagggggg ggaggtgtga   1920
```

```
gagatagcat ctcaacattt atcaatgcca gcttgtatgc cgcgatccac agcagaccga   1980
cctgaccgac cgtgtcattg ctacttgcct acttgaacat atcacataca acattggcag   2040
cttttgtacc gtttaagagt cctgcggcgt gtagcctgga agaatttcca gcaggggtcc   2100
ttcctgatga gtttgacagc tcgcatagtt gtaaaagcgg caagtccaca aaaacagcga   2160
ttttatgtta cattgcgtga cgaggaggta atgagagcat gagacgagca ttttgcaacc   2220
ttgaactggg ccgagcacct gagagaaaga tgcaacgccg atgaggaaga atcatggtga   2280
tgatgtatgt ataggcatgc gatggcatgt gctggcgacg attgggaaga ggcggaaggg   2340
tcgcttgggg cgggaaaaca ctgcaggctg caggcgtgct cgaggagaga tagacacgct   2400
acgtgattac tacgccagcc ctctcaggct gtaatgatcg ttcatcaaag ttggttagag   2460
tgggctggtg atgatgcatc ttgtgtcggt gcgtggcacg atggactatg ggaggcaagt   2520
ttggcgtact agtaggtcta taaggatgat gtgaaatatg tgggtatgcc agtcatccaa   2580
cctaccattt acgtcacgat gctaagcctc atcgccacac atctgaaaag ctggtcctcc   2640
acgtgaagtg aggaatcatg aaagtcattt ttgcttggaa ggaaagccca tgcgactcag   2700
taaactctac taagacacga aacgaacgat gttgcacatg agatcctatg tcagtctcgc   2760
acagcatagg cactttcgga ccatcctcgc cggctacctt gggccgcccg aactgccaac   2820
tcagttccgt cgatggtcca ttggggaact caaaactgaa atggaggacc agaatcacaa   2880
gcgcagcctg gcaattgtca agtcaaaaat gaataaaaac cggcaggagt ttcgccatac   2940
cttcatctcc agcaaggcga ggtctcttcc cggacacagc ctttggccag caccgaaagt   3000
caatagattt cggtagccgg gtactttctc ccttcttcct ttcttatgac catcaacttc   3060
cagccacctg cttggatcga atgtcgccgc atccggtccc cacaacgtct ctgatatatt   3120
cattcctcct aaagggatgc ggagacggtg cctttcctca cgaacaagct gtcgatcatc   3180
gctccagatg cagttcgtat gggatccgtc agcggtatca catcgtcttc ggctgcctag   3240
tcgaaaagat cgtcatcata aaaagatagg gatgaaagga agggacgaac cacgcgggtt   3300
agtaccattt ctgagggatg taacctcagt atctcggata taaaagcatc gaggtatttc   3360
agatcctttg tcagctggtc gtatgtaggg cgttctccgt ctgccaagca ctccttgagt   3420
tcggcacgga gagtctcttg aatttctgcc cggcgagcaa gctcaatgag ggaccactga   3480
gggaaagctc ggcgatggat ctcttgtaga taaataacat taccgtcatg gcaactgtga   3540
acagcatagt tagtggatta tgagatcatc ggactgctag tcatagaact tacttgccgt   3600
agtttcatac ccggccaaga caagaccacc cttcggttat atcaggtcag agtggataca   3660
aaagagattg catagggaca tacagcctac aaaggatgtt gatcgagcac cgacgccgat   3720
gtgtgaagca acttacctgg gccgtgatct cgggaagtga taaacggacg ttagcatttt   3780
catttttgga cttgactata tataggaaag ctgaaatctc cttacacgtg gtcaggatag   3840
aggtaacata cgcataaccc caaggattga ttggtgaacg gcgctatctt caggcgcctc   3900
acgtgcttcc cgcagaaagc cagtcgcgag tactttaaag tgcgctgcca gttcctcaaa   3960
ctgcttttct ttggcattcg gtaaggtaat cttgaagagg ttataaagta tctcgcgggt   4020
aaacacaata aaccttatgt aaaggcctga agggctgact gcgtggaaag catccaagtc   4080
agctaagatc gaacacgtat ggcccctcat gttgccgaag tcatacgaca atacagcttt   4140
tccaatatta tccatgctag gaatatattg caggtgagaa gaatggggca gagtaaaggt   4200
tgcgagtcat acgtgtaaca gttcatcctt gggcacataa tgaaccaatt aaatgaaggc   4260
```

```
tagaaggaaa gcaactcacc atttctctgc atcaagcacg atagcacggt tcgaattgtt   4320
tgacaactgg aaacatgaat cccatgatgc tttgagctat catttgtgct gttcaatcga   4380
ctgactctca aagctggaac cgtcctgacc tgataggcgg aatccaaaca cataggagtg   4440
aaattgcgga ttgccgagac cgacagggga gaagacaaga ccctccgtat tctataatcc   4500
gttcaatatt aaatttatgc catgttttca agcagtcaag agcgaccaac ctcttgtggg   4560
tctccccttc cgtgagcacc aaaatatcac caaactggaa caagttaagt ctgacagctc   4620
gggaaaacgc tggaacaaac gctcaccaac ttccgcccca tgtctttctg cctagcaggc   4680
tgagaatatg tgacagtgtc cttggaaaat aagtgtgtga gagccttggg atcgttcaat   4740
acgacgtggt tggagccaaa gccagaggct atttcataga cgggcccgta agtctgctcc   4800
aaaccttgat acaccaaact gaggttggct gaagggaaga tcttcctagc attgccgagg   4860
atgaagctct ccatgtgtgg tccttgcagt ctcggcgttc taggacctcg acggcttcgg   4920
taaatggaaa caacgacgag caaggatatg ccagaggcta ttatcctcat cgaattgact   4980
ttgaggtact ccgcgacata aggccaaagg ctgctgaaat tgaggttcaa catcgcgaag   5040
agagcgatcg cgggccgtta cagaggtgag accaccagta ggccatccag atatggatac   5100
gactcaagat agaaaatggg gtcctcacca aaaaaggatg ccaaactggc gagtctccaa   5160
gtcatttcca tcaagggcgg acagcctcag cgggatttac tattggccca actggatatg   5220
gatagtgtgg ggtgaatagt ataatattgt gaagaagaag atgatgagtg gcggacagca   5280
tgaatgcaag atctgtcgct gaaaaaggat gaaaggtcac tgatgatcta tgatcagatt   5340
gctttcgacg attcggccga agggatcaca ttctattctt gccgacggtt tatttcctat   5400
gggtgacggt ttgcacgctt acggccgcgc gggtgggaac gctgcgaaag aactttccgt   5460
ttgtatcgcg ccggtaaatc ccgaggcgcg actggccacg ctgagccaaa caaatgagcg   5520
tcactgcgga ttcacgcacc ctaactacac gcagaagccc tacttcggtg ctcatctact   5580
gatagctaat gaatattgag gccaactcac gaggcctcgt aggtggctgt ggtaatcact   5640
gtttggcgca ggtatgtctc atctttcgaa ctgggcgtcg catttggatt taccatcaac   5700
cagtcgcggt tgcggccgca tgtccttgac agggcaggtt tcaggctgac ttcataccag   5760
agatctgatg tcgcaaacat cgccagtgat ttcgttccgt tgtcttacta gagtttgctg   5820
agctgcatgg gctttccttc caagcaaata tgattttcgt gattcctcac ttcacgtcgg   5880
gagcccagct tttcagatat gcggcgactg cctcccatgg tccattgtgc ccgcgtcgac   5940
acaagatacc tcatcaccag cccttccccc gcgactttag ccaactttaa tgaacggccc   6000
ttgagagact ggcgtagtaa tcgcgtagcg tgtctatctc tccaatcgtc gcccgtgttc   6060
gcctacacac atgcgatcgc attatgccta catcatcgcc attctctcct ccccctcgtc   6120
atcggggttg ctgagcctgc tttttcccgg gtgtagttca aagttgcaaa ttgctcgtct   6180
catgctcctc gtcacgcaat gtaacataaa ttcactgttt ttgtgaactt gccgacttcc   6240
acaactatgc gagctatcaa actcatcata aaagaccctt ctttgaaatt cctccaggtt   6300
atacgcccca cggcttttca atggtacaac agctgcctat gtgatatgtg atatgttgct   6360
gacaagtagc aatgataagg acagtcagga cggtcaagct ctggcgacag cagcatgcgc   6420
tcggattgct aaacgctctc ttactgacaa cacacacaca tacacacaca agtatattgc   6480
attccatagt acagctcgga tcatttacgt gggttttata tgagaatgag aaagaatgag   6540
aaataacgtg agtcgtctaa tccaagttgg ctcgctgctt atcacagaaa aacttgaagg   6600
ccttacttcc gatgcaggct caacgctcca agcctaacat tgtcaacaac ttgcgtcgtc   6660
```

-continued

```
cactactaca tcgaagtaag taccatgacc atgcattgtc atcaagaaat cagaggcgga   6720
taccttgact agtggatgag acatttagca aaggctggta cacgacacat aagtacattg   6780
ctacattatt aaatggaatt ttgagctcac ctctcaccac gagtgaggag acggttgacg   6840
tcgtcaccga cgcatgggca gtctacaagc caagcaggaa gacgggtggc attgatgtca   6900
gacattgtga tttagagtag aggtcttggg ttcgagttcg aatgggaggt aagtaatatt   6960
gacagctgag ccgcatccaa cgccttttat ctgtttcagt cacgaattcg caagattgga   7020
aaaccgcaga aagtacgata gataagagaa tcttgtcctg acacggagat gagaagacaa   7080
attggcgcaa aatctccata agcgtttgtc tgatcggtct tcccatgaat cattcatgct   7140
gtcccccact ctttatcaca caggctccac gcttactata tggaatccgt gaacttcttt   7200
gtttttaggg gcgttcggtt tctgcggaca ttcagccggg caagacggtg caatacaatg   7260
gcaaccccgt caaaagttgt tgaatcacat caagggagtc ttgaccttaa gcttacactt   7320
ttcatcgtat cctgcgtgtt ggcgatttat gccgaactgg gcataacgcg tttcgaacac   7380
cacttagcac agcctctctt tgtctgtcct ggtggtcaca gattaaacag ttaagtggca   7440
gtcctacaga ccgatagata ggtgttttgt cccaaaatgg acatgtatga gaatgattat   7500
cgggcgtgtg tatttaagaa tcccttcggc cgagttcccg atcattcggc tccatcttgc   7560
gctcacactt gtgttgcatc atacgaacgt ttcgtctgtt ctttcccgga atcggatctg   7620
tccctatcca ccttcacggt aagatggacc cccaacaccg tccccggaga tagataggtc   7680
aagcatttat cgcgcctggt tacggtttcg ggtcctcaga aacattttcc tcgcattcgc   7740
gcaacttgat cgccttccac ggctcgtcca cttcgtgatg ttgaacctca acttcaacgg   7800
cctctggcct gatgtagcag agtatttcaa aggcgattcg atgaggattg tgacctctgc   7860
ctttacgttg ctcgtcgtca tttctatcta tcgaagacgc cgaggtatca gaacgcccag   7920
actgcaagga ccacgcagcg agagcttcat cttcggtaac accaagaaga tcttcccttc   7980
ggcgaacctc agtgtggtat atcgggattg ggaacgaatg tatgggcccg tttacgagat   8040
acccactggc atcggctcca gccatgttgt attaagcgat cccaaggctc tcacacacat   8100
atattccaag gataccacca catattgtcg gctcgcaggg acaaccgctt tgagccggaa   8160
gttggcgagt atctgttttg caccattttt cttagctgcc agccttattt acgttccagt   8220
atggtgatgt tgtatctatt tctgagggcg agactcacaa gcggtcggtc actctttatc   8280
gctcaacgat cagggcataa acttaacatg atcgcagact acggagaggc ctgtcttctc   8340
cactgtcggt ctcagcaatt cgcaatctca ctcccgtgtg cttggattct gcctatcagg   8400
ttagaatggt tccattctta aaacaatcgg ccgattgacc aacataaatg acagctcaaa   8460
gcagcatggg attcatgttc tccgtcatca gagcactcaa acaaccccgt cataattgat   8520
gtcgtgaaat ggcaagttgc tgtatctatc tcccccattg ttagttaacc ttgttctctg   8580
tgcccaagga tgaattctgt cacgtacgtt gcgcagcctt cattccgccc ttgccctgaa   8640
atgttcctag attggacact atagggaaag ctatattgtc gcatgacttt ggaactctaa   8700
ggggccgcac gtccttgatg atggccgcct ttgactctat ccacacagtc aagccttccc   8760
cctttataag gcttattcac tttctgtcac cgatactcta tgccctgttt aaagttaccc   8820
tcatgagcgt cagagaagag aagctcgcac aatcagtagc acacttgaat aggcttacaa   8880
ctaacagcct gaacaaggca tgtaaggaac cggaagatac tgtcaacgaa tcagtccttg   8940
ggattctggg tatgtcacca atatatgagg tgatgtttct tcgtgcctac gcttccctgt   9000
```

```
atagtcaagt cagaaaacgc aaatcccaac agccgtttgt cactctccga gatcacggcc   9060
caggtatgta gcccaagtgc acatcggctt gatgcctaat caacatactt tgtaggccgt   9120
acgtaccttt gccactcctc tgatattctc tgtaagttaa tataaccgaa gagtttcctt   9180
ttcatggctg catatgaaac aacagcaagt aagttctgcg aacggttgtc cttgtttatc   9240
aaagatctca taaactatga cccgtgctgc tcatagtcac cttaacggta atcttcgcct   9300
acgagtgttc aagctgttct attactgagc cttcactcag tggtctctca ttgaacttgc   9360
acgccggcca gaaatccaag agagcctccg tgctgagctc tcagaatgtt tggcaaaggg   9420
agaacgtcct acatacgacc agctaacaaa ggatctgaaa tacctcgatg cttttatagc   9480
cgagatactg agactccatg cccccgaaat gcaatcaatc cgtgtggttc gtcttcattg   9540
tttaattcct tcccgcatcc ccctattatc ttggcaggca gccgaagacg atgtgatacc   9600
gttgacaaat cccatacgta ttgcatctgg agcgacgatc gatagcttgt ttttgaagaa   9660
aggtatggtc gtccgtatac ccttgggggg agtgaatatg tcggaagcgt tgtgggggcc   9720
agacgcgggc atgttcgatc caagcagatg gctggacgct gagggtcata agaaaggaaa   9780
caagggagaa ctagctggct accggggtct cttaactttc ggtgctggtc ccaggatgtg   9840
tccaggcaga gacctcgccg tactggaggt gaaggtacga ttgaacccca tgtcagcggt   9900
ttggttgttt gactgcacaa tctctaggct gtgctgtcgg ttctggtcag atattttgcc   9960
tttgagctcc ccaatgggcc atcgacggaa ctgagttggc attttacgcg ccccaaggta  10020
gctggcgagg atggtacaaa agttcctctt cttgtgcgaa agttaacata ggcgttcccc  10080
gtaccactgt ttttgtacta gggtagaaaa catggtggtg gtgctcgcct acttgataag  10140
cagactcgtg cgaaacacca tgtcaatcga tgacgggcat aagagaccac gacattgggg  10200
cgatgaagtc ggtggtgact catacgagtc gtattgtaaa tttttgcttg ggaagtcatg  10260
gcatgtcgca acagttggcc ccactgatgt cattcaacca accgacatct cgaggcttgc  10320
gctaaagtct cccgccatta acgccgcgtt ccaatgctgc gtcatccgca gtgcctgcac  10380
cgtcagaacg catttagtag tggcaagaag cttctgtcaa attcaatcgc taaccggttc  10440
tttgacgggc tagaaccctg gttatgaact aaacttcggc ggcagctcgc atgctcaagc  10500
tcttttccat cctccacatt ttactctcat catttctcag ccccgaactc agttcgtaat  10560
tgactgctat gtaatatcat agatgccagt acaaactcca cacagtggtc cctagacctc  10620
taggtataat gaaccacgag gcgcgttaac ttcgagcttt atatggcttg atgagcagcg  10680
ggagctgata acggcccggg tccgtggtca aaatcggtcg gttacttagt ccactttcca  10740
cagaaatttg ctccgctggc acagccaagt caaattcgag ggcacggact agtgtgaaga  10800
gtagagcttt cattcttgtc gttaccagtg tcagcactat atcttcgaaa tgctagagaa  10860
aacttgctca ctcggcgata gcaaatctga atccgataca cgaacgtgga ccaccccaaa  10920
aactgagcaa atggctccag acgcctggga tggtattgac gccttcaggt agacattccc  10980
atcgttctgg tctatcaaaa ctgaatgact caggagccaa cagcgacgtg caatatttac  11040
ctgaagtcta aagcatcttc accccatatc gacttgtcct tgtggatggc agaaatggga  11100
attatgacta cttgccctct tttgatacta taagaccggt gaacgctaaa aagaaatatg  11160
ggaacgaccg aatcctcacc taatactgga gaataggttt cctctccggt cggtgatcgg  11220
cttagccaaa ggtaaaatgt cgtccttggc acacaccctc gagtggccta gatgaaggat  11280
acagacgtag cgtctcccta attaccatat ccaaatatga aagtgcattg agctggtccg  11340
tcgttggctg acaggtatcg accgtgagca gctctctacg cagcttagcc tggatttcac  11400
```

```
ggttttttgc cagagaaaat aaagcccacg ccattacgtt actaccaatc aaatattcga  11460
gaatagtcct taaacagata aacagactca gacttacatc ggactttcac gtccagcaat  11520
tacaaatgag ataacctcta aataaaaaga tcaggtatac tcgcagtgac aaatacatca  11580
gcctcacgcg ctttgacttc gtcatcggat agacgacggt gctctggcac atcgggggac  11640
atattggtgc gaaccaaaag cgataggaga tctcgactgc cggaattgtc attattcgta  11700
cgtacggatc ccttgctctc gttcagaagc cgactcgtaa tccgagaaag ggtctgcttg  11760
atatcgtcta gttgtgtctc tacaggatca ggctagacaa cgcgatgaga actccgttac  11820
agtgatttgg aatttccata ctatgaacca tagaagtggg atgaatcttc ggagttgcca  11880
acgaatcagg ttcaattgag ataaaattgt agccacacgg ctaaagtcac tttcacgatc  11940
cagggaatca agctcgtaac ggaagccttt ccatcgaatg gcatcggtaa acactaataa  12000
gtatgctggc aacatcagac atacctgttg agctgatgat gtccatcacc accttaccaa  12060
ggcctaccat aatgtctaag cggcaagtac caccttgttt cgagcattca gtagcccaag  12120
agtcttggag ctaggcgaag ttcatcactg gtagcatgga tgagtagtaa aaaccgaccc  12180
gttttgattt ttttacgaag caatctgtga attcgcgaat gcggaccgga ccaaaggcag  12240
gattctggtt gtgattgaga cactgatgga ccacgatttg gaatggatag atagtcacca  12300
aaatcttccg ctgttaaacg taatatatca taatacgaac taggttgagg caacggaagt  12360
acgcacctgc tttttatgtt gatccccttc gacaaaaggg agacctgacg tatggttgga  12420
tcatcgcctc ttaagtatgg taggtgaaaa agcacctgga ccccacaact tgccgatctg  12480
gcggcgagta aacgatggtt tggtgtaaac gtaaccattc gtcaaaatgt ggttcaaggc  12540
ctgcggatcc gtcacatata aatgcgaaag ctaaacttga ttgttatcta tatcagaata  12600
aatggattgg ttcttacacc gagaaatcca tttagtctta tcatcggccc atattgtgaa  12660
tgccaatgat atgtctgtgg taatagtggt taacaatggg tgggtaggtg ggtgattttg  12720
tacttacatc tgtccagagc tgtttgagat taccaagaaa tatattggcg tttgctggac  12780
cggggagatg gcgtattgga gaagtcagct caacataaat tacacgagtg actctgtaaa  12840
gtccatagat agtcaatgca gctgcagata gcttgaggaa ttggaatata agcctgaaag  12900
tgacgagagc tgaatacgag atggtgtgca agtcgaccat tgttattaac ttggtaacgg  12960
gcaaacgttt caaacttgta ggtggatcgg ttaaatctcc gattgaagat gatgctgagt  13020
ttcgtaggtt gcactgatgg ttccgattcg tccctttttt tcggtgagag acacattatc  13080
ttcattactg tatcttttgg atttactagc tccccccctgt caccgtctcc actttccatc  13140
atcgattatc gattctatcc atttctggtt atgctacgct cccatcatgg acatcgccgc  13200
ccttcggctg cgatgtgctg aaaatagtga aacttctctg acttctctcc gatc        13254
```

<210> SEQ ID NO 613
<211> LENGTH: 226
<212> TYPE: PRT
<213> ORGANISM: Galerina marginata

<400> SEQUENCE: 613

```
Ala Pro Thr Arg Leu His Leu Arg Val Arg Thr Arg Phe Ser Tyr Leu
1               5                   10                  15

Ser Ser Phe Pro Arg Phe Leu Gln Pro Cys Glu Phe Val Thr Glu Thr
            20                  25                  30

Asp Lys Arg Arg Trp Ile Gln Leu Ser Ile Gln Tyr Ser Ile Leu Thr
        35                  40                  45
```

```
Ser His Ser Asn Ser Ser Pro Arg Pro Leu Leu Ile Thr Met Ser Asp
    50                  55                  60

Ile Asn Ala Thr Arg Leu Pro Ala Trp Leu Val Asp Cys Pro Cys Val
65                  70                  75                  80

Gly Asp Asp Val Asn Arg Leu Leu Thr Arg Gly Glu Arg Ala Gln Asn
                85                  90                  95

Ser Ile Cys Ser Asn Gly Leu Met Cys Arg Val Ser Ala Phe Ala Lys
            100                 105                 110

Cys Leu Ile His Ser Arg Tyr Pro Pro Arg Ile Ser Arg Arg Val Ile
        115                 120                 125

Val Leu Thr Met Thr Lys Ala Asn Cys Arg Thr Arg Leu Ala Cys Lys
    130                 135                 140

Ala Met Ile Val Pro Leu Asn Gln Arg Leu Lys Asp Cys Arg Asp Asn
145                 150                 155                 160

His Arg Gly His Leu Ala Asn Thr Thr Glu Val His Tyr Pro Ser Tyr
                165                 170                 175

Phe Ser Phe Val Asn Leu Tyr Pro Pro Gln Cys Ser Glu Leu Cys Asn
            180                 185                 190

Ala Met His Arg Arg Gly Gly Arg Cys Glu Arg His Leu Asn Ile Tyr
        195                 200                 205

Gln Cys Gln Leu Val Cys Arg Asp Pro Gln Gln Thr Asp Leu Thr Asp
    210                 215                 220

Arg Val
225


<210> SEQ ID NO 614
<211> LENGTH: 260
<212> TYPE: PRT
<213> ORGANISM: Galerina marginata

<400> SEQUENCE: 614

Leu Cys Asp Lys Glu Trp Gly Thr Ala Met Ile His Gly Lys Thr Asp
1               5                   10                  15

Gln Thr Asn Ala Tyr Gly Asp Phe Ala Pro Ile Cys Leu Leu Ile Ser
            20                  25                  30

Val Ser Gly Gln Asp Ser Leu Ile Tyr Arg Thr Phe Cys Gly Phe Pro
        35                  40                  45

Ile Leu Arg Ile Arg Asp Asn Arg Lys Ala Leu Asp Ala Ala Gln Leu
    50                  55                  60

Ser Ile Leu Leu Thr Ser His Ser Asn Ser Asn Pro Arg Pro Leu Leu
65                  70                  75                  80

Ile Thr Met Ser Asp Ile Asn Ala Thr Arg Leu Pro Ala Trp Leu Val
                85                  90                  95

Asp Cys Pro Cys Val Gly Asp Asp Val Asn Arg Leu Leu Thr Arg Gly
            100                 105                 110

Glu Arg Ala Gln Asn Ser Ile Cys Ser Asn Val Leu Met Cys Arg Val
        115                 120                 125

Pro Ala Phe Ala Lys Cys Leu Ile His Ser Arg Tyr Pro Pro Leu Ile
    130                 135                 140

Ser Gln Cys Met Val Met Val Leu Thr Ser Met Trp Thr Thr Gln Val
145                 150                 155                 160

Val Asp Asn Val Arg Leu Gly Ala Leu Ser Leu His Arg Lys Gly Leu
                165                 170                 175

Gln Val Phe Leu Ala Ala Ser Gln Leu Gly Leu Asp Asp Ser Arg Tyr
```

```
            180                 185                 190

Phe Ser Phe Phe Leu Ile Leu Ile Asn Pro Arg Lys Ser Glu Leu Tyr
        195                 200                 205

Tyr Gly Met Gln Tyr Thr Cys Val Cys Met Cys Val Cys Cys Gln Glu
    210                 215                 220

Ser Val Gln Ser Glu Arg Met Leu Leu Ser Pro Glu Leu Asp Arg Pro
225                 230                 235                 240

Asp Cys Pro Tyr His Cys Tyr Leu Ser Ala Thr Tyr His Ile Ser His
                245                 250                 255

Arg Gln Leu Leu
            260


<210> SEQ ID NO 615
<211> LENGTH: 1512
<212> TYPE: DNA
<213> ORGANISM: Galerina marginata

<400> SEQUENCE: 615

atgtttgcga catcagatct ctggtatgaa gtcagcctga aacctgccct gtcaaggaca      60

tgcggccgca accgcgactg gttgatggta aatccaaatg cgacgcccag ttcgaaagat     120

gagacatacc tgcgccaaac agtgattacc acagccacct acgaggcctc cgtggccagt     180

cgcgcctcgg gatttaccgg cgcgatacaa acggaaagtt ctttcgcagc gttcccaccc     240

gcgcggcccc tttggcctta tgtcgcggag tacctcaaag tcaattcgat gaggataata     300

gcctctggca tatccttgct cgtcgttgtt tccatttacc gaagccgtcg aggtcctaga     360

acgccgagac tgcaaggacc acacatggag agcttcatcc tcggcaatgc taggaagatc     420

ttcccttcag ccaacctcag tttggtgtat caaggtttgg agcagactta cgggcccgtc     480

tatgaaatag cctctggctt tggctccaac cacgtcgtat tgaacgatcc caaggctctc     540

acacacttat tttccaagga cactgtcaca tattctcagc ctgctaggca gaaagacatg     600

gggcggaagt tgaatacgga gggtcttgtc ttctcccctg tcggtctcgg caatccgcaa     660

tttcactcct atgtgtttgg attccgccta tcaggtcagg acggttccag ctttgagaca     720

tcatgggatt catgtttcca gttgtcaaac aattcgaacc gtgctatcgt gcttgatgca     780

gagaaatgca tggataatat tggaaaagct gtattgtcgt atgacttcgg caacatgagg     840

ggccatacgt gttcgatctt agctgacttg gatgctttcc acgcagtcag cccttcaggc     900

ctttacataa ggtttattgt gtttacccgc gagatacttt ataacctctt caagattacc     960

ttaccgaatg ccaaagaaaa gcagtttgag gaactggcag cgcactttaa agtactcgcg    1020

actggctttc tgcgggaagc acgtgaggcg cctgaagata gcgccgttca ccaatcaatc    1080

cttggggtta tgctcaagtc caaaaatgaa aatgctaacg tccgtttatc acttcccgag    1140

atcacggccc aggctggtgg tcttgtcttg gccgggtatg aaactacggc aaagatccat    1200

cgccgagctt tccctcagtg gtccctcatt gagcttgctc gccgggcaga aattcaagag    1260

actctccgtg ccgaactcaa ggagtgcttg gcagacggag aacgccctac atacgaccag    1320

ctgacaaagg atctgaaata cctcgatgct tttatatccg agatactgag gttacatccc    1380

tcagaaatgg tactaacccg cgtggcagcc gaagacgatg tgataccgct gacggatccc    1440

atacgaactg catctggagc gatgatcgac agcttgttcg tgaggaaagg caccgtctcc    1500

gcatcccttt ag                                                        1512


<210> SEQ ID NO 616
```

<211> LENGTH: 503
<212> TYPE: PRT
<213> ORGANISM: Galerina marginata

<400> SEQUENCE: 616

```
Met Phe Ala Thr Ser Asp Leu Trp Tyr Glu Val Ser Leu Lys Pro Ala
1               5                   10                  15

Leu Ser Arg Thr Cys Gly Arg Asn Arg Asp Trp Leu Met Val Asn Pro
            20                  25                  30

Asn Ala Thr Pro Ser Ser Lys Asp Glu Thr Tyr Leu Arg Gln Thr Val
        35                  40                  45

Ile Thr Thr Ala Thr Tyr Glu Ala Ser Val Ala Ser Arg Ala Ser Gly
    50                  55                  60

Phe Thr Gly Ala Ile Gln Thr Glu Ser Ser Phe Ala Ala Phe Pro Pro
65                  70                  75                  80

Ala Arg Pro Leu Trp Pro Tyr Val Ala Glu Tyr Leu Lys Val Asn Ser
                85                  90                  95

Met Arg Ile Ile Ala Ser Gly Ile Ser Leu Leu Val Val Val Ser Ile
            100                 105                 110

Tyr Arg Ser Arg Arg Gly Pro Arg Thr Pro Arg Leu Gln Gly Pro His
        115                 120                 125

Met Glu Ser Phe Ile Leu Gly Asn Ala Arg Lys Ile Phe Pro Ser Ala
    130                 135                 140

Asn Leu Ser Leu Val Tyr Gln Gly Leu Glu Gln Thr Tyr Gly Pro Val
145                 150                 155                 160

Tyr Glu Ile Ala Ser Gly Phe Gly Ser Asn His Val Val Leu Asn Asp
                165                 170                 175

Pro Lys Ala Leu Thr His Leu Phe Ser Lys Asp Thr Val Thr Tyr Ser
            180                 185                 190

Gln Pro Ala Arg Gln Lys Asp Met Gly Arg Lys Leu Asn Thr Glu Gly
        195                 200                 205

Leu Val Phe Ser Pro Val Gly Leu Gly Asn Pro Gln Phe His Ser Tyr
    210                 215                 220

Val Phe Gly Phe Arg Leu Ser Gly Gln Asp Gly Ser Ser Phe Glu Thr
225                 230                 235                 240

Ser Trp Asp Ser Cys Phe Gln Leu Ser Asn Asn Ser Asn Arg Ala Ile
                245                 250                 255

Val Leu Asp Ala Glu Lys Cys Met Asp Asn Ile Gly Lys Ala Val Leu
            260                 265                 270

Ser Tyr Asp Phe Gly Asn Met Arg Gly His Thr Cys Ser Ile Leu Ala
        275                 280                 285

Asp Leu Asp Ala Phe His Ala Val Ser Pro Ser Gly Leu Tyr Ile Arg
    290                 295                 300

Phe Ile Val Phe Thr Arg Glu Ile Leu Tyr Asn Leu Phe Lys Ile Thr
305                 310                 315                 320

Leu Pro Asn Ala Lys Glu Lys Gln Phe Glu Glu Leu Ala Ala His Phe
                325                 330                 335

Lys Val Leu Ala Thr Gly Phe Leu Arg Glu Ala Arg Glu Ala Pro Glu
            340                 345                 350

Asp Ser Ala Val His Gln Ser Ile Leu Gly Val Met Leu Lys Ser Lys
        355                 360                 365

Asn Glu Asn Ala Asn Val Arg Leu Ser Leu Pro Glu Ile Thr Ala Gln
    370                 375                 380

Ala Gly Gly Leu Val Leu Ala Gly Tyr Glu Thr Thr Ala Lys Ile His
```

385 390 395 400

Arg Arg Ala Phe Pro Gln Trp Ser Leu Ile Glu Leu Ala Arg Arg Ala
405 410 415

Glu Ile Gln Glu Thr Leu Arg Ala Glu Leu Lys Glu Cys Leu Ala Asp
420 425 430

Gly Glu Arg Pro Thr Tyr Asp Gln Leu Thr Lys Asp Leu Lys Tyr Leu
435 440 445

Asp Ala Phe Ile Ser Glu Ile Leu Arg Leu His Pro Ser Glu Met Val
450 455 460

Leu Thr Arg Val Ala Ala Glu Asp Asp Val Ile Pro Leu Thr Asp Pro
465 470 475 480

Ile Arg Thr Ala Ser Gly Ala Met Ile Asp Ser Leu Phe Val Arg Lys
485 490 495

Gly Thr Val Ser Ala Ser Leu
500

<210> SEQ ID NO 617
<211> LENGTH: 35
<212> TYPE: PRT
<213> ORGANISM: Galerina marginata

<400> SEQUENCE: 617

Met Ser Asp Ile Asn Ala Thr Arg Leu Pro Ile Trp Gly Ile Gly Cys
1 5 10 15

Asn Pro Cys Ile Gly Asp Asp Val Thr Thr Leu Leu Thr Arg Gly Glu
20 25 30

Ala Leu Cys
35

<210> SEQ ID NO 618
<211> LENGTH: 17
<212> TYPE: PRT
<213> ORGANISM: Galerina marginata

<400> SEQUENCE: 618

Cys Ile Gly Asp Asp Val Thr Thr Leu Leu Thr Arg Gly Glu Ala Leu
1 5 10 15

Cys

<210> SEQ ID NO 619
<211> LENGTH: 34
<212> TYPE: PRT
<213> ORGANISM: Galerina marginata

<400> SEQUENCE: 619

Met Ser Asp Ile Asn Ala Thr Arg Leu Pro Ala Trp Leu Val Asp Cys
1 5 10 15

Pro Cys Val Gly Asp Asp Val Asn Arg Leu Leu Thr Arg Gly Glu Ser
20 25 30

Leu Cys

<210> SEQ ID NO 620

<400> SEQUENCE: 620

000

<210> SEQ ID NO 621

<400> SEQUENCE: 621

000

<210> SEQ ID NO 622

<400> SEQUENCE: 622

000

<210> SEQ ID NO 623
<211> LENGTH: 17
<212> TYPE: PRT
<213> ORGANISM: Galerina marginata

<400> SEQUENCE: 623

Met Ser Asp Ile Asn Ala Thr Arg Leu Pro Ala Trp Leu Val Asp Cys
1               5                   10                  15

Pro

<210> SEQ ID NO 624

<400> SEQUENCE: 624

000

<210> SEQ ID NO 625
<211> LENGTH: 15
<212> TYPE: PRT
<213> ORGANISM: Galerina marginata

<400> SEQUENCE: 625

Cys Val Gly Asp Asp Val Asn Arg Leu Leu Thr Arg Ser Leu Cys
1               5                   10                  15

<210> SEQ ID NO 626
<211> LENGTH: 33
<212> TYPE: PRT
<213> ORGANISM: Galerina marginata

<400> SEQUENCE: 626

Met Ala Asp Ile Asn Ala Thr Arg Leu Pro Ile Trp Gly Ile Gly Cys
1               5                   10                  15

Asn Pro Cys Ile Gly Asp Asp Val Thr Thr Leu Leu Thr Arg Ala Leu
            20                  25                  30

Cys

<210> SEQ ID NO 627
<211> LENGTH: 24
<212> TYPE: PRT
<213> ORGANISM: Galerina marginata

<400> SEQUENCE: 627

Met Ser Asp Ile Asn Ala Thr Arg Leu Pro Trp Cys Pro Cys Gly Asp
1               5                   10                  15

Asp Val Leu Leu Thr Arg Leu Cys
            20

<210> SEQ ID NO 628
<211> LENGTH: 32
<212> TYPE: PRT
<213> ORGANISM: Galerina marginata

<400> SEQUENCE: 628

```
Met Ser Asp Ile Asn Ala Thr Arg Leu Pro Ala Trp Leu Val Asp Cys
1               5                   10                  15

Pro Cys Val Gly Asp Asp Val Asn Arg Leu Leu Thr Arg Ser Leu Cys
            20                  25                  30


<210> SEQ ID NO 629
<211> LENGTH: 110
<212> TYPE: DNA
<213> ORGANISM: Amanita bisporigera

<400> SEQUENCE: 629

acccttccgc aatgtctgac gtcaatgaca cccgtcttcc cttcaacttc ttccgctttc     60

cctacccctg catcggtgac gacagcggaa gtgtcctcag gctcggcgag               110


<210> SEQ ID NO 630
<211> LENGTH: 3237
<212> TYPE: DNA
<213> ORGANISM: Puccinia graminis

<400> SEQUENCE: 630

atgaccaaac ctactaagaa cccatgggac cctaaggcaa caccttatcc ccccgttcgc     60

agggatccag actcatcgga ggtcttccag agtaagcaga atggctcggt caccgtccca    120

gatcccttac agttggctac acgagccacc caagcagagc aaagacactc aggtgcgccc    180

cgtcaaaacc aaaaaaaaaa catgacttat tctgatctcc ttcctatttc agcaatttgt    240

caccagtcaa caggccttga ccaaggatta cctaagcaaa taccctcatc gagactcact    300

tcatgcggca gtcacaaaga cttgggacta tgctcgattc agttgtccat cgctgaagcc    360

ggatggatac tactatttca gcttcaactc tggcctccag gcccagtcga tcatctatcg    420

ggtcaagaag gggcaggaag aggatgcact caagcgggcc accgacccca aacagcccgc    480

aggcgagctc ttcctcgatc ccaacctgtt ctccatcgat ggcactaccg cactctcatt    540

ctccgccaca tccgagtcag gcatctatat ggcgtacggt gtctcccgct ctggaagcga    600

cagtcagact atctacgtcc gtcgcaccga ctctccccac acaaagtctg ccgccgatgg    660

tggcaagagg ggcgaggacc ctggccggat ggaggacaca gtcgagaagg ttaaattcag    720

tagcctcagt tggatgaaag acgattctgg tcagtccaaa aaatcaaaaa aaaaaaaaaa    780

attccttcat cagagcccgg tgggggacaa tcgatcgatc tcctgcttgc tgactgaatt    840

gtgatcgaac gattatcagg tttcttttat tcaagattcc ctgacgaaca ggccaaagct    900

gagaagccct ccgggcccgg ggcggatgtt caaggagaag tagagattga tgccgggaca    960

gatactaagg ctgatctcaa tcacatggta agcattcatt ccgtgagctc tgcagtgact   1020

tataaaaaaa actaatccca attctttctt tctgtagctc tactttcaca aacttggtga   1080

gccacagagt aaagatctgt tgatagtcga ggtcagaaga tttcgaacct gtttctctga   1140

tcggaggctc gtgtcctgag aataaaattt acttttgatc tggctcacag gatccagcga   1200

atccatccta tatgtgggga gctgaagtct cggatgagtg ggtgacttga ttttatttaa   1260

ctgccacatt cccgcatcga ctgatatgat ctgtgttctt ccagcgccaa gtacctcatc   1320

ttgacgacct ccaaggatac cggccgttcg aatcgactct gggttgccga tctgacctct   1380

caacccctat cgagtgagat gaaatggcaa aagattgtca atgagtttgg caacgagtac   1440

atcttcgcgg ccaatgatgg cagtcaacta tatttcatga ccaacaagga cgcgcctaaa   1500

cgcaagggta agaactccac agccatcaat catcgccaca gaagttttcc atcataccaa   1560
```

-continued caagacatta cttcgtagtg gtgacgtatg acttgagtaa gcccgaagaa ggctttaaag 1620
acttgatccc agaggatcct caggcggtcc tggagggtta ttatcccacc aacaaagaat 1680
tcaccgttct gagctattct cgagatgtca aagatgagct atacctccac gagatcaagt 1740
cgggcaagcg gatcaaacgg atcggcggag acttgattgg cacgatcggg ggcctttccg 1800
gccgccgtaa acacgacgag ttcttcttcc agatcagtag cttcttgagc cccggcacgg 1860
tctaccggta agtgatcggc tgtaacattt ttttttggta atgtgtatgg ttgtcctgat 1920
ggcactctcc aatttgctgg gttatggatt tttctttgcc tggaacctct tgcagctacc 1980
gtttcgatcg tcaagaggat caggaattgg tcgaattcag gaagactctg attccgggat 2040
tcaattccaa cgatttcgtt tccaaacagg tattctatga atcaaaggac gggaccaaag 2100
tcccgatgtt tatcgttcac aagaaagact tccagcagga cggtactgcg ccagctcttc 2160
agtacggata cgtaggcccc ccttttttta catattcttt ccatcatccg gtcagctcgc 2220
gaaaaccgga cagctaaggt gaactgttct ccagggtgga ttttcgatca gtatctcgcc 2280
ctacttttcg ccctctttca tgagctttgt agcccattat ggaggggtat tggctgtccc 2340
taacatccga gggggtggag agtatggaga ggactggcac ttggcaggct ggtcagtacc 2400
ctgaatgttc tcccttgaag ggtgtaaatt gaacgctaat tgattcgatg gaatctcatg 2460
gatcgtggat gggtacagct ttgagaaaaa acagaacgtg ttcgacgact tccagtacgc 2520
taccaaatat ctggttgcca atcagtacgc ggcgcccgac aaggtgacca tcatgggcgg 2580
cagtaacgga ggtctcctgg tggcagcctg cgtgaaccag gctcccgagc tctttggagc 2640
cgcgcttgcc gaggtgggcg tgttggacat gttgaggttc catcggttca cgattgggta 2700
agggtcactt tatccaatca ccgccatcct ctctctctct ccgttctctt gagcttgagc 2760
ttactctccc cgcgccctgc gtcacgtttc cagacgggct tggatcgctg actatggaga 2820
cccagaagac cccgaagcat tcgactactt gatcaaatat tccccccttac ataacgtcaa 2880 cccggccgcg gaatatccgg ctctcatgct actcacagcg ggtcagtgcc agacccatcc 2940
catctcatct atcgacacgc cacatgatta ttcttaggat ctgttggagc cccactactg 3000
atgaggaggt tcgaatatct acaacatata gaccatgacg atcgggtggt ccctctgcac 3060
agcttcaagt acgctgctgc cgttcaacac gccctcccga cgaacaaaca accttgcttg 3120
ttgaggctcg atctcaaggc aggtcatgga gccgggaaga gcacggagat gaagatcaac 3180
tcggtcgtcg accaacgtct gtcctccagt ccttcaactt cttccccttg tttttga 3237

<210> SEQ ID NO 631
<211> LENGTH: 2190
<212> TYPE: DNA
<213> ORGANISM: Puccinia graminis

<400> SEQUENCE: 631
atgaccaaac ctactaagaa cccatgggac cctaaggcaa caccttatcc ccccgttcgc 60
agggatccag actcatcgga ggtcttccag agtaagcaga atggctcggt caccgtccca 120
gatcccttac agttggctac acgagccacc caagcagagc aaagacactc agtcacaaag 180
acttgggact atgctcgatt cagttgtcca tcgctgaagc cggatggata ctactatttc 240
agcttcaact ctggcctcca ggcccagtcg atcatctatc gggtcaagaa ggggcaggaa 300
gaggatgcac tcaagcgggc caccgacccc aaacagcccg caggcgagct cttcctcgat 360
cccaacctgt tctccatcga tggcactacc gcactctcat tctccgccac atccgagtca 420
ggcatctata tggcgtacgg tgtctcccgc tctggaagcg acagtcagac tatctacgtc 480

```
cgtcgcaccg actctcccca cacaaagtct gccgccgatg gtggcaagag gggcgaggac    540

cctggccgga tggaggacac agtcgagaag gttaaattca gtagcctcag ttggatgaaa    600

gacgattctg gtttctttta ttcaagattc cctgacgaac aggccaaagc tgagaagccc    660

tccgggcccg gggcggatgt tcaaggagaa gtagagattg atgccgggac agatactaag    720

gctgatctca atcacatgct ctactttcac aaacttggtg agccacagag taaagatctg    780

ttgatagtcg aggatccagc gaatccatcc tatatgtggg gagctgaagt ctcggatgac    840

gccaagtacc tcatcttgac gacctccaag gataccggcc gttcgaatcg actctgggtt    900

gccgatctga cctctcaacc cctatcgagt gagatgaaat ggcaaaagat tgtcaatgag    960

tttggcaacg agtacatctt cgcggccaat gatggcagtc aactatattt catgaccaac   1020

aaggacgcgc ctaaacgcaa ggtggtgacg tatgacttga gtaagcccga agaaggcttt   1080

aaagacttga tcccagagga tcctcaggcg gtcctggagg gttattatcc caccaacaaa   1140

gaattcaccg ttctgagcta ttctcgagat gtcaaagatg agctatacct ccacgagatc   1200

aagtcgggca agcggatcaa acggatcggc ggagacttga ttggcacgat cgggggcctt   1260

tccggccgcc gtaaacacga cgagttcttc ttccagatca gtagcttctt gagccccggc   1320

acggtctacc gctaccgttt cgatcgtcaa gaggatcagg aattggtcga attcaggaag   1380

actctgattc cgggattcaa ttccaacgat ttcgtttcca aacaggtatt ctatgaatca   1440

aaggacggga ccaaagtccc gatgtttatc gttcacaaga aagacttcca gcaggacggt   1500

actgcgccag ctcttcatat ctcgccctac ttttcgccct ctttcatgag ctttgtagcc   1560

cattatggag ggtattggc tgtccctaac atccgagggg gtggagagta tggagaggac   1620

tggcacttgg caggctgctt tgagaaaaaa cagaacgtgt tcgacgactt ccagtacgct   1680

accaaatatc tggttgccaa tcagtacgcg gcgcccgaca aggtgaccat catgggcggc   1740

agtaacggag gtctcctggt ggcagcctgc gtgaaccagg ctcccgagct ctttggagcc   1800

gcgcttgccg aggtgggcgt gttggacatg ttgaggttcc atcggttcac gattggacgg   1860

gcttggatcg ctgactatgg agacccagaa gaccccgaag cattcgacta cttgatcaaa   1920

tattccccct tacataacgt caacccggcc gcggaatatc cggctctcat gctactcaca   1980

gcggaccatg acgatcgggt ggtccctctg cacagcttca agtacgctgc tgccgttcaa   2040

cacgccctcc cgacgaacaa acaaccttgc ttgttgaggc tcgatctcaa ggcaggtcat   2100

ggagccggga agagcacgga gatgaagatc aactcggtcg tcgaccaacg tctgtcctcc   2160

agtccttcaa cttcttcccc ttgtttttga                                    2190
```

<210> SEQ ID NO 632
<211> LENGTH: 40
<212> TYPE: PRT
<213> ORGANISM: Puccinia graminis

<400> SEQUENCE: 632

```
Met Thr Lys Pro Thr Lys Asn Pro Trp Asp Pro Lys Ala Thr Pro Tyr
1               5                   10                  15

Pro Pro Val Arg Arg Asp Pro Asp Ser Ser Glu Val Phe Gln Ser Lys
            20                  25                  30

Gln Asn Gly Ser Val Thr Val Pro
        35                  40
```

<210> SEQ ID NO 633
<211> LENGTH: 8

<212> TYPE: PRT
<213> ORGANISM: Artificial Sequence
<220> FEATURE:
<223> OTHER INFORMATION: A synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 633

Ala Ile Xaa Lys Ala Gly Xaa Ala
1 5

<210> SEQ ID NO 634
<211> LENGTH: 6
<212> TYPE: PRT
<213> ORGANISM: Artificial Sequence
<220> FEATURE:
<223> OTHER INFORMATION: A synthetic peptide

<400> SEQUENCE: 634

Arg Gly Lys Pro Lys Gly
1 5

<210> SEQ ID NO 635
<211> LENGTH: 6
<212> TYPE: PRT
<213> ORGANISM: Artificial Sequence
<220> FEATURE:
<223> OTHER INFORMATION: A synthetic peptide

<400> SEQUENCE: 635

Thr Gly Lys Pro Lys Gly
1 5

<210> SEQ ID NO 636
<211> LENGTH: 7
<212> TYPE: PRT
<213> ORGANISM: Artificial Sequence
<220> FEATURE:
<223> OTHER INFORMATION: A synthetic peptide

<400> SEQUENCE: 636

Phe Thr Ser Gly Ser Thr Gly
1 5

<210> SEQ ID NO 637
<211> LENGTH: 7
<212> TYPE: PRT
<213> ORGANISM: Artificial Sequence
<220> FEATURE:
<223> OTHER INFORMATION: A synthetic peptide

<400> SEQUENCE: 637

Tyr Thr Ser Gly Ser Thr Gly
1 5

<210> SEQ ID NO 638
<211> LENGTH: 5
<212> TYPE: PRT
<213> ORGANISM: Artificial Sequence
<220> FEATURE:
<223> OTHER INFORMATION: A synthetic peptide

<400> SEQUENCE: 638

Tyr Gly Pro Thr Glu
1 5

<210> SEQ ID NO 639
<211> LENGTH: 6
<212> TYPE: PRT
<213> ORGANISM: Artificial Sequence
<220> FEATURE:
<223> OTHER INFORMATION: A synthetic peptide

<400> SEQUENCE: 639

Pro Cys Thr Pro Leu Gln
1 5

<210> SEQ ID NO 640
<211> LENGTH: 7
<212> TYPE: PRT
<213> ORGANISM: Artificial Sequence
<220> FEATURE:
<223> OTHER INFORMATION: A synthetic peptide

<400> SEQUENCE: 640

Tyr Arg Thr Gly Asp Leu Val
1 5

<210> SEQ ID NO 641
<211> LENGTH: 6
<212> TYPE: PRT
<213> ORGANISM: Artificial Sequence
<220> FEATURE:
<223> OTHER INFORMATION: A synthetic peptide
<220> FEATURE:
<221> NAME/KEY: MISC_FEATURE
<222> LOCATION: (3)..(3)
<223> OTHER INFORMATION: The residue at this position could be Gly or Ala.

<400> SEQUENCE: 641

Glu Leu Xaa Glu Ile Glu
1 5

<210> SEQ ID NO 642
<211> LENGTH: 5
<212> TYPE: PRT
<213> ORGANISM: Artificial Sequence
<220> FEATURE:
<223> OTHER INFORMATION: A synthetic peptide

<400> SEQUENCE: 642

Ile Ser Asp Gly Trp
1 5

<210> SEQ ID NO 643
<211> LENGTH: 6
<212> TYPE: PRT
<213> ORGANISM: Artificial Sequence
<220> FEATURE:
<223> OTHER INFORMATION: A synthetic peptide

<400> SEQUENCE: 643

Glu Gly His Gly Arg Glu
1 5

<210> SEQ ID NO 644
<211> LENGTH: 6
<212> TYPE: PRT
<213> ORGANISM: Artificial Sequence
<220> FEATURE:
<223> OTHER INFORMATION: A synthetic peptide

<400> SEQUENCE: 644

Gln Glu Gly Met Leu Ala
1 5

<210> SEQ ID NO 645
<211> LENGTH: 6
<212> TYPE: PRT
<213> ORGANISM: Artificial Sequence
<220> FEATURE:
<223> OTHER INFORMATION: A synthetic peptide

<400> SEQUENCE: 645

Gln Glu Gly Leu Met Ala
1 5

<210> SEQ ID NO 646

<400> SEQUENCE: 646

000

<210> SEQ ID NO 647
<211> LENGTH: 7
<212> TYPE: PRT
<213> ORGANISM: Artificial Sequence
<220> FEATURE:
<223> OTHER INFORMATION: A synthetic peptide

<400> SEQUENCE: 647

Gly Glu Leu Ile Ile Gly Gly
1 5

<210> SEQ ID NO 648
<211> LENGTH: 6
<212> TYPE: PRT
<213> ORGANISM: Artificial Sequence
<220> FEATURE:
<223> OTHER INFORMATION: A synthetic peptide

<400> SEQUENCE: 648

Tyr Lys Thr Gly Asp Leu
1 5

<210> SEQ ID NO 649
<211> LENGTH: 6
<212> TYPE: PRT
<213> ORGANISM: Artificial Sequence
<220> FEATURE:
<223> OTHER INFORMATION: A synthetic peptide

<400> SEQUENCE: 649

Lys Asp Thr Gln Val Lys
1 5

<210> SEQ ID NO 650
<211> LENGTH: 7
<212> TYPE: PRT
<213> ORGANISM: Artificial Sequence
<220> FEATURE:
<223> OTHER INFORMATION: A synthetic peptide
<220> FEATURE:
<221> NAME/KEY: MISC_FEATURE
<222> LOCATION: (6)..(6)
<223> OTHER INFORMATION: The residue in this position could be Ala or Thr

<400> SEQUENCE: 650

Gly Gly Asp Ser Ile Xaa Ala
1 5

<210> SEQ ID NO 651
<211> LENGTH: 7
<212> TYPE: PRT
<213> ORGANISM: Artificial Sequence
<220> FEATURE:
<223> OTHER INFORMATION: A synthetic peptide
<220> FEATURE:
<221> NAME/KEY: MISC_FEATURE
<222> LOCATION: (6)..(6)
<223> OTHER INFORMATION: The residue at this position can be Ala or Thr

<400> SEQUENCE: 651

Gly Gly His Ser Ile Xaa Ala
1 5

<210> SEQ ID NO 652
<211> LENGTH: 61
<212> TYPE: DNA
<213> ORGANISM: Amanita bisporigera

<400> SEQUENCE: 652
atgtctgaca tcaatgccac ccgtcttccc gcttggcttg tagactgccc atgcgtcggt 60
g 61

<210> SEQ ID NO 653
<211> LENGTH: 7
<212> TYPE: PRT
<213> ORGANISM: Artificial Sequence
<220> FEATURE:
<223> OTHER INFORMATION: A synthetic peptide
<220> FEATURE:
<221> NAME/KEY: MISC_FEATURE
<222> LOCATION: (4)..(4)
<223> OTHER INFORMATION: The residue at this position could be Tyr or Phe.
<220> FEATURE:
<221> NAME/KEY: MISC_FEATURE
<222> LOCATION: (5)..(5)
<223> OTHER INFORMATION: The residue at this position could be Ala or Pro.

<400> SEQUENCE: 653

Glu Asp Val Xaa Xaa Cys Thr
1 5

<210> SEQ ID NO 654
<211> LENGTH: 10
<212> TYPE: PRT
<213> ORGANISM: Amanita bisporigera

<400> SEQUENCE: 654

Met Ser Asp Ile Asn Val Thr Arg Leu Pro
1 5 10

<210> SEQ ID NO 655
<211> LENGTH: 8
<212> TYPE: PRT
<213> ORGANISM: Amanita bisporigera

<400> SEQUENCE: 655

Ile Trp Gly Ile Gly Cys Val Leu
1 5

<210> SEQ ID NO 656
<211> LENGTH: 6
<212> TYPE: PRT
<213> ORGANISM: Burkholderia ambifaria

<400> SEQUENCE: 656

Ala Trp Leu Val Asp Cys
1 5

<210> SEQ ID NO 657
<211> LENGTH: 7
<212> TYPE: PRT
<213> ORGANISM: Pseudomonas aeruginosa

<400> SEQUENCE: 657

Ala Trp Val Val Asp Cys Pro
1 5

<210> SEQ ID NO 658
<211> LENGTH: 5
<212> TYPE: PRT
<213> ORGANISM: Galerina marginata

<400> SEQUENCE: 658

Tyr Leu Leu Asn Val
1 5

<210> SEQ ID NO 659
<211> LENGTH: 20
<212> TYPE: PRT
<213> ORGANISM: Amanita bisporigera

<400> SEQUENCE: 659

Thr Asn Phe Gly Ser Arg Ile Gly Thr Ile Thr Thr Pro Arg Leu Phe
1 5 10 15

Ala Thr Val Arg
20

<210> SEQ ID NO 660
<211> LENGTH: 13
<212> TYPE: PRT
<213> ORGANISM: Amanita bisporigera

<400> SEQUENCE: 660

Ile Arg Leu Ser Leu Tyr Arg Ser Leu Phe Ser Val Ile
1 5 10

<210> SEQ ID NO 661
<211> LENGTH: 5
<212> TYPE: PRT
<213> ORGANISM: Amanita bisporigera

<400> SEQUENCE: 661

Lys Leu Gln Ala Met
1 5

<210> SEQ ID NO 662
<211> LENGTH: 6
<212> TYPE: PRT
<213> ORGANISM: Amanita bisporigera

<400> SEQUENCE: 662

Gly Ser Pro Arg Pro Pro 1 5

<210> SEQ ID NO 663
<211> LENGTH: 48
<212> TYPE: PRT
<213> ORGANISM: Amanita bisporigera

<400> SEQUENCE: 663

Val Leu Leu Arg Ala Val Cys Gln Ser Gly Gln Arg Tyr Thr Ser Ala
1 5 10 15

Arg Val Leu Leu Asp Leu Pro Pro Ile Trp Asn Phe Pro Met Gly Trp
20 25 30

Ser Asp Ala Leu Arg Ser Gln Asn Ser Thr Asn Glu Asp Ser Ser Ser
35 40 45

<210> SEQ ID NO 664
<211> LENGTH: 10
<212> TYPE: PRT
<213> ORGANISM: Amanita bisporigera

<400> SEQUENCE: 664

Trp Arg Arg Lys Cys Leu Gly Pro Leu Phe
1 5 10

<210> SEQ ID NO 665
<211> LENGTH: 85
<212> TYPE: PRT
<213> ORGANISM: Amanita bisporigera
<220> FEATURE:
<221> NAME/KEY: MISC_FEATURE
<222> LOCATION: (63)..(70)
<223> OTHER INFORMATION: Predicted amanitin region.

<400> SEQUENCE: 665

Lys Phe Thr Val Leu Arg Ser Arg Cys Tyr Phe Leu Thr His Gln Leu
1 5 10 15

Tyr Ser Val Leu Glu Arg Asp Lys Arg Arg Ser Ser Val Gln Ala Asp
20 25 30

Leu Gln Ser Pro Asn Ala Asn Ser Leu Asn Gln Arg Phe Phe Phe Ala
35 40 45

Leu Thr Ser Thr Met Phe Asp Thr Asn Ala Thr Arg Leu Pro Ile Trp
50 55 60

Gly Ile Gly Cys Asn Pro Trp Thr Ala Glu His Val Asp Gln Thr Leu
65 70 75 80

Ala Ser Gly Asn Glu
85

<210> SEQ ID NO 666
<211> LENGTH: 33
<212> TYPE: PRT
<213> ORGANISM: Homo sapiens

<400> SEQUENCE: 666

Gln Thr Val Gln Ile Phe Tyr Pro Ser Lys Asp Gly Thr Lys Ile Pro
1 5 10 15

Met Phe Ile Val His Lys Lys Ser Thr Lys Leu Asp Gly Ser His Pro
20 25 30

Ala

<210> SEQ ID NO 667
<211> LENGTH: 32

<212> TYPE: PRT
<213> ORGANISM: Homo sapiens

<400> SEQUENCE: 667

Ile Phe Tyr Pro Ser Lys Asp Gly Thr Lys Ile Pro Met Phe Ile Val
1               5                   10                  15

His Lys Lys Ser Ile Lys Leu Asp Gly Ser His Pro Ala Phe Leu Tyr
            20                  25                  30

<210> SEQ ID NO 668
<211> LENGTH: 26
<212> TYPE: PRT
<213> ORGANISM: Homo sapiens

<400> SEQUENCE: 668

Lys Arg Leu Thr Ile Asn Gly Gly Ser Asn Gly Gly Leu Leu Val Ala
1               5                   10                  15

Ala Cys Ala Asn Gln Arg Pro Asp Leu Phe
            20                  25

<210> SEQ ID NO 669
<211> LENGTH: 27
<212> TYPE: PRT
<213> ORGANISM: Homo sapiens

<400> SEQUENCE: 669

Ser Asp Asp Gly Thr Val Ala Leu Arg Gly Tyr Ala Phe Ser Glu Asp
1               5                   10                  15

Gly Glu Tyr Phe Ala Tyr Gly Leu Ser Ala Ser
            20                  25

<210> SEQ ID NO 670
<211> LENGTH: 20
<212> TYPE: PRT
<213> ORGANISM: Homo sapiens

<400> SEQUENCE: 670

Pro Leu Leu Ile His Val Asp Thr Lys Ala Gly His Gly Ala Gly Lys
1               5                   10                  15

Pro Thr Ala Lys
            20

<210> SEQ ID NO 671
<211> LENGTH: 16
<212> TYPE: PRT
<213> ORGANISM: Homo sapiens

<400> SEQUENCE: 671

Asp Gly Thr Lys Ile Pro Met Phe Ile Val His Lys Lys Ser Thr Lys
1               5                   10                  15

<210> SEQ ID NO 672
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 672
atgttcgaca ccaactccac t                                              21

<210> SEQ ID NO 673
<211> LENGTH: 23

<212> TYPE: DNA
<213> ORGANISM: Artificial Sequence
<220> FEATURE:
<223> OTHER INFORMATION: A synthetic oligonucleotide

<400> SEQUENCE: 673
cgctacgtaa cggcatgaca gtg 23

<210> SEQ ID NO 674
<211> LENGTH: 5
<212> TYPE: PRT
<213> ORGANISM: Amanita bisporigera

<400> SEQUENCE: 674

Met Ser Asp Ile Asn
1 5

<210> SEQ ID NO 675
<211> LENGTH: 5
<212> TYPE: PRT
<213> ORGANISM: Galerina marginata

<400> SEQUENCE: 675

Met Phe Asp Thr Asn
1 5

<210> SEQ ID NO 676
<211> LENGTH: 5
<212> TYPE: PRT
<213> ORGANISM: Artificial Sequence
<220> FEATURE:
<223> OTHER INFORMATION: A synthetic peptide

<400> SEQUENCE: 676

Ala Thr Arg Leu Pro
1 5

<210> SEQ ID NO 677
<211> LENGTH: 5
<212> TYPE: PRT
<213> ORGANISM: Artificial Sequence
<220> FEATURE:
<223> OTHER INFORMATION: A synthetic peptide

<400> SEQUENCE: 677

Ser Thr Arg Leu Pro
1 5

<210> SEQ ID NO 678
<211> LENGTH: 5
<212> TYPE: PRT
<213> ORGANISM: Galerina marginata
<220> FEATURE:
<221> NAME/KEY: MISC_FEATURE
<222> LOCATION: (2)..(2)
<223> OTHER INFORMATION: The residue in this position can be either A or
S.

<400> SEQUENCE: 678

Asn Xaa Thr Arg Leu
1 5

<210> SEQ ID NO 679
<211> LENGTH: 10
<212> TYPE: PRT
<213> ORGANISM: Galerina marginata

<400> SEQUENCE: 679

Met Phe Asp Thr Asn Ala Thr Arg Leu Pro
1 5 10

<210> SEQ ID NO 680
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 680
atgttcgaca ccaactccac t 21

<210> SEQ ID NO 681
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 681
cgctacgtaa cggcatgaca gtg 23

<210> SEQ ID NO 682
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 682
ctccaatccc ccaaccacaa a 21

<210> SEQ ID NO 683
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 683
gtcgaacacg gcaacaacag 20

<210> SEQ ID NO 684
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 684
gaaaaccgaa tctccaatcc tc 22

<210> SEQ ID NO 685
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 685
agctcactcg ttgccactaa 20

<210> SEQ ID NO 686

<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 686
ccaacgacag gcgggacacg 20

<210> SEQ ID NO 687
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 687 gaccttttg ctttaacatc taca 24

<210> SEQ ID NO 688
<211> LENGTH: 26
<212> TYPE: DNA
<213> ORGANISM: Artificial Sequence
<220> FEATURE:
<223> OTHER INFORMATION: A synthetic oligonucleotide

<400> SEQUENCE: 688
gtcaacaagt ccaggagaca ttcaac 26

<210> SEQ ID NO 689
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 689
accgaatctc caatcctcca acca 24

<210> SEQ ID NO 690
<211> LENGTH: 55
<212> TYPE: PRT
<213> ORGANISM: Artificial Sequence
<220> FEATURE:
<223> OTHER INFORMATION: A synthetic peptide

<400> SEQUENCE: 690

```
Ser Pro Ile Pro Gln Pro Gln Thr His Leu Thr Lys Asp Leu Phe Ala
1               5                   10                  15

Leu Thr Ser Thr Met Phe Asp Thr Asn Ala Thr Arg Leu Pro Ile Trp
            20                  25                  30

Gly Ile Gly Cys Asn Pro Trp Thr Ala Glu His Val Asp Gln Thr Leu
        35                  40                  45

Ala Ser Gly Asn Asp Ile Cys
    50                  55
```

<210> SEQ ID NO 691
<211> LENGTH: 60
<212> TYPE: PRT
<213> ORGANISM: Artificial Sequence
<220> FEATURE:
<223> OTHER INFORMATION: A synthetic peptide

<400> SEQUENCE: 691

```
Met Gln Val Lys Thr Glu Ser Pro Ile Leu Gln Pro Ser Thr Gln Pro
```

```
1               5                   10                  15

Lys Ile Phe Ala Leu Ala Leu Ile Ser Ala Phe Asp Thr Asn Ser Thr
            20                  25                  30

Arg Leu Pro Ile Trp Gly Ile Gly Cys Asn Pro Trp Thr Ala Glu His
        35                  40                  45

Val Asp Gln Thr Leu Val Ser Gly Asn Asp Ile Cys
    50                  55                  60
```

<210> SEQ ID NO 692
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 692
tttagggcag tgatttcgtg aca 23

<210> SEQ ID NO 693
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 693
aacagggagg cgattattca ac 22

<210> SEQ ID NO 694
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 694
gaacaatcga acccatgaca agaa 24

<210> SEQ ID NO 695
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 695
cccccattga ttgttacctt gtc 23

<210> SEQ ID NO 696
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 696
cggcgttcca aggcgatgat aata 24

<210> SEQ ID NO 697
<211> LENGTH: 25
<212> TYPE: DNA
<213> ORGANISM: Artificial Sequence
<220> FEATURE:
<223> OTHER INFORMATION: A synthetic oligonucleotide

<400> SEQUENCE: 697
catctccatc gacccctttt tcagc 25

<210> SEQ ID NO 698
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 698
agtctgccgt ccgtgccttg g 21

<210> SEQ ID NO 699
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 699
cggtacgact tcacggctcc aga 23

<210> SEQ ID NO 700
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 700
gcgtggatat gtcctgcggg 20

<210> SEQ ID NO 701
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 701
ccatacaagc caaccacggc 20

<210> SEQ ID NO 702
<211> LENGTH: 8
<212> TYPE: PRT
<213> ORGANISM: Artificial Sequence
<220> FEATURE:
<223> OTHER INFORMATION: A synthetic peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 702

Xaa Trp Xaa Xaa Xaa Cys Xaa Pro
1 5

<210> SEQ ID NO 703

<400> SEQUENCE: 703

000

<210> SEQ ID NO 704
<211> LENGTH: 35
<212> TYPE: PRT
<213> ORGANISM: Galerina marginata

<400> SEQUENCE: 704

Met Phe Asp Thr Asn Ala Thr Arg Leu Pro Ile Trp Gly Ile Gly Cys
1 5 10 15

Asn Pro Trp Thr Ala Glu His Val Asp Gln Thr Leu Ala Ser Gly Asn
20 25 30

Asp Ile Cys
35

<210> SEQ ID NO 705
<211> LENGTH: 35
<212> TYPE: PRT
<213> ORGANISM: Galerina marginata

<400> SEQUENCE: 705

Met Phe Asp Thr Asn Ser Thr Arg Leu Pro Ile Trp Gly Ile Gly Cys
1 5 10 15

Asn Pro Trp Thr Ala Glu His Val Asp Gln Thr Leu Val Ser Gly Asn
20 25 30

Asp Ile Cys
35

<210> SEQ ID NO 706
<211> LENGTH: 33
<212> TYPE: PRT
<213> ORGANISM: Artificial Sequence
<220> FEATURE:
<223> OTHER INFORMATION: A synthetic peptide

<400> SEQUENCE: 706

Met Phe Asp Thr Asn Thr Arg Leu Pro Ile Trp Gly Ile Gly Cys Asn
1 5 10 15

Pro Trp Thr Ala Glu His Val Asp Gln Thr Leu Ser Gly Asn Asp Ile
20 25 30

Cys

<210> SEQ ID NO 707
<211> LENGTH: 34
<212> TYPE: PRT
<213> ORGANISM: Artificial Sequence
<220> FEATURE:
<223> OTHER INFORMATION: A synthetic peptide
<220> FEATURE:
<221> NAME/KEY: MISC_FEATURE
<222> LOCATION: (2)..(2)
<223> OTHER INFORMATION: The residue in this position can be either F or S.
<220> FEATURE:
<221> NAME/KEY: MISC_FEATURE
<222> LOCATION: (4)..(4)
<223> OTHER INFORMATION: The residue in this position can be either T or I.
<220> FEATURE:
<221> NAME/KEY: MISC_FEATURE
<222> LOCATION: (6)..(6)
<223> OTHER INFORMATION: The residue in this position can be either A or S.

<220> FEATURE:
<221> NAME/KEY: MISC_FEATURE
<222> LOCATION: (19)..(19)
<223> OTHER INFORMATION: The residue in this position can be either W or C.
<220> FEATURE:
<221> NAME/KEY: MISC_FEATURE
<222> LOCATION: (20)..(20)
<223> OTHER INFORMATION: The residue in this position can be either T or I.
<220> FEATURE:
<221> NAME/KEY: MISC_FEATURE
<222> LOCATION: (21)..(21)
<223> OTHER INFORMATION: The residue in this position can be either A or G.
<220> FEATURE:
<221> NAME/KEY: MISC_FEATURE
<222> LOCATION: (22)..(22)
<223> OTHER INFORMATION: The residue in this position can be either E or D.
<220> FEATURE:
<221> NAME/KEY: MISC_FEATURE
<222> LOCATION: (23)..(23)
<223> OTHER INFORMATION: The residue in this position can be either H or D.
<220> FEATURE:
<221> NAME/KEY: MISC_FEATURE
<222> LOCATION: (25)..(25)
<223> OTHER INFORMATION: The residue in this position can be either Q or T.
<220> FEATURE:
<221> NAME/KEY: MISC_FEATURE
<222> LOCATION: (26)..(26)
<223> OTHER INFORMATION: The residue in this position can be either T or L.
<220> FEATURE:
<221> NAME/KEY: MISC_FEATURE
<222> LOCATION: (28)..(28)
<223> OTHER INFORMATION: The residue in this position can be either A or V or T.
<220> FEATURE:
<221> NAME/KEY: MISC_FEATURE
<222> LOCATION: (29)..(29)
<223> OTHER INFORMATION: The residue in this position can be either R or S.
<220> FEATURE:
<221> NAME/KEY: MISC_FEATURE
<222> LOCATION: (31)..(31)
<223> OTHER INFORMATION: The residue in this position can be either N or E.
<220> FEATURE:
<221> NAME/KEY: MISC_FEATURE
<222> LOCATION: (32)..(32)
<223> OTHER INFORMATION: The residue in this position can be either D or A or S.
<220> FEATURE:
<221> NAME/KEY: MISC_FEATURE
<222> LOCATION: (33)..(33)
<223> OTHER INFORMATION: The residue in this position can be either I or L.

<400> SEQUENCE: 707

```
Met Xaa Asp Xaa Asn Xaa Thr Arg Leu Pro Ile Trp Gly Ile Gly Cys
1               5                   10                  15

Asn Pro Xaa Xaa Xaa Xaa Xaa Val Xaa Xaa Leu Xaa Xaa Gly Xaa Xaa
            20                  25                  30

Xaa Cys
```

<210> SEQ ID NO 708
<211> LENGTH: 34
<212> TYPE: PRT
<213> ORGANISM: Artificial Sequence
<220> FEATURE:
<223> OTHER INFORMATION: A synthetic peptide
<220> FEATURE:

<221> NAME/KEY: MISC_FEATURE
<222> LOCATION: (2)..(2)
<223> OTHER INFORMATION: The residue in this position can be either F or S.
<220> FEATURE:
<221> NAME/KEY: MISC_FEATURE
<222> LOCATION: (4)..(4)
<223> OTHER INFORMATION: The residue in this position can be either T or I.
<220> FEATURE:
<221> NAME/KEY: MISC_FEATURE
<222> LOCATION: (6)..(6)
<223> OTHER INFORMATION: The residue in this position can be either A or S.
<220> FEATURE:
<221> NAME/KEY: MISC_FEATURE
<222> LOCATION: (11)..(11)
<223> OTHER INFORMATION: The residue in this position can be either I or A.
<220> FEATURE:
<221> NAME/KEY: MISC_FEATURE
<222> LOCATION: (13)..(13)
<223> OTHER INFORMATION: The residue in this position can be either G or L.
<220> FEATURE:
<221> NAME/KEY: MISC_FEATURE
<222> LOCATION: (14)..(14)
<223> OTHER INFORMATION: The residue in this position can be either I or V.
<220> FEATURE:
<221> NAME/KEY: MISC_FEATURE
<222> LOCATION: (15)..(15)
<223> OTHER INFORMATION: The residue in this position can be either G or D.
<220> FEATURE:
<221> NAME/KEY: MISC_FEATURE
<222> LOCATION: (17)..(17)
<223> OTHER INFORMATION: The residue in this position can be either N or any other amino acid.
<220> FEATURE:
<221> NAME/KEY: MISC_FEATURE
<222> LOCATION: (19)..(19)
<223> OTHER INFORMATION: The residue in this position can be either W or C.
<220> FEATURE:
<221> NAME/KEY: MISC_FEATURE
<222> LOCATION: (20)..(20)
<223> OTHER INFORMATION: The residue in this position can be either T or I or V.
<220> FEATURE:
<221> NAME/KEY: MISC_FEATURE
<222> LOCATION: (21)..(21)
<223> OTHER INFORMATION: The residue in this position can be either A or G.
<220> FEATURE:
<221> NAME/KEY: MISC_FEATURE
<222> LOCATION: (22)..(22)
<223> OTHER INFORMATION: The residue in this position can be either E or D.
<220> FEATURE:
<221> NAME/KEY: MISC_FEATURE
<222> LOCATION: (23)..(23)
<223> OTHER INFORMATION: The residue in this position can be either H or D.
<220> FEATURE:
<221> NAME/KEY: MISC_FEATURE
<222> LOCATION: (25)..(25)
<223> OTHER INFORMATION: The residue in this position can be either Q or T or R.
<220> FEATURE:
<221> NAME/KEY: MISC_FEATURE
<222> LOCATION: (26)..(26)
<223> OTHER INFORMATION: The residue in this position can be either T or L.
<220> FEATURE:
<221> NAME/KEY: MISC_FEATURE
<222> LOCATION: (28)..(28)
<223> OTHER INFORMATION: The residue in this position can be either A or V or T.

<220> FEATURE:
<221> NAME/KEY: MISC_FEATURE
<222> LOCATION: (29)..(29)
<223> OTHER INFORMATION: The residue in this position can be either R or S.
<220> FEATURE:
<221> NAME/KEY: MISC_FEATURE
<222> LOCATION: (31)..(31)
<223> OTHER INFORMATION: The residue in this position can be either N or E.
<220> FEATURE:
<221> NAME/KEY: MISC_FEATURE
<222> LOCATION: (32)..(32)
<223> OTHER INFORMATION: The residue in this position can be either D or A or S.
<220> FEATURE:
<221> NAME/KEY: MISC_FEATURE
<222> LOCATION: (33)..(33)
<223> OTHER INFORMATION: The residue in this position can be either I or L.

<400> SEQUENCE: 708

```
Met Xaa Asp Xaa Asn Xaa Thr Arg Leu Pro Xaa Trp Xaa Xaa Xaa Cys
1               5                   10                  15

Xaa Pro Xaa Xaa Xaa Xaa Xaa Val Xaa Xaa Leu Xaa Xaa Gly Xaa Xaa
            20                  25                  30

Xaa Cys
```

<210> SEQ ID NO 709
<211> LENGTH: 177
<212> TYPE: DNA
<213> ORGANISM: Galerina marginata

<400> SEQUENCE: 709

```
gatgctctaa gatcacagaa ctccaccaat gaagacaggt cctcgtaatg gcgtcgaaaa     60

tgttcttgga tctttattct agaagttcac agcttgcgga gtcgctgcta tttcctaact    120

catcagctct attcggtcct cgagagagat aaaaggcgtt cgtcagtgag agctgat       177
```

<210> SEQ ID NO 710
<211> LENGTH: 59
<212> TYPE: DNA
<213> ORGANISM: Galerina marginata

<400> SEQUENCE: 710

```
ctccaatccc ccaaccacaa actcacttaa ccaaagacct ttttgcttta acatctaca      59
```

<210> SEQ ID NO 711
<211> LENGTH: 498
<212> TYPE: DNA
<213> ORGANISM: Galerina marginata

<400> SEQUENCE: 711

```
atgttcgaca ccaacgctac tcgtctccca atctggggta ttggctgcaa cccatggact     60

gctgagcacg tcgaccagac tctcgctagt ggcaacgagt aagcttggtt tctgttgttg    120

ccgtgttcga cgtactcatg ttgtgcgtta gcatttgctg aacgtgtccc gcctgtcgtt    180

ggcccgccgc tttaacacga aggtgtggct atcttactac tctcaaagca ttgcattcaa    240

caggcctgat atttccgagc agtgggcaac gatacttatc gacgatgtta ggcttggaac    300

attgagcctt ttcgtaggtc agaccttgtg ctttattacg tggtattaag gagtactgac    360

ccatctactg tttttccttc atctagccat tctttctctt ttgtaaatcg ataaaaccat    420

acaccaactc gcatttgtaa attgataaac cctacgttga tgatcctcac cgttgaaata    480
```

aatgtaaatt ttgagcca 498

<210> SEQ ID NO 712
<211> LENGTH: 583
<212> TYPE: DNA
<213> ORGANISM: Galerina marginata

<400> SEQUENCE: 712
cgtcgaaaat gttcgagcca tctggaagtt tacaactttc cgaaagtaat gcgaagcggg 60
tgcttccttt cctatctcgt cggctctgtt tcgtccttgg gagagataaa agcagcccat 120
gcaagtgaaa accgaatctc caatcctcca accatcaact caaccaaaga tcttcgccct 180
tgccttaata tctgccatgt tcgacaccaa ctccactcgt cttccaatct ggggtattgg 240
ctgcaaccca tggactgctg aacacgtcga tcaaactctc gttagtggca acgagtgagc 300
tcaatttccg ttgttgacat gttcgacgta ctcatgcgtt gtacgttagc atttgttgaa 360
tgtctcctgg acttgttgac aatattaggc ttggcccgtt gagcctttac cgcaggtcag 420
accatgcatc tcatcagtgg ttttgagaaa tgctgacttg cccgttattt ctctttgtct 480
aggacacgtt ctgtaacatt tctgacccgt gatatgtaaa ttgtaaaacc ctacgtcgac 540
gatcgttact gtttgaatga atgtaacgtt tgattcattg cat 583

<210> SEQ ID NO 713
<211> LENGTH: 409
<212> TYPE: DNA
<213> ORGANISM: Galerina marginata

<400> SEQUENCE: 713
gaagcgggtg cttcctttcc tatctcgtcg gctctgtttc gtccttggga gagataaaag 60
cagcccatgc aagtgaaaac cgaatctcca atcctccaac catcaactca accaaagatc 120
ttcgcccttg ccttaatatc tgccatgttc gacaccaact ccactcgtct tccaatctgg 180
ggtattggct gcaacccatg gactgctgaa cacgtcgatc aaactctcgt tagtggcaac 240
gacatttgtt gaatgtctcc tggacttgtt gacaatatta ggcttggccc gttgagcctt 300
taccgcagga cacgttctgt aacatttctg acccgtgata tgtaaattgt aaaaccctac 360
gtcgacgatc gttactgttt gaatgaatgt aacgtttgat tcattgcat 409

<210> SEQ ID NO 714
<211> LENGTH: 108
<212> TYPE: DNA
<213> ORGANISM: Galerina marginata

<400> SEQUENCE: 714
atgttcgaca ccaactccac tcgtcttcca atctggggta ttggctgcaa cccatggact 60
gctgaacacg tcgatcaaac tctcgttagt ggcaacgaca tttgttga 108

<210> SEQ ID NO 715
<211> LENGTH: 2427
<212> TYPE: DNA
<213> ORGANISM: Galerina marginata
<220> FEATURE:
<221> NAME/KEY: misc_feature
<222> LOCATION: (2386)..(2386)
<223> OTHER INFORMATION: n is a, c, g, or t

<400> SEQUENCE: 715
ggctgtccct ccgttccctc ccctttccta ggtctctaag acgcgttttc acactgtata 60
ggcgctcctc gtcgtctcct gcgaacatgg cccgaacacc gtggcttccc aacgcatatc 120

```
caccagctcg tcgttccgat cacgttgaca tctataagag cgcccttcgt ggcgacgtac    180
gcgttcagga cccgtaccag tggctagagg aatacaccga tgagacagac aaatggacga    240
ctgctcaaga ggttttcaca aggacttacc tagacaaaaa ccctgacctc cctcggcttg    300
aaaaagcgtt tcaggcttgc aatgattatc ccaagtccta tgccccttac ttacatgatg    360
acaaccgatg gtactggtac tacaattctg gcctggagcc gcagacggcg ttgtaccggt    420
ccaaagacag cagtttaccg gatctctcta cagccgatgg cagtggtggc gatttattct    480
ttgatcccaa tgccctttcc aacgacggaa ctgccgctct ttcaacctat gccttctcgg    540
attgtggcaa atattttgcg tatgggatct ctttctctgg cagtgatttc gtgacaatct    600
acgtgcggtt gacggattcc cctctcacta aagatgtgga cgcgaagaac gacaaaggtc    660
gccttccaga ggaaatcaaa tttgtcaaat tttcatccat aggatggaca cctgattcca    720
agggcttttt ttatcagcgt tacccagata cctccaccgt cacccaagag aacgggccta    780
tcgcgacaga aggtgacctg gatgccatgg tatattatca tcgccttgga acaccgcggt    840
cggaagatac tctgatctac caagacaaag aacataggga ctggatgttc agcattgatg    900
tcacggacga cggcaattac ctcctccttt acattctcaa ggacagctca aggcaaaact    960
tactttggat tgctgcattt gatcctgcaa atcttggtcc caatatcaag tggcagaggg   1020
tcttcgatga atatcactca gaatacgaga ttatcacaaa caagggctca ttgttctatg   1080
ttagaactaa cgaatccgct ccccagtaca gagtcataac ggttgacatt gccaaaggga   1140
atgaaatcaa tgaactcatc cctgaaaccg atgcatactt gtccagcatt accagcgtaa   1200
ataagggcta ctttgccctc gtttacaagc gcaatgtaaa agatgaggta tatgtgtatt   1260
cgcatgctgg aaaccagctc gctcgcctgg ctgaggactt tgtgggcgct gctcatgtgt   1320
ctgggcgtga aaagcattcc tccttctttg tcgaactgaa tggctttacc tcacctggca   1380
caactggtag atacaagttt accgatcctg aggagcagcg gtggagcatt taccgaacaa   1440
ccaaactcaa cggcctaaat acagaggatt tcgaagctag ccaagtatgg tatgagagca   1500
aggacggcac aggcatccca acgtttatcg ttcgtcacaa atcaacgaaa tttgatggca   1560
ctgccccagt catacaatac ggttatggtg gattcagcat ctccatcgac cccttttca   1620
gcgcgacaat tcttacattc ctccaaaaat acggcgtcgt gtttgcgctt ccaaatatca   1680
ggggtggcgg agaattcggc gaggactggc acttggctgg atgtagagaa aagaagggaa   1740
attgcytcga cgattttatc gccgcaaccc aataccttgt gaagaataag tacgcagctc   1800
ctgacaaggt aacaatcaat ggggggtcga atggcggttt gttggtttct gcttgcgtga   1860
accgcgcccc ggagggtacg tttggctgcg ctgtagccga cgtcggagta cacgatcttc   1920
tcaagttcca caagtttact attggtaaag cctggaccag tgattacggt aaccctgacg   1980
atccaaacga ctttgatttc attttcccca tatccccgct gcaaaacata ccgaaagaca   2040
aggtgttccc tccaatgtta cttctaactg ctgaccatga tgatcgcgtc gtgcccatgc   2100
attccttcaa gctagctgct gagctccaat actcgctccc acacaacccg aacccgttgc   2160
tcatccgaat agacaagaaa gccggtcatg gagctggcaa atcaactcaa caaaagatca   2220
aagagagcgc ggacaagtgg ggatttgtcg cgcaatcgct cggacttgtt tggaaagact   2280
ccactgagca acccaatctc tgatccatta ttgaaagttg ctaatcgtag aatccagctc   2340
atgagtatgt tactctctcg tctgggcatg ttgtaattcg gcctcncctc atgacttttc   2400
tatgatataa tggtatatac ttgggtc                                        2427
```

<210> SEQ ID NO 716
<211> LENGTH: 738
<212> TYPE: PRT
<213> ORGANISM: Galerina marginata
<220> FEATURE:
<221> NAME/KEY: misc_feature
<222> LOCATION: (554)..(554)
<223> OTHER INFORMATION: Xaa can be any naturally occurring amino acid

<400> SEQUENCE: 716

Met Ala Arg Thr Pro Trp Leu Pro Asn Ala Tyr Pro Pro Ala Arg Arg
1               5                   10                  15

Ser Asp His Val Asp Ile Tyr Lys Ser Ala Leu Arg Gly Asp Val Arg
            20                  25                  30

Val Gln Asp Pro Tyr Gln Trp Leu Glu Glu Tyr Thr Asp Glu Thr Asp
        35                  40                  45

Lys Trp Thr Thr Ala Gln Glu Val Phe Thr Arg Thr Tyr Leu Asp Lys
    50                  55                  60

Asn Pro Asp Leu Pro Arg Leu Glu Lys Ala Phe Gln Ala Cys Asn Asp
65                  70                  75                  80

Tyr Pro Lys Ser Tyr Ala Pro Tyr Leu His Asp Asp Asn Arg Trp Tyr
                85                  90                  95

Trp Tyr Tyr Asn Ser Gly Leu Glu Pro Gln Thr Ala Leu Tyr Arg Ser
            100                 105                 110

Lys Asp Ser Ser Leu Pro Asp Leu Ser Thr Ala Asp Gly Ser Gly Gly
        115                 120                 125

Asp Leu Phe Phe Asp Pro Asn Ala Leu Ser Asn Asp Gly Thr Ala Ala
    130                 135                 140

Leu Ser Thr Tyr Ala Phe Ser Asp Cys Gly Lys Tyr Phe Ala Tyr Gly
145                 150                 155                 160

Ile Ser Phe Ser Gly Ser Asp Phe Val Thr Ile Tyr Val Arg Leu Thr
                165                 170                 175

Asp Ser Pro Leu Thr Lys Asp Val Asp Ala Lys Asn Asp Lys Gly Arg
            180                 185                 190

Leu Pro Glu Glu Ile Lys Phe Val Lys Phe Ser Ser Ile Gly Trp Thr
        195                 200                 205

Pro Asp Ser Lys Gly Phe Phe Tyr Gln Arg Tyr Pro Asp Thr Ser Thr
    210                 215                 220

Val Thr Gln Glu Asn Gly Pro Ile Ala Thr Glu Gly Asp Leu Asp Ala
225                 230                 235                 240

Met Val Tyr Tyr His Arg Leu Gly Thr Pro Arg Ser Glu Asp Thr Leu
                245                 250                 255

Ile Tyr Gln Asp Lys Glu His Arg Asp Trp Met Phe Ser Ile Asp Val
            260                 265                 270

Thr Asp Asp Gly Asn Tyr Leu Leu Leu Tyr Ile Leu Lys Asp Ser Ser
        275                 280                 285

Arg Gln Asn Leu Leu Trp Ile Ala Ala Phe Asp Pro Ala Asn Leu Gly
    290                 295                 300

Pro Asn Ile Lys Trp Gln Arg Val Phe Asp Glu Tyr His Ser Glu Tyr
305                 310                 315                 320

Glu Ile Ile Thr Asn Lys Gly Ser Leu Phe Tyr Val Arg Thr Asn Glu
                325                 330                 335

Ser Ala Pro Gln Tyr Arg Val Ile Thr Val Asp Ile Ala Lys Gly Asn
            340                 345                 350

Glu Ile Asn Glu Leu Ile Pro Glu Thr Asp Ala Tyr Leu Ser Ser Ile

```
        355                 360                 365

Thr Ser Val Asn Lys Gly Tyr Phe Ala Leu Val Tyr Lys Arg Asn Val
    370                 375                 380

Lys Asp Glu Val Tyr Val Tyr Ser His Ala Gly Asn Gln Leu Ala Arg
385                 390                 395                 400

Leu Ala Glu Asp Phe Val Gly Ala Ala His Val Ser Gly Arg Glu Lys
                405                 410                 415

His Ser Ser Phe Phe Val Glu Leu Asn Gly Phe Thr Ser Pro Gly Thr
            420                 425                 430

Thr Gly Arg Tyr Lys Phe Thr Asp Pro Glu Glu Gln Arg Trp Ser Ile
        435                 440                 445

Tyr Arg Thr Thr Lys Leu Asn Gly Leu Asn Thr Glu Asp Phe Glu Ala
    450                 455                 460

Ser Gln Val Trp Tyr Glu Ser Lys Asp Gly Thr Gly Ile Pro Thr Phe
465                 470                 475                 480

Ile Val Arg His Lys Ser Thr Lys Phe Asp Gly Thr Ala Pro Val Ile
                485                 490                 495

Gln Tyr Gly Tyr Gly Gly Phe Ser Ile Ser Ile Asp Pro Phe Phe Ser
            500                 505                 510

Ala Thr Ile Leu Thr Phe Leu Gln Lys Tyr Gly Val Val Phe Ala Leu
        515                 520                 525

Pro Asn Ile Arg Gly Gly Gly Glu Phe Gly Glu Asp Trp His Leu Ala
    530                 535                 540

Gly Cys Arg Glu Lys Lys Gly Asn Cys Xaa Asp Asp Phe Ile Ala Ala
545                 550                 555                 560

Thr Gln Tyr Leu Val Lys Asn Lys Tyr Ala Ala Pro Asp Lys Val Thr
                565                 570                 575

Ile Asn Gly Gly Ser Asn Gly Gly Leu Leu Val Ser Ala Cys Val Asn
            580                 585                 590

Arg Ala Pro Glu Gly Thr Phe Gly Cys Ala Val Ala Asp Val Gly Val
        595                 600                 605

His Asp Leu Leu Lys Phe His Lys Phe Thr Ile Gly Lys Ala Trp Thr
    610                 615                 620

Ser Asp Tyr Gly Asn Pro Asp Asp Pro Asn Asp Phe Asp Phe Ile Phe
625                 630                 635                 640

Pro Ile Ser Pro Leu Gln Asn Ile Pro Lys Asp Lys Val Phe Pro Pro
                645                 650                 655

Met Leu Leu Leu Thr Ala Asp His Asp Asp Arg Val Val Pro Met His
            660                 665                 670

Ser Phe Lys Leu Ala Ala Glu Leu Gln Tyr Ser Leu Pro His Asn Pro
        675                 680                 685

Asn Pro Leu Leu Ile Arg Ile Asp Lys Lys Ala Gly His Gly Ala Gly
    690                 695                 700

Lys Ser Thr Gln Gln Lys Ile Lys Glu Ser Ala Asp Lys Trp Gly Phe
705                 710                 715                 720

Val Ala Gln Ser Leu Gly Leu Val Trp Lys Asp Ser Thr Glu Gln Pro
                725                 730                 735

Asn Leu
```

<210> SEQ ID NO 717
<211> LENGTH: 2435
<212> TYPE: DNA
<213> ORGANISM: Galerina marginata

<400> SEQUENCE: 717
ctacttctcc cttttgtcca gaagcccttt atcatatcta aaatcgtgac agtggcacgg 60
accgtggacg ttatcccaaa ccaaccctat tggtaccctt aaaaaacagg gtttttcgat 120
gtccgtcttc cagccgtatc gctgacccca caattgcgga aaactatgtc gtctgtaacc 180
tgggctcctg gaaattatcc ctctacccgt cgttctgacc atgtcgatac ctatcagagc 240
gcgtccaagg gcgaagtacc tgtgccggac ccctaccaat ggctggaaga gagcaccgat 300
gaagtagaca aatggacgac tgctcaggcc gatcttgccc aatcatatct tgatcagaac 360
gcggatattc agaaacttgc ggagaaattt cgtgcgagta gaaactacgc aaagttttcc 420
gcaccgactc tgctcgatga cggacattgg tattggttct acaaccgagg cctgcaatcg 480
cagtcagttc tttaccgctc caacgaaccg gcgcttcctg atttctccaa tggcgacgat 540
aatgttggcg acgtattctt cgacccgaat gtactcgcta ctgatggcag cgccggtatg 600
gtcctctgta aattctcccc cgatggcaaa tttttcgcct atgcagtgtc ccatttggga 660
ggcgattatt caactatcta tattcgttca acgagctcgc cattgtctca ggcgtcggca 720
gtccaaggca cggacggcag actgtcggat gaagtaaagt ggttcaagtt ttcaacgata 780
atctggacga aggactccaa aggtttttctt taccagcgat atcctgctcg tgaacgtcat 840
gaagggacac gcagcgacag aaatgctatg atgtgctacc acaaagttgg aacgactcaa 900
gaggaggata ttatcgtgta tcaagacaat gaacacccag agtggatata tggagcagat 960
acgtcagaag atgggaaata tctctacttg tatcagttca aggatacctc gaagaaaaac 1020
cttctgtggg ttgcagaact caacgaggat ggcgtcaagt cggggattca gtggcgaaaa 1080
gtcgttaatg agtatgtggc cgactacaac gttataacga accacggatc attggtgtac 1140
atcaagacca atctcaatgc accccagtat aaggtcatca ccatcgacct atcgaaagac 1200
gaacctgaaa ttcgtgattt tatcccggaa gagaaagatg caaagctcgc tcaagttaat 1260
tgcgccaacg aagaatactt tgtggcaatc tacaagcgca atgtcaagga tgaaatatat 1320
ctctactcga aggctggcgt acaactcacc cgtcttgcgc cggactttgt tggcgctgcg 1380
tctatagcga acagacagaa acaaactcat ttcttcctca cgctgtctgg attcaataca 1440
cctggcacca ttgctcggta cgacttcacg gctccagaaa cgcaacgctt cagcatcctt 1500
cggacgacra aggtcaatga actggatcca gatgactttg agtccacgca agtctggtat 1560
gagagtaaag atggcacraa aattcccatg ttcattgttc gtcacaaatc tacaaaattc 1620
gatggaacgg csgcggcgat tcaatayggt tacggtggat ttgccacttc ggcagatcca 1680
ttctttagtc caattattct cacatttttg caaacatacg gcgcaatctt tgctgttcct 1740
agtattcgag gtggaggtga attcggtgaa gaatggcaca agggtggacg aagagaaacc 1800
aaggtaaata cattcgatga tttcattgcc gccgcacagt ttctggtcaa gaacaagtat 1860
gcggctcctg gcaaggtggc tatcaacggc gcatccaatg gcggtcttct tgtcatgggt 1920
tcgattgttc gagcaccgga ggggaccttc ggcgccgcgg tccctgaggg tggcgttgca 1980
gacctcctca agttccacaa gttcaccggg gggcaagctt ggatcagtga atacggaaat 2040
ccttccattc ctgaagagtt cgactacatc tatccattat ctcctgtaca caatgtgcgg 2100
accgacaagg ttatgccagc tacgttaatc acggtcaata ttggcgacgg ccgggttgtg 2160
cccatgcatt ccttcaagtt cattgcaaca cttcagcata acgtgcctca gaaccctcat 2220
ccattgctga tcaaaattga caagtcctgg cttggtcatg gtatggggaa accaacggac 2280
aaaaatgtca aagacgcggc tgataaatgg ggtttcatcg cacgagcgct cggacttgaa 2340
ttgaaaacag ttgaataggc tttattgcta tcgaggactt ggcattgaat gtatgtacat 2400
acatttgatg gtggcaatat acctgcgtca tttga 2435

<210> SEQ ID NO 718

<400> SEQUENCE: 718

000

<210> SEQ ID NO 719

<400> SEQUENCE: 719

000

<210> SEQ ID NO 720

<400> SEQUENCE: 720

000

<210> SEQ ID NO 721

<400> SEQUENCE: 721

000

<210> SEQ ID NO 722
<211> LENGTH: 730
<212> TYPE: PRT
<213> ORGANISM: Galerina marginata

<400> SEQUENCE: 722

```
Met Ser Ser Val Thr Trp Ala Pro Gly Asn Tyr Pro Ser Thr Arg Arg
1               5                   10                  15

Ser Asp His Val Asp Thr Tyr Gln Ser Ala Ser Lys Gly Glu Val Pro
            20                  25                  30

Val Pro Asp Pro Tyr Gln Trp Leu Glu Glu Ser Thr Asp Glu Val Asp
        35                  40                  45

Lys Trp Thr Thr Ala Gln Ala Asp Leu Ala Gln Ser Tyr Leu Asp Gln
    50                  55                  60

Asn Ala Asp Ile Gln Lys Leu Ala Glu Lys Phe Arg Ala Ser Arg Asn
65                  70                  75                  80

Tyr Ala Lys Phe Ser Ala Pro Thr Leu Leu Asp Asp Gly His Trp Tyr
                85                  90                  95

Trp Phe Tyr Asn Arg Gly Leu Gln Ser Gln Ser Val Leu Tyr Arg Ser
            100                 105                 110

Asn Glu Pro Ala Leu Pro Asp Phe Ser Asn Gly Asp Asp Asn Val Gly
        115                 120                 125

Asp Val Phe Phe Asp Pro Asn Val Leu Ala Thr Asp Gly Ser Ala Gly
    130                 135                 140

Met Val Leu Cys Lys Phe Ser Pro Asp Gly Lys Phe Phe Ala Tyr Ala
145                 150                 155                 160

Val Ser His Leu Gly Gly Asp Tyr Ser Thr Ile Tyr Ile Arg Ser Thr
                165                 170                 175

Ser Ser Pro Leu Ser Gln Ala Ser Ala Val Gln Gly Thr Asp Gly Arg
            180                 185                 190

Leu Ser Asp Glu Val Lys Trp Phe Lys Phe Ser Thr Ile Ile Trp Thr
        195                 200                 205
```

```
Lys Asp Ser Lys Gly Phe Leu Tyr Gln Arg Tyr Pro Ala Arg Glu Arg
    210                 215                 220

His Glu Gly Thr Arg Ser Asp Arg Asn Ala Met Met Cys Tyr His Lys
225                 230                 235                 240

Val Gly Thr Thr Gln Glu Glu Asp Ile Ile Val Tyr Gln Asp Asn Glu
                245                 250                 255

His Pro Glu Trp Ile Tyr Gly Ala Asp Thr Ser Glu Asp Gly Lys Tyr
            260                 265                 270

Leu Tyr Leu Tyr Gln Phe Lys Asp Thr Ser Lys Lys Asn Leu Leu Trp
        275                 280                 285

Val Ala Glu Leu Asn Glu Asp Gly Val Lys Ser Gly Ile Gln Trp Arg
    290                 295                 300

Lys Val Val Asn Glu Tyr Val Ala Asp Tyr Asn Val Ile Thr Asn His
305                 310                 315                 320

Gly Ser Leu Val Tyr Ile Lys Thr Asn Leu Asn Ala Pro Gln Tyr Lys
                325                 330                 335

Val Ile Thr Ile Asp Leu Ser Lys Asp Glu Pro Glu Ile Arg Asp Phe
            340                 345                 350

Ile Pro Glu Glu Lys Asp Ala Lys Leu Ala Gln Val Asn Cys Ala Asn
        355                 360                 365

Glu Glu Tyr Phe Val Ala Ile Tyr Lys Arg Asn Val Lys Asp Glu Ile
    370                 375                 380

Tyr Leu Tyr Ser Lys Ala Gly Val Gln Leu Thr Arg Leu Ala Pro Asp
385                 390                 395                 400

Phe Val Gly Ala Ala Ser Ile Ala Asn Arg Gln Lys Gln Thr His Phe
                405                 410                 415

Phe Leu Thr Leu Ser Gly Phe Asn Thr Pro Gly Thr Ile Ala Arg Tyr
            420                 425                 430

Asp Phe Thr Ala Pro Glu Thr Gln Arg Phe Ser Ile Leu Arg Thr Thr
        435                 440                 445

Lys Val Asn Glu Leu Asp Pro Asp Asp Phe Glu Ser Thr Gln Val Trp
    450                 455                 460

Tyr Glu Ser Lys Asp Gly Thr Lys Ile Pro Met Phe Ile Val Arg His
465                 470                 475                 480

Lys Ser Thr Lys Phe Asp Gly Thr Ala Ala Ala Ile Gln Tyr Gly Tyr
                485                 490                 495

Gly Gly Phe Ala Thr Ser Ala Asp Pro Phe Phe Ser Pro Ile Ile Leu
            500                 505                 510

Thr Phe Leu Gln Thr Tyr Gly Ala Ile Phe Ala Val Pro Ser Ile Arg
        515                 520                 525

Gly Gly Gly Glu Phe Gly Glu Glu Trp His Lys Gly Gly Arg Arg Glu
    530                 535                 540

Thr Lys Val Asn Thr Phe Asp Asp Phe Ile Ala Ala Ala Gln Phe Leu
545                 550                 555                 560

Val Lys Asn Lys Tyr Ala Ala Pro Gly Lys Val Ala Ile Asn Gly Ala
                565                 570                 575

Ser Asn Gly Gly Leu Leu Val Met Gly Ser Ile Val Arg Ala Pro Glu
            580                 585                 590

Gly Thr Phe Gly Ala Ala Val Pro Glu Gly Gly Val Ala Asp Leu Leu
        595                 600                 605

Lys Phe His Lys Phe Thr Gly Gly Gln Ala Trp Ile Ser Glu Tyr Gly
    610                 615                 620
```

```
Asn Pro Ser Ile Pro Glu Glu Phe Asp Tyr Ile Tyr Pro Leu Ser Pro
625                 630                 635                 640

Val His Asn Val Arg Thr Asp Lys Val Met Pro Ala Thr Leu Ile Thr
                645                 650                 655

Val Asn Ile Gly Asp Gly Arg Val Val Pro Met His Ser Phe Lys Phe
            660                 665                 670

Ile Ala Thr Leu Gln His Asn Val Pro Gln Asn Pro His Pro Leu Leu
        675                 680                 685

Ile Lys Ile Asp Lys Ser Trp Leu Gly His Gly Met Gly Lys Pro Thr
    690                 695                 700

Asp Lys Asn Val Lys Asp Ala Ala Asp Lys Trp Gly Phe Ile Ala Arg
705                 710                 715                 720

Ala Leu Gly Leu Glu Leu Lys Thr Val Glu
                725                 730
```

<210> SEQ ID NO 723
<211> LENGTH: 916
<212> TYPE: DNA
<213> ORGANISM: Artificial Sequence
<220> FEATURE:
<223> OTHER INFORMATION: A synthetic oligonucleotide

<400> SEQUENCE: 723

```
accttgtcag gagctgcgta cttattcttc acaaggtatt ggctgtgaca ggaaagttat      60

tgccggcaga gtaaaaagaa gcaagatgcg tacgttgcgg cgataaaatc gtcgaagcaa     120

tttccctgca ggacatcatg agcagctgat gaaataccaa gagttaaagg aacaagggac     180

cttcttttct ctacatccag ccaagtgcca gtcctcgccg aattctccgc cacccctgat     240

atttggaagc gcaaacacga cgccgtattt ttggaggaat gtaagaattg tcgcgctgaa     300

aaaggggtcg atggagatgc tgaatccacc ataacctgga gagcgtgagg cgtaaatacg     360

tgtgccatta aaattttcga tcggatatgg tcagtcaccg tattgtatga ctggggcagt     420

gccatcaaat ttcgttgatt tgtgacgaac gataaacatt gggatgcttg tgccgtcctt     480

gctctcatac catacctgcc aagacaaggt cagtaaatgg accagctaag aggtgggcag     540

caagtacttg gctagcttcg aaatcctctg tatttaggcc gttgagtttg gttgttcggt     600

aaatgctcca ccgctgctcc tcaggatcgg taaacttgta tctaccaatt gtgccaggtg     660

aggtaaaacc attcagttcg acaaagaagg aggaatgctt ttcacgccca gacacatgag     720

cagcgcccac aaagtcctca gccaggcgag cgagctggtt tccagcatgc gaatacacat     780

atacctcatc ttttacctgc ataaggtggc cgataacgtt attgttatat acttcgtatg     840

atggatgggt cttacattgc gcttgtaaac gagggcaaag tagcccttat ttacgctggt     900

aatgctggac aagtat                                                     916
```

<210> SEQ ID NO 724
<211> LENGTH: 87
<212> TYPE: PRT
<213> ORGANISM: Amanita bisporigera

<400> SEQUENCE: 724

```
Ser Thr Gln Val Trp Tyr Lys Ser Lys Asp Gly Thr Lys Val Pro Met
1               5                   10                  15

Phe Ile Val Arg His Lys Ser Thr Lys Phe Asp Gly Thr Ala Pro Ala
            20                  25                  30

Ile Gln Asn Gly Tyr Gly Gly Phe Ala Ile Thr Ala Asp Pro Phe Phe
        35                  40                  45
```

```
Ser Pro Ile Met Leu Thr Phe Met Gln Thr Tyr Gly Ala Ile Leu Ala
    50                  55                  60

Val Pro Asn Ile Arg Gly Gly Gly Glu Phe Gly Gly Glu Trp His Lys
65                  70                  75                  80

Ala Gly Arg Arg Glu Thr Lys
                85


<210> SEQ ID NO 725
<211> LENGTH: 107
<212> TYPE: PRT
<213> ORGANISM: Galerina marginata

<400> SEQUENCE: 725

Ser Trp Gln Val Trp Tyr Glu Ser Lys Asp Gly Thr Ser Ile Pro Met
1               5                   10                  15

Phe Ile Val Arg His Lys Ser Thr Lys Phe Asp Gly Thr Ala Pro Val
            20                  25                  30

Ile Gln Tyr Gly Asp Pro Tyr Pro Ile Glu Asn Phe Asn Gly Thr Arg
        35                  40                  45

Ile Tyr Ala Ser Arg Ser Pro Gly Tyr Gly Gly Phe Ser Ile Ser Ile
    50                  55                  60

Asp Pro Phe Phe Ser Ala Thr Ile Leu Thr Phe Leu Gln Lys Tyr Gly
65                  70                  75                  80

Val Val Phe Ala Leu Pro Asn Ile Arg Gly Gly Gly Glu Phe Gly Glu
                85                  90                  95

Asp Trp His Leu Ala Gly Cys Arg Glu Lys Lys
            100                 105


<210> SEQ ID NO 726
<211> LENGTH: 84
<212> TYPE: PRT
<213> ORGANISM: Amanita bisporigera

<400> SEQUENCE: 726

Val Lys Asp Glu Ile Tyr Leu Tyr Ser Lys Ala Gly Asp Gln Leu Ser
1               5                   10                  15

Arg Leu Ala Ser Asp Phe Ile Gly Val Ala Ser Ile Thr Asn Arg Glu
            20                  25                  30

Lys Gln Pro His Ser Phe Leu Thr Phe Ser Gly Phe Asn Thr Pro Gly
        35                  40                  45

Thr Ile Ser Arg Tyr Asp Phe Thr Ala Pro Asp Thr Gln Arg Leu Ser
    50                  55                  60

Ile Leu Arg Thr Thr Lys Leu Asn Gly Leu Asn Ala Asp Asp Phe Glu
65                  70                  75                  80

Ser Thr Gln Val


<210> SEQ ID NO 727
<211> LENGTH: 84
<212> TYPE: PRT
<213> ORGANISM: Galerina marginata

<400> SEQUENCE: 727

Val Lys Asp Glu Val Tyr Val Tyr Ser His Ala Gly Asn Gln Leu Ala
1               5                   10                  15

Arg Leu Ala Glu Asp Phe Val Gly Ala Ala His Val Ser Gly Arg Glu
            20                  25                  30

Lys His Ser Ser Phe Phe Val Glu Leu Asn Gly Phe Thr Ser Pro Gly
```

35 40 45

Thr Ile Gly Arg Tyr Lys Phe Thr Asp Pro Glu Glu Gln Arg Trp Ser
50 55 60

Ile Tyr Arg Thr Thr Lys Leu Asn Gly Leu Asn Thr Glu Asp Phe Glu
65 70 75 80

Ala Ser Gln Val

<210> SEQ ID NO 728
<211> LENGTH: 25
<212> TYPE: PRT
<213> ORGANISM: Amanita bisporigera

<400> SEQUENCE: 728

Lys Gly Asn Thr Phe Asp Asp Phe Ile Ala Ala Ala Gln Phe Leu Val
1 5 10 15

Lys Asn Lys Tyr Ala Ala Pro Gly Lys
20 25

<210> SEQ ID NO 729
<211> LENGTH: 41
<212> TYPE: PRT
<213> ORGANISM: Galerina marginata

<400> SEQUENCE: 729

Gln Gly Asn Cys Phe Asp Asp Phe Ile Ala Ala Thr Tyr Ala Ser Cys
1 5 10 15

Phe Phe Leu Leu Cys Arg Gln Leu Ser Cys His Ser Gln Tyr Leu Val
20 25 30

Lys Asn Lys Tyr Ala Ala Pro Asp Lys
35 40

<210> SEQ ID NO 730
<211> LENGTH: 21
<212> TYPE: PRT
<213> ORGANISM: Amanita bisporigera

<400> SEQUENCE: 730

Leu Thr Gln Val Lys Cys Val Asn Lys Gly Tyr Phe Val Ala Ile Tyr
1 5 10 15

Lys Arg Asn Val Lys
20

<210> SEQ ID NO 731
<211> LENGTH: 21
<212> TYPE: PRT
<213> ORGANISM: Galerina marginata

<400> SEQUENCE: 731

Leu Ser Ser Ile Thr Ser Val Asn Lys Gly Tyr Phe Ala Leu Val Tyr
1 5 10 15

Lys Arg Asn Val Arg
20

<210> SEQ ID NO 732
<211> LENGTH: 1036
<212> TYPE: DNA
<213> ORGANISM: Amanita bisporigera

<400> SEQUENCE: 732
tctctctaca gccgatggca gtggtggcga tttattcttt gatgtgggcc agctttctgc 60

```
caatcgcatg cctttgctga tgttcgtgaa gcccaatgcc ctttccaacg acggaactgc    120

cgctctttca acctatgcct tctcggattg tggcaaatat tttgcgtatg ggatctcttt    180

ctctgtatgt acattgatac acttcaaact actcgagcat gtattaactc atctatttag    240

ggcagtgatt tcgtgacaat ctacgtgcgg ttgacggatt cccctctcac taaagatgtg    300

gacgcgaaga acgacaaagg tcgccttcca gaggaaatca aatttgtcaa attttcatcc    360

ataggatgga cacctgattc caagggcttt ttttatcagg tcattccctg gaccgcgtgg    420

catcgctatt gggctaactt cattgtagcg ttacccagat acctccaccg tcacccaaga    480

gaacgggcct atcgcgacag aaggtgacct ggatgccatg gtatattatc atcgccttgg    540

aacgccgcag tgtatgcact ttccgttttt tctggaatca tgattgacgg gcagataact    600

gtttagcgga agatactctg atctaccaag acaaagaaca tagggactgg atgttcagca    660

ttgatgtcac agacgacggc aattacctcc tcctttacat tctcaaggac agctcaaggg    720

taatgcgctt attattaatt tctttttatg atgtctaaat cgccatgtag caaaacttac    780

tttggattgc tgcatttgat cctgcaaatc ttggtcccaa tatcaagtgg cagaaggtct    840

tcgatgaata tcactcagaa tacgagatgt atggccctga ttcttccttg tgtttggttg    900

atcaatgacc ttggtaccag tatcacaaac aagggctcat tgttctatgt tagaactaac    960

gaatccgctc cccagtacag agtcataacg gttgacattg ccaaagggaa tgaaatcaat   1020

gaactcatcc ctgaaa                                                   1036


<210> SEQ ID NO 733
<211> LENGTH: 80
<212> TYPE: PRT
<213> ORGANISM: Amanita bisporigera

<400> SEQUENCE: 733

Glu Asp Ile Ile Val Gln Gln Asp Lys Glu Asn Pro Asp Trp Thr Tyr
1               5                   10                  15

Gly Thr Asp Ala Ser Glu Asp Gly Lys Tyr Ile Tyr Leu Val Val Tyr
            20                  25                  30

Lys Asp Ala Ser Lys Gln Asn Leu Leu Trp Val Ala Glu Phe Asp Lys
        35                  40                  45

Asp Gly Val Lys Pro Glu Ile Pro Trp Arg Lys Val Ile Asn Glu Phe
    50                  55                  60

Gly Ala Asp Tyr His Val Ile Thr Asn His Gly Ser Leu Ile Tyr Val
65                  70                  75                  80


<210> SEQ ID NO 734
<211> LENGTH: 95
<212> TYPE: PRT
<213> ORGANISM: Galerina marginata

<400> SEQUENCE: 734

Glu Asp Thr Leu Ile Tyr Gln Asp Lys Glu His Arg Asp Trp Met Phe
1               5                   10                  15

Ser Ile Asp Val Thr Asp Asp Gly Asn Tyr Leu Leu Leu Tyr Ile Leu
            20                  25                  30

Lys Asp Ser Ser Arg Val Met Arg Leu Leu Leu Ile Ser Phe Tyr Asp
        35                  40                  45

Val Ile Ala Met Gln Asn Leu Leu Trp Ile Ala Ala Phe Asp Pro Ala
    50                  55                  60

Asn Leu Gly Pro Asn Ile Lys Trp Gln Lys Val Phe Asp Glu Tyr His
65                  70                  75                  80
```

```
Ser Glu Tyr Glu Met Tyr Gly Pro Asp Ser Ser Leu Cys Leu Val
                85                  90                  95


<210> SEQ ID NO 735
<211> LENGTH: 56
<212> TYPE: PRT
<213> ORGANISM: Amanita bisporigera

<400> SEQUENCE: 735

Gly Val Asp Tyr Phe Thr Ile Tyr Val Arg Pro Thr Ser Ser Ser Leu
1               5                   10                  15

Ser Gln Ala Pro Glu Ala Glu Gly Gly Asp Gly Arg Leu Ser Asp Gly
            20                  25                  30

Val Lys Trp Cys Lys Phe Thr Thr Ile Thr Trp Thr Lys Asp Ser Lys
        35                  40                  45

Gly Phe Leu Tyr Gln Arg Tyr Pro
    50                  55


<210> SEQ ID NO 736
<211> LENGTH: 56
<212> TYPE: PRT
<213> ORGANISM: Galerina marginata

<400> SEQUENCE: 736

Gly Ser Asp Phe Val Thr Ile Tyr Val Arg Leu Thr Asp Ser Pro Leu
1               5                   10                  15

Thr Lys Asp Val Asp Ala Lys Asn Asp Lys Gly Arg Leu Pro Glu Glu
            20                  25                  30

Ile Lys Phe Val Lys Phe Ser Ser Ile Gly Trp Thr Pro Asp Ser Lys
        35                  40                  45

Gly Phe Phe Tyr Gln Val Ile Pro
    50                  55


<210> SEQ ID NO 737
<211> LENGTH: 55
<212> TYPE: PRT
<213> ORGANISM: Amanita bisporigera

<400> SEQUENCE: 737

Ile Pro Trp Arg Lys Val Ile Asn Glu Phe Gly Ala Asp Tyr His Val
1               5                   10                  15

Ile Thr Asn His Gly Ser Leu Ile Tyr Val Lys Thr Asn Val Asn Ala
            20                  25                  30

Pro Gln Tyr Lys Val Val Thr Ile Asp Leu Ser Thr Gly Glu Pro Glu
        35                  40                  45

Ile Arg Asp Phe Ile Pro Glu
    50                  55


<210> SEQ ID NO 738
<211> LENGTH: 51
<212> TYPE: PRT
<213> ORGANISM: Galerina marginata

<400> SEQUENCE: 738

Leu Pro Cys Val Trp Leu Ile Asn Asp Leu Gly Thr Ser Ile Thr Asn
1               5                   10                  15

Lys Gly Ser Leu Phe Tyr Val Arg Thr Asn Glu Ser Ala Pro Gln Tyr
            20                  25                  30

Arg Val Ile Thr Val Asp Ile Ala Lys Gly Asn Glu Ile Asn Glu Leu
```

```
        35                  40                  45

Ile Pro Glu
    50


<210> SEQ ID NO 739
<211> LENGTH: 33
<212> TYPE: PRT
<213> ORGANISM: Amanita bisporigera

<400> SEQUENCE: 739

Val Tyr Phe Asp Pro Asn Val Leu Ser Ala Asp Gly Thr Ala Ile Met
1               5                   10                  15

Gly Thr Cys Arg Phe Ser Pro Ser Gly Glu Tyr Phe Ala Tyr Ala Val
            20                  25                  30

Ser


<210> SEQ ID NO 740
<211> LENGTH: 33
<212> TYPE: PRT
<213> ORGANISM: Galerina marginata

<400> SEQUENCE: 740

Met Phe Val Lys Pro Asn Ala Leu Ser Asn Asp Gly Thr Ala Ala Leu
1               5                   10                  15

Ser Thr Tyr Ala Phe Ser Asp Cys Gly Lys Tyr Phe Ala Tyr Gly Ile
            20                  25                  30

Ser


<210> SEQ ID NO 741
<211> LENGTH: 1169
<212> TYPE: DNA
<213> ORGANISM: Amanita bisporigera

<400> SEQUENCE: 741

gtggttcaag ttttcaacga taatctggac gaaggactcc aaaggttttc tgtaccaagt     60

atggtccacc atttaagcca tcgttgatca acgcgctgac acgatccttg cagcgatatc    120

ctgctcgtga acgtcatgag gggacacgca gcgatagaaa tgctatgatg tgttaccaca    180

aggttggaac gactcaaggt aagctgagat agcatcctgg ccttccctaa ttcaattccg    240

tgtgacagag gaggatatta tcgtgtatca agataatgaa cacccggaat ggatttatgg    300

agcagatacg tcagaggatg ggaaatatct ctacttgtat cagttcaagg atacctcgaa    360

ggtaaggctc tgagatttat tgcgcgacat caatgaatct cgtactgtca gaaaaacctt    420

ctgtgggttg cagaactcga cgaagatggg gtcaagtcag ggattcactg gcgaaaagtc    480

gttaatgagt atgcggccga ctataacatg tgaaaatctt ttattatctc caaatcaccc    540

tgtttaactt tgtataacac agtataacga accacggatc gctggtatac atcaagacca    600

atctcaatgc accccagtat aaggtcatca ccatcgacct atcaaaagac gaacctgaaa    660

tccgtgattt tatcccggaa gagaaagatg caaagctcgc tcaagttaat tgcgccaacg    720

aagaatactt tgtggccatc tacaagcgca atgtaatttc gttcgtgact ttctttgaat    780

ttcgctaatg ttggtacgac acccgcaggt caaagacgaa atatatctct actcgaaggc    840

tggagttcaa ctgacccgtc ttgcgccaga ctttgttggc gctgcgtcta ttgcgaacag    900

acagaaacaa actcatttct tcctcacact gtccggattt aatacacctg gcaccattgc    960

tcggtacgac ttcacggctc cagaaacaca acgcttcagc atccttcgga cgacaaaggt   1020
```

```
caatgaactg gatccagatg actttgagtc cacgcaagtc tggtatgaga gtaaagatgg   1080

cacaaaaatt cccatgttca ttgttcgtca acaaatctac aaaattcgat ggaacggcgg   1140

cggcgattca atatggtaat ccttttcgc                                     1169


<210> SEQ ID NO 742
<211> LENGTH: 105
<212> TYPE: PRT
<213> ORGANISM: Amanita bisporigera

<400> SEQUENCE: 742

Val Lys Asp Glu Ile Tyr Leu Tyr Ser Lys Ala Gly Asp Gln Leu Ser
1               5                   10                  15

Arg Leu Ala Ser Asp Phe Ile Gly Val Ala Ser Ile Thr Asn Arg Glu
            20                  25                  30

Lys Gln Pro His Ser Phe Leu Thr Phe Ser Gly Phe Asn Thr Pro Gly
        35                  40                  45

Thr Ile Ser Arg Tyr Asp Phe Thr Ala Pro Asp Thr Gln Arg Leu Ser
    50                  55                  60

Ile Leu Arg Thr Thr Lys Leu Asn Gly Leu Asn Ala Asp Asp Phe Glu
65                  70                  75                  80

Ser Thr Gln Val Trp Tyr Lys Ser Lys Asp Gly Thr Lys Val Pro Met
                85                  90                  95

Phe Ile Val Arg His Lys Ser Thr Lys
            100                 105


<210> SEQ ID NO 743
<211> LENGTH: 105
<212> TYPE: PRT
<213> ORGANISM: Galerina marginata

<400> SEQUENCE: 743

Val Lys Asp Glu Ile Tyr Leu Tyr Ser Lys Ala Gly Val Gln Leu Thr
1               5                   10                  15

Arg Leu Ala Pro Asp Phe Val Gly Ala Ala Ser Ile Ala Asn Arg Gln
            20                  25                  30

Lys Gln Thr His Phe Phe Leu Thr Leu Ser Gly Phe Asn Thr Pro Gly
        35                  40                  45

Thr Ile Ala Arg Tyr Asp Phe Thr Ala Pro Glu Thr Gln Arg Phe Ser
    50                  55                  60

Ile Leu Arg Thr Thr Lys Val Asn Glu Leu Asp Pro Asp Asp Phe Glu
65                  70                  75                  80

Ser Thr Gln Val Trp Tyr Glu Ser Lys Asp Gly Thr Lys Ile Pro Met
                85                  90                  95

Phe Ile Val Arg Gln Gln Ile Tyr Lys
            100                 105


<210> SEQ ID NO 744
<211> LENGTH: 181
<212> TYPE: PRT
<213> ORGANISM: Amanita bisporigera

<400> SEQUENCE: 744

His Val Ile Thr Asn His Gly Ser Leu Ile Tyr Val Lys Thr Asn Val
1               5                   10                  15

Asn Ala Pro Gln Tyr Lys Val Val Thr Ile Asp Leu Ser Thr Gly Glu
            20                  25                  30

Pro Glu Ile Arg Asp Phe Ile Pro Glu Gln Lys Asp Ala Lys Leu Thr
```

35 40 45

Gln Val Lys Cys Val Asn Lys Gly Tyr Phe Val Ala Ile Tyr Lys Arg
50 55 60

Asn Val Lys Asp Glu Ile Tyr Leu Tyr Ser Lys Ala Gly Asp Gln Leu
65 70 75 80

Ser Arg Leu Ala Ser Asp Phe Ile Gly Val Ala Ser Ile Thr Asn Arg
85 90 95

Glu Lys Gln Pro His Ser Phe Leu Thr Phe Ser Gly Phe Asn Thr Pro
100 105 110

Gly Thr Ile Ser Arg Tyr Asp Phe Thr Ala Pro Asp Thr Gln Arg Leu
115 120 125

Ser Ile Leu Arg Thr Thr Lys Leu Asn Gly Leu Asn Ala Asp Asp Phe
130 135 140

Glu Ser Thr Gln Val Trp Tyr Lys Ser Lys Asp Gly Thr Lys Val Pro
145 150 155 160

Met Phe Ile Val Arg His Lys Ser Thr Lys Phe Asp Gly Thr Ala Pro
165 170 175

Ala Ile Gln Asn Gly
180

<210> SEQ ID NO 745
<211> LENGTH: 198
<212> TYPE: PRT
<213> ORGANISM: Galerina marginata

<400> SEQUENCE: 745

His Ser Ile Thr Asn His Gly Ser Leu Val Tyr Ile Lys Thr Asn Leu
1 5 10 15

Asn Ala Pro Gln Tyr Lys Val Ile Thr Ile Asp Leu Ser Lys Asp Glu
20 25 30

Pro Glu Ile Arg Asp Phe Ile Pro Glu Glu Lys Asp Ala Lys Leu Ala
35 40 45

Gln Val Asn Cys Ala Asn Glu Glu Tyr Phe Val Ala Ile Tyr Lys Arg
50 55 60

Asn Val Ile Ser Phe Val Thr Phe Phe Glu Phe Arg Cys Trp Tyr Asp
65 70 75 80

Thr Arg Arg Ser Lys Thr Lys Tyr Ile Ser Thr Arg Arg Leu Glu Phe
85 90 95

Asn Pro Val Leu Arg Gln Thr Leu Leu Ala Leu Arg Leu Leu Arg Thr
100 105 110

Asp Arg Asn Lys Leu Ile Ser Ser Ser His Cys Pro Asp Leu Ile His
115 120 125

Leu Ala Pro Leu Leu Gly Thr Thr Ser Arg Leu Gln Lys His Asn Ala
130 135 140

Ser Ala Ser Phe Gly Arg Gln Arg Ser Met Asn Trp Ile Gln Met Thr
145 150 155 160

Leu Ser Pro Arg Lys Ser Gly Met Arg Val Lys Met Ala Gln Lys Phe
165 170 175

Pro Cys Ser Leu Phe Val Asn Lys Ser Thr Lys Phe Asp Gly Thr Ala
180 185 190

Ala Ala Ile Gln Tyr Gly
195

<210> SEQ ID NO 746
<211> LENGTH: 88

-continued

<212> TYPE: PRT
<213> ORGANISM: Amanita bisporigera

<400> SEQUENCE: 746

Trp Cys Lys Phe Thr Thr Ile Thr Trp Thr Lys Asp Ser Lys Gly Phe
1               5                   10                  15

Leu Tyr Gln Arg Tyr Pro Ala Arg Glu Ser Leu Val Ala Lys Asp Arg
            20                  25                  30

Asp Lys Asp Ala Met Val Cys Tyr His Arg Val Gly Thr Thr Gln Leu
        35                  40                  45

Glu Asp Ile Ile Val Gln Gln Asp Lys Glu Asn Pro Asp Trp Thr Tyr
    50                  55                  60

Gly Thr Asp Ala Ser Glu Asp Gly Lys Tyr Ile Tyr Leu Val Val Tyr
65                  70                  75                  80

Lys Asp Ala Ser Lys Gln Asn Leu
                85

<210> SEQ ID NO 747
<211> LENGTH: 118
<212> TYPE: PRT
<213> ORGANISM: Galerina marginata

<400> SEQUENCE: 747

Trp Phe Lys Phe Ser Thr Ile Ile Trp Thr Lys Asp Ser Lys Gly Phe
1               5                   10                  15

Leu Tyr Gln Val Trp Ser Thr Ile Ala Ile Val Asp Gln Arg Ala Asp
            20                  25                  30

Thr Ile Leu Ala Ala Ile Ser Cys Ser Thr Ser Gly Asp Thr Gln Arg
        35                  40                  45

Lys Cys Tyr Asp Val Leu Pro Gln Gly Trp Asn Asp Ser Arg Ala Glu
    50                  55                  60

Ile Ala Ser Trp Pro Ser Leu Ile Gln Phe Arg Val Thr Glu Glu Asp
65                  70                  75                  80

Ile Ile Val Tyr Gln Asp Asn Glu His Pro Glu Trp Ile Tyr Gly Ala
                85                  90                  95

Asp Thr Ser Glu Asp Gly Lys Tyr Leu Tyr Leu Tyr Gln Phe Lys Asp
            100                 105                 110

Thr Ser Lys Val Arg Leu
        115

<210> SEQ ID NO 748
<211> LENGTH: 34
<212> TYPE: PRT
<213> ORGANISM: Amanita bisporigera

<400> SEQUENCE: 748

Lys Gln Asn Leu Leu Trp Val Ala Glu Phe Asp Lys Asp Gly Val Lys
1               5                   10                  15

Pro Glu Ile Pro Trp Arg Lys Val Ile Asn Glu Phe Gly Ala Asp Tyr
            20                  25                  30

His Val

<210> SEQ ID NO 749
<211> LENGTH: 34
<212> TYPE: PRT
<213> ORGANISM: Galerina marginata

<400> SEQUENCE: 749

```
Gln Lys Asn Leu Leu Trp Val Ala Glu Leu Asp Glu Asp Gly Val Lys
1               5                   10                  15

Ser Gly Ile His Trp Arg Lys Val Val Asn Glu Tyr Ala Ala Asp Tyr
            20                  25                  30

Asn Met


<210> SEQ ID NO 750
<211> LENGTH: 1306
<212> TYPE: PRT
<213> ORGANISM: Amanita bisporigera

<400> SEQUENCE: 750

Thr Cys Ala Gly Gly Cys Thr Thr Ala Thr Gly Cys Ala Gly Gly Ala
1               5                   10                  15

Cys Thr Cys Gly Ala Gly Thr Thr Thr Thr Cys Cys Ala Thr Cys Cys
            20                  25                  30

Ala Ala Gly Ala Gly Thr Gly Gly Cys Cys Thr Cys Gly Cys Gly Ala
        35                  40                  45

Gly Cys Gly Thr Thr Gly Thr Thr Ala Ala Ala Thr Gly Gly Cys Thr
    50                  55                  60

Thr Thr Thr Thr Gly Gly Ala Thr Ala Cys Thr Gly Ala Ala Gly Gly
65                  70                  75                  80

Thr Thr Gly Gly Thr Gly Ala Gly Thr Cys Thr Gly Ala Thr Thr Gly
                85                  90                  95

Ala Gly Thr Gly Ala Thr Thr Ala Thr Gly Thr Ala Cys Ala Cys Gly
            100                 105                 110

Ala Ala Gly Thr Cys Ala Ala Thr Cys Ala Gly Gly Gly Thr Gly Gly
        115                 120                 125

Thr Ala Cys Thr Thr Gly Gly Gly Ala Cys Thr Thr Gly Gly Ala Gly
    130                 135                 140

Gly Ala Cys Ala Gly Gly Ala Cys Thr Thr Thr Cys Thr Thr Ala Gly
145                 150                 155                 160

Gly Ala Cys Thr Thr Ala Cys Thr Cys Cys Ala Cys Ala Cys Gly Cys
                165                 170                 175

Thr Cys Ala Thr Ala Ala Thr Ala Thr Cys Ala Cys Gly Thr Cys Gly
            180                 185                 190

Gly Thr Ala Thr Thr Cys Cys Ala Thr Cys Thr Thr Cys Cys Cys Thr
        195                 200                 205

Gly Thr Cys Ala Gly Thr Thr Thr Thr Thr Gly Ala Cys Cys Cys Cys
    210                 215                 220

Ala Ala Gly Ala Thr Thr Gly Thr Ala Ala Thr Ala Ala Cys Ala Cys
225                 230                 235                 240

Thr Cys Gly Thr Cys Ala Gly Gly Thr Gly Ala Gly Cys Thr Thr Cys
                245                 250                 255

Ala Cys Ala Gly Ala Ala Ala Thr Ala Thr Ala Thr Gly Gly Cys Ala
            260                 265                 270

Gly Gly Ala Gly Ala Ala Ala Thr Gly Ala Thr Ala Cys Thr Gly Ala
        275                 280                 285

Ala Ala Ala Ala Gly Cys Ala Gly Thr Thr Gly Cys Cys Cys Thr Thr
    290                 295                 300

Ala Cys Ala Cys Ala Thr Ala Gly Cys Gly Thr Thr Cys Ala Thr Gly
305                 310                 315                 320

Ala Ala Ala Thr Thr Cys Gly Gly Cys Ala Thr Gly Thr Thr Gly Cys
                325                 330                 335
```

-continued

```
Ala Cys Thr Thr Cys Thr Gly Ala Thr Ala Gly Ala Ala Cys Ala Gly
            340                 345                 350

Thr Cys Ala Thr Cys Cys Ala Ala Ala Thr Ala Ala Cys Thr Gly Gly
        355                 360                 365

Thr Thr Cys Ala Ala Gly Gly Cys Thr Thr Thr Ala Thr Thr Thr Cys
    370                 375                 380

Ala Cys Ala Cys Cys Cys Ala Gly Thr Gly Thr Thr Gly Thr Thr Thr
385                 390                 395                 400

Ala Thr Gly Gly Gly Cys Cys Cys Cys Cys Ala Thr Gly Ala Thr Cys
                405                 410                 415

Cys Ala Thr Thr Cys Thr Thr Thr Gly Thr Cys Thr Cys Gly Ala Thr
            420                 425                 430

Gly Ala Ala Ala Cys Gly Cys Cys Cys Thr Cys Ala Thr Cys Gly Gly
        435                 440                 445

Ala Cys Gly Cys Gly Cys Gly Ala Cys Gly Gly Ala Ala Thr Thr Thr
    450                 455                 460

Gly Ala Ala Ala Ala Thr Thr Ala Gly Gly Thr Gly Gly Ala Cys Thr
465                 470                 475                 480

Gly Ala Ala Thr Thr Thr Gly Ala Ala Ala Thr Gly Thr Gly Thr Thr
                485                 490                 495

Gly Ala Thr Gly Gly Cys Ala Gly Ala Ala Cys Thr Thr Thr Gly Gly
            500                 505                 510

Cys Thr Thr Gly Thr Cys Ala Cys Thr Thr Ala Cys Thr Ala Cys Thr
        515                 520                 525

Thr Cys Thr Cys Cys Cys Thr Thr Thr Thr Gly Thr Cys Cys Ala Gly
    530                 535                 540

Ala Ala Gly Cys Cys Cys Thr Thr Thr Ala Thr Cys Ala Thr Ala Thr
545                 550                 555                 560

Cys Thr Ala Ala Ala Ala Thr Cys Gly Thr Gly Ala Cys Ala Gly Thr
                565                 570                 575

Gly Gly Cys Ala Cys Gly Gly Ala Cys Cys Gly Thr Gly Gly Ala Cys
            580                 585                 590

Gly Thr Thr Ala Thr Cys Cys Cys Ala Ala Ala Cys Cys Ala Ala Cys
        595                 600                 605

Cys Cys Thr Ala Thr Thr Gly Gly Thr Ala Cys Cys Cys Thr Thr Ala
    610                 615                 620

Ala Ala Ala Ala Ala Cys Ala Gly Gly Gly Thr Thr Thr Thr Thr Cys
625                 630                 635                 640

Gly Ala Thr Gly Thr Cys Cys Gly Thr Cys Thr Thr Cys Cys Ala Gly
                645                 650                 655

Cys Cys Gly Thr Ala Thr Cys Gly Cys Thr Gly Ala Cys Cys Cys Cys
            660                 665                 670

Ala Cys Ala Ala Thr Thr Gly Cys Gly Gly Ala Ala Ala Ala Cys Thr
        675                 680                 685

Ala Thr Gly Thr Cys Gly Thr Cys Thr Gly Thr Ala Ala Cys Cys Thr
    690                 695                 700

Gly Gly Gly Cys Thr Cys Cys Thr Gly Gly Ala Ala Ala Thr Thr Ala
705                 710                 715                 720

Thr Cys Cys Cys Thr Cys Thr Ala Cys Cys Cys Gly Thr Cys Gly Thr
                725                 730                 735

Thr Cys Thr Gly Ala Cys Cys Ala Thr Gly Thr Cys Gly Ala Thr Ala
            740                 745                 750

Cys Cys Thr Ala Thr Cys Ala Gly Ala Gly Cys Gly Cys Gly Thr Cys
```

```
        755                 760                 765

Cys Ala Ala Gly Gly Gly Cys Gly Ala Ala Gly Thr Ala Cys Cys Thr
    770                 775                 780

Gly Thr Gly Cys Cys Gly Gly Ala Cys Cys Cys Cys Thr Ala Cys Cys
785                 790                 795                 800

Ala Ala Thr Gly Gly Cys Thr Gly Gly Ala Ala Gly Ala Gly Ala Gly
            805                 810                 815

Cys Ala Cys Cys Gly Ala Thr Gly Ala Ala Gly Thr Ala Gly Ala Cys
            820                 825                 830

Ala Ala Ala Thr Gly Gly Ala Cys Gly Ala Cys Thr Gly Cys Thr Cys
        835                 840                 845

Ala Gly Gly Cys Cys Gly Ala Thr Cys Thr Thr Gly Cys Cys Cys Ala
    850                 855                 860

Ala Thr Cys Ala Thr Ala Thr Cys Thr Thr Gly Ala Thr Cys Ala Gly
865                 870                 875                 880

Ala Ala Cys Gly Cys Gly Gly Ala Thr Ala Thr Thr Cys Ala Gly Ala
            885                 890                 895

Ala Ala Cys Thr Thr Gly Cys Gly Gly Ala Gly Ala Ala Ala Thr Thr
            900                 905                 910

Thr Cys Gly Thr Gly Cys Gly Ala Gly Thr Ala Gly Ala Ala Ala Cys
        915                 920                 925

Thr Ala Cys Gly Cys Ala Ala Ala Gly Gly Thr Ala Ala Thr Thr Thr
    930                 935                 940

Ala Thr Cys Gly Thr Ala Thr Ala Ala Ala Gly Thr Cys Gly Thr Ala
945                 950                 955                 960

Ala Cys Thr Thr Ala Thr Cys Ala Thr Cys Thr Gly Gly Cys Thr Gly
            965                 970                 975

Ala Ala Ala Cys Cys Cys Gly Thr Thr Cys Thr Cys Cys Thr Ala Gly
            980                 985                 990

Thr Thr Thr Thr Cys Cys Gly Cys  Ala Cys Cys Gly Ala  Cys Thr Cys
        995                 1000                1005

Thr Gly  Cys Thr Cys Gly Ala  Thr Gly Ala Cys Gly  Gly Ala Cys
    1010                1015                1020

Ala Thr  Thr Gly Gly Thr Ala  Thr Thr Gly Gly Thr  Thr Cys Thr
    1025                1030                1035

Ala Cys  Ala Ala Cys Cys Gly  Ala Gly Gly Cys Cys  Thr Gly Cys
    1040                1045                1050

Ala Ala  Thr Cys Gly Cys Ala  Gly Thr Cys Ala Gly  Gly Thr Ala
    1055                1060                1065

Gly Ala  Thr Ala Thr Thr Thr  Ala Thr Thr Thr Gly  Thr Cys Cys
    1070                1075                1080

Thr Ala  Cys Gly Ala Gly Gly  Gly Thr Gly Cys Ala  Ala Ala Ala
    1085                1090                1095

Cys Thr  Cys Ala Gly Ala Cys  Ala Thr Thr Thr Thr  Ala Cys Ala
    1100                1105                1110

Ala Gly  Thr Thr Cys Thr Thr  Thr Ala Cys Cys Gly  Cys Thr Cys
    1115                1120                1125

Cys Ala  Ala Gly Gly Ala Ala  Cys Cys Gly Gly Cys  Gly Cys Thr
    1130                1135                1140

Thr Cys  Cys Thr Gly Ala Thr  Thr Thr Cys Thr Cys  Cys Ala Ala
    1145                1150                1155

Gly Gly  Gly Cys Gly Ala Cys  Gly Ala Thr Ala Ala  Thr Gly Thr
    1160                1165                1170
```

```
Thr Gly  Gly Cys Gly Ala Cys  Gly Thr Ala Thr Thr  Cys Thr Thr
    1175                 1180                 1185

Cys Gly  Ala Cys Gly Thr Ala  Gly Gly Gly Gly Cys  Cys Thr Cys
    1190                 1195                 1200

Cys Thr  Thr Cys Ala Cys Thr  Gly Cys Cys Thr Cys  Ala Gly Ala
    1205                 1210                 1215

Cys Gly  Thr Cys Thr Thr Cys  Thr Cys Thr Gly Ala  Ala Thr Gly
    1220                 1225                 1230

Cys Gly  Thr Thr Cys Thr Thr  Ala Ala Ala Ala Gly  Cys Cys Ala
    1235                 1240                 1245

Ala Ala  Thr Gly Thr Ala Cys  Thr Cys Gly Cys Thr  Gly Cys Thr
    1250                 1255                 1260

Gly Ala  Thr Gly Gly Cys Ala  Gly Cys Gly Cys Cys  Gly Gly Thr
    1265                 1270                 1275

Ala Thr  Gly Gly Thr Cys Cys  Thr Cys Thr Gly Thr  Ala Ala Ala
    1280                 1285                 1290

Thr Thr  Cys Thr Cys Cys Cys  Cys Cys Gly Ala Thr  Gly
    1295                 1300                 1305
```

<210> SEQ ID NO 751
<211> LENGTH: 134
<212> TYPE: PRT
<213> ORGANISM: Amanita bisporigera

<400> SEQUENCE: 751

```
Arg Ile Met Ser Ser Thr Gln Trp Thr Pro Asn Met Tyr Pro Ser Ala
1               5                   10                  15

Arg Arg Ser Asp His Ile Asp Thr Tyr Arg Ser Glu Thr Arg Gly Glu
            20                  25                  30

Val Lys Val Pro Asp Pro Tyr His Trp Leu Glu Glu Tyr Ser Glu Glu
        35                  40                  45

Thr Asp Lys Trp Thr Ser Asp Gln Glu Glu Phe Thr Arg Thr Tyr Leu
    50                  55                  60

Asp Ser Asn Pro Asp Arg Lys Lys Leu Glu Asp Ala Phe Arg Lys Ser
65                  70                  75                  80

Met Asp Tyr Pro Lys Phe Ser Ala Pro Phe Leu Asn Asp Asp Lys Arg
                85                  90                  95

Trp Tyr Trp Phe Tyr Asn Thr Gly Leu Gln Ala Gln Thr Val Ile Cys
            100                 105                 110

Arg Ser Lys Asp Glu Thr Leu Pro Asp Phe Ser Glu Ser Asp Tyr Val
        115                 120                 125

Gly Glu Thr Phe Phe Asp
    130
```

<210> SEQ ID NO 752
<211> LENGTH: 167
<212> TYPE: PRT
<213> ORGANISM: Galerina marginata

<400> SEQUENCE: 752

```
Lys Thr Met Ser Ser Val Thr Trp Ala Pro Gly Asn Tyr Pro Ser Thr
1               5                   10                  15

Arg Arg Ser Asp His Val Asp Thr Tyr Gln Ser Ala Ser Lys Gly Glu
            20                  25                  30

Val Pro Val Pro Asp Pro Tyr Gln Trp Leu Glu Glu Ser Thr Asp Glu
        35                  40                  45
```

```
Val Asp Lys Trp Thr Thr Ala Gln Ala Asp Leu Ala Gln Ser Tyr Leu
    50                  55                  60

Asp Gln Asn Ala Asp Ile Gln Lys Leu Ala Glu Lys Phe Arg Ala Ser
65                  70                  75                  80

Arg Asn Tyr Ala Lys Val Ile Tyr Arg Ile Lys Ser Leu Ile Ile Trp
                85                  90                  95

Leu Lys Pro Val Leu Leu Val Phe Arg Thr Asp Ser Ala Arg Arg Thr
            100                 105                 110

Leu Val Leu Val Leu Gln Pro Arg Pro Ala Ile Ala Val Arg Ile Phe
        115                 120                 125

Ile Cys Pro Thr Arg Val Gln Asn Ser Asp Ile Leu Gln Val Leu Tyr
    130                 135                 140

Arg Ser Lys Glu Pro Ala Leu Pro Asp Phe Ser Lys Gly Asp Asp Asn
145                 150                 155                 160

Val Gly Asp Val Phe Phe Asp
                165
```

<210> SEQ ID NO 753
<211> LENGTH: 35
<212> TYPE: PRT
<213> ORGANISM: Artificial Sequence
<220> FEATURE:
<223> OTHER INFORMATION: A synthetic peptide
<220> FEATURE:
<221> NAME/KEY: MISC_FEATURE
<222> LOCATION: (11)..(11)
<223> OTHER INFORMATION: The residue in this position can be either I or A.
<220> FEATURE:
<221> NAME/KEY: MISC_FEATURE
<222> LOCATION: (13)..(13)
<223> OTHER INFORMATION: The residue in this position can be either G or L.
<220> FEATURE:
<221> NAME/KEY: MISC_FEATURE
<222> LOCATION: (14)..(14)
<223> OTHER INFORMATION: The residue in this position can be either I or V.
<220> FEATURE:
<221> NAME/KEY: MISC_FEATURE
<222> LOCATION: (15)..(15)
<223> OTHER INFORMATION: The residue in this position can be either G or D.
<220> FEATURE:
<221> NAME/KEY: MISC_FEATURE
<222> LOCATION: (17)..(17)
<223> OTHER INFORMATION: The residue in this position can be either N or any amino acid.
<220> FEATURE:
<221> NAME/KEY: MISC_FEATURE
<222> LOCATION: (20)..(20)
<223> OTHER INFORMATION: The residue in this position can be either I or V.
<220> FEATURE:
<221> NAME/KEY: MISC_FEATURE
<222> LOCATION: (25)..(25)
<223> OTHER INFORMATION: The residue in this position can be either T or N.
<220> FEATURE:
<221> NAME/KEY: MISC_FEATURE
<222> LOCATION: (26)..(26)
<223> OTHER INFORMATION: The residue in this position can be either T or R.
<220> FEATURE:
<221> NAME/KEY: MISC_FEATURE
<222> LOCATION: (33)..(33)
<223> OTHER INFORMATION: The residue in this position can be either A or S.

<400> SEQUENCE: 753

-continued

```
Met Ser Asp Ile Asn Ala Thr Arg Leu Pro Xaa Trp Xaa Xaa Xaa Cys
1               5                   10                  15

Xaa Pro Cys Xaa Gly Asp Asp Val Xaa Xaa Leu Leu Thr Arg Gly Glu
            20                  25                  30

Xaa Leu Cys
        35


<210> SEQ ID NO 754
<211> LENGTH: 6
<212> TYPE: PRT
<213> ORGANISM: Artificial Sequence
<220> FEATURE:
<223> OTHER INFORMATION: A synthetic peptide

<400> SEQUENCE: 754

Asn Ala Thr Arg Leu Pro
1               5


<210> SEQ ID NO 755
<211> LENGTH: 17
<212> TYPE: PRT
<213> ORGANISM: Artificial Sequence
<220> FEATURE:
<223> OTHER INFORMATION: A synthetic peptide

<400> SEQUENCE: 755

Met Ser Asp Ile Asn Ala Thr Arg Leu Pro Ala Trp Leu Ala Thr Cys
1               5                   10                  15

Pro


<210> SEQ ID NO 756
<211> LENGTH: 6
<212> TYPE: PRT
<213> ORGANISM: Artificial Sequence
<220> FEATURE:
<223> OTHER INFORMATION: A synthetic peptide

<400> SEQUENCE: 756

Ala Trp Leu Ala Thr Cys
1               5
```

UNITED STATES PATENT AND TRADEMARK OFFICE
CERTIFICATE OF CORRECTION

PATENT NO. : 9,932,571 B2
APPLICATION NO. : 15/437359
DATED : April 3, 2018
INVENTOR(S) : Hallen-Adams et al.

It is certified that error appears in the above-identified patent and that said Letters Patent is hereby corrected as shown below:

On the Title Page

On page 2, in Column 2, under "Other Publications", Line 59, delete "ofthe" and insert --of the-- therefor On page 2, in Column 2, under "Other Publications", Line 69, delete "grarninearum)," and insert --graminearum),-- therefor On page 2, in Column 2, under "Other Publications", Line 71, delete "ofiethal" and insert --of lethal-- therefor On page 3, in Column 1, under "Other Publications", Line 22, delete "alpha-Arnanitin."," and insert --alpha-Amanitin.",-- therefor On page 3, in Column 1, under "Other Publications", Lines 34-36, delete "376-380 May, J.P., et al., "Tryptathionine Bridges in Peptide Synthesis", Biopolymers, 88(5), (2007), 714-724." and insert --376-380.-- therefor On page 3, in Column 1, under "Other Publications", Line 51, delete "Exogenornics"," and insert --Exogenomics",-- therefor On page 3, in Column 1, under "Other Publications", Line 60, delete "[D-Ala2]deltorphin" and insert --[D-Ala$^2$]deltorphin-- therefor On page 3, in Column 1, under "Other Publications", Line 62, delete "derrnorphin-related" and insert --dermorphin-related-- therefor On page 3, in Column 2, under "Other Publications", Line 7, delete "hornobasidiomycete" and insert --homobasidiomycete-- therefor Signed and Sealed this
Fourth Day of June, 2019

Andrei Iancu
*Director of the United States Patent and Trademark Office*

CERTIFICATE OF CORRECTION (continued)
U.S. Pat. No. 9,932,571 B2

On page 3, in Column 2, under "Other Publications", Line 12, delete "Intolerence" and insert --Intolerance-- therefor On page 3, in Column 2, under "Other Publications", Line 46, delete "fFngi" and insert --Fungi:-- therefor On page 3, in Column 2, under "Other Publications", Line 69, delete "cultureof" and insert --culture of-- therefor